United States Patent
Natunen et al.

(10) Patent No.: US 9,695,454 B2
(45) Date of Patent: Jul. 4, 2017

(54) PRODUCTION OF FUCOSYLATED GLYCOPROTEINS

(71) Applicants: Glykos Finland OY, Helsinki (FI); Novartis AG, Basel (CH)

(72) Inventors: Jari Natunen, Vantaa (FI); Ann Westerholm-Parvinen, Kirkkonummi (FI); Hanna Salo, Helsinki (FI); Jussi Joensuu, Tervakoski (FI); Heli Viskari, Nummela (FI); Christopher Landowski, Helsinki (FI); Anne Huuskonen, Helsinki (FI); Anne Kanerva, Helsinki (FI); Anna-Liisa Hanninen, Helsinki (FI); Noora Salovuori, Helsinki (FI); Merja Penttila, Helsinki (FI); Juhani Saarinen, Helsinki (FI); Markku Saloheimo, Helsinki (FI)

(73) Assignee: GLYKOS FINLAND OY, Helsinki (FI)

(*) Notice: Subject to any disclaimer, the term of this patent is extended or adjusted under 35 U.S.C. 154(b) by 284 days.

(21) Appl. No.: 14/402,837

(22) PCT Filed: May 23, 2013

(86) PCT No.: PCT/EP2013/060627
§ 371 (c)(1),
(2) Date: Nov. 21, 2014

(87) PCT Pub. No.: WO2013/174927
PCT Pub. Date: Nov. 28, 2013

(65) Prior Publication Data
US 2015/0176044 A1    Jun. 25, 2015

Related U.S. Application Data

(60) Provisional application No. 61/650,910, filed on May 23, 2012.

(51) Int. Cl.
| | | |
|---|---|---|
| C12R 1/885 | (2006.01) |
| C12P 21/00 | (2006.01) |
| C07K 14/435 | (2006.01) |
| C12N 9/04 | (2006.01) |
| C12N 9/10 | (2006.01) |
| C12N 9/58 | (2006.01) |
| C12N 9/88 | (2006.01) |
| C12N 15/52 | (2006.01) |
| C07K 16/00 | (2006.01) |
| C12N 15/80 | (2006.01) |

(52) U.S. Cl.
CPC ...... *C12P 21/005* (2013.01); *C07K 14/43545* (2013.01); *C07K 16/00* (2013.01); *C12N 9/0006* (2013.01); *C12N 9/1051* (2013.01); *C12N 9/58* (2013.01); *C12N 9/88* (2013.01); *C12N 15/52* (2013.01); *C12N 15/80* (2013.01); *C07K 2319/01* (2013.01)

(58) Field of Classification Search
CPC ................. C12R 1/885; C12P 21/15
See application file for complete search history.

(56) References Cited

U.S. PATENT DOCUMENTS

| | | |
|---|---|---|
| 4,758,512 A | 7/1988 | Goldberg et al. |
| 5,116,964 A | 5/1992 | Capon et al. |
| 5,428,130 A | 6/1995 | Capon et al. |
| 5,455,165 A | 10/1995 | Capon et al. |
| 5,514,582 A | 5/1996 | Capon et al. |
| 5,674,728 A | 10/1997 | Buxton et al. |
| 5,693,520 A | 12/1997 | Branner et al. |
| 5,756,338 A | 5/1998 | Buxton et al. |
| 5,776,730 A | 7/1998 | Stuart |
| 5,821,104 A | 10/1998 | Holm et al. |
| 5,840,570 A | 11/1998 | Berka et al. |
| 5,846,802 A | 12/1998 | Buxton et al. |
| 5,968,774 A | 10/1999 | Lehmbeck |
| 5,989,889 A | 11/1999 | Rey et al. |
| 6,013,452 A | 1/2000 | Christensen et al. |
| 6,013,489 A | 1/2000 | Musters et al. |
| 6,025,185 A | 2/2000 | Christensen et al. |
| 6,291,209 B1 | 9/2001 | Lehmbeck |
| 6,352,841 B1 | 3/2002 | Lehmbeck |
| 6,509,171 B1 | 1/2003 | Berka et al. |

(Continued)

FOREIGN PATENT DOCUMENTS

| | | |
|---|---|---|
| EP | 1 266 011 B1 | 5/2010 |
| WO | 96/36718 A1 | 11/1996 |
| WO | 97/12045 A1 | 4/1997 |
| WO | 97/46689 A1 | 12/1997 |
| WO | 00/46375 A2 | 8/2000 |
| WO | 2004/067709 A2 | 8/2004 |
| WO | 2005/055944 A2 | 6/2005 |
| WO | 2005/087922 A1 | 9/2005 |
| WO | 2008/074499 A1 | 6/2008 |
| WO | 2008/112092 A2 | 9/2008 |
| WO | 2010/036898 A1 | 4/2010 |
| WO | 2011/075677 A2 | 6/2011 |
| WO | 2011/106389 A1 | 9/2011 |

OTHER PUBLICATIONS

Ahamed, et al. Chymostatin can combine with pepstatin to eliminate extracellular protease activity in cultures of Aspergillus niger NRRL-3. J. Ind. Microbiol. Biotechnol. 34: 165-169 (2007).

Baldwin, et al. Develop Systems for Manufacturing 100,000,000 Doses of an Emergency Pharmaceutical (e.g. Vaccine or Monoclonal Antibody) Within 2 Months of Product Identification, Genencor International (Jun. 6, 2009).

(Continued)

*Primary Examiner* — Karen Cochrane Carlson
(74) *Attorney, Agent, or Firm* — Patrick J. Halloran

(57) ABSTRACT

Described herein are compositions including filamentous fungal cells, such as *Trichoderma* fungal cells, having reduced protease activity and expressing fucosylation pathway. Further described herein are methods for producing a glycoprotein having fucosylated N-glycan, using genetically modified filamentous fungal cells, for example, *Trichoderma* fungal cells, as the expression system.

17 Claims, 21 Drawing Sheets

(56) References Cited

U.S. PATENT DOCUMENTS

| | | |
|---|---|---|
| 6,602,684 B1 | 8/2003 | Umaña et al. |
| 6,806,062 B1 | 10/2004 | Hjort et al. |
| 6,946,292 B2 | 9/2005 | Kanda et al. |
| 7,029,872 B2 | 4/2006 | Gerngross |
| 7,094,530 B1 | 8/2006 | Sasaki et al. |
| 7,122,330 B2 | 10/2006 | Emalfarb et al. |
| 7,163,804 B1 | 1/2007 | Royer et al. |
| 7,198,938 B2 | 4/2007 | Shuster et al. |
| 7,303,877 B2 | 12/2007 | Connelly et al. |
| 7,323,327 B2 | 1/2008 | Edens et al. |
| 7,691,621 B2 | 4/2010 | Wang |
| 7,771,971 B2 | 8/2010 | Connelly et al. |
| 7,794,974 B2 | 9/2010 | Peij et al. |
| 7,858,360 B2 | 12/2010 | Hansen et al. |
| 7,968,312 B2 | 6/2011 | Sagt et al. |
| 7,977,067 B2 | 7/2011 | Power et al. |
| 8,017,341 B2 | 9/2011 | Nikolaev et al. |
| 8,119,171 B2 | 2/2012 | Lopez et al. |
| 8,288,517 B2 | 10/2012 | Clarkson et al. |
| 8,389,269 B2 | 3/2013 | Sagt et al. |
| 8,426,164 B2 | 4/2013 | Hjort et al. |
| 8,450,098 B2 | 5/2013 | Kim et al. |
| 8,633,010 B2 | 1/2014 | Lehmbeck et al. |
| 8,647,856 B2 | 2/2014 | Shasky et al. |
| 8,680,252 B2 | 3/2014 | Emalfarb et al. |
| 8,716,004 B2 | 5/2014 | Wang |
| 8,741,654 B2 | 6/2014 | Bodie et al. |
| 8,812,247 B2 | 8/2014 | Roubos et al. |
| 8,916,363 B2 | 12/2014 | Gusakov et al. |
| 8,986,974 B2 * | 3/2015 | Maiyuran ............ C12N 9/58 435/254.1 |
| 2002/0058313 A1 | 5/2002 | Renkonen et al. |
| 2002/0132320 A1 | 9/2002 | Wang et al. |
| 2003/0157108 A1 | 8/2003 | Presta |
| 2003/0175884 A1 | 9/2003 | Umana et al. |
| 2004/0014170 A1 | 1/2004 | Miura et al. |
| 2004/0018573 A1 | 1/2004 | Power et al. |
| 2004/0018590 A1 | 1/2004 | Gerngross et al. |
| 2004/0072290 A1 | 4/2004 | Umana et al. |
| 2004/0093621 A1 | 5/2004 | Shitara et al. |
| 2004/0136986 A1 | 7/2004 | Raju |
| 2004/0171826 A1 | 9/2004 | Hamilton |
| 2004/0191256 A1 | 9/2004 | Raju |
| 2004/0230042 A1 | 11/2004 | Hamilton |
| 2004/0241817 A1 | 12/2004 | Umana et al. |
| 2004/0259150 A1 | 12/2004 | Nakamura et al. |
| 2005/0170452 A1 | 8/2005 | Wildt et al. |
| 2005/0208617 A1 | 9/2005 | Bobrowicz et al. |
| 2005/0276805 A1 | 12/2005 | Hanai et al. |
| 2005/0277154 A1 | 12/2005 | Dukler et al. |
| 2006/0000996 A1 | 1/2006 | Soldo |
| 2006/0040353 A1 | 2/2006 | Davidson et al. |
| 2006/0160179 A1 | 7/2006 | Bobrowicz et al. |
| 2006/0211085 A1 | 9/2006 | Bobrowicz |
| 2006/0234345 A1 | 10/2006 | Schwartz et al. |
| 2006/0286637 A1 | 12/2006 | Hamilton |
| 2007/0037248 A1 | 2/2007 | Bobrowicz et al. |
| 2007/0067855 A1 | 3/2007 | Jarvis et al. |
| 2008/0206816 A1 | 8/2008 | Idiris et al. |
| 2008/0305525 A1 | 12/2008 | Kang et al. |
| 2009/0176219 A1 | 7/2009 | Parenicova et al. |
| 2009/0221030 A1 | 9/2009 | Bao et al. |
| 2009/0253173 A1 | 10/2009 | Wang |
| 2009/0275079 A1 | 11/2009 | Edens et al. |
| 2010/0062485 A1 | 3/2010 | Kang et al. |
| 2010/0137565 A1 | 6/2010 | Javaud et al. |
| 2011/0111977 A1 | 5/2011 | Retallack |
| 2011/0283422 A1 | 11/2011 | Nelson et al. |
| 2011/0294191 A1 | 12/2011 | Wang |
| 2012/0030839 A1 | 2/2012 | Emalfarb et al. |
| 2012/0107856 A1 | 5/2012 | Punt et al. |
| 2012/0149064 A1 | 6/2012 | Wang et al. |
| 2012/0213728 A1 | 8/2012 | Meehl et al. |
| 2012/0231502 A1 | 9/2012 | Hamilton et al. |
| 2012/0232007 A1 | 9/2012 | Bobrowicz et al. |
| 2012/0276075 A1 | 11/2012 | Monod et al. |
| 2012/0288892 A1 | 11/2012 | Maiyuran et al. |
| 2012/0328626 A1 | 12/2012 | Sethuraman et al. |
| 2013/0011875 A1 | 1/2013 | Meehl et al. |
| 2014/0212977 A1 | 7/2014 | Yaver et al. |

OTHER PUBLICATIONS

Hintz et al., Improved gene expression in Aspergillus nidulans. Can. Jo. Bot. 73 (Supp. 1): S876-S884 (1995).

Idiris, et al. Enhanced protein secretion from multiprotease-deficient fission yeast by modification of its vacuolar protein sorting pathway. Appl. Microbiol. Biotechnol. 85: 667-677 (2010).

Krysan, et al. Yapsins are a family of aspartyl proteases required for cell wall integrity in saccharomyces cerevisiae. Eukaryotic Cell. 4(8): 1364-1374 (2005).

Kuroda, et al. Antibody expression in protease-deficient strains of the methlotrophic yeast ogataea minuta. FEMS Yeast Res. 7: 1307-1316 (2007).

Martinez, et al. Genome sequencing and analysis of the biomass-degrading fungus Trichoderma reesei (syn. Hypocrea jecorina). Nature Biotech. 26(5): 553-560 (2008).

Martinez, et al. Uniprot GORG34, XP002712642 (Oct. 19, 2011).
Martinez, et al. Uniprot GORIW3, XP002712643 (Oct. 19, 2011).
Martinez, et al. Uniprot GORHO5, XP002712644 (Oct. 19, 2011).
Martinez, et al. Uniprot GORSP8, XP002712645 (Oct. 19, 2011).
Martinez, et al. Uniprot GORVKO, XP002712646 (Oct. 19, 2011).
Martinez, et al. Uniprot GOR8TO, XP002712647 (Oct. 19, 2011).

Van Den Hobergh, et al. Disruption of three acid proteases in Aspergillus niger. Eur. J. Biochem. 247: 605-613 (1997).

Yoon, et al. Construction of quintuple protease gene disruptant for heterologous protein production in aspergillus oryzae Appl. Microbiol. Biotechnol. 82: 691-701 (2009).

Yoon, et al. Disruption of ten protease genes in the filamentous fungus aspergillus oryzae highly improves production of heterologous proteins. Appl. Microbiol. Biotechnol. (Oct. 19, 2010).

Adav et al., "Proteomic Analysis of pH and Strains Dependent Protein Secretion of Trichoderma Reesei", J Proteome Res., (10)10, Oct. 7, 2011, pp. 4579-4596.

Archer et al., "Proteolytic Degradation of Heterologous Proteins Expressed in Aspergillus Niger", Biotechnology Letters, vol. 14, Issue 5, May 5, 1992, pp. 357-362.

Behnsen et al., "Secreted Aspergillus Fumigatus Protease Alp1 Degrades Human Complement Proteins C3, C4, and C5", Infect Immun., 78(8), Aug. 2010, pp. 3585-3594.

Berka et al., "Molecular Cloning and Deletion of the Gene Encoding Aspergillopepsin a from Aspergillus Awamori", Gene., 86(2), Feb. 14, 1990, pp. 153-162.

Broekhuijsen et al., "Secretion of Heterologous Proteins by Aspergillus Niger: Production of Active Human Interleukin-6 in a Protease-Deficient Mutant by KEX2-like Processing of a Glucoamylase-hIL6 Fusion Protein", Journal of Biotechnology, 31(2), Nov. 1993, pp. 135-145.

Dal Degan et al., "Purification and Characterization of two Serine Carboxypeptidases from Aspergillus Niger and their use in C-terminal Sequencing of Proteins and Peptide Synthesis", Applied and Environment Microbiology, 58(7), Jul. 1992, pp. 2144-2152.

Delgado-Jarana et al., "Overproduction of Beta-1,6-glucanase in Trichoderma Harzianum is Controlled by Extracellular Acidic Proteases and pH", Biochimca et Biophysica Acta, 1481(2), Sep. 29, 2000, pp. 289-296.

Delgado-Jarana et al., "Aspartyl Protease from Trichoderma Harzianum CECT 2413: Cloning and Characterization" Microbiology, 148(Pt 5), May 2002, pp. 1305-1315.

Diener et al., "Characterization of the Protein Processing and Secretion Pathways in a Comprehensive Set of Expressed Sequence Tags from Trichoderma reesei", FEMS Microbiology Letters, 230(2), Jan. 30, 2004, pp. 275-282.

Dienes et al., "Identification of a trypsin-like Serine Protease from Trichoderma reesei QM9414", Enzyme and Microbial Technology, vol. 40, Issue 5, Apr. 3, 2007, pp. 1087-1094.

(56) References Cited

OTHER PUBLICATIONS

Durand-Poussereau et al., "Characterization of a Protease Deficient Strain of Penicillium Roqueforti Generated by Heterologous Plasmid Integration: Potential use for Protein Production", Journal of Biotechnology, 51(1), Oct. 18, 1996, pp. 97-105.
Edens et al.,"Extracellular Prolyl Endoprotease from Aspergillus Niger and its use in the Debittering of Protein Hydrolysates", Journal of Agricultural and Food Chemistry, 53(20), Oct. 5, 2005, pp. 7950-7957.
Eneyskaya et al., "Acid protease from Trichoderma reesei: Limited Proteolysis of Fungal Carbohydrases", Applied Microbiology and Biotechnology, vol. 52, Issue 52, Aug. 1999, pp. 226-231.
Foreman et al., "Transcriptional Regulation of Biomass-degrading Enzymes in the Filamentous Fungus *Trichoderma reesei*", Journal of Biological Chemistry, vol. 278, No. 34, Aug. 22, 2003, pp. 31988-31997.
Frenken et al., "Recent Advances in the Large-scale Production of Antibody Fragments using Lower Eukaryotic Microorganisms", Research in Immunology, vol. 149, Issue 6, Jul. 1998, pp. 589-599.
Fujinaga et al., "The Molecular Structure and Catalytic Mechanism of a Novel Carboxyl Peptidase from Scytalidium Lignicolum", Proc Natl Acad Sci U S A, vol. 101, No. 10, Mar. 9, 2004, pp. 3364-3369.
Gagnon-Arsenault et al., "Fungal Yapsins and Cell Wall: a Unique Family of Aspartic Peptidases for a Distinctive Cellular Function", FEMS Yeast Research, 6(7), Nov. 2006, pp. 966-978.
Gouka et al., "Efficient Production of Secreted Proteins by Aspergillus: Progress, Limitations and Prospects", Applied Microbiology and Biotechnology, vol. 47, Issue 1, Jan. 1997, pp. 1-11.
Haab et al., "Formation of the Extracellular Proteases from Trichoderma reesei QM 9414 Involved in Cellulase Degradation", Journal of Biotechnology, vol. 16, Issue 3-4, Nov. 1990, pp. 187-198.
Hagspiel et al., "Protease Activity and Proteolytic Modification of cellulases from a Trichoderma reesei QM 9414 selectant", Applied Microbiology and Biotechnology, vol. 32, Issue 1, Nov. 1989, pp. 61-67.
Huang et al., "Identification of a Glutamic Acid and an Aspartic Acid Residue Essential for Catalytic Activity of Aspergillopepsin II, a non-pepsin type Acid Proteinase", The Journal of Biological Chemistry, vol. 275, No. 34, Aug. 25, 2000, pp. 26607-26614.
Inoue et al., "The Gene and Deduced Protein Sequences of the Zymogen of Aspergillus Niger acid Proteinase A", The Journal of Biological Chemistry, vol. 266, No. 29, Oct. 15, 1991, pp. 19484-19489.
Janas, "Production of Extracellular Enzymes by Low-protease Mutants of Trichoderma reesei", Technologia Alimentaria, Issue 2(2), 2003, pp. 103-114.
Jarai et al., "Cloning and Characterization of the pepE Gene of Aspergillus Niger Encoding a new Aspartic Protease and Regulation of pepE and pepC", Gene., 145(2), Aug. 1994, pp. 171-178.
Jin et al., "Double Disruption of the Proteinase Genes, tppA and pepE, Increases the Production Level of Human Lysozyme by Aspergillus Oryzae", Applied Microbiology and Biotechnology, vol. 76, Issue 5, Oct. 2007, pp. 1059-1068.
Kakimori et al., "Nucleotide Sequence of the Gene Encoding Pepstatin-insensitive Acid Protease B, Scytalidopepsin B, of Scytalidium Lignicolum", Bioscience Biotechnology and Biochemistry, 60(7), 1996, pp. 1210-1211.
Kataoka et al., "Catalytic residues and substrate specificity of scytalidoglutamic peptidase, the first member of the eqolisin in family (G1) of peptidases", FEBS Letters, 579(14), Jun. 6, 2005, pp. 2991-2994.
Kimura et al., "Monitoring Global Gene Expression of Proteases and Improvement of Human Lysozyme Production in the nptB gene disruptant of Aspergillus oryzae" Bioscience, Biotechnology, and Biochemistry, vol. 72, Issue 2, Feb. 2008, pp. 499-505.
Kruszewska, "Heterologous expression of genes in filamentous fungi", Acta Biochimica Polonica, vol. 46, No. 1, 1999, 181-195.

Liu et al., "A new Serine Protease Gene from Trichoderma Harzianum is Expressed in Saccharomyces Cerevisiae", Prikl Biokhim Mikrobiol., 45(1), Jan.-Feb. 2009, pp. 28-32.
Lu et al., "Molecular Cloning of a cDNA for Proctase B from *Aspergillus niger* Var. Macrosporus and Sequence Comparison with Other Aspergillopepsins I", Bioscience, Biotechnology, and Biochemistry, 59(5), 1995, pp. 954-955.
Lubertozzi et al., "Developing Aspergillus as a Host for Heterologous Expression", Biotechnology Advances, 27(1), Jan.-Feb. 2009, pp. 53-75.
Maita et al., "Complete Amino Acid Sequence of Scytalidium Lignicolum Acid Protease B", Journal of Biochemistry, 95(2), Feb. 1984, pp. 465-475.
Margolles-Clark et al., "Improved Production of Trichoderma Harzianum Endochitinase by Expression in Trichoderma Reesei", Applied and Environmental Microbiology, vol. 2, No. 6, Jun. 1996, pp. 2145-2151.
Maruyama et al., "Multiple Gene Disruptions by Marker Recycling with Highly Efficient Gene-Targeting Background (DeltaligD) in Aspergillus Oryzae", Biotechnol Letters, vol. 30, Issue 10, Oct. 2008, pp. 1811-1817.
Mattern et al., "Isolation and Characterization of Mutants of Aspergillus Niger Deficient in Extracellular Proteases", Molecular and General Genetics MGG, vol. 234, Issue 2, Aug. 1992, pp. 332-336.
Moralejo et al., "Thaumatin Production in Aspergillus Awamori by Use of Expression Cassettes with Strong Fungal Promoters and High Gene Dosage", Applied and Environmental Microbiology, vol. 65 No. 3, Mar. 1999, pp. 1168-1174.
Moralejo et al., "Overexpression and Lack of Degradation of Thaumatin in an Aspergillopepsin A-Defective Mutant of Aspergillus Awamori Containing an Insertion in the pepA gene", Applied Microbiology and Biotechnology, vol. 54, Issue 6, Dec. 2000, pp. 772-777.
Moralejo et al., "Silencing of the Aspergillopepsin B (pepB) Gene of Aspergillus Awamori by Antisense RNA Expression or Protease Removal by Gene Disruption Results in a Large Increase in Thaumatin Production", Applied and Environmental Microbiology, vol. 68, No. 7, Jul. 2002, pp. 3550-3559.
Morya et al., "In Silico Characterization of Alkaline Proteases from Different Species of Aspergillus", Applied Biochemistry and Biotechnology, vol. 166, Issue 1, Jan. 2012, pp. 243-257.
Mäntylä et al., "Industrial mutants and recombinant strains of Trichoderma reesei", In: Trichoderma and Gliocladium, vol. 2, 1998, pp. 291-309.
Nascimento et al., "Statistical Coupling Analysis of Aspartic Proteinases Based on Crystal Structures of the Trichoderma Reesei Enzyme and its Complex with Pepstatin A", Journal of Molecular Biology, vol. 382, Issue 3, Oct. 10, 2008, pp. 763-778.
Nemoto et al., "Isolation of Aspergillus Oryzae Mutants for Heterologous Protein Production from a Double Proteinase Gene Disruptant" Applied Microbiology and Biotechnology, vol. 82, Issue 6, Apr. 2009, pp. 1105-1114.
Oda et al., "Nucleotide Sequence of the Gene Encoding the Precursor Protein of Pepstatin Insensitive Acid Protease B, Scytalidopepsin B, from Scytalidium Lignicolum", Bioscience, Biotechnology, and Biochemistry, 62(8), Aug. 1998, pp. 1637-1639.
O'Donoghue et al., "Inhibition of a Secreted Glutamic Peptidase Prevents Growth of the Fungus *Talaromyces emersonii*", Journal of Biological Chemistry, vol. 283. No. 43, Oct. 24, 2008, pp. 29186-29195.
Pillai et al., "Crystal Structure of Scytalidoglutamic Peptidase with its First Potent Inhibitor Provides Insights into Substrate Specificity and Catalysis", Journal of Molecular Biology, vol. 365, Issue 2, 2007, pp. 343-361.
Pozo et al., "Functional Analysis of tvsp1, a Serine Protease-Encoding Gene in the Biocontrol Agent Trichoderma Virens", Fungal Genetics and Biology, 41, 2004, pp. 336-348.
Reichard et al., "Molecular Cloning and Sequencing of the Gene Encoding an Extracellular Aspartic Proteinase from Aspergillus Fumigatus", FEMS Microbioly Letters, 130, 1995, pp. 69-74.

(56) References Cited

OTHER PUBLICATIONS

Reichard et al., "Molecular Cloning and Targeted Deletion of PEP2 Which Encodes a Novel Aspartic Proteinase from Aspergillus Fumigatus", Int. J. Med. Microbiol., 290, 2000, pp. 85-96.
Reichard et al., "Sedolisins, a New Class of Secreted Proteases from Aspergillus Fumigatus with Endoprotease or Tripeptidyl-Peptidase Activity at acidic pHs", Applied and Environmental Microbiology, vol. 72, No. 3, Mar. 2006, pp. 1739-1748.
Kainz et al., "N-Glycan Modification in Aspergillus Species", Applied and Environmental Microbiology, vol. 74, No. 4, Feb. 15, 2008, pp. 1076-1086.
Pourcq et al., "Engineering of Glycosylation in Yeast and Other Fungi: Current State and Perspectives", Applied Microbiology and Biotechnology, Springer, Berlin, DE, vol. 87, No. 5, Jun. 29, 2010, pp. 1617-1631.
Hamilton et al., "Glycosylation Engineering in Yeast: the Advent of Fully Humanized Yeast", Current Opinion in Biotechnology, London, GB, vol. 18, No. 5, Oct. 24, 2007, pp. 387-392.
Punt et al., "Filamentous Fungi as Cell Factories for Heterologous Protein Production", Trends in Biotechnology, Elsevier Publications, Cambridge, GB, vol. 20, No. 5, May 1, 2002, pp. 200-206.
Van Den Hombergh et al., "Aspergillus as a Host for Heterologous Protein Production: the Problem of Proteases", Trends in Biotechnology, Elsevier Publications, Cambridge, GB, vol. 15, No. 7, Jul. 1, 1997, pp. 256-263.
Baldwin et al., "Develop Systems for Manufacturing 100,000,000 Doses of an Emergency Pharmaceutical (e.g. Vaccine or Monoclonal Antibody) Within 2 Months of Product Identification", Genencor International, Jun. 2006, 21 pages.
Hintz et al., "Improved Gene Expression in Aspergillus Nidulans", Canadian Journal of Botany, 1995, pp. 876-884.
Chigira et al., "Engineering of a mammalian O-glycosylation Pathway in the Yeast Saccharomyces Cerevisiae : production of 0-fucosylated epidermal growth factor domains", Glycobiology, Apr. 2008, vol. 18, No. 4, pp. 303-314.
Jarvinen et al., "Cloning and expression of Helicobacter pylori GDP-L-fucose synthesizing enzymes (GMD and GMER) in Saccharomyces Cerevisiae", Eur. J. Biochem, vol. 268, No. 24, Dec. 2001, pp. 6458-6464.
Ma et al., "Fucosylation in Prokaryotes and Eukaryotes", Glycobiology, vol. 16, No. 12, Dec. 2006, pp. 158R-184R.
Mattila et al., "Functional expression of *Escherichia coli* enzymes Synthesizing GDP-L-Fucose from Inherent GDP-D-mannose in Saccharomyces cerevisiae", Glycobiology, vol. 10, No. 10, Oct. 2000, pp. 1041-1047.
Wildt et al., "The humanization of N-glycosylation Pathways in Yeast", Nature reviews, Microbiology, vol. 3, No. 2, Feb. 2005, pp. 119-128.
Hayashi et al., "Molecular Cloning of Mouse Alpha-1,6-fucosyltransferase and Expression of its mRNA in the Developing Cerebrum", DNA Seq. vol. 11, No. (1-2), 2000, pp. 91-96.
Tonetti et al., "Synthesis of GDP-L-fucose by the Human FX Protein", J Biol Chem. Nov. 1996, vol. 271, No. 44, pp. 27274-27279.
Uozumi et al., "Purification and cDNA cloning of porcine brain GDP-L-Fuc:N-acetyl-beta-D-glucosaminide alpha1—>6 fucosyltransferase", J Biol Chem. vol. 271, No. 44, Nov. 1, 1996, pp. 27810-27817.
Paschinger et al., "Fucosyltransferase substrate specificity and the order of fucosylation in invertebrates", Glycobiology. vol. 15, No. 5, May 2005, pp. 463-474.
Becker et al., "Fucose: biosynthesis and biological function in mammals", Glycobiology. vol. 13 No. 7, Jul. 2003, pp. 41R-53R.
Breton et al., "Conserved structural features in eukaryotic and prokaryotic fucosyltransferases", Glycobiology, vol. 8, No. 1, Jan. 1998, pp. 87-94.
Choi et al., "Use of combinatorial genetic libraries to humanize N-linked glycosylation in the yeast *Pichia pastoris*", PNAS, vol. 100, No. 9, Apr. 29, 2003, pp. 5022-5027.

Clarke et al., "Expression of human alpha-l-fucosyltransferase gene homologs in monkey kidney COS cells and modification of potential fucosyltransferase acceptor substrates by an endogenous glycosidase", Glycobiology. vol. 9, No. 2, Feb. 1999, pp. 191-202.
Hamilton et al., "Production of complex human glycoproteins in yeast", Science, vol. 301, No. 5637, Aug. 29, 2003, pp. 1244-1246.
Hamilton et al., "Humanization of Yeast to Produce Complex Terminally Sialylated Glycoproteins", Science, vol. 313, No. 5792, Sep. 8, 2006, pp. 1441-1443.
Bobrowicz et al., "Engineering of an artificial glycosylation pathway blocked in core oligosaccharide assembly in the yeast Pichia pastoris: production of complex humanized glycoproteins with terminal galactose", Glycobiology, vol. 14, No. 9, Sep. 2004, pp. 757-766.
Wang et al., "Modification of epidermal growth factor-like repeats with O-fucose. Molecular cloning and expression of a novel GDP-fucose protein O-fucosyltransferase", J Biol Chem., vol. 276, No. 43, Oct. 26, 2001, pp. 40338-40345.
Nakayama et al., "Interaction of GDP-4-keto-6-deoxymannose-3,5-epimerase-4-reductase with GDP-mannose-4,6- dehydratase stabilizes the enzyme activity for formation of GDP-fucose from GDP-mannose", Glycobiology. vol. 13, No. 10, Oct. 2003, pp. 673-680.
Rhomberg et al., "Reconstitution in vitro of the GDP-fucose biosynthetic pathways of Caenorhabditis elegans and Drosophila melanogaster", FEBS J., vol. 273, No. 10, May 2006, pp. 2244-2256.
International Search Report and Written Opinion received for International PCT application No. PCT/EP2013/060627, dated Jul. 26, 2013, 16 pages.
Roberts et al., "Heterologous Gene Expression in Aspergillus Niger: a Glucoamylase-Porcine Pancreatic Prophospholipase A2 Fusion Protein is Secreted and Processed to Yield Mature Enzyme", Gene., 122, 1992, pp. 155-161.
Sharma et al., "Approaches for Refining Heterologous Protein Production in Filamentous Fungi", World J Microbiol Biotechnol, 25, 2009, pp. 2083-2094.
Sharon et al., "Transcription Factor PrtT Controls Expression of Multiple Secreted Proteases in the Human Pathogenic Mold Aspergillus Fumigatus", Infection and Immunity, vol. 77, No. 9, Sep. 2009, pp. 4051-4060.
Simkovic et al., "Induction of Secretion of Extracellular Proteases from Trichoderma Viride", Acta Chimica Slovaca, vol. 1, No. 1, 2008, pp. 250-264.
Sims et al., "Glutamic Protease Distribution is Limited to Filamentous Fungi", FEMS Microbiology Letters, 239, 2004, pp. 95-101.
Sriranganadane et al., "Secreted Glutamic Protease Rescues Aspartic Protease Pep Deficiency in Aspergillus Fumigatus During Growth in Acidic Protein Medium", Microbiology, 157, 2011, pp. 1541-1550.
Suárez et al., "Characterization of Genes Encoding Novel Peptidases in the Biocontrol Fungus Trichoderma Harzianum CECT 2413 Using the TrichoEST Functional Genomics Approach", Curr Genet, 51, 2007, pp. 331-342.
Uusitalo et al., Enzyme Production by Recombinant Trichoderma Reesei Strains. Journal of Biotechnology, 17, 1991, pp. 35-50.
Van Den Hombergh et al., "New Protease Mutants in Aspergillus Niger Result in Strongly Reduced in Vitro Degradation of Target Proteins; Genetical and Biochemical Characterization of Seven Complementation Groups", Curr Genet, 28, 1995, pp. 299-308.
Van Den Hombergh et al., "Improve the Efficiency of Protein Expression in Fungi", Chemtech 26, Feb. 1996, pp. 30-37.
Van Den Hombergh et al., "Aspergillus as a Host for Heterologous Protein Production: The Problem of Proteases", Tibtech, vol. 15, Jul. 1997, pp. 256-263.
Van Den Hombergh et al., "Production of the Homologous Pectin Lyase B Protein in Six Genetically Defined Protease-Deficient Aspergillus Niger Mutant Strains", Curr Genet, vol. 32, Jul. 1997, pp. 73-81.
Van Kuyk et al., "Analysis of Two Aspergillus Nidulans Genes Encoding Extracellular Proteases", Fungal Genetics and Biology, vol. 29, Apr. 2000, pp. 201-210.

(56) References Cited

OTHER PUBLICATIONS

Vázquez-Laslop et al., "Characterization of a Vacuolar Protease in Neurospora Crassa and the Use of Gene Riping to Generate Protease-Deficient Strains", The Journal of Biological Chemistry, vol. 271, No. 36, Sep. 1996, pp. 21944-21949.

Vinterová et al., "Evidence for the Presence of Proteolytically Active Secreted Aspartic Proteinase of Candida Parapsilosis in the Cell Wall", Protein Science, vol. 20, Dec. 2011, pp. 2004-2012.

Wang et al., "Bioprocessing Strategies to Improve Heterologous Protein Production in Filamentous Fungal Fermentations", Biotechnology Advances, vol. 23, Mar. 2005, pp. 115-129.

Wang et al., "Isolation of Four Pepsin-Like Protease Genes from Aspergillus Niger and Analysis of the Effect of Disruptions on Heterologous Laccase Expression", Fungal Genetics and Biology, vol. 45, Jan. 2008, pp. 17-27.

Xu et al., "Increased Heterologous Protein Production in Aspergillus Niger Fermentation through Extracellular Proteases Inhibition by Pelleted Growth", Biotechnol Prog., vol. 16, No. 2, Mar.-Apr. 2000, pp. 222-227.

Yan et al., "Cloning and Heterologous Expression of SS10, A Subtilisin-Like Protease Displaying Antifungal Activity from Trichoderma Harzianum", FEMS Microbiology Letters, vol. 290, Jan. 2009, pp. 54-61.

Zhu et al., "Improved Heterologous Protein Production by a Tripeptidyl Peptidase Gene (Aosedd) Disruptant of the Filamentous Fungus Aspergillus Oryzae", The Journal of General and Applied Microbiology, vol. 58, 2012, pp. 199-209.

Zhu et al., "Further Enhanced Production of Heterologous Proteins by Double-Gene Disruption ($\Delta$AosedD $\Delta$Aovps10) in a Hyper-Producing Mutant of Aspergillus Oryzae", Applied Microbiology and Biotechnology, vol. 97, 2013, pp. 6347-6357.

\* cited by examiner

FIG. 8A

FX alignment

CLUSTAL 2.1 multiple sequence alignment [overall sequence homology >62%]

```
EcaballusFX     ------------------------------------------------------------
ClupusFX        ------------------------------------------------------------
HsapiensFX      ------------------------------------------------------------
RnorvegicusFX   ------------------------------------------------------------
MmusculusFX     ------------------------------------------------------------
CgriseusFX      ------------------------------------------------------------
BtaurusFX       ------------------------------------------------------------
GgallusFX       ------------------------------------------------------------
XlaevisFX       ------------------------------------------------------------
DrerioFX        ------------------------------------------------------------
AsuumFX         ------------------------------------------------------------
BmalayiFX       MASSSRRLKKELTDIQSSDSRTFCCVEFDENNLLHWTGLLVPDKEPYNKGAFKVAIDFPV  60
CelegansFX      ------------------------------------------------------------

EcaballusFX     ------------------------------------------------------------
ClupusFX        ------------------------------------------------------------
HsapiensFX      ------------------------------------------------------------
RnorvegicusFX   ------------------------------------------------------------
MmusculusFX     ------------------------------------------------------------
CgriseusFX      ------------------------------------------------------------
BtaurusFX       ------------------------------------------------------------
GgallusFX       ------------------------------------------------------------
XlaevisFX       ------------------------------------------------------------
DrerioFX        ------------------------------------------------------------
AsuumFX         ------------------------------------------------------------
BmalayiFX       EYPFKPPKITFLTKIYHPNVDEKGQVCLPIISPDNWKPATKTEQVMNALLGLITEPEPDH  120
CelegansFX      ------------------------------------------------------------

EcaballusFX     ------------------------------------MGEPQGSMRILVTGSSGL   18
ClupusFX        ------------------------------------MSEPGGSVRILVTGGSGL   18
HsapiensFX      ------------------------------------MGEPQGSMRILVTGGSGL   18
RnorvegicusFX   ------------------------------------MGEPHGSMRILVTGGSGL   18
MmusculusFX     ------------------------------------MGEPHGSMRILVTGGSGL   18
CgriseusFX      ------------------------------------MGEPQGSRRILVTGGSGL   18
BtaurusFX       ------------------------------------MGDPRGTRRILVTGGSGL   18
GgallusFX       ----------------------------------MTEALGAKPKRILVTGGTGL   20
XlaevisFX       ----------------------------------------MEGKRILVTGGSGL   14
DrerioFX        ------------------------------------MNGTVEPMRVLVTGGSGL   18
AsuumFX         -----------------------------------MASEKQMIVLVTGCTGL    17
BmalayiFX       PLRADLAEEFTKDRKKFNKTAEDYTKKYAVKRPDGWFETRHKIMDREQSMTVLVTGGTGL 180
CelegansFX      --------------------------------------------MKTILVTGGTGL   12
                                                            :****.:**

EcaballusFX     VGRAIQKVVADGARLPGEDWVFVSSKDADLTDAAQTRALFEKVRPTHVIHLAAMVGGLFR  78
ClupusFX        VGRAIQKVVADGAGLPGEDWVFVSSKDADLTDAAQTRALFEKVRPTHVIHLAAMVGGLFR  78
HsapiensFX      VGKAIQKVVADGAGLPGEDWVFVSSKDADLTDTAQTRALFEKVQPTHVIHLAAMVGGLFR  78
RnorvegicusFX   VGRAIQKVVADGAGLPGEEWVFVSSKDADLTDAAQTQALFQKVQPTHVIHLAAMVGGLFR  78
MmusculusFX     VGRAIQKVVADGAGLPGEEWVFVSSKDADLTDAAQTQALFQKVQPTHVIHLAAMVGGLFR  78
CgriseusFX      VGRAIQKVVADGAGLPGEEWVFVSSKDADLTDAAQTQALFQKVQPTHVIHLAAMVGGLFR  78
BtaurusFX       VGRAIQKVEDGARLPGEDWVFVSSKDADLTDAAQTRALFQQVQPTHVIHLAAMVGGLFR  78
GgallusFX       VGRAIQEVVANGEGRPDEEWVFVSSRDADLTSAVETKALFEKHKPTHVIHLAAMVGGLFK  80
XlaevisFX       VGKAIEKVVADGEGRPDEQWIFISSKDADLTNAADTKCLFEKHKPTHVIHLAAMVGGLFR  74
DrerioFX        VGRAIERVVKD-EGREGEEWTFLSSKDANLLSAEETRAIFQKYRPTHVIHLAAMVGGLFR  77
AsuumFX         VGKAIEKIVKTEESRPNERWIFIGSKDCDLSDLEATRKLFAKHKPTHVIHLAAMVGGLFH  77
BmalayiFX       VGRSIEKIITTEEARPNETWIFVGRNDCDLTDIEATRKLFMKCRPSHVIHLAAMVGGLFH 240
CelegansFX      VGSAIKKVVETTEKRDDEKWVFIGSKDCDLENLEETRELFESVKPTHVIHLAAMVGGLFH  72
                **  :*:.::          .* * *:. .*.:*  .   *: :*  . :*;**************:
```

FIG. 8B

```
EcaballusFX     NIKYNLDFWRKNVHINDNVLHSAFEVGARKVVSCLSTCIFPDKTTYPIDETMIHNGPPHS  138
ClupusFX        NIKYNLDFWRKNVHINDNVLHSAFEVGVRKVVSCLSTCIFPDKTTYPIDETMIHNGPPHN  138
HsapiensFX      NIKYNLDFWRKNVHMNDNVLHSAFEVGARKVVSCLSTCIFPDKTTYPIDETMIHNGPPHN  138
RnorvegicusFX   NIKYNLDFWRKNVHINDNVLHSAFEVGTRKVVSCLSTCIFPDKTTYPIDETMIHNGPPHS  138
MmusculusFX     NIKYNLDFWRKNVHINDNVLHSAFEVGARKVVSCLSTCIFPDKTTYPIDETMIHNGPPHS  138
CgriseusFX      NIKYNLDFWRKNVHINDNVLHSAFEVGTRKVVSCLSTCIFPDKTTYPIDETMIHNGPPHS  138
BtaurusFX       NIKYNLDFWRKNIHINDNVLHSAFEVGVRKVVSCLSTCIFPDKTTYPIDETMIHNGPPHS  138
GgallusFX       NIRCNLDFWRRNIHINDNVLHSAYECGVQKVVSCLSTCIFPDKTTYPIDETMIHNGPPHS  140
XlaevisFX       NMKYNLDFLRNNLHINDNVLHSAYEMGVQKVVSCLSTCIFPDKTTYPIDETMIHNGPPHT  134
DrerioFX        NMRQNLDFWRNNVFINDNVLQTANEFGVVKVVSCLSTCIFPDKTTYPIDETMIHNGPPHD  137
AsuumFX         NLQHNLQFFRKNMQINDNVLAVCDENDIEKCVSCLSTCIFPDKTTYPIDETMVHNGPPHD  137
BmalayiFX       NLHCNLQFFRKNMQINDNVLMACNEFDVVKCISCLSTCVFPDKTTYPIDETMVHNGPPHS  300
CelegansFX      NLAHNLQFFRKNMAINDNVLALCHEFDVIKCVSCLSTCIFPDKTSYPIDETMVHLGPPHD  132
                *:  **:* *.*: :*****   .  *  .  * :******:*****:*********:* ****

EcaballusFX     SNFGYSYAKRMIDVQNRAYFQQHGCTFTAVIPTNVFGPHDNFNIEDGHVLPGLIHKVHLA  198
ClupusFX        SNFGYSYAKRMIDVQNRAYFQQHGCTFTAVIPTNVFGPHDNFNIEDGHVLPGLIHKVHLA  198
HsapiensFX      SNFGYSYAKRMIDVQNRAYFQQYGCTFTAVIPTNVFGPHDNFNIEDGHVLPGLIHKVHLA  198
RnorvegicusFX   SNFGYSYAKRMIDVQNRAYFQQHGCTFTSVIPTNVFGPYDNFNIEDGHVLPGLIHKVHLA  198
MmusculusFX     SNFGYSYAKRMIDVQNRAYFQQHGCTFTAVIPTNVFGPYDNFNIEDGHVLPGLIHKVHLA  198
CgriseusFX      SNFGYSYAKRMIDVQNRAYFQQHGCTFTAVIPTNVFGPHDNFNIEDGHVLPGLIHKVHLA  198
BtaurusFX       SNFGYSYAKRMIDVQNRAYFQQHGCTFTAVIPTNVFGPHDNFSIEDGHVLPGLIHKVHLA  198
GgallusFX       SNFGYSYAKRMIDVQNRGYFEQHGCRFTAVIPTNVFGPHDNFNIEDGHVLPGLIHKVYLA  200
XlaevisFX       SNFGYSYAKRMIDVQNRAYYEQHGCKFTSVIPTNVFGPHDNFNIDDGHVLPGLIHKVYSA  194
DrerioFX        SNFGYAFAKRMIDVQNRTCFKQYGRRYTSVIPTNVFGAHDNFNIDDGHVLPGLIHKTYLA  197
AsuumFX         SNFGYSYAKRMIDVLNRGYAQERGRKYTSVVPCNVFGPYDNYNLEYGHVIPALIHKTFIA  197
BmalayiFX       SNFGYSYAKRMIDVLNRGYAQEFGRKYTSVIPCNVFGPHDNYNLKDGHVIPALIHKTYIA  360
CelegansFX      SNFGYSYAKRMIDVLNKGYAQEHGRKYTSVVPCNVFGPHDNYNLQSGHVLPALIHKAYVA  192
                *****: ******* *:     :: *  :*:*:* ****.:**:. . ***:*.****.. *

EcaballusFX     KSSGSALTVWGTGKPRRQFIYSLDLARLFIWVLREYNEVEPIILSVGEEDEVSIQEAAEA  258
ClupusFX        KSSGSALTVWGTGKPRRQFIYSLDLARLFIWVLREYNEVEPIILSVGEEDEVSIQEAAEA  258
HsapiensFX      KSSGSALTVWGTGNPRRQFIYSLDLAQLFIWVLREYNEVEPIILSVGEEDEVSIKEAAEA  258
RnorvegicusFX   KSSGSALTVWGTGKPRRQFIYSLDLARLFIWVLREYNEVEPIILSVGEEDEVSIKEAAEA  258
MmusculusFX     KSSDSALTVWGTGKPRRQFIYSLDLARLFIWVLREYSEVEPIILSVGEEDEVSIKEAAEA  258
CgriseusFX      KSNGSALTVWGTGKPRRQFIYSLDLARLFIWVLREYNEVEPIILSVGEEDEVSIKEAAEA  258
BtaurusFX       KSSGSALTVWGTGRPRRQFIYSLDLAPLFIWALREYDEVEPIILSVGEEDEVSVQEAAEA  258
GgallusFX       KQNGSALTVWGTGKPRRQFIYSLDLARLFVWVLREYEEVEPIILSVGEEDEVSIREAAEA  260
XlaevisFX       KQNGTALSIWGTGQPRRQFIYSLDLARLFIWVLREYNEVDPIILSVGEEDEVSIKEAAES  254
DrerioFX        KKEGKPLQVWGSGKPLRQFIYSLDLARLFLWVLREYDEVDPIILSVGEEDELSIKDCADA  257
AsuumFX         KRDGKPLEVFGSGAPLRQFIYSLDLARLFVWVLRNYEEIEPIILSVGEEDEVSIMDAVNA  257
BmalayiFX       KHEGTPLEVFGSSTPLRQFIYSLDLARLFIWVARSYEEIDPIILSVGEEDEVSIMDAVHA  420
CelegansFX      QRDGTPLQVYGSSTPLRQFIYSIDLARLFIRVVREYDVEPIILSVNESDEVSIRDAVSA  252
                :  ...,*  ::*:* * ******:***:*: . *.*.::::*****.*.**:*: :.. :

EcaballusFX     VVEAMDFHGDVTFDTTKSDGQFKKTASNGKLRAYLPDFRFTPFKQAVKETCAWFTDNYEQ  318
ClupusFX        VVEAMDFHGEVTFDTTKSDGQFKKTASNGKLRTYLPDFRFTPFKQAVKETCAWFTHNYEQ  318
HsapiensFX      VVEAMDFHGEVTFDTTKSDGQFKKTASNSKLRTYLPDFRFTPFKQAVKETCAWFTDNYEQ  318
RnorvegicusFX   VVEAMDFSGEVTFDSTKSDGQYKKTASNGKLRSYLPDFCFTPFKQAVKETCAWFTENYEQ  318
MmusculusFX     VVEAMDFNGEVTFDSTKSDGQYKKTASNGKLRSYLPDFRFTPFKQAVKETCTWFTDNYEQ  318
CgriseusFX      VVEAMDFCGEVTFDSTKSDGQYKKTASNGKLRAYLPDFRFTPFKQAVKETCAWFTDNYEQ  318
BtaurusFX       VVEAMDFHGEVTFDTTKSDGQFKKTASNAKLRAYLPDFRFTPFKQAVKETCAWFTDNYEQ  318
GgallusFX       IVEAMDFRGELIFDTTKADGQFKKTASNAKLRHYLPNFQFTPFRQAVKETCTWFSTNYAS  320
XlaevisFX       IVAAMEFKGELIFDSTKSDGQFKKTASNHKLRKYLPDFQFTPFNKAVQETCNWFNSNYAQ  314
DrerioFX        VVDALGFKGDVIYDTSKADGQFKKTASNAKLRQYLPDFQFTPFREAIKETCDWFVANYDI  317
AsuumFX         IVKAFDFKGGIVQDKSKADGQYKKTASNAKLRKYLPDFKFTPFDVAIKESVDWFVANYED  317
BmalayiFX       VVRAFDFKGEIVHDKTKADGQYKKTASNAKLRKYLPNFKFTPFEIAIKESVDWFIDNYDN  480
CelegansFX      VVKAIDFTGDVEYDTSKADGQFKKTASNEKLLKLFPDFQFTPFEQAIQESVQWFVDNYET  312
                :*  *: * *  :   *.:*:***:***** **    :*:* ****  *:;*: ** **
```

FIG. 8C

```
EcaballusFX      ARK 321
ClupusFX         ARK 321
HsapiensFX       ARK 321
RnorvegicusFX    ARK 321
MmusculusFX      ARK 321
CgriseusFX       ARK 321
BtaurusFX        ARK 321
GgallusFX        ARK 323
XlaevisFX        ARK 317
DrerioFX         ARK 320
AsuumFX          ARK 320
BmalayiFX        ARK 483
CelegansFX       ARK 315
                 ***
```

FIG. 9A

GMD alignment, eukaryotic

CLUSTAL 2.1 multiple sequence alignment [overall sequence homology >59%]

```
MmusculusGMD         ------------------------MAQAPAKCPS---------------YPGSGDGEMG  20
RnorvegicusGMD       ------------------------MAHAPASCRR---------------YPGSGDGEMG  20
CgriseusGMD          ------------------------MAHAPASCPS---------------SRNSGDGDKG  20
HsapiensGMD          ------------------------MAHAPARCPS---------------ARGSGDGEMG  20
BtaurusGMD           ------------------------MAQAAAHYPG---------------ACGAGDAETG  20
XlaevisGMF           ------------------------MAQNQGNCSC---------------SPSNSS---G  17
DrerioGMD            ------------------------MAQCTATTTG---------------GGMNGD--SK  18
SsalarGMD            ------------------------MAQCTEPSTS---------------TGANGE--LK  18
CintestinalisGMD     ------------------------MADSSCNGKRK-------------NGDSCDTETK  21
AgambiaeGMD          -----------------------------------------------MEGEAAVTNP  10
AaegyptiGMD          ------------------MSLENGSNKKPRLSLEN------HLATESEGSSSSD  30
DmelanogasterGMD     --------------MLNTRLIAMSTSDGAPETKKQRPESSSNGSKDQNGTEAGAEGD  43
AmelliferaGMD        ------------------------------------------------MKMATD  6
LloaGMD              ------------------MNTEALEDCLGNRHS------------MKPISEVEKCKF  27
BmalayiGMD           -----------MTINATKMNTETQENCLGNRSS------------MKTISEVERYKC  34
CelegansGMD          MPTGKSESSDISEVVGNMEISKVEGLEACIGMSHE-----------VSTTPAAELAAF  47

MmusculusGMD         KLRKVALITGITGQDGSYLAEFLLEKGYEVHGIVRRSSSFNTGRIEHLYKNPQAHI-EGN  79
RnorvegicusGMD       KLRKVALITGITGQDGSYLAEFLLEKGYEVHGIVRRSSSFNTGRIEHLYKNPQAHI-EGN  79
CgriseusGMD          KPRKVALITGITGQDGSYLAEFLLEKGYEVHGIVRRSSSFNTGRIEHLYKNPQAHI-EGN  79
HsapiensGMD          KPRNVALITGITGQDGSYLAEFLLEKGYEVHGIVRRSSSFNTGRIEHLYKNPQAHI-EGN  79
BtaurusGMD           KPRKVALITGITGQDGSYLAEFLLEKGYEVHGIVRRSSSFNTGRIEHLYKNPQAHI-EGN  79
XlaevisGMF           KPRKVALITGITGQDGSYLAEFLLEKGYEVHGIVRRSSSFNTGRIEHLYKNPHAHT-EGN  76
DrerioGMD            RKRKVALITGITGQDGSYLAELLLAKGYEVHGILRRSSSFNTGRIEHLYKNPQTHT-EGN  77
SsalarGMD            KPRKVAVITGITGQDGSYLAEFLLEKGYEVHGILRRSSSFNTGRIEHLYQNPQTHT-EGN  77
CintestinalisGMD     KQKKTALVTGITGQDGSYLAELLIEKGYEVHGIIRRASQPNTARIEHLYADRATHK-EGS  80
AgambiaeGMD          VDRKVALITGITGQDGSYLAEFLLDKGYEVHGIIRRASTFNTSRIEHLYADPRTHR-EGK  69
AaegyptiGMD          PNRRVALITGITGQDGSYLAEFLLKKDYEVHGIIRRASTFNTSRIEHLYADPHSHK-QGK  89
DmelanogasterGMD     SRDKVALITGITGQDGSYLAEFLLKKDYEVHGIIRRASTFNTTRIEHLYADPKAHK-GGR  102
AmelliferaGMD        SRRRVALITGITGQDGSYLAEFLLEKGYDVHGIIRRASSFNTARIQHLYEDPKCHR-QGK  65
LloaGMD              RTPKIALITGISGQDGSYLAELLLSKGYEVHGIIRRSSSFNTSRIEHLYSNPVTHHADSS  87
BmalayiGMD           RARKIALITGISGQDGSYLAELLLSKGYEVHGIIRRSSSFNTARIEHLYSNPITHHADSS  94
CelegansGMD          RARKVALITGISGQDGSYLAELLLSKGYKVHGIIRRSSSFNTARIEHLYSNPITHHGDSS  107
                       *:.***:**********:*:  *.*.****:**:*   **.**:***    *    .

MmusculusGMD         MKLHYGDLTDSTCLVKIINEVKPTEIYNLGAQSHVKISFDLAEYTADVDGVGTLRLLDAI  139
RnorvegicusGMD       MKLHYGDLTDSTCLVKIINEVKPTEIYNLGAQSHVKISFDLAEYTADVDGVGTLRLLDAI  139
CgriseusGMD          MKLHYGDLTDSTCLVKIINEVKPTEIYNLGAQSHVKISFDLAEYTADVDGVGTLRLLDAI  139
HsapiensGMD          MKLHYGDLTDSTCLVKIINEVKPTEIYNLGAQSHVKISFDLAEYTADVDGVGTLRLLDAV  139
BtaurusGMD           MKLHYGDLTDSTCLVKIINEVKPTEIYNLGAQSHVKISFDLAEYTADVDGVGTLRLLDAV  139
XlaevisGMF           MKLHYGDLTDSTCLVKIINEVKPTEIYNLGAQSHVKISFDLAEYTADVDGLGTLRLLDAT  136
DrerioGMD            MKLHYGDLTDSTCLVKIINEVKPTEIYNLGAQSHVKISFDLAEYTADVDGVGTLRLLDAV  137
SsalarGMD            MKLHYGDLTDSTCLVKIINQVKPTEIYNLGAQSHVKISFELAEYTANVDGVGTLRLLDAI  137
CintestinalisGMD     MKLHYGDLTDSSCLVKIINQVKPNEIYNLGAMSHVKVSFDLAEYTADVDGVGTLRLLDAI  140
AgambiaeGMD          MKLHYGDMTDSSALVKIIAQVRPSEIYNLAAQSHVKSFDLSEYTAEVDAVGTLRLLDAI  129
AaegyptiGMD          MKLHYGDMTDSSCLVKIISSVRPSEIYNLAAQSHVKVSFDLSEYTAEVDAVGTLRLLDAI  149
DmelanogasterGMD     MKLHYGDMTDSSSLVKIINMVKPTEIYNLAAQSHVKVSFDLSEYTAEVDAVGTLRILDAI  162
AmelliferaGMD        MKLHYGDMTDSSSLIKVISSVQPTEIYNLAAQSHVMVSFEVSEYTAEVDAVGTVRLLDAI  125
LloaGMD              FTLHYGDMTDSSCLIKLVSQIQPTEVYHLAAQSHVKVSFDLPEYTAEVDAVGTLRLLDSI  147
BmalayiGMD           FTLHYGDMTDSSCLIKIVSQIQPTEVYHLAAQSHVKVSFDLPEYTAEVDAVGTLRLLDSI  154
CelegansGMD          FSLHYGDMTDSSCLIKLISTIEPTEVYHLAAQSHVKVSFDLPEYTAEVDAVGTLRLLDAI  167
                     :.*****:***:.*:*::   :.*.*:*:*.* *** :**::.*****:**.:**:*:*:
```

FIG. 9B

```
MmusculusGMD      KTCGLINSVKFYQASTSELYGKVQEIPQKETTPFYPRSPYGAAKLYAYWIVVNFREAYNL 199
RnorvegicusGMD    KTCGLINSVKFYQASTSELYGKVQEIPQKETTPFYPRSPYGAAKLYAYWIVVNFREAYNL 199
CgriseusGMD       KTCGLINSVKFYQASTSELYGKVQEIPQKETTPFYPRSPYGAAKLYAYWIVVNFREAYNL 199
HsapiensGMD       KTCGLINSVKFYQASTSELYGKVQEIPQKETTPFYPRSPYGAAKLYAYWIVVNFREAYNL 199
BtaurusGMD        KTCGLISSVRFYQASTSELYGKVQEIPQKETTPFYPRSPYGAAKLYAYWIVVNFREAYNL 199
XlaevisGMF        KTCGLINTVKFYQASTSELYGKVQEIPQKETTPFYPRSPYGAAKLYAYWIVVNFREAYNL 196
DrerioGMD         KTCGLTDTVRFYQASTSELYGKVQEIPQKETTPFYPRSPYGAAKLYAYWIVINFREAYNL 197
SsalarGMD         KTCGLTNSVKFYQASTSELYGKVQEIPQKETTPFYPRSPYGAAKLYAYWIVVNFREAYNL 197
CintestinalisGMD  RTCGMSDSVRFYQASTSEMFGKVQEIPQKETTPFYPRSPYAAAKVYAYWIVVNYREAYGM 200
AgambiaeGMD       RTVGQERTVRFYQASTSELYGKVAETPQNEKTPFYPRSPYACAKMYGYWIVINYREAYDM 189
AaegyptiGMD       RTCGLEKSVRFYQASTSELYGKVVETPQNEKTPFYPRSPYACAKMYGYWIVINYREAYNM 209
DmelanogasterGMD  RTCGMEKNVRFYQASTSELYGKVVETPQNEQTPFYPRSPYACAKMYGFWIVINYREAYNM 222
AmelliferaGMD     RTCGLEKSVKFYHASTSELYGRVTQVPQNEKTPFYPRSPYACAKLYSFWIVINYREAYNM 185
LloaGMD           HACGLTNKVRFYQASTSELYGKVQEVPQKETTPFYPRSPYAAAKLYSYWIVVNYREAYNM 207
BmalayiGMD        HACGLTNKVKFYQASTSELYGKVQEVPQKETTPFYPRSPYAAAKLYSYWIVVNYREAYSM 214
CelegansGMD       HACRLTEKVRFYQASTSELYGKVQEIPQSEKTPFYPRSPYAVAKMYGYWIVVNYREAYNM 227
                  ::   .*:**:*****;:*;*  :  **.* *********. **:*.:***;*:****.:

MmusculusGMD      FAVNGILFNHESPRRGANFVTRKISRSVAKIYLGQLECFSLGNLDAKRDWGHAKDYVEAM 259
RnorvegicusGMD    FAVNGILFNHESPRRGANFVTRKISRSVAKIYLGQLECFSLGNLDAKRDWGHAKDYVEAM 259
CgriseusGMD       FAVNGILFNHESPRRGANFVTRKISRSVAKIYLGQLECFSLGNLDAKRDWGHAKDYVEAM 259
HsapiensGMD       FAVNGILFNHESPRRGANFVTRKISRSVAKIYLGQLECFSLGNLDAKRDWGHAKDYVEAM 259
BtaurusGMD        FAVNGILFNHESPRRGANFVTRKISRSVAKIHLGQLECFSLGNLDAKRDWGHAKDYVEAM 259
XlaevisGMF        FAVNGILFNHESPRRGANFVTRKISRSVAKIHLGQMESFSLGNLDAKRDWGHAKDYVEAM 256
DrerioGMD         FAVNGILFNHESPRRGSNFVTRKISRSVAKIHLGQLECFSLGNLDSMRDWGHAKDYVEAM 257
SsalarGMD         FAVNGILFNHESPRRGANFVTRKISRSVAKIHLGQLESFSLGNLDSKRDWGHAKDYVEAM 257
CintestinalisGMD  HASNGILFNHESPRRGFNFVTRKITRSVAKIHLGLQELITLGNLDSKRDWGHARDYVKGM 260
AgambiaeGMD       FACNGILFNHESPRRGENFVTRKITRSVAKISLGQQEYLELGNLDSKRDWGHAKDYVEAM 249
AaegyptiGMD       FACNGILFNHESPRRGENFVTRKITRSVAKISLNQMDCLELGNLDSKRDWGHAQDYVEAM 269
DmelanogasterGMD  YACNGILFNHESPRRGENFVTRKITRSVAKIYHKQMEYFELGNLDSKRDWGHASDYVEAM 282
AmelliferaGMD     FACNGILFNHESPRRGENFVTRKVTRSIAKIHLGLQDILELGNLDAKRDWGHAKDYVEAM 245
LloaGMD           FACNGILFNHESPRRGETFVTRKITRAVAKIALGQQEILELGNLSSSRDWGHAKEYVEAM 267
BmalayiGMD        FACNGILFNHESPRRGETFVTRKITRAVAKIALGQQEVLELGNLSSSRDWGHAKEYVEAM 274
CelegansGMD       FACNGILFNHESPRRGETFVTRKITRSVAKISLGQQESIELGNLSALRDWGHAREYVEAM 287
                  .* ************ .*****;:*;;***   : : ****.: ****** :**:.*

MmusculusGMD      WLMLQNDEPEDFVIATGEVHSVREFVEKSFMHIGKTIVWEGKNENEVGRCKETGKVHVTV 319
RnorvegicusGMD    WLMLQNDEPEDFVIATGEVHSVREFVEKSFMHIGKTIVWEGKNENEVGRCKETGKIHVTV 319
CgriseusGMD       WLMLQNDEPEDFVIATGEVHSVREFVEKSFMHIGKTIVWEGKNENEVGRCKETGKIHVTV 319
HsapiensGMD       WLMLQNDEPEDFVIATGEVHSVREFVEKSFLHIGKTIVWEGKNENEVGRCKETGKVHVTV 319
BtaurusGMD        WLMLQKDEPEDFVIATGEVHSVREFVEKSFLHIGKTIVWEGKNENEVGRCKETGKIHVTV 319
XlaevisGMF        WLMLQTDEPEDFVISTGEVHSVREFVEKAFKHIGKTIVWEGKNENEVGRCSETGKIHVKV 316
DrerioGMD         WLMLQQEEPVDFVIATGEVHSVRERAPKHVGKTIVWEGKDEKEVGRCQETGVIHVRV 317
SsalarGMD         WLMLQQEEPEDLVIATGEVHSVREFVEKSFKHVGKTIVWEGKDENEVGRCQETGVIHVKV 317
CintestinalisGMD  WMMMQHDEPGDYVLSTNETHSVREFVEKSFKHIGVELEWQGEGVNEIGVDKSTGVKRVQI 320
AgambiaeGMD       WLMMQQERPEDFVIATGETHSVREFVEQAFRYIGREIEWRGTGVDEVGVEKGTDTVRVRI 309
AaegyptiGMD       WMMLQQPQPQDYVIATGECHSVREFVEHSFRHIGREIEWRGEGLNEVGVEKGTDTVRVRI 329
DmelanogasterGMD  WMMLQRESPSDYVIATGETHSVREFVEAAFKHIDREITWKGKGVDEVGVENGTGIVRVRI 342
AmelliferaGMD     WLMLQQPTADDYVIATGETHSVREFVEAAFQYVGRTIKWEGEGINEIGQDVQTGQVLVKV 305
LloaGMD           WKILQYDQPDDFVIATGKSYTVRRFAELAFEEIGKTIIWEGEGVHEVGKEKDTGIIRVRV 327
BmalayiGMD        WRILQYDKPDDFVIATGKSYTVRRFAELAFEEIGKKIIWEGEGVHEVGKEEDTGIVRVRV 334
CelegansGMD       WRILQHDSPDDFVIATGKQFSVREFCNLAFAEIGEVLQWEGEGVEEVGKNKD-GVIRVKV 346
                  * ::*   . * *::*.:  .:**.* : :* .  :  *.* . ..*:* .  *  :
```

FIG. 9C

```
MmusculusGMD      DLKYYRPTEVDFLQGDCSKAQQKLNWKPRVAFDELVREMVQADVELMRTNPNA 372
RnorvegicusGMD    DLKYYRPTEVDFLQGDCSKAQQKLNWKPRVAFDELVREMVQADVELMRTNPNA 372
CgriseusGMD       DLKYYRPTEVDFLQGDCSKAQQKLNWKPRVAFDELVREMVQADVELMRTNPNA 372
HsapiensGMD       DLKYYRPTEVDFLQGDCTKAKQKLNWKPRVAFDELVREMVHADVELMRTNPNA 372
BtaurusGMD        DLKYYRPTEVDFLQGDCSKARQKLSWKPRVAFDELVREMVEADVELMRTNPHA 372
XlaevisGMF        DLKYYRPTEVDFLQGDCSQAKNKLGWTPKVSFDELVKEMVESDVKLMATNPNA 369
DrerioGMD         DPKYYRPTEVDYLQGDSSKAFKVLGWKPRVTFEELVKEMVDADIKLMQNNPNA 370
SsalarGMD         DSKYYRPTEVEYLQGDSTKALTKLGWKAKITFEELVKEMVDADIHLMKNNPNA 370
CintestinalisGMD  SERYYRPTEVEFLLGDYSKAKKVLGWSPDIKFNELVKEMVEADINLMKKTPNA 373
AgambiaeGMD       NPKFFRPTEVDLLLGDASKAKAQLGWSPKVTFLELIADMMAADIQLMKNNPSA 362
AaegyptiGMD       NPKFFRPTEVDLLLGDASKAKRELGWTPKVSFLQLVSDMMVADIELMKKNPNA 382
DmelanogasterGMD  NPKYFRPTEVDLLQGDASKANRELNWTPKVTFVELVSDMMKADIELMRKNPIA 395
AmelliferaGMD     NPKYFRPTEVDVLLGDATKAKEKIGWKPTITFENLVKDMMDSDLELMSKNPNA 358
LloaGMD           SPKYYRPTEVDLLIGDPTKAKQKLNWEAKITLEELVKEMVASDLQLMKSNPMA 380
BmalayiGMD        SSKYYRPTEVDLLIGDSTKAKQKLNWEAKTTLEELVKEMVASDLQLMKSNPMA 387
CelegansGMD       SPKYYRPTEVETLLGNAEKAKKTLGWEAKVTVPELVKEMVASDIILMKSNPMA 399
                  . :::*****: * *:  :*    :.* .   . :*: :*: :*: ** ..* *
```

FIG. 10A

FUT8 alignment

CLUSTAL 2.1 multiple sequence alignment [overall sequence homology >77%]

```
MmusculusFUT8      LEPEYNVSSLSSRKIEDRVETLKMRAWTGSWRWIMLILFAWGTLLFYIGGHLVRDNDHP  60
RnorvegicusFUT8    ------------------------MRAWTGSWRWIMLILFAWGTLLFYIGGHLVRDNDHP  36
CgriseusFUT8       ------------------------MRAWTGSWRWIMLILFAWGTLLFYIGGHLVRDNDHP  36
BtaurusFUT8        ------------------------MRPWTGSWRWIMLILFAWGTLLFYIGGHLVRDNDHP  36
ClupusFUT8         ------------------------MRPWTGSWRWIMLILFAWGTLLFYIGGHLVRDNDHP  36
HsapiensFUT8       ------------------------MRPWTGSWRWIMLILFAWGTLLFYIGGHLVRDNDHP  36
GgallusFUT8        ------------------------MRPWTGSWRWIMLILFAWGTLLFYIGGHLVRDSEHP  36
StropicalisFUT8    ------------------------MRPWTGSWRWIMLILFAWGTLLFYIGGHLVRDNENP  36
DrerioFUT8         ------------------------MRPWTGSWRWIALVLLAWGTLLFYIGGHLVKDSEHA  36
                                           **.********* *.*.***************.*..:.

MmusculusFUT8      DHSSRELSKILAKLERLKQQNEDLRRMAESLRIPEGPIDQGTATGRVRVLEEQLVKAKEQ 120
RnorvegicusFUT8    DHSSRELSKILAKLERLKQQNEDLRRMAESLRIPEGPIDQGTATGRVRVLEEQLVKAKEQ  96
CgriseusFUT8       DHSSRELSKILAKLERLKQQNEDLRRMAESLRIPEGPIDQGTATGRVRVLEEQLVKAKEQ  96
BtaurusFUT8        DHSSRELSKILAKLERLKQQNEDLRRMAESLRIPEGPIDQGPASGRIRALEEQLVKAKEQ  96
ClupusFUT8         DHSSRELSKILAKLERLKQQNEDLRRMAESLRIPEGPIDQAPASGRVRALEEQLLKAKEQ  96
HsapiensFUT8       DHSSRELSKILAKLERLKQQNEDLRRMAESLRIPEGPIDQGPAIGRVRVLEEQLVKAKEQ  96
GgallusFUT8        DHSSRELSKILAKLERLKQQNEDLRRMAESLRIPDGPIDQGPAAGKVHALEEQLLKAKEQ  96
StropicalisFUT8    DHSSRELSKILAKLERLKQQNEDLRRMAESLRIPEGPIEQGAAAGRIRALEEQLLKAKEQ  96
DrerioFUT8         PRSSRELAKILTKLERLKQQNEDLRRMAQSLRIPEGQSDGPISSGRLRSLEEQLSRAKQK  96
                    :****.***:*********** ***.****.*   :   : *::: ***** :**::

MmusculusFUT8      IENYKKQARN---GLGKDHEILRRRIENGAKELWFFLQSELKKLKHLEGNELQRHADEIL 177
RnorvegicusFUT8    IENYKKQARN---GLGKDHEILRRRIENGAKELWFFLQSELKKLKHLEGNELQRHADEIL 153
CgriseusFUT8       IENYKKQARN---DLGKDHEILRRRIENGAKELWFFLQSELKKLKKLEGNELQRHADEIL 153
BtaurusFUT8        IENYKKQTRN---GLGKDHEILRRRIENGAKELWFFLQSELKKLKNLEGNELQRHADEFL 153
ClupusFUT8         IENYKKQTRN---GLGKDHEILRRPIENGAKELWFFLQSELKKLKNLEGNVLQRHADEFL 153
HsapiensFUT8       IENYKKQTRN---GLGKDHEILRRRIENGAKELWFFLQSELKKLKNLEGNELQRHADEFL 153
GgallusFUT8        IENYKKQTGD---GLGKDHEILRRIENGAKELWFFLQSELKKLKHLEGSELQRRIDEFL 153
StropicalisFUT8    IEMYKKQQSSNAVSGLGKDHEILRRAIENGAKEFWYFVQSEVKKLKHLDRNELQRHVDEII 156
DrerioFUT8         IQSFQRLSGE---GPGKDHEELRRKVENGVRELWYFVRSEVKKLPLMETGAMHKHVDTLM 153
                   *:  :::  :      ***** *** :***.:*:*:*:**:***   :: . :::: * ::

MmusculusFUT8      LDLGHHERSIMTDLYYLSQTDGAGDWREKEAKDLTELVQRRITYLQNPKDCSKARKLVCN 237
RnorvegicusFUT8    LDLGHHERSIMTDLYYLSQTDGAGDWREKEAKDLTELVQRRITYLQNPKDCSKARKLVCN 213
CgriseusFUT8       LDLGHHERSIMTDLYYLSQTDGAGEWREKEAKDLTELVQRRITYLQNPKDCSKARKLVCN 213
BtaurusFUT8        SDLGHHERSIMTDLYYLSQTDGAGDWREKEAKDLTELVQRRITYLQNPKDCSKAKKLVCN 213
ClupusFUT8         SDLGHHERSIMTDLYYLSQTDGAGDWREKEAKDLTELVQRRITYLQNPKDCSKAKKLVCN 213
HsapiensFUT8       LDLGHHERSIMTDLYYLSQTDGAGDWREKEAKDLTELVQRRITYLQNPKDCSKAKKLVCN 213
GgallusFUT8        SDLGHQERSIMTDLYYLSQTDGAGDWREKEAKDLTDLVQRRITYLQNPKDCSKAKKLVCN 213
StropicalisFUT8    IDMGHQQRSVMTDLYYLSQTDGAGDWREKEANELSDLVQNRIMYLQNPQDCSKARKLVCN 216
DrerioFUT8         QDLGHQQRSVMTDLYHLSQADGAGDWREKEANELSDLVQNRIMYLQNPQDCSKARKLVCN 213
                    *:*:*.:**:*****:***:***:*******::*:*:**.**:*****:****:****

MmusculusFUT8      INKGCGYGCQLHHVVYCFMIAYGTQRTLILESQNWRYATGGWETVFRPVSETCTDRSGLS 297
RnorvegicusFUT8    INKGCGYGCQLHHVVYCFMIAYGTQRTLILESQNWRYATGGWETVFRPVSETCTDRSGLS 273
CgriseusFUT8       INKGCGYGCQLHHVVYCFMIAYGTQRTLILESQNWRYATGGWETVFRPVSETCTDRSGLS 273
BtaurusFUT8        INKGCGYGCQLHHVVYCFMIAYGTQRTLILESHNWRYATGGWETVFRPVSETCTDRSGVS 273
ClupusFUT8         INKGCGYGCQLHHVVYCFMIAYGTQRTLILESQNWRYATGGWETVFRPVNETCTDRSGTS 273
HsapiensFUT8       INKGCGYGCQLHHVVYCFMIAYGTQRTLILESQNWRYATGGWETVFRPVSETCTDRSGIS 273
GgallusFUT8        INKGCGYGCQLHHVVYCFMIAYGTQRTLILESQNWRYATGGWETVFRPVSETCTDRSGTT 273
StropicalisFUT8    INKGCGYGCQLHHVVYCFMIAYGTQRTLILESQSWRYATGGWETVFKPVSETCTDRSGSS 276
DrerioFUT8         INKGCGYGCQLHHVVYCFMIAYGTQRTLILESQNWRYATGGWETVFKPVSDTCTDRTGAS 273
                   ********************************:.**********:**.:****:*  :
```

FIG. 10B

```
MmusculusFUT8    TGHWSGEVNDKNIQVVELPIVDSLHPRPPYLPLAVPEDLADRLLRVHGDPAVWWVSQFVK 357
RnorvegicusFUT8  TGHWSGEVNDKNIQVVELPIVDSLHPRPPYLPLAVPEDLADRLVRVHGDPAVWWVSQFVK 333
CgriseusFUT8     TGHWSGEVKDKNVQVVELPIVDSLHPRPPYLPLAVPEDLADRLLRVHGDPAVWWVSQFVK 333
BtaurusFUT8      TGHWSGEIKDKNVQVVELPIVDSLHPRPPYLPLAVPEDLADRLVRVHGDPAVWWVSQFVK 333
ClupusFUT8       TGHWSGEVKDKNVQVVELPIVDSLHPRPPYLPLAVPEDLADRLVRVHGDPAVWWVSQFVK 333
HsapiensFUT8     TGHWSGEVKDKNVQVVELPIVDSLHPRPPYLPLAVPEDLADRLVRVHGDPAVWWVSQFVK 333
GgallusFUT8      TGHWSGETNDKDVQVVELPIVDSLHPRPPYLPLAVPEDLADRLIRVHGDPAVWWVSQFVK 333
StropicalisFUT8  TGHWSGEANDKNVQVVELPIVDSLHPRPPYLPLGVPEDLADRLIRLHGDPAVWWVSQFVK 336
DrerioFUT8       TGHWSGEAHDRDVQVVELPIVDSLHPRPPYLPLAVPEDLAPRLQRLHGDPSVWWVSQFVK 333
                 ******  :*.::*******************.****.** *:****.*********

MmusculusFUT8    YLIRPQPWLEKEIEEATKKLGFKHPVIGVHVRRTDKVGTEAAFHPIEEYMVHVEEHFQLL 417
RnorvegicusFUT8  YLIRPQPWLEKEIEEATKKLGFKHPVIGVHVRRTDKVGTEAAFHPIEEYMVHVEEHFQLL 393
CgriseusFUT8     YLIRPQPWLEREIEETTKKLGFKHPVIGVHVRRTDKVGTEAAFHPIEEYMVHVEEHFQLL 393
BtaurusFUT8      YLIRPQPWLEKEIEEATKKLGFKHPVIGVHVRRTDKVGTEAAFHPIEEYMVHVEEHFQLL 393
ClupusFUT8       YLIRPQPWLEKEIEEATKKLGFNIPVIGVHVRRTDKVGTEAAFHPIEEYMVHVEEHFQLL 393
HsapiensFUT8     YLIRPQPWLEKEIEEATKKLGFKHPVIGVHVRRTDKVGTEAAFHPIEEYMVHVEEHFQLL 393
GgallusFUT8      YLIRPQPWLEKEIEEATRKLGFKHPVIGVHVRRTDKVGTEAAFHPIEEYMVHVEERFELL 393
StropicalisFUT8  YLIRPQPWLEKEIEESTKKLGFKHPVIGVHVRRTDKVGTEAAFHPIEEYMVHVEEHFQLL 396
DrerioFUT8       FLVRPQAWLEKEIQETCLKLGFKHPIIGVHVRRTDKVGTEAAFHPIEEYMVHVEDHYQSL 393
                 :*:***.***:**:*:    ****: *:*************************:::: *

MmusculusFUT8    ARRMQVDKKRVYLATDDPTLLKEAKTKYSNYEFISDNSISWSAGLHNRYTENSLRGVILD 477
RnorvegicusFUT8  ARRMQVDKKRVYLATDDPALLKEAKTKYSNYEFISDNSISWSAGLHNRYTENSLRGVILD 453
CgriseusFUT8     ERRMKVDKKRVYLATDDPSLLKEAKTKYSNYEFISDNSISWSAGLHNRYTENSLRGVILD 453
BtaurusFUT8      ARRMQVDKKRVYLATDDPSLLKEAKTKYPHYEFISDNSISWSAGLHNRYTENSLRGVILD 453
ClupusFUT8       ARRMQVDKKRVYLATDDPSLLKEAKTKYPTYEFISDNSISWSAGLHNRYTENSLRGVILD 453
HsapiensFUT8     ARRMQVDKKRVYLATDDPSLLKEAKTKYPNYEFISDNSISWSAGLHNRYTENSLRGVILD 453
GgallusFUT8      ARRMHVDKKRVYLATDDPSLLQEAKSKYPNYEFISDNSISWSAGLHNRYTENSLRGVILD 453
StropicalisFUT8  ARRMQIDKKRVYLATDDPTLLQEAKAKYPQYEFISDNSISWSAGLHNRYTENSLRGVILD 456
DrerioFUT8       AQRMHVDKKRVYLATDDPSLLQEAKTKYPDYEFISDNSISWSAGLHNRYTENSLRGVILD 453
                 :**::**:**********:**:***.**. ******************************

MmusculusFUT8    IHFLSQADFLVCTFSSQVCRVAYEIMQTLHPDASANFHSLDDIYYFGGQNAHNQIAVYPH 537
RnorvegicusFUT8  IHFLSQADFLVCTFSSQVCRVAYEIMQTLHPDASANFHSLDDIYYFGGQNAHNQIAVYPH 513
CgriseusFUT8     IHFLSQADFLVCTFSSQVCRVAYEIMQTLHPDASANFHSLDDIYYFGGQNAHNQIAVYPH 513
BtaurusFUT8      IHFLSQADFLVCTFSSQVCRVAYEIMQTLHPDASANFHSLDDIYYFGGQNAHNQIAIYPH 513
ClupusFUT8       IHFLSQADFLVCTFSSQVCRVAYEIMQTLHPDASANFHSLDDIYYFGGQNAHNQIAIYPH 513
HsapiensFUT8     IHFLSQADFLVCTFSSQVCRVAYEIMQTLHPDASANFHSLDDIYYFGGQNAHNQIAIYAH 513
GgallusFUT8      IHFLSQADFLVCTFSSQVCRVPYEIMQTLHPDASAYFHSLDDIYYFGGQNAHNQIAVYAH 513
StropicalisFUT8  IHFLSQADFLVCTFSSQVCRVAYEIMQTLHPDASAHFHSLDDIYYFGGQNAHNQLAIYPH 516
DrerioFUT8       IHFLSRTNYLVCTFSSQVCRVAYEIMQTLHPDASSYFYSLDDIYYFGGQNAHNQIAIYPH 513
                 *****::::*********.**********: *:****************:*:*.*

MmusculusFUT8    KPRTEEEIPMEPGDIIGVAGNHWDGYSKGINRKLGKTGLYPSYKVREKIETVKYPTYPEA 597
RnorvegicusFUT8  KPRTDEEIPMEPGDIIGVAGNHWDGYSKGVNRKLGKTGLYPSYKVREKIETVKYPTYPEA 573
CgriseusFUT8     QPRTKEEIPMEPGDIIGVAGNHWNGYSKGVNRKLGKTGLYPSYKVREKIETVKYPTYPEA 573
BtaurusFUT8      EPRTADEIPMEPGDIIGVAGNHWDGYSKGVNRKLGRTGLYPSYKVREKIETVKYPTYPEA 573
ClupusFUT8       QPRTADEIPMEPGDIIGVAGNHWDGYSKGVNRKLGRTGLYPSYKVREKIETVKYPTYPEA 573
HsapiensFUT8     QPRTADEIPMEPGDIIGVAGNHWDGYSKGVNRKLGRTGLYPSYKVREKIETVKYPTYPEA 573
GgallusFUT8      HPRTADEIPMEPGDIIGVAGNHWDGYSKGINRKLGKTGLYPSYKVKEKIETVKYPTYPEA 573
StropicalisFUT8  QPRNAEEIPLEPGDIIGVAGNHWDGYSKGINRKLGRTGLYPSYKVKEKIETVKYPTYQEA 576
DrerioFUT8       QPRNSDDIPLEPGDVIGVAGNHWDGYSKGINRKTGRTGLYPSYKVKEKIETVKYPTYPEA 573
                 .**. ::**:****.*******.*****:*** *:********:************ **

MmusculusFUT8    EK----- 599
RnorvegicusFUT8  EK----- 575
CgriseusFUT8     EK----- 575
BtaurusFUT8      EK----- 575
ClupusFUT8       EK----- 575
HsapiensFUT8     EK----- 575
GgallusFUT8      EK----- 575
StropicalisFUT8  EK----- 578
DrerioFUT8       DKLLKKP 580
                 :*
```

FIG. 11A

FucT8 alignment

CLUSTAL 2.1 multiple sequence alignment [overall sequence homology >46%]

```
HsapiensFucT       -----MNRAPLKRSRILHMALTGASDPSAEAEA--NGEKPFLLRALQIALVVSLYWVTSIS 54
HsapiensFucT2      ------------------MALTGASDPSAEAEA--NGEKPFLLRALQIALVVSLYWVTSIS 41
ClupusFucT         -----MNRAPLKRSRILHMALMGASDPLGEAEA--IKEKPFLLRALQITLVVSLYWVTSIS 54
BtaurusFucT        -----MNRASLKRSKILHMALMGTSDPSGEAEA--SQEKPFVLRALQIALVVSLYWVTSIS 54
MmusculusFucT      -----MNRAPLKRSRILRMALTGVSAVSEESE---SGNKPFLLRALQIALVVSLYWVTSIS 53
MmusculusFucT2     ------------------MALTGVSAVSEESE---SGNKPFLLRALQIALVVSLYWVTSIS 40
RnorvegicusFucT    -----MNRVPLKRSRILPMALTGASAVSEEAD---SENKPFLLRALQIALVVSLYWVTSIS 53
CgriseusFucT       -----MNRAPLKRSRILRMALTGGSTASEEADED-SRNKPFLLRALQIALVVSLYWVTSIS 55
GgallusFucT        -----MSRSQLTRTGILRMALGGAADPLLPAEGAGGRRTPFVLRALRIALVVSLYWFVSIT 56
XtropicalisFucT    -----MN----FKRSSILRMALMGAGEGDQEKVS-----RESFLVRAVKIALVVTLYWFISIT 49
DrerioFucT         ---------------MAFTDSTRPGDKEE--------PFFMRATKIALVVTLYWFISIS 36
AsuumFucT          MHHDSKITPVATIHLLPKGLGRGLLLQQFAMKNGRQHETLAQKSIKIVLAVSAYWICSIG 60
LloaFucT           ------------------------------------------------------------
CelegansFucT       ---------------------MKLHEENNKALFEAMRNRENPTKWESYKQVITAVSAYWVFSIG 43

HsapiensFucT       MVFLNKYLLDSPS--LRLDTPIFVTFYQCLVTTLLCKGLSALAACCPG-AVDFPSLRLDL 111
HsapiensFucT2      MVFLNKYLLDSPS--LRLDTPIFVTFYQCLVTTLLCKGLSALAACCPG-AVDFPSLRLDL 98
ClupusFucT         MVFLNKYLLDSPS--LQLDTPIFVTFYQCLVTSLLCKGLSTLAAFCPG-AMDFPTLRLDL 111
BtaurusFucT        MVFLNKYLLDSPS--LRLDTPIFVTFYQCLVTVLLCKGLSSLATCCPG-TVDFPALHLDL 111
MmusculusFucT      MVFLNKYLLDSPS---LQLDTPIFVTFYQCLVTSLLCKGLSTLATCCPG-MVDFPTLNLDV 110
MmusculusFucT2     MVFLNKYLLDSPS--LQLDTPIFVTFYQCLVTSLLCKGLSTLATCCPG-MVDFPTLNLDL 97
RnorvegicusFucT    MVFLNKYLLDSPS--LQLDTPIFVTFYQCLVTSLLCKGLSTLATCCPG-MVDFPTLNLDL 110
CgriseusFucT       MVFLNKYLLDSPS--LQLDTPIFVTFYQCLVTSLLCKGLSTLATCCPG-TVDFPTLNLDL 112
GgallusFucT        MVFLNKYLLDSPS--LLDAPLFVTFFQCAVTAALCLGLSLGAACGP---CAALPALRLDL 112
XtropicalisFucT    MVFLNKYLLDSPS--LKLDAPLFVTFYQCVVTVVLCKGLSLLTHVVPSHILEFPSLRFDL 107
DrerioFucT         MVFLNNYLLDSK----ELDAPVFITFFQCVVSVGLCLLMSFLSSLCPG-SVDFPSLKFDL 91
AsuumFucT          LVFLNKYLLSS--ENLKLNAPLFITWYQCLVTVVLCYTCSYLSRIFPS-RFSFPSIAFDH 117
LloaFucT           ----MSKYSLSSSYTGKLLNAPLFVTWYQCFVTVLLCCVFCWVSKQYPS-LVTFPFVGFDH 56
CelegansFucT       LVFLNKYLLSS----VQLDAPLFITWYQCLVTVFLCLFLSKTSKAYG--LFKFPSMPIDA 97
                    ::* *.*      *::*:*:*::**  *:  **  .  :        :*  : :*

HsapiensFucT       RVARSVLPLSVVFIGMITFNNLCLKYVGVAFYNVGRSLTTVFNVLLSYLLLKQTTSFYAL 171
HsapiensFucT2      RVARSVLPLSVVFIGMITFNNLCLKYVGVAFYNVGRSLTTVFNVLLSYLLLKQTTSFYAL 158
ClupusFucT         RVARSVLPLSVVFIGMITFNNLCLKYVGVAFYNVGRSLTTVFNVLLSYLLLKQTTSFYAL 171
BtaurusFucT        KVARSVLPLSVVFIGMITFNNLCLKYVGVAFYNVGRSLTTVFNVLLSYLLLKQTTSFYAL 171
MmusculusFucT      KVARSVLPLSVVFIGMITFNNLCLKYVGVPFYNVGRSLTTVFNVLLSYLLLKQTTSFYAL 170
MmusculusFucT2     KVARSVLPLSVVFIGMITFNNLCLKYVGVPFYNVGRSLTTVFNVLLSYLLLKQTTSFYAL 157
RnorvegicusFucT    KVARSVLPLSVVFIGMITFNNLCLKYVGVAFYNVGRSLTTVFNVLLLKQTTSFYAL 170
CgriseusFucT       KVARSVLPLSVVFIGMISFNNLCLKYVGVAFYNVGRSLTTVFNVLLSYLLLKQTTSFYAL 172
GgallusFucT        KVSRSVLPLSVVFIGMVTSNNLCLKHVGVAFYNVGRSLTTVFNVLLSYLLLKQTTSLYAL 172
XtropicalisFucT    KVLRTVLPLSIVFIGMITFNNLCLKYLGVAFYTVGRCLSTVFNVLLSYIMLKQTTSMYAL 167
DrerioFucT         RVSREILPLTIVFISMITFNNLCLKYVGVAFYTVGRSLSTVFNVILSYVVLKQTTSLYAV 151
AsuumFucT          RISREVLPLSFVFVAMITTNNLCLKYVGVSFYYVGRSLTTVFNVCSYLILGQGTSWRAL 177
LloaFucT           RISREVLPLSFVFVAMIATNNLCLKYVGVSFYYIGRSLTTVFNVICSYIILGQLTSLKTI 116
CelegansFucT       KISREVLPLSVVFVAMISFNNLCLKYVGVSFYYVGRSLTTVFNVVCTYLILGQKTSGQAI 157
                    :: *  :***:.**:.*::  *****:;**.**  ;**.*;*****;  :*;:* * **    ::
```

FIG. 11B

```
HsapiensFucT       LTCGIIIGGFWLGVDQEGAE-------------GTLSWLGTVFGVLASLCVSLNAIYTTKVLP 221
HsapiensFucT2      LTCGIIIGGFWLGVDQEGAE-------------GTLSWLGTVFGVLASLCVSLNAIYTTKVLP 208
ClupusFucT         LTCGIIIGGFWLGVDQEGAE-------------GTLSWTGTLFGVLASLCVSLNAIYTKKVLP 221
BtaurusFucT        LTCSVIIGGFWLGVDQEGAE-------------GTLSWTGTLFGVLASLCVSLNAIYTKKVLP 221
MmusculusFucT      LTCGVIIGGFWLGIDQEGAE-------------GTLSLTGTIFGVLASLCVSLNAIYTKKVLP 220
MmusculusFucT2     LTCGVIIGGFWLGIDQEGAE-------------GTLSLTGTIFGVLASLCVSLNAIYTKKVLP 207
RnorvegicusFucT    LTCAIIIGGFWLGIDQEGAE-------------GTLSLTGTIFGVLASLCVSLNAIYTKKVLP 220
CgriseusFucT       LTCGIIIGGFWLGIDQEGAE-------------GTLSLIGTIFGVLASLCVSLNAIYTKKVLP 222
GgallusFucT        LACGIIIGGFWLGVDQEGAE-------------GTLSWTGIIFGILASLCVSLNAIYTKKVLP 222
XtropicalisFucT    MSCGVILGGFWLGIDQEGAE-------------GTLSWAGIFFGVLASLCVSLNAIYTKKVLP 217
DrerioFucT         LCCGVILGGFWLGVDQEAVA-------------GSLSWAGVVFGVIASLCVSLNAIFTKKVLP 201
AsuumFucT          LCCAVIIGGFFLGVDQEDA----------AGSLSVLGVVYGVAASLCVALNAIYTQRTLP 227
LloaFucT           LCCALIGGFVLGVDQEDATAQFFLPRTFLGTLSVTGVIFGVAASMFVALNAIYTQRTLP 176
CelegansFucT       GCCALIIFGFLLGVDQEGVT-------------GTLSYTGVIFGVLASLSVALNAIYTRKVLS 207
                    *.:*: ** **;***  .                *:**    *  .:*:  **: *;****:*  :.*.

HsapiensFucT       AVDGSIWRLTFYNNVNACILFLPLLLLLGELQALRDFAQLGSAHFWGMMTLGGLFGFAIG 281
HsapiensFucT2      AVDGSIWRLTFYNNVNACILFLPLLLLLGELQALRDFAQLGSAHFWGMMTLGGLFGFAIG 268
ClupusFucT         AVDGSIWRLTFYNNVNACVLFLPLLLLLGELQTLLNFSQLGSAHFWGMMTLGGLFGFAIG 281
BtaurusFucT        AVDGSIWRLTFYNNANACVLFLPLLLALGELRALLAFPQLGSAHFWAMMTLGGLFGFAIG 281
MmusculusFucT      AVDHSIWRLTFYNNVNACVLFLPLMIVLGELRALLAFTHLSSAHFWLMMTLGGLFGFAIG 280
MmusculusFucT2     AVDHSIWRLTFYNNVNACVLFLPLMIVLGELRALLAFTHLSSAHFWLMMTLGGLFGFAIG 267
RnorvegicusFucT    AVDHSIWRLTFYNNVNACVLFLPLMVVLGELHALLAFAHLNSAHFWVMMTLGGLFGFAIG 280
CgriseusFucT       AVDNSIWRLTFYNNVNACVLFLPLMVLLGELRALLDFAHLYSAHFWLMMTLGGLFGFAIG 282
GgallusFucT        VVDGSIWHLTFYNNMMNACVLFLPLMMITGEFHTLYHFDKLGSPSFWGMMTLGGVFGFAIG 282
XtropicalisFucT    AVDGSIWRLTFYNNVNACFLFTPLLFIFGEVGTLFTFDKLFAFSFWGMMTLGGIFGFAIG 277
DrerioFucT         VVDGNIWKLSYYNNLNAIVLFLPLLIILGEVKSVFEFSRLTDLRFWGMMTLGGVFGFAIG 261
AsuumFucT          AVGDSVARLTMYNNTNAVVLFIPLMLFSGEFGEIIYFPYLLSTHFWALMTISGVFGFLMG 287
LloaFucT           SVGDSITQLTLYNNINALVLFIPVMLFSGDISEVFYFRYSSSLRFWTLMTLSGIFGFLMS 236
CelegansFucT       SVGDCLWRLTMYNNLNALVLFLPLMLFNGEFGAVFYFDKLFDTTPFWILMTLGGVFGFMMG 267
                    *.   :  :*: *** **  .** *::.   *:.    :   *        **  :**:.*:*** :.

HsapiensFucT       YVTGLQIKFTSPLTHNVSGTAKACAQTVLAVLYYEETKSFLWWTSNMMVLGGSSAYTWVR 341
HsapiensFucT2      YVTGLQIKFTSPLTHNVSGTAKACAQTVLAVLYYEETKSFLWWTSNMMVLGGSSAYTWVR 328
ClupusFucT         YVTGLQIKFTSPLTHNVSGTAKACAQTVLAVLYYEETKSFLWWTSNMMVLGGSSAYTWVR 341
BtaurusFucT        YVTGLQIKFTSPLTHNVSGTAKACAQTVLAVLYYEEAKSFLWWTSNMMVLGGSSAYTWVR 341
MmusculusFucT      YVTGLQIKFTSPLTHNVSGTAKACAQTVLAVLYYEEIKSFLWWTSNLMVLGGSSAYTWVR 340
MmusculusFucT2     YVTGLQIKFTSPLTHNVSGTAKACAQTVLAVLYYEEIKSFLWWTSNLMVLGGSSAYTWVR 327
RnorvegicusFucT    YVTGLQIKFTSPLTHNVSGTAKACAQTVLAVLYYEEIKSFLWWTSNLMVLGGSSAYTWVR 340
CgriseusFucT       YVTGLQIKFTSPLTHNVSGTAKACAQTVLAVLYYEETKSFLWWTSNLMVLGGSSAYTWVR 342
GgallusFucT        YVTGLQIKFTSPLTHNVSGTAKACAQTVLAVVYFEETKSLLWWTSNLMVLGGSFAYTWVK 342
XtropicalisFucT    YVTGLQIQFTSPLTHNISGTAKACAQTVLAVMYYHQIKSFLWWTSNLMVLGGSFSYTWVK 337
DrerioFucT         YVTGLQIKFTSPLTHNVSGTAKSCAQTVLAVVYWASEKSTLWWTSNLMVLGGSFAYTWVK 321
AsuumFucT          YVTGWQIQVTSPLTHNISGTAKAAAQTVIAVAWWQEVKSVLWWVSNVVVLGGSAAYTAVK 347
LloaFucT           YVTGWQIQVTSSLTHNISGTAKAAAQTVIAVVWWQEMKSLLWWISNVIVLGGSAIYTMIK 296
CelegansFucT       YVTGWQIQATSPLTHNISGTAKAAAQTVMAVVWYSELKTLLWWTSNFVVLFGSGMYTVQ 327
                    ****  **: **:*****;:.****;**  ::   .  *:  *** **.:** ** **  ::

HsapiensFucT       GWEMKKTPEEP--SPKDSEKS--------------AMGV 364
HsapiensFucT2      GWEMKKTPEEP--SPKDSEKS--------------AMGV 351
ClupusFucT         GWEMKKIQEDP--SPKEDEKS--------------SMGV 364
BtaurusFucT        GREMKKTQEEP--HPRENEKS--------------NMEV 364
MmusculusFucT      GWEMQKTQEDP--SSKDGEKS--------------AIRV 363
MmusculusFucT2     GWEMQKTQEDP--SSKDGEKS--------------AIRV 350
RnorvegicusFucT    GWEMQKTQEDP--SSKEGEKS--------------AIGV 363
CgriseusFucT       GWEMQKTQEDP--SSKEGEKS--------------AIRV 365
GgallusFucT        GLEMRKAQEDP--NLKSSEKN--------------ETGV 365
XtropicalisFucT    GLEMKKSQGETNQSQSNGEKN----------------SVGV 362
DrerioFucT         GMEMKKAPVPTETQSLNPQKNKE------------DLGV 348
AsuumFucT          RKEMIANHESNAKPRGSVSPDREPILSSKSSGDTSEDV 385
LloaFucT           RKEMVDKYDTN--KSKLNENIERQAVLFGLS---DEDETV 331
CelegansFucT       KR--VMDKKNSG--ASPASEAKSDKVKLLGRDGNAAEESV 363
                                 :               .   .        *
```

PRODUCTION OF FUCOSYLATED GLYCOPROTEINS

The present invention relates to compositions and methods useful for the production of glycoproteins, e.g. recombinant antibodies, having fucosylated N-glycans, in filamentous fungal cells.

BACKGROUND

Posttranslational modification of eukaryotic proteins, particularly therapeutic proteins such as immunoglobulins, is often necessary for proper protein folding and function. Because standard prokaryotic expression systems lack the proper machinery necessary for such modifications, alternative expression systems have to be used in production of these therapeutic proteins. Yeast and fungi are attractive options for expressing proteins as they can be easily grown at a large scale in simple media, which allows low production costs, and yeast and fungi have posttranslational machinery and chaperones that perform similar functions as found in mammalian cells. Moreover, tools are available to manipulate the relatively simple genetic makeup of yeast and fungal cells as well as more complex eukaryotic cells such as mammalian or insect cells (De Pourcq et al., Appl Microbiol Biotechnol, 87(5):1617-31). Despite these advantages, many therapeutic proteins are still being produced in mammalian cells, which produce therapeutic proteins with posttranslational modifications most resembling the native human proteins, whereas the posttranslational modifications naturally produced by yeast and fungi often differ from those found in mammalian cells.

To address this deficiency, new strains of yeast and fungi are being developed that produce posttranslational modifications that more closely resemble those found in native human proteins. More specifically, news strains of yeast and fungi have been genetically modified so that they express recombinant proteins having N-glycan patterns resembling that of native human proteins. The general strategies include the elimination of endogenous glycosylation enzymes that are involved in producing high mannose N-glycans (such as och1p or Alg3p in yeast), and the introduction of certain glycosyltransferases in order to reproduce the sequential reaction steps of the mammalian glycosylation pathway, including α1,2 mannosidase, GnTI, mannosidase II, GnTII, GalT, SiaT enzymes (Wildt and Gerngross, 2005, Nature, 3: 119-127; De Pourcq et al., 2010, Appl Microbiol Biotechnol, 87:1617-1631).

Mammalian and human cells express fucosyltransferase (FucTs) activities and FucTs are therefore one of the enzyme families of interest for remodeling N-glycan patterns on the surface of recombinant glycoproteins produced in yeast or fungi. The presence of fucosylated structures on glycoproteins has indeed been shown to be advantageous in some cases. More specifically, in the production of monoclonal antibodies, immunoglobulin and related glycoproteins comprising Fc fragment, it is well known that the presence of fucosylated N-glycans influence antibody dependent cytotoxicity (ADCC) activity. In some cases, it is desirable to produce antibodies with fucosylated N-glycans, in order to decrease ADCC activity of the resulting protein. It is further well known that the presence of fucosylated N-glycans influence antibody dependent cellular phagocytosis (ADCP) activity (Shibata-Koyama et al. 2009. Exp Hematol 37:309-21). In some cases, it is desirable to produce antibodies with fucosylated N-glycans, in order to decrease ADCP activity of the resulting protein.

WO 2008/112092 reports materials and methods for making lower eukaryotic expression systems that can be used to produce recombinant, fucosylated glycoproteins. The genetic modification of yeast *P. pastoris* strain capable of producing glycoproteins that include fucose is described, including the insertion of polynucleotides encoding human GDP-mannose-4,6 dehydratase (GMD), human GDP-4-keto-6-deoxy-D-mannose-3,5-epimerase/4-reductase (FX) and human α1,6 fucosyltransferase (FUT8) proteins in such host cell.

Other reports have suggested genetic modification of yeast strains to produce the GDP-L-fucose, the substrate of fucosyltransferase (Chigira et al. 2008, Glycobiology 18 no. 4 pp 303-314; Jä rvinen et al. 2001, Eur J Biochem 268, 6458-6464), and/or human-like fucosylated glycoforms (Ma et al., 2006, Glycobiology 16(12) pp 158-184, US 20050170452, US 2010137565, US2010062485).

Reports of fungal cell expression systems expressing human-like fucosylated N-glycans are lacking. Indeed, due to the industry's focus on mammalian cell culture technology for such a long time, the fungal cell expression systems such as *Trichoderma* are not as well established for therapeutic protein production as mammalian cell culture and therefore suffer from drawbacks when expressing mammalian proteins. In particular, a need remains in the art for improved filamentous fungal cells, such as *Trichoderma* fungus cells, that can stably produce heterologous proteins with mammalian-like N-glycan patterns, preferably at high levels of expression.

The invention now provides fungal cell expression system, more specifically *Trichoderma* cells, or related species such as *Neurospora, Myceliophtora, Fusarium, Aspergillus, Penicillium* and *Chrysosporium* species, having reduced protease activity and capable of expressing fucosylated glycoproteins, for example with mammalian-like complex fucosylated N-glycans.

SUMMARY

Described herein are compositions including filamentous fungal cells, such as *Trichoderma* fungal cells, expressing fucosylation pathway. More specifically, described herein are compositions including filamentous fungal cells with reduced protease activity and expressing fucosylation pathway. Further described herein are methods for producing a glycoprotein, e.g. an antibody, having fucosylated N-glycan, using genetically modified filamentous fungal cells, for example, *Trichoderma* fungal cells, as the expression system. Thus, a particular aspect of the invention includes filamentous fungal cells, such as

*Trichoderma* fungal cells, comprising at least a mutation that reduces an endogenous protease activity compared to a parental filamentous fungal cell which does not have such mutation and comprising a polynucleotide encoding a polypeptide having fucosyltransferase activity. In certain embodiments, the filamentous fungal cell is selected from the group consisting of *Trichoderma, Neurospora, Myceliophthora, Fusarium, Aspergillus, Penicillium* and *Chrysosporium* cell.

In certain embodiments, said mutation is a deletion or a disruption of the gene encoding said endogenous protease activity. In certain embodiments, the expression level of at least two, or at least three proteases is reduced. In certain embodiments that may be combined with the preceding embodiments, the cell has a mutation in one or more proteases selected from the group consisting of pep1, pep2, pep3, pep4, pep5, pep7, pep8, pep11, pep12, tpp1, tsp1, slp1, slp2, slp3, slp5, slp6, slp7, slp8, gap1 and gap2. In one embodiment that may be combined with the preceding embodiments, said cell comprises mutations that reduce or eliminate the activity of
a) the three endogenous proteases pep1, tsp1 and slp1,
b) the three endogenous proteases gap1, slp1 and pep1,
c) three endogenous proteases selected from the group consisting of pep1, pep2, pep3, pep4, pep5, pep8, pep11, pep12, tsp1, slp1, slp2, slp3, slp7, gap1 and gap2,
d) three to six proteases selected from the group consisting of pep1, pep2, pep3, pep4, pep5, tsp1, slp1, slp2, slp3, gap1 and gap2,
e) seven to ten proteases selected from the group consisting of pep1, pep2, pep3, pep4, pep5, pep7, pep8, tsp1, slp1, slp2, slp3, slp5, slp6, slp7, slp8, tpp1, gap1 and gap2.

In certain embodiments that may be combined with the preceding embodiments, said fucosyltransferase activity (FucT) is selected from the group consisting of: α1,2 FucT, α1,3/α1,4, α1,6 FucT and O-FucTs. An example of a polynucleotide encoding a polypeptide having fucosyltransferase activity comprises either the polynucleotide of SEQ ID NO:1, or a functional variant polynucleotide encoding a polypeptide having at least 50%, at least 60%, at least 70%, at least 90%, or at least 95% identity with SEQ ID NO:6, said polypeptide has α1,6 fucosyltransferase activity.

In certain embodiments that may be combined with the preceding embodiments, the filamentous fungal cell further comprises one or more polynucleotides encoding a polypeptide having GDP-fucose synthesis activity and, optionally, GDP-fucose transporter activivity. In certain embodiments, said one or more polynucleotides encoding a polypeptide having GDP-fucose synthesis activity comprises
a) GMD polynucleotide or a functional variant polynucleotide encoding a polypeptide having GDP-mannose-dehydratase activity; and,
b) FX polynucleotide or a functional variant polynucleotide encoding a polypeptide having both GDP-keto-deoxy-mannose-epimerase and GDP-keto-deoxy-galactose-reductase activities.

An example of said one or more polynucleotides encoding the polypeptide encoding GDP-fucose synthesis activity comprises
a) *C. elegans* GMD polynucleotide of SEQ ID NO:2 or a functional variant polynucleotide encoding a polypeptide having at least 50%, at least 60%, at least 70%, at least 90%, or at least 95% identity with SEQ ID NO:7, wherein said polypeptide has GDP-mannose-dehydratase activity; and,
b) *C. elegans* FX polynucleotide of SEQ ID NO:3 or a functional variant polynucleotide encoding a polypeptide having at least 50%, at least 60%, at least 70%, at least 90%, or at least 95% identity with SEQ ID NO:8, wherein said polypeptide has both GDP-keto-deoxy-mannose-epimerase and GDP-keto-deoxy-galactose-reductase activities.

In certain embodiments that may be combined with the preceding embodiments, the filamentous fungal cell further comprises a polynucleotide of SEQ ID NO:4 encoding *C. elegans* GDP-fucose transporter or a functional variant polynucleotide encoding a polypeptide having at least 50%, at least 60%, at least 70%, at least 90%, or at least 95% identity with SEQ ID NO:9 and encoding GDP fucose transporter.

In certain embodiments that may be combined with the preceding embodiments, said polynucleotide encoding a polypeptide having fucosyltransferase activity further comprises a Golgi targeting sequence for targeting expression of said polypeptide in the ER/Golgi compartment of said filamentous fungal cell. An example of said Golgi targeting sequence comprises a polynucleotide sequence encoding a N-terminal portion of the polypeptide of SEQ ID NO:10, or a functional variant polynucleotide suitable for targeting said fucosyltransferase activity in the Golgi compartment of said filamentous fungal cell.

In certain embodiments that may be combined with the preceding embodiments, the filamentous fungal cell is genetically modified to produce a complex N-glycan as an acceptor substrate for said fucosyltransferase activity.

In certain embodiments that may be combined with the preceding embodiments, the filamentous fungal cell has a mutation that reduces the level of expression of an ALG3 gene compared to the level of expression in a parent cell which does not have such mutation. In certain embodiments that may be combined with the preceding embodiment, the filamentous fungal cell further comprises a first polynucleotide encoding N-acetylglucosaminyltransferase I catalytic domain and a second polynucleotide encoding N-acetylglucosaminyltransferase II catalytic domain.

In certain embodiments that may be combined with the preceding embodiments, the filamentous fungal cell further comprises one or more polynucleotides selected from the group consisting of:
i. a polynucleotide encoding α1,2 mannosidase,
ii. a polynucleotide encoding N-acetylglucosaminyltransferase I catalytic domain,
iii. a polynucleotide encoding α mannosidase II,
iv. a polynucleotide encoding N-acetylglucosaminyltransferase II catalytic domain.

In certain embodiments that may be combined with the preceding embodiments, the filamentous fungal cell further comprises a polynucleotide encoding β1,4 galactosyltransferase.

In certain embodiments that may be combined with the preceding embodiments, the filamentous fungal cell further comprises one or more polynucleotides selected from the group consisting of:
i. a polynucleotide encoding glucosamine UDP-N-acetylglucosamine-2-epimerase/N-acetylmannosamine kinase,
ii. a polynucleotide encoding N-acetylneuraminic acid synthase,
iii. a polynucleotide encoding N-acetylneuraminic acid phosphatase,
iv. a polynucleotide encoding cytidine monophosphate N-acetylneuraminic acid synthetase,
v. a polynucleotide encoding CMP-sialic acid transporter, and
vi. a polynucleotide encoding sialyltransferase.

In certain embodiments that may be combined with the preceding embodiments, the filamentous fungal cell further comprises mutations in one or more genes encoding glycosyl hydrolases, wherein said mutation eliminates or reduces activity of the corresponding hydrolases, and wherein said hydrolases are selected from the group consisting xylanase, cellobiohydrolase, and endoglucanase.

Another aspect includes a method for producing a glycoprotein, e.g. an antibody, having fucosylated N-glycan, comprising:
a) providing a filamentous fungal cell as defined above, and comprising a polynucleotide encoding a glycoprotein,
b) culturing the filamentous fungal cell to produce said glycoprotein having fucosylated N-glycan.

In certain embodiments that may be combined with the preceding embodiments, the fucose of the N-glycan is in an α1,6 linkage. For example, said fucosylated N-glycan is selected from the group consisting of $Man_3GlcNAc_2(Fuc)$, $GlcNAcMan_3GlcNAc_2(Fuc)$, $GlcNAc_2Man_3GlcNAc_2(Fuc)$, $Gal_{1-2}GlcNAc_2Man_3GlcNAc_2(Fuc)$, $Neu5Ac_{1-2}Gal_{1-2}GlcNAc_2Man_3GlcNAc_2(Fuc)$. In certain embodiments, at least 5 mol %, at least 10 mol % or at least 15 mol % of the total secreted neutral N-glycans consist of $GlcNAc_2Man_3GlcNAc_2(Fuc)$ glycoform.

In certain embodiments that may be combined with the preceding embodiments, said polynucleotide encoding a glycoprotein, e.g. an antibody, is a recombinant polynucleotide encoding a heterologous glycoprotein. For example, said heterologous glycoprotein is a mammalian glycoprotein selected from the group consisting of an antibody, an immunoglobulin, a single chain antibody, a monomeric or multimeric single domain antibody, a FAb-fragment, a FAb2-fragment, their antigen-binding fragments or a protein fusion comprising Fc fragment of an immunoglobulin.

In one embodiment, said polynucleotide encoding said glycoprotein further comprises a polynucleotide encoding CBH1 catalytic domain and linker as a carrier protein and/or cbh1 promoter.

In an embodiment that may be combined with one or more of the preceding embodiments less than 0.1%, 0.01%, 0.001% or 0% of the N-glycans of the glycoprotein (or secreted glycoprotein) comprises Neu5Gc and/or Galα-structure. In an embodiment that may be combined with the preceding embodiments, less than 0.1%, 0.01%, 0.001% or 0% of the N-glycans of the antibody (or secreted antibody) comprises Neu5Gc and/or Galα-structure.

In an embodiment that may be combined with one or more of the preceding embodiments, less than 1.0%, 0.5%, 0.1%, 0.01%, 0.001%, or 0% of the glycoprotein (or secreted glycoprotein) comprises glycation structures. In an embodiment that may be combined with the preceding embodiments, less than 1.0%, 0.5%, 0.1%, 0.01%, 0.001%, or 0% of the antibody (or secreted antibody) comprises glycation structures.

DETAILED DESCRIPTION

Figure 1:
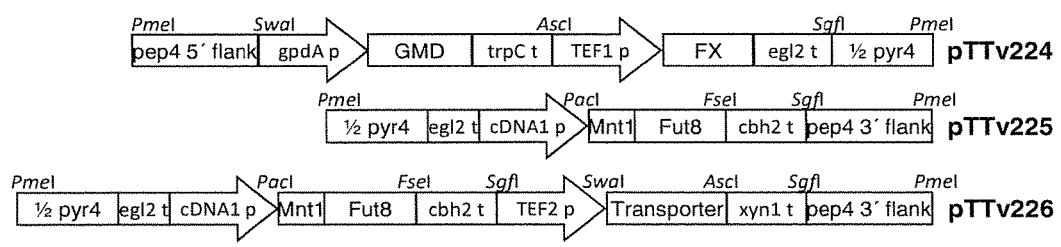
FIG. 1. Schematic expression cassette design for plasmids pTTv224, pTTv225 and pTTv226.

The present invention relates to improved methods for producing glycoproteins with fucosylated N-glycans, and more specifically, fucosylated glycoproteins, such as antibodies or related immunoglobulins or protein fusion comprising Fc fragments.

The present invention is based in part on the surprising discovery that filamentous fungal cells, such as *Trichoderma* cells, can be genetically modified to produce fucosylated glycoproteins, and in particular fucosylated glycoproteins with complex fucosylated N-glycans, at a high yield.

In one aspect, the invention relates to a fungal cell, including a filamentous fungal cell that produces core fucosylated N-glycan. In one embodiment, the cell comprises reduced or deleted alg3 enzyme activity. In other embodiments, the core fucosylated N-glycans are produced on secreted glycoproteins. In other embodiments, the secreted glycoproteins are heterologous and/or homologous glycoproteins. In other embodiments, the cell is a fungal cell or filamentous fungal cell.

A particular aspect of the invention relates to a filamentous fungal cell, comprising at least a mutation that reduces an endogenous protease activity compared to a parental filamentous fungal cell which does not have such mutation and comprising a polynucleotide encoding fucosyltransferase activity, and, optionally, other polynucleotides encoding GDP fucose synthesis and/or GDP-fucose transporter.

Such filamentous fungal cells are useful as an expression system for the production of heterologous glycoproteins, preferably heterologous mammalian glycoproteins, such as an immunoglobulin, an antibody, a single chain antibody, a monomeric or multimeric single domain antibody, a Fab fragment, a Fab2 fragment or a protein fusion comprising an Fc fragment of an immunoglobulin or their antigen-binding fragment.

Typically, the method for producing fucosylated glycoproteins comprises the steps of:

a) providing a filamentous fungal cell genetically modified as defined below, and comprising a polynucleotide encoding a glycoprotein, for example encoding an immunoglobulin, an antibody, a single chain antibody, a monomeric or multimeric single domain antibody, a Fab fragment, a Fab2 fragment or a protein fusion comprising an Fc fragment of an immunoglobulin or their antigen-binding fragment, and b) culturing the filamentous fungal cell to produce said glycoprotein having fucosylated N-glycan c) optionally, purifying said fucosylated glycoprotein.

Definitions

As used herein, an "expression system" or a "host cell" refers to the cell that is genetically modified to enable the transcription, translation and proper folding of a polypeptide or a protein of interest, typically a mammalian protein.

As used herein, a "polynucleotide" or "oligonucleotide" or "nucleic acid" are used interchangeably and refers to a polymer of at least two nucleotides joined together by a phosphodiester bond and may consist of either ribonucleotides or deoxynucleotides or their derivatives that can be introduced into a host cell for genetic modification of such host cell. For example, a polynucleotide may encode a coding sequence of a protein, and/or comprise control or regulatory sequences of a coding sequence of a protein, such as enhancer or promoter sequences or terminator. A polynucleotide may for example comprise native coding sequence of a gene or their fragments, or variant sequences that have been optimized for optimal gene expression in a specific host cell (for example to take into account codon bias).

As used herein, the term, "optimized" with reference to a polynucleotide means that a polynucleotide has been altered to encode an amino acid sequence using codons that are preferred in the production cell or organism, for example, a filamentous fungal cell such as a *Trichoderma* cell. The optimized nucleotide sequence is typically modified to retain completely or as much as possible the amino acid sequence originally encoded by the starting nucleotide sequence, which is also known as the "parental" sequence. The optimized sequences herein have been engineered to have codons that are preferred in the corresponding production cell or organism, for example the filamentous fungal cell. The amino acid sequences encoded by optimized nucleotide sequences may also be referred to as optimized.

As used herein, a "peptide" or a "polypeptide" is an amino acid sequence including a plurality of consecutive polymerized amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide or a combination of more than one peptide or polypeptide assembled together by covalent or non-covalent bonds. Unless specified, the term "protein" may encompass one or more amino acid sequences with their post-translation modifications, and in particular with N-glycan modifications. As used herein, the term "glycoprotein" refers to a protein which comprises at least one N-linked glycan attached to at least one asparagine residue of a protein.

As used herein, "glycan" refers to an oligosaccharide chain that can be linked to a carrier such as an amino acid, peptide, polypeptide, lipid or a reducing end conjugate. In certain embodiments, the invention relates to N-linked glycans ("N-glycan") conjugated to a polypeptide N-glycosylation site such as -Asn-Xxx-Ser/Thr- by N-linkage to sidechain amide nitrogen of asparagine residue (Asn), where Xxx is any amino acid residue except Pro. The invention may further relate to glycans as part of dolichol-phospho-oligosaccharide (Dol-P-P-OS) precursor lipid structures, which are precursors of N-linked glycans in the endoplasmic reticulum of eukaryotic cells. The precursor oligosaccharides are linked from their reducing end to two phosphate residues on the dolichol lipid. For example, α3-mannosyl-transferase Alg3 modifies the Dol-P-P-oligosaccharide precursor of N-glycans. Generally, the glycan structures described herein are terminal glycan structures, where the non-reducing residues are not modified by other monosaccharide residue or residues.

As used throughout the present disclosure, glycolipid and carbohydrate nomenclature is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 29). It is assumed that Gal (galactose), Glc (glucose), GlcNAc (N-acetylglucosamine), GalNAc (N-acetylgalactosamine), Man (mannose), and Neu5Ac are of the D-configuration, Fuc of the L-configuration, and all the monosaccharide units in the pyranose form (D-Galp, D-Glcp, D-GlcpNAc, D-GalpNAc, D-Manp, L-Fucp, D-Neup5Ac). The amine group is as defined for natural galactose and glucosamines on the 2-position of GalNAc or GlcNAc. Glycosidic linkages are shown partly in shorter and partly in longer nomenclature, the linkages of the sialic acid SA/Neu5X-residues α3 and α6 mean the same as α2-3 and α2-6, respectively, and for hexose monosaccharide residues α1-3, α1-6, β1-2, β1-3, β1-4, and β1-6 can be shortened as α3, α6, β2, β3, β4, and β6, respectively. Lactosamine refers to type II N-acetyllactosamine, Galβ4GlcNAc, and/or type I N-acetyllactosamine. Galβ3GlcNAc and sialic acid (SA) refer to N-acetylneuraminic acid (Neu5Ac), N-glycolyl-neuraminic acid (Neu5Gc), or any other natural sialic acid including derivatives of Neu5X. Sialic acid is referred to as NeuNX or Neu5X, where preferably X is Ac or Gc. Occasionally Neu5Ac/Gc/X may be referred to as NeuNAc/NeuNGc/NeuNX.

The sugars typically constituting N-glycans found in mammalian glycoprotein, include, without limitation, N-acetylglucosamine (abbreviated hereafter as "GlcNAc"), mannose (abbreviated hereafter as "Man"), glucose (abbreviated hereafter as "Glc"), galactose (abbreviated hereafter as "Gal"), and sialic acid (abbreviated hereafter as "Neu5Ac"). N-glycans share a common pentasaccharide referred as the "core" structure $Man_3GlcNAc_2$. When a fucose is attached to the core structure, the N-glycan may be represented as $Man_3GlcNAc_2(Fuc)$. A "complex N-glycan" refers to a N-glycan which has one GlcNAc residue on terminal 1,3 mannose arm of the core structure and one GlcNAc residue on terminal 1,6 mannose arm of the core structure. Such complex N-glycans include $GlcNAc_2Man_3GlcNAc_2$ (also referred as G0 glycoform), $Gal_{1-2}GlcNAc_2Man_3GlcNAc_2$ (also referred as G1 glycoform), and $Neu5Ac_{1-2}Gal_{1-2}GlcNAc_2Man_3GlcNAc_2$ (also referred as G2 glycoform), and their core fucosylated glycoforms FG0, FG1 and FG2, respectively $GlcNAc_2Man_3GlcNAc_2(Fuc)$, $Gal_{1-2}GlcNAc_2Man_3GlcNAc_2(Fuc)$, and $Neu5Ac_{1-2}Gal_{1-2}GlcNAc_2Man_3GlcNAc_2(Fuc)$.

"Increased" or "Reduced activity of an endogenous enzyme": The filamentous fungal cell may have increased or reduced levels of activity of various endogenous enzymes. A reduced level of activity may be provided by inhibiting the activity of the endogenous enzyme with an inhibitor, an antibody, or the like. In certain embodiments, the filamentous fungal cell is genetically modified in ways to increase or reduce activity of various endogenous enzymes. "Genetically modified" refers to any recombinant DNA or RNA method used to create a prokaryotic or eukaryotic host cell that expresses a polypeptide at elevated levels, at lowered levels, or in a mutated form. In other words, the host cell has been transfected, transformed, or transduced with a recombinant polynucleotide molecule, and thereby been altered so as to cause the cell to alter expression of a desired protein.

"Genetic modifications" which result in a decrease in gene expression, in the function of the gene, or in the function of the gene product (i.e., the protein encoded by the gene) can be referred to as inactivation (complete or partial), deletion, disruption, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete (disruption) or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action of proteins discussed herein generally refers to any genetic modification in the host cell in question, which results in decreased expression and/or functionality (biological activity) of the proteins and includes decreased activity of the proteins (e.g., decreased catalysis), increased inhibition or degradation of the proteins as well as a reduction or elimination of expression of the proteins. For example, the action or activity of a protein can be decreased by blocking or reducing the production of the protein, reducing protein action, or inhibiting the action of the protein. Combinations of some of these modifications are also possible. Blocking or reducing the production of a protein can include placing the gene encoding the protein under the control of a promoter that requires the presence of an inducing compound in the growth medium. By establishing conditions such that the inducer becomes depleted from the medium, the expression of the gene encoding the protein (and therefore, of protein synthesis) could be turned off. Blocking or reducing the action of a protein could also include using an excision technology approach similar to that described in U.S. Pat. No. 4,743,546. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In general, according to the present invention, an increase or a decrease in a given characteristic of a mutant or modified protein (e.g., enzyme activity) is made with reference to the same characteristic of a parent (i.e., normal, not modified) protein that is derived from the same organism (from the same source or parent sequence), which is measured or established under the same or equivalent conditions. Similarly, an increase or decrease in a characteristic of a genetically modified host cell (e.g., expression and/or biological activity of a protein, or production of a product) is made with reference to the same characteristic of a wild-type host cell of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the host cell is measured, as well as the type of assay used, the host cell that is evaluated, etc. As discussed above, equivalent conditions are conditions (e.g., culture conditions) which are similar, but not necessarily identical (e.g., some conservative changes in conditions can be tolerated), and which do not substantially change the effect on cell growth or enzyme expression or biological activity as compared to a comparison made under the same conditions.

Preferably, a genetically modified host cell that has a genetic modification that increases or decreases the activity of a given protein (e.g., an enzyme) has an increase or decrease, respectively, in the activity or action (e.g., expression, production and/or biological activity) of the protein, as compared to the activity of the protein in a parent host cell (which does not have such genetic modification), of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are certain when comparing an isolated modified nucleic acid molecule or protein directly to the isolated wild-type nucleic acid molecule or protein (e.g., if the comparison is done in vitro as compared to in vivo).

In another aspect of the invention, a genetically modified host cell that has a genetic modification that increases or decreases the activity of a given protein (e.g., an enzyme) has an increase or decrease, respectively, in the activity or action (e.g., expression, production and/or biological activity) of the protein, as compared to the activity of the wild-type protein in a parent host cell, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

As used herein, the terms "identical" or percent "identity," in the context of two or more nucleic acid or amino acid sequences, refers to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8): 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22): 10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Functional variant" as used herein refers to a coding sequence or a protein having sequence similarity with a reference sequence, typically, at least 30%, 40%, 50%, 60%, 70%, 80%, 90% or 95% identity with the reference coding sequence or protein, and retaining substantially the same function as said reference coding sequence or protein. A functional variant may retain the same function but with reduced or increased activity. Functional variants include natural variants, for example, homologs from different species or artificial variants, resulting from the introduction of a mutation in the coding sequence. Functional variant may be a variant with only conservatively modified mutations.

"Conservatively modified mutations" as used herein include individual substitutions, deletions or additions to an encoded amino acid sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Filamentous fungal cells

As used herein, "filamentous fungal cells" include cells from all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). Filamentous fungal cells are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Preferably, the filamentous fungal cell is not adversely affected by the transduction of the necessary nucleic acid sequences, the subsequent expression of the proteins (e.g., mammalian proteins), or the resulting intermediates. General methods to disrupt genes of and cultivate filamentous fungal cells are disclosed, for example, for *Penicillium*, in Kopke et al. (2010) Appl Environ Microbiol. 76(14):4664-74. doi: 10.1128/AEM.00670-10, for *Aspergillus*, in Maruyama and Kitamoto (2011), Methods in Molecular Biology, vol. 765, DOI10.1007/978-1-61779-197-0_27; for *Neurospora*, in Collopy et al. (2010) Methods Mol Biol. 2010; 638:33-40. doi: 10.1007/978-1-60761-611-5_3; and for *Myceliophthora* or *Chrysosporium* PCT/NL2010/000045 and PCT/EP98/06496.

Examples of suitable filamentous fungal cells include, without limitation, cells from an *Acremonium, Aspergillus, Fusarium, Humicola, Mucor, Myceliophthora, Neurospora, Penicillium, Scytalidium, Thielavia, Tolypocladium*, or *Trichoderma* strain. In certain embodiments, the filamentous fungal cell is from a *Trichoderma* sp., *Acremonium, Aspergillus, Aureobasidium, Cryptococcus, Chrysosporium, Chrysosporium lucknowense, Filibasidium, Fusarium, Gibberella, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia,* or *Tolypocladium* strain.

In some embodiments, the filamentous fungal cell is a *Trichoderma* cell or related species such as *Myceliophthora* or *Chrysosporium, Fusarium, Neurospora, Penicillium,* or *Aspergillus* cell.

*Aspergillus* fungal cells of the present disclosure may include, without limitation, *Aspergillus aculeatus, Aspergillus awamori, Aspergillus clavatus, Aspergillus flavus, Aspergillus foetidus, Aspergillus fumigatus, Aspergillus japonicus, Aspergillus nidulans, Aspergillus niger, Aspergillus oryzae,* or *Aspergillus terreus*.

*Neurospora* fungal cells of the present disclosure may include, without limitation, *Neurospora crassa*. *Myceliophthora* fungal cells of the present disclosure may include, without limitation, *Myceliophthora thermophila*.

In a preferred embodiment, the filamentous fungal cell is a *Trichoderma* fungal cell. *Trichoderma* fungal cells of the present disclosure may be derived from a wild-type *Trichoderma* strain or a mutant thereof. Examples of suitable *Trichoderma* fungal cells include, without limitation, *Trichoderma harzianum, Trichoderma koningii, Trichoderma longibrachiatum, Trichoderma reesei, Trichoderma atroviride, Trichoderma virens, Trichoderma viride*; and alternative sexual form thereof (i.e., *Hypocrea*).

In a more preferred embodiment, the filamentous fungal cell is a *Trichoderma reesei*, and for example, strains derived from ATCC 13631 (QM 6a), ATCC 24449 (radiation mutant 207 of QM 6a), ATCC 26921 (QM 9414; mutant of ATCC 24449), VTT-D-00775 (Selinheimo et al., FEBS J., 2006, 273: 4322-4335), Rut-C30 (ATCC 56765), RL-P37 (NRRL 15709) or *T. harzianum* isolate T3 (Wolffhechel, H., 1989).

Proteases with reduced activity

The invention described herein relates to filamentous fungal cells, such as *Trichoderma* fungal cells, that have reduced activity in at least one endogenous protease and comprises at least a polynucleotide encoding fucosyltransferase, for use in the production of glycoproteins with fucosylated N-glycans.

It has been found that reducing protease activity enables to increase substantially the production of heterologous mammalian glycoprotein. Indeed, such proteases found in filamentous fungal cells that express a heterologous polypeptide normally catalyze significant degradation of the expressed recombinant glycoprotein. Thus, by reducing the activity of proteases in filamentous fungal cells that express a heterologous glycoprotein, the stability of the expressed glycoprotein is increased, resulting in an increased level of production of the fucosylated glycoprotein, and in some circumstances, improved quality of the produced fucosylated glycoprotein (e.g., full-length instead of degraded).

Proteases include, without limitation, aspartic proteases, trypsin-like serine proteases, subtilisin proteases, glutamic proteases, and sedolisin proteases. Such proteases may be identified and isolated from filamentous fungal cells and tested to determine whether reduction in their activity affects the production of a recombinant polypeptide from the filamentous fungal cell. Methods for identifying and isolating proteases are well known in the art, and include, without limitation, affinity chromatography, zymogram assays, and gel electrophoresis. An identified protease may then be tested by deleting the gene encoding the identified protease from a filamentous fungal cell that expresses a recombinant polypeptide, such a heterologous or mammalian polypeptide, and determining whether the deletion results in a decrease in total protease activity of the cell, and an increase in the level of production of the expressed recombinant polypeptide. Methods for deleting genes, measuring total protease activity, and measuring levels of produced protein are well known in the art and include the methods described herein.

Aspartic Proteases

Aspartic proteases are enzymes that use an aspartate residue for hydrolysis of the peptide bonds in polypeptides and proteins. Typically, aspartic proteases contain two highly-conserved aspartate residues in their active site which are optimally active at acidic pH. Aspartic proteases from eukaryotic organisms such as *Trichoderma* fungi include pepsins, cathepsins, and renins. Such aspartic proteases have a two-domain structure, which is thought to arise from an ancestral gene duplication. Consistent with such a duplication event, the overall fold of each domain is similar, though the sequences of the two domains have begun to diverge. Each domain contributes one of the catalytic aspartate residues. The active site is in a cleft formed by the two domains of the aspartic proteases. Eukaryotic aspartic proteases further include conserved disulfide bridges, which can assist in identification of the polypeptides as being aspartic acid proteases.

Nine aspartic proteases have been identified in *Trichoderma reesei* fungal cells: pep1 (tre74156); pep2 (tre53961); pep3 (tre121133); pep4 (tre77579), pep5 (tre81004), and pep7 (tre58669), pep8 (EGR48424), pep11 (EGR49498) and pep12 (EGR52517).

Examples of suitable aspartic proteases include, without limitation, *Trichoderma reesei* pep1 (SEQ ID NO: 17), *Trichoderma reesei* pep2 (SEQ ID NO: 18), *Trichoderma reesei* pep3 (SEQ ID NO: 19); pep4 (SEQ ID NO: 20), *Trichoderma reesei* pep5 (SEQ ID NO: 21), *Trichoderma reesei* pep7 (SEQ ID NO:23), *Trichoderma reesei* pep8 (SEQ ID NO:410), *Trichoderma reesei* pep11 (SEQ ID NO:411) and *Trichoderma reesei* pep12 (SEQ ID NO:412) and homologs thereof. Examples of homologs of pep1, pep2, pep3, pep4, pep5, pep7, pep8, pep11 or pep12 proteases identified in other organisms are also described in U.S. provisional application 61/583,559 or PCT/EP2013/050126, the content of which being incorporated by reference.

Trypsin-Like Serine Proteases

Trypsin-like serine proteases are enzymes with substrate specificity similar to that of trypsin. Trypsin-like serine proteases use a serine residue for hydrolysis of the peptide bonds in polypeptides and proteins. Typically, trypsin-like serine proteases cleave peptide bonds following a positively-charged amino acid residue. Trypsin-like serine proteases from eukaryotic organisms such as *Trichoderma* fungi include trypsin 1, trypsin 2, and mesotrypsin. Such trypsin-like serine proteases generally contain a catalytic triad of three amino acid residues (such as histidine, aspartate, and serine) that form a charge relay that serves to make the active site serine nucleophilic. Eukaryotic trypsin-like serine proteases further include an "oxyanion hole" formed by the backbone amide hydrogen atoms of glycine and serine, which can assist in identification of the polypeptides as being trypsin-like serine proteases.

One trypsin-like serine protease has been identified in *Trichoderma* fungal cells: tsp1 (tre73897). As discussed below, tsp1 has been demonstrated to have a significant impact on expression of recombinant glycoproteins, such as immunoglobulins.

Examples of suitable tsp1 proteases include, without limitation, *Trichoderma reesei* tsp1 (SEQ ID NO: 24) and homologs thereof. Examples of homologs of tsp1 proteases identified in other organisms are described in U.S. provisional application 61/583,559 or PCT/EP2013/050126.

Subtilisin Proteases

Subtilisin proteases are enzymes with substrate specificity similar to that of subtilisin. Subtilisin proteases use a serine residue for hydrolysis of the peptide bonds in polypeptides and proteins. Generally, subtilisin proteases are serine proteases that contain a catalytic triad of the three amino acids aspartate, histidine, and serine. The arrangement of these catalytic residues is shared with the prototypical subtilisin from *Bacillus licheniformis*. Subtilisin proteases from eukaryotic organisms such as *Trichoderma* fungi include furin, MBTPS1, and TPP2. Eukaryotic trypsin-like serine proteases further include an aspartic acid residue in the oxyanion hole.

Seven subtilisin proteases have been identified in *Trichoderma* fungal cells: slp1 (tre51365); slp2 (tre123244); slp3 (tre123234); slp5 (tre64719), slp6 (tre121495), slp7 (tre123865), and slp8 (tre58698).

Examples of suitable slp proteases include, without limitation, *Trichoderma reesei* slp1 (SEQ ID NO: 25), slp2 (SEQ ID NO: 26); slp3 (SEQ ID NO: 27); slp5 (SEQ ID NO: 28), slp6 (SEQ ID NO: 29), slp7 (SEQ ID NO: 30), and slp8 (SEQ ID NO: 31), and homologs thereof. Examples of homologs of slp proteases identified in other organisms are described in U.S. provisional application 61/583,559 or PCT/EP2013/050126.

Glutamic Proteases

Glutamic proteases are enzymes that hydrolyze the peptide bonds in polypeptides and proteins. Glutamic proteases are insensitive to pepstatin A, and so are sometimes referred to as pepstatin insensitive acid proteases. While glutamic proteases were previously grouped with the aspartic proteases and often jointly referred to as acid proteases, it has been recently found that glutamic proteases have very different active site residues than aspartic proteases.

Two glutamic proteases have been identified in *Trichoderma* fungal cells: gap1 (tre69555) and gap2 (tre106661).

Examples of suitable gap proteases include, without limitation, *Trichoderma reesei* gap1 (SEQ ID NO: 32), *Trichoderma reesei* gap2 (SEQ ID NO: 33), and homologs thereof. Examples of homologs of gap proteases identified in other organisms are described in U.S. provisional application 61/583,559 or PCT/EP2013/050126.

Sedolisin Proteases and homologs of proteases

Sedolisin proteases are enzymes that use a serine residue for hydrolysis of the peptide bonds in polypeptides and proteins. Sedolisin proteases generally contain a unique catalytic triad of serine, glutamate, and aspartate. Sedolisin proteases also contain an aspartate residue in the oxyanion hole. Sedolisin proteases from eukaryotic organisms such as *Trichoderma* fungi include tripeptidyl peptidase.

Examples of suitable tpp1 proteases include, without limitation, *Trichoderma reesei* tpp1 (SEQ ID NO: 34) and homologs thereof. Examples of homologs of tpp1 proteases identified in other organisms are described in U.S. provisional application 61/583,559 or PCT/EP2013/050126.

As used in reference to protease, the term "homolog" refers to a protein which has protease activity and exhibit sequence similarity with a known (reference) protease sequence. Homologs may be identified by any method known in the art, preferably, by using the BLAST tool to compare a reference sequence to a single second sequence or fragment of a sequence or to a database of sequences. As described in the "Definitions" section, BLAST will compare sequences based upon percent identity and similarity.

Preferably, a homologous protease has at least 30% identity with (optionally 30%, 40%, 45%, 50%, 55%, 60%, 65%, 70%, 75%, 80%, 85%, 90%, 95%, 99% or 100% identity over a specified region, or, when not specified, over the entire sequence), when compared to one of the protease sequences listed above, including *T. reesei* pep1, pep2, pep3, pep4, pep5, pep7, pep8, pep 11, pep 12, tsp1, slp1, slp2, slp3, slp5, slp6, slp7, slp8, tpp1, gap1 and gap2.

Reducing the Activity of Proteases in the filamentous fungal cell of the invention The filamentous fungal cells according to the invention have reduced activity of at least one endogenous protease, typically 2, 3, 4, 5 or more, in order to improve the stability and production of the glycoprotein with fucosylated N-glycans in said filamentous fungal cell.

The activity of proteases found in filamentous fungal cells can be reduced by any method known to those of skill in the art. In some embodiments reduced activity of proteases is achieved by reducing the expression of the protease, for example, by promoter modification or RNAi.

In other embodiments, reduced activity of proteases is achieved by modifying the gene encoding the protease. Examples of such modifications include, without limitation, a mutation, such as a deletion or disruption of the gene encoding said endogenous protease activity.

Accordingly, the invention relates to a filamentous fungal cell, such as a *Trichoderma* cell, which has a mutation that reduces at least one endogenous protease activity compared to a parental filamentous fungal cell which does not have such mutation, said filamentous fungal cell further comprising a polynucleotide encoding fucosyltransferase activity.

Deletion or disruption mutation includes without limitation knock-out mutation, a truncation mutation, a point mutation, a missense mutation, a substitution mutation, a frameshift mutation, an insertion mutation, a duplication mutation, an amplification mutation, a translocation mutation, or an inversion mutation, and that results in a reduction in the corresponding protease activity. Methods of generating at least one mutation in a protease encoding gene of interest are well known in the art and include, without limitation, random mutagenesis and screening, site-directed mutagenesis, PCR mutagenesis, insertional mutagenesis, chemical mutagenesis, and irradiation.

In certain embodiments, a portion of the protease encoding gene is modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, without limitation, a leader sequence, a propeptide sequence, a signal sequence, a transcription terminator, and a transcriptional activator.

Protease encoding genes that are present in filamentous fungal cells may also be modified by utilizing gene deletion techniques to eliminate or reduce expression of the gene. Gene deletion techniques enable the partial or complete removal of the gene thereby eliminating their expression. In such methods, deletion of the gene may be accomplished by homologous recombination using a plasmid that has been constructed to contiguously contain the 5' and 3' regions flanking the gene.

The protease encoding genes that are present in filamentous fungal cells may also be modified by introducing, substituting, and/or removing one or more nucleotides in the gene, or a control sequence thereof required for the transcription or translation of the gene. For example, nucleotides may be inserted or removed for the introduction of a stop codon, the removal of the start codon, or a frame-shift of the open reading frame. Such a modification may be accomplished by methods known in the art, including without limitation, site-directed mutagenesis and peR generated mutagenesis (see, for example, Botstein and Shortie, 1985, Science 229: 4719; Lo et al., 1985, Proceedings of the National Academy of Sciences USA 81: 2285; Higuchi et al., 1988, Nucleic Acids Research 16: 7351; Shimada, 1996, Meth. Mol. Bioi. 57: 157; Ho et al., 1989, Gene 77: 61; Horton et al., 1989, Gene 77: 61; and Sarkar and Sommer, 1990, BioTechniques 8: 404).

Additionally, protease encoding genes that are present in filamentous fungal cells may be modified by gene disruption techniques by inserting into the gene a disruptive nucleic acid construct containing a nucleic acid fragment homologous to the gene that will create a duplication of the region of homology and incorporate construct nucleic acid between the duplicated regions. Such a gene disruption can eliminate gene expression if the inserted construct separates the promoter of the gene from the coding region or interrupts the coding sequence such that a nonfunctional gene product results. A disrupting construct may be simply a selectable marker gene accompanied by 5' and 3' regions homologous to the gene. The selectable marker enables identification of transformants containing the disrupted gene.

The disruptive nucleic acid construct may comprise one or more polynucleotides encoding fucosylation pathway proteins, a polynucleotide encoding GMD activity, a polynucleotide encoding FX activity, a polynucleotide encoding GDP-fucose transporter, and a polynuceotide encoding $\alpha 1,6$ fucosyltransferase activity. Further, the disruptive nucleic acid construct may comprise one or more polynucleotides encoding an $\alpha$-1,2 mannosidase, an N-acetylglucosaminyltransferase I catalytic domain, an $\alpha$ mannosidase II, an N-acetylglucosaminyltransferase II catalytic domain, a $\beta 1,4$ galactosyltransferase, a glucosamine UDP-N-acetylglucosamine-2-epimerase/N-acetylmannosamine kinase, an N-acetylneuraminic acid synthase, an N-acetylneuraminic acid phosphatase, a cytidine monophosphate N-acetylneuraminic acid synthetase, a CMP-sialic acid transporter, and/or a sialyltransferase.

Protease encoding genes that are present in filamentous fungal cells may also be modified by the process of gene conversion (see, for example, Iglesias and Trautner, 1983, Molecular General Genetics 189:5 73-76). For example, in the gene conversion a nucleotide sequence corresponding to the gene is mutagenized in vitro to produce a defective nucleotide sequence, which is then transformed into a Trichoderma strain to produce a defective gene. By homologous recombination, the defective nucleotide sequence replaces the endogenous gene. It may be desirable that the defective nucleotide sequence also contains a marker for selection of transformants containing the defective gene.

Protease encoding genes of the present disclosure that are present in filamentous fungal cells that express a recombinant polypeptide may also be modified by established anti-sense techniques using a nucleotide sequence complementary to the nucleotide sequence of the gene (see, for example, Parish and Stoker, 1997, FEMS Microbiology Letters 154: 151-157). In particular, expression of the gene by filamentous fungal cells may be reduced or inactivated by introducing a nucleotide sequence complementary to the nucleotide sequence of the gene, which may be transcribed in the strain and is capable of hybridizing to the mRNA produced in the cells. Under conditions allowing the complementary anti-sense nucleotide sequence to hybridize to the mRNA, the amount of protein translated is thus reduced or eliminated.

Protease encoding genes that are present in filamentous fungal cells may also be modified by random or specific mutagenesis using methods well known in the art, including without limitation, chemical mutagenesis (see, for example, Hopwood, The Isolation of Mutants in Methods in Microbiology (J. R. Norris and D. W. Ribbons, eds.) pp. 363-433, Academic Press, New York, 25 1970). Modification of the gene may be performed by subjecting filamentous fungal cells to mutagenesis and screening for mutant cells in which expression of the gene has been reduced or inactivated. The mutagenesis, which may be specific or random, may be performed, for example, by use of a suitable physical or chemical mutagenizing agent, use of a suitable oligonucleotide, subjecting the DNA sequence to peR generated mutagenesis, or any combination thereof. Examples of physical and chemical mutagenizing agents include, without limitation, ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the Trichoderma cells to be mutagenized in the presence of the mutagenizing agent of choice under suitable conditions, and then selecting for mutants exhibiting reduced or no expression of the gene.

In certain embodiments, the at least one mutation or modification in a protease encoding gene of the present disclosure results in a modified protease that has no detectable protease activity. In other embodiments, the at least one modification in a protease encoding gene of the present disclosure results in a modified protease that has at least 25% less, at least 50% less, at least 75% less, at least 90%, at least 95%, or a higher percentage less protease activity compared to a corresponding non-modified protease.

In a preferred embodiment, a filamentous fungal cell according to the invention is a Trichoderma cell which has a deletion or disruption in at least 3 endogenous proteases, resulting in no detectable activity for such deleted or disrupted endogenous proteases and further comprising at least one or more polynucleotides encoding fucosylation pathway. In one embodiment, that may be combined with the preceding embodiments, said cell may comprise mutations that reduce or eliminate the activity of
a) the three endogenous proteases pep1, tsp1 and slp1,
b) the three endogenous proteases gap1, slp1 and pep1,
c) three endogenous proteases selected from the group consisting of pep1, pep2, pep3, pep4, pep5, pep8, pep11, pep12, tsp1, slp1, slp2, slp3, slp7, gap1 and gap2,
d) three to six proteases selected from the group consisting of pep1, pep2, pep3, pep4, pep5, tsp1, slp1, slp2, slp3, gap1 and gap2, or
e) seven to ten proteases selected from the group consisting of pep1, pep2, pep3, pep4, pep5, pep7, pep8, tsp1, slp1, slp2, slp3, slp5, slp6, slp7, slp8, tpp1, gap1 and gap2.

In certain embodiments, the filamentous fungal cell or Trichoderma cell, has reduced or no detectable protease activity in pep1, tsp1, and slp1. Advantageously, in such triple deletion mutant, the protease activity may be reduced by more than 3 fold. In certain embodiments, the filamentous fungal cell or Trichoderma cell, has reduced or no detectable protease activity in gap1, slp1, and pep1. In certain embodiments, the filamentous fungal cell or Trichoderma cell, has reduced or no detectable protease activity in slp2, pep1 and gap1. In certain embodiments, the filamentous fungal cell or Trichoderma cell, has reduced or no detectable protease activity in pep1, tsp1, slp1, and gap1. Advantageously, in such quadruple deletion mutant, the protease activity may be reduced by more than 7 fold. In certain embodiments, the filamentous fungal cell or Trichoderma cell, has reduced or no detectable protease activity in pep1, tsp1, slp1, gap1, and gap2. Advantageously, in such 5-fold deletion mutant, the protease activity may be reduced by more than 10 fold. In certain embodiments, the filamentous fungal cell or Trichoderma cell, has reduced or no detectable protease activity in pep1, tsp1, slp1, gap1, gap2, and pep4. Advantageously, in such 6-fold deletion mutant, the protease activity may be reduced by more than 15 fold. In certain embodiments, the filamentous fungal cell or Trichoderma cell, has reduced or no detectable protease activity in pep1, tsp1, slp1, gap1, gap2, pep4, and pep3. Advantageously, in such 7-fold deletion mutant, the protease activity may be reduced by more than 18 fold. In certain embodiments, the filamentous fungal cell or Trichoderma cell, has reduced or no detectable protease activity in pep1, tsp1, slp1, gap1, gap2, pep4, pep3, and pep5. In certain embodiments, the filamentous fungal cell or Trichoderma cell, has reduced or no detectable protease activity in pep1, tsp1, slp1, gap1, gap2, pep4, pep3, pep5, and pep2. In certain embodiments, the filamentous fungal cell or Trichoderma cell, has reduced or no detectable protease activity in pep1, tsp1, slp1, gap1, gap2, pep4, pep3, pep5, pep2, and pep11. In certain embodiments, the filamentous fungal cell or Trichoderma cell, has reduced or no detectable protease activity in pep1, tsp1, slp1, gap1, gap2, pep4, pep3, and slp2. In certain embodiments, the filamentous fungal cell or Trichoderma cell, has reduced or no detectable protease activity in pep1, tsp1, slp1, gap1, gap2, pep4, pep3, pep5, and pep12.

Polynucleotides encoding fucosylation pathway

Genes and proteins involved in the fucosylation pathways of prokaryotes and eukaryotes have been identified and characterized in the art (see for a review, Ma et al, 2006, Glycobiology, 16(12) 158-144).

As used herein the term "fucosylation pathway" relates to the sequential enzymatic steps required for in vivo fucosylation of a glycoprotein. There is no fucosylation pathway in filamentous fungal cells, such as Trichoderma cells. One of the major goals of the present invention is to provide tools and materials for the production of glycoproteins with fucosylated N-glycans, for example of fucosylated G0 glycoform, in a filamentous fungal cell.

In vivo fucosylation requires at least expression of one enzyme of the fucosyltransferase family. Accordingly, a filamentous fungal cell with reduced protease activity according to the invention comprises at least one polynucleotide encoding fucosyltransferase activity.

If GDP-fucose is not provided in the medium or naturally synthesized in the filamentous fungal cell, the filamentous fungal cell according to the invention may advantageously contain one or more polynucleotides encoding GDP-fucose synthesis and, optionally, GDP-fucose transporter.

Depending on the structure of the fucosylated N-glycan that is desired to be produced by the filamentous fungal cell according to the invention, the skilled person will select the appropriate sequences encoding polypeptides with fucosyltransferase activity.

Various fucosyltransferase enzymes and their coding sequences have been identified in the art. Fucosyltransferase (FucTs) are indeed widely expressed in vertebrates such as mammalian and human cells, invertebrates, plants and bacteria. FucT belong to the glycosyltransferase superfamily (EC 2.4.1.x.y) which is defined in the category of Carbohydrate-Active enzymes (CAZY) available on the internet.

More specifically, as use herein, the term "fucosyltransferase" or "FucTs" refers to the enzyme catalysing the reaction that transfers the donor guanosine-diphosphate fucose (GDP-Fuc) to an acceptor glycoprotein.

FucTs thus include enzymes with $\alpha 1,2$ fucosyltransferase activity (encoded for example by human FUT1 and FUT2 genes), $\alpha 1,3/\alpha 1,4$ fucosyltransferase activity (encoded for example by human FUT9 and FUT5 genes), O-FucTs (encoded for example by plant O-FUT1 and 2) and $\alpha 1,6$ fucosyltransferase activity (encoded for example by human FUT8 gene), which is further described in detail below.

In a preferred embodiment, the filamentous fungal cell according to the invention comprises a polynucleotide encoding a polypeptide having $\alpha 1,6$ fucosyltransferase activity. $\alpha 1,6$ FucT adds fucose to the innermost GlcNAc moiety of the chitobiose unit of the core Asn-linked glycans at an $\alpha 1,6$ linkage. In mammals, $\alpha 1,6$ fucosyltransferase acting at late Golgi cisternae requires an unsubstituted $\beta 1,2$ linked GlcNAc on the $\alpha 1,3$ mannose arm of the core N-glycan. $\alpha 1,6$ fucosyltransferase activity is useful in particular in methods for producing fucosylated complex N-glycans such as the FG0, FG1 or FG2 glycoforms.

Human $\alpha 1,6$ FucT encoded by FUT8 gene is widely expressed in human tissues. Polynucleotide sequences encoding $\alpha 1,6$ FucT that may be used in the present invention includes without limitation the human FUT8 coding sequence of SEQ ID NO:1, FUT8 isoforms or other homologous FUT8 coding sequences from mammalian species, including without limitation any one of SEQ ID NOs 142-149.

In one embodiment, said filamentous fungal cell of the invention comprises a polynucleotide of human FUT8 coding sequence (SEQ ID NO:1), or a functional variant polynucleotide encoding a polypeptide having at least 50%, at least 60%, at least 70%, at least 90%, or at least 95% identity with SEQ ID N0:6, said functional variant encoding $\alpha 1,6$ fucosyltransferase activity.

Expression of $\alpha 1,6$ fucosyltransferase activity in a filamentous fungal cell of the invention may be determined by structural analysis of N-glycans produced by such filamentous fungal cell, as described in the Examples below.

The substrate of fucosyltransferase is GDP-fucose. In order to obtain in vivo fucosylation, it is therefore advantageous to provide filamentous fungal cells which further comprise enzymes required for GDP-fucose synthesis and its transport into the ER/Golgi compartment where fucosyltransferase reaction occurs. Accordingly, the filamentous fungal cell may advantageously further comprise one or more polynucleotides encoding GDP-fucose synthesis and, optionally, GDP-fucose transporter.

In eukaryote, GDP-fucose synthesis can be synthesized either by the de novo pathway or the minor salvage pathway. The de novo pathway starts from GDP-D-mannose which is dehydrated by GDP-mannose-4,6 dehydratase (hereafter referred as "GMD"). This leads to the formation of an unstable GDP-4-keto-6-deoxy-D-mannose, which undergoes a subsequent 3,5 epimerization and then a NADPH-dependent reduction with the consequent formation of GDP-L-fucose. These two last steps are catalysed by GDP-4-keto-6-deoxy-D-mannose-3,5-epimerase/4-reductase (hereafter referred as "FX").

Accordingly, in a specific embodiment, the filamentous fungal cell of the invention, for example Trichoderma cell further comprises one or more polynucleotides encoding a polypeptide having GDP-fucose synthesis activity, selected from the group consisting of:
i. GMD polynucleotide or a functional variant polynucleotide encoding a polypeptide having GDP-mannose-dehydratase activity; and,
ii. FX polynucleotide or a functional variant polynucleotide encoding a polypeptide having both GDP-keto-deoxy-mannose-epimerase and GDP-keto-deoxy-galactose-reductase activities.

GMD encoding polynucleotide sequences have been described in the art and include without limitation *C. elegans* GMD optimized polynucleotide of SEQ ID NO:2, *H. pylori* GMD optimized polynucleotide of SEQ ID NO:16, or polynucleotides encoding homologous eukaryotic proteins of any one of SEQ ID NOs:124-138 or polynucleotides encoding homologous prokaryotic proteins of any one of SEQ ID NOs: 139-141, or their functional variant polynucleotide encoding polypeptides having at least 50%, at least 60%, at least 70%, at least 90%, or at least 95% identity with said any one of SEQ ID NO:7, SEQ ID NO:15 or SEQ ID NOs: 124-141, and having GDP-mannose-dehydratase activity (see also Mattila et al., 2000, Glycobiology 10(10) pp 1041-1047 and Järvinen et al, 2001, Eur J Biochem 268, 6458-6464).

FX encoding polynucleotide sequences have also been described in the art and include without limitation *C. elegans* FX polynucleotide of SEQ ID NO: 3, *H. pylori* FX polynucleotide of SEQ ID NO: 14 or a homologous FX polynucleotide encoding any one of SEQ ID NOs 112-123, or their functional variant polynucleotide encoding a polypeptide having at least 50%, at least 60%, at least 70%, at least 90%, or at least 95% identity with any one of said polynucleotide sequences of SEQ ID NO:8, SEQ ID NO:13 or SEQ ID NOs: 112-123 and having both GDP-keto-deoxy-mannose-epimerase and GDP-keto-deoxy-galactose-reductase activities (see also Mattila et al., 2000, Glycobiology 10(10) pp 1041-1047 and Järvinen et al, 2001, Eur J Biochem 268, 6458-6464).

In one specific embodiment, the filamentous fungal cell of the invention, such as a *Trichoderma* cell, further comprises said one or more polynucleotides encoding polypeptides with GDP-fucose synthesis activity comprising
i. *C. elegans* GMD polynucleotide of SEQ ID NO:2 or a functional variant polynucleotide encoding a polypeptide having at least 50%, at least 60%, at least 70%, at least 90%, or at least 95% identity with SEQ ID NO:7 and having GDP-mannose-dehydratase activity; and,
ii. *C. elegans* FX polynucleotide of SEQ ID NO:3 or a functional variant polynucleotide encoding a polypeptide having at least 50%, at least 60%, at least 70%, at least 90%, or at least 95% identity with SEQ ID NO:8 and having both GDP-keto-deoxy-mannose-epimerase and GDP-keto-deoxy-galactose-reductase activities.

GDP-fucose synthesis may be detected in vivo for example by purification and MALDI-TOF MS analysis of GDP-L-fucose as described in Mattila et al 2000, supra.

GDP-fucose synthesis takes place in the cytosol whereas fucosyltransferase activity occurs in vivo in the Golgi compartment. Therefore, it may be advantageous to further introduce into the filamentous fungal cell of the invention a polynucleotide encoding GDP fucose transporter (hereafter referred as "GFTr").

GDP fucose transporter encoding genes have been cloned and characterized from various organisms. GDP fucose transporter encoding polynucleotide includes without limitation *C. elegans* GDP fucose transporter polynucleotide of SEQ ID NO: 4, a homologous FX polynucleotide encoding any one of SEQ ID NOs: 150-162, or their functional variant polynucleotide encoding a polypeptide at least 50%, at least 60%, at least 70%, at least 90%, or at least 95% identity with any one of SEQ ID NO:9, or SEQ ID NOs: 150-162 and having GDP fucose transporter.

In one specific embodiment, the filamentous fungal cell of the invention, such as a *Trichoderma* cell, further comprises a GDP-fucose transporter *C. elegans* GFTr polynucleotide of SEQ ID NO:4 or a functional variant polynucleotide encoding a polypeptide having at least 50%, at least 60%, at least 70%, at least 90%, or at least 95% identity with SEQ ID NO:9 and having GDP fucose transporter.

To increase Golgi targeting of fucosyltransferase, it may be required to include Golgi targeting sequence in the polynucleotide encoding fucosyltransferase activity that is introduced in the filamentous fungal cell according to the invention.

Accordingly, the filamentous fungal cell of the invention comprises a polynucleotide encoding fucosyltransferase linked to a Golgi targeting sequence for targeting expression of said fucosyltransferase activity in the Golgi compartment.

In specific embodiments, the filamentous fungal cell of the invention further comprises a polynucleotide encoding GnTI, GnTII, GalT, or sialyltransferase linked to a Golgi targeting sequence for targeting expression of said GnTI, GnTII, GalT, or sialyltransferase activity in the Golgi compartment.

To increase Golgi targeting of GnTI, GnTII, GalT, or sialyltransferase, the Golgi targeting sequence can be linked to the polynucleotide encoding GnTI, GnTII, GalT, or sialyltransferase activity that is introduced in the filamentous fungal cell of the invention, such that the targeting sequence and the GnTI, GnTII, GalT, or sialyltransferase is expressed as a single polypeptide.

Examples of Golgi targeting polynucleotide sequences that may be used for targeting fucosyltransferase, GnTI, GnTII, GalT, or sialyltransferase in the Golgi compartment are described in PCT/EP2011/070956 and include without limitation, N-terminal portion of SEQ ID NO: 5. Other targeting sequences that may be used are described more in details in the next section.

In a specific embodiment, a filamentous fungal cell according to the invention, such as *Trichoderma* cell, further comprises a polynucleotide encoding the N-terminal portion of Golgi targeting sequence of SEQ ID NO:10, or a functional variant polynucleotide having at least 50%, at least 60%, at least 70%, at least 90%, or at least 95% identity with SEQ ID NO:5 linked to the polynucleotide sequence encoding fucosyltransferase activity, such as SEQ ID NO:1. In such embodiment, a preferred filamentous fungal cell is a *Trichoderma reesei* cell.

In a specific embodiment, a filamentous fungal cell of the invention, preferably a *Trichoderma* cell, and more preferably a *Trichoderma reesei* cell, may advantageously comprise the following features:
a) a mutation in at least one endogenous protease that reduces the activity of said endogenous protease, preferably the protease activity of two or three or more endogenous proteases is reduced, in order to improve production or stability of the glycoprotein with fucosylated N-glycans to be produced,
b) a polynucleotide encoding a glycoprotein, preferably a heterologous glycoprotein, such as an immunoglobulin, an antibody, or a protein fusion comprising Fc fragment of an immunoglobulin.

c) a polynucleotide encoding GMD and FX activities for GDP-fucose synthesis,
d) a polynucleotide encoding GDP-fucose transporter, for transporting GDP-fucose transporter in the Golgi compartment where fucosyltansferase activity occurs in vivo,
e) a polynuceotide encoding α1,6 fucosyltransferase activity linked with a Golgi targeting sequence for targeting said α1,6 fucosylytransferase activity to the Golgi compartment.

Targeting Sequences

In certain embodiments, recombinant enzymes, such as α1,6 fucosyltransferase, or other glycosyltransferases introduced into the filamentous fungal cells, include a targeting peptide linked to the catalytic domains. The term "linked" as used herein means that two polymers of amino acid residues in the case of a polypeptide or two polymers of nucleotides in the case of a polynucleotide are either coupled directly adjacent to each other or are within the same polypeptide or polynucleotide but are separated by intervening amino acid residues or nucleotides. A "targeting peptide", as used herein, refers to any number of consecutive amino acid residues of the recombinant protein that are capable of localizing the recombinant protein to the endoplasmic reticulum (ER) or Golgi apparatus (Golgi) within the host cell. The targeting peptide may be N-terminal or C-terminal to the catalytic domains. In certain embodiments, the targeting peptide is N-terminal to the catalytic domains. In certain embodiments, the targeting peptide provides binding to an ER or Golgi component, such as to a mannosidase II enzyme. In other embodiments, the targeting peptide provides direct binding to the ER or Golgi membrane.

Components of the targeting peptide may come from any enzyme that normally resides in the ER or Golgi apparatus. Such enzymes include mannosidases, mannosyltransferases, glycosyltransferases, Type 2 Golgi proteins, and MNN2, MNN4, MNN6, MNN9, MNN10, MNS1, KRE2, VAN1, and OCH1 enzymes. Such enzymes may come from a yeast or fungal species such as those of *Acremonium, Aspergillus, Aureobasidium, Cryptococcus, Chrysosporium, Chrysosporium lucknowense, Filobasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, and *Trichoderma*. Sequences for such enzymes can be found in the GenBank sequence database.

In certain embodiments the targeting peptide comes from the same enzyme and organism as one of the catalytic domains of the recombinant protein. For example, if the recombinant protein includes a human GnTII catalytic domain, the targeting peptide of the recombinant protein is from the human GnTII enzyme. In other embodiments, the targeting peptide may come from a different enzyme and/or organism as the catalytic domains of the recombinant protein.

Examples of various targeting peptides for use in targeting proteins to the ER or Golgi that may be used for targeting the recombinant enzymes, such as α1,6 fucosyltransferase or other glycosyltransferases, include: Kre2/Mnt1 N-terminal peptide fused to galactosyltransferase (Schwientek, JBC 1996, 3398), HDEL for localization of mannosidase to ER of yeast cells to produce Man5 (Chiba, JBC 1998, 26298-304; Callewaert, FEBS Lett 2001, 173-178), OCH1 targeting peptide fused to GnTI catalytic domain (Yoshida et al, Glycobiology 1999, 53-8), yeast N-terminal peptide of Mns1 fused to α2-mannosidase (Martinet et al, Biotech Lett 1998, 1171), N-terminal portion of Kre2 linked to catalytic domain of GnTI or β4GalT (Vervecken, Appl. Environ Microb 2004, 2639-46), various approaches reviewed in Wildt and Gerngross (Nature Rev Biotech 2005, 119), full-length GnTI in *Aspergillus nidulans* (Kalsner et al, Glycocon. J 1995, 360-370), full-length GnTI in *Aspergillus oryzae* (Kasajima et al, Biosci Biotech Biochem 2006, 2662-8), portion of yeast Sec12 localization structure fused to *C. elegans* GnTI in *Aspergillus* (Kainz et al 2008), N-terminal portion of yeast Mnn9 fused to human GnTI in *Aspergillus* (Kainz et al 2008), N-terminal portion of *Aspergillus* Mnn10 fused to human GnTI (Kainz et al, Appl. Environ Microb 2008, 1076-86), and full-length human GnTI in *T. reesei* (Maras et al, FEBS Lett 1999, 365-70).

In certain embodiments the targeting peptide is an N-terminal portion of the Mnt1 targeting peptide having the amino acid sequence of SEQ ID NO: 10 (for example encoded by the polynucleotide of SEQ ID NO:5).

Further examples of sequences that may be used for targeting peptides include the sequences listed in Table 1 below.

TABLE 1

Targeting peptides. Putative transmembrane domains are underlined. In KRE2/MNT1, the stem domain enabling Golgi localization is underlined and double-underlined. Other01 and Other02 are putative mannosylation-related proteins.

| Homologous to | Cytoplasmic | Transmembrane | Luminal |
|---|---|---|---|
| KRE2 | SEQ ID NO: 171 | SEQ ID NO: 172 | SEQ ID NO: 173 |
| KRE2 alternative1 | SEQ ID NO: 174 | SEQ ID NO: 175 | SEQ ID NO: 176 |
| OCH1 | SEQ ID NO: 177 | SEQ ID NO: 178 | SEQ ID NO: 179 |
| OCH1 alternative1 | SEQ ID NO: 180 | SEQ ID NO: 181 | SEQ ID NO: 182 |
| MNN9 | SEQ ID NO: 183 | SEQ ID NO: 184 | SEQ ID NO: 185 |
| MNN9 alternative1 | SEQ ID NO: 186 | SEQ ID NO: 187 | SEQ ID NO: 188 |
| MNN9 alternative2 | SEQ ID NO: 189 | SEQ ID NO: 190 | SEQ ID NO: 191 |
| MNN10 | SEQ ID NO: 192 | SEQ ID NO: 193 | SEQ ID NO: 194 |
| MNN10 alternative1 | SEQ ID NO: 195 | SEQ ID NO: 196 | SEQ ID NO: 197 |
| MNS1 | SEQ ID NO: 198 | SEQ ID NO: 199 | SEQ ID NO: 200 |
| MNS1 alternative1 | SEQ ID NO: 201 | SEQ ID NO: 202 | SEQ ID NO: 203 |
| MNS1 alternative2 | SEQ ID NO: 204 | SEQ ID NO: 205 | SEQ ID NO: 206 |
| MNS1 alternative3 | SEQ ID NO: 207 | SEQ ID NO: 208 | SEQ ID NO: 209 |
| MNS1 alternative4 | — | SEQ ID NO: 210 | SEQ ID NO: 211 |
| VAN1 | SEQ ID NO: 212 | SEQ ID NO: 213 | SEQ ID NO: 214 |
| VAN1 alternative1 | SEQ ID NO: 215 | SEQ ID NO: 216 | SEQ ID NO: 217 |
| VAN1 alternative2 | SEQ ID NO: 218 | SEQ ID NO: 219 | SEQ ID NO: 220 |
| Other01 | SEQ ID NO: 221 | SEQ ID NO: 222 | SEQ ID NO: 223 |
| Other02 | SEQ ID NO: 224 | SEQ ID NO: 225 | SEQ ID NO: 226 |

Uncharacterized sequences may be tested for use as targeting peptides by expressing enzymes of the glycosylation pathway in a host cell, where one of the enzymes contains the uncharacterized sequence as the sole targeting peptide, and measuring the glycans produced in view of the cytoplasmic localization of glycan biosynthesis (e.g. as in Schwientek JBC 1996 3398), or by expressing a fluorescent reporter protein fused with the targeting peptide, and analyzing the localization of the protein in the Golgi by immunofluorescence or by fractionating the cytoplasmic membranes of the Golgi and measuring the location of the protein.

Filamentous fungal cell for producing glycoproteins with complex fucosylated N-glycans The filamentous fungal cells according to the present invention may be useful in particular for producing glycoproteins with mammalian-like fucosylated N-glycan, such as complex fucosylated N-glycans.

Accordingly, in one aspect, the filamentous fungal cell is genetically modified to produce a complex N-glycan as an acceptor substrate for the fucosyltransferase activity, thereby enabling in vivo production of glycoprotein with complex fucosylated N-glycans. In certain embodiments, this aspect includes methods of producing glycoproteins with human-like fucosylated N-glycans in a *Trichoderma* cell or related species such as *Neurospora, Myceliophtora, Fusarium, Aspergillus, Penicillium* and *Chrysosporium* species.

In certain embodiment, the complex fucosylated N-glycan includes any glycan having the formula [GlcNAcβ2]$_z$Manα3([GlcNAcβ2]$_w$Manα6)Man{β4GlcNAcβ[(Fucαx)4GlcNAc]}, where x is 3 or 6, where ( ) defines a branch in the structure, where [ ] or { } define a part of the glycan structure either present or absent in a linear sequence, and where z and w are 0 or 1. Preferably w and z are 1.

In certain embodiments, the complex fucosylated N-glycan includes GlcNAcβ2Manα3(GlcNAcβ2Manα6)Manβ4GlcNAcβ4(Fucα6)GlcNAc, GlcNAcβ2Manα3(Manα6)Manβ4GlcNAcβ4(Fucα6)GlcNAc, and Manα3(Manα6)Manβ4GlcNAcβ4(Fucα6)GlcNAc.

In certain embodiments, the filamentous fungal cell generates a mixture of different N-glycans. The secreted complex fucosylated neutral N-glycans may constitute at least 1%, at least 3%, at least 5%, at least 10%, at least 15%, at least 20%, at least 25%, at least 50%, or at least 75% or more of total secreted (mol %) neutral N-glycans of the filamentous fungal cells. In certain embodiment, the filamentous fungal cell generates core fucosylated FG0 N-glycan structure GlcNAcβ2Manα3[GlcNAcβ2Manα6]Manβ4GlcNAcβ4(Fucα6)GlcNAc. In specific embodiments, the filamentous fungal cell generates the trimannosyl N-glycan structure Manα3[Manα6]Manβ4GlcNAcβ4GlcNAc. In certain embodiments, total secreted N-glycans comprises less than 60%, 50%, 40%, 30%, or less than 20% of the non-fucosylated Manα3[Manα6]Manβ4GlcNAcβ4GlcNAc structure.

In other embodiments, the filamentous fungal cell generates the G0 N-glycan structure GlcNAcβ2Manα3[GlcNAcβ2Manα6]Manβ4GlcNAcβ4GlcNAc.

In certain embodiments, total secreted N-glycans comprises less than 60%, 50%, 40%, 30%, or less than 20% of the non-fucosylated G0 glycans. In other embodiments, less than 0.5%, 0.1%, 0.05%, or less than 0.01% of the N-glycan comprises galactose. In certain embodiments, none of the secreted N-glycans comprise galactose.

In certain embodiments, the glycoprotein comprises the complex fucosylated N-glycan, as a major fucosylated glycoform, GlcNAcβ2Manα3(GlcNAcβ2Manα6)Manβ4GlcNAcβ4(Fucα6)GlcNAc. In an embodiment the glycoform is the major glycoform of the neutral complex type glycoforms.

In certain embodiments, the glycoprotein comprises the complex fucosylated N-glycan, as a major fucosylated glycoform, Galβ4GlcNAcβ2Manα3(Galβ4GlcNAcβ2Manα6)Manβ4GlcNAcβ4(Fucα6)GlcNAc. In an embodiment the glycoform is the major glycoform of the neutral complex type glycoforms In certain embodiments, the glycoprotein comprises the complex fucosylated N-glycan, as a major fucosylated glycoform, GlcNAcβ2Manα3(Galβ4GlcNAcβ2Manα6)Manβ4GlcNAcβ4(Fucα6)GlcNAc or Galβ4GlcNAcβ2Manα3(GlcNAcβ2Manα6)Manβ4GlcNAcβ4(Fucα6)GlcNAc. In an embodiment the glycoform is the major glycoform of the neutral complex type glycoforms.

In certain embodiments, the glycoprotein comprises the complex fucosylated N-glycan, as a major fucosylated glycoform, GlcNAcβ2Manα3(Manα6)Manβ4GlcNAcβ4(Fucα6)GlcNAc. In an embodiment the glycoform is the major glycoform of the neutral complex type glycoforms.

In certain embodiments, the glycoprotein comprises the complex fucosylated N-glycan, as a major fucosylated glycoform, Manα3(Manα6)Manβ4GlcNAcβ4(Fucα6)GlcNAc.

In certain embodiments, the filamentous fungal cell of the invention produces glycoprotein composition with a mixture of different fucosylated N-glycans.

In some embodiments, GlcNAcβ2Manα3(GlcNAcβ2Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least at least 30%, at least 40%, at least 50%, at least 60%, at least 70%, at least 80%, at least 90% or more of total (mol %) neutral or complex type N-glycans of a heterologous glycoprotein, as expressed in a filamentous fungal cells of the invention.

In other embodiments, GlcNAcβ2Manα3(Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% or more of total (mol %) neutral or complex type N-glycans of a heterologous glycoprotein, as expressed in a filamentous fungal cells of the invention.

In other embodiments, Manα3(Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least at least 30%, at least 40%, at least 50%, at least 60%, at least 70%, at least 80%, at least 90% or more of total (mol %) neutral N-glycans of a heterologous glycoprotein, as expressed in a filamentous fungal cells of the invention.

In some embodiments, less than 0.5%, 0.1%, 0.05%, or less than 0.01% of the fucosylated N-glycan of the glycoprotein produced by the host cell of the invention, comprises galactose. In certain embodiments, none of fucosylated N-glycans comprise galactose.

The Neu5Gc and Galα-(non-reducing end terminal Galα3Galβ4GlcNAc) structures are known xenoantigenic (animal derived) modifications of heterologous proteins such as antibodies which are produced in animal cells such as CHO cells. The structures may be antigenic and, thus, harmful even at low concentrations. The filamentous fungi of the present invention lack biosynthetic pathways to produce the terminal Neu5Gc and Galα-structures. In an embodiment that may be combined with the preceding embodiments less than 0.1%, 0.01%, 0.001% or 0% of the fucosylated N-glycans of the glycoprotein comprises Neu5Gc and/or Galα-structure. In an embodiment that may be combined with the preceding embodiments, less than 0.1%, 0.01%, 0.001% or 0% of the fucosylated N-glycans of the antibody comprises Neu5Gc and/or Galα-structure.

The terminal Galβ4GlcNAc structure of N-glycan of mammalian cell produced glycans affects bioactivity of antibodies and Galβ3GlcNAc may be xenoantigenic structure. In an embodiment that may be combined with one or more of the preceding embodiments, less than 0.1%, 0.01%, 0.001%, or 0% of fucosylated N-glycan of the glycoprotein comprises terminal galactose epitopes Galβ3/4GlcNAc. In an embodiment that may be combined with one or more of the preceding embodiments, less than 0.1%, 0.01%, 0.001%, or 0% of the fucosylated N-glycan of the antibody comprises terminal galactose epitopes Galβ3/4GlcNAc.

Glycation is a common post-translational modification of proteins, resulting from the chemical reaction between reducing sugars such as glucose and the primary amino groups on protein. Glycation occurs typically in neutral or slightly alkaline pH in cell cultures conditions, for example, when producing antibodies in CHO cells and analysing them (see, for example, Zhang et al. (2008) Unveiling a glycation hot spot in a recombinant humanized monoclonal antibody. Anal Chem. 80(7):2379-2390). As filamentous fungi of the present invention are typically cultured in acidic pH, occurrence of glycation is reduced. In an embodiment that may be combined with the preceding embodiments, less than 1.0%, 0.5%, 0.1%, 0.01%, 0.001%, or 0% of the fucosylated glycoprotein comprises glycation structures. In an embodiment that may be combined with the preceding embodiments, less than 1.0%, 0.5%, 0.1%, 0.01%, 0.001%, or 0% of the antibody comprises glycation structures.

Fucosylated structures and their quantitation may also be determined as mole % of fucosylated (non-fucosylated) per total polypeptide as produced by the host cell of the invention. Analytical methods, such as MALDI TOF MS analysis may be used to determine fucosylation level are described in detail in the Examples below. In brief, a polypeptide as produced by a filamentous fungal cell is purified to determine its fucosylation level. Non-fucosylated and fucosylated structure of the polypeptide are separated and quantified by MALDI-TOF MS analysis. For example, the quantification of fucosylation level may be performed by determining area values or intensity of the different peaks of MALDI-TOF MS spectrum.

The complex fucosylated N-glycan is attached to a molecule such as an amino acid, a peptide, or a polypeptide. The asparagine residue is in aminoglycosidic linkage from the side-chain amide (a biologic mammalian polypeptide N-glycan linkage structure) and may be part of a peptide chain such as a dipeptide, an oligopeptide, or a polypeptide. The glycan may be a reducing end derivative such as an N-, O-, or C-linked, preferably glycosidic, derivative of the reducing GlcNAc or Man, such as a spacer or terminal organic residue with a certain glycan linked structure selected from the group of an amino acid, alkyl, heteroalkyl, acyl, alkyloxy, aryl, arylalkyl, and heteroarylalkyl. The spacer may be further linked to a polyvalent carrier or a solid phase. In certain embodiments, alkyl-containing structures include methyl, ethyl, propyl, and C4-C26 alkyls, lipids such as glycerolipids, phospholipids, dolichol-phospholipids and ceramides and derivatives. The reducing end may also be derivatized by reductive amination to a secondary amine linkage or a derivative structure. Certain carriers include biopoly- or oligomers such as (poly)peptides, poly(saccharides) such as dextran, cellulose, amylose, or glycosaminoglycans, and other organic polymers or oligomers such as plastics including polyethylene, polypropylene, polyamides (e.g., nylon or polystyrene), polyacrylamide, and polylactic acids, dendrimers such as PAMAM, Starburst or Starfish dendrimers, or polylysine, and polyalkylglycols such as polyethylene glycol (PEG). Solid phases may include microtiter wells, silica particles, glass, metal (including steel, gold and silver), polymer beads such as polystyrene or resin beads, polylactic acid beads, polysaccharide beads or organic spacers containing magnetic beads.

In certain embodiments, the complex fucosylated N-glycan is attached to a heterologous polypeptide. In certain embodiments, the heterologous polypeptide is a therapeutic protein. Therapeutic proteins may include immunoglubulin, or a protein fusion comprising a Fc fragment or other therapeutic glycoproteins, such as antibodies, erythropoietins, interferons, growth hormones, enzymes, or blood-clotting factors and may be useful in the treatment of humans or animals. For example, the glycoproteins with complex fucosylated N-glycan as produced by the filamentous fungal cell may be a therapeutic glycoprotein such as rituximab. In an embodiment, the heterologous protein or heterologous glycoprotein is selected from the group consisting of: an immunoglubulin, such as IgG, a light chain or heavy chain of an immunoglobulin, a heavy chain or a light chain of an antibody, a single chain antibody, a monomeric or multimeric single domain antibody, a FAb-fragment, a FAb2-fragment, and, their antigen-binding fragments.

Methods for generating complex N-glycans as acceptor substrate for fucosyltransferase are described for example in PCT/EP2011/070956 which content is incorporated by reference.

In one aspect, the filamentous fungal cell according to the invention as described above, is further genetically modified to mimick the traditional pathway of mammalian cells, starting from Man5 N-glycans as acceptor substrate for GnTI, and followed sequentially by GnT1, mannosidase II and GnTII reaction steps (hereafter referred as the "traditional pathway" for producing G0 glycoforms). In one variant, a single recombinant enzyme comprising the catalytic domains of GnTI and GnTII, is used.

Alternatively, in a second aspect, the filamentous fungal cell according to the invention as described above is further genetically modified to have alg3 reduced expression, allowing the production of core $Man_3GlcNAc_2$ N-glycans, as acceptor substrate for GnTI and GnTII subsequent reactions and bypassing the need for mannosidase α1,2 or mannosidase II enzymes (the reduced "alg3" pathway). In one variant, a single recombinant enzyme comprising the catalytic domains of GnTI and GnTII, is used.

In such embodiments for mimicking the traditional pathway for producing glycoproteins with complex fucosylated N-glycans, a $Man_5$ expressing filamentous fungal cell, such as T. reesei strain, may be transformed with a GnTI or a GnTII/GnTI fusion enzyme using random integration or by targeted integration to a known site known not to affect Man5 glycosylation. Strains that produce GlcNAcMan5 are selected. The selected strains are further transformed with a catalytic domain of a mannosidase II-type mannosidase capable of cleaving Man5 structures to generate GlcNAc-Man3. In certain embodiments mannosidase II-type enzymes belong to glycoside hydrolase family 38 (cazy.org/GH38_all.html). Characterized enzymes include enzymes listed in cazy.org/GH38_characterized.html. Especially useful enzymes are Golgi-type enzymes that cleaving glycoproteins, such as those of subfamily α-mannosidase II (Man2A1;ManA2). Examples of such enzymes include human enzyme AAC50302, D. melanogaster enzyme (Van den Elsen J. M. et al (2001) EMBO J. 20: 3008-3017), those with the 3D structure according to PDB-reference 1 HTY, and others referenced with the catalytic domain in PDB. For cytoplasmic expression, the catalytic domain of the mannosidase is typically fused with an N-terminal targeting peptide (for example as disclosed in the above Section) or expressed with endogenous animal or plant Golgi targeting structures of animal or plant mannosidase II enzymes. After transformation with the catalytic domain of a mannosidase II-type mannosidase, strains are selected that produce Glc-NAcMan3 (if GnTI is expressed) or strains are selected that effectively produce GlcNAc2Man3 (if a fusion of GnTI and GnTII is expressed). For strains producing GlcNAcMan3, such strains are further transformed with a polynucleotide encoding a catalytic domain of GnTII and transformant strains that are capable of producing GlcNAc2Man3GlcNAc2 are selected.

In embodiments using the reduced alg3 pathway, the filamentous fungal cell, such as a *Trichoderma* cell, has a reduced level of activity of a dolichyl-P-Man:Man(5)Glc-NAc(2)-PP-dolichyl mannosyltransferase compared to the level of activity in a parent host cell. Dolichyl-P-Man:Man (5)GlcNAc(2)-PP-dolichyl mannosyltransferase (EC 2.4.1.130) transfers an alpha-D-mannosyl residue from dolichyl-phosphate D-mannose into a membrane lipid-linked oligosaccharide. Typically, the dolichyl-P-Man:Man (5)GlcNAc(2)-PP-dolichyl mannosyltransferase enzyme is encoded by an alg3 gene. In certain embodiments, the filamentous fungal cell for producing glycoproteins with complex fucosylated N-glycans has a reduced level of expression of an alg3 gene compared to the level of expression in a parent strain.

More preferably, the filamentous fungal cell comprises a mutation of alg3. The ALG3 gene may be mutated by any means known in the art, such as point mutations or deletion of the entire alg3 gene. For example, the function of the alg3 protein is reduced or eliminated by the mutation of alg3. In certain embodiments, the alg3 gene is disrupted or deleted from the filamentous fungal cell, such as *Trichoderma* cell. In certain embodiments, the filamentous fungal cell is a *T. reesei* cell. SEQ ID NOs: 163 and 164 provide the nucleic acid and amino acid sequences of the alg3 gene in *T. reesei*, respectively.

In certain embodiments, the filamentous fungal cell has a reduced level of activity of a alpha-1,6-mannosyltransferase compared to the level of activity in a parent strain. Alpha-1,6-mannosyltransferase (EC 2.4.1.232) transfers an alpha-D-mannosyl residue from GDP-mannose into a protein-linked oligosaccharide, forming an elongation initiating alpha-(1->6)-D-mannosyl-D-mannose linkage in the Golgi apparatus. Typically, the alpha-1,6-mannosyltransferase enzyme is encoded by an och1 gene. In certain embodiments, the filamentous fungal cell has a reduced level of expression of an och1 gene compared to the level of expression in a parent filamentous fungal cell. In certain embodiments, the och1 gene is deleted from the filamentous fungal cell.

The filamentous fungal cells used in the methods of producing glycoprotein with complex fucosylated N-glycans may further contain a polynucleotide encoding an N-acetylglucosaminyltransferase I catalytic domain (GnTI) that catalyzes the transfer of N-acetylglucosamine to a terminal Manα3 and a polynucleotide encoding an N-acetylglucosaminyltransf erase II catalytic domain (GnTII), that catalyses N-acetylglucosamine to a terminal Manα6 residue of an acceptor glycan to produce a complex N-glycan. In one embodiment, said polynucleotides encoding GnTI and GnTII are linked so as to produce a single protein fusion comprising both catalytic domains of GnTI and GnTII.

As disclosed herein, N-acetylglucosaminyltransferase I (GlcNAc-TI; GnTI; EC 2.4.1.101) catalyzes the reaction UDP-N-acetyl-D-glucosamine+3-(alpha-D-mannosyl)-beta-D-mannosyl-R<=>UDP+3-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase I catalytic domain is any portion of an N-acetylglucosaminyltransferase I enzyme that is capable of catalyzing this reaction. GnTI enzymes are listed in the CAZy database in the glycosyltransferase family 13 cazy.org/GT13_all). Enzymatically characterized species includes *A. thaliana* AAR78757.1 (U.S. Pat. No. 6,653,459), *C. elegans* AAD03023.1 (Chen S. et al J. Biol. Chem 1999; 274(1): 288-97), *D. melanogaster* AAF57454.1 (Sarkar & Schachter Biol Chem. 2001 February; 382(2):209-17); *C. griseus* AAC52872.1 (Puthalakath H. et al J. Biol. Chem 1996 271(44):27818-22); *H. sapiens* AAA52563.1 (Kumar R. et al Proc Natl Acad Sci USA. 1990 December;87(24):9948-52); *M. auratus* AAD04130.1 (Opat As et al Biochem J. 1998 Dec. 15; 336 (Pt 3):593-8), (including an example of deactivating mutant), Rabbit, *O. cuniculus* AAA31493.1 (Sarkar M et al. Proc Natl Acad Sci USA. 1991 Jan. 1; 88(1):234-8). Amino acid sequences for N-acetylglucosaminyltransferase I enzymes from various organisms are described for example in PCT/EP2011/070956. Additional examples of characterized active enzymes can be found at cazy.org/GT13_characterized. The 3D structure of the catalytic domain of rabbit GnTI was defined by X-ray crystallography in Unligil U M et al. EMBO J. 2000 Oct. 16; 19(20):5269-80. The Protein Data Bank (PDB) structures for GnTI are 1FO8, 1FO9, 1FOA, 2AM3, 2AM4, 2AM5, and 2APC. In certain embodiments, the N-acetylglucosaminyltransferase I catalytic domain is from the human N-acetylglucosaminyltransferase I enzyme (SEQ ID NO: 165), or variants thereof. In certain embodiments, the N-acetylglucosaminyltransferase I catalytic domain contains a sequence that is at least 70%, at least 75%, at least 80%, at least 85%, at least 90%, at least 95%, at least 96%, at least 97%, at least 98%, at least 99%, or 100% identical to amino acid residues 84-445 of SEQ ID NO: 165. In some embodiments, a shorter sequence can be used as a catalytic domain (e.g. amino acid residues 105-445 of the human enzyme or amino acid residues 107-447 of the rabbit enzyme; Sarkar et al. (1998) Glycoconjugate J 15:193-197). Additional sequences that can be used as the GnTI catalytic domain include amino acid residues from about amino acid 30 to 445 of the human enzyme or any C-terminal stem domain starting between amino acid residue 30 to 105 and continuing to about amino acid 445 of the human enzyme, or corresponding homologous sequence of another GnTI or a catalytically active variant or mutant thereof. The catalytic domain may include N-terminal parts of the enzyme such as all or part of the stem domain, the transmembrane domain, or the cytoplasmic domain.

As disclosed herein, N-acetylglucosaminyltransferase II (GlcNAc-TII; GnTII; EC 2.4.1.143) catalyzes the reaction UDP-N-acetyl-D-glucosamine+6-(alpha-D-mannosyl)-beta-D-mannosyl-R<=>UDP+6-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase II catalytic domain is any portion of an N-acetylglucosaminyltransferase II enzyme that is capable of catalyzing this reaction. Amino acid sequences for N-acetylglucosaminyltransferase II enzymes from various organisms are listed in PCT/EP2011/070956. In certain embodiments, the N-acetylglucosaminyltransferase II catalytic domain is from the human N-acetylglucosaminyltransferase II enzyme (SEQ ID NO: 166), or variants thereof. Additional GnTII species are listed in the CAZy database in the glycosyltransferase family 16 (cazy.org/GT16_all). Enzymatically characterized species include GnTII of *C. elegans, D. melanogaster, Homo sapiens, Rattus norvegicus, Sus scrofa* (cazy.org/GT16_characterized). In certain embodiments, the N-acetylglucosaminyltransferase II catalytic domain contains a sequence that is at least 70%, at least 75%, at least 80%, at least 85%, at least 90%, at least 95%, at least 96%, at least 97%, at least 98%, at least 99%, or 100% identical to amino acid residues from about 30 to about 447 of SEQ ID NO: 166. The catalytic domain may include N-terminal parts of the enzyme such as all or part of the stem domain, the transmembrane domain, or the cytoplasmic domain.

In embodiments where the filamentous fungal cell contains a fusion protein of the invention, the fusion protein may further contain a spacer in between the N-acetylglucosaminyltransferase I catalytic domain and the N-acetylglucosaminyltransferase II catalytic domain. In certain preferred embodiments, the spacer is an EGIV spacer, a 2×G4S spacer, a 3×G4S spacer, or a CBHI spacer. In other embodiments, the spacer contains a sequence from a stem domain.

For ER/Golgi expression the N-acetylglucosaminyltransferase I and/or N-acetylglucosaminyltransferase II catalytic domain is typically fused with a targeting peptide or a part of an ER or early Golgi protein, or expressed with an endogenous ER targeting structures of an animal or plant N-acetylglucosaminyltransferase enzyme. In certain preferred embodiments, the N-acetylglucosaminyltransferase I and/or N-acetylglucosaminyltransferase II catalytic domain contains any of the targeting peptides of the invention as described in the section entitled "Targeting sequences." Preferably, the targeting peptide is linked to the N-terminal end of the catalytic domain. In some embodiments, the targeting peptide contains any of the stem domains of the invention as described in the section entitled "Targeting sequences." In certain preferred embodiments, the targeting peptide is a Kre2/Mnt1 targeting peptide. In other embodiments, the targeting peptide further contains a transmembrane domain linked to the N-terminal end of the stem domain or a cytoplasmic domain linked to the N-terminal end of the stem domain. In embodiments where the targeting peptide further contains a transmembrane domain, the targeting peptide may further contain a cytoplasmic domain linked to the N-terminal end of the transmembrane domain. Further examples of sequences that may be used for targeting peptides include the targeting sequences as described in WO2012/069593 or PCT/EP2013/050126.

The filamentous fungal cells may also contain a polynucleotide encoding a UDP-GlcNAc transporter. The polynucleotide encoding the UDP-GlcNAc transporter may be endogenous (i.e., naturally present) in the host cell, or it may be heterologous to the filamentous fungal cell.

In certain embodiments, the filamentous fungal cell may further contain a polynucleotide encoding a α-1,2-mannosidase. The polynucleotide encoding the α-1,2-mannosidase may be endogenous in the host cell, or it may be heterologous to the host cell. Heterologous polynucleotides are especially useful for a host cell expressing high-mannose glycans transferred from the Golgi to the ER without effective exo-α-2-mannosidase cleavage. The α-1,2-mannosidase may be a mannosidase I type enzyme belonging to the glycoside hydrolase family 47 (cazy.org/GH47_all.html). In certain embodiments the α-1,2-mannosidase is an enzyme listed at cazy.org/GH47_characterized.html. In particular, the α-1,2-mannosidase may be an ER-type enzyme that cleaves glycoproteins such as enzymes in the subfamily of ER α-mannosidase I EC 3.2.1.113 enzymes. Examples of such enzymes include human α-2-mannosidase 1B (AAC26169), a combination of mammalian ER mannosidases, or a filamentous fungal enzyme such as α-1,2-mannosidase (MDS1) (*T. reesei* AAF34579; Maras M et al J Biotech. 77, 2000, 255). For cytoplasmic expression the catalytic domain of the mannosidase is typically fused with a targeting peptide, such as HDEL, KDEL, or part of an ER or early Golgi protein, or expressed with an endogenous ER targeting structures of an animal or plant mannosidase I enzyme.

In certain embodiments, the filamentous fungal cell may also further contain a polynucleotide encoding a galactosyltransferase. Galactosyltransferases transfer β-linked galactosyl residues to terminal N-acetylglucosaminyl residue. In certain embodiments the galactosyltransferase is a β-1,4-galactosyltransferase. Generally, β-1,4-galactosyltransferases belong to the CAZy glycosyltransferase family 7 (cazy.org/GT7_all.html) and include β-N-acetylglucosaminyl-glycopeptide β-1,4-galactosyltransferase (EC 2.4.1.38), which is also known as N-acetylactosamine synthase (EC 2.4.1.90). Useful subfamilies include β4-GalT1, β4-GalT-II, -III, -IV, -V, and -VI, such as mammalian or human β4-GalTI or β4GalT-II, -III, -IV, -V, and -VI or any combinations thereof. β4-GalT1, β4-GalTII, or β4-GalTIII are especially useful for galactosylation of terminal GlcNAcβ2-structures on N-glycans such as GlcNAcMan3, GlcNAc2Man3, or GlcNAcMan5 (Guo S. et al. Glycobiology 2001, 11:813-20). The three-dimensional structure of the catalytic region is known (e.g. (2006) J. Mol. Biol. 357: 1619-1633), and the structure has been represented in the PDB database with code 2FYD. The CAZy database includes examples of certain enzymes. Characterized enzymes are also listed in the CAZy database at cazy.org/GT7_characterized.html. Examples of useful β4GalT enzymes include β4GalT1, e.g. bovine *Bos taurus* enzyme AAA30534.1 (Shaper N. L. et al Proc. Natl. Acad. Sci. U.S.A. 83 (6), 1573-1577 (1986)), human enzyme (Guo S. et al. Glycobiology 2001, 11:813-20), and *Mus musculus* enzyme AAA37297 (Shaper, N. L. et al. 1998 J. Biol. Chem. 263 (21), 10420-10428); β4GalTII enzymes such as human β4GalTII BAA75819.1, Chinese hamster *Cricetulus griseus* AAM77195, *Mus musculus* enzyme BAA34385, and Japanese Medaka fish *Oryzias latipes* BAH36754; and β4GalTIII enzymes such as human β4GalTIII BAA75820.1, Chinese hamster *Cricetulus griseus* AAM77196 and *Mus musculus* enzyme AAF22221.

The galactosyltransferase may be expressed in the cytoplasm of the host cell. A heterologous targeting peptide, such as a Kre2 peptide described in Schwientek J. Biol. Chem 1996 3398, may be used. Promoters that may be used for expression of the galactosyltransferase include constitutive promoters such as gpd, promoters of endogenous glycosylation enzymes and glycosyltransferases such as mannosyltransferases that synthesize N-glycans in the Golgi or ER, and inducible promoters of high-yield endogenous proteins such as the cbh1 promoter.

In certain embodiments of the invention where the filamentous fungal cell contains a polynucleotide encoding a galactosyltransferase, the filamentous fungal cell also contains a polynucleotide encoding a UDP-Gal 4 epimerase and/or UDP-Gal transporter. In certain embodiments of the invention where the filamentous fungal cell contains a polynucleotide encoding a galactosyltransferase, lactose may be used as the carbon source instead of glucose when culturing the host cell. The culture medium may be between pH 4.5 and 7.0 or between 5.0 and 6.5. In certain embodiments of the invention where the filamentous fungal cell contains a polynucleotide encoding a galactosyltransferase and a polynucleotide encoding a UDP-Gal 4 epimerase and/or UDP-Gal transporter, a divalent cation such as Mn2+, Ca2+ or Mg2+ may be added to the cell culture medium.

In certain embodiments, the filamentous fungal cell contains a polynucleotide encoding a sialyltransferase. A sialyltransferase transfers α3- or α6-linked sialic acid, such as Neu5Ac, to the terminal Gal of galactosylated complex glycans. Examples of suitable sialyltransferases can be found in the glycosylation protein family 29 (cazy.org/GT29.html). Useful α3- or α6-sialyltransferases include β-galactoside α-2,6-sialyltransferase (EC 2.4.99.1) with a certain subfamily ST6Gal-I, and N-acetylactosaminide α-2,3-sialyltransferase (EC 2.4.99.6) with possible cross-reactivity with β-galactoside α-2,3-sialyltransferase (EC 2.4.99.4). Useful subtypes of α3-sialyltransferases include ST3Gal-III and ST3Gal-IV. Certain enzymatically characterized species of these are listed as characterized in the CAZy database of carbohydrate active enzymes (cazy.org/GT29_characterized.html). The polynucleotide encoding the α3- or α6-linked sialyltransferase may be endogenous to the host cell, or it may be heterologous to the host cell. Sialylation in the host cell may require expression of enzymes synthesizing the donor CMP-sialic acid (CMP-Sia) such as CMP-Neu5Ac, especially in fungal, plant, nematode/parasite, or insect cells.

Enzymes involved in sialylation pathway result a cellular pool of CMP-Sia in the filamentous fungal cell which can be utilized in the production of sialylated glycans on glycoproteins of interest.

The synthesis of the CMP-Sia donor molecule in e.g. mammals is a multiple reaction process starting with the substrate UDP-GlcNAc and resulting in CMP-Sia. The process initiates in the cytoplasm producing sialic acid which is then converted to CMP-Sia by CMP-sialic acid synthase (NANS). Subsequently, CMP-Sia is then transported into the Golgi where sialyltransferases catalyze the transfer of sialic acid onto the acceptor glycan on a glycoprotein.

Using standard techniques known to those skilled in the art, nucleic acid molecules encoding one or more enzymes (or catalytically active fragments thereof) involved in the sialylation pathway, i.e. GNE, NANS, NANP, CMAS, SLC35A1, and a sialyltransferase (see Example 9) inserted into appropriate expression vectors under the transcriptional control of promoters and/or other expression control sequences capable of driving transcription in a filamentous fungal cell of the invention. The functional expression of such enzymes in the filamentous fungal cell of the invention can be detected using e.g. by measuring the intermediates formed by the enzymes or detaching and analyzing the glycans on glycoproteins using the methods described in the Examples.

Accordingly, in certain embodiments, the filamentous fungal cell of the invention, for example, selected among *Neurospora, Trichoderma, Fusarium, Aspergillus, Penicillium, Myceliophthora*, or *Chrysosporium* cell, and more preferably a *Trichoderma* cell and even more preferably *Trichoderma reesei* cell, may comprise the following features:

a) a mutation in at least one endogenous protease that reduces the activity of said endogenous protease, for example, pep4 protease, preferably the protease activity of two or three or more endogenous proteases is reduced, in order to improve production or stability of the glycoprotein with fucosylated N-glycans to be produced, b) a polynucleotide encoding a glycoprotein, preferably a heterologous glycoprotein, such as an immunoglobulin, an antibody, or a protein fusion comprising Fc fragment of an immunoglobulin.

c) one or more polynucleotides encoding polypeptides with GMD and FX activities for GDP-fucose synthesis, d) a polynucleotide encoding GDP-fucose transporter, for transporting GDP-fucose transporter in the Golgi compartment where fucosyltansferase activity occurs in vivo, e) a polynuceotide encoding α1,6 fucosyltransferase activity linked with a Golgi targeting sequence for targeting said α1,6 fucosylytransferase activity to the Golgi compartment, f) a deletion or disruption of the alg3 gene, g) a polynucleotide encoding N-acetylglucosaminyltransferase I catalytic domain and a polynucleotide encoding N-acetylglucosaminyltransferase II catalytic domain, h) optionally, a polynucleotide encoding β1,4 galactosyltransferase, i) optionally, a polynucleotide or polynucleotides encoding UDP-Gal 4 epimerase and/or transporter, j) optionally, a polynucleotide or polynucleotides encoding sialylation pathway enzymes and transporter.

In certain embodiments, said polynucleotides encoding sialylation pathway enzymes and transporter include one or more of the polynucleotides selected from the group consisting of:

i) a polynucleotide encoding glucosamine UDP-N-acetylglucosamine-2-epimerase/N-acetylmannosamine kinase, ii) a polynucleotide encoding N-acetylneuraminic acid synthase, iii) a polynucleotide encoding N-acetylneuraminic acid phosphatase, iv) a polynucleotide encoding cytidine monophosphate N-acetylneuraminic acid synthetase, v) a polynucleotide encoding CMP-sialic acid transporter, and vi) a polynucleotide encoding sialyltransferase.

Methods for producing a glycoprotein having fucosylated N-glycan

The filamentous fungal cells as described above are useful in methods for producing a glycoprotein, e.g., an antibody, having fucosylated N-glycan.

Accordingly, in another aspect, the invention relates to a method for producing a glycoprotein, e.g., an antibody, having fucosylated N-glycan, comprising:

a. providing a filamentous fungal cell according to the invention as described above, and comprising a polynucleotide encoding a glycoprotein, b. culturing the filamentous fungal cell to produce said glycoprotein having fucosylated N-glycan.

In methods of the invention, typically, cells are grown at 35° C. in appropriate media. Certain growth media in the present invention include, for example, common commercially-prepared media such as Luria-Bertani (LB) broth, Sabouraud Dextrose (SD) broth or Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and Ollis 1986). In certain embodiments the pH of cell culture is between 3.5 and 7.5, between 4.0 and 7.0, between 4.5 and 6.5, between 5 and 5.5, or at 5.5.

In some embodiments, the glycoprotein is a heterologous glycoprotein, preferably a mammalian glycoprotein. In other embodiments, the heterologous glycoprotein is a non-mammalian glycoprotein.

In certain embodiments, the mammalian glycoprotein is selected from an immunoglobulin, immunoglobulin heavy chain, an immunoglobulin light chain, a monoclonal antibody, a Fab fragment, a single chain antibody, a hybrid antibody, an F(ab')2 antibody fragment, a monomeric or multimeric single domain antibody, a functional antibody fragment comprising a Fc fragment of an immunoglobulin, an immunoadhesin, a protein fusion comprising a Fc fragment of an immunoglobulin, or their antigen-binding fragments. A fragment of a protein, as used herein, consists of at least 10, 20, 30, 40, 50, 60, 70, 80, 90, 100 consecutive amino acids of a reference protein.

As used herein, an "immunoglobulin" refers to a multimeric protein containing a heavy chain and a light chain covalently coupled together and capable of specifically combining with antigen. Immunoglobulin molecules are a large family of molecules that include several types of molecules such as IgM, IgD, IgG, IgA, and IgE.

As used herein, an "antibody" refers to intact immunoglobulin molecules, as well as fragments thereof which are capable of binding an antigen. These include hybrid (chimeric) antibody molecules (see, e.g., Winter et al. Nature 349:293-99225, 1991; and U.S. Pat. No. 4,816,567 226); F(ab')2 molecules; non-covalent heterodimers [227, 228]; dimeric and trimeric antibody fragment constructs; humanized antibody molecules (see e.g., Riechmann et al. Nature 332, 323-27, 1988; Verhoeyan et al. Science 239, 1534-36, 1988; and GB 2,276,169); and any functional fragments obtained from such molecules, as well as antibodies obtained through non-conventional processes such as phage display or transgenic mice. Preferably, the antibodies are classical antibodies with Fc region. Methods of manufacturing antibodies are well known in the art.

As used herein the term "Fc", "Fc region" or "Fc fragment" refers to the constant region of an immunoglobulin. An Fc fragment comprises at least the CH2 and CH3 domain, optionally, the hinge region which is located between the heavy chain CH1 domain and CH2. Fc fragments could be obtained for example by papain digestion of an immunoglobulin. Fc fragment include at least one asparagine residue in the hinge region which is linked with N-glycan. As used herein, the term Fc fragment further include Fc variants of native Fc domain into which a substitution, deletion or insertion of at least one amino acid has been introduced. In one embodiment, the hinge region is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the fusion protein. In another embodiment, the Fc region is modified to increase its biological half-life. Various approaches are possible. For example, one or more of the following mutations can be introduced: T252L, T254S, T256F, as described in U.S. Pat. No. 6,277,375 to Ward. In yet other embodiments, the Fc region is altered by replacing at least one amino acid residue with a different amino acid residue to alter the effector functions of the Fc portion. For example, one or more amino acids can be replaced with a different amino acid residue such that the Fc portion has an altered affinity for an effector ligand. This approach is described in further detail in U.S. Pat. Nos. 5,624,821 and 5,648,260, both by Winter et al. In yet another embodiment, the Fc region is modified to increase or decrease the ability of the fusion polypeptide to mediate antibody dependent ceflular cytotoxicity (ADCC) and/or to increase or decrease the affinity of the Fc region for an Fc receptor by modifying one or more amino acids. This approach is described further in PCT Publication WO 00742072 by Presta. Moreover, the binding sites on human IgG1 for FcγRI, FcγRII, FcγRIII and FcRn have been mapped and variants with improved or reduced binding have been described (see Shields, R L. et al. 2001 J. Biol. Chem. 276:6591-6604). In one embodiment, the Fc domain is of human origin and may be from any of the immunoglobulin classes, such as IgG or IgA and from any subtype such as human IgG1, IgG2, IgG3 and IgG4. In other embodiments the Fc domain is from a nonhuman animal, for example, but not limited to, a mouse, rat, rabbit, camel, shark, nonhuman primate or hamster. In certain embodiments, the Fc domain of IgG1 isotype is used. In some specific embodiments, a mutant variant of IgG1 Fc fragment is used, e.g. a mutant IgG1 Fc which reduces or eliminates the ability of the fusion protein to mediate antibody dependent cellular cytotoxicity (ADCC) and/or to bind to an Fcγ receptor. An example of an IgG1 isotype silent mutant, is a so-called LALA mutant, wherein Leucine residue is replaced by Alanine residue at amino acid positions 234 and 235 as described in J. Virol 2001 by Hezareh et al.

In further embodiments, the yield of the mammalian glycoprotein is at least 0.5, at least 1, at least 2, at least 3, at least 4, or at least 5 grams per liter. In certain embodiments, the mammalian glycoprotein is an antibody, optionally, IgG1, IgG2, IgG3, or IgG4. In further embodiments, the yield of the antibody is at least 0.5, at least 1, at least 2, at least 3, at least 4, or at least 5 grams per liter. In further embodiments, the mammalian glycoprotein is an antibody, and the antibody contains at least 70%, at least 80%, at least 90%, at least 95%, or at least 98% of a natural antibody C-terminus and N-terminus without additional amino acid residues. In other embodiments, the mammalian glycoprotein is an antibody, and the antibody contains at least 70%, at least 80%, at least 90%, at least 95%, or at least 98% of a natural antibody C-terminus and N-terminus that do not lack any C-terminal or N-terminal amino acid residues.

In certain embodiments where the mammalian glycoprotein is purified from cell culture, the culture containing the mammalian glycoprotein contains polypeptide fragments that make up a mass percentage that is less than 50%, less than 40%, less than 30%, less than 20%, or less than 10% of the mass of the produced polypeptides. In certain preferred embodiments, the mammalian glycoprotein is an antibody, and the polypeptide fragments are heavy chain fragments and/or light chain fragments. In other embodiments, where the mammalian glycoprotein is an antibody and the antibody purified from cell culture, the culture containing the antibody contains free heavy chains and/or free light chains that make up a mass percentage that is less than 50%, less than 40%, less than 30%, less than 20%, or less than 10% of the mass of the produced antibody. Methods of determining the mass percentage of polypeptide fragments are well known in the art and include, measuring signal intensity from an SDS-gel.

In certain embodiments, where the mammalian glycoprotein is purified from cell culture, the culture contains at least 5%, 10%, 15%, 20%, 25%, 30% of secreted complex fucosylated neutral N-glycans (mol %) compared to total secreted neutral N-glycans (as measured for example as described in the Examples). In certain embodiments where the mammalian glycoprotein is purified from cell culture, and where the strain is a *Trichoderma* cell genetically engineered to produce complex N-glycans as acceptor substrate for α1,6 fucosyltransferase activity, the culture comprises at least 5%, 10%, 15%, 20%, 25%, 30% of secreted complex fucosylated neutral N-glycans (mol %) compared to total secreted neutral N-glycans (as measured for example as described in the Examples). In certain embodiments, the purified mammalian glycoprotein comprises the core fucosylated FG0 N-glycan structure GlcNAcβ2Manα3[GlcNAcβ2Manα6]Manβ4GlcNAcβ4(Fucα6)GlcNAc. In some embodiments, GlcNAcβ2Manα3(GlcNAcβ2Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% or more of total (mol %) neutral or complex type N-glycans of a glycoprotein. In some embodiments, Galβ4GlcNAcβ2Manα3(Galβ4GlcNAcβ2Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least at least 30%, at least 40%, at least 50%, at least 60%, at least 70%, at least 80%, at least 90% or more of total (mol %) neutral or complex type N-glycans of a glycoprotein. In some embodiments, GlcNAcβ2Manα3(Galβ4GlcNAcβ2Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least at least 30%, at least 40%, at least 50%, at least 60%, at least 70%, at least 80%, at least 90% or more of total (mol %) neutral or complex type N-glycans of a glycoprotein. In some embodiments, Galβ4GlcNAcβ2Manα3(GlcNAcβ2Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least at least 30%, at least 40%, at least 50%, at least 60%, at least 70%, at least 80%, at least 90% or more of total (mol %) neutral or complex type N-glycans of a glycoprotein.

In other embodiments, the culture comprises the trimannosyl N-glycan structure Manα3[Manα6]Manβ4GlcNAcβ4GlcNAc. In other embodiments, the culture comprises less than 60%, 50%, 40%, 30%, 20% of the Manα3[Manα6]Manβ4GlcNAcβ4GlcNAc structure compared to the amount (mol %) of total secreted N-glycans or the amount (mol %) of G0 glycans. In other embodiments, the culture comprises the G0 N-glycan structure GlcNAcβ2Manα3[GlcNAcβ2Manα6]Manβ4GlcNAcβ4GlcNAc. In other embodiments, the culture comprises less than 60%, 50%, 40%, 30%, 20% of the non-fucosylated G0 glycoform compared to the amount (mol %) of total secreted N-glycans or the amount of secreted fucosylated FG0 N-glycans. In other embodiments, the culture comprises less than 0.5%, 0.1%, 0.05%, 0.01% galactosylated N-glycans. In certain embodiments, the culture comprises no galactosylated N-glycans. In some embodiments, Manα3(Manα6)Manβ4GlcNAcβ4(Fucα6)GlcNAc represents at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% or more of total (mol %) neutral N-glycans of a glycoprotein.

In some embodiments, GlcNAcβ2Manα3(GlcNAcβ2Manα6)Manβ4GlcNAcβ4(Fucα6)GlcNAc and GlcNAcβ2Manα3(GlcNAcβ2Manα6)Manβ4GlcNAcβ4GlcNAc represents at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% (mol %) of total complex type neutral N-glycans of a glycoprotein. In certain embodiments, at least 40%, 50% or 55% of complex type glycans are fucosylated.

In some embodiments, Galβ4GlcNAcβ2Manα3(Galβ4GlcNAcβ2Manα6)Manβ4GlcNAcβ4(Fucα6)GlcNAc and Galβ4GlcNAcβ2Manα3(Galβ4GlcNAcβ2Manα6)Manβ4GlcNAcβ4GlcNAc represents at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90% (mol %) of total complex type neutral N-glycans of a glycoprotein. In certain embodiments, at least 40%, 50% or 55% of complex type glycans are fucosylated.

In present invention the "complex type N-glycan" comprises at least core structure GlcNAcβ2Manα3(Manα6)Manβ4GlcNAcβ4GlcNAc, which may be elongated to GlcNAcβ2Manα3(GlcNAcβ2Manα6)Manβ4GlcNAcβ4GlcNAc and to galactosylated and/or fucosylated variants [Galβ4]$_a$GlcNAcβ2Manα3([Galβ4]$_b$GlcNAcβ2Manα6)Manβ4GlcNAcβ4(Fucα6)$_c$GlcNAc, wherein a, b and c or integers 0 or 1, independently.

In certain embodiments of any of the disclosed methods, the method includes the further step of providing one or more, two or more, three or more, four or more, or five or more protease inhibitors. In certain embodiments, the protease inhibitors are peptides that are co-expressed with the mammalian polypeptide. In other embodiments, the inhibitors inhibit at least two, at least three, or at least four proteases from a protease family selected from aspartic proteases, trypsin-like serine proteases, subtilisin proteases, and glutamic proteases.

In certain embodiments of any of the disclosed methods, the filamentous fungal cell or *Trichoderma* fungal cell also contains a carrier protein. As used herein, a "carrier protein" is portion of a protein that is endogenous to and highly secreted by a filamentous fungal cell or *Trichoderma* fungal cell. Suitable carrier proteins include, without limitation, those of *T. reesei* mannanase I (Man5A, or MANI), *T. reesei* cellobiohydrolase II (Cel6A, or CBHII) (see, e.g., Paloheimo et al Appl. Environ. Microbiol. 2003 December; 69(12): 7073-7082) or *T. reesei* cellobiohydrolase I (CBHI). In some embodiments, the carrier protein is CBH1. In other embodiments, the carrier protein is a truncated *T. reesei* CBH1 protein that includes the CBH1 core region and part of the CBH1 linker region. In some embodiments, a carrier such as a cellobiohydrolase or its fragment is fused to a glycoprotein, for example, an antibody light chain and/or an antibody heavy chain. In some embodiments, a carrier-antibody fusion polypeptide comprises a Kex2 cleavage site. In certain embodiments, Kex2, or other carrier cleaving enzyme, is endogenous to a filamentous fungal cell. In certain embodiments, carrier cleaving protease is heterologous to the filamentous fungal cell, for example, another Kex2 protein derived from yeast or a TEV protease. In certain embodiments, carrier cleaving enzyme is overexpressed. In certain embodiments, the carrier consists of about 469 to 478 amino acids of N-terminal part of the *T. reesei* CBH1 protein GenBank accession No. EGR44817.1.

In certain embodiments, the filamentous fungal cell of the invention overexpress KEX2 protease. In an embodiment the heterologous protein is expressed as fusion construct comprising an endogenous fungal polypeptide, a protease site such as a Kex2 cleavage site, and the heterologous protein such as an antibody heavy and/or light chain. Useful 2-7 amino acids combinations preceding Kex2 cleavage site have been described, for example, in Mikosch et al. (1996) J. Biotechnol. 52:97-106; Goller et al. (1998) Appl Environ Microbiol. 64:3202-3208; Spencer et al. (1998) Eur. J. Biochem. 258:107-112; Jalving et al. (2000) Appl. Environ. Microbiol. 66:363-368; Ward et al. (2004) Appl. Environ. Microbiol. 70:2567-2576; Ahn et al. (2004) Appl. Microbiol. Biotechnol. 64:833-839; Paloheimo et al. (2007) Appl Environ Microbiol. 73:3215-3224; Paloheimo et al. (2003) Appl Environ Microbiol. 69:7073-7082; and Margolles-Clark et al. (1996) Eur J Biochem. 237:553-560.

The invention further relates to the glycoprotein composition, for example the antibody composition, obtainable or obtained by the method as disclosed above.

In specific embodiment, such antibody composition obtainable or obtained by the methods of the invention, comprises at least 10%, 20%, 30%, 40%, 50%, 60%, 70%, 80%, 90%, 95%, or 100% of the antibodies that are fucosylated (mol %, as determined for example by MALDI TOF MS analysis, and measuring area or intensity of peaks as described in Examples). In other specific embodiments, such antibody composition further comprises at least 2%, 3%, 4%, 5%, 6%, 7%, 8%, 9%, 10%, 20%, 30%, 40%, 50%, 60%, 70% or 80% (mole % neutral N-glycan) or more, of the following glycoform:

(i) Manα3(Manα6)Manβ4GlcNAβ4(Fucα6)GlcNAc;
(ii) Galβ4GlcNAcβ2Manα3(Galβ4GlcNAcβ2Manα6) Manβ4GlcNAcβ4(Fucα6)GlcNAc (FG2);
(iii) GlcNAcβ2Manα3(Galβ4GlcNAcβ2Manα6) Manβ4GlcNAcβ4(Fucα6)GlcNAc (FG1),
(iv) Galβ4GlcNAcβ2Manα3(GlcNAcβ2Manα6) Manβ4GlcNAcβ4(Fucα6)GlcNAc (FG1);
(v) GlcNAcβ2Manα3(GlcNAcβ2Manα6) Manβ4GlcNAcβ4(Fucα6)GlcNAc (FG0);
(vi) GlcNAcβ2Manα3(Manα6)Manβ4GlcNAcβ4 (Fucα6)GlcNAc.

In some embodiments the N-glycan composition according to i-v comprises less than 15%, 10%, 7%, 5%, 3%, 1% or 0.5% or is devoid of Man5 glycan (Manα3[Manα6 (Manα3)Manα6]Manβ4GlcNAβ4GlcNAc) and/or Man5 glycan (Manα3(Manα6)Manβ4GlcNAβ4GlcNAc.

Pharmaceutical Compositions Containing Glycoprotein with Complex Fucosylated N-Glycans Produced by the Methods of the Invention In another aspect, the present invention provides a composition, e.g., a pharmaceutical composition, containing glycoproteins with complex fucosylated N-glycans produced by the methods of the invention, formulated together with a pharmaceutically acceptable carrier. Pharmaceutical compositions of the invention also can be administered in combination therapy, i.e., combined with other agents. For example, the combination therapy can include a glycoprotein with fucosylated N-glycans (e.g. complex fucosylated N-glycans) according to the present invention combined with at least one other therapeutic agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the fucosylated N-glycan attached to a heterologous molecule according to the invention, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the certain methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the glycoprotein with fucosylated N-glycans, in particular where such glycoprotein is an antibody, the dosage ranges from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Certain dosage regimens for antibodies with fucosylated N-glycan include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively a glycoprotein with fucosylated N-glycan according to the invention can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a glycoprotein of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Certain routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a glycoprotein with fucosylated N-glycan according to the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a certain embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

In certain embodiments, the use of the glycoprotein with fucosylated N-glycan according to the invention is for the treatment of any disease that may be treated with therapeutic antibodies, more specifically silent therapeutic antibodies, with low or no ADCC activity, including without limitation antibodies for use in treating autoimmune and inflammatory disorders, and/or to prevent from graft rejection.

It is to be understood that, while the invention has been described in conjunction with the certain specific embodiments thereof, the foregoing description is intended to illustrate and not limit the scope of the invention. Other aspects, advantages, and modifications within the scope of the invention will be apparent to those skilled in the art to which the invention pertains.

EXAMPLES

Example 1

Cloning and deletion of *T. reesei* Alg3 and generation of GnTII/I fusion protein The gene encoding the ALG3 mannosyltransferase was identified in the *Trichoderma reesei* genome sequence. A disruption construct was designed to insert the acetamidase selection marker between 1000 bp 5' and 3' flanking region fragments of the alg3 gene. The flanking region fragments were amplified by PCR, and the construct was made by homologous recombination cloning in *Saccharomyces cerevisiae*. The disruption cassette was released from its backbone vector by digestion and transformed into the *T. reesei* strain M124 (mus53 deletion of M44 (VTT-D-00775; Selinheimo et al., FEBS J. 2006, 273(18): 4322-35). Transformants were selected on acetamidase medium and screened by PCR with a forward primer outside the 5' flanking region fragment of the construct and the reverse primer inside the AmdS selection marker.

A vector having the chimeric GnTII/GnTI sequence (SEQ ID NO: 240) under the control of the cbh1 promoter was constructed with a pyr4 gene loopout marker and subcloned into a backbone vector between alg3 flanking region fragments for targeted integration, resulting in plasmid pTTv110. A PmeI-digested expression cassette was transformed into *T. reesei* strain M127 (pyr4-strain of M124). After plate selection, the clones were PCR-screened and purified through single spores. Five PCR positive transformants indicating correct integration to the alg3 locus in the M127 transformation were cultivated in a 300 ml volume for seven days at +28° C. in a media containing TrMM, pH 5.5, supplemented with 40 g/l lactose, 20 g/l spent grain extract, and 100 mM PIPPS. To avoid bacterial contamination, 100 mg/l ampicillin was added into the flasks at the time of inoculation.

Example 2

Cloning of *C. elegans* GMD, FX, GDP fucose transporter and human FUT8

The coding sequences of the *Ceanorhabditis elegans* GMD, FX, GDP-fucose transporter and human FUT8 transferase were optimized for *Trichoderma reesei* expression. The GMD and Fut8 genes were cloned into a *T. reesei* expression vector between the gpdA promoter and TrpC terminator, and the FX and GDP-fucose transporter were cloned into an *E. coli* cloning plasmid.

A plasmid containing expression cassettes for both *C. elegans* GMD and FX was generated from the optimized sequences. The plasmid was cloned using yeast homologous recombination and, as vector backbone, the yeast vector pRS426, EcoRI-XhoI digested, was used (Colot et al., PNAS 2006, 103(27):10352-7). The GMD expression cassette was digested with NotI-HindIII, resulting in a 4.3 kb fragment, containing the gpdA promoter and trpC terminator flanking the ORF. The FX ORF was digested with KpnI and SacI, and the tef1 promoter and egl2 terminator for the FX expression were created by PCR from genomic DNA from parent strain M124. The pep4 5' integration flank and the first half of the pyr4 marker were obtained by PCR, using a pep4 deletion plasmid (pTTv181) with pyr4 marker as a template (see pep4 deletion plasmid construction below). The primers used are listed in Table 2. The digested fragments and PCR products were separated with agarose gel electrophoresis and the correct fragments were isolated from the gel with a gel extraction kit (Qiagen) according to manufacturer's protocol. The plasmid was constructed using the yeast homologous recombination method, using overlapping oligonucleotides for the recombination of the GMD fragment. The plasmid DNA was rescued from yeast and transformed into electro competent TOP10 E. coli that were plated on ampicillin (100 µg/ml) selection plates. Miniprep plasmid preparations were made from several colonies. The presence of the GMD and FX genes was confirmed by digesting the prepared plasmids with SacI-SacII and two positive clones were sequenced to verify the sequence. One correct clone was chosen to be the final vector pTTv224.

A vector was constructed by yeast cloning using the EcoRI-XhoI pRS426 as backbone, and the human optimized FUT8 sequence. For targeting of the FUT8 to Golgi, the transmembrane region of a *T. reesei* native mannosyltransferase MNT1 was used. The first 85 amino acids of the MNT1 were fused to human FUT8 without the transmembrane domain (amino acids 1-31). The mnt1 localisation fragment was generated by PCR from a vector containing genomic DNA of the mnt1, and the FUT8 fragment was generated by PCR from the optimized sequence. The cdna1 promoter and cbh2 terminator were chosen for the FUT8 expression and these were generated by PCR from vectors containing *T. reesei* cdna1 promoter, and cbh2 terminator, respectively. The pep4 3' integration flank and the second half of the pyr4 marker were obtained by PCR, using the pep4 deletion plasmid pTTv181 as a template. There is an overlap of 900 bp between the two parts of the pyr4 marker, which enables efficient recombination of the two different fragments in *T. reesei*. The 300 bp egl2 terminator repetitive sequence was created by PCR from genomic DNA from the strain M124. The cloning was performed as described above, but the presence of the human FUT8 gene was confirmed by digestion with NcoI-PvuI. One correct clone was chosen to be the final vector pTTv225.

The pTTv225 vector was linearised with SgfI, and the *C. elegans* GDP-fucose transporter, together with the *tef2* promoter and xyn1 terminator, was inserted by yeast recombination. The optimized transporter coding sequence was digested with KpnI and SacI, and the *tef2* promoter and xyn1 terminator were created by PCR from genomic DNA from strain M124. The cloning was performed as described for pTTv224, but the presence of the transporter gene was checked by digestion with XhoI. One correct clone was chosen to be the final vectors pTTv226. The primers used for sequencing the vectors are listed in Table 3.

TABLE 2

List of primers used for cloning vectors pTTv224, pTTv225 and pTTv226

| Fragment | Primer | Primer sequence |
|---|---|---|
| pep4 5'flank | T298_77579_5f | GTAACGCCAGGGTTTTCCCAGTCACGAC GGTTTAAACTCAGGTCAACCACCGAGGA C (SEQ ID NO: 35) |
| | T_758_pTTv224_1 | TTCTTCTTATTGATTTGAGCCTGTGTGTAG AGATACAAGGATTTAAATTGAATGGGATG GTTCGATTGCT (SEQ ID NO: 36) |
| GMD 5' overlapping oligos | T729_pTTv227_3 | AAGTTCCCTTCCTCTGGCAGCAATCGAAC CATCCCATTCAATTTAAATCCTTGTATCTC TACACACAGGCTCAAATCAATAAGAAGAA (SEQ ID NO: 37) |
| | T730_pTTv227_4 | TTCTTCTTATTGATTTGAGCCTGTGTGTAG AGATACAAGGATTTAAATTGAATGGGATG GTTCGATTGCTGCCAGAGGAAGGGAACT T (SEQ ID NO: 38) |
| GMD 3' overlapping oligos | T731_pTTv227_5 | AAGCGCCCACTCCACATCTCCACTCGAC CTGCAGGCATGCGGCGCGCCACTGGGA GCTGTGCCGAGTTTGCTGGCTACTTACCT AGTC (SEQ ID NO: 39) |
| | T732_pTTv227_6 | GACTAGGTAAGTAGCCAGCAAACTCGGC ACAGCTCCCAGTGGCGCGCCGCATGCCT GCAGGTCGAGTGGAGATGTGGAGTGGGC GCTT (SEQ ID NO: 40) |
| tef1 promoter | T733_pTTv227_7 | AAGCGCCCACTCCACATCTCCACTCGAC CTGCAGGCATGCGGCGCGCCACTGGGA GCTGTGCCGAGTTTG (SEQ ID NO: 41) |
| | T734_pTTv227_8 | CCACCAGACCAGTGCCGCCCGTGACGAG GATGGTTTTCATTTTGACGGTTTGTGTGAT GTAGCGT (SEQ ID NO: 42) |
| egl2 terminator | T735_pTTv227_9 | CCAGTGGTTCGTTGACAACTACGAAACCG CCCGGAAGTAACACTCTGAGCTGAATGC AGAAGC (SEQ ID NO: 43) |
| | T759_pTTv224_2 | TACAATAACACAGATCTTTTATGACGG (SEQ ID NO: 44) |

TABLE 2-continued

List of primers used for cloning vectors pTTv224, pTTv225 and pTTv226

| Fragment | Primer | Primer sequence |
|---|---|---|
| First part of pyr4 marker | T760_pTTv224_3 | TTGTAATGTTCTACCGTCATAAAAGATCTG TGTTATTGTAGCGATCGCCTAGCATCGAC TACTGCTGCTCT (SEQ ID NO: 45) |
| | T761_pTTv224_4 | GCGGATAACAATTTCACACAGGAAACAGC GTTTAAACCTCCACCGACCGATCCGTTGG (SEQ ID NO: 46) |
| Second part of pyr4 marker | T762_pTTv225_1 | GTAACGCCAGGGTTTTCCCAGTCACGAC GGTTTAAACTCAAGCTCATGGACCTCAAG GC (SEQ ID NO: 47) |
| | T763_pTTv225_2 | CCATGCAAAGATACACATCAATCG (SEQ ID NO: 48) |
| egl2 terminator loop-out | T764_pTTv225_3 | GATTGTACCCCAGCTGCGATTGATGTGTA TCTTTGCATGGGGCATCCGTAGTTGTCGC AAGAA (SEQ ID NO: 49) |
| | T759_pTTv224_2 | TACAATAACACAGATCTTTTATGACGG (SEQ ID NO: 50) |
| cDNA1 promoter | T765_pTTv225_4 | TTGTAATGTTCTACCGTCATAAAAGATCTG TGTTATTGTAGGTCTGAAGGACGTGGAAT GATG (SEQ ID NO: 51) |
| | T738_pTTv228_2 | GTTGAGAGAAGTTGTTGGATTGATCA (SEQ ID NO: 52) |
| mnt1 1-85 | T739_pTTv228_3 | AACCAAAGACTTTTTGATCAATCCAACAA CTTCTCTCAACTTAATTAAAATGGCGTCAAC AAATGCGCGCTAT (SEQ ID NO: 53) |
| | T740_pTTv228_4 | GTTCATTCGAGGGCCGGGA (SEQ ID NO: 54) |
| FUT8 32-575 | T741_pTTv228_5 | CAACGACCTCGTCGGCATCGCTCCCGGC CCTCGAATGAACGACAACGACCACCCTG ATCATTC (SEQ ID NO: 55) |
| | T742_pTTV228_6 | TTACTTCTCGGCCTCGGGGTAG (SEQ ID NO: 56) |
| cbh2 terminator | T743_pTTv228_7 | GACTGTTAAGTACCCGACCTACCCCGAG GCCGAGAAGTAAGGCCGGCCGGCTTTCG TGACCGGGCTTCAAA (SEQ ID NO: 57) |
| | T744_pTTV228_8 | GTATCAGTCAGCGAGCAAGCCATT (SEQ ID NO: 58) |
| pep4 5'flank | T766_pTTv225_5 | ATGATGCCTTTGCAGAAATGGCTTGCTCG CTGACTGATACGCGATCGCAGGTAGACG CTTTGCGAGTGTG (SEQ ID NO: 59) |
| | T301_77579_3r | GCGGATAACAATTTCACACAGGAAACAGC GTTTAAACTGAACTGACGCGGACTGA (SEQ ID NO: 60) |
| tef2 promoter | T780_pTTv226_1 | GCCTTTGCAGAAATGGCTTGCTCGCTGAC TGATACGCGATCGCTTGGTGCTCGTATTA GTGCCAATG (SEQ ID NO: 61) |
| | T781_pTTv226_2 | CCTCGAACAGGGCCTTGTTGTTTTCCTCG TGGAGCTTCATATTTAAATCTTGGCGGTA TTGCGGCTCGG (SEQ ID NO: 62) |
| xyn1 terminator | T782_pTTv226_3 | CCTGGGCAGAGATGGTAACGCCGCCGAG GAATCCGTTTAAGGCGCGCCGTTCTGTTG ATGTTGACTTGGAGT (SEQ ID NO: 63) |
| | T783_pTTv226_4 | CTTCTTAGATACACACACACTCGCAAAGC GTCTACCTGCGATCGCTGGGGGCGGATA GAGGAGCAG (SEQ ID NO: 64) |

TABLE 3

List of primers used for sequencing vectors pTTv224, pTTv225 and pTTv226

| Primer | Sequence |
| --- | --- |
| T023_pRS426_5.1sekv | GGCGAAAGGGGGATGTGCTG (SEQ ID NO: 65) |
| T228_pRS426_3.1sekv | CCCAGGCTTTACACTTTATG (SEQ ID NO: 66) |
| T094_pyr4_F | TAGCATCGACTACTGCTGC (SEQ ID NO: 67) |
| T770_alg3_3pr_int_pyr4_F | CAGCCTCTCTCAGCCTCATC (SEQ ID NO: 68) |
| T785 | GCCAAAGCACCCAAGTACC (SEQ ID NO: 69) |
| T786 | GACGAGCCCGACATTAAAGC (SEQ ID NO: 70) |
| T787 | GCACGGCTTCCTCATCTTCG (SEQ ID NO: 71) |
| T790 | GAAGTAATCTCTGCAGATCTTTCG (SEQ ID NO: 72) |
| T791 | ATTTGCTTTCCAGGCTGAG (SEQ ID NO: 73) |
| T792 | CCCTACAACGACCATCAAAGTC (SEQ ID NO: 74) |
| T793 | GAGAATATGGAGCTTCATCGA (SEQ ID NO: 75) |
| T794 | CAGTATATTCATCTTCCCATCC (SEQ ID NO: 76) |
| T795 | TTCTCCCTCCACTACGG (SEQ ID NO: 77) |
| T796 | CGAGTACGTCGAGGCTATGTG (SEQ ID NO: 78) |
| T797 | CAAGCAGCAAAGAGTGC (SEQ ID NO: 79) |
| T798 | TTTACAACTCTCCTATGAGTCG (SEQ ID NO: 80) |
| T799 | CAATCGGAAGGGTGTCG (SEQ ID NO: 81) |
| T800 | AGCCACTGGCACTTGCA (SEQ ID NO: 82) |
| T801 | CCGGTGAAGTCGATTGC (SEQ ID NO: 83) |
| T802 | CAGTGCGAGAACGTTGTC (SEQ ID NO: 84) |
| T803 | GGCCTCTTCCACAACCT (SEQ ID NO: 85) |
| T804 | CTCAGCGTGAACGAGTC (SEQ ID NO: 86) |
| T805 | TGTAACTCAGGTTAATTGTTGGGC (SEQ ID NO: 87) |
| T809 | TGAAGGACGTGGAATGATGG (SEQ ID NO: 88) |
| T810 | AAACAAGCAACCTTGAACC (SEQ ID NO: 89) |
| T811 | ACACAGATAAACCACCAACTC (SEQ ID NO: 90) |
| T812 | CGATTGACCAAGGCCCA (SEQ ID NO: 91) |
| T813 | ACGCTGATCTTGGAGTC (SEQ ID NO: 92) |
| T814 | CCTCGCTGCTCAAAGAG (SEQ ID NO: 93) |
| T815 | CCGGGCTTCAAACAATGATGTG (SEQ ID NO: 94) |
| T816 | GGAGCATGAGCCTATGG (SEQ ID NO: 95) |
| T817 | CTGAGGACGGGCAATTCAAGTC (SEQ ID NO: 96) |
| T818 | CACATCAACCGTTGACAAGG (SEQ ID NO: 97) |
| T819 | TTTCTTCCTCCTACACCAC (SEQ ID NO: 98) |
| T820 | ACGTCGTCTGCACCTACCT (SEQ ID NO: 99) |
| T821 | CTGTTGTGGTGGACGTC (SEQ ID NO: 100) |
| T824 | CTGCGAGGTCAAGACGT (SEQ ID NO: 101) |
| T825 | CAGGGCCAGCAGTACAACAC (SEQ ID NO: 102) |

The pTTv224 vector contains the first part of the pyr4 marker; the pyr4 promoter and pyr4 ORF nucleotides 1-979. The pTTv225 and pTTv226 vectors contain the second part of the marker, the pyr4 ORF nucleotides 81-1146 and the pyr4 terminator. The 300 bp egl2 terminator fragment after the pyr4 marker enables loopout of the pyr4 marker. The constructs were targeted to the aspartic protease locus pep4 (tre77579) using the pep4 sequence from the 5' and 3' flanks of the gene (see above sequences). These listed sequences were included in the cassette to allow the cassette to integrate into the pep4 locus via homologous recombination.

Transformation into G0 *T. reesei* strain

To prepare the vectors for transformation, the vectors were cut with PmeI to release the expression cassettes (FIG. 1). The fragments were separated with agarose gel electrophoresis and the correct fragment was isolated from the gel with a gel extraction kit (Qiagen) according to manufacturer's protocol. The purified expression cassette DNA (5 μg) was then co-transformed into protoplasts of the *Trichoderma reesei* M289 G0 strain expressing fusion protein GNT2/1 in the alg3 locus (obtained by transforming pyr4-strain of M124 with GnTII/I to alg3 locus in Example 1), the ALG3 deficient strains expressing GnTII and GnTI as fusion protein GNT2/1 are also described in International Patent Application No. PCT/EP2011/070956. Preparation of protoplasts and transformation were carried out essentially according to methods in Penttilä et al. (1987, Gene 61:155-164) and Gruber et al (1990, Curr. Genet. 18:71-76) for pyr4 selection. The transformed protoplasts were plated onto *Trichoderma* minimal media (TrMM) plates containing sorbitol.

Transformants were then streaked onto TrMM plates with 0.1% TritonX-100. Transformants growing fast as selective streaks were screened by PCR using the primers listed in Table 4. DNA from mycelia was purified and analyzed by PCR to look at the integration of the 5' and 3' flanks of cassette and the existence of the pep4 ORF. The cassette was targeted into the pep4 locus; therefore the open reading frame was not present in the positively integrated transformants, purified to single cell clones. To screen for 5' integration, sequence outside of the 5' integration flank was used to create a forward primer that would amplify genomic DNA flanking pep4 and the reverse primer was made from sequence in the gpdA promoter of the cassette. To check for proper integration of the cassette in the 3' flank, a reverse primer was made from sequence outside of the 3' integration flank that would amplify genomic DNA flanking pep4 and the forward primer was made from sequence in the cbh2 terminator for pTTv225 and GDP-fucose transporter for pTTv226. Thus, one primer would amplify sequence from genomic DNA outside of the cassette and the other would amplify sequence from DNA in the cassette. The transformation efficiency and integration of the split marker fragments was comparable to that of one expression construct carrying the full pyr4 marker.

TABLE 4

List of primers used for PCR screening of *T. reesei* transformants

| 5' flank screening primers: | 1361 bp product |
|---|---|
| T302_77579_5int | GATTCATCACAGGGGCAGTC (SEQ ID NO: 103) |
| T018_pgpdA_5rev | GAGCAGGCTCGACGTATTTC (SEQ ID NO: 104) |
| 3' flank screening primers, pTTv225: | 1318 bp product |
| T816 | GGAGCATGAGCCTATGG (SEQ ID NO: 105) |
| T415_77579_3screen | ACGCCGTTGCTGAGCCTTG (SEQ ID NO: 106) |
| 3' flank screening primers, pTTv226: | 1666 bp product |
| T821 | CTGTTGTGGTGGACGTC (SEQ ID NO: 107) |
| T415_77579_3screen | ACGCCGTTGCTGAGCCTTG (SEQ ID NO: 106) |
| pep4 ORF primers: | 1347 bp product |
| T416_77579_probeF | GAGCCCATCATCAACACCTC (SEQ ID NO: 108) |
| T417_77579_probeR | TGCCAAGGTCGTAGACGGA (SEQ ID NO: 109) |

Fermentation of strain M525, clone 43A

*T. reesei* strain M525 (pTTv224+pTTv226 transformant 43A) was grown on lactose—whole spent grain in 2 l batch mode fermentation (Sartorius, Biostat B plus) with 1 litre working volume for 9 days. 100 µl of M525 spores were cultivated in 100 ml of 30 g/l glucose, 15 g/l whole spent grain, 5 g/l KH2PO4, 5 g/l (NH4)2SO4-medium, pH 5.5 at +30° C. with 200 rpm for 4 days. To avoid contaminations 100 µg/ml ampicillin was added in the inoculum medium. 90 ml of seed was used as the fermenter inoculum.

Fermentation was performed on 60 g/l lactose, 40 g/l whole spent grain, 40 g/l cellobiose, 20 g/l glucose, 1 ml/l 1000× TrTES, (Ilmèn et al, 1997, AEM 63:1298-1306), 5 g/l KH2PO4, 5 g/l (NH4)2SO4-medium, pH 5.5. 1.5 ml of Struktol J633 antifoam (Schill-Seilacher) was added in the medium. Medium was sterilized by autoclaving at +121° C. for 40 min. 2.4 ml of 1M MgSO4 and 4.1 ml of 1M CaCl2 were added in the medium after autoclave. Fermentation was conducted at +28° C. and agitation speed was 715 rpm (tip speed 2.05 m/s) with aerating rate of 0.4 vvm. The pH of the medium was adjusted with 5% NH3 and with 15% H3PO4. Struktol J633 diluted in RO-water (2:1) was used as an antifoam agent. Sampling was performed on days 0, 2, 3, 4, 7 and 9 and samples were filtered through the GF/A filters (Millipore, cat no APFA04700).

N-Glycan analysis

Six *T. reesei* fucosylation transformants containing *C. elegans* GMD, FX and human FUT8 (pTTv224+pTTv225; clones 40A, 40D, 43A, 43D, 57A, 57D), seven transformants containing *C. elegans* GMD, FX, human FUT8 and *C. elegans* GDP-Fuc transporter (pTTv224+pTTv226; clones 2B, 3B, 4B, 5B, 5D, 12C, 12D) and parental M289 G0 strain were cultivated in shake flasks in TrMM, 40 g/l lactose, 20 g/l spent grain extract, pH 5.0, at +28° C. The protein concentrations of the day 5 and 3 or 7 culture supernatants were measured by Bradford based assay (BioRad Quickstart Bradford Protein Assay) using BSA as a standard, and the N-glycans were analysed in triplicate from 10 µg of EtOH precipitated and SDS denatured supernatant proteins using 0.625 mU PNGase F (Europa Bioproducts) in 20 mM sodium phosphate buffer, pH 7.3, in overnight reaction at +37° C. The released N-glycans were purified with Hypersep C-18 and Hypersep Hypercarb (Thermo Scientific) and analysed with MALDI-TOF MS. Native fragmentation analysis was performed on signal m/z 1485, 1485 [M+Na]$^+$ corresponding to FG0.

For protein specific N-glycan analysis 80 µl of culture supernatant (~15 µg of protein) of fucosylation clone 40A was run in reducing SDS-PAGE and blotted to PVDF membrane, where from ~70 kDa and ~55 kDa bands were excised. The N-glycans were released from the membrane with 2.5 mU PNGase F (Europa Bioproducts) in 20 mM sodium phosphate buffer, pH 7.3, in overnight reaction at +37° C. The released N-glycans were purified with Hypersep C-18 and Hypersep Hypercarb (Thermo Scientific) and analysed with MALDI-TOF MS.

Results

Figure 2A:
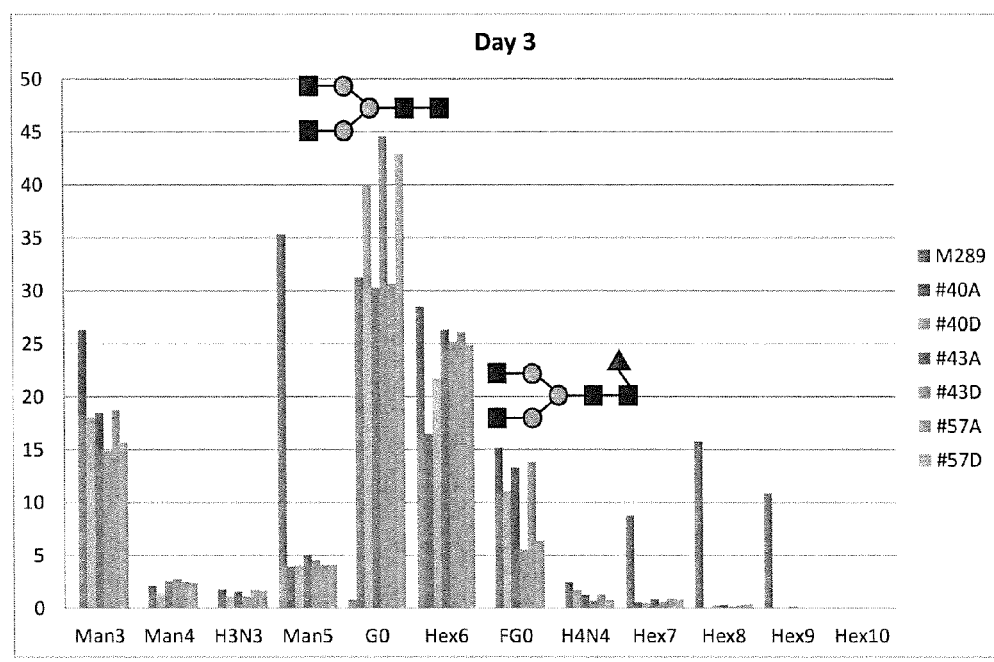
FIG. 2. Neutral N-glycans from day 3 (A) and day 5 (B) supernatant proteins of *T. reesei* fucosylation transformants (pTTv224+pTTv225) and parental strain M289.
Figure 2B:
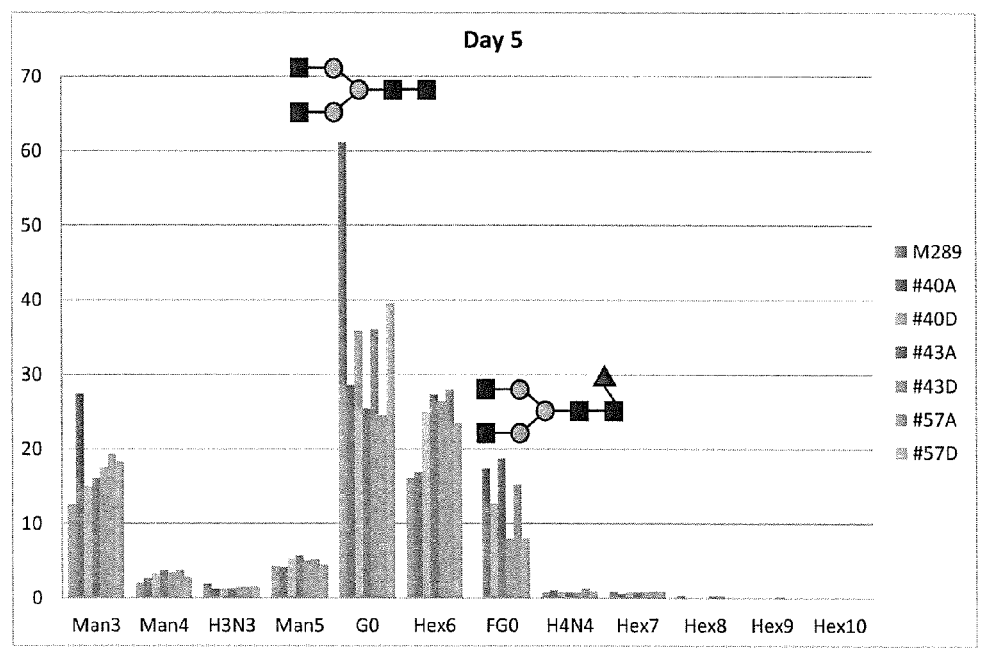
Figure 3:
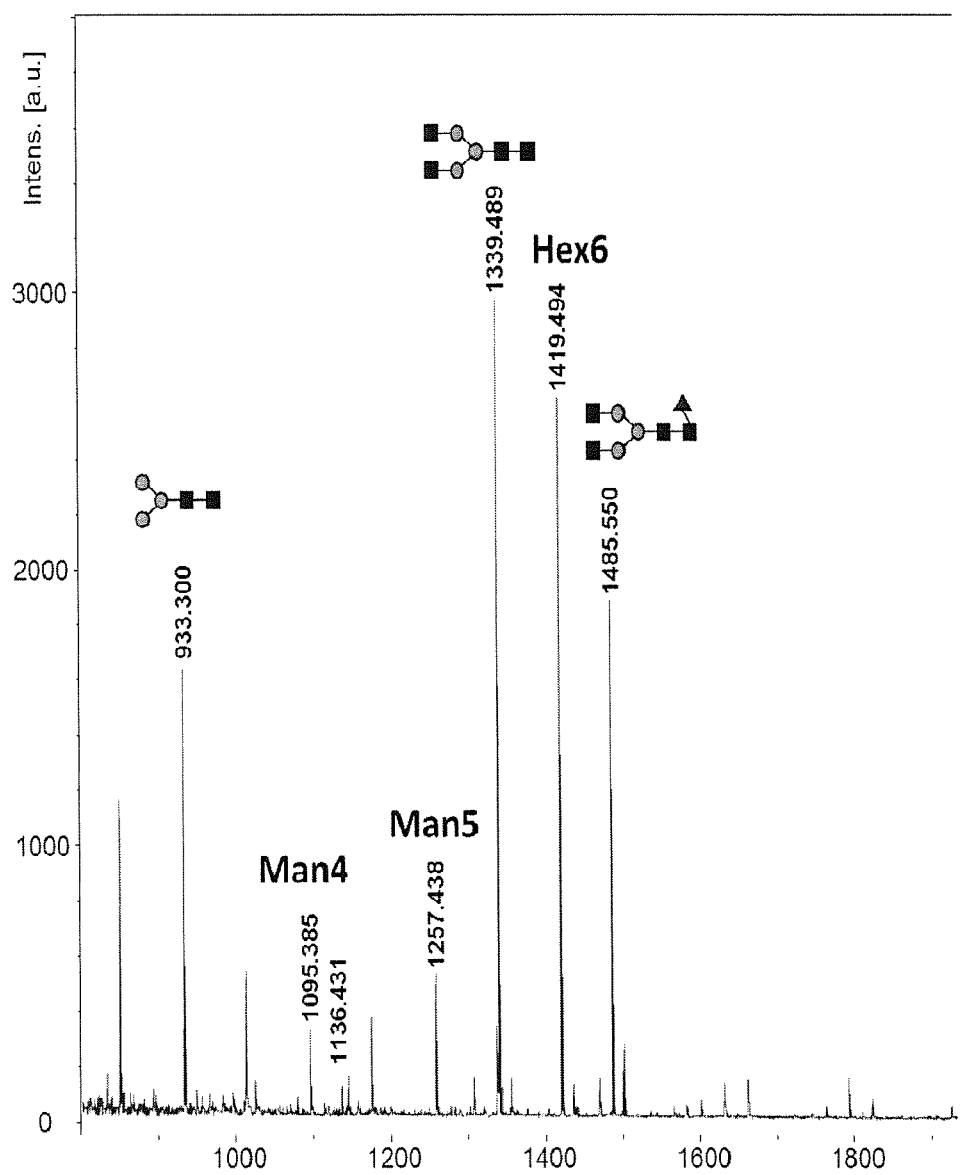
FIG. 3. Neutral N-glycans of day 5 supernatant proteins from *T. reesei* fucosylation transformant 43A.
Figure 7:
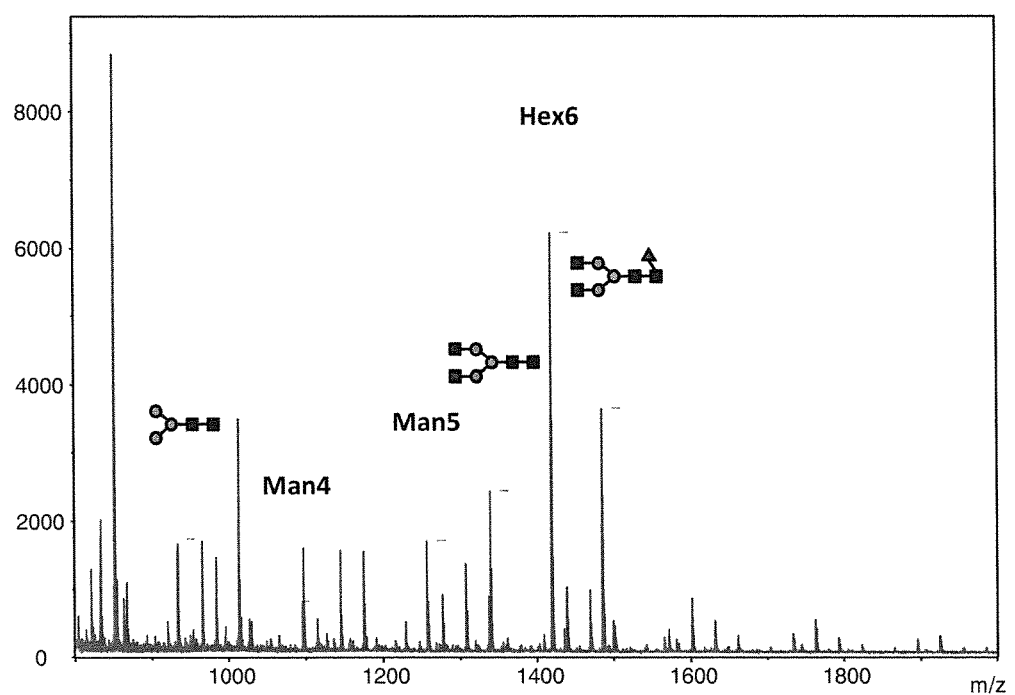
FIG. 7. Neutral N-glycans of day 5 supernatant proteins from fermentation of *T. reesei* fucosylation transformant 12D with GDP fucose transporter FIGS. 8A-C. Alignment of FX proteins of different species FIGS. 9A-C. Alignment of GMD proteins of different species FIGS. 10A-B. Alignment of FUT8 proteins of different species FIGS. 11A-B. Alignment of fucose transporter proteins of different species FIG. 12. Normalised protease activity of day 5 supernatants taken from shake flask cultures done with the M289 parent strain, four pTTv224+pTTv225 transformants 40A, 43A, 7G and 51E and two pTTv224+pTTv226 transformants 4B and 12D. Fluorescent casein was incubated with the diluted supernatants (1:4) in citrate buffer pH 4.5 to detect protease activity.

The N-glycan analysis revealed that all the fucosylation transformants containing *C. elegans* GMD, FX and human FUT8 produced 6-15% of fucosylated G0 (FG0) on supernatants proteins in three days of cultivation in shake flasks (FIG. 2A, Table 5) and 8-19% in five days (FIG. 2B, Table 6). The best clones were 40A, 43A (FIGS. 3) and 57A. All the fucosylation transformants with GDP-Fuc transporter produced over 11% of FG0 on supernatant proteins in five days of cultivation in shake flasks (Table 4), the best clone being 12D with 25% of FG0 (FIG. 7).

Figure 4:
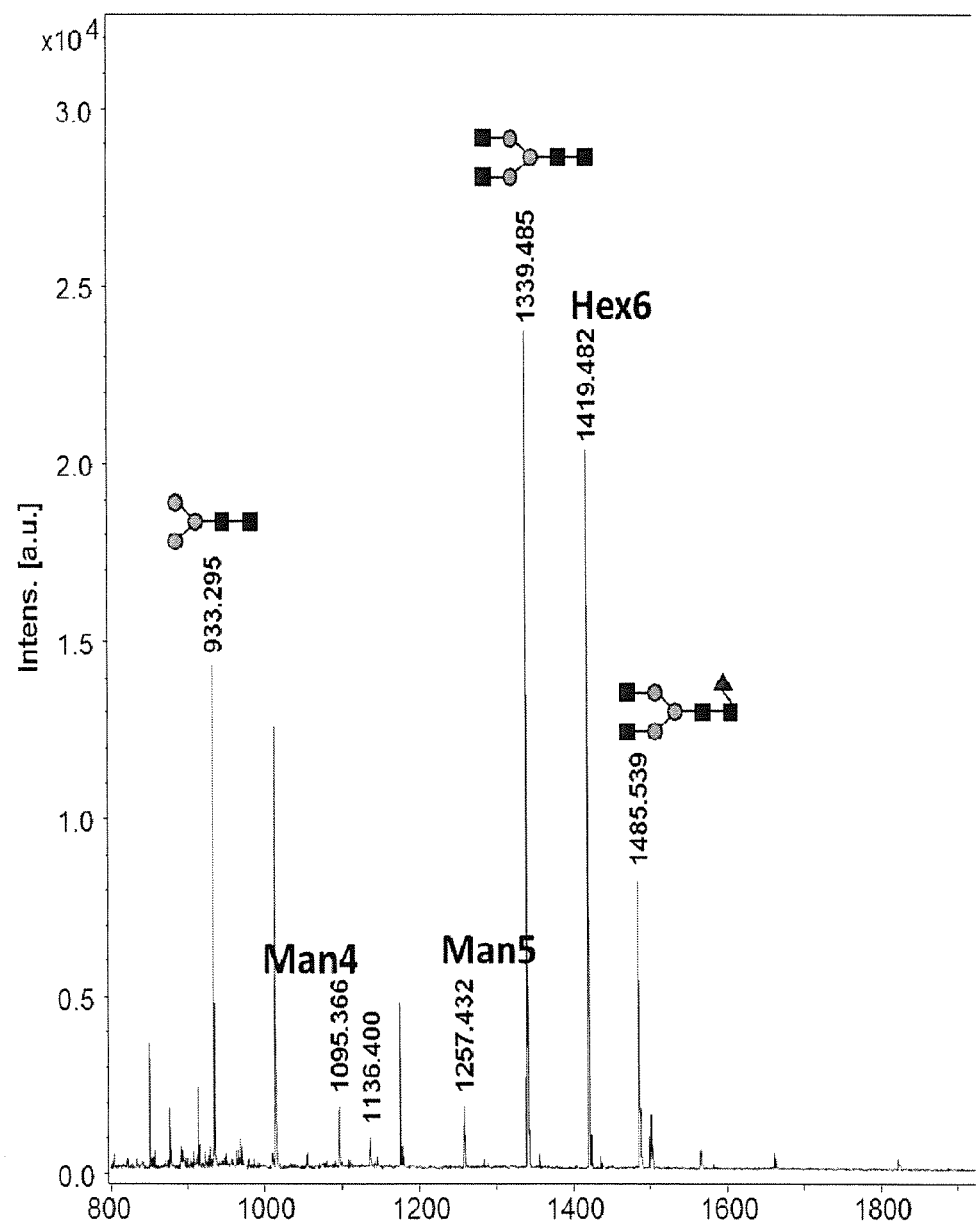
FIG. 4. Protein specific N-glycosylation (70 kDa supernatant protein).

The protein specific N-glycan analysis showed that there is FG0 both in ~70 kDa and ~55 kDa supernatant proteins (FIG. 4) ruling out the possibility that it would originate from the medium.

Figure 5:
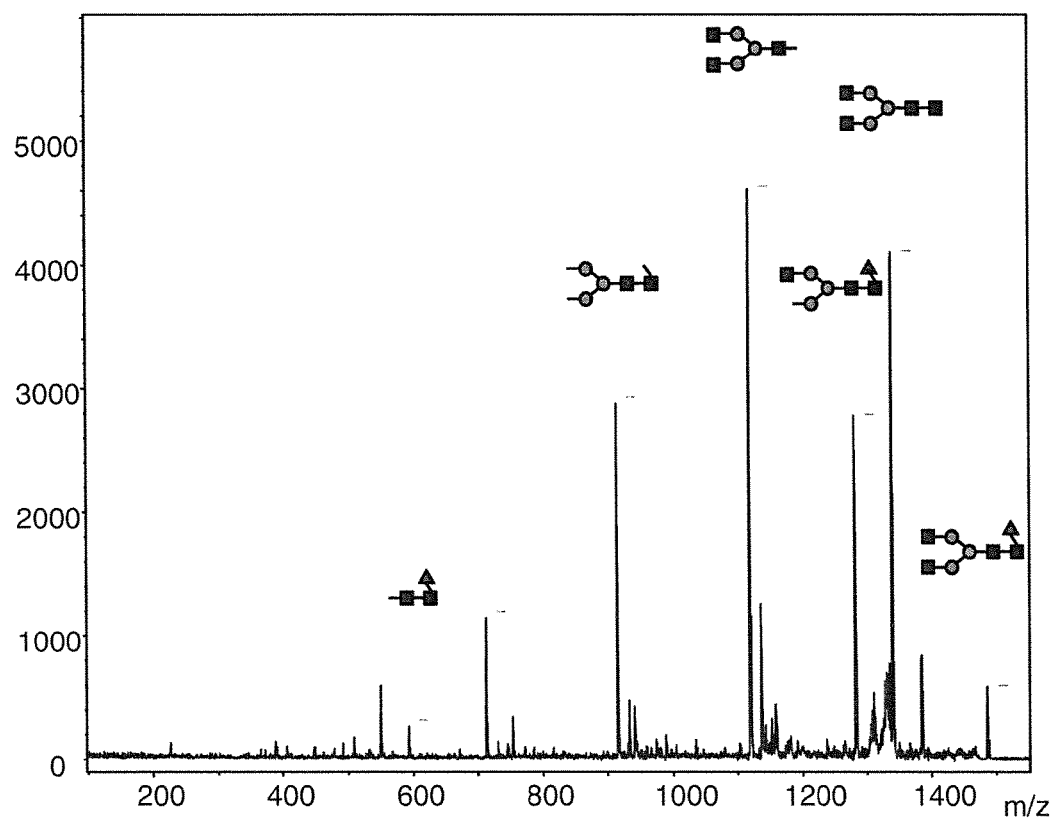
FIG. 5. Fragmentation analysis of m/z 1485 (FG0)

The fragmentation analysis of signal m/z 1485 [M+Na]$^+$ in its native form brought further proof that this signal is FG0 (FIG. 5). The signal m/z 1339 demonstrates the loss of fucose and the signal m/z 593 proves that the fucose is in N-glycan core.

Figure 6:
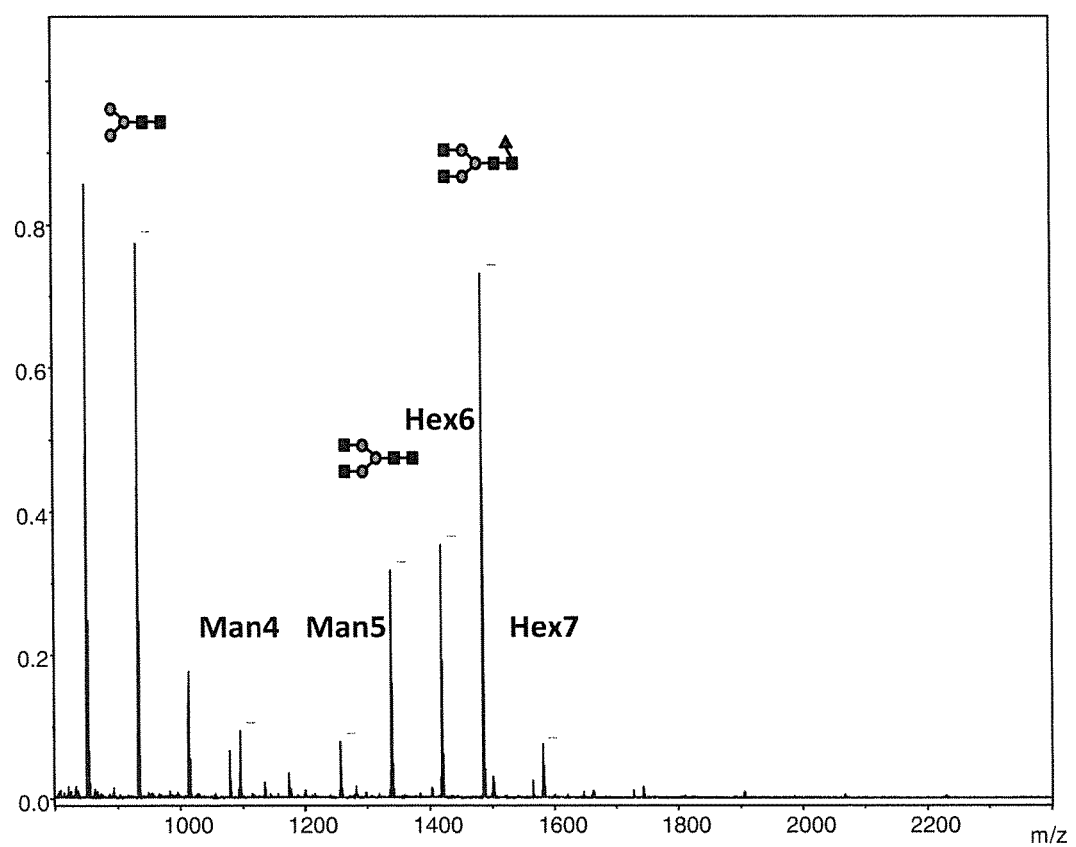
FIG. 6. Neutral N-glycans of day 7 supernatant proteins from fermentation of *T. reesei* fucosylation transformant 43A (M525).

In fermentation of the fucosylation transformant clone 43A (strain M525) the amount of FG0 increased until day 7 when there was 28% of FG0 (Table 7, FIG. 6).

TABLE 5

Relative proportions of neutral N-glycans from day 3 supernatant proteins of *T. reesei* fucosylation transformants (pTTv224 + pTTv225) and parental strain M289.

| | | | day 3 | | | | | | |
|---|---|---|---|---|---|---|---|---|---|
| Composition | Short | m\z | M289 % | #40A % | #40D % | #43A % | #43D % | #57A % | #57D % |
| Hex3HexNAc2 | Man3 | 933.31 | 0.00 | 26.31 | 18.08 | 18.47 | 14.89 | 18.70 | 15.68 |
| Hex4HexNAc2 | Man4 | 1095.37 | 0.00 | 2.12 | 1.37 | 2.56 | 2.72 | 2.45 | 2.38 |
| Hex3HexNAc3 | H3N3 | 1136.40 | 0.00 | 1.78 | 1.12 | 1.56 | 1.09 | 1.74 | 1.64 |
| Hex5HexNAc2 | Man5 | 1257.42 | 35.32 | 3.92 | 4.10 | 5.04 | 4.55 | 4.07 | 4.03 |
| Hex3HexNAc4 | G0 | 1339.48 | 0.84 | 31.28 | 40.02 | 30.22 | 44.59 | 30.58 | 42.92 |
| Hex6HexNAc2 | Hex6 | 1419.48 | 28.46 | 16.48 | 21.72 | 26.30 | 25.20 | 26.07 | 24.88 |
| Hex3HexNAc4dHex | FG0 | 1485.53 | 0.00 | 15.12 | 11.00 | 13.31 | 5.52 | 13.78 | 6.36 |
| Hex4HexNAc4 | H4N4 | 1501.53 | 0.00 | 2.41 | 1.72 | 1.24 | 0.66 | 1.31 | 0.81 |
| Hex7HexNAc2 | Hex7 | 1581.53 | 8.78 | 0.58 | 0.52 | 0.85 | 0.61 | 0.90 | 0.85 |
| Hex8HexNAc2 | Hex8 | 1743.58 | 15.77 | 0.00 | 0.26 | 0.30 | 0.18 | 0.31 | 0.37 |
| Hex9HexNAc2 | Hex9 | 1905.63 | 10.84 | 0.00 | 0.00 | 0.14 | 0.00 | 0.00 | 0.00 |
| Hex10HexNAc2 | Hex10 | 2067.69 | 0.00 | 0.00 | 0.10 | 0.00 | 0.00 | 0.10 | 0.08 |

TABLE 6

Relative proportions of neutral N-glycans from day 5 supernatant proteins of *T. reesei* fucosylation transformants (pTTv224 + pTTv225) and parental strain M289.

| | | | day 5 | | | | | | |
|---|---|---|---|---|---|---|---|---|---|
| Composition | Short | m\z | M289 % | #40A % | #40D % | #43A % | #43D % | #57A % | #57D % |
| Hex3HexNAc2 | Man3 | 933.31 | 12.53 | 27.43 | 15.03 | 16.11 | 17.63 | 19.30 | 18.28 |
| Hex4HexNAc2 | Man4 | 1095.37 | 2.01 | 2.60 | 3.26 | 3.74 | 3.41 | 3.75 | 2.78 |
| Hex3HexNAc3 | H3N3 | 1136.40 | 1.90 | 1.22 | 1.25 | 1.29 | 1.47 | 1.48 | 1.56 |
| Hex5HexNAc2 | Man5 | 1257.42 | 4.31 | 4.12 | 5.28 | 5.67 | 5.01 | 5.13 | 4.44 |
| Hex3HexNAc4 | G0 | 1339.48 | 61.17 | 28.65 | 35.89 | 25.43 | 36.03 | 24.59 | 39.55 |
| Hex6HexNAc2 | Hex6 | 1419.48 | 16.08 | 16.89 | 24.99 | 27.35 | 26.47 | 28.00 | 23.56 |
| Hex3HexNAc4dHex | FG0 | 1485.53 | 0.00 | 17.40 | 12.70 | 18.75 | 7.95 | 15.23 | 7.98 |
| Hex4HexNAc4 | H4N4 | 1501.53 | 0.73 | 1.04 | 0.80 | 0.83 | 0.73 | 1.26 | 0.96 |
| Hex7HexNAc2 | Hex7 | 1581.53 | 0.89 | 0.57 | 0.80 | 0.83 | 0.78 | 0.93 | 0.89 |
| Hex8HexNAc2 | Hex8 | 1743.58 | 0.37 | 0.00 | 0.00 | 0.00 | 0.35 | 0.31 | 0.00 |
| Hex9HexNAc2 | Hex9 | 1905.63 | 0.00 | 0.08 | 0.00 | 0.00 | 0.17 | 0.00 | 0.00 |
| Hex10HexNAc2 | Hex10 | 2067.69 | 0.00 | 0.00 | 0.00 | 0.00 | 0.00 | 0.00 | 0.00 |

TABLE 7

Relative proportions of neutral N-glycans from supernatant proteins of *T. reesei* strain M525 (pTTv224 + pTTv225 transformant clone 43A) fermented for 3, 4, 7 and 9 days.

| | | | M525 | | | |
|---|---|---|---|---|---|---|
| Composition | Short | m\z | d 3 % | d 4 % | d 7 % | d 9 % |
| Hex3HexNAc2 | Man3 | 933.31 | 11.96 | 19.40 | 30.87 | 38.24 |
| Hex4HexNAc2 | Man4 | 1095.37 | 5.35 | 3.68 | 4.09 | 3.70 |
| Hex3HexNAc3 | GnMan3 | 1136.40 | 0.00 | 1.16 | 0.96 | 1.07 |
| Hex5HexNAc2 | Man5 | 1257.42 | 7.56 | 4.10 | 3.25 | 3.13 |
| Hex3HexNAc3dHex | GnMan3F | 1282.45 | 0.00 | 0.94 | 0.78 | 0.89 |
| Hex3HexNAc4 | G0 | 1339.48 | 8.25 | 10.86 | 11.80 | 11.75 |
| Hex6HexNAc2 | Hex6 | 1419.48 | 54.34 | 35.42 | 14.74 | 12.64 |
| Hex3HexNAc4dHex | FG0 | 1485.53 | 6.45 | 19.62 | 27.93 | 20.88 |
| Hex4HexNAc4 | H4N4 | 1501.53 | 0.13 | 1.06 | 1.24 | 1.18 |
| Hex7HexNAc2 | Hex7 | 1581.53 | 5.30 | 3.19 | 3.11 | 3.42 |
| Hex8HexNAc2 | Hex8 | 1743.58 | 0.68 | 0.37 | 0.62 | 1.49 |
| Hex9HexNAc2 | Hex9 | 1905.63 | 0.00 | 0.14 | 0.38 | 1.02 |
| Hex10HexNAc2 | Hex10 | 2067.69 | 0.00 | 0.05 | 0.22 | 0.57 |

TABLE 8

Relative proportions of neutral N-glycans from day 5 supernatant proteins of *T. reesei* fucosylation transformants with GDP-Fuc transporter (pTTv224 + pTTv226).

| | | | d 5 | | | | | | | |
|---|---|---|---|---|---|---|---|---|---|---|
| Composition | Short | m\z | M289 % | #2B % | #3B % | #4B % | #5B % | #5D % | #12C % | #12D % |
| Hex3HexNAc2 | Man3 | 933.31 | 11.10 | 12.17 | 10.82 | 8.48 | 9.54 | 8.68 | 9.78 | 9.53 |
| Hex4HexNAc2 | Man4 | 1095.37 | 4.72 | 5.55 | 5.45 | 4.73 | 6.31 | 6.20 | 4.57 | 3.83 |

TABLE 8-continued

Relative proportions of neutral N-glycans from day 5 supernatant proteins of *T. reesei* fucosylation transformants with GDP-Fuc transporter (pTTv224 + pTTv226).

| | | | d 5 | | | | | | | |
|---|---|---|---|---|---|---|---|---|---|---|
| Composition | Short | m\z | M289 % | #2B % | #3B % | #4B % | #5B % | #5D % | #12C % | #12D % |
| Hex3HexNAc3 | GnMan3 | 1136.40 | 1.48 | 1.10 | 1.39 | 1.26 | 1.25 | 2.02 | 1.57 | 1.49 |
| Hex5HexNAc2 | Man5 | 1257.42 | 10.29 | 11.37 | 9.81 | 10.22 | 12.23 | 11.95 | 9.27 | 9.46 |
| Hex3HexNAc3dHex | GnMan3F | 1282.45 | 0.00 | 0.68 | 0.00 | 0.64 | 0.00 | 0.00 | 0.00 | 0.57 |
| Hex3HexNAc4 | G0 | 1339.48 | 40.88 | 20.12 | 25.76 | 16.66 | 12.88 | 17.64 | 29.43 | 14.29 |
| Hex6HexNAc2 | Hex6 | 1419.48 | 28.06 | 26.32 | 32.20 | 32.31 | 39.34 | 40.03 | 28.98 | 33.66 |
| Hex3HexNAc4dHex | FG0 | 1485.53 | 0.00 | 20.67 | 12.91 | 23.88 | 16.81 | 11.74 | 14.58 | 25.13 |
| Hex4HexNAc4 | G0 + Hex | 1501.53 | 0.61 | 0.58 | 0.31 | 0.28 | 0.22 | 0.24 | 0.73 | 0.32 |
| Hex7HexNAc2 | Hex7 | 1581.53 | 1.48 | 0.87 | 1.12 | 0.87 | 1.04 | 1.07 | 0.94 | 1.11 |
| Hex8HexNAc2 | Hex8 | 1743.58 | 0.69 | 0.33 | 0.23 | 0.44 | 0.38 | 0.16 | 0.14 | 0.60 |
| Hex9HexNAc2 | Hex9 | 1905.63 | 0.69 | 0.26 | 0.00 | 0.24 | 0.00 | 0.28 | 0.00 | 0.00 |

Protease assay

Figure 12:
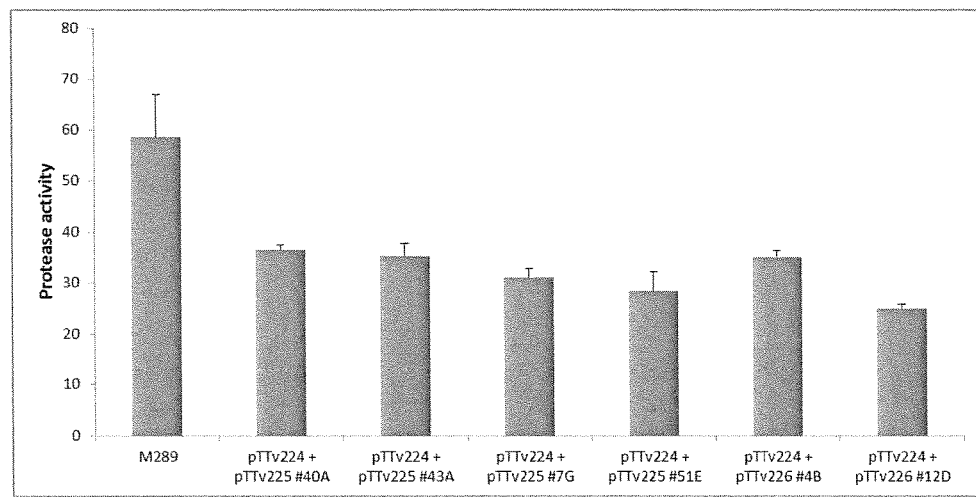

Total protease activity was measured with BODIPY casein FL (enzCheck protease assay kit #E6638, Molecular Probes) according to the manufacturer's protocol. The day 5 shake flask culture supernatants were analysed and the protease activity was normalised to the protein concentration (FIG. 12). All transformants showed decrease in protease activity by 40-55%, when compared to the parent strain M289.

Example 3

Cloning of *H. pylori* GMD and FX and Transformation into *T. reesei* and Production of GDP-Fucose The coding sequences of the *Helicobacter pylori* GMD and FX were codon optimized for *Trichoderma reesei* expression. The GMD and FX genes were cloned into a *T. reesei* expression vector between the gpdA promoter and trpC terminator. The GMD and FX expression plasmids were introduced into the *T. reesei* M124 strain by co-transformation with hygromycin resistance gene as the selective marker. 5 µg of circular plasmids were used for all three plasmids. The hygromycin marker gene is under the gpdA promoter and trpC terminator in the (pBluekan) plasmid used. Preparation of protoplasts and transformation were carried out essentially according to methods in Penttilä et al. (1987, Gene 61:155-164) and Gruber et al (1990, Curr. Genet. 18:71-76) for pyr4 selection. The transformed protoplasts were plated onto *Trichoderma* minimal media (TrMM) plates containing sorbitol and 150 µg/ml Hygromycin B.

Transformants were then streaked onto TrMM plates with 0.1% TritonX-100 and 125 µg/ml Hygromycin B for two successive rounds. Transformants growing fast as second selective streaks were screened by PCR using the primers listed in Table 9. DNA from mycelia was purified and analyzed by PCR to confirm the presence of the GMD, FX and hygromycin marker in the transformants. The genes are not targeted to specific loci in the genome and therefore ectopic integration will occur at random sites in the genome.

TABLE 9

List of primers used for PCR screening of *T. reesei* transformants

| GMD screening primers: | 664 bp product |
|---|---|
| Hp GMD forw | AAGATCGCCCTCATTACCGGCGT (SEQ ID NO: 110) |
| Hp GMD rev | TCCGAAGGGTATATCCGCCGT (SEQ ID NO: 111) |
| FX screening primers: | 1123 bp product |
| Hp FX forw | AGCGAGCTGTGCCTCTTGGA (SEQ ID NO: 167) |
| Hp FX rev | AGTCGAGCACTTGCGCGACCT (SEQ ID NO: 168) |
| Hygromycin resistance marker: | 1666 bp product |
| Ann 79 hph | TTTGTTGCCATATTTTCCTGC (SEQ ID NO: 169) |
| Hph-gene 3.1 PCR | TTGCCAGTGATACACATGGG (SEQ ID NO: 170) |

Nine transformants out of forty-two screened, were PCR positive for the presence of the GMD, FX and hygromycin marker. These transformants were purified to single cell clones and cultivated in shake flask cultures.

Quantification of relative amounts of GDP-Fuc from *T. reesei* strains expressing *H. pylori* GMD and FX Purification of nucleotide sugars from *T. reesei*. 80 ml of *T. reesei* cell culture medium was pelleted and boiled (diluted in 10 mM ammonium bicarbonate) for 5 minutes prior to homogenization with glass beads. Parallel 15 ml samples were collected for dry weight determination. The samples were stored at −20° C. The purification and analysis method has been described earlier in Räbinä et al, 2001, Glycoconjugate Journal, 18:799-805. The pellet from cell lysate was discarded and the solution was applied in carbograph column (sample equivalent to 9.6 mg of dry weight; Extract Clean Carbo 150 mg/4 ml column from Alltech; the column was equilibrated first with 4 ml of methanol and then with 8 ml of MQ-$H_2O$). The column was washed with 1) 2 ml of MQ-$H_2O$, 2) 2 ml of 25% ACN (acetonitrile), and 3) 2 ml of 50 mM TEAA (triethylammonium acetate) buffer, pH 7.0. Nucleotide sugars were eluted with 2 ml of 25% ACN in 50 mM TEAA buffer.

The sample was treated with 0.25 U of alkaline phosphatase (Shrimp alkaline phosphatase, Fermentas) in 50 it of 10 mM Tris-HCl pH 7.5, 10 mM $MgCl_2$, 0.1 mg/ml BSA at 37° C. for 4 h. The sample (dissolved in 10 mM $NH_4HCO_3$) was purified in DEAE Sepharose Fast Flow—column (1.3 ml, GE Healthcare, equilibrated with 10 mM $NH_4HCO_3$) by washing with 5 ml of 10 mM $NH_4HCO_3$ and eluting with 5 ml 250 mM $NH_4HCO_3$. Finally, prior to HPLC, the sample was purified with carbograph column as described above and dried. The sample was diluted in 15 it of 20 mM TEAA buffer (pH 6.0), 5 it was analyzed with ion-pair reversed phase UPLC.

Ion-pair reversed phase UPLC. For screening the transfected strains of *T. reesei*, nucleotide sugars were separated with ion-pair reversed phase UPLC using Acquity UPLC BEH C18-column (2.1×100 mm, 1.7 μm, Waters) and following gradient: Isocratic 20 mM TEAA buffer (pH 6.0) for 2.2 min, then linear gradient of 10% ACN in 20 mM TEAA buffer (pH 6.0) up to 20% over 2.8 min. Finally, the column was washed rising to 40% of 10% ACN in 20 mM TEAA buffer (pH 6.0) in 0.3 min and keeping there for 1 min. The amounts of nucleotide sugars were quantified integrating peak areas and comparing them to external standards.

Results

Nucleotide sugars from wild type (WT M124) and *T. reesei* strains transfected with *H. pylori* (pTTv19+21 51a) GDP-fucose synthesizing enzymes were quantified. A sample equal to 9.6 mg (cell pellet dry weight) was purified and one third was analyzed with ion-pair reversed phase UPLC. Samples from two culture media (with either lactose or glucose) and three time points were analyzed (days 3, 5, and 7). Quantification was performed by comparing to external nucleotide sugar standards. The relative amounts of GDP-fucose from transfected strains cultured in lactose containing medium were 18, 6, and 4 pmol/mg at days 3, 5, and 7, respectively, and in glucose containing medium 5, 4, and 4 pmol/mg at days 3, 5, and 7, respectively. No GDP-fucose was detected in wild type strain.

Example 4

Generation of single, double, triple, 4-, 5-, 6-, and 7-fold protease deletion strains

TABLE 10

Overview of generation of the single, double, triple, 4, 5, 6, 7, 8, 9, and 10-fold deletion strains.

| Strain | Vector | Clone | Strain transformed | Locus | Proteases k/o |
|---|---|---|---|---|---|
| M127 | 5-FOA of M124 | | | pyr4 mutant | None |
| M195 | pTTv71 | 9-35A-1 | M127 | K/o pep1 | pep1 |
| M196 | 5-FOA of M195 | 9-35A-1-1A | M195 | pyr4- of pyr4 loopout | pep1 |
| M219 | pTTv72 | 16-5AA | M196 | K/o tsp1 | pep1 tsp1 |
| M228 | 5-FOA of M219 | 16-5AA-1AA | M219 | pyr4- of pyr4 loopout | pep1 tsp1 |
| M277 | pTTv126 | 18-5A | M228 | K/o slp1 | pep1 tsp1 slp1 |
| M306 | 5-FOA of M277 | 2A | M277 | pyr4- of pyr4 loopout | pep1 tsp1 slp1 |
| M307 | pTTv117 | 117-37A | M306 | K/o gap1 | pep1 tsp1 slp1 gap1 |
| M321 | 5-FOA of M307 | 9A | M307 | pyr4- of pyr4 loopout | pep1 tsp1 slp1 gap1 |
| M369 | pTTv145 | 7-30A | M321 | K/o gap2 | pep1 tsp1 slp1 gap1 gap2 |
| M381 | 5-FOA of M369 | 14 | M369 | pyr4- of pyr4 loopout | pep1 tsp1 slp1 gap1 gap2 |
| M396 | pTTv181 | 25-120A | M381 | K/o pep4 | pep1 tsp1 slp1 gap1 gap2 pep4 |
| M402 | 5-FOA of M396 | 25-120A-62 | M396 | pyr4- of pyr4 loopout | pep1 tsp1 slp1 gap1 gap2 pep4 |
| M486 | pTTv205 | 34-14A-a | M402 | pep3 | pep1 tsp1 slp1 gap1 gap2 pep4 pep3 |
| M496 | 5-FOA of M486 | 2A-a | M486 | pyr4- of pyr4 loopout | pep1 tsp1 slp1 gap1 gap2 pep4 pep3 |
| M504 | pTTv229 | 38-48A | M496 | pep5 (Trire81004) | pep1 tsp1 slp1 gap1 gap2 pep4 pep3 pep5 |
| M521 | 5-FOA of M504 | 1a-1 | M504 | pyr4- of pyr4 loopout | pep1 tsp1 slp1 gap1 gap2 pep4 pep3 pep5 |
| M575 | pTTv245 | 42-45B | M521 | pep12 (tre119876) | pep1 tsp1 slp1 gap1 gap2 pep4 pep3 pep5 pep12 |
| M574 | pTTv246 | 41-45G | M521 | pep2 (tre53961) | pep1 tsp1 slp1 gap1 gap2 pep4 pep3 pep5 pep2 |
| M597 | 5-FOA of M574 | 1AA | M574 | pyr4- of pyr4 loopout | pep1 tsp1 slp1 gap1 gap2 pep4 pep3 pep5 pep2 |
| M658 | pTTv312 | 47-62B-1 | M597 | pep11 | pep1 tsp1 slp1 gap1 gap2 pep4 pep3 pep5 pep2 pep11 |

Deletion of pep1

1066 bp of 5' flanking region and 1037 bp of 3' flanking region were selected as the basis of the pep1 deletion plasmid. Fragments were produced by PCR. Products were separated with agarose gel electrophoresis and correct fragments were isolated from the gel with a gel extraction kit (Qiagen) using standard laboratory methods. Template DNA used in the amplification of the flanking regions was from the *T. reesei* wild type strain QM6a (ATCC13631).

For the yeast homologous recombination system used in cloning, overlapping sequences for the vector and the selection marker were placed to the appropriate PCR-primers. To enable marker switch in the construct, NotI restriction sites were introduced between the flanking regions and the selection marker. PmeI restriction sites were placed between the vector and the flanking regions for removal of vector sequence prior to transformation into *T. reesei*. Vector backbone pRS426 was digested with restriction enzymes (EcoRI and XhoI). The restriction fragments were then separated with agarose gel electrophoresis, and the correct fragments were isolated from the gel with a gel extraction kit (Qiagen) using standard laboratory methods.

To construct the deletion plasmid, the vector backbone and the appropriate marker and flanking region fragments were transformed into *Saccharomyces cerevisiae* (strain H3488/FY834). The yeast transformation protocol was based on the method for homologous yeast recombination described in the *Neurospora* knockouts workshop material of Colot and Collopy, (Dartmouth *Neurospora* genome protocols website), and the Gietz laboratory protocol (University of Manitoba, Gietz laboratory website). The plasmid DNA from the yeast transformants was rescued by transformation into *Escherichia coli*. A few clones were cultivated, plasmid DNA was isolated and digested to screen for correct recombination using standard laboratory methods. A few clones with correct insert sizes were sequenced and stored.

The first deletion plasmid for pep1 (plasmid pTTv41, Table 11) used another selection marker, bar. The flanking region and marker fragments were produced by PCR and assembled to a plasmid using the yeast recombination method described above. To clone the second pep1 deletion plasmid (pTTv71, Table 11), the bar marker was removed from the deletion plasmid pTTv41 with NotI digestion and replaced by the pyr4 blaster cassette using the yeast homologous recombination system. The pyr4 blaster cassette contains *T. reesei* pyr4 gene followed by 310 bp direct repeat from pyr4 5' untranslated region. The direct repeat enables removal of pyr4 gene under 5-FOA selection pressure via homologous recombination of the sequences and thus recycling of the selection marker. These deletion plasmids for pep1 (pTTv41 and pTTv71) result in 1874 bp deletion in the pep1 locus and cover the complete coding sequence of PEP1.

TABLE 11

Primers for generating pep1 deletion plasmids.

| Deletion plasmid pTTv41 for pep1 (TreID74156), vector backbone pRS426 | |
|---|---|
| Primer | Sequence |
| 5flankfw | GTAACGCCAGGGTTTTCCCAGTCACGACGGTTTAAAC GTATTGCGATGAGCAGCAGA (SEQ ID NO: 241) |
| 5flankrev | ATCCACTTAACGTTACTGAAATCTGGTCTCCTAACCCA CCAAG (SEQ ID NO: 242) |
| 3flankfw | CTCCTTCAATATCATCTTCTGTCTGTGAAATGAGGTCC CTTCC (SEQ ID NO: 243) |
| 3flankrev | GCGGATAACAATTTCACACAGGAAACAGCGTTTAAAC CAAACGCAGCAGAAACCATA (SEQ ID NO: 244) |
| PTfwd | GATTTCAGTAACGTTAAGTGGATGCGGCCGCGACAGA AGATGATATTGAAG (SEQ ID NO: 245) |
| PTrev | GACAGAAGATGATATTGAAGGAGGCGGCCGCTTAAG TGGATCCCGGTGAC (SEQ ID NO: 246) |

| Deletion plasmid pTTv71 for pep1 (TreID74156), vector backbone pTTv41 | |
|---|---|
| Primer | Sequence |
| T315_pyr4_for | GGTGGGTTAGGAGACCAGATTTCAGTAACGTTAAGTG GATGCGGCCGCCTAGCATCGACTACTGCTGC (SEQ ID NO: 247) |
| T316_pyr4_rev | GCAGCAGTAGTCGATGCTAGGCGCGCCATGCAAAGA TACACATCAA (SEQ ID NO: 248) |
| T317_yr4_loop_for | TTGATGTGTATCTTTGCATGGCGCGCCTAGCATCGAC TACTGCTGC (SEQ ID NO: 249) |
| T318_pyr4_loop_rev | AGGGACCTCATTTCACAGACAGAAGATGATATTGAAG GAGGCGGCCGCGGCTGATGAGGCTGAGAGAG (SEQ ID NO: 250) |

To enable recycling of the selection marker and allow rapid deletion of subsequent protease genes, pep1 was deleted from M127 (pyr4⁻ mutant of the basic strain M124) using the pyr4 blaster cassette described above. To remove the vector sequence, plasmid pTTv71 (Δpep1-pyr4) was digested with PmeI and the correct fragment was purified from an agarose gel using QIAquick Gel Extraction Kit (Qiagen). Approximately 5 µg of the pep1 deletion cassette was used to transform strain M127. Preparation of protoplasts and transformation for pyr4 selection were carried out essentially according to methods in Penttilä et al. (1987, Gene 61:155-164) and Gruber et al (1990, *Curr. Genet.* 18:71-76).

200 clones were picked as selective streaks and 24 transformants growing fast as selective streaks were screened by PCR using the primers listed in Table 12 for the correct integration using standard laboratory methods. Seven putative disruptants were purified to single cell clones. Deletion of pep1 was verified by Southern analyses from these clones. Southern analyses also verified that four of the clones were single integrants. Three clones indicated multiple or inaccurate integration of the deletion cassette and were discarded. Two pure clones were designated with strain numbers M181 (9-20A-1) and M195 (9-35A-1).

as the selection marker. The flanking region fragments were produced by PCR using the primers listed in Table 13. The products were separated with agarose gel electrophoresis and the correct fragments were isolated from the gel with gel extraction kit (Qiagen). Template DNA used in the PCR of the flanking regions was from the *T. reesei* wild type strain QM6a. The bar marker was obtained from pTTv41 with NotI digestion. The vector backbone was EcoRI/XhoI digested pRS426 as above. The plasmid was constructed using the yeast homologous recombination method as described above.

TABLE 12

Primers for screening integration of pep1 deletion constructs

For screening integration of pTTv41

| Primer | Sequence |
| --- | --- |
| T075_74156_5int | TCGCTGTAACGAACTTCTGT (SEQ ID NO: 251) |
| T032_Bar_end_for | CATTGTTGACCTCCACTAGC (SEQ ID NO: 252) |
| T076_74156_3int | GCTGCTGATCGGACATTTTT (SEQ ID NO: 253) |
| T031_Bar_begin_rev2 | GTTTCTGGCAGCTGGACT (SEQ ID NO: 254) |

For screening integration of pTTv71

| Primer | Sequence |
| --- | --- |
| T075_74156_5int | TCGCTGTAACGAACTTCTGT (SEQ ID NO: 255) |
| T027_Pyr4_orf_start_rev | TGCGTCGCCGTCTCGCTCCT (SEQ ID NO: 256) |

For screening deletion of pep1 ORF

| Primer | Sequence |
| --- | --- |
| T077_74156_5orf_pcr | CGACGATCTACAGCCATCTG (SEQ ID NO: 257) |
| T078_74156_3orf_pcr | ACCCAAAGCGTCCTTCATTA (SEQ ID NO: 22) |

Generation of pep1tsp1 double deletion strain M219

The deletion plasmids for the trypsin-like serine protease tsp1 (TreID71322/TreID73897) were constructed essentially as described for the pep1 deletion plasmids. 953 bp of 5' flanking region and 926 bp of 3' flanking region were selected as the basis of the tsp1 deletion plasmids. As for pep1, the first deletion plasmid for tsp1 (pTTv42) used bar as the selection marker.

To clone the second tsp1 deletion plasmid (pTTv72), the bar marker was removed from the deletion plasmid pTTv42 with NotI digestion. The pyr4 blaster cassette was obtained from pTTv71 with NotI digestion, ligated to NotI cut pTTv42 and transformed into *E. coli*. A few transformants were cultivated, plasmid DNA isolated and digested to screen for correct ligation and orientation of the pyr4 blaster cassette. One clone with correct insert size and orientation was sequenced and stored. These deletion plasmids for tsp1 (pTTv42 and pTTv72) result in a 1252 bp deletion in the tsp1 locus and cover the complete coding sequence of TSP1.

TABLE 13

Primers for generating tsp1 deletion plasmids.

Deletion plasmid pTTv42 for tsp1 (TreID71322/TreID73897), vector backbone pRS426

| Primer | Sequence |
| --- | --- |
| T303_71322_5f | GTAACGCCAGGGTTTTCCCAGTCACGACGGTTTAAACTGCTGTTGCTGTTTGTTGATG (SEQ ID NO: 259) |
| T304_71322_5r_pt | CCCGTCACCGAGATCTGATCCGTCACCGGGATCCACTTAAGCGGCCGCCTGTGGTGAGATCTCCAGACG (SEQ ID NO: 260) |
| T305_71322_3f_pt | GCCAAGCCCAAAAAGTGCTCCTTCAATATCATCTTCTGTCGCGGCCGCACTGTGCCCAACAATAAGCAG (SEQ ID NO: 261) |
| T306_71322_3r | GCGGATAACAATTTCACACAGGAAACAGCGTTTAAACCCAAGGCGCTGGCTGTTA (SEQ ID NO: 262) |

TABLE 13-continued

Primers for generating tsp1 deletion plasmids.

Deletion plasmid pTTv72 for tsp1 (TreID71322/TreID73897), vector backbone pTTv42

| Primer | Sequence |
|---|---|
| no new primers, pTTv42 digested with NotI and ligated with pyr4-loopout fragment from pTTv71 | |

To reuse pyr4 as the selection marker, removal of the pyr4 blaster cassette from the pep1 deletion strain M195 was carried out. Spores were spread onto minimal medium plates containing 20 g/l glucose, 2 g/l proteose peptone, 1 ml/l Triton X-100, 5 mM uridine and 1.5 g/l 5-FOA, pH 4.8. 5-FOA resistant colonies were picked after 5-7 days to 0.9% NaCl, suspended thoroughly by vortexing and filtrated through a cotton-filled pipette tip. To purify clones to single cell clones, filtrates were spread again onto plates described above. Purified clones were sporulated on plates containing 39 g/l potato dextrose agarose.

integration of the deletion cassette and also for the deletion of the tsp1 ORF. Four putative Δtsp1 clones were purified to single cell clones. Deletion of tsp1 was verified by Southern analyses. Southern analyses indicated that four transformants (clones 16-5AA, 16-5BA, 16-11 AA, 16-11 BA) were single integrants. The other clones were determined to carry additional copies somewhere else in the genome and were discarded. The clone (16-5AA) used in removal of the pyr4 blaster cassette (and to generate the triple deletion strain M277) was designated with strain number M219 (Δpep1Δtsp1).

TABLE 14

Primers for screening removal of pyr4 blaster cassette and for screening tsp1 integration and strain purity.

For screening removal of pyr4 blaster cassette from M195

| T083_74156_5a_seq | GATCGACAAAGGTTCCAGCG (SEQ ID NO: 263) |
| T084_74156_3a_seq | AATTGTATCATTCCGAGGCT (SEQ ID NO: 264) |

For screening integration of pTTv72

| Primer | Sequence |
|---|---|
| T307_71322_5int | CTGTTTGGCCCTCGAAACT (SEQ ID NO: 265) |
| T027_Pyr4_orf_start_rev | TGCGTCGCCGTCTCGCTCCT (SEQ ID NO: 266) |
| T308_71322_3int | TTCGCCATCCAAATTTCTTC (SEQ ID NO: 267) |
| T028_Pyr4_flank_rev | CATCCTCAAGGCCTCAGAC (SEQ ID NO: 268) |

For screening deletion of tsp/ORF

| T309_71322_5orfpcr | CCCAAGTCGTCTCAGCTCTC (SEQ ID NO: 269) |
| T310_71322_3orfpcr | TCGAAGGCTTCAGTGAGGTAA (SEQ ID NO: 270) |

These clones were tested for uridine auxotrophy by plating spores onto minimal medium plates (20 g/l glucose, 1 ml/l Triton X-100) where no growth was observed, indicating that the selected clones were pyr4-. All clones were further tested by PCR (using the primers listed in Table 14) for the removal of the blaster cassette and were shown to be correct. The clone (9-35A-1A-a) used to generate the double protease deletion strain (M219) was designated with strain number M196 (Δpep1, pyr4-).

To remove vector sequence, plasmid pTTv72 (Δtsp1-pyr4 loopout) was digested with PmeI and the correct fragment was purified from an agarose gel. Approximately 5 μg of the tsp1 deletion cassette was used to transform M196 (Δpep1, pyr4-). Preparation of protoplasts and transformation were carried out using pyr4 selection essentially as described for the pep1 deletion strains M181 and M195 as described above.

Over 100 colonies were picked and 48 were screened by PCR using the primers listed in Table 14 for the correct Generation of pep1 tsp1 slp1 triple deletion strain M277

The deletion plasmid for the subtilisin-like protease slp1 (TreID51365) was constructed essentially as described for pep1 deletion plasmid pTTv41. 1094 bp of 5' flanking regions and 1247 bp of 3' flanking region were selected as the basis of the slp1 deletion plasmid. Fragments were produced by PCR using the primers listed in Table 15. The products were separated with agarose gel electrophoresis and the correct fragments were isolated from the gel with gel extraction kit (Qiagen) using standard laboratory methods. Template used in the PCR of the flanking regions was from the *T. reesei* wild type strain QM6a. The pyr4 blaster cassette was obtained from pTTv71 with NotI digestion. The vector backbone was EcoRI/XhoI digested pRS426 and the plasmid was constructed using the yeast homologous recombination method as described above. This deletion plasmid for slp1 (pTTv126) results in 2951 bp deletion in the slp1 locus and covers the complete coding sequence of SLP1.

TABLE 15

Primers for generating slp1 deletion plasmid.
Deletion plasmid pTTv126 for slp1 (TreID51365), vector backbone pRS426

| Primer | Sequence |
|---|---|
| 5flankfw_vect | GTAACGCCAGGGTTTTCCCAGTCACGACGGTTTAAACAT CTCGGAGTGATGCTTCCT (SEQ ID NO: 271) |
| slp1_5flankrev_pyr4Prom | GCGCTGGCAACGAGAGCAGAGCAGCAGTAGTCGATGCT AGGCGGCCGCATCAGACGAAACCAGACGAG (SEQ ID NO: 272) |
| slp1_3flankfw_pyr4Term | CAACCAGCCGCAGCCTCAGCCTCTCTCAGCCTCATCAG CCGCGGCCGCGCGAATCGAGTTGATGATTC (SEQ ID NO: 273) |
| 3flankrev_vect | GCGGATAACAATTTCACACAGGAAACAGCGTTTAAACCT GGTTGGGATCTGACCACT (SEQ ID NO: 274) |

To generate a marker-free triple protease deletion strain, the looping out of the pyr4 marker was applied to strain M219 essentially as described above for looping out pyr4 from the single protease deletion strain Δpep1. Three consecutive 5-FOA selection steps were carried out to ensure that the clones selected were originating from single cells. Final clones were verified for the looping out of pyr4 by PCR (using the primers listed in Table 16); no specific signals were seen with primers annealing with the looped out part of the pyr4. The looping out was further verified by plating the clones onto minimal medium plates with or without 5 mM uridine. The clone used to generate the triple protease deletion strain was designated with strain number M228 (Δpep1Δtsp1, pyr4-).

To remove vector sequence, plasmid pTTv126 (Δslp1-pyr4 loopout) was digested with PmeI and the correct fragment purified from an agarose gel using QIAquick Gel Extraction Kit (Qiagen). Approximately 5 µg of the slp1 deletion cassette was used to transform M228 (Δpep1Δtsp1, pyr4-) above. Preparation of protoplasts and transformation were carried out essentially as described above for the strains M181 and M195 using pyr4 selection.

200 clones were picked as first streaks and 48 of these streaks were screened by PCR using the primers listed in Table 16 for the correct integration. Five putative triple protease disruptants were purified to single cell clones. Deletion of slp1 was verified by Southern analyses of the five clones and three of the clones were single integrants. The clone used in removal of the pyr4 blaster cassette (and to generate the quadruple protease deletion strain M307 below) was designated with strain number M277 (Δpep1Δtsp1Δslp1).

TABLE 16

Primers for screening removal of pyr4 blaster cassette and for screening slp1 integration and strain purity.

For screening removal of pyr4 blaster cassette from M219

| Primer | Sequence |
|---|---|
| T307_71322_5int | CTGTTTGGCCCTCGAAACT (SEQ ID NO: 275) |
| T026_Pyr4_orf_5rev2 | CCATGAGCTTGAACAGGTAA (SEQ ID NO: 276) |
| T308_71322_3int | TTCGCCATCCAAATTTCTTC (SEQ ID NO: 277) |
| T028_Pyr4_flank_rev | CATCCTCAAGGCCTCAGAC (SEQ ID NO: 278) |

For screening integration of pTTv126

| Primer | Sequence |
|---|---|
| T079_slp1_scrn_5forw | GCAGACAAACAGAGCAACGA (SEQ ID NO: 279) |
| T026_Pyr4_orf_5rev2 | CCATGAGCTTGAACAGGTAA (SEQ ID NO: 280) |
| T080_slp1_scrn_3rev | TAGAGGGTGTCGATGGAAGC (SEQ ID NO: 281) |
| T028_Pyr4_flank_rev | CATCCTCAAGGCCTCAGAC (SEQ ID NO: 282) |

For screening deletion of slp/ORF

| Primer | Sequence |
|---|---|
| T081_slp1_orf_fw | GGTCTCTTCTTTGCCAGCAC (SEQ ID NO: 283) |
| T082_slp1_orf_rev | TGTCGCTGAACTGAATTTGC (SEQ ID NO: 284) |

Generation of quadruple protease deletion strain M307

To generate a marker-free triple protease deletion strain, removal of the pyr4 blaster cassette was applied to strain M277 essentially as described above. Three consecutive 5-FOA selection steps were carried out to ensure that the clones selected were originating from single cells. Final clones were verified for the removal of the blaster cassette by PCR using the primers listed in Table 18 and by plating the clones onto minimal medium plates with or without 5 mM uridine. The clone used to generate the quadruple protease deletion strain was designated with strain number M306 (Δpep1Δtsp1Δslp1, pyr4-).

The deletion plasmid pTTv117 for the glutamic protease gap1 (TreID69555) was constructed essentially as described for pep1 deletion plasmid pTTv41. 1000 bp of 5' flanking region and 1100 bp of 3' flanking region were selected as the basis of the gap1 deletion plasmid. Flanking region fragments were produced by PCR using the primers listed in Table 17. The products were separated with agarose gel electrophoresis and the correct fragments were isolated from the gel with gel extraction kit (Qiagen). Template DNA used in the PCR of the flanking regions was from the *T. reesei* wild type strain QM6a. The pyr4 blaster cassette was obtained from pTTv71 with NotI digestion. The vector backbone was EcoRI/XhoI digested pRS426 and the plasmid was constructed using the yeast homologous recombination method as described above. This deletion plasmid for gap1 (pTTv117) resulted in a 1037 bp deletion in the gap1 locus and covers the complete coding sequence of GAP1.

TABLE 17

Primers for generating gap1 deletion plasmid.
Deletion plasmid pTTv117 for gap1 (TreID69555), vector backbone pRS426

| Primer | Sequence |
| --- | --- |
| JJ-045 primer | GATTAAGTTGGGTAACGCCAGGGTTTTCCCAGTCACGACG GTTTAAACACCTCATGAGGGACTATGG (SEQ ID NO: 285) |
| JJ-046 primer | GCGCTGGCAACGAGAGCAGAGCAGCAGTAGTCGATGCTAG GCGGCCGCCAAGAAGAGGCAGAGGGTAAT (SEQ ID NO: 286) |
| JJ-047 primer | CAACCAGCCGCAGCCTCAGCCTCTCTCAGCCTCATCAGCC GCGGCCGCCTATACATACTGATGATACA (SEQ ID NO: 287) |
| JJ-048 primer | TGGAATTGTGAGCGGATAACAATTTCACACAGGAAACAGCG TTTAAACGCCCCATGTATGGACTCTAC (SEQ ID NO: 288) |

To remove vector sequence, plasmid pTTv117 was digested with PmeI and the correct fragment purified from an agarose gel using QIAquick Gel Extraction Kit (Qiagen). Approximately 5 μg of the gap1 deletion cassette was used to transform M306 (Δpep1Δtsp1Δslp1, pyr4-) above. Preparation of protoplasts and transformation were carried out essentially as described for the strains M181 and M195 using pyr4 selection.

150 clones were picked as first streaks and 48 of these streaks were screened by PCR using the primers listed in Table 18 for the correct integration. Eight putative quadruple protease disruptants were purified to single cell clones. Deletion of gap1 was verified by Southern analyses of the eight clones and it verified that three of the clones were single integrants. The clone used in removal of the pyr4 blaster cassette (and to generate the quintuple protease deletion strain M369 below) was designated with strain number M307 (Δpep1Δtsp1Δslp1Δgap1).

TABLE 18

Primers for screening removal of pyr4 blaster cassette and for screening gap1 integration and strain purity.

For screening removal of pyr4 blaster cassette from M277

| Primer | Sequence |
| --- | --- |
| T079_slp1_scrn_5forw | GCAGACAAACAGAGCAACGA (SEQ ID NO: 289) |
| T026_Pyr4_orf_5rev2 | CCATGAGCTTGAACAGGTAA (SEQ ID NO: 290) |
| T080_slp1_scrn_3rev | TAGAGGGTGTCGATGGAAGC (SEQ ID NO: 291) |
| T028_Pyr4_flank_rev | CATCCTCAAGGCCTCAGAC (SEQ ID NO: 292) |

For screening integration of pTTv117

| Primer | Sequence |
| --- | --- |
| T052_gap1_5screen_F | CTCAGAAAGGTTGTAGTTGTGA (SEQ ID NO: 293) |
| T026_Pyr4_orf_5rev2 | CCATGAGCTTGAACAGGTAA (SEQ ID NO: 294) |
| T053_gap1_3screen_R | GATGTTGTGTTTTCAGTCTGCA (SEQ ID NO: 295) |
| T028_Pyr4_flank_rev | CATCCTCAAGGCCTCAGAC (SEQ ID NO: 296) |

TABLE 18-continued

Primers for screening removal of pyr4 blaster cassette and for screening gap1 integration and strain purity.

For screening deletion of gap1 ORF

| | |
|---|---|
| T109_gap1_ORF_F | ATGTTCATCGCTGGCGTCG (SEQ ID NO: 297) |
| T110_gap1_ORF_R | CTAAACGTAAGAGCAGGTCAA (SEQ ID NO: 298) |

Generation of quintuple Protease deletion strain M369

To generate a marker-free quadruple protease deletion strain, removal of the pyr4 blaster cassette was applied to strain M307 essentially as described above. Three consecutive 5-FOA selection steps were carried out and the final clones were verified for the removal of the blaster cassette by PCR using the primers listed in Table 20 and by plating the clones onto minimal medium plates with or without 5 mM uridine. The clone used to generate the quintuple protease deletion strain was designated with strain number M321 (Δpep1Δtsp1Δslp1Δgap1, pyr4-).

The pTTv145 deletion plasmid for the glutamic protease gap2 (TreID106661) was constructed essentially as described for pep1 deletion plasmid pTTv41. 1021 bp of 5' flanking region and 1010 bp of 3' flanking region were selected as the basis of the gap2 deletion plasmid. In this plasmid the direct repeat fragment of the pyr4 blaster cassette was changed from pyr4 5'UTR to 320 bp direct repeat from the end of gap2 5' flanking region and no AscI site was added between the pyr4 and the 5' direct repeat. Fragments were produced by PCR using the primers listed in Table 19 and the products were separated with agarose gel electrophoresis and the correct fragments were isolated from the gel with gel extraction kit (Qiagen). Template DNA used in the PCR of the flanking regions was the *T. reesei* wild type strain QM6a. The pyr4 marker gene was obtained from pHHO5 with NotI digestion and the vector backbone was EcoRI/XhoI digested pRS426. The plasmid was constructed using the yeast homologous recombination method as described above. This deletion plasmid for gap2 (pTTv145) results in a 944 bp deletion in the gap2 locus and covers the complete coding sequence of GAP2.

TABLE 19

Primers for generating gap2 deletion plasmid.
Deletion plasmid pTTv145 for gap2 (TreID106661), vector backbone pRS426

| Primer | Sequence |
|---|---|
| T101_gap2_5flank_F_pRS426 | GATTAAGTTGGGTAACGCCAGGGTTTTCCCAGTCA CGACGGTTTAAACGCTACTACGCGAGCAAGTG (SEQ ID NO: 299) |
| T102_gap2_5flank_R_pyr4 | GGAACTGTCGGCGATTGGGAGAATTTCGTGCGAT CGCGGCGGCCGCCGGATGAAGATGTGCAGTTG (SEQ ID NO: 300) |
| T103gap2-loop_F_pyr4 | AGGGAACATATCACCCTCGGGCATTTTTCATTTGG TAGGCGGCCGCTAAGATATCTTCAAGCTTATGCG (SEQ ID NO: 301) |
| T104gap2-loop_R | CGGATGAAGATGTGCAGTTG (SEQ ID NO: 302) |
| T105gap2_3flank_F_loop | TGTCTCACTTCCACCCATCTCAACTGCACATCTTC ATCCGAGCAACAACATGAGGTTCGAA (SEQ ID NO: 303) |
| T106_gap2_3flank_R_pRS426 | CCTATGTTGTGTGGAATTGTGAGCGGATAACAATT TCACAGTTTAAACACAACGCATGTCCAGCTTTTG (SEQ ID NO: 304) |

To remove vector sequence, plasmid pTTv145 (Δgap2-pyr4 loopout) was digested with PmeI and the correct fragment purified from an agarose gel using QIAquick Gel Extraction Kit (Qiagen). Approximately 5 μg of the gap2 deletion cassette was used to transform M321. Preparation of protoplasts and transformation were carried out essentially as described above.

100 clones were picked as first streaks and all 20 growing streaks were screened by PCR using the primers listed in Table 20 for the correct integration. 10 putative quintuple protease disruptants (Δpep1Δtsp1Δslp1Δgap1Δgap2) were purified to single cell clones and rescreened by PCR and one purified clone was negative for the gap2 ORF. The gap2 deletion was verified by Southern analyses of the clone. The clone 7-30A was designated with strain number M369 (Δpep1Δtsp1Δslp1Δgap1Δgap2) and it was used for removal of the pyr4 blaster cassette and to generate the 6-fold protease deletion strain M396.

TABLE 20

Primers for screening removal of pyr4 blaster cassette and for screening gap2 integration and strain purity.

For screening removal of pyr4 blaster cassette from M307

| Primer | Sequence |
| --- | --- |
| T052_gap1_5screen_F | CTCAGAAAGGTTGTAGTTGTGA (SEQ ID NO: 305) |
| T026_Pyr4_orf_5rev2 | CCATGAGCTTGAACAGGTAA (SEQ ID NO: 306) |
| T053_gap1_3screen_R | GATGTTGTGTTTTCAGTCTGCA (SEQ ID NO: 307) |
| T028_Pyr4_flank_rev | CATCCTCAAGGCCTCAGAC (SEQ ID NO: 308) |

For screening integration of pTTv145

| Primer | Sequence |
| --- | --- |
| T048_gap2_5screen_F | GCTTGGCATCACGGAAGCT (SEQ ID NO: 309) |
| T026_Pyr4_orf_5rev2 | CCATGAGCTTGAACAGGTAA (SEQ ID NO: 310) |
| T049_gap2_3screen_R | TTGACAAGAAAGGTCCGGTTG (SEQ ID NO: 311) |
| T028_Pyr4_flank_rev | CATCCTCAAGGCCTCAGAC (SEQ ID NO: 312) |

For screening deletion of gap2 ORF

| T107_gap2_ORF_F | ATGGATGCTATCCGAGCCAG (SEQ ID NO: 313) |
| --- | --- |
| T108_gap2_ORF-R | CTATTCATACTCAACAGTCACA (SEQ ID NO: 314) |

Generation of 6-fold protease deletion strains M396

To generate a marker-free quintuple protease deletion strain, removal of the pyr4 marker was applied to strain M369 essentially as described above. Three consecutive 5-FOA selection steps were carried out to ensure that the clones selected were originating from single cells and the final clones were verified by PCR using the primers listed in Table 22. Removal was further verified by plating the clones onto minimal medium plates with or without 5 mM uridine and by Southern analyses. The clone used to generate the 6-fold protease deletion strain was designated with strain number M381 (Δpep1Δtsp1Δslp1Δgap1Δgap2, pyr4-).

The deletion plasmid pTTv181 for the sixth protease gene, aspartic protease pep4 (TreID77579) was constructed essentially as described above for the pTTv1. 959 bp of 5' flanking region and 992 bp of 3' flanking region were selected as the basis of the pep4 deletion plasmid. As for pep1, the first deletion plasmid for pep4 (pTTv43, Table 21) carried another selection marker, bar, which was replaced with the pyr4 blaster cassette. The blaster cassette was obtained from pTTv71 with NotI digestion, ligated to NotI cut pTTv43, and then transformed into E. coli. A few transformants were cultivated, plasmid DNA isolated and digested to screen for correct ligation and orientation of the pyr4 blaster cassette. One clone with correct insert size and orientation was sequenced and stored (pTTv73, Table 21).

The blaster cassette was changed: the direct repeat fragment used in removal of pyr4 was changed from 308 bp of pyr4 5'UTR to 300 bp direct repeat from the end of pep4 5' flanking region (as in pTTv145, gap2-pyr4). This was made by removing the existing pyr4 blaster cassette from pTTv73 with NotI digestion. The pyr4 gene was amplified by PCR using pTTv73 as a template using the primers in Table 21. For the yeast homologous recombination system used in cloning, overlapping sequences for the vector were placed to the appropriate PCR-primers. To enable marker switch in the construct, NotI restriction sites were introduced on both sides of the pyr4 selection marker and for additional cloning steps an AscI site was introduced between the pep4 5'direct repeat and 3' flank. This type of blaster cassette should not leave any additional sequence to the locus of the deleted gene after excision. The 300 bp pep4 5'direct repeat was amplified by PCR using the T. reesei wild type strain QM6a as a template. Products were separated with agarose gel electrophoresis and the correct fragments were isolated from the gel with gel extraction kit (Qiagen). A few of the clones obtained from the recombination were cultivated, and plasmid DNA was isolated and digested to screen for correct recombination. These deletion plasmids for pep4 (pTTv43, pTTv73 and pTTv181, Table 21) result in a 1413 bp deletion in the pep4 locus and cover the complete coding sequence of PEP4.

TABLE 21

Primers for generating pep4 deletion plasmids.

Deletion plasmid pTTv43 for pep4 (TreID77579), vector backbone pRS426

| Primer | Sequence |
| --- | --- |
| T298_77579_5f | GTAACGCCAGGGTTTTCCCAGTCACGACGGTTTAAA CTCAGGTCAACCACCGAGGAC (SEQ ID NO: 35) |
| T299_77579_5r_pt | CCCGTCACCGAGATCTGATCCGTCACCGGGATCCAC TTAAGCGGCCGCTGAATGGGATGGTTCGATTG |
| T300_77579_3f_pt | GCCAAGCCCAAAAAGTGCTCCTTCAATATCATCTTCT GTCGCGGCCGCAGGTAGACGCTTTGCGAGTG |

TABLE 21-continued

Primers for generating pep4 deletion plasmids.

| | |
|---|---|
| T301_77579_3r | GCGGATAACAATTTCACACAGGAAACAGCGTTTAAAC TGAACTGACGCGGACTGA (SEQ ID NO: 60) |

Deletion plasmid pTTv73 for pep4 (TreID77579), vector backbone pTTv43

| Primer | Sequence |
|---|---|
| no new primers, pTTv43 digested with NotI and ligated with pyr4-loopout fragment from pTTv71 | |

Deletion plasmid pTTv181 for pep4 (TreID77579), vector backbone pTTv73

| Primer | Sequence |
|---|---|
| T209_pyr4_f_recpep4_5f | AAGTTCCCTTCCTCTGGCAGCAATCGAACCATCCCAT TCAGCGGCCGCCTAGCATCGACTACTGCTGC (SEQ ID NO: 315) |
| T210_pyr4_r | CATGCAAAGATACACATCAA (SEQ ID NO: |
| T211_pep4_loop_f_recpyr4 | TGATTGTACCCCAGCTGCGATTGATGTGTATCTTTGC ATGGCGGCCGCTCAATGTTGACTGCCCCAGG (SEQ ID NO: 316) |
| T212_pep4_loop_r_recpep4_3f | GCACTTCTTAGATACACACACTCGCAAAGCGTCTA CCTGGCGCGCCTGAATGGGATGGTTCGATTG (SEQ ID NO: 317) |

To remove vector sequence, plasmid pTTv181 (Δpep4-pyr4 loopout) was digested with PmeI and the correct fragment purified from an agarose gel using QIAquick Gel Extraction Kit (Qiagen). Approximately 5 μg of the pep4 deletion cassette was used to transform M381. Preparation of protoplasts and transformation were carried out essentially as described above.

Over 200 transformants were picked as first streaks and 32 growing streaks were screened by PCR using the primers listed in Table 22 for correct integration. Seven clones gave the expected signals and were purified to single cell clones and rescreened by PCR using the primers of Table 22. Deletion of pep4 was verified also by Southern analyses from five clones. Southern analyses also indicated that all transformants were single integrants. Clone 25-120A used for removal of the pyr4 blaster cassette (and in generation of the 7-fold protease deletion strain) was designated with strain number M396.

Generation of 7-Fold deletion strain M486

The first deletion plasmid pTTv188 for the seventh protease gene, aspartic protease pep3 (TreID121133) was constructed essentially as described for Δpep1 plasmid pTTv41 above. 1215 bp of 5' flanking region and 1082 bp of 3' flanking region were selected as the basis of the pep3 deletion plasmid. In this plasmid the direct repeat fragment is a 300 bp stretch from the end of pep3 5' flanking region. Fragments were produced by PCR using the primers listed in Table 23. NotI restriction sites were introduced on both sides of the pyr4 selection marker and for additional cloning steps and AscI site was introduced between the pep3 5'direct repeat and 3' flank. The products were separated with agarose gel electrophoresis and the correct fragments were isolated from the gel with gel extraction kit (Qiagen). Template used in the PCR of the flanking regions was the *T. reesei* wild type strain QM6a. The pyr4 marker gene was obtained from pTTv181 with NotI digestion. The vector backbone was EcoRI/XhoI digested pRS426 and the plas-

TABLE 22

Primers for screening removal of pyr4 blaster cassette from M369 and for screening pep4 integration and strain purity.

For screening removal of pyr4 blaster cassette from M369

| Primer | Sequence |
|---|---|
| T222_gap2_5f_f2 | GGCAGGTCGCAGAGCAAGACA (SEQ ID NO: 318) |
| T049_gap2_3screen_R | TTGACAAGAAAGGTCCGGTTG (SEQ ID NO: 319) |

For screening integration of pTTv181

| Primer | Sequence |
|---|---|
| T302_77579_5int | GATTCATCACAGGGGCAGTC (SEQ ID NO: 320) |
| T027_Pyr4_orf_start_rev | TGCGTCGCCGTCTCGCTCCT (SEQ ID NO: 321) |
| T415_77579_3screen | ACGCCGTTGCTGAGCCTTG (SEQ ID NO: 322) |
| T061_pyr4_orf_screen_2F | TTAGGCGACCTCTTTTTCCA (SEQ ID NO: 323) |

For screening deletion of pep4 ORF

| Primer | Sequence |
|---|---|
| T416_77579_probeF | GAGCCCATCATCAACACCTC (SEQ ID NO: 324) |
| T417_77579_probeR | TGCCAAGGTCGTAGACGGA (SEQ ID NO: 325) | mid was constructed using the yeast homologous recombination method as described above.

The second deletion plasmid for the aspartic protease pep3 (TreID121133), pTTv192, was constructed using the plasmid pTTv188 above as the backbone. This second plasmid carries a native KEX2 (TreID123156) overexpression cassette and uses acetamidase (AmdS) gene from *Aspergillus nidulans* as the selection marker. The pyr4 blaster cassette was removed from pTTv188 with NotI-AscI double digestion. The fragments for cDNA1 promoter (template: pTHN3 plasmid DNA), native kex2 (template: *T. reesei* QM6a genomic DNA), trpC terminator (template: pHHO2 plasmid DNA) and AmdS marker (template: pHHO1 plasmid DNA) were produced by PCR using the primers listed in Table 23. As for pTTv188 above, to enable marker switch in the construct, NotI restriction sites were introduced on both sides of the AmdS selection marker. The products were separated with agarose gel electrophoresis and the correct fragments were isolated from the gel with gel extraction kit (Qiagen) and the plasmid was constructed using the yeast homologous recombination method as described above.

The third deletion plasmid for the aspartic protease pep3 (TreID121133), pTTv205, was constructed using the plasmid pTTv192 above as the backbone. The AmdS marker was removed from pTTv192 with NotI digestion. Fragments for a new pyr4 blaster cassette (located after the KEX2 overexpression cassette) were produced by PCR using the primers listed in Table 23. In this blaster cassette, the direct repeat is a 300 bp stretch from the beginning of the pep3 3' flanking region and located before the pyr4 gene. As for pTTv192 above, to enable marker switch in the construct, NotI restriction sites were introduced on both sides of the pyr4 blaster cassette. The products were separated with agarose gel electrophoresis and the correct fragments were isolated from the gel with gel extraction kit (Qiagen) and the plasmid was constructed using the yeast homologous recombination method as described above.

These deletion plasmids for pep3 (pTTv188, pTTv192 and pTTv205, Table 23) result in a 2590 bp deletion in the pep3 locus and cover the complete coding sequence of PEP3.

TABLE 23

Primers for generating pep3 deletion plasmids.

Deletion plasmid pTTv188 for pep3 (TreID121133), vector backbone pRS426

| Primer | Sequence |
| --- | --- |
| T346_pep3_5f_for | GGTAACGCCAGGGTTTTCCCAGTCACGACGGTTTAAA CGTCGAGCCCCCTGGACACCT (SEQ ID NO: 326) |
| T347_pep3_5f_rev | GCGCTGGCAACGAGAGCAGAGCAGCAGTAGTCGATG CTAGGCGGCCGCCATCGCCGTCGCGGACATGA (SEQ ID NO: 327) |
| T348_pep3_loop_for | TGATTGTACCCCAGCTGCGATTGATGTGTATCTTTGC ATGGCGGCCGCTCGACGTTGTATCTGCACTC (SEQ ID NO: 328) |
| T349_pep3_loop_rev | GTACGTTCTGATTGCCAACTACGGACCAGACCAGGG CTCCGGCGCGCCCATCGCCGTCGCGGACATGA (SEQ ID NO: 329) |
| T350_pep3_3f_for | GGAGCCCTGGTCTGGTCCGT (SEQ ID NO: 330) |
| T351_pep3_3f_rev | AGCGGATAACAATTTCACACAGGAAACAGCGTTTAAA CACGCGCTTCAACATGCCCCA (SEQ ID NO: 331) |

Deletion plasmid pTTv192 for pep3 (TreID121133), vector backbone pTTv188

| Primer | Sequence |
| --- | --- |
| T389_cDNApromoter_pep3flank | GCTGGCCGCTGGGAATAGCGTCATGTCCGCGACGGC GATGGAATTCGGTCTGAAGGACGT (SEQ ID NO: 332) |
| T138_cDNA1_Rev | GTTGAGAGAAGTTGTTGGATTG (SEQ ID NO: 333) |
| T139_123561For_cDNA1 | AACCAAAGACTTTTTGATCAATCCAACAACTTCTCTCA ACATGAAGATTTCCTCGATCCTTG (SEQ ID NO: 334) |
| 123561Rev | TCAGCGCCGTAACCTCTGC (SEQ ID NO: 335) |
| trpCterm_For_123561 | TGATGGTGATGAGGCGGAAAAGCAGAGGTTACGGCG CTGAGGATCCACTTAACGTTACTGA (SEQ ID NO: 336) |
| T390_trpCtermR_AmdS | TCTCTCAAAGGAAGAATCCCTTCAGGGTTGCGTTTCC AGTGCGGCCGCTCTCCTTCTAGAAAGAAGGATTA (SEQ ID NO: 337) |
| T391_AmdS_endR | ACTGGAAACGCAACCCTGAA (SEQ ID NO: 338) |
| T390_trpCtermR_AmdS | TCTGATTGCCAACTACGGACCAGACCAGGGCTCCGG CGCGGCGGCCGCTAGATCTACG (SEQ ID NO: 339) |

Deletion plasmid pTTv205 for pep3 (TreID121133), vector backbone pTTv192

| Primer | Sequence |
| --- | --- |
| T428_pep3_3flankDR_F-trpCterm | GTACACTTGTTTAGAGGTAATCCTTCTTTCTAGAAGGA GAGCGGCCGCGGAGCCCTGGTCTGGTCC (SEQ ID NO: 340) |
| T429_pep3_3flankDR_R-pyr4 | GCGCTGGCAACGAGAGCAGAGCAGCAGTAGTCGATG CTAGAAGCTGACGGGCGTCAACG (SEQ ID NO: 341) |
| T094_pyr4_F | TAGCATCGACTACTGCTGC (SEQ ID NO: 342) |
| T430_pyr4_R-pep3_3flank | GTACGTTCTGATTGCCAACTACGGACCAGACCAGGG CTCCGCGGCCGCCATGCAAAGATACACATCAATC (SEQ ID NO: 343) |

To generate a marker-free 6-fold protease deletion strain, removal of the pyr4 marker was applied to the 6-fold deletion strain M396 essentially as described above. Four consecutive 5-FOA selection steps were carried out to ensure that the clones selected were originating from single cells.

Final clones were verified by PCR using the primers listed in Table 24 and removal of the blaster cassette was further verified by plating the clones onto minimal medium plates with or without 5 mM uridine and by Southern analyses. The clone (25-120A-62) used to generate the 7-fold protease deletion strain was designated with strain number M402.

Transformation was carried out with pTTv205 (KEX2 overexpression included). To remove vector sequence, plasmid pTTv205 was digested with PmeI and the correct fragment purified from agarose gel using QIAquick Gel Extraction Kit (Qiagen). Approximately 5 µg of the deletion cassette was used to transform M402 (Δpep1Δtsp1Δslp1Δgap1Δgap2Δpep4, pyr4-). Preparation of protoplasts and transformation were carried out essentially as described above.

Transformants were picked as first streaks and growing streaks were screened by PCR (using the primers listed in Table 24) for correct integration. Clones giving the expected signals were purified to single cell clones and rescreened by PCR using the primers listed in Table 24. Deletion of pep3 was verified by Southern analyses from selected clones.

TABLE 24

Primers for screening removal of pyr4 blaster cassette from M396 and for screening pep3 integration and strain purity

| For screening removal of pyr4 blaster cassette from M396 | |
|---|---|
| Primer | Sequence |
| T302_77579_5int | GATTCATCACAGGGGCAGTC (SEQ ID NO: 344) |
| T214_pep4_3f_seq_r1 | CCGCTCTCAAACTGCCCAAA (SEQ ID NO: 345) |
| For screening integration of pTTv205 | |
| T625_pep3_5int_new | ACGTGAAGTTGCCCATCAA (SEQ ID NO: 346) |
| T140_cDNA1promoter_seqR1 | TAACTTGTACGCTCTCAGTTCGAG (SEQ ID NO: 347) |
| T626_pep3_3int_new | GACCAATGGCTTCACGAAGT (SEQ ID NO: 348) |
| T061_pyr4_orf_screen_2F | TTAGGCGACCTCTTTTTCCA (SEQ ID NO: 349) |
| For screening deletion of pep3 ORF | |
| T352_pep3_orf_for | CAGCAGCACCGCATCCACCA (SEQ ID NO: 350) |
| T353_pep3_orf_rev | GCCGAATCGCTGGTTGCCCT (SEQ ID NO: 351) |

Generation of 8, 9, and 10-Fold Deletion Strains

Generation of 8, 9, and 10-Fold deletion strains are described in the International Patent Application PCT/EP2013/050126.

Briefly, to generate an 8-fold protease deletion strain, removal of the pyr4 marker was applied to the 7-fold deletion strain M486 essentially as described above. Four consecutive 5-FOA selection steps were carried out to ensure that the clones selected were originating from single cells. Final clones were verified by PCR using the primers listed in Table 24b, removal of the blaster cassette was further verified by plating the clones onto minimal medium plates with or without 5 mM uridine, and with Southern analyses. A pyr4-clone was designated as M496.

To remove vector sequence, plasmid pTTv229 (Example 5) was digested with PmeI+XbaI and the correct fragment purified from an agarose gel using a QIAquick Gel Extraction Kit (Qiagen). Approximately 5 µg of the deletion cassette was used to transform protoplasts of M496. Transformants were picked as first streaks, growing streaks were screened by PCR (using the primers listed in Table 24b) for correct integration and clones giving the expected signals were purified to single cell clones and rescreened by PCR using the primers listed in Table 24b. Deletion of pep5 was verified by Southern analyses. An 8-fold deletion strain clone was designated as M504.

TABLE 24b

Primers for screening removal of pyr4 blaster cassette from 7-fold strain and for screening integration of pep5 deletion plasmid pTTv229 integration and strain purity.

For screening removal of pyr4 blaster cassette from M486 and strain purity

| Primer | Sequence |
| --- | --- |
| T047_trpC_term_end_F | CCTATGAGTCGTTTACCCAGA (SEQ ID NO: 413) |
| T854_pep3_3f_r2 | TGGCCGAGTCTATGCGTA (SEQ ID NO: 414) |
| T488_pyr4_5utr_rev | GGAGTTGCTTTAATGTCGGG (SEQ ID NO: 415) |
| T061_pyr4_orf_screen_2F | TTAGGCGACCTCTTTTTCCA (SEQ ID NO: 416) |
| T855_pep3_orf_f3 | GTAAGACGCCCCGTCTC (SEQ ID NO: 417) |
| T754_pep3_orf_rev2 | TGGATCATGTTGGCGACG (SEQ ID NO: 418) |

For screening integration of pTTv229

| Primer | Sequence |
| --- | --- |
| T627_pep5_5int_new | GTCGAAGATGTCCTCGAGAT (SEQ ID NO: 419) |
| T488_pyr4_5utr_rev | GGAGTTGCTTTAATGTCGGG (SEQ ID NO: 420) |
| T061_pyr4_orf_screen_2F | TTAGGCGACCTCTTTTTCCA (SEQ ID NO: 421) |
| T628_pep5_3int_new | TAGTCCATGCCGAACTGC (SEQ ID NO: 422) |

For screening deletion of pep5 ORF

| Primer | Sequence |
| --- | --- |
| T418_pep5_orf_for | CCGGACCTGCACCGCAAGTT (SEQ ID NO: 423) |
| T419_pep5_orf_rev | AGGGCAATGTCGCCCAGCAC (SEQ ID NO: 424) |
| T859_pep5_orf_f2 | GACCTGCACCGCAAGTT (SEQ ID NO: 425) |
| T860_pep5_orf_f3 | GTCGAGCGTCTGATATTCAC (SEQ ID NO: 426) |
| T861_pep5_orf_r2 | GACGGAGACCTCCCACA (SEQ ID NO: 427) |

Generation of 9-fold Protease Deletion Strain Having Deletions
Δpep1Δtsp1Δslp1Δgap1Δgap2Δpep4Δpep3Δpep5Δpep12
Generation of pep12 deletion plasmids The first deletion plasmid, pTTv209, for the aspartic protease pep12 (tre119876) was constructed essentially as described for pTTv41 above but a second selection marker cassette (bar) of *Streptomyces* ssp., was placed after the pyr4 gene creating a deletion plasmid with a double selection marker blaster cassette. The second deletion plasmid for the aspartic protease pep12 (pTTv245) was constructed using the plasmid pTTv209 above as the backbone. The pyr4-bar double marker was removed from pTTv209 with NotI digestion and the new pyr4 marker gene was obtained from pTTv181 with NotI digestion. 1019 bp of 5' flanking region and 895 bp of 3' flanking region were selected as the basis of the pep12 deletion plasmids. A 300 bp stretch from the end of pep12 5' flank was used as the direct repeat fragment. These fragments were amplified by PCR using the primers listed in Table 24c. The double marker (pyr4-bar) was digested from pTTv202 (Δpep5-pyr4-bar) with NotI. To enable removal of the complete double marker cassette, NotI restriction sites were introduced on both sides of the double marker cassette. AscI site was introduced between the pep12 5'direct repeat and 3' flank. Vector backbone was EcoRI/XhoI digested pRS426. The plasmid pTTv209 was constructed using the yeast homologous recombination method as described. These deletion plasmids for pep12 (pTTv209 and pTTv245, Table 24c) result in a 2198 bp deletion in the pep12 locus and cover the complete coding sequence of PEP12.

TABLE 24c

Primers for generating pep12 deletion plasmids.

Deletion plasmid pTTv209 (Δpep12-pyr4-bar), vector backbone pRS426

| Primer | Sequence |
| --- | --- |
| T477_pep12_5f_for | GGTAACGCCAGGGTTTTCCCAGTCACGACGGTTTAAAC CGACAGCACGTTGTGTGCTCC (SEQ ID NO: 428) |
| T478_pep12_5f_rev | GCGCTGGCAACGAGAGCAGAGCAGCAGTAGTCGATGCTA GGCGGCCGCTGGAGACCCAGCAGCCAGCA (SEQ ID NO: 429) |
| T479_pep12_DR_for | CCCGTCACCGAGATCTGATCCGTCACCGGGATCCACTTAA GCGGCCGCTCAGAGGGAGGCTGCCCAAC (SEQ ID NO: 430) |
| T480_pep12_DR_rev | GAGACTCGAACAAAGACATCTTTGCGACCTCGTCCAC GGCGGCGCGCCTGGAGACCCAGCAGCCAGCA (SEQ ID NO: 431) |

TABLE 24c-continued

Primers for generating pep12 deletion plasmids.

| | |
|---|---|
| T481_pep12_3f_for | GCCGTGGACGAGGTCGCAAA (SEQ ID NO: 432) |
| T482_pep12_3f_rev | AGCGGATAACAATTTCACACAGGAAACAGCGTTTAAAC CCCTGCGCCCTCTTCTGCAC (SEQ ID NO: 433) |

Deletion plasmid pTTv245 (Δpep12-pyr4)

| Primer | Sequence |
|---|---|
| no new primers, pTTv209 digested with NotI and ligated with pyr4 fragment from pTTv181 | |

Generation of 9-fold protease deletion strain with pep12 (tre119876); M575

To generate a 9-fold protease deletion strain, removal of the pyr4 marker was applied to the 8-fold deletion strain M504 essentially as described above using primers listed in Table 24d and resulting in a pyr4-clone designated as M521. To remove vector sequence, plasmid pTTv245 was digested with MssI and approximately 5 µg of the deletion cassette was used to transform M521.

Transformants were picked as first streaks and growing streaks were screened by PCR using the primers listed in Table 24d for correct integration. Clones giving the expected signals were purified to single cell clones and rescreened by PCR using the primers listed in Table 24d. Deletion of pep12 was verified by Southern analyses from selected clones. Clone 42-45B was designated with strain number M575.

cassette carrying hygromycin phosphotransferase gene (hph), was placed after the pyr4 gene creating a deletion plasmid with a double selection marker blaster cassette. In addition to the double marker, the first deletion plasmid contained also an overexpression cassette for native KEX2 (tre123561; promoter cDNA1, terminator cbh2). The second deletion plasmid for the aspartic protease pep2 (pTTv232) was constructed using the plasmid pTTv213 above as the backbone. The kex2 overexpression cassette (pcDNA1-kex2-tcbh2) was removed from pTTv213 with AscI digestion. The third deletion plasmid for the aspartic protease pep2 (pTTv246) was constructed using the plasmid pTTv232 above as the backbone. The pyr4-hph double marker was removed from pTTv232 with NotI digestion. The pyr4 marker gene was obtained from pTTv181 (Δpep4-pyr4 above) with NotI digestion.

TABLE 24d

Primers for screening removal of pyr4 blaster cassette from 8-fold protease deletion strain and for screening pTTv245/Δpep12-pyr4 integration and strain purity.

For screening removal of pyr4 blaster cassette from M504 and strain purity

| Primer | Sequence |
|---|---|
| T858_pep5_5f_f3 | GGAATCGTCACCAAGGAG (SEQ ID NO: 434) |
| T755_pep5_3f_rev3 | CTTCTGGTGACATTCCGAC (SEQ ID NO: 435) |
| T627_pep5_5int_new | GTCGAAGATGTCCTCGAGAT (SEQ ID NO: 436) |
| T488_pyr4_5utr_rev | GGAGTTGCTTTAATGTCGGG (SEQ ID NO: 437) |
| T860_pep5_orf_f3 | GTCGAGCGTCTGATATTCAC (SEQ ID NO: 438) |
| T861_pep5_orf_r2 | GACGGAGACCTCCCACA (SEQ ID NO: 439) |

For screening integration of pTTv245 (Δpep12-pyr4)

| Primer | Sequence |
|---|---|
| T517_pep12_5int | AGCAGTCCACCTGCTCAAAA (SEQ ID NO: 440) |
| T026_Pyr4_orf_5rev2 | CCATGAGCTTGAACAGGTAA (SEQ ID NO: 441) |
| T061_pyr4_orf_screen_2F | TTAGGCGACCTCTTTTTCCA (SEQ ID NO: 442) |
| T518_pep12_3int | GATTCACACCAATGAGTCGG (SEQ ID NO: 443) |

For screening deletion of pep12 (tre119876) ORF

| Primer | Sequence |
|---|---|
| T486_pep12_orf_probef | CCCCGACTTTGCCCCGTCAC (SEQ ID NO: 444) |
| T487_pep12_orf_prober | TCGTCAGAGTCGTCGCCCGT (SEQ ID NO: 445) |
| T1057_pep12_orf_probef2 | GCGCAGCTAATGTCCTCTGT (SEQ ID NO: 446) |
| T1058_pep12_orf_prober2 | TTGTTGAGCCAGAGTCGAGA (SEQ ID NO: 447) |

Generation of 9-fold Protease Deletion Strain Having Deletions
Δpep1Δtsp1Δslp1Δgap1Δgap2Δpep4Δpep3Δpep5Δpep2
Generation of pep2 deletion plasmids The first deletion plasmid, pTTv213, for the aspartic protease pep2 (tre0053961) was constructed essentially as for pTTv41 above but an additional second selection marker 1000 bp of 5' flanking region and 1020 bp of 3' flanking region were selected as the basis of the pep2 deletion plasmids. A 300 bp stretch from the end of pep2 5' flank was used as the direct repeat fragment. These fragments as well as the second selection marker cassette (hph), cDNA1 promoter, native kex2 gene and cbh2 terminator were ampli fied by PCR using the primers listed in Table 24e and cloned. The pyr4 selection marker was obtained from pTTv181 (Δpep4-pyr4 above) with NotI digestion. To enable removal of the complete double marker cassette in pTTv213, NotI restriction sites were introduced on both sides of the double marker cassette, and a SwaI site between the two selection markers. AscI sites were introduced on both sides of the kex2 overexpression cassette (between pep2 5'direct repeat and 3' flank). Vector backbone was EcoRI/XhoI digested pRS426 and the plasmid pTTv213 was constructed using the yeast homologous recombination method described. These deletion plasmids for pep2 (pTTv213, pTTv232 and pTTv246, Table 24e) result in a 1580 bp deletion in the pep2 locus and cover the complete coding sequence of PEP2.

TABLE 24e

Primers for generating pep2 deletion plasmids.

Deletion plasmid pTTv213, vector backbone pRS426

| Primer | Sequence |
| --- | --- |
| T431_pep2-5flankF-pRS426 | GATTAAGTTGGGTAACGCCAGGGTTTTCCCAGTCACGACGG TTTAAACCGGTTGTCCATTTCATCCTTC (SEQ ID NO: 448) |
| T629_pep2_5f_rev_pyr4 | GCGCTGGCAACGAGAGCAGAGCAGCAGTAGTCGATGCTAG GCGGCCGCGGGGAAGCAAGTTTCGAAGT (SEQ ID NO: 449) |
| T630_pep2_5DR_for_trpC | GTACACTTGTTTAGAGGTAATCCTTCTTTCTAGAAGGAGAGC GGCCGCCTCCACGCTCTTGGCCAC (SEQ ID NO: 450) |
| T631_pep2_5DR_rev_cDNA1 | GTCATTAAGTCCATCATTCCACGTCCTTCAGACCGAATTCGG CGCGCCGGGGAAGCAAGTTTCGAAGT (SEQ ID NO: 451) |
| T632_pep2_3f_for_tcbh2 | ATGATGCCTTTGCAGAAATGGCTTGCTCGCTGACTGATACG GCGCGCCTATCGCGAAAGTAGCCAATA (SEQ ID NO: 452) |
| T633_pep2_3f_rev | AGCGGATAACAATTTCACACAGGAAACAGCGTTTAAACCATC CTTTTCCTCACCACGA (SEQ ID NO: 453) |
| T491_hph_recpyr4_for3 | TGATTGTACCCCAGCTGCGATTGATGTGTATCTTTGCATGAT TTAAATTCTCCTTAGCTCTGTACAGT (SEQ ID NO: 454) |
| T492_hph_rev2 | GCGGCCGCTCTCCTTCTAGAAAGAAGGA (SEQ ID NO: 455) |
| T495_cDNA1_for | GAATTCGGTCTGAAGGACGT (SEQ ID NO: 456) |
| T138_cDNA1_Rev | GTTGAGAGAAGTTGTTGGATTG (SEQ ID NO: 457) |
| T139_123561 For cDNA1 | AACCAAAGACTTTTTGATCAATCCAACAACTTCTCTCAACAT GAAGATTTCCTCGATCCTTG (SEQ ID NO: 458) |
| T516_123561Rev | TCAGCGCCGTAACCTCTGC (SEQ ID NO: 459) |
| T496_tcbh2_for | TGATGGTGATGAGGCGGAAAAGCAGAGGTTACGGCGCTGA GGCTTTCGTGACCGGGCTTC (SEQ ID NO: 460) |
| T497_tcbh2_rev | GTATCAGTCAGCGAGCAAGC (SEQ ID NO: 461) |

Deletion plasmid pTTv232

| Primer | Sequence |
| --- | --- |
| no new primers, pTTv213 digested with AscI (to remove kex2 overexpression cassette) and self-ligated | |

Deletion plasmid pTTv246

| Primer | Sequence |
| --- | --- |
| no new primers, pTTv232 digested with NotI and ligated with pyr4/NotI-fragment from pTTv181 | |

Generation of 9-Fold Protease Deletion Strain with Pep2 (Tre53961); M574

To generate a 9-fold protease deletion strain, removal of the pyr4 marker was applied to the 8-fold deletion strain M504 essentially as described above using consecutive 5-FOA selection steps. Clones were verified by PCR using the primers listed in Table 24f and plating the clones onto minimal medium plates with or without 5 mM uridine. The strain used in generation of 9-fold protease deletion strain was designated with strain number M521.

To remove vector sequence, plasmid pTTv246 (Δpep2-pyr4) was digested with MssI, purified and approximately 5 μg of the deletion cassette was used to transform strain M521. Growing streaks were screened by PCR (using the primers listed in Table 24f) for correct integration. Clones giving the expected signals were purified to single cell clones and rescreened by PCR using the primers listed in Table 24f, and deletion of pep2 was verified by Southern analyses. The clone 41-45G was designated with strain number M574.

TABLE 24f

Primers for screening removal of pyr4 blaster cassette from 8-fold protease
deletion strain and for screening pTTv246/Δpep2-pyr4 integration and strain purity.

For screening removal of pyr4 blaster cassette from M504 and strain purity

| Primer | Sequence |
| --- | --- |
| T858_pep5_5f_f3 | GGAATCGTCACCAAGGAG (SEQ ID NO: 462) |
| T755_pep5_3f_rev3 | CTTCTGGTGACATTCCGAC (SEQ ID NO: 463) |
| T627_pep5_5int_new | GTCGAAGATGTCCTCGAGAT (SEQ ID NO: 464) |
| T488_pyr4_5utr_rev | GGAGTTGCTTTAATGTCGGG (SEQ ID NO: 465) |
| T860_pep5_orf_f3 | GTCGAGCGTCTGATATTCAC (SEQ ID NO: 466) |
| T861_pep5_orf_r2 | GACGGAGACCTCCCACA (SEQ ID NO: 467) |

For screening integration of pTTv246 (Δpep2-pyr4)

| Primer | Sequence |
| --- | --- |
| T596_pep2 fwd 5'flank screen | CCTCTGCGTTGAGCAACATA (SEQ ID NO: 468) |
| T026_Pyr4_orf_5rev2 | CCATGAGCTTGAACAGGTAA (SEQ ID NO: 469) |
| T061_pyr4_orf_screen_2F | TTAGGCGACCTCTTTTTCCA (SEQ ID NO: 470) |
| T600_pep2 rev 3'flank screen | CGAAAGCGTGGAGTCTTCTC (SEQ ID NO: 471) |

For screening deletion of pep2 (tre53961) ORF

| Primer | Sequence |
| --- | --- |
| T601_pep2 fwd | GACGTGGTACGACAACATCG (SEQ ID NO: 472) |
| T623_pep2 rev | TATCAAGGTACCGGGGACAG (SEQ ID NO: 473) |
| T1077_pep2_orf_probef2 | AACAAAGCCTTCACAGGCC (SEQ ID NO: 474) |
| T1078_pep2_orf_prober2 | TGAGGCTCCTTCCAACTTTT (SEQ ID NO: 475) |

Generation of 10-Fold Protease Deletion Strain Having Deletions Δpep1Δtsp1Δslp1Δgap1Δgap2Δpep4Δpep3Δpep5Δpep2 Δpep11
Generation of pep11 Deletion Plasmid The deletion plasmid pTTv312 for the aspartic protease pep11 (tre121306) was constructed essentially as described above. 956 bp of 5' flanking region and 943 bp of 3' flanking region were selected as the basis of the pep11 deletion plasmid. A 307 bp stretch from the end of pep11 5' flank was used as the direct repeat fragment. These fragments were amplified by PCR using the primers listed in Table 24g and the products were isolated from the gel. The pyr4 cassette was obtained from pTTv181 (Δpep4-pyr4 above) with NotI digestion. To enable removal of the marker cassette, NotI restriction sites were introduced on both sides of the cassette. AscI site was introduced between the pep11 5'direct repeat and 3' flank. Vector backbone was EcoRI/XhoI digested pRS426 and the plasmid was constructed using the yeast homologous recombination method as described. This deletion plasmid for pep11 (pTTv312, Table 24g) results in 2624 bp deletion in the pep11 locus and covers the complete coding sequence of PEP11.

TABLE 24g

Primers for generating pep11 deletion plasmids.
Deletion plasmid pTTv312 (Δpep11-pyr4), vector backbone pRS426

| Primer | Sequence |
| --- | --- |
| T1009_pep11_5flkfw_vector | GTAACGCCAGGGTTTTCCCAGTCACGACGGTTTAAAC ATGAGCGTGATCGACAAGTG (SEQ ID NO: 476) |
| T1010_pep11_5flkrev_pyr4Prom | GCGCTGGCAACGAGAGCAGAGCAGCAGTAGTCGATGCTAG GCGGCCGCCCTCTGAGGTCGAGATGGAG (SEQ ID NO: 477) |
| T1144_pep11_5dr_for | TGATTGTACCCCAGCTGCGATTGATGTGTATCTTTGCAT GGCGGCCGCACGACTAATATCCACTGCCG (SEQ ID NO: 478) |
| T1145_pep11_5dr_rev | AACCAAAGTGTACAATGCTCATCTCGTATTCACATGCAAA GGCGCGCCCTCTGAGGTCGAGATGGAG (SEQ ID NO: 479) |
| T1146_pep11_3f_for | TTTGCATGTGAATACGAGATGA (SEQ ID NO: 480) |
| T1012_pep11_3flrev_vector | GCGGATAACAATTTCACACAGGAAACAGCGTTTAAAC TGCTCGATCCTACTCCAAGG (SEQ ID NO: 481) |

Generation of 10-Fold Protease Deletion Strain with Pep11 (Tre121306); M658

To generate a 10-fold protease deletion strain, removal of the pyr4 marker was applied to the 9-fold deletion strain M574 essentially as described above using consecutive 5-FOA selection steps. Final clones were verified by PCR using the primers listed in Table 24h and by plating the clones onto minimal medium plates with or without 5 mM uridine. Resulting strain used in generation of 10-fold protease deletion strain was designated with strain number M597.

To remove vector sequence, plasmid pTTv312 (Δpep11-pyr4) was digested with MssI and approximately 5 μg of the deletion cassette was used to transform M597. Transformants were picked as first streaks and growing streaks were screened by PCR (using the primers listed in Table 24h) for correct integration. Clones were purified to single cell clones and rescreened by PCR using the primers listed in Table 24h and deletion of pep11 was verified by Southern analyses. Clone 47-62B was designated with strain number M632. An additional single cell purification step was applied to strain M632 to obtain 10-fold protease deletion strain M658.

the Δpep1 plasmid pTTv41 but an additional second selection marker cassette, bar, was placed after the pyr4 gene creating a deletion plasmid with a double selection marker blaster cassette.

1348 bp of 5' flanking region and 1164 bp of 3' flanking region were selected as the basis of the pep5 deletion plasmid. A 300 bp stretch from the end of pep5 5' flank was used as the direct repeat fragment. These fragments as well as the second selection marker cassette, bar, were amplified by PCR using the primers listed in Table 25. The products were separated with agarose gel electrophoresis and the correct fragments were isolated from the gel with a gel extraction kit (Qiagen). To enable removal of the complete double marker cassette, NotI restriction sites were introduced on both sides of the double marker cassette, and an As/S1 site between the two selection markers. An AscI site was introduced between the pep5 5'direct repeat and 3' flank. Vector backbone was EcoRI/XhoI digested pRS426. The pyr4 selection marker was obtained from pTTv181 (Δpep4-pyr above) with NotI digestion. The plasmid was constructed using the yeast homologous recombination method TABLE 24h Primers for screening removal of pyr4 blaster cassette from 9-fold protease deletion strain and for screening pTTv312/Δpep11-pyr4 integration and strain purity.

For screening removal of pyr4 blaster cassette from M574 and strain purity

| Primer | Sequence |
|---|---|
| T1162_pep2_5f_f2 | CTGTAAAGGCAGCATCGG (SEQ ID NO: 482) |
| T1163_pep2_3f_r2 | TCAGAACGGCTTCAATCATT (SEQ ID NO: 483) |
| T1162_pep2_5f_f2 | CTGTAAAGGCAGCATCGG (SEQ ID NO: 484) |
| T488_pyr4_5utr_rev | GGAGTTGCTTTAATGTCGGG (SEQ ID NO: 485) |
| T601_pep2 fwd | GACGTGGTACGACAACATCG (SEQ ID NO: 486) |
| T623_pep2 rev | TATCAAGGTACCGGGGACAG (SEQ ID NO: 487) |

For screening integration of pTTv312 (Δpep11-pyr4)

| Primer | Sequence |
|---|---|
| T1013_pep11_screen_5flk_fwd | TTACGACTCGATCCCTGTCC (SEQ ID NO: 488) |
| T488_pyr4_5utr_rev | GGAGTTGCTTTAATGTCGGG (SEQ ID NO: 489) |
| T061_pyr4_orf_screen_2F | TTAGGCGACCTCTTTTTCCA (SEQ ID NO: 490) |
| T1016_pep11_screen_3flk_rev | GCCGCTAGGATCGTGATAAG (SEQ ID NO: 491) |

For screening deletion of pep11 ORF

| Primer | Sequence |
|---|---|
| T1017_pep11_orf_fwd | GTGTCCCAGGACGACAACTT (SEQ ID NO: 492) |
| T1018_pep11_orf_rev | TGAAGGTTGCAGTGATCTCG (SEQ ID NO: 493) |

Example 5

Generations of Deletion Plasmids for pep5, pep7, pep8, tpp1, slp2, slp3, slp5, slp6, slp7 and slp8

The deletion plasmid for the aspartic protease pep5 (TreID81004) was constructed essentially as described for as described. This deletion plasmid for pep5 (pTTv202, Table 25) results in a 1687 bp deletion in the pep5 locus and covers the complete coding sequence of PEP5. pTTv229 was cloned by removing pyr4-bar double selection marker with NotI digestion and ligating pyr4 marker (NotI fragment from pTTv181) into it.

TABLE 25

Primers for generating pep5 deletion plasmid.

Deletion plasmid pTTv202 for pep5 (TreID81004), vector backbone pRS426

| Primer | Sequence |
|---|---|
| T372_pep5_5f_for | GGTAACGCCAGGGTTTTCCCAGTCACGACGGTTTAAA CGGAGGCTGCGACACCGTCTG (SEQ ID NO: 352) |

TABLE 25-continued

Primers for generating pep5 deletion plasmid.

| Primer | Sequence |
| --- | --- |
| T373_pep5_5f_rev | GCGCTGGCAACGAGAGCAGAGCAGCAGTAGTCGATG CTAGGCGGCCGCCCCGGCCTGAAACGACCTCCC (SEQ ID NO: 353) |
| T376_pep5_5DR_for | CCCGTCACCGAGATCTGATCCGTCACCGGGATCCAC TTAAGCGGCCGCGAGAGAGAAACAAAACAGTG (SEQ ID NO: 354) |
| T377_pep5_5DR_rev | ACATTCCGACCGTTTACTGATCCAAGCCGTGCAACCG ACTGGCGCGCCCCGGCCTGAAACGACCTCCC (SEQ ID NO: 355) |
| T378_pep5_3f_for | AGTCGGTTGCACGGCTTGGA (SEQ ID NO: 356) |
| T379_pep5_3f_rev | AGCGGATAACAATTTCACACAGGAAACAGCGTTTAAA CGAGACGGACGCCTGCACCAC (SEQ ID NO: 357) |
| T374_bar_recpyr4_for2 | TGATTGTACCCCAGCTGCGATTGATGTGTATCTTTGC ATGGCGATCGCGACAGAAGATGATATTGAAG (SEQ ID NO: 358) |
| T375_bar_rev | TTAAGTGGATCCCGGTGACG (SEQ ID NO: 359) |

Deletion plasmid pTTv229 for pep5 (TreID81004), vector backbone pTTv202

| Primer | Sequence |
| --- | --- |
| no new primers, pTTv202 digested with NotI and ligated with pyr4 fragment from pTTv181 | |

The deletion plasmid for the aspartic protease pep7 (TreID58669) is constructed essentially as described for pep1 deletion plasmid pTTv41. 1062 bp of 5' flanking regions and 1121 bp of 3' flanking region are selected as the basis of the pep7 deletion plasmid. Fragments are produced by PCR using the primers listed in Table 26. This deletion plasmid for pep7 results in deletion in the pep7 locus and covers the complete coding sequence of PEP7

TABLE 26

Primers for generating pep7 deletion plasmids.

Deletion plasmid for pep7 (TreID58669), vector backbone pRS426

| Primer | Sequence |
| --- | --- |
| 5flankfw_pRS426 | GTAACGCCAGGGTTTTCCCAGTCACGACGGTTTAAACCATAA ACTTGCGCAGTCGAA (SEQ ID NO: 360) |
| 5flankrev_pyr4 | GCGCTGGCAACGAGAGCAGAGCAGCAGTAGTCGATGCTAG GCGGCCGCCTTCTAGGATGGAGCGCTTG (SEQ ID NO: 361) |
| 3flankfw_pyr4 | CAACCAGCCGCAGCCTCAGCCTCTCTCAGCCTCATCAGCCG CGGCCGCAGACGGCTTCTTCCAAAACA (SEQ ID NO: 362) |
| 3flankrev_pRS426 | GCGGATAACAATTTCACACAGGAAACAGCGTTTAAACCCCCA GGGAGGCTATTCTAC (SEQ ID NO: 363) |

For screening integration of pep7 deletion cassette

| Primer | Sequence |
| --- | --- |
| scrn_5forw | CTTTCCAAGCGTTTGAGTCC (SEQ ID NO: 364) |
| T026_Pyr4_orf_5rev2 | CCATGAGCTTGAACAGGTAA (SEQ ID NO: 365) |
| scrn_3rev | GCGTGTTTTATCCTGGTGCT (SEQ ID NO: 366) |
| T028_Pyr4_flank_rev | CATCCTCAAGGCCTCAGAC (SEQ ID NO: 367) |

For screening deletion of pep7 ORF

| Primer | Sequence |
| --- | --- |
| orf_fw | CACCTCCGTCGATGAGTTTT (SEQ ID NO: 368) |
| orf_rev | AGAAGAAGGTGGTGGTGGTG (SEQ ID NO: 369) |

A deletion plasmid pTTv319 for aspartic protease pep8 (tre122076) was constructed essentially as described above. The second deletion plasmid for pep8 (pTTv328) was constructed using the plasmid pTTv319 above as the backbone. The pyr4 marker was removed from pTTv319 with NotI digestion. The pyr4-hph cassette was obtained from pTTv210 (Δsep1-pyr4-hph) with NotI digestion. Cloning of the plasmid pTTv328 was done with standard ligation using T4 DNA ligase at room temperature and part of the ligation mixture was transformed into E. coli with electroporation. Correct ligation and orientation of the marker was further verified by sequencing.

1095 bp of 5' flanking region and 988 bp of 3' flanking region were selected as the basis of the pep8 deletion plasmids. A 324 bp stretch from the end of pep8 5' flank was used as the direct repeat fragment. These fragments were amplified by PCR using the primers listed in Table 26-1. The pyr4 selection marker used in pTTv319 was obtained from pTTv181. To enable removal of the pyr4 marker cassette, NotI restriction sites were introduced on both sides of the cassette and AscI site was introduced between the pep8 5'direct repeat and 3' flank. Vector backbone was EcoRI/XhoI digested pRS426. These deletion plasmids for pep8 (pTTv319 and pTTv328, Table 26-1) result in a 1543 bp deletion in the pep8 locus and cover the complete coding sequence of PEP8.

TABLE 26-1

Primers for generating pep8 deletion plasmid.

Deletion plasmid pTTv319 (Δpep8-pyr4), vector backbone pRS426

| Primer | Sequence |
|---|---|
| T1019_pep8_5flkfw_vector | GTAACGCCAGGGTTTTCCCAGTCACGACGGTTTAAAC AGGTTTGGGTTGTGAGATCG (SEQ ID NO: 494) |
| T1020_pep8_5flkrev_ pyr4Prom | GCGCTGGCAACGAGAGCAGAGCAGCAGTAGTCGATGCTA GGCGGCCGCGCGCAAAGCTACTGGGCTAT (SEQ ID NO: 495) |
| T1167_pep8_5DR_for | TGATTGTACCCCAGCTGCGATTGATGTGTATCTTTGCAT GGCGGCCGCTCTGCTCTGCTCTGTTCTGC (SEQ ID NO: 496) |
| T1168_pep8_5DR_rev | AAAGTTCGTCAAAGAGCACTCATAGGGCTGAGAAAA GCCAGGCGCGCCGCGCAAAGCTACTGGGCTAT (SEQ ID NO: 497) |
| T1169_pep8_3f_for2 | TGGCTTTTCTCAGCCCTATG (SEQ ID NO: 498) |
| T1022_pep8_3flkrev_vector | GCGGATAACAATTTCACACAGGAAACAGCGTTTAAAC CAATGTGTGCCTGTTTTTCG (SEQ ID NO: 499) |

Deletion plasmid pTTv328 (Δpep8-pyr4-hph)

| Primer | Sequence |
|---|---|
| no new primers, pTTv319 digested with NotI and ligated with pyr4-hph fragment from pTTv210 | |

The third deletion plasmid pTTv266 for pep8 was constructed essentially as described above. 1095 bp of 5' flanking region and 988 bp of 3' flanking region were selected as the basis. These fragments were amplified by PCR using the primers listed in Table 26-2. The pyr4-hph selection marker was obtained from pTTv194 (Δpep4-pyr-hph) with NotI digestion. To enable removal of the pyr4-hph marker cassette, NotI restriction sites were introduced on both sides of the cassette. Vector backbone was EcoRI/XhoI digested pRS426. The plasmid pTTv266 was constructed with the 5' flank, 3' flank, pyr4-hph marker, and vector backbone using the yeast homologous recombination method. The deletion plasmids for pep8 (pTTv266, Table 26-2) result in a 1543 bp deletion in the pep8 locus and cover the complete coding sequence of PEP8.

The deletion plasmid pTTv331 (2152 bp deletion in the tpp1 locus and covers the complete coding sequence of TPP1) for tripeptidyl peptidase tpp1 (tre82623) was constructed essentially as described above with the marker used for selection was a double marker pyr4-hph. 1245 bp of 5' flanking region and 1025 bp of 3' flanking region were selected as the basis. A 311 bp stretch from the end of tpp1 5' flank was used as the direct repeat fragment and these fragments were amplified using the primers of Table 26-3. The pyr4-hph cassette was obtained from pTTv210 (Δsep1-pyr4-hph) with NotI digestion. To enable removal of the complete double marker cassette, NotI restriction sites were introduced on both sides of the double marker cassette. AscI site was introduced between the tpp1 5'direct repeat and 3' flank. Vector backbone was EcoRI/XhoI digested pRS426.

TABLE 26-2

Primers for generating pep8 deletion plasmid.
Deletion plasmid pTTv266 (Δpep8-pyr4-hph), vector backbone pRS426

| Primer | Sequence |
|---|---|
| T1019_pep8_5flkfw_vector | GTAACGCCAGGGTTTTCCCAGTCACGACGGTTTAAAC AGGTTTGGGTTGTGAGATCG (SEQ ID NO: 500) |
| T1020_pep8_5flkrev_pyr4Prom | GCGCTGGCAACGAGAGCAGAGCAGCAGTAGTCGATG CTAGGCGGCCGCGCGCAAAGCTACTGGGCTAT (SEQ ID NO: 501) |
| T1021_pep8_3flkfw_pyr4loop | CAACCAGCCGCAGCCTCAGCCTCTCTCAGCCTCATCA GCCGCGGCCGCTGGCTTTTCTCAGCCCTATG (SEQ ID NO: 502) |
| T1022_pep8_3flkrev_vector | GCGGATAACAATTTCACACAGGAAACAGCGTTTAAAC CAATGTGTGCCTGTTTTTCG (SEQ ID NO: 503) |

TABLE 26-3

Primers for generating tpp1 deletion plasmid.
Deletion plasmid pTTv331 (Δtpp1-pyr4-hph), vector backbone pRS426

| Primer | Sequence |
| --- | --- |
| T311_82623_5for | GTAACGCCAGGGTTTTCCCAGTCACGACGGTTTAAAC CGCATTACGAATGCACAAAG (SEQ ID NO: 504) |
| T1190_tpp1_5f_rev2 | GCGCTGGCAACGAGAGCAGAGCAGCAGTAGTCGATGCTA GGCGGCCGCCCATGTCAGCTCAGACCAAT (SEQ ID NO: 505) |
| T1191_tpp1_5dr_for | GTACACTTGTTTAGAGGTAATCCTTCTTTCTAGAAGGAGA GCGGCCGCAGGCCCTGGACTGCTAGTTT (SEQ ID NO: 506) |
| T1192_tpp1_5dr_rev | CGAGCCATCCGCCGCGGCCCTATATTCCACCCGAGTCCT CGGCGCGCCCCATGTCAGCTCAGACCAAT (SEQ ID NO: 507) |
| T1193_tpp1_3f_for2 | GAGGACTCGGGTGGAATATAGG (SEQ ID NO: 508) |
| T314_82623_3rev | GCGGATAACAATTTCACACAGGAAACAGCGTTTAAAC TTGGTCTTGAATGAAAGGTGTG (SEQ ID NO: 509) |

The deletion plasmids for the subtilisin-like proteases slp2 (TreID123244) and slp3 (TreID123234) were constructed essentially as described for pep1 deletion plasmid pTTv41. 1000 bp of 5' and 1100 bp of 3' flanking regions were selected as the basis of the slp2 deletion plasmid. For slp3, 1000 bp of 5' and 1100 bp of 3' flanking regions were selected. Fragments were produced by PCR using the primers listed in Table 26-4. Template used in the PCR of the flanking regions was from the *T. reesei* wild type strain QM6a. The pyr4 blaster cassette was obtained from pTTv71 with NotI digestion. The vector backbone was EcoRI/XhoI digested pRS426 and the plasmids were constructed using the yeast homologous recombination method described above. The deletion plasmid for slp2 (pTTv115) results in a 2114 bp deletion in the slp2 locus and covers the complete coding sequence of SLP2. The deletion plasmid for slp3 (pTTv116) results in a 1597 bp deletion in the slp3 locus and covers the complete coding sequence of SLP3.

TABLE 26-4

Primers used for plasmids.

Deletion plasmid pTTv115 for slp2 (TreID123244), vector backbone pRS426

| Primer | Sequence |
| --- | --- |
| JJ-037 primer | GATTAAGTTGGGTAACGCCAGGGTTTTCCCAGTCACGACGG TTTAAACGCAGTCTATCCCATCCCTG (SEQ ID NO: 510) |
| JJ-038 primer | GCGCTGGCAACGAGAGCAGAGCAGCAGTAGTCGATGCTAG GCGGCCGCGCGGATGATGAAGGAAGAAG (SEQ ID NO: 511) |
| JJ-039 primer | CAACCAGCCGCAGCCTCAGCCTCTCTCAGCCTCATCAGCC GCGGCCGCAACAGCTGTTCGCACGCGTG (SEQ ID NO: 512) |
| JJ-040 primer | TGGAATTGTGAGCGGATAACAATTTCACACAGGAAACAGCG TTTAAACGGCTGGGCATTGGGGCCG (SEQ ID NO: 513) |

Deletion plasmid pTTv116 for slp3 (TreID123234), vector backbone pRS426

| Primer | Sequence |
| --- | --- |
| JJ-041 primer | GATTAAGTTGGGTAACGCCAGGGTTTTCCCAGTCACGACGG TTTAAACAAACAAGGCACAAAGGCCTG (SEQ ID NO: 514) |
| JJ-042 primer | GCGCTGGCAACGAGAGCAGAGCAGCAGTAGTCGATGCTAG GCGGCCGCATCCAAGGATGAGGAGAAC (SEQ ID NO: 515) |
| JJ-043 primer | CAACCAGCCGCAGCCTCAGCCTCTCTCAGCCTCATCAGCC GCGGCCGCACCTAATGGTTTCTTCGTTTTTC (SEQ ID NO: 516) |
| JJ-044 primer | TGGAATTGTGAGCGGATAACAATTTCACACAGGAAACAGCG TTTAAACCGGTCCGAAGGGTGTTTTGG (SEQ ID NO: 517) |

The deletion plasmid for the aspartic protease slp5 (TreID64719) is constructed essentially as described above. 1044 bp of 5' flanking regions and 1003 bp of 3' flanking region are selected as the basis of the slp5 deletion plasmid. Fragments are produced by PCR using the primers listed in Table 27. This deletion plasmid for slp5 results in deletion in the slp5 locus and covers the complete coding sequence of SLP5.

TABLE 27

Primers for generating slp5 deletion plasmids.

Deletion plasmid for slp5 (TreID64719), vector backbone pRS426

| Primer | Sequence |
| --- | --- |
| 5flankfw_pRS426 | GTAACGCCAGGGTTTTCCCAGTCACGACGGTTTAAACGTTT GAGCATTCTCCCAAGC (SEQ ID NO: 370) |
| 5flankrev_pyr4 | GCGCTGGCAACGAGAGCAGAGCAGCAGTAGTCGATGCTAG GCGGCCGCCGCCATTTTGAAGAAGATGC (SEQ ID NO: 371) |
| 3flankfw_pyr4 | CAACCAGCCGCAGCCTCAGCCTCTCTCAGCCTCATCAGCC GCGGCCGCATGCTCCCTCGTCATTAAGC (SEQ ID NO: 372) |
| 3flankrev_pRS426 | GCGGATAACAATTTCACACAGGAAACAGCGTTTAAACACAA CACCTTCTCCGACACC (SEQ ID NO: 373) |

For screening integration of slp5 deletion cassette

| Primer | Sequence |
| --- | --- |
| scrn_5forw | ATGCCCAAGTTTCGTACCTG (SEQ ID NO: 374) |
| T026_Pyr4_orf_5rev2 | CCATGAGCTTGAACAGGTAA (SEQ ID NO: 375) |
| scrn_3rev | GGCGCATTCAGAAGAAGAAC (SEQ ID NO: 376) |
| T028_Pyr4_flank_rev | CATCCTCAAGGCCTCAGAC (SEQ ID NO: 377) |

For screening deletion of slp5 ORF

| Primer | Sequence |
| --- | --- |
| orf_fw | CACTTGATGAACGCTGGCTA (SEQ ID NO: 378) |
| orf_rev | CGTAATGGCGTTGTTGACAG (SEQ ID NO: 379) |

A deletion plasmid for the aspartic protease slp6 (TreID121495) is based on 1192 bp of 5' flanking regions and 1114 bp of 3' flanking regions. Fragments are produced by PCR using the primers listed in Table 28. This deletion plasmid for slp6 results in deletion in the slp6 locus and covers the complete coding sequence of SLP6.

TABLE 28

Primers for generating slp6 deletion plasmids.

Deletion plasmid for slp6 (TreID121495), vector backbone pRS426

| Primer | Sequence |
| --- | --- |
| 5flankfw_pRS426 | GTAACGCCAGGGTTTTCCCAGTCACGACGGTTTAAACGAG GCAGCCAAAAAGTGAAG (SEQ ID NO: 380) |
| 5flankrev_pyr4 | GCGCTGGCAACGAGAGCAGAGCAGCAGTAGTCGATGCTAG GCGGCCGCTGAAAGAAGGCAGGACCAGT (SEQ ID NO: 381) |
| 3flankfw_pyr4 | CAACCAGCCGCAGCCTCAGCCTCTCTCAGCCTCATCAGCC GCGGCCGCAAGAGGCTCGGACAAAGACA (SEQ ID NO: 382) |
| 3flankrev_pRS426 | GCGGATAACAATTTCACACAGGAAACAGCGTTTAAACGATC GTGGTGCACGAGACTA (SEQ ID NO: 383) |

For screening integration of slp6 deletion cassette

| Primer | Sequence |
| --- | --- |
| scrn_5forw | GCACTGCGTTGCCTTTCTAT (SEQ ID NO: 384) |
| T026_Pyr4_orf_5rev2 | CCATGAGCTTGAACAGGTAA (SEQ ID NO: 385) |
| scrn_3rev | GAAAGCATGGCTCGTTTCTC (SEQ ID NO: 386) |
| T028_Pyr4_flank_rev | CATCCTCAAGGCCTCAGAC (SEQ ID NO: 387) |

For screening deletion of slp6 ORF

| Primer | Sequence |
| --- | --- |
| orf_fw | ACCCGGCTCAACTAGCTACA (SEQ ID NO: 388) |
| orf_rev | AGCTGGCCTTTCGTTACAGA (SEQ ID NO: 389) |

The deletion plasmid for the aspartic protease slp7 (TreID123865) is based on 1134 bp of 5' flanking regions and 1005 bp of 3' flanking regions. Fragments are produced by PCR using the primers listed in Table 29-1. This deletion plasmid for slp7 results in deletion in the slp7 locus and covers the complete coding sequence of SLP7. Alternatively, a deletion plasmid pTTv269 for slp7 (tre123865) was constructed with the marker pyr4-hph from pTTv194. This plasmid has 949 bp of 5' flanking region and 1025 bp of 3' flanking region and the plasmid was constructed using the primers listed in Table 29-2. This deletion plasmid for slp7(pTTv269, Table 29-2) results in a 2019 bp deletion in the slp7 locus and covers the complete coding sequence of SLP7.

The deletion plasmid for the aspartic protease slp8 (TreID58698) is based on 1123 bp of 5' flanking regions and 1062 bp of 3' flanking regions. Fragments are produced by PCR using the primers listed in Table 30-1. This deletion plasmid for slp8 results in deletion in the slp8 locus and covers the complete coding sequence of SLP8. Alternatively, a deletion plasmid pTTv330 for slp8 was constructed with a double marker pyr4-hph and using 975 bp of 5' flanking region and 1038 bp of 3' flanking regions as the basis. A 298 bp stretch from the end of slp8 5' flank was used as the direct repeat fragment. These fragments were amplified by PCR using the primers listed in Table 30-2. The pyr4-hph cassette was obtained from pTTv210 (Δsep1-pyr4-hph) with NotI digestion. NotI restriction sites were introduced on both sides of the double marker cassette and AscI site was introduced between the slp8 5'direct repeat and 3' flank. The deletion plasmid for slp8 (pTTv330, Table 30-2) results in a 1433 bp deletion in the slp8 locus and cover the complete coding sequence of SLP8.

TABLE 29-1

Primers for generating slp7 deletion plasmids.

Deletion plasmid for slp7 (TreID123865), vector backbone pRS426

| Primer | Sequence |
| --- | --- |
| 5flankfw_pRS426 | GTAACGCCAGGGTTTTCCCAGTCACGACGGTTTAAACTTGG TTTGAACAGCTGCAAG (SEQ ID NO: 390) |
| 5flankrev_pyr4 | GCGCTGGCAACGAGAGCAGAGCAGCAGTAGTCGATGCTAG GCGGCCGCTTTGCAGCAAGATGTCGTTC (SEQ ID NO: 391) |
| 3flankfw_pyr4 | CAACCAGCCGCAGCCTCAGCCTCTCTCAGCCTCATCAGCC GCGGCCGCGCTGTGAAGACGGGCTTATC (SEQ ID NO: 392) |
| 3flankrev_pRS426 | GCGGATAACAATTTCACACAGGAAACAGCGTTTAAACCAAG AACAGCATCGAGGACA (SEQ ID NO: 393) |

For screening integration of slp7 deletion cassette

| Primer | Sequence |
| --- | --- |
| scrn_5forw | GGGCGACGACGAGTTTTAT (SEQ ID NO: 394) |
| T026_Pyr4_orf_5rev2 | CCATGAGCTTGAACAGGTAA (SEQ ID NO: 395) |
| scrn_3rev | GAATGGATCAAGTCGCTGCT (SEQ ID NO: 396) |
| T028_Pyr4_flank_rev | CATCCTCAAGGCCTCAGAC (SEQ ID NO: 397) |

For screening deletion of slp7 ORF

| Primer | Sequence |
| --- | --- |
| orf_fw | CTCAGGCTCTGCTTGGATTC (SEQ ID NO: 398) |
| orf_rev | ATGCCAAAAAGACTGCTGCT (SEQ ID NO: 399) |

TABLE 29-2

Primers for generating slp7 deletion plasmids.
Deletion plasmid pTTv269 (Δslp7-pyr4-hph), vector backbone pRS426

| Primer | Sequence |
| --- | --- |
| T1088_slp7_5flkfw_vector | GTAACGCCAGGGTTTTCCCAGTCACGACGGTTTAAAC TCCCATATGCCTCTTGAAGG (SEQ ID NO: 518) |
| T1089_slp7_5flkrev_pyr4Prom | GCGCTGGCAACGAGAGCAGAGCAGCAGTAGTCGATG CTAGGCGGCCGCTTTGCAGCAAGATGTCGTTC (SEQ ID NO: 391) |
| T1090_slp7_3flkfw_pyr4loop | CAACCAGCCGCAGCCTCAGCCTCTCTCAGCCTCATCA GCCGCGGCCGCTGGGTGATAAGCTTGGGTTT (SEQ ID NO: 519) |
| T1091_slp7_3flkrev_vector | GCGGATAACAATTTCACACAGGAAACAGCGTTTAAACA TCATGATGACCCATCGACA (SEQ ID NO: 520) |

TABLE 30-1

Primers for generating slp8 deletion plasmids.

Deletion plasmid for slp8 (TreID58698), vector backbone pRS426

| Primer | Sequence |
| --- | --- |
| 5flankfw_pRS426 | GTAACGCCAGGGTTTTCCCAGTCACGACGGTTTAAACGCCT CCCTGGTATTCAGACA (SEQ ID NO: 400) |
| 5flankrev_pyr4 | GCGCTGGCAACGAGAGCAGAGCAGCAGTAGTCGATGCTAG GCGGCCGCGACGCCAGAAAGAAATGCTC (SEQ ID NO: 401) |
| 3flankfw_pyr4 | CAACCAGCCGCAGCCTCAGCCTCTCTCAGCCTCATCAGCC GCGGCCGCGACCTGGTCAGCTGCTCTTT (SEQ ID NO: 402) |
| 3flankrev_pRS426 | GCGGATAACAATTTCACACAGGAAACAGCGTTTAAACTGGA ACCACATCGACTTCAC (SEQ ID NO: 403) |

For screening integration of slp8 deletion cassette

| Primer | Sequence |
| --- | --- |
| scrn_5forw | AACCACCTTGTCACCGTCTC (SEQ ID NO: 404) |
| T026_Pyr4_orf_5rev2 | CCATGAGCTTGAACAGGTAA (SEQ ID NO: 405) |
| scrn_3rev | GTCGTCGAGGCTGCTTTATC (SEQ ID NO: 406) |
| T028_Pyr_flank_rev | CATCCTCAAGGCCTCAGAC (SEQ ID NO: 407) |

For screening deletion of slp8 ORF

| Primer | Sequence |
| --- | --- |
| orf_fw | GATCTCGAATCCGAGGACAA (SEQ ID NO: 408) |
| orf_rev | CCGGTAGCGTTAGAGAGACG (SEQ ID NO: 258) |

TABLE 30-2

Primers for generating slp8 deletion plasmid.
Deletion plasmid pTTv330 (Δslp8-pyr4-hph), vector backbone pRS426

| Primer | Sequence |
| --- | --- |
| T1203_slp8_5f_f | GATTAAGTTGGGTAACGCCAGGGTTTTCCCAGTCACGACG GTTTAAACATCGTGCTTGGGCTATTCTG (SEQ ID NO: 521) |
| T1204_slp8_5f_r | GCGCTGGCAACGAGAGCAGAGCAGCAGTAGTCGATGCTAG GCGGCCGCGGAAAGACGCCAGAAAGAAA (SEQ ID NO: 522) |
| T1205_slp8_5dr_f | GTACACTTGTTTAGAGGTAATCCTTCTTTCTAGAAGGAGA GCGGCCGCCGCTCGATGTGGATGATACT (SEQ ID NO: 523) |
| T1206_slp8_5dr_r | ATCTATACTGTCTGCACCAAAAGTACAACAACGCAAA CCGGGCGCGCCGGAAAGACGCCAGAAAGAAA (SEQ ID NO: 524) |
| T1207_slp8_3f_f | CGGTTTGCGTTGTTGTACTT (SEQ ID NO: 525) |
| T1208_slp8_3f_r | TGGAATTGTGAGCGGATAACAATTTCACACAGGAAACAGC GTTTAAACACAACCCAACGTTCTCTCGT (SEQ ID NO: 526) |

The pyr4 blaster cassette is obtained from pTTv71 with NotI digestion. Templates to be used in the PCR of the flanking regions is from the *T. reesei* wild type strain QM6a; the vector backbone is EcoRI/XhoI digested pRS426 and the plasmids are constructed using the yeast homologous recombination method described above.

Example 6

Generation of MAB01 Antibody Producing Seven-Fold Protease Deletion Strain M507

To generate an MAB01 antibody producing strain in the seven-fold protease deletion strain, M486 (Δpep1Δtsp1Δslp1Δgap1Δgap2Δpep4Δpep3) as described in U.S. provisional application 61/583,559 or PCT/EP2013/050126 and in example 4 was transformed with MAB01 light and heavy chain tandem construct (pTTv223) using acetamide selection for the transformation. Transformants were screened by PCR for correct integration into the cbh1 locus and purified to single cell clones. One MAB01 antibody producing strain was designated with the number M507. To reuse pyr4 as the selection marker, removal of the pyr4 blaster cassette from the pep3 deletion locus was carried out. Spores were spread onto minimal medium plates containing 20 g/l glucose, 2 g/l proteose peptone, 1 ml/l Triton X-100, 5 mM uridine and 1.5 g/l 5-FOA, pH 4.8. 5-FOA resistant colonies were picked after 5-7 days to 0.9% NaCl, suspended thoroughly by vortexing and filtrated through a cotton-filled pipette tip. To purify clones to single cell clones, filtrates were spread again onto plates described above. Purified clones were sporulated on plates containing 39 g/l potato dextrose agarose. These clones were tested for uridine auxotrophy by plating spores onto minimal medium plates (20 g/l glucose, 1 ml/l Triton X-100) where no growth was observed, indicating that the selected clones were pyr4-. Clones were further tested by PCR for the removal of the blaster cassette and were shown to be correct. One clone was designated with strain number M564.

Generation of Fucosylated G0 in Seven-Fold Protease Deletion Strain

The PmeI fragments of pTTv224 and pTTv225 or pTTv226 plasmids from example 2 are transformed into the seven-fold protease deletion *Trichoderma reesei* strain M564 (Δpep1Δtsp1Δslp1Δgap1Δgap2Δpep4Δpep3pyr4) expressing codon optimized MAB01 antibody, essentially as described in Example 2. 5 μg of purified expression cassette DNA is co-transformed into protoplasts of the strain M564. Preparation of protoplasts and transformation are carried out essentially according to methods in Penttilä et al. (1987, Gene 61:155-164) and Gruber et al (1990, Curr. Genet. 18:71-76) for pyr4 selection. The transformed protoplasts are plated onto *Trichoderma* minimal media (TrMM) plates containing sorbitol.

Transformants are streaked onto TrMM plates with 0.1% TritonX-100. Transformants growing fast as selective streaks are screened by PCR using the primers listed in Table 4. DNA from mycelia are purified and analyzed by PCR to look at the integration of the 5' and 3' flanks of cassette and the existence of the pep4 ORF, as explained in example 2. Positively integrated transformants are purified to single cell clones.

The pyr4 marker of pTTv110 (Example 1), containing chimeric GnTII/GnTI sequence, is changed to hygromycin resistance marker by NotI digestion and ligation. 5 μg of purified expression cassette DNA from this plasmid is transformed into protoplasts of a strain containing pTTv224 and pTTv225 or pTTv226. The transformed protoplasts are plated onto *Trichoderma* minimal media (TrMM) plates containing sorbitol and hygromycin (150 μg/ml). Transformants are streaked onto TrMM plates containing hygromycin (125 μg/ml) and 0.1% TritonX-100 and screened by PCR for correct integration into the alg3 locus and loss of the alg3 ORF. Positively integrated transformants are purified to single cell clones. Pure strains are cultivated in shake flask cultures as described in Example 2.

Samples are taken from shake flask cultures in days 3, 5, and 7 and MAB01 is purified with Protein G affinity chromatography. PNGase F reactions are performed for ~10 μg of denatured protein. The released N-glycans are first purified with Hypersep C-18 and then with Hypersep Hypercarb (both from Thermo Scientific). The purification steps are performed in 96-well format. Neutral N-glycans are analyzed by MALDITOF MS as described in Example 2.

Generation of G0 Producing Strain M629

Generation of G0 producing strain M629 is described in the International Patent

Application PCT/EP2013/050126. Briefly, the vector pTTg173 (having *T. reesei* Kre2 signal peptide fused to human GnT1 and native human GnT2 targeted to *T. reesei* alg3 locus) was transformed to *T reesei*. Transformants were picked onto selective plates and on the basis of PCR screening clones with positive results were selected for single spore platings and re-screening for integration and alg3 deletion. PCR-screened strains were subjected to shake flask cultivation and glycan analysis. Final G0 MAB01 producing strain was named as M629.

Generation of MAB01 Antibody Producing Double Protease Deletion Strains M292 and M295

To generate the MAB01 antibody producing strain, the pep1 deletion strain M181 was transformed with MAB01 light and heavy chain constructs (pTTv98+pTTv67) using hygromycin and acetamide in selection. The removal of the pyr4 blaster cassette from pep1 locus was carried out essentially as described for M195 above. This pyr4-strain was designated with number M285.

To remove vector sequence, plasmids pTTv115 and pTTv116 were digested with PmeI and approximately 5 μg of either deletion cassette was used to transform M285 separately. Colonies growing on transformation plates were picked as selective streaks and clones growing fast were screened by PCR using the primers listed in Table 30-3 for the correct integration. Putative disruptants were purified to single cell clones. No pure clones were obtained even after repeated purification steps. However, clones having Δpep1Δslp2 and Δpep1Δslp3 were designated as M292 and M295, respectively.

TABLE 30-3

Primers for screening slp2 (pTTv115) and slp3 (pTTv116) integration and strain purity.

| For screening integration of pTTv115 | |
|---|---|
| Primer | Sequence |
| T054_slp2_5screen_F | GATGCACCGCTGCGGCC (SEQ ID NO: 327) |
| T026_Pyr4_orf_5rev2 | CCATGAGCTTGAACAGGTAA (SEQ ID NO: 328) |
| T028_Pyr4_flank_rev | CATCCTCAAGGCCTCAGAC (SEQ ID NO: 329) |
| T055_slp2_3screen_R | GGCGTTGCTCCCCATGCG (SEQ ID NO: 330) |
| For screening deletion of slp2 ORF | |
| T111_slp2_ORF_F | ATGCGGTCCGTTGTCGCC (SEQ ID NO: 331) |
| T112_slp2_ORF_R | TTACTCGGAGAGCTCAGAGA (SEQ ID NO: 332) |
| For screening integration of pTTv116 | |
| Primer | Sequence |
| T056_slp3_5screen_F | GTGAATGGGTGGCAACATGA (SEQ ID NO: 333) |
| T026_Pyr4_orf_5rev2 | CCATGAGCTTGAACAGGTAA (SEQ ID NO: 334) |
| T028_Pyr4_flank_rev | CATCCTCAAGGCCTCAGAC (SEQ ID NO: 335) |
| T057_slp3_3screen_R | CATCAAGTTGACCACCATTGT (SEQ ID NO: 336) |

TABLE 30-3-continued

Primers for screening slp2 (pTTv115) and slp3 (pTTv116) integration and strain purity.

For screening deletion of slp3 ORF

| | |
|---|---|
| T113_slp3_ORF_F | ATGCGGTTGTCCGTCCTCC (SEQ ID NO: 337) |
| T114_slp3_ORF_R | TTAACCGGAAGGGTTGCCGT (SEQ ID NO: 338) |

Generation of MAB01 Producing Triple Protease Deletion Strain M304

To generate the MAB01 antibody producing strain the Δpep1Δtsp1 double protease deletion strain M194 was transformed with MAB01 light and heavy chain constructs (pTTv99+pTTv67) using hygromycin and acetamide in selection. This MAB01 strain with Δpep1Δtsp1 was designated with number M252. Removal of the pyr4 blaster cassette from pep1 locus was carried out essentially as described above. This pyr4⁻ strain was designated with number M284.

The third protease deletion to M284 was obtained by using slp1 deletion construct pTTv128. This construct contains a native KEX2 overexpression cassette targeted to the slp1 locus. The resulting strain was designated M304. M304 comprises MAB01 light chain fused to *T. reesei* truncated CBH1 carrier with NVISKR Kex2 cleavage sequence and MAB01 heavy chain fused to *T. reesei* truncated CBH1 carrier with AXE1 [DGETVVKR] Kex2 cleavage sequence.

Generation of MAB01 Producing Quadruple Protease Deletion Strain M371

Removal of the pyr4 blaster cassette from slp1 locus from strain M304 was carried out essentially as described above. This pyr4⁻ strain was designated with number M317. Gap1 was deleted from M317 using deletion construct pTTv117 above. A strain producing MAB01 and having quadruple protease deletion was designated as M371.

Generation of MAB01 Producing 8-Fold Protease Deletion Strain M646

The M646 slp2 deletion strain was made by transforming the pTTv115 deletion cassette into M564 (pyr4-version of M507). The M564 pyr4-strain was created essentially as described above. Approximately 5 μg of the deletion cassette was used to transform the MAB01 production strain M564. Growing streaks were screened by PCR (using the primers listed in Table 30-4) for correct integration and loss of slp2 ORF. Clones giving the expected signals were purified to single cell clones and rescreened by PCR using the primers listed in Table 30-4. A correct clone was designated as strain M646.

TABLE 30-4

Primers for screening pTTv115/Δslp2-pyr4 cassette integration and strain purity.

| For screening integration of pTTv115 (Δslp2-pyr4) | |
|---|---|
| Primer | Sequence |
| T054_slp2_5screen_F | GATGCACCGCTGCGGCC (SEQ ID NO: 527) |
| T1084_screen_5flk_pyr_rev | TCTTGAGCACGACAATCGAC (SEQ ID NO: 528) |
| T055_slp2_3screen_R | GGCGTTGCTCCCCATGCG (SEQ ID NO: 529) |
| T028_Pyr4_flank_rev | CATCCTCAAGGCCTCAGAC (SEQ ID NO: 530) |
| For screening deletion of slp2 (tre123244) ORF | |
| T111_slp2_ORF_F | ATGCGGTCCGTTGTCGCC (SEQ ID NO: 531) |
| T112_slp2_ORF_R | TTACTCGGAGAGCTCAGAGA (SEQ ID NO: 532) |

Generation of Antibody Fragments

Generation of various antibody fragments is described in the International Patent Application PCT/EP2013/050126.

TABLE 31-1

Overview of generation of the protease deletion strains having having MAB01 antibody. pTTv99/67 plasmids include MAB01 light chain fused to *T. reesei* truncated CBH1 carrier with NVISKR Kex2 cleavage sequence and MAB01 heavy chain fused to *T. reesei* truncated CBH1 carrier with AXE1 [DGETVVKR] Kex2 cleavage sequence.

| Strain | Vector | Clone | Strain transformed | Proteases k/o | Markers in strain |
|---|---|---|---|---|---|
| M181 | pTTv71 | 9-20A-1 | M127 | pep1 | pyr4 |
| M194 | pTTv42 | 13-172D | M181 | pep1 tsp1 | pyr4 bar |
| M252 | pTTv99/67 | 6.14A | M194 | pep1 tsp1 | AmdS/HygR |
| M284 | 5-FOA of M252 | 3A | pyr4- of M252 | pep1 tsp1 | none |
| M304 | pTTv128 | 12A | M284 | pep1 tsp1 slp1 | pyr4 |
| M317 | 5-FOA of M304 | 1A | pyr4- of M304 | pep1 tsp1 slp1 | None |
| M371 | pTTv117 | 44A | M317 | pep1 tsp1 slp1 gap1 | pyr4 |
| M244 | pTTv98/67 | 1.3Apep1 | M181 | pep1 | AmdS/HygR |
| M285 | 5-FOA of M244 | 2A / | pyr4- of M244 | pep1 | none |
| M292 | pTTv115 | 11A | M285 | pep1 slp2 | pyr4 |
| M295 | pTTv116 | 82A | M285 | pep1 slp3 | pyr4 |
| M507 | pTTv223 | 19B | M486 | pep1 tsp1 slp1 gap1 gap2 pep4 pep3 | AmdS |
| M564 | 5-FOA of M507 | | pyr4- of M507 | pep1 tsp1 slp1 gap1 gap2 pep4 pep3 | none |
| M646 | pTTv115 | | M564 | pep1 tsp1 slp1 gap1 gap2 pep4 pep3 slp2 | pyr4 |

Example 7

Fungal Strain Producing Man5

A filamentous fungal cell of the invention can also be engineered to produce Man5 as the substrate for fucosylation and production of FG0 glycans (i.e traditional pathway). If a filamentous fungus does not produce endogenously sufficient levels of Man5, an α1-2-mannosidase expression can be introduced to the filamentous fungal cell.

In addition to introducing GnTI and GnTII or a recombinant GnTII/I fusion protein into a Man5-producing strain, a mannosidase II activity is further needed to remove two mannoses from the GlcNAcMan5 glycan structure so that GnTII can use GlcNAcMan3 as an acceptor molecule.

Mannosidase II activity is introduced to the e.g. MAB01 antibody expressing *Trichoderma reesei* strain by designing a mannosidase II-containing expression cassette with a promoter for driving the mannosidase II expression. Useful promoters are those from e.g. gpdA or cbh1. Mannosidase II activity can be transformed by random or targeted integration followed by screening of strains with most suitable expression level. The expression cassette is linked with a proprietary selection marker gene, or a selection marker is co-transformed as a separate expression cassette. Transformation is performed according to methods described above.

For ER/Golgi expression, the catalytic domain of the mannosidase II may be fused with an N-terminal targeting peptide. Exemplary targeting peptide is an N-terminal portion of *T. reesei* KRE2.

After transformation of *Trichoderma* with the mannosidase II construct described above, *Trichoderma* strains are selected, streaked on selective medium for two successive rounds, and tested by PCR for integration of the expression constructs into the genome. Selected transformants of *Trichoderma* strains producing Man5 and expressing the GnTI and GnTII, mannosidase II, and MAB01 antibody are then cultured in shake flasks or fermentor conditions and analyzed for glycan content as described above.

The resulting strains are then subjected to transformation of GMD, FX and FUT8.

Example 8

Generation of a Fungal Strain Producing Galactosylated Glycans on an Antibody In order for a fungal strain to produce galactosylated and fucosylated glycans on an antibody, a β-1,4-galactosyltransferase gene is generated, cloned into a fungal expression plasmid followed by transformation into the fungal cell expressing an antibody of the above examples.

For example, a human β-1,4-galactosyltransferase I gene (GenBank accession P15291; gene NM_001497) is artificially synthesized and cloned into a *Trichoderma* expression cassette with a promoter for driving the galactosyltransferase expression. Useful promoters are those from gpdA or cbh1. In order to enhance galactosyltransferase targeting to ER/Golgi, targeting peptide derived from *Trichoderma* (or host cell) Kre2/Mnt1 (described in Schwientek et al. (1996)) can be used to generate a fusion construct. Targeting peptide is ligated in-frame to an N-terminal amino acid deletion of the galactosyltransferase. The encoded fusion protein localizes in the ER/Golgi by means of the KRE2 targeting peptide sequence while retaining its galactosyltransferase catalytic domain activity and is capable of transferring galactose onto GlcNAc(1-2)Man3GlcNAc2. The KRE2 targeting peptide may comprise the amino acids from about 1 to about 106 or from about 1 to about 83, or shorter, e.g. from about 1 to about 51 amino acids.

Kre2 (Tre21576) aa 1-106

(SEQ ID NO: 229)
MASTNARYVRYLLIAFFTILVFYFVSNSKYEGVDLNKGTFTAPDSTKTTP

KPPATGDAKDFPLALTPNDPGFNDLVGIAPGPRMNATFVTLARNSDVWDI

ARSIRQ

Kre2 aa 1-83

(SEQ ID NO: 230)
MASTNARYVRYLLIAFFTILVFYFVSNSKYEGVDLNKGTFTAPDSTKTTP

KPPATGDAKDFPLALTPNDPGFNDLVGIAPGPR

Kre2 aa 1-51

(SEQ ID NO: 231)
MASTNARYVRYLLIAFFTILVFYFVSNSKYEGVDLNKGTFTAPDSTKTTP

K

The galactosyltransferase expression cassette can be targeted to, for example, the cbh2 or a protease locus of *T. reesei*, using methods essentially as described above. Alternatively, galactosyltransferase activity can be transformed by random integration.

After transformation of *Trichoderma* with the galactosyltransferase construct described above, *Trichoderma* strains are selected, streaked on selective medium for two successive rounds, and tested by PCR for integration of the expression constructs into the genome. Selected transformants of *Trichoderma* strains producing galactosylated (and fucosylated) antibody are then cultured in shake flasks or fermentor conditions and analyzed for glycan content as described above.

Optionally, the fungal strain in the examples can be made to express UDP-galactose (UDP-Gal) transporter. Human UDP-galactose (UDP-Gal) transporter has been cloned and shown to be active in *S. cerevisiae*. (e.g. GenBank accession NP_005651; Kainuma, M., et al. 1999 Glycobiology 9(2): 133-141).

Further, to increase endogenous pool of UDP galactose expression of a UDP-galactose 4 epimerase (e.g. GenBank accession AAB86498) in a fungal cell may be introduced.

Example 9

Generation of Fungal Strain Producing Sialylated Glycans

The galactosylated glycans of previous example are substrates in the formation of sialylated glycoproteins produced in a filamentous fungus. The fungal cell is engineered to express enzymes needed in production and transport of sialylation pathway molecules. The following genes may be introduced, for example, into the fungal cell producing galactosylated and fucosylated glycans.

TABLE 31-2

| Gene name | Species | GenBank accession # |
|---|---|---|
| Glucosamine UDP-N-acetylglucosamine-2-epimerase/N-acetylmannosamine kinase | *Homo sapiens* glucosamine UDP-N-acetylglucosamine-2-epimerase/N-acetylmannosamine kinase (GNE) | Q6QNY5 (SEQ ID NO: 232) NP_001121699 (SEQ ID NO: 233) |

TABLE 31-2-continued

| Gene name | Species | GenBank accession # |
|---|---|---|
| N-acetylneuraminic acid synthase | Homo sapiens N-acetylneuraminic acid synthase (NANS) | NP_061819 (SEQ ID NO: 234) |
| N-acetylneuraminic acid phosphatase | Homo sapiens N-acetylneuraminic acid phosphatase (NANP; optional) | NP_689880 (SEQ ID NO: 235) |
| Cytidine monophosphate N-acetylneuraminic acid synthetase | Homo sapiens cytidine monophosphate N-acetylneuraminic acid synthetase (CMAS) | NP_061156 (SEQ ID NO: 236) |
| CMP-sialic acid transporter | Mus musculus solute carrier family 35 member 1 (SLC35A1) | Q61420 (SEQ ID NO: 237) |
| Sialyltransferase | Mus musculus β-galactoside α2,6-sialyltransferase 1 (St6gal1) | NP_001239434 (SEQ ID NO: 238) |
| | Homo sapiens β-galactoside α2,3-sialyltransferase 4 (ST3GAL4) | NP_006269 (SEQ ID NO: 239) |

Briefly, open reading frames for the above genes UDP-N-acetylglucosamine-2-epimerase/N-acetylmannosamine kinase (human, GNE), N-acetylneuraminic acid synthase (human, NANS), N-acetylneuraminic acid phosphatase (human, NANP, this enzyme is optional), cytidine monophosphate N-acetylneuraminic acid synthetase (human, CMAS), solute carrier family 35 member 1 (M. musculus, SLC35A1), β-galactoside α2,6-sialyltransferase 1 (M. musculus, ST6GAL1) and β-galactoside α2,3-sialyltransferase 4 (human, ST3GAL4) are codon-optimized and synthesized for Trichoderma expression. The resultant synthetic DNAs for GNE, NANS, NANP, CMAS, SLC35A1, ST6GAL1 and ST3GAL4 are generated with appropriate restriction sites and cloned into expression vector(s). Tandem constructs/expression cassettes may be also generated with two or more genes to reduce number of transformations and loci to be transformed.

Sialyltransferase catalytic domain may be fused to a Trichoderma targeting peptide, for example, Kre2 described above.

The sialylation pathway gene expression cassettes can be targeted to, for example, the cbh2, egL2, or a protease locus of T. reesei, using methods essentially as described above. Alternatively, sialylation pathway genes can be transformed by random integration.

After transformation of Trichoderma with the sialylation pathway gene constructs described above, Trichoderma strains are selected, streaked on selective medium for two successive rounds, and tested by PCR for integration of the expression constructs into the genome. Selected transformants of Trichoderma strains producing sialylated (and fucosylated) antibody are then cultured in shake flasks or fermentor conditions and analyzed for glycan content as described above. Neutral N-glycans are detected in positive ion reflector mode as [M+Na]+ ions, and acidic N-glycans are detected in negative ion linear mode as [M-H]– ions and as described above.

Example 10

Proteases of the invention may also be silenced using RNAi technology. Examples of RNAi constructs to silence slp2 is described in the International Patent Application PCT/EP2013/050126.

Example 11

Generation of Fucosylated Antibody Glycoform Producing T. reesei strains

A pyr4-strain was created from M629 and the expression cassettes of pTTv224 and pTTv225 were transformed to the strain, however, N-glycan analysis showed that GNT2 activity was lost during the pyr4-loopout and therefore a clone (60-1; M905) was chosen to be retransformed with GnTs and GalT.

Figure 13:
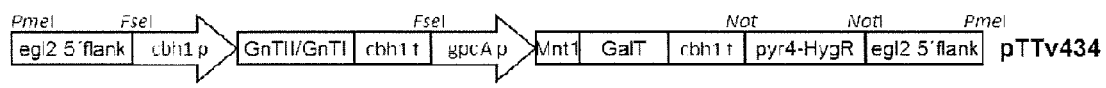
FIG. 13. Schematic expression cassette design for plasmids pTTv434

The coding sequence of human β-1,4-galactosyltransferase 1 (GalTI, SEQ ID NO:409) was optimized for T. reesei expression. A plasmid containing expression cassettes for human GalTI and chimeric GnTII/GnTI was generated (GnTII/GnTI fusion protein has been described in WO2012069593). The plasmid was cloned in two steps using yeast homologous recombination; first plasmid pTTv363 to which expression cassette for GNT2/1 was added generating plasmid pTTv434 (see FIG. 13). For pTTv363 plasmid pTTv264 (described in International patent application PCT/EP2013/050126) was used as backbone vector. This plasmid contains integration flanks for egl2 locus, gpdA promoter, cbh1 terminator and hygromycin marker. The plasmid was digested with PacI-NotI and all three fragments were utilised in cloning the plasmid pTTv363. For targeting of the GalTI to Golgi, the transmembrane region of a T. reesei native mannosyltransferase KRE2 (MNT1) was used. The first 85 amino acids of the KRE2 were fused to human GalTI without the transmembrane domain (amino acids 1-77). The kre2 localisation fragment was generated by PCR from genomic DNA and the GalTI fragment was generated by PCR from the vector containing the optimised GalTI sequence (Table 32). pyr4 marker, egl2 direct repeat and cbh2 terminator fragments were generated by PCR from genomic DNA, in order to generate a plasmid containing pyr4-hygromycin double marker. In addition to pTTv363, alternative GalTI plasmid pTTv362 was cloned. This plasmid has shorter truncation in the N-terminus of the human GalTI (amino acids 1-43). Otherwise the plasmid is like pTTv363 described above. The clonings of these plasmids were performed as described in Example 2. Clones were sequenced to verify the sequence and one correct clone for each plasmid were chosen to be the final vectors pTTv362 and pTTv363.

TABLE 32

List of primers used for cloning vectors pTTv362 and pTTv363.

| Fragment | Primer | Primer sequence |
|---|---|---|
| KRE2 | T1372_kre2_recgpda_for | ACTAACAGCTACCCCGCTTGAGCAGACATCA TGGCGTCAACAAATGCGCG (SEQ ID NO: 533) |
| | T337_21576_r | GTTCATTCGAGGGCCGGGAG (SEQ ID NO: 534) |

TABLE 32-continued

List of primers used for cloning vectors pTTv362 and pTTv363.

| Fragment | Primer | Primer sequence |
|---|---|---|
| GalTI Δ43 | T1373_galt_44_for | GTCGGCATCGCTCCCGGCCCTCGAATGAACG GCAGGGACCTCAGCCGCCT (SEQ ID NO: 535) |
| | T1374_galt_rev | ACCGGTGCGTCAGGCTTTCGCCACGGAGCTT CAGCTGGGGGTGCCGATGT (SEQ ID NO: 536) |
| GalTI Δ77 | T1375_galt_78_for | GTCGGCATCGCTCCCGGCCCTCGAATGAACC GAACCGGCGGCGCCCGCCC (SEQ ID NO: 537) |
| | T1374_galt_rev | ACCGGTGCGTCAGGCTTTCGCCACGGAGCTT CAGCTGGGGGTGCCGATGT (SEQ ID NO: 538) |
| pyr4 | T1369_pyr4_for | CTAGCATCGACTACTGCTGC (SEQ ID NO: 539) |
| | T1370_pyr4_rechphnew_rev | AAGGGGACCGGCCGCTAGTCTCACCGTTATC ATGCAAAGATACACATCAA (SEQ ID NO: 540) |
| egl2 3DR | T1367_egl2_3dr_for | TCCGTTGCGAGGCCAACTTGCATTGCTGTCAAGA CGATGAGGATCCCACTCTGAGCTGAATGCAGA (SEQ ID NO: 541) |
| | T1368_egl2_3dr_rev | GCGCTGGCAACGAGAGCAGAGCAGCAGTAGTCG ATGCTAGGCGGCCGCTGCGACAACTACGGATGC (SEQ ID NO: 542) |
| cbh2 term | T161_tcbh2_seq_f2 | CAGCTGCGGAGCATGAGCCT (SEQ ID NO: 543) |
| | T1371_tcbh2_recelg2_rev | TGGCGAGGCTTCTGCATTCAGCTCAGAGTGG CGGCCGCGTGCTGCGGAATCATTATCA (SEQ ID NO: 544) |

The pTTv363 vector was linearised with FseI, and the human chimeric GnTII/GnTI, together with the cbh1 promoter and terminator, was inserted by yeast recombination with long overlapping primers as described in example 2 (Table 33). The GnTII/GnTI expression cassette was digested from plasmid pTTv110 with SoI (pTTv110 is described in WO2012069593). The presence of the GnTII/GnTI gene was confirmed by digesting the prepared plasmids with SacI and one correct clone was chosen to be the final vector pTTv434.

The PmeI expression construct fragment of pTTv434 was prepared and transformed to the M905 strain essentially as described in Example 2. Transformation plates contained hygromycin (150 μg/ml). Transformants were streaked onto TrMM plates containing hygromycin (125 μg/ml) and 0.1% TritonX-100 and visible amounts of the $2^{nd}$ streaks (total sum 51) were denaturised by boiling in 1% SDS followed by addition of 10% n-octyl-13-D-glucopyranoside to eliminate SDS. PNGase F (*Elizabethkingia meningosepticum*, Prozyme) was performed as an overnight reaction in 20 mM sodium phosphate buffer, pH 7.3. The released N-glycans

TABLE 33

List of primers used for cloning vector pTTv434.

| Fragment | Primer | Primer sequence |
|---|---|---|
| GNT2/1 overlapping oligos 5' | T1560 | ACACTCTCAGAATAAATTCATCGCCAATTTGACAGGCCGGCC ATTCTCACGGTGAATGTAGGCCTTTTGTAGGGTAGGAATT (SEQ ID NO: 545) |
| | T1561 | AATTCCTACCCTACAAAAGGCCTACATTCACCGTGAGAATGG CCGGCCTGTCAAATTGGCGATGAATTTATTCTGAGAGTGT (SEQ ID NO: 546) |
| GNT2/1 overlapping oligos 3' | T1562 | TTGCATTGCTGTCAAGACGATGACAACGTAGCCGAGGACCG GCCGGCCCCTTGTATCTCTACACACAGGCTCAAATCAATAAG AAG (SEQ ID NO: 547) |
| | T1563 | CTTCTTATTGATTTGAGCCTGTGTGTAGAGATACAAGGGGCC GGCCGGTCCTCGGCTACGTTGTCATCGTCTTGACAGCAATG CAA (SEQ ID NO: 548) | were purified using Hypersep C18 and Hypersep Hypercarb 10 mg (Thermo Scientific) and analysed by MALDI-TOF MS. Clones positive for galactosylated N-glycans were selected for shake flask cultures. Streaks were also screened by PCR for correct integration into the egl2 locus and loss of the egl2 ORF (Table 34). Promising transformants were cultivated in a 50 ml volume for seven days at +28° C. in a media containing TrMM, pH 5.5, supplemented with 40 g/l lactose, 20 g/l spent grain extract, 9 g/l casamino acids and 100 mM PIPPS.

TABLE 34

List of primers used for PCR screening of T. reesei transformants

| | |
|---|---|
| 5' flank screening primers: | 1932 bp product |
| T1410_egl2_5int_f3 | GCTCGAGACGTACGATTCAC (SEQ ID NO: 549) |
| T176_pcbh1_seq_r4 | CTCCGGGTTCGCAGCAGCTT (SEQ ID NO: 550) |
| 3' flank screening primers: | 1168 bp product |
| T1158_egl2_3pr_intR2 | GGCGAAATAAGCTCACTCAG (SEQ ID NO: 551) |
| T1411_cbh2t_end_f | CCAATAGCCCGGTGATAGTC (SEQ ID NO: 552) |
| egl1_ORF_primers: | 368 bp product |
| T1412_egl2_orf_f1 | AACAAGTCCGTGGCTCCATT (SEQ ID NO: 553) |
| T1413_egl2_orf_r1 | CCAACTTTTCAGCCAGCAAC (SEQ ID NO: 554) |

For N-glycan analysis the antibody was purified from day 5 culture supernatants using Protein G HP MultiTrap 96-well filter plate (GE Healthcare) basically according to manufacturer's instructions, but as an elution buffer 0.1 M citrate buffer, pH 2.6, was used. The antibody concentrations were determined via UV absorbance against MAB01 standard curve and the N-glycans were analysed from 15-20 µg of purified antibody as described in Example 2. N-glycans were analysed from total of eleven pTTv434 clones and four of them turned out to produce fucosylated or fucosylated and galactosylated glycoforms on antibody (Table 35).

TABLE 35

Relative proportions of neutral N-glycans from purified antibody from pTTv434 clones #3, #41, #48 and #64.

| Composition | Short | m\z | #3 % | #41 % | #48 % | #64 % |
|---|---|---|---|---|---|---|
| Hex3HexNAc2 | Man3 | 933.310 | 31.7 | 0.0 | 4.7 | 20.2 |
| Hex4HexNAc2 | Man4 | 1095.370 | 3.9 | 0.0 | 3.0 | 5.5 |
| Hex3HexNAc3 | GnMan3 | 1136.400 | 3.3 | 0.0 | 0.0 | 17.9 |
| Hex5HexNAc2 | Man5 | 1257.420 | 4.4 | 12.4 | 22.9 | 5.3 |
| Hex3HexNAc3dHex | FGnMan3 | 1282.450 | 0.0 | 0.0 | 0.0 | 8.3 |
| Hex3HexNAc4 | G0 | 1339.480 | 18.6 | 0.0 | 0.0 | 0.0 |
| Hex6HexNAc2 | Hex6 | 1419.480 | 32.5 | 48.3 | 39.3 | 42.7 |
| Hex3HexNAc4dHex | FG0 | 1485.530 | 3.3 | 0.0 | 0.0 | 0.0 |
| Hex4HexNAc4 | G1 | 1501.530 | 0.9 | 0.0 | 0.0 | 0.0 |
| Hex7HexNAc2 | Hex7 | 1581.530 | 1.4 | 16.1 | 13.1 | 0.0 |
| Hex5HexNAc4 | G2 | 1663.580 | 0.0 | 7.9 | 1.9 | 0.0 |
| Hex8HexNAc2 | Hex8 | 1743.580 | 0.0 | 8.3 | 8.9 | 0.0 |
| Hex5HexNAc4dHex | FG2 | 1809.640 | 0.0 | 6.9 | 1.8 | 0.0 |
| Hex9HexNAc2 | Hex9 | 1905.630 | 0.0 | 0.0 | 3.5 | 0.0 |
| Hex10HexNAc2 | Hex10 | 2067.690 | 0.0 | 0.0 | 0.9 | 0.0 |

Example 12

Protease Activity Measurement of Protease Deficient T reesei Strains

The protein concentrations were determined from supernatant samples from day 2-7 of 1-7× protease deficient strains according to EnzChek protease assay kit (Molecular probes #E6638, green fluorescent casein substrate). Briefly, the supernatants were diluted in sodium citrate buffer to equal total protein concentration and equal amounts of the diluted supernatants were added into a black 96 well plate, using 3 replicate wells per sample. Casein FL diluted stock made in sodium citrate buffer was added to each supernatant containing well and the plates were incubated covered in plastic bag at 37° C. The fluorescence from the wells was measured after 2, 3, and 4 hours. The readings were done on the Varioskan fluorescent plate reader using 485 nm excitation and 530 nm emission. Some protease activity measurements were performed using succinylated casein (QuantiCleave protease assay kit, Pierce #23263) according to the manufacturer's protocol.

The pep1 single deletion reduced the protease activity by 1.7-fold, the pep1/tsp1 double deletion reduced the protease activity by 2-fold, the pep1/tsp1/slp1 triple deletion reduced the protease activity by 3.2-fold, the pep1/tsp1/slp1/gap1 quadruple deletion reduced the protease activity by 7.8-fold compared to the wild type M124 strain, the pep1/tsp1/slp1/gap1/gap2 5-fold deletion reduced the protease activity by 10-fold, the pep1/tsp1/slp1/gap1/gap2/pep4 6-fold deletion reduced the protease activity by 15.9.fold, and the pep1/tsp1/slp1/gap1/gap2/pep4/pep3 7-fold deletion reduced the protease activity by 18.2-fold.

Figure 14:
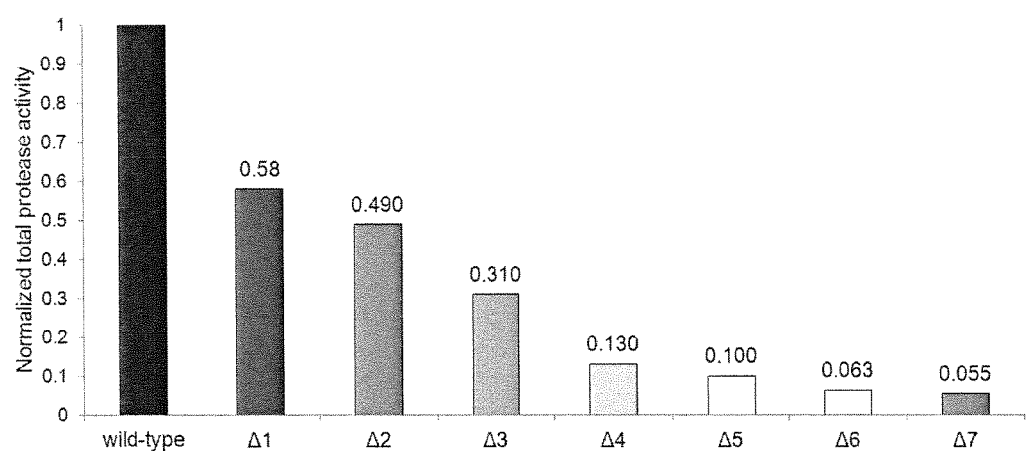
FIG. 14 graphically depicts normalized protease activity data from culture supernatants from each of the protease deletion supernatants and the parent strain M124. Protease activity was measured at pH 5.5 in first 5 strains and at pH 4.5 in the last three deletion strains. Protease activity is against green fluorescent casein. The six protease deletion strain has only 6% of the wild type parent strain and the 7 protease deletion strain protease activity was about 40% less than the 6 protease deletion strain activity.

The FIG. 14 graphically depicts normalized protease activity data from culture supernatants from each of the protease deletion supernatants (from 1-fold to 7-fold deletion mutant) and the parent strain M124. Protease activity was measured at pH 5.5 in first 5 strains and at pH 4.5 in the last three deletion strains. Protease activity is against green fluorescent casein. The six-fold protease deletion strain has only 6% of the wild type parent strain and the 7-fold protease deletion strain protease activity was about 40% less than the 6-fold protease deletion strain activity.

Example 13

Useful Polynucleotide and Amino Acid Sequences for Practicing the Invention

| SEQ | |
|---|---|
| 1 | Human FUT8 optimized coding sequence (as present in transformed strains) |
| 2 | C. elegans GMD optimized coding sequence (as present in transformed strains) |
| 3 | C. elegans FX optimized coding sequence (as present in transformed strains) |
| 4 | C. elegans GDP-fucose transporter optimized coding sequence (as present in transformed strains) |
| 5 | T. reesei KRE2/MNT1 coding sequence used for Golgi targeting |
| 6 | Human FUT8 protein sequence |
| 7 | C. elegans GMD protein sequence |
| 8 | C. elegans FX protein sequence |
| 9 | C. elegans GDP-fucose transporter |
| 10 | T. reesei KRE2/MNT1 protein sequence used for Golgi targeting |
| 11 | 5' flank nucleic acid sequence of pep4 in the cassette used for integration |
| 12 | 3' flank nucleic acid sequence of pep4 in the cassette used for integration |
| 13 | H. pylori FX protein sequence |
| 14 | H. pylori optimized FX coding sequence |
| 15 | H. pylori GMD protein sequence |
| 16 | H. pylori optimized GMD coding sequence |
| 17 | T. reesei amino acid pep1 |
| 18 | T. reesei amino acid pep2 |
| 19 | T. reesei amino acid pep3 |
| 20 | T. reesei amino acid pep4 |
| 21 | T. reesei amino acid pep5 |
| 22 | T078__74156__3orf__pcr (primer) |
| 23 | T. reesei amino acid pep7 |
| 24 | T. reesei amino acid tsp1 |
| 25 | T. reesei amino acid slp1 |
| 26 | T. reesei amino acid slp2 |
| 27 | T. reesei amino acid slp3 |
| 28 | T. reesei amino acid slp5 |
| 29 | T. reesei amino acid slp6 |
| 30 | T. reesei amino acid slp7 |
| 31 | T. reesei amino acid slp8 |
| 32 | T. reesei amino acid gap1 |
| 33 | T. reesei amino acid gap2 |
| 34 | T. reesei amino acid tpp1 |
| 35 | T298__77579__5f (primer) |
| 36 | T__758__pTTv224__1(primer) |
| 37 | T729__pTTv227__3(primer) |
| 38 | T730__pTTv227__4(primer) |
| 39 | T731__pTTv227__5(primer) |
| 40 | T732__pTTv227__6(primer) |
| 41 | T733__pTTv227__7(primer) |
| 42 | T734__pTTv227__8(primer) |
| 43 | T735__pTTv227__9(primer) |
| 44 | T759__pTTv224__2(primer) |
| 45 | T760__pTTv224__3(primer) |
| 46 | T761__pTTv224__4(primer) |
| 47 | T762__pTTv225__1(primer) |
| 48 | T763__pTTv225__2(primer) |
| 49 | T764__pTTv225__3(primer) |
| 50 | T759__pTTv224__2(primer) |
| 51 | T765__pTTv225__4(primer) |
| 52 | T738__pTTv228__2(primer) |
| 53 | T739__pTTv228__3(primer) |
| 54 | T740__pTTv228__4(primer) |
| 55 | T741__pTTv228__5(primer) |
| 56 | T742__pTTV228__6(primer) |
| 57 | T743__pTTv228__7(primer) |
| 58 | T744__pTTv228__8(primer) |
| 59 | T766__pTTv225__5(primer) |
| 60 | T301__77579__3r (primer) |
| 61 | T780__pTTv226__1(primer) |
| 62 | T781__pTTv226__2(primer) |
| 63 | T782__pTTv226__3(primer) |
| 64 | T783__pTTv226__4(primer) |
| 65 | T023__pRS426__5.1sekv(primer) |
| 66 | T228__pRS426__3.1sekv(primer) |
| 67 | T094__pyr4__F(primer) |
| 68 | T770__alg3__3pr__int__pyr4__F(primer) |
| 69 | T785(primer) |
| 70 | T786(primer) |
| 71 | T787(primer) |

-continued

| SEQ | |
|---|---|
| 72 | T790(primer) |
| 73 | T791(primer) |
| 74 | T792(primer) |
| 75 | T793(primer) |
| 76 | T794(primer) |
| 77 | T795(primer) |
| 78 | T796(primer) |
| 79 | T797(primer) |
| 80 | T798(primer) |
| 81 | T799(primer) |
| 82 | T800(primer) |
| 83 | T801(primer) |
| 84 | T802(primer) |
| 85 | T803(primer) |
| 86 | T804(primer) |
| 87 | T805(primer) |
| 88 | T809(primer) |
| 89 | T810(primer) |
| 90 | T811(primer) |
| 91 | T812(primer) |
| 92 | T813(primer) |
| 93 | T814(primer) |
| 94 | T815(primer) |
| 95 | T816(primer) |
| 96 | T817(primer) |
| 97 | T818(primer) |
| 98 | T819(primer) |
| 99 | T820(primer) |
| 100 | T821(primer) |
| 101 | T824(primer) |
| 102 | T825(primer) |
| 103 | T302__77579__5int(primer) |
| 104 | T018__pgpdA__5rev(primer) |
| 105 | T816(primer) |
| 106 | T415__77579__3screen(primer) |
| 107 | T821(primer) |
| 108 | T416__77579__probeF(primer) |
| 109 | T417__77579__probeR(primer) |
| 110 | Hp GMD forw(primer) |
| 111 | Hp GMD rev(primer) |
| 112 | gi│324519268│gb│ADY47333.1│GDP-L-fucose synthase [*Ascaris suum*] |
| 113 | gi│170576679│ref│XP__001893725.1│GDP-L-fucose synthetase [*Brugia malayi*] |
| 114 | gi│363731098│ref│XP__418405.3│PREDICTED: GDP-L-fucose synthase isoform 2 [*Gallus gallus*] |
| 115 | gi│116267961│ref│NP__001070752.1│uncharacterized protein LOC768139 [*Danio rerio*] |
| 116 | gi│116063448│gb│AAI23105.1│LOC398450 protein [*Xenopus laevis*] |
| 117 | gi│114051291│ref│NP__001039604.1│GDP-L-fucose synthase [*Bos taurus*] |
| 118 | │149757572│ref│XP__001505053.1│PREDICTED: GDP-L-fucose synthase [*Equus caballus*] |
| 119 | gi│73974844│ref│XP__532346.2│PREDICTED: GDP-L-fucose synthase [*Canis lupus familiaris*] |
| 120 | gi│4507709│ref│NP__003304.1│GDP-L-fucose synthase [*Homo sapiens*] |
| 121 | gi│350538233│ref│NP__001233708.1│GDP-L-fucose synthase [*Cricetulus griseus*] |
| 122 | gi│188536096│ref│NP__001120927.1│GDP-L-fucose synthase [*Rattus norvegicus*] |
| 123 | gi│13654268│ref│NP__112478.1│GDP-L-fucose synthase [*Mus musculus*] |
| 124 | gi│312070424│ref│XP__003138140.1│GDP-mannose 4,6-dehydratase [*Loa loa*] |
| 125 | gi│170587907│ref│XP__001898715.1│GDP-mannose 4,6-dehydratase [*Brugia malayi*] |
| 126 | gi│118778930│ref│XP__308963.3│AGAP006783-PA [*Anopheles gambiae* str. PEST] |
| 127 | gi│157108166│ref│XP__001650108.1│gdp mannose-4,6-dehydratase [*Aedes aegypti*] |
| 128 | gi│156523058│ref│NP__001095945.1│GDP-mannose 4,6 dehydratase isoform 1 [*Danio rerio*] |
| 129 | gi│213515196│ref│NP__001134845.1│GDP-mannose 4,6 dehydratase [*Salmo salar*] |
| 130 | gi│328790131│ref│XP__395164.3│PREDICTED: GDP-mannose 4,6 dehydratase-like [*Apis mellifera*] |
| 131 | gi│24158427│ref│NP__608888.2│GDP-mannose 4,6-dehydratase [*Drosophila melanogaster*] |
| 132 | gi│147899928│ref│NP__001080352.1│GDP-mannose 4,6 dehydratase [*Xenopus laevis*] |
| 133 | gi│122692409│ref│NP__001073800.1│GDP-mannose 4,6 dehydratase [*Bos taurus*] |
| 134 | Article I. gi│350539705│ref│NP__001233625.1│GDP-mannose 4,6 dehydratase [*Cricetulus griseus*] |
| 135 | gi│22122523│ref│NP__666153.1│GDP-mannose 4,6 dehydratase [*Mus musculus*] |

| SEQ | |
|---|---|
| 136 | gi|88853855|ref|NP_001034695.1|GDP-mannose 4,6 dehydratase [*Rattus norvegicus*] |
| 137 | gi|4504031|ref|NP_001491.1|GDP-mannose 4,6 dehydratase isoform 1 [*Homo sapiens*] |
| 138 | gi|198423994|ref|XP_002131034.1|PREDICTED: similar to GDP-mannose 4,6-dehydratase [*Ciona intestinalis*] |
| 139 | gi|337754860|ref|YP_004647371.1|GDP-mannose 4,6-dehydratase [*Francisella* sp. TX077308] |
| 140 | gi|380558719|gb|EIA81894.1|GDP-D-mannose dehydratase [*Campylobacter coli* 59-2] |
| 141 | gi|325287517|ref|YP_004263307.1|GDP-mannose 4,6-dehydratase [*Cellulophaga lytica* DSM 7489] |
| 142 | gi|296482935|gb|DAA25050.1|alpha-(1,6)-fucosyltransferase [*Bos taurus*] |
| 143 | gi|52546726|ref|NP_001005262.1|alpha-(1,6)-fucosyltransferase [*Canis lupus familiaris*] |
| 144 | gi|148704495|gb|EDL36442.1|fucosyltransferase 8, isoform CRA_b [*Mus musculus*] |
| 145 | gi|149051511|gb|EDM03684.1|rCG62185, isoform CRA_a [*Rattus norvegicus*] |
| 146 | gi|354479164|ref|XP_003501783.1|PREDICTED: alpha-(1,6)-fucosyltransferase [*Cricetulus griseus*] |
| 147 | gi|52345460|ref|NP_001004766.1|alpha-(1,6)-fucosyltransferase [*Gallus gallus*] |
| 148 | gi|47575776|ref|NP_001001232.1|alpha-(1,6)-fucosyltransferase [*Xenopus (Silurana) tropicalis*] |
| 149 | gi|51467976|ref|NP_001003855.1|alpha-(1,6)-fucosyltransferase [*Danio rerio*] |
| 150 | gi|324513182|gb|ADY45426.1|GDP-fucose transporter [*Ascaris suum*] |
| 151 | gi|312066547|ref|XP_003136322.1|GDP-fucose transporter [*Loa loa*] |
| 152 | gi|157820319|ref|NP_001101218.1|GDP-fucose transporter 1 [*Rattus norvegicus*] |
| 153 | gi|350538845|ref|NP_001233737.1|GDP-fucose transporter [*Cricetulus griseus*] |
| 154 | gi|74194961|dbj|BAE26053.1|unnamed protein product [*Mus musculus*] |
| 155 | gi|22003876|ref|NP_665831.1|GDP-fucose transporter 1 isoform 2 [*Mus musculus*] |
| 156 | gi|313851048|ref|NP_001186580.1|GDP-fucose transporter 1 [*Gallus gallus*] |
| 157 | gi|301609135|ref|XP_002934120.1|PREDICTED: GDP-fucose transporter 1-like isoform 1 [*Xenopus (Silurana) tropicalis*] |
| 158 | gi|56693251|ref|NP_001008590.1|GDP-fucose transporter 1 [*Danio rerio*] |
| 159 | gi|155372141|ref|NP_001094680.1|GDP-fucose transporter 1 [*Bos taurus*] |
| 160 | gi|308235937|ref|NP_001184118.1|GDP-fucose transporter 1 [*Canis lupus familiaris*] |
| 161 | gi|223671915|ref|NP_060859.4|GDP-fucose transporter 1 isoform a [*Homo sapiens*] |
| 162 | gi|223671917|ref|NP_001138737.1|GDP-fucose transporter 1 isoform b [*Homo sapiens*] |
| 163 | Nucleic acid sequence of *T. reesei* alg3 gene |
| 164 | Amino acid sequence of *T. reesei* alg3 protein |
| 165 | Human GnTI amino acid sequence |
| 166 | Human GnTII amino acid sequence |
| 167 | Hp FX forw(primer) |
| 168 | Hp FX rev(primer) |
| 169 | Ann 79 hph(primer) |
| 170 | Hph-gene 3.1 PCR(primer) |
| 171-173 | KRE2 targeting peptide (cytoplasmic, transmembrane, luminal) |
| 174-176 | KRE2 alternative1 (cytoplasmic, transmembrane, luminal) |
| 177-179 | OCH1 (cytoplasmic, transmembrane, luminal) |
| 180-182 | OCH1 alternative1 (cytoplasmic, transmembrane, luminal) |
| 183-185 | MNN9 targeting peptide (cytoplasmic, transmembrane, luminal) |
| 186-188 | MNN9 alternative1 targeting peptide (cytoplasmic, transmembrane, luminal) |
| 189-191 | MNN9 alternative2 targeting peptide (cytoplasmic, transmembrane, luminal) |
| 192-194 | MNN10 targeting peptide (cytoplasmic, transmembrane, luminal) |
| 195-197 | MNN10 alternative1 targeting peptide (cytoplasmic, transmembrane, luminal) |
| 198-200 | MNS1 targeting peptide (cytoplasmic, transmembrane, luminal) |
| 201-203 | MNS1 alternative1 targeting peptide (cytoplasmic, transmembrane, luminal) |
| 204-206 | MNS1 alternative2 targeting peptide (cytoplasmic, transmembrane, luminal) |
| 207-209 | MNS1 alternative3 targeting peptide (cytoplasmic, transmembrane, luminal) |

| SEQ | |
|---|---|
| 210-211 | MNS1 alternative4 targeting peptide (transmembrane, luminal) |
| 212-214 | VAN1 targeting peptide (cytoplasmic, transmembrane, luminal) |
| 215-217 | VAN1 alternative1 targeting peptide (cytoplasmic, transmembrane, luminal) |
| 218-220 | VAN1 alternative2 targeting peptide (cytoplasmic, transmembrane, luminal) |
| 221-223 | Other01 targeting peptide (cytoplasmic, transmembrane, luminal) |
| 224-226 | Other02 targeting peptide (cytoplasmic, transmembrane, luminal) |
| 227 | >gi\|74583855\|sp\|Q12520.1\|HUT1_YEAST RecName: Full = UDP-galactose transporter homolog 1; AltName: Full = Multicopy suppressor of leflunomide-sensitivity protein 6 |
| 228 | >gi\|1119217\|gb\|AAB86498.1\|UDP-galactose-4-epimerase [*Homo sapiens*] |
| 229 | Kre2 (Tre21576) amino acids 1-106 |
| 230 | Kre2 (Tre21576) amino acids 1-83 |
| 231 | Kre2 (Tre21576) amino acids 1-51 |
| 232 | *Homo sapiens* glucosamine UDP-N-acetylglucosamine-2-epimerase/N-acetylmannosamine kinase (GNE) Q6QNY5 |
| 233 | *Homo sapiens* glucosamine UDP-N-acetylglucosamine-2-epimerase/N-acetylmannosamine kinase (GNE) NP_001121699 |
| 234 | *Homo sapiens* N-acetylneuraminic acid synthase (NANS) NP_061819 |
| 235 | *Homo sapiens* N-acetylneuraminic acid phosphatase (NANP) NP_689880 |
| 236 | *Homo sapiens* cytidine monophosphate N-acetylneuraminic acid synthetase (CMAS) NP_061156 |
| 237 | *Mus musculus* solute carrier family 35 member 1 (SLC35A1) Q61420 |
| 238 | *Mus musculus* β-galactoside α2,6-sialyltransferase 1 (St6gal1) NP_001239434 |
| 239 | *Homo sapiens* β-galactoside α2,3-sialyltransferase 4 (ST3GAL4) NP_006269 |
| 240 | Chimeric GnTII/GnTI amino acid sequence |
| 241 | 5flankfw |
| 242 | 5flankrev |
| 243 | 3flankfw |
| 244 | 3flankrev |
| 245 | PTfwd |
| 246 | PTrev |
| 247 | T315_pyr4_for |
| 248 | T316_pyr4_rev |
| 249 | T317_pyr4_loop_for |
| 250 | T318_pyr4_loop_rev |
| 251 | T075_74156_5int |
| 252 | T032_Bar_end_for |
| 253 | T076_74156_3int |
| 254 | T031_Bar_begin_rev2 |
| 255 | T075_74156_5int |
| 256 | T027_Pyr4_orf_start_rev |
| 257 | T077_74156_5orf_pcr |
| 258 | orf_rev |
| 259 | T303_71322_5f |
| 260 | T304_71322_5r_pt |
| 261 | T305_71322_3f_pt |
| 262 | T306_71322_3r |
| 263 | T083_74156_5a_seq |
| 264 | T084_74156_3a_seq |
| 265 | T307_71322_5int |
| 266 | T027_Pyr4_orf_start_rev |
| 267 | T308_71322_3int |
| 268 | T028_Pyr4_flank_rev |
| 269 | T309_71322_5orfpcr |
| 270 | T310_71322_3orfpcr |
| 271 | 5flankfw_vect |
| 272 | slp1_5flankrev_pyr4Prom |
| 273 | slp1_3flankfw_pyr4Term |
| 274 | 3flankrev_vect |
| 275 | T307_71322_5int |
| 276 | T026_Pyr4_orf_5rev2 |
| 277 | T308_71322_3int |
| 278 | T028_Pyr4_flank_rev |
| 279 | T079_slp1_scrn_5forw |
| 280 | T026_Pyr4_orf_5rev2 |
| 281 | T080_slp1_scrn_3rev |
| 282 | T028_Pyr4_flank_rev |
| 283 | T081_slp1_orf_fw |
| 284 | T082_slp1_orf_rev |
| 285 | JJ-045 primer |
| 286 | JJ-046 primer |

-continued

| SEQ | |
|---|---|
| 287 | JJ-047 primer |
| 288 | JJ-048 primer |
| 289 | T079_slp1_scrn_5forw |
| 290 | T026_Pyr4_orf_5rev2 |
| 291 | T080_slp1_scrn_3rev |
| 292 | T028_Pyr4_flank_rev |
| 293 | T052_gap1_5screen_F |
| 294 | T026_Pyr4_orf_5rev2 |
| 295 | T053_gap1_3screen_R |
| 296 | T028_Pyr4_flank_rev |
| 297 | T109_gap1_ORF_F |
| 298 | T110_gap1_ORF_R |
| 299 | T101_gap2_5flank_F_pRS426 |
| 300 | T102_gap2_5flank_R_pyr4 |
| 301 | T103gap2-loop_F_pyr4 |
| 302 | T104gap2-loop_R |
| 303 | T105gap2_3flank_F_loop |
| 304 | T106_gap2_3flank_R_pRS426 |
| 305 | T052_gap1_5screen_F |
| 306 | T026_Pyr4_orf_5rev2 |
| 307 | T053_gap1_3screen_R |
| 308 | T028_Pyr4_flank_rev |
| 309 | T048_gap2_5screen_F |
| 310 | T026_Pyr4_orf_5rev2 |
| 311 | T049_gap2_3screen_R |
| 312 | T028_Pyr4_flank_rev |
| 313 | T107_gap2_ORF_F |
| 314 | T108_gap2_ORF_R |
| 315 | T209_pyr4_f_recpep4_5f |
| 316 | T211_pep4_loop_f_recpyr4 |
| 317 | T212_pep4_loop_r_recpep4_3f |
| 318 | T222_gap2_5f_f2 |
| 319 | T049_gap2_3screen_R |
| 320 | T302_77579_5int |
| 321 | T027_Pyr4_orf_start_rev |
| 322 | T415_77579_3screen |
| 323 | T061_pyr4_orf_screen_2F |
| 324 | T416_77579_probeF |
| 325 | T417_77579_probeR |
| 326 | T346_pep3_5f_for |
| 327 | T347_pep3_5f_rev |
| 328 | T348_pep3_loop_for |
| 329 | T349_pep3_loop_rev |
| 330 | T350_pep3_3f_for |
| 331 | T351_pep3_3f_rev |
| 332 | T389_cDNApromoter_pep3flank |
| 333 | T138_cDNA1_Rev |
| 334 | T139_123561For_cDNA1 |
| 335 | 123561Rev |
| 336 | trpCtermFor_123561 |
| 337 | T390_trpCtermR_AmdS |
| 338 | T391_AmdS_endR |
| 339 | T390_trpCtermR_AmdS |
| 340 | T428_pep3_3flankDR_F-trpCterm |
| 341 | T429_pep3_3flankDR_R-pyr4 |
| 342 | T094_pyr4_F |
| 343 | T430_pyr4_R-pep3_3flank |
| 344 | T302_77579_5int |
| 345 | T214_pep4_3f_seq_r1 |
| 346 | T625_pep3_5int_new |
| 347 | T140_cDNA1promoter_seqR1 |
| 348 | T626_pep3_3int_new |
| 349 | T061_pyr4_orf_screen_2F |
| 350 | T352_pep3_orf_for |
| 351 | T353_pep3_orf_rev |
| 352 | T372_pep5_5f_for |
| 353 | T373_pep5_5f_rev |
| 354 | T376_pep5_5DR_for |
| 355 | T377_pep5_5DR_rev |
| 356 | T378_pep5_3f_for |
| 357 | T379_pep5_3f_rev |
| 358 | T374_bar_recpyr4_for2 |
| 359 | T375_bar_rev |
| 360 | 5flankfw_pRS426 |
| 361 | 5flankrev_pyr4 |
| 362 | 3flankfw_pyr4 |
| 363 | 3flankrev_pRS426 |

-continued

| SEQ | |
|---|---|
| 364 | scrn_5forw |
| 365 | T026_Pyr4_orf_5rev2 |
| 366 | scrn_3rev |
| 367 | T028_Pyr4_flank_rev |
| 368 | orf_fw |
| 369 | orf_rev |
| 370 | 5flankfw_pRS426 |
| 371 | 5flankrev_pyr4 |
| 372 | 3flankfw_pyr4 |
| 373 | 3flankrev_pRS426 |
| 374 | scrn_5forw |
| 375 | T026_Pyr4_orf_5rev2 |
| 376 | scrn_3rev |
| 377 | T028_Pyr4_flank_rev |
| 378 | orf_fw |
| 379 | orf_rev |
| 380 | 5flankfw_pRS426 |
| 381 | 5flankrev_pyr4 |
| 382 | 3flankfw_pyr4 |
| 383 | 3flankrev_pRS426 |
| 384 | scrn_5forw |
| 385 | T026_Pyr4_orf_5rev2 |
| 386 | scrn_3rev |
| 387 | T028_Pyr4_flank_rev |
| 388 | orf_fw |
| 389 | orf_rev |
| 390 | 5flankfw_pRS426 |
| 391 | 5flankrev_pyr4 |
| 392 | 3flankfw_pyr4 |
| 393 | 3flankrev_pRS426 |
| 394 | scrn_5forw |
| 395 | T026_Pyr4_orf_5rev2 |
| 396 | scrn_3rev |
| 397 | T028_Pyr4_flank_rev |
| 398 | orf_fw |
| 399 | orf_rev |
| 400 | 5flankfw_pRS426 |
| 401 | 5flankrev_pyr4 |
| 402 | 3flankfw_pyr4 |
| 403 | 3flankrev_pRS426 |
| 404 | scrn_5forw |
| 405 | T026_Pyr4_orf_5rev2 |
| 406 | scrn_3rev |
| 407 | T028_Pyr4_flank_rev |
| 408 | orf_fw |
| 409 | Coding sequence of human GalT1 |
| 410 | *Trichoderma reesei* pep8 |
| 411 | *Trichoderma reesei* pep11 |
| 412 | *Trichoderma reesei* pep12 |
| 413 | T047_trpC_term_end_F |
| 414 | T854_pep3_3f_r2 |
| 415 | T488_pyr4_5utr_rev |
| 416 | T061_pyr4_orf_screen_2F |
| 417 | T855_pep3_orf_f3 |
| 418 | T754_pep3_orf_rev2 |
| 419 | T627_pep5_5int_new |
| 420 | T488_pyr4_5utr_rev |
| 421 | T061_pyr4_orf_screen_2F |
| 422 | T628_pep5_3int_new |
| 423 | T418_pep5_orf_for |
| 424 | T419_pep5_orf_rev |
| 425 | T859_pep5_orf_f2 |
| 426 | T860_pep5_orf_f3 |
| 427 | T861_pep5_orf_r2 |
| 428 | T477_pep12_5f_for |
| 429 | T478_pep12_5f_rev |
| 430 | T479_pep12_DR_for |
| 431 | T480_pep12_DR_rev |
| 432 | T481_pep12_3f_for |
| 433 | T482_pep12_3f_rev |
| 434 | T858_pep5_5f_f3 |
| 435 | T755_pep5_3f_rev3 |
| 436 | T627_pep5_5int_new |
| 437 | T488_pyr4_5utr_rev |
| 438 | T860_pep5_orf_f3 |
| 439 | T861_pep5_orf_r2 |
| 440 | T517_pep12_5int |

| SEQ | |
|---|---|
| 441 | T026__Pyr4__orf__5rev2 |
| 442 | T061__pyr4__orf__screen__2F |
| 443 | T518__pep12__3int |
| 444 | T486__pep12__orf__probef |
| 445 | T487__pep12__orf__prober |
| 446 | T1057__pep12__orf__probef2 |
| 447 | T1058__pep12__orf__prober2 |
| 448 | T431__pep2-5flankF-pRS426 |
| 449 | T629__pep2__5f__rev__pyr4 |
| 450 | T630__pep2__5DR__for__trpC |
| 451 | T631__pep2__5DR__rev__cDNA1 |
| 452 | T632__pep2__3f__for__tcbh2 |
| 453 | T633__pep2__3f__rev |
| 454 | T491__hph__recpyr4__for3 |
| 455 | T492__hph__rev2 |
| 456 | T495__cDNA1__for |
| 457 | T138__cDNA1__Rev |
| 458 | T139__123561For__cDNA1 |
| 459 | T516__123561Rev |
| 460 | T496__tcbh2__for |
| 461 | T497__tcbh2__rev |
| 462 | T858__pep5__5f__f3 |
| 463 | T755__pep5__3f__rev3 |
| 464 | T627__pep5__5int__new |
| 465 | T488__pyr4__5utr__rev |
| 466 | T860__pep5__orf__f3 |
| 467 | T861__pep5__orf__r2 |
| 468 | T596__pep2 fwd 5'flank screen |
| 469 | T026__Pyr4__orf__5rev2 |
| 470 | T061__pyr4__orf__screen__2F |
| 471 | T600__pep2 rev 3'flank screen |
| 472 | T601__pep2 fwd |
| 473 | T623__pep2 rev |
| 474 | T1077__pep2__orf__probef2 |
| 475 | T1078__pep2__orf__prober2 |
| 476 | T1009__pep11__5flkfw__vector |
| 477 | T1010__pep11__5flkrev__pyr4Prom |
| 478 | T1144__pep11__5dr__for |
| 479 | T1145__pep11__5dr__rev |
| 480 | T1146__pep11__3f__for |
| 481 | T1012__pep11__3flkrev__vector |
| 482 | T1162__pep2__5f__f2 |
| 483 | T1163__pep2__3f__r2 |
| 484 | T1162__pep2__5f__f2 |
| 485 | T488__pyr4__5utr__rev |
| 486 | T601__pep2 fwd |
| 487 | T623__pep2 rev |
| 488 | T1013__pep11__screen__5flk__fwd |
| 489 | T488__pyr4__5utr__rev |
| 490 | T061__pyr4__orf__screen__2F |
| 491 | T1016__pep11__screen__3flk__rev |
| 492 | T1017__pep11__orf__fwd |
| 493 | T1018__pep11__orf__rev |
| 494 | T1019__pep8__5flkfw__vector |
| 495 | T1020__pep8__5flkrev__pyr4Prom |
| 496 | T1167__pep8__5DR__for |
| 497 | T1168__pep8__5DR__rev |
| 498 | T1169__pep8__3f__for2 |
| 499 | T1022__pep8__3flkrev__vector |
| 500 | T1019__pep8__5flkfw__vector |
| 501 | T1020__pep8__5flkrev__pyr4Prom |
| 502 | T1021__pep8__3flkfw__pyr4loop |
| 503 | T1022__pep8__3flkrev__vector |
| 504 | T311__82623__5for |
| 505 | T1190__tpp1__5f__rev2 |
| 506 | T1191__tpp1__5dr__for |
| 507 | T1192__tpp1__5dr__rev |
| 508 | T1193__tpp1__3f__for2 |
| 509 | T314__82623__3rev |
| 510 | JJ-037 primer |
| 511 | JJ-038 primer |
| 512 | JJ-039 primer |
| 513 | JJ-040 primer |
| 514 | JJ-041 primer |
| 515 | JJ-042 primer |
| 516 | JJ-043 primer |
| 517 | JJ-044 primer |

| SEQ | |
|---|---|
| 518 | T1088_slp7_5flkfw_vector |
| 519 | T1090_slp7_3flkfw_pyr4loop |
| 520 | T1091_slp7_3flkrev_vector |
| 521 | T1203_slp8_5f_f |
| 522 | T1204_slp8_5f_r |
| 523 | T1205_slp8_5dr_f |
| 524 | T1206_slp8_5dr_r |
| 525 | T1207_slp8_3f_f |
| 526 | T1208_slp8_3f_r |
| 527 | T054_slp2_5screen_F |
| 528 | T1084_screen_5flk_pyr_rev |
| 529 | T055_slp2_3screen_R |
| 530 | T028_Pyr4_flank_rev |
| 531 | T111_slp2_ORF_F |
| 532 | T112_slp2_ORF_R |
| 533 | T1372_kre2_recgpda_for |
| 534 | T337_21576_r |
| 535 | T1373_galt_44_for |
| 536 | T1374_galt_rev |
| 537 | T1375_galt_78_for |
| 538 | T1374_galt_rev |
| 539 | T1369_pyr4_for |
| 540 | T1370_pyr4_rechphnew_rev |
| 541 | T1367_egl2_3dr_for |
| 542 | T1368_egl2_3dr_rev |
| 543 | T161_tcbh2_seq_f2 |
| 544 | T1371_tcbh2_recelg2_rev |
| 545 | T1560 |
| 546 | T1561 |
| 547 | T1562 |
| 548 | T1563 |
| 549 | T1410_egl2_5int_f3 |
| 550 | T176_pcbh1_seq_r4 |
| 551 | T1158_egl2 3pr intR2 |
| 552 | T1411_cbh2t_end_f |
| 553 | T1412_egl2_orf_f1 |
| 554 | T1413_egl2_orf_r1 |

The invention claimed is:

1. A *Trichoderma* cell for producing glycoproteins with mammalian-like fucosylated N-glycans, comprising:
   1) at least a deletion or disruption mutation in an endogenous protease encoding gene, which mutation reduces the expressed endogenous protease compared to a parental filamentous fungal cell which does not have the mutation,
   2) an exogenous polynucleotide encoding a polypeptide having α1,6 fucosyltransferase activity, and
   3) one or more exogenous polynucleotides encoding a polypeptide having GDP-fucose synthesis activity, wherein GDP-fucose synthesis activity comprises:
      a) a polynucleotide or a functional variant polynucleotide encoding a polypeptide having GDP-mannose-dehydratase (GMD) activity and,
      b) a polynucleotide or a functional variant polynucleotide encoding a polypeptide having both GDP-keto-deoxy-mannose-epimerase and GDP-keto-deoxy-galactose-reductase (FX) activities.

2. The *Trichoderma* cell of claim 1, wherein the cell further has GDP-fucose transporter activity.

3. The *Trichoderma* cell of claim 1, wherein said polynucleotide encoding the polypeptide having α1,6 fucosyltransferase activity comprises either the polynucleotide having SEQ ID NO: 1, or a functional variant polynucleotide encoding a polypeptide having at least 50%, at least 60%, at least 70%, at least 90%, or at least 95% identity with SEQ ID NO: 6, wherein said polypeptide has α1,6 fucosyltransferase activity.

4. The *Trichoderma* cell of claim 1, wherein said one or more polynucleotides encoding the polypeptide having GDP-fucose synthesis activity comprises:
   a) *C. elegans* GMD polynucleotide having SEQ ID NO: 2 or a functional variant polynucleotide encoding a polypeptide having at least 50%, at least 60%, at least 70%, at least 90%, or at least 95% identity with SEQ ID NO: 7, wherein said polypeptide has GDP-mannose-dehydratase activity; and,
   b) *C. elegans* FX polynucleotide having SEQ ID NO: 3 or a functional variant polynucleotide encoding a polypeptide having at least 50%, at least 60%, at least 70%, at least 90%, or at least 95% identity with SEQ ID NO: 8, wherein said polypeptide has both GDP-keto-deoxy-mannose-epimerase and GDP-keto-deoxy-galactose-reductase activities.

5. The *Trichoderma* cell of claim 2 wherein the GDP fucose transporter activity encoded by the GDP-fucose transporter *C. elegans* GFTr having SEQ ID NO: 4 or a functional variant polynucleotide encoding a polypeptide having at least 50%, at least 60%, at least 70%, at least 90%, or at least 95% identity with SEQ ID NO: 9.

6. The *Trichoderma* cell of claim 1, wherein said polypeptide having α1,6 fucosyltransferase activity further comprises a Golgi targeting sequence comprising the N-terminal portion of the polypeptide having SEQ ID NO: 10.

7. The *Trichoderma* cell of claim 1, further comprising a mutation that reduces the level of expression of an ALG3 gene compared to the level of expression in a parent cell which does not have such mutation.

8. The *Trichoderma* cell of claim 1, further comprising one or more polynucleotides encoding a polypeptide selected from the group consisting of:
   i) α1,2 mannosidase,
   ii) N-acetylglucosaminyltransferase I catalytic domain,
   iii) a mannosidase II,
   iv) N-acetylglucosaminyltransferase II catalytic domain, and,
   v) β1,4 galactosyltransferase.

9. The *Trichoderma* cell of claim 1, further comprising an N-acetylglucosaminyltransferase I, an α mannosidase II, an N-acetylglucosaminyltransferase II, and/or a β1,4 galactosyltransferase, wherein the α1,6 fucosyltransferase, N-acetylglucosaminyltransferase I, an α mannosidase II, an N-acetylqlucosaminvltransferase II, and/or a β1,4 galactosyltransferase comprise a Golgi targeting sequence selected from the group consisting of: N-terminal portion of GnTI, N-terminal portion of human GnTI, N-terminal portion of GnTI I, N-terminal portion of human GnTII, N-terminal portion of Kre2, and N-terminal portion of T. reesei Kre2.

10. The *Trichoderma* cell of claim 1, further comprising one or more polynucleotides encoding a polypeptide selected from the group consisting of:
   i) glucosamine UDP-N-acetylglucosamine-2-epimerase/ N-acetylmannosamine kinase,
   ii) N-acetylneuraminic acid synthase,
   iii) N-acetylneuraminic acid phosphatase, iv) cytidine monophosphate N-acetylneuraminic acid synthetase,
v) CMP-sialic acid transporter, and
vi) sialyltransferase.

11. The *Trichoderma* cell of claim 1, wherein said mutation reduces the endogenous protease selected from the group consisting of *Trichoderma reesei* pep1 (SEQ ID NO: 17), *Trichoderma reesei* pep2(SEQ ID NO: 18), *Trichoderma reesei* pep3 (SEQ ID NO: 19), *Trichoderma reesei* pep4 (SEQ ID NO: 20), *Trichoderma reesei* pep5 (SEQ ID NO: 21), *Trichoderma reesei* pep7 (SEQ ID NO: 23), *Trichoderma reesei* pep8 (SEQ ID NO: 410), *Trichoderma reesei* pep11 (SEQ ID NO: 411), *Trichoderma reesei* pep12 (SEQ ID NO: 412), *Trichoderma reesei* tpp1 (SEQ ID NO: 34), *Trichoderma reesei*tsp1 (SEQ ID NO: 24), *Trichoderma reesei* slp1 (SEQ ID NO: 25), *Trichoderma reesei* slp2 (SEQ ID NO: 26), *Trichoderma reesei* slp3 (SEQ ID NO: 27), *Trichoderma reesei* slp5 (SEQ ID NO: 28), *Trichoderma reesei* slp6 (SEQ ID NO: 29), *Trichoderma reesei* slp7 (SEQ ID NO: 30), *Trichoderma reesei* slp8 (SEQ ID NO: 31), *Trichoderma reesei* gap1 (SEQ ID NO: 32), and *Trichoderma reesei* gap2 (SEQ ID NO: 33).

12. The *Trichoderma* cell of claim 11, wherein said cell comprises mutations that reduce or eliminate the activity of:
a) the three endogenous proteases pep1, tsp1 and slp1 in *Trichoderma reesei*',
b) the three endogenous proteases gap1, slp1 and pep1 in *Trichoderma reesei*',
c) three endogenous proteases selected from the group consisting of pep1, pep2, pep3, pep4, pep5, pep8, pep11, pep12, tsp1, slp1, slp2, slp3, slp7, gap1 and gap2 in *Trichoderma reesei*;
d) three to six proteases selected from the group consisting of pep1, pep2, pep3, pep4, pep5, tsp1, slp1, slp2, slp3, gap1 and gap2 in *Trichoderma reesei*', or
e) seven to ten proteases selected from the group consisting of pep1, pep2, pep3, pep4, pep5, pep7, pep8, tsp1, slp1, slp2, slp3, slp5, slp6, slp7, slp8, tpp1, gap1 and gap2 in *Trichoderma reesei*.

13. The *Trichoderma* cell of claim 1, wherein the cell further comprises mutations in one or more genes encoding glycosyl hydrolases, wherein said mutation eliminates or reduces activity of the corresponding hydrolases, and wherein said hydrolases are selected from the group consisting xylanase, cellobiohydrolase, and endoglucanase.

14. A method for producing a glycoprotein or antibody with fucosylated N-glycan, comprising:
a) providing the *Trichoderma* cell of claim 1, wherein the cell comprises a polynucleotide encoding a glycoprotein or an antibody, and
b) culturing the *Trichoderma* cell to produce said glycoprotein or antibody with fucosylated N-glycan.

15. The method of claim 14, wherein said fucosylated N-glycan is selected from the group consisting of $Man_3GlcNAc_2(Fuc)$, $GlcNAcMan_3GlcNAc_2(Fuc)$, $GlcNAc_2Man_3GlcNAc_2(Fuc)$, $Gal_{1-2}GlcNAc_2Man_3GlcNAc_2(Fuc)$, and $Neu5Ac_{1-2}Gal_{1-2}GlcNAc_2Man_3GlcNAc_2(Fuc)$.

16. The method of claim 15 wherein at least 5 mol %, at least 10 mol %, or at least 15 mol % of the total secreted N-glycans consist of $GlcNAc_2Man_3GlcNAc_2(Fuc)$.

17. The method of claim 14, wherein said polynucleotide encoding a glycoprotein or an antibody is a recombinant polynucleotide encoding a heterologous glycoprotein or heterologous antibody.

\* \* \* \* \*

SEQUENCE LISTING

<160> NUMBER OF SEQ ID NOS: 408

<210> SEQ ID NO 1
<211> LENGTH: 1728
<212> TYPE: DNA
<213> ORGANISM: Homo sapiens

<400> SEQUENCE: 1

```
atgcgcccct ggaccggcag ctggcggtgg atcatgctca ttctgttcgc ctggggtacg      60 ctccttttt  acatcggcgg acacctggtc cgagacaacg accaccctga tcattcctct     120
cgcgagttgt ctaagatcct ggctaagctc gagaggctca agcagcagaa cgaggacctg     180
cgccgtatgg ccgaaagcct tcgcatcccc gagggccga ttgaccaagg cccagcgatc     240
ggccgagtca gagtgctcga ggaacagctg gttaaggcca agagcagat tgagaattac     300 aagaagcaga ctcggaacgg cctcggtaag gatcacgaga tcttgcgccg taggatcgag     360
aacggcgcaa agaactctg gttcttcctg cagtccgagc tgaagaagct caagaacctt     420
gagggaaacg agctgcaacg ccacgccgac gagtttctct ggacctggg ccaccatgaa     480 cgatcaatta tgaccgatct ctactatctc tcgcagacag acggcgctgg cgactggcgc     540
gagaaagagg ccaaggacct gaccgagctt gtccagcgcc ggatcacgta cctccagaac     600
cccaaggatt gcagcaaggc gaagaagctg gtctgcaata ttaacaaggg ctgcggttac     660
ggatgtcaac tccaccacgt cgtgtattgc ttcatgatcg cctacggcac ccagcgaacg     720
```

| | |
|---|---|
| ctgatcttgg agtcccagaa ctggcgttac gcaaccggcg ggtgggaaac tgttttccgc | 780 |
| cctgtcagtg agacatgcac ggacaggtct ggcattagca ccggccactg gtcgggtgag | 840 |
| gtcaaggaca agaacgtcca ggtggtggag cttccgatcg ttgactccct ccatcccaga | 900 |
| ccccttacc tcccctggc cgtcccggaa gatctcgctg accgcctggt ccgagtgcac | 960 |
| ggcgacccag ccgtctggtg ggtcagccag tttgttaagt atctcatccg cccccaacct | 1020 |
| tggttggaga aagagattga ggaagcgact aagaagctgg gattcaagca ccccgtcatc | 1080 |
| ggcgtccacg tgcgccggac cgataaggtt ggaaccgagg ccgcttttcca cccgatcgaa | 1140 |
| gagtacatgg tccacgtgga ggaacatttt cagctgcttg cccgtaggat gcaggtcgac | 1200 |
| aagaagcgcg tctacctcgc cacggacgac ccctcgctgc tcaaagaggc aaagacgaag | 1260 |
| taccctaact atgagttcat cagcgataat tccatttctt ggtcagccgg cctccacaac | 1320 |
| cgatacaccg agaactccct gcgcggtgtt atccttgaca ttcactttt gtcgcaggcg | 1380 |
| gacttcctcg tctgtacttt cagctcccag gtctgccggg tggcttacga gatcatgcaa | 1440 |
| acactgcatc cagatgccag cgccaacttt cactctctcg acgacatcta ctatttcggc | 1500 |
| ggccagaacg cccacaacca gattgctatc tacgcgcacc agcccagaac cgccgacgag | 1560 |
| atccccatgg aaccgggcga tatcattggt gtcgcaggca atcattggga cggatactcg | 1620 |
| aaggggtga accgcaagct cggccgtacg ggcctgtacc cttcctataa ggtccgagag | 1680 |
| aagatcgaga ctgttaagta cccgacctac cccgaggccg agaagtaa | 1728 |

<210> SEQ ID NO 2
<211> LENGTH: 1200
<212> TYPE: DNA
<213> ORGANISM: Caenorhabditis elegans

<400> SEQUENCE: 2

| | |
|---|---|
| atgccaaccg gcaagtctga atcttctgat atttctgaag ttgttggtaa catggaaata | 60 |
| tctaaagttg agggtcttga agcgtgtatc ggaatgagcc acgaagtgtc cactactcca | 120 |
| gctgctgagt tggctgctt cagagcacgc aaggttgctc tgattactgg aatttctgga | 180 |
| caagacggtt catatcttgc tgagcttctt ctttcaaaag gatacaaagt tcacggaatc | 240 |
| atccgtcgtt catcttcatt caataccgca agaatcgaac atctgtacag taatccaatt | 300 |
| actcatcacg gtgattcttc attctctctt cactatggag atatgactga ttcatcttgt | 360 |
| ctcatcaagc tcatttcaac tatcgagcca accgaagtgt atcatttggc tgctcaatct | 420 |
| cacgtcaaag tgtcttttga tttgccagaa tacactgctg aagtagacgc tgttggaact | 480 |
| cttcgccttc tcgatgcaat ccatgcttgt cgtttgactg aaaaagttcg attctatcaa | 540 |
| gcatccacat ccgaattgta tggaaaagtt caagagattc acaaagtgaa aagactcca | 600 |
| ttctatccaa gatctccata tgctgttgcc aagatgtacg ggtactggat gttgttaac | 660 |
| tatcgtgaag cctacaatat gtttgcttgc aatggaattt tgttcaacca tgagagtcca | 720 |
| agaagaggag agacattcgt gactcgtaag atcactcgtt cagtcgctaa aatcagtttg | 780 |
| gggcaacagg aaagcattga gctcggaaat ctgagtgctc ttcgtgattg gggacacgcc | 840 |
| agagagtatg ttgaagcaat gtggagaatt cttcaacacg actcaccaga tgattttgtg | 900 |
| attgcaactg gaaaacaatt cagtgtcaga gagttttgta atcttgcatt tgctgaaatt | 960 |
| ggagaagtat tgcaatggga aggagaaggt gttgaggaag ttggaaagaa taaagatgga | 1020 |
| gttattcgag ttaaagttag tccaaagtac tacagaccaa ctgaagtgga gacttttattg | 1080 |
| ggaaatgctg aaaaagcaaa gaagactctt ggatgggaag caaaggttac ggttccggaa | 1140 |

```
ctcgtcaaag agatggttgc aagcgacatt atccttatga agtccaatcc aatggcttaa   1200
```

<210> SEQ ID NO 3
<211> LENGTH: 948
<212> TYPE: DNA
<213> ORGANISM: Caenorhabditis elegans

<400> SEQUENCE: 3

```
atgaaaacca tcctcgtcac gggcggcact ggtctggtgg aagcgccat taagaaggtc     60
gttgagacaa ccgagaagcg cgacgatgaa aagtgggtct ttatcggctc caaggactgc   120
gacctcgaga accttgagga aacgcgagag ctgttcgagt cggtcaagcc cacccacgtg   180
atccatttgg ccgctatggt cgggggcctc ttccacaacc tcgcgcacaa tctgcagttc   240
tttcggaaga acatggccat caacgacaac gttctcgcac tgtgccacga gttcgatgtc   300
atcaagtgcg tgagctgcct ttctacctgt atcttccctg acaagacgtc ctacccgatt   360
gacgagacta tggtccacct cggcccaccc catgactcaa actttggcta ctcgtatgcc   420
aagcgcatga tcgatgtcct gaacaagggt tacgctcaag agcacggacg taagtacacc   480
agcgtggttc cctgcaatgt cttttggccct cacgacaact acaacttgca gtccggccat   540
gtcctcccgg ccctgatcca aaggcctat gtcgcgcaga gggacggcac gcccttcag    600
gtgtacggca gtggtacacc cctgcgccag ttcatctact ctattgatct cgtcgcctg    660
ttcattcgag tcgttagaga atacgaggac gtcgagccta tcatcctcag cgtgaacgag   720
tccgacgaag tctcgattcg cgacgccgtc agcgccgtgg ttaaggcaat cgacttcacc   780
ggggacgtcg agtatgatac ttccaaagcg gatggacagt tcaagaaaac cgcctcgaac   840
gagaagctcc tgaagttgtt tccggacttc caattcacgc cctttgagca ggctatccaa   900
gagtcagtcc agtggttcgt tgacaactac gaaaccgccc ggaagtaa              948
```

<210> SEQ ID NO 4
<211> LENGTH: 1092
<212> TYPE: DNA
<213> ORGANISM: Caenorhabditis elegans

<400> SEQUENCE: 4

```
atgaagctcc acgaggaaaa caacaaggcc ctgttcgagg ctatgcgcaa ccgagagaat    60
cccaccaagt gggagagcta caagcaggtc atcacggccg tgtccgcgta ctgggtcttt   120
tcgattggcc tcgttttcct gaacaagtat cttttgtcta gcgtccagct cgacgcccct   180
ctgttcatca cttggtatca atgcctcgtc accgtgttcc tctgcctgtt tctttcaaag   240
acatccaagg catacggtct gttcaaattt ccctcgatgc cgatcgatgc caagattagc   300
cgtgaggtcc tcccattgtc cgtcgtgttc gttgctatga tcagttcaa caacctctgt   360
ctgaagtacg tcggcgtttc tttttactac gtcggacgca gcctgaccac ggtgttcaac   420
gtcgtctgca cctacctcat ccttggccag aaaacgtcgg gccaggccat ggggtgctgc   480
gcgctgatca tcttcggctt tctcttgggt gtggaccagg aaggcgtcac cggaacgctg   540
tcctacactg gcgtcatttt cggcgttctc gccagcctct ccgtcgccct gaatgctatc   600
tatacccgta aggtcctttc gtcagtgggc gactgtctgt ggaggctcac aatgtacaac   660
aacctcaacg cactcgttct gtttctgccc cttatgttgt caacggcga gttcggtgcc   720
gtcttttact tcgacaagct cttttgatacc acttttctgga ttctcatgac gctgggcgga   780
gtgttcggct tcatgatggg ctacgtcacc gggtggcaga tccaagcgac cagccctctc   840
```

```
acgcacaata tctctggtac tgccaaggcc gctgcccaga cagtcatggc agtcgtttgg    900
tattccgagc ttaagaccct gttgtggtgg acgtcgaact tcgtcgtgct gtttggcagc    960
ggaatgtaca cctacgtgca aaagcgcgtc atggacaaga agaactccgg cgccagcccg   1020
gcttcggagg cgaagtctga caaggtcaag ctcctgggca gagatggtaa cgccgccgag   1080
gaatccgttt aa                                                       1092
```

<210> SEQ ID NO 5
<211> LENGTH: 1431
<212> TYPE: DNA
<213> ORGANISM: Trichoderma reesei

<400> SEQUENCE: 5

```
atggcgtcaa caaatgcgcg ctatgtgcgc tatctactaa tcgccttctt cgtacgtcac     60
cctacagact cgacacctct gtccctatg cagttgttgc taacatagaa gaatagacaa    120
tcctcgtctt ctactttgtc tccaattcaa agtatgaggg cgtcgatctc aacaagggca    180
ccttcacagc tccggattcg accaagacga caccaaagcc gccagccact ggcgatgcca    240
aagactttcc tctggccctg acgccgaacg atccaggctt caacgacctc gtcggcatcg    300
ctcccggccc tcgaatgaac gccaccttg tcaccctcgc cgaaacagc gacgtctggg     360 acattgcacg ctcgatccgc caggtcgagg atcgcttcaa cgacggtac aactacgact    420 gggtgttcct caacgacaag ccgttttgaca cacccttcaa gaaggtcacg acgtccctgg   480
tgtcgggcaa gacgcactat ggcgagattg cgcccgagca ctggtcgttc cccgactgga   540
tcgaccagga caaggccaag aaggtgcgcg aggacatggc tgagcgcaaa atcatctacg   600
gcgactcggt cagctaccgc cacatgtgcc gcttcgagtc gggcttcttc ttccgccagc   660
cgctgatgat gaactacgaa tactactggc gcgtggagcc ctccatcgag ctctactgcg   720
acatccacta cgacccttc cgcctgatgg ttgagcaggg caaaaagtac agcttcgtca   780
tcagcctgta cgagtaccg gccacgattg ccacgctgtg ggagagcacc aagaagttta   840
tgaagaacca tccggagcac attgcccccg acaactcgat gcgcttcctg agcgatgacg   900
gcggcgagac gtacaacaac tgccacttcg taagcttccc tgcccgttga cttttctctc   960
tctctctttt gtctgccttc caccccggcaa catgatggct aacatgagga tagtggtcca   1020
actttgagat tggcagcctg gagtggctgc gcagcaagca gtacattgac ttttcgagt    1080 ccctggacaa ggacggcggc ttcttctacg agcgatgggg cgacgctccc gtccactcca   1140
ttgccgccgg cctgatgctc aacaggagcg agattcactt cttcaacgac attgcctact   1200
ggcatgtgcc ctttacccac tgccccacgg gcgagaagac gagactggat ctgaaatgcc   1260
actgcgaccc caaggagaac tttgattgga agggctactc ttgtaagcgc tctagatacc   1320
tttgtgccaa cagaaatctg tgactaacac gcctctgtca taggcacatc ccgattcttt   1380
gagatgaacg gcatggacaa gcccgaaggc tgggagaacc agcaagacta a            1431
```

<210> SEQ ID NO 6
<211> LENGTH: 575
<212> TYPE: PRT
<213> ORGANISM: Homo sapiens

<400> SEQUENCE: 6

```
Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30
```

```
Asn Asp His Pro Asp His Ser Ser Arg Glu Leu Ser Lys Ile Leu Ala
         35                  40                  45

Lys Leu Glu Arg Leu Lys Gln Gln Asn Glu Asp Leu Arg Arg Met Ala
 50                  55                  60

Glu Ser Leu Arg Ile Pro Glu Gly Pro Ile Asp Gln Gly Pro Ala Ile
 65                  70                  75                  80

Gly Arg Val Arg Val Leu Glu Glu Gln Leu Val Lys Ala Lys Glu Gln
                 85                  90                  95

Ile Glu Asn Tyr Lys Lys Gln Thr Arg Asn Gly Leu Gly Lys Asp His
                100                 105                 110

Glu Ile Leu Arg Arg Ile Glu Asn Gly Ala Lys Glu Leu Trp Phe
                115                 120                 125

Phe Leu Gln Ser Glu Leu Lys Lys Leu Lys Asn Leu Glu Gly Asn Glu
130                 135                 140

Leu Gln Arg His Ala Asp Glu Phe Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
                180                 185                 190

Arg Arg Ile Thr Tyr Leu Gln Asn Pro Lys Asp Cys Ser Lys Ala Lys
                195                 200                 205

Lys Leu Val Cys Asn Ile Asn Lys Gly Cys Gly Tyr Gly Cys Gln Leu
                210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Ile
                260                 265                 270

Ser Thr Gly His Trp Ser Gly Glu Val Lys Asp Lys Asn Val Gln Val
                275                 280                 285

Val Glu Leu Pro Ile Val Asp Ser Leu His Pro Arg Pro Pro Tyr Leu
                290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
                340                 345                 350

Leu Gly Phe Lys His Pro Val Ile Gly Val His Val Arg Arg Thr Asp
                355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Pro Asn Tyr Glu Phe Ile Ser Asp Asn Ser Ile
                420                 425                 430

Ser Trp Ser Ala Gly Leu His Asn Arg Tyr Thr Glu Asn Ser Leu Arg
                435                 440                 445
```

```
Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Ile Tyr Ala
                500                 505                 510

His Gln Pro Arg Thr Ala Asp Glu Ile Pro Met Glu Pro Gly Asp Ile
                515                 520                 525

Ile Gly Val Ala Gly Asn His Trp Asp Gly Tyr Ser Lys Gly Val Asn
530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 7
<211> LENGTH: 399
<212> TYPE: PRT
<213> ORGANISM: Caenorhabditis elegans

<400> SEQUENCE: 7

Met Pro Thr Gly Lys Ser Glu Ser Ser Asp Ile Ser Glu Val Val Gly
1               5                   10                  15

Asn Met Glu Ile Ser Lys Val Glu Gly Leu Glu Ala Cys Ile Gly Met
            20                  25                  30

Ser His Glu Val Ser Thr Thr Pro Ala Ala Glu Leu Ala Ala Phe Arg
        35                  40                  45

Ala Arg Lys Val Ala Leu Ile Thr Gly Ile Ser Gly Gln Asp Gly Ser
    50                  55                  60

Tyr Leu Ala Glu Leu Leu Leu Ser Lys Gly Tyr Lys Val His Gly Ile
65                  70                  75                  80

Ile Arg Arg Ser Ser Ser Phe Asn Thr Ala Arg Ile Glu His Leu Tyr
                85                  90                  95

Ser Asn Pro Ile Thr His His Gly Asp Ser Ser Phe Ser Leu His Tyr
            100                 105                 110

Gly Asp Met Thr Asp Ser Ser Cys Leu Ile Lys Leu Ile Ser Thr Ile
        115                 120                 125

Glu Pro Thr Glu Val Tyr His Leu Ala Ala Gln Ser His Val Lys Val
    130                 135                 140

Ser Phe Asp Leu Pro Glu Tyr Thr Ala Glu Val Asp Ala Val Gly Thr
145                 150                 155                 160

Leu Arg Leu Leu Asp Ala Ile His Ala Cys Arg Leu Thr Glu Lys Val
                165                 170                 175

Arg Phe Tyr Gln Ala Ser Thr Ser Glu Leu Tyr Gly Lys Val Gln Glu
            180                 185                 190

Ile Pro Gln Ser Glu Lys Thr Pro Phe Tyr Pro Arg Ser Pro Tyr Ala
        195                 200                 205

Val Ala Lys Met Tyr Gly Tyr Trp Ile Val Val Asn Tyr Arg Glu Ala
    210                 215                 220

Tyr Asn Met Phe Ala Cys Asn Gly Ile Leu Phe Asn His Glu Ser Pro
225                 230                 235                 240

Arg Arg Gly Glu Thr Phe Val Thr Arg Lys Ile Thr Arg Ser Val Ala
                245                 250                 255
```

```
Lys Ile Ser Leu Gly Gln Gln Glu Ser Ile Glu Leu Gly Asn Leu Ser
            260                 265                 270

Ala Leu Arg Asp Trp Gly His Ala Arg Glu Tyr Val Glu Ala Met Trp
        275                 280                 285

Arg Ile Leu Gln His Asp Ser Pro Asp Phe Val Ile Ala Thr Gly
    290                 295                 300

Lys Gln Phe Ser Val Arg Glu Phe Cys Asn Leu Ala Phe Ala Glu Ile
305                 310                 315                 320

Gly Glu Val Leu Gln Trp Gly Glu Gly Val Glu Val Gly Lys
                325                 330                 335

Asn Lys Asp Gly Val Ile Arg Val Lys Val Ser Pro Lys Tyr Tyr Arg
            340                 345                 350

Pro Thr Glu Val Glu Thr Leu Leu Gly Asn Ala Glu Lys Ala Lys Lys
        355                 360                 365

Thr Leu Gly Trp Glu Ala Lys Val Thr Val Pro Glu Leu Val Lys Glu
    370                 375                 380

Met Val Ala Ser Asp Ile Ile Leu Met Lys Ser Asn Pro Met Ala
385                 390                 395

<210> SEQ ID NO 8
<211> LENGTH: 315
<212> TYPE: PRT
<213> ORGANISM: Caenorhabditis elegans

<400> SEQUENCE: 8

Met Lys Thr Ile Leu Val Thr Gly Gly Thr Gly Leu Val Gly Ser Ala
1               5                   10                  15

Ile Lys Lys Val Val Glu Thr Thr Glu Lys Arg Asp Asp Glu Lys Trp
            20                  25                  30

Val Phe Ile Gly Ser Lys Asp Cys Asp Leu Glu Asn Leu Glu Glu Thr
        35                  40                  45

Arg Glu Leu Phe Glu Ser Val Lys Pro Thr His Val Ile His Leu Ala
    50                  55                  60

Ala Met Val Gly Gly Leu Phe His Asn Leu Ala His Asn Leu Gln Phe
65                  70                  75                  80

Phe Arg Lys Asn Met Ala Ile Asn Asp Asn Val Leu Ala Leu Cys His
                85                  90                  95

Glu Phe Asp Val Ile Lys Cys Val Ser Cys Leu Ser Thr Cys Ile Phe
            100                 105                 110

Pro Asp Lys Thr Ser Tyr Pro Ile Asp Glu Thr Met Val His Leu Gly
        115                 120                 125

Pro Pro His Asp Ser Asn Phe Gly Tyr Ser Tyr Ala Lys Arg Met Ile
    130                 135                 140

Asp Val Leu Asn Lys Gly Tyr Ala Gln Glu His Gly Arg Lys Tyr Thr
145                 150                 155                 160

Ser Val Val Pro Cys Asn Val Phe Gly Pro His Asp Asn Tyr Asn Leu
                165                 170                 175

Gln Ser Gly His Val Leu Pro Ala Leu Ile His Lys Ala Tyr Val Ala
            180                 185                 190

Gln Arg Asp Gly Thr Pro Leu Gln Val Tyr Gly Ser Gly Thr Pro Leu
        195                 200                 205

Arg Gln Phe Ile Tyr Ser Ile Asp Leu Ala Arg Leu Phe Ile Arg Val
    210                 215                 220

Val Arg Glu Tyr Glu Asp Val Glu Pro Ile Ile Leu Ser Val Asn Glu
```

```
                225                 230                 235                 240
Ser Asp Glu Val Ser Ile Arg Asp Ala Val Ser Ala Val Val Lys Ala
                245                 250                 255

Ile Asp Phe Thr Gly Asp Val Glu Tyr Asp Thr Ser Lys Ala Asp Gly
                260                 265                 270

Gln Phe Lys Lys Thr Ala Ser Asn Glu Lys Leu Leu Lys Leu Phe Pro
                275                 280                 285

Asp Phe Gln Phe Thr Pro Phe Glu Gln Ala Ile Gln Glu Ser Val Gln
                290                 295                 300

Trp Phe Val Asp Asn Tyr Glu Thr Ala Arg Lys
305                 310                 315

<210> SEQ ID NO 9
<211> LENGTH: 363
<212> TYPE: PRT
<213> ORGANISM: caenorhabditis elegans

<400> SEQUENCE: 9

Met Lys Leu His Glu Glu Asn Asn Lys Ala Leu Phe Glu Ala Met Arg
1               5                   10                  15

Asn Arg Glu Asn Pro Thr Lys Trp Glu Ser Tyr Lys Gln Val Ile Thr
                20                  25                  30

Ala Val Ser Ala Tyr Trp Val Phe Ser Ile Gly Leu Val Phe Leu Asn
            35                  40                  45

Lys Tyr Leu Leu Ser Ser Val Gln Leu Asp Ala Pro Leu Phe Ile Thr
        50                  55                  60

Trp Tyr Gln Cys Leu Val Thr Val Phe Leu Cys Leu Phe Leu Ser Lys
65                  70                  75                  80

Thr Ser Lys Ala Tyr Gly Leu Phe Lys Phe Pro Ser Met Pro Ile Asp
                85                  90                  95

Ala Lys Ile Ser Arg Glu Val Leu Pro Leu Ser Val Val Phe Val Ala
            100                 105                 110

Met Ile Ser Phe Asn Asn Leu Cys Leu Lys Tyr Val Gly Val Ser Phe
        115                 120                 125

Tyr Tyr Val Gly Arg Ser Leu Thr Thr Val Phe Asn Val Val Cys Thr
    130                 135                 140

Tyr Leu Ile Leu Gly Gln Lys Thr Ser Gly Gln Ala Ile Gly Cys Cys
145                 150                 155                 160

Ala Leu Ile Ile Phe Gly Phe Leu Leu Gly Val Asp Gln Glu Gly Val
                165                 170                 175

Thr Gly Thr Leu Ser Tyr Thr Gly Val Ile Phe Gly Val Leu Ala Ser
            180                 185                 190

Leu Ser Val Ala Leu Asn Ala Ile Tyr Thr Arg Lys Val Leu Ser Ser
        195                 200                 205

Val Gly Asp Cys Leu Trp Arg Leu Thr Met Tyr Asn Asn Leu Asn Ala
    210                 215                 220

Leu Val Leu Phe Leu Pro Leu Met Leu Phe Asn Gly Glu Phe Gly Ala
225                 230                 235                 240

Val Phe Tyr Phe Asp Lys Leu Phe Asp Thr Thr Phe Trp Ile Leu Met
                245                 250                 255

Thr Leu Gly Gly Val Phe Gly Phe Met Met Gly Tyr Val Thr Gly Trp
            260                 265                 270

Gln Ile Gln Ala Thr Ser Pro Leu Thr His Asn Ile Ser Gly Thr Ala
        275                 280                 285
```

```
Lys Ala Ala Gln Thr Val Met Ala Val Val Trp Tyr Ser Glu Leu
290                 295                 300

Lys Thr Leu Leu Trp Trp Thr Ser Asn Phe Val Leu Phe Gly Ser
305                 310                 315                 320

Gly Met Tyr Thr Tyr Val Gln Lys Arg Val Met Asp Lys Asn Ser
            325                 330                 335

Gly Ala Ser Pro Ala Ser Glu Ala Lys Ser Asp Lys Val Lys Leu Leu
            340                 345                 350

Gly Arg Asp Gly Asn Ala Ala Glu Glu Ser Val
            355                 360
```

<210> SEQ ID NO 10
<211> LENGTH: 406
<212> TYPE: PRT
<213> ORGANISM: Trichoderma reesei

<400> SEQUENCE: 10

```
Met Ala Ser Thr Asn Ala Arg Tyr Val Arg Tyr Leu Leu Ile Ala Phe
1               5                   10                  15

Phe Thr Ile Leu Val Phe Tyr Phe Val Ser Asn Ser Lys Tyr Glu Gly
                20                  25                  30

Val Asp Leu Asn Lys Gly Thr Phe Thr Ala Pro Asp Ser Thr Lys Thr
            35                  40                  45

Thr Pro Lys Pro Pro Ala Thr Gly Asp Ala Lys Asp Phe Pro Leu Ala
50                  55                  60

Leu Thr Pro Asn Asp Pro Gly Phe Asn Asp Leu Val Gly Ile Ala Pro
65                  70                  75                  80

Gly Pro Arg Met Asn Ala Thr Phe Val Thr Leu Ala Arg Asn Ser Asp
                85                  90                  95

Val Trp Asp Ile Ala Arg Ser Ile Arg Gln Val Glu Asp Arg Phe Asn
                100                 105                 110

Arg Arg Tyr Asn Tyr Asp Trp Val Phe Leu Asn Asp Lys Pro Phe Asp
            115                 120                 125

Asn Thr Phe Lys Lys Val Thr Thr Ser Leu Val Ser Gly Lys Thr His
130                 135                 140

Tyr Gly Glu Ile Ala Pro Glu His Trp Ser Phe Pro Asp Trp Ile Asp
145                 150                 155                 160

Gln Asp Lys Ala Lys Lys Val Arg Glu Asp Met Ala Glu Arg Lys Ile
                165                 170                 175

Ile Tyr Gly Asp Ser Val Ser Tyr Arg His Met Cys Arg Phe Glu Ser
            180                 185                 190

Gly Phe Phe Phe Arg Gln Pro Leu Met Met Asn Tyr Glu Tyr Tyr Trp
        195                 200                 205

Arg Val Glu Pro Ser Ile Glu Leu Tyr Cys Asp Ile His Tyr Asp Pro
210                 215                 220

Phe Arg Leu Met Val Glu Gln Gly Lys Lys Tyr Ser Phe Val Ile Ser
225                 230                 235                 240

Leu Tyr Glu Tyr Pro Ala Thr Ile Ala Thr Leu Trp Glu Ser Thr Lys
                245                 250                 255

Lys Phe Met Lys Asn His Pro Glu His Ile Ala Pro Asp Asn Ser Met
            260                 265                 270

Arg Phe Leu Ser Asp Asp Gly Gly Glu Thr Tyr Asn Asn Cys His Phe
        275                 280                 285

Trp Ser Asn Phe Glu Ile Gly Ser Leu Glu Trp Leu Arg Ser Lys Gln
290                 295                 300
```

Tyr Ile Asp Phe Phe Glu Ser Leu Asp Lys Asp Gly Gly Phe Phe Tyr
305                 310                 315                 320

Glu Arg Trp Gly Asp Ala Pro Val His Ser Ile Ala Ala Gly Leu Met
            325                 330                 335

Leu Asn Arg Ser Glu Ile His Phe Phe Asn Asp Ile Ala Tyr Trp His
        340                 345                 350

Val Pro Phe Thr His Cys Pro Thr Gly Glu Lys Thr Arg Leu Asp Leu
            355                 360                 365

Lys Cys His Cys Asp Pro Lys Glu Asn Phe Asp Trp Lys Gly Tyr Ser
    370                 375                 380

Cys Thr Ser Arg Phe Phe Glu Met Asn Gly Met Asp Lys Pro Glu Gly
385                 390                 395                 400

Trp Glu Asn Gln Gln Asp
                405

<210> SEQ ID NO 11
<211> LENGTH: 959
<212> TYPE: DNA
<213> ORGANISM: Trichoderma reesei

<400> SEQUENCE: 11
tcaggtcaac caccgaggac cagcctttga ccgccattgc tcccgttcgt gccggcagag      60
ttgggtctgg atacgccgtc ttcataccta tccagctctc accatgcagg gtttccatct     120
gtttgaagca tccattcgca gcgcgcgaga ccgctactgc ttcgtgacta tacagtacat     180
gtaataccaa caggagtcga ggatacgagt actaagtacc acctattaat ctgctgctcg     240
tgcctcgtcc gcattgaaag cgaggtaagg taggcagaac cgctgacccg tcccccatca     300
ggtgatgata caacagggta gtactgcggt gacctcgaga taaagtacac ctcgtgtctct    360 ggacgccggc aacggtaccc aatccgagg tccaaatctg ctcgcgcggc ctgaggcaga     420
gacaccaccg tttgttgatc tcggttgccc catcagccag ccagcgcacc tcagttaggc     480
tcggacctgg gcaaaagttg gggtaacaaa ggccggcggc caaagcaccc aagtacctct     540
gcccgccatt gcgggtgcag aggtgacttc cgcgggccat acggtggcg cccccttgcag    600 ggagtggtgc gtcatcggct cgtcagcacg gccaatagac gcaaccggcg gccctgcttt     660
caatgttgac tgccccaggc cgagtccagt gaccacccga tagcaccatc gcagccaccc     720
caaatgcgac ctgcaccgcg ctggccaggg cccttcgggg cgcctgttag tgcctgcggt     780
tgctcggcgg gcgggctgct taacgtgctt tgcgtgctga gctgcctgcc tgccgcccgc     840
tcgccttatc taatgcccgc tacctctcct ccgtactccg tccctacaaa gaggctggtt     900
cctagcttcg tcatcctcca agttcccttc ctctggcagc aatcgaacca tcccattca     959

<210> SEQ ID NO 12
<211> LENGTH: 992
<212> TYPE: DNA
<213> ORGANISM: Trichoderma reesei

<400> SEQUENCE: 12
aggtagacgc tttgcgagtg tgtgtgtatc taagaagtgc acatcctgta tgtttgcaga      60
atgctgggta gttttggtta tttgggcagt ttgagagcgg aagacagtcc tactgctgcg     120
gaggagtctg gatcaagatt gcaacgtcgt ttatgtaata actataatgg agactggccg     180
tcgtctgctg ccgctatttg gttcggtgtc atgatctcgt gcctttgcga ggcgctcatc     240
tcgattgatt gattgattgg cctgtctcga catgtcgata ctaaccttgc cgcggccgaa     300

```
cgattccatt tttgcttgct tggtcaattg tactggtgtc gccgggacct tgtcagagc    360 gagctgcccg tacctaccaa ctacctagta ggtgccatca aatgacgtgc tgcaagctat    420
cgcgaccagc caggtcagcc gcgtgtcaca tgtaaggtca gagctaataa gatgcgacat    480
tctgtgcatt gctagcaccg ccaatactag cacgaaacgg ctttggcacc tcagtggcag    540
gccgaagttc gcgtgggatg ggatccattt attaccctgc attatacggg gagagctaca    600
ggtcttgagc gagtatcatc aacgggcag ttgtttataa ggatcaaagg acaggttgtt     660
aataccgaat ttacattaag aagtagaatg caagatgagt tgtgaactgt aatctcctgt    720
gtttactgcc caaggtaggt ggcttagcat gttagcagca atacattctt acctgtagca    780
tctggcgccg ctacctagta tcaatatgat ccaggcacta aggcgtgttc cgcctcgact    840
acctcacaga tgcatgatgc aagttttgat ggaaaatgtc cgcgtctctg ctttcaacaa    900
aggccgccaa ccgcccgctc cagccaaaca gaacgcggc tgcaataccc atcatctttc     960
acagacaagc cgaatcagtc cgcgtcagtt ca                                   992

<210> SEQ ID NO 13
<211> LENGTH: 310
<212> TYPE: PRT
<213> ORGANISM: Helicobacter pylori

<400> SEQUENCE: 13

Met Asn Glu Ile Ile Leu Ile Thr Gly Ala Tyr Gly Met Val Gly Gln
1               5                   10                  15

Asn Thr Ala Leu Tyr Phe Lys Lys Asn Lys Pro Asp Val Thr Leu Leu
            20                  25                  30

Thr Pro Lys Lys Ser Glu Leu Cys Leu Leu Asp Lys Asp Asn Val Gln
        35                  40                  45

Ala Tyr Leu Lys Glu Tyr Lys Pro Thr Gly Ile Ile His Cys Ala Gly
    50                  55                  60

Arg Val Gly Gly Ile Val Ala Asn Met Asn Asp Leu Ser Thr Tyr Met
65                  70                  75                  80

Val Glu Asn Leu Leu Met Gly Leu Tyr Leu Phe Ser Ser Ala Leu Asp
                85                  90                  95

Ser Gly Val Lys Lys Ala Ile Asn Leu Ala Ser Ser Cys Ala Tyr Pro
            100                 105                 110

Lys Phe Ala Pro Asn Pro Leu Lys Glu Ser Asp Leu Leu Asn Gly Ser
        115                 120                 125

Leu Glu Pro Thr Asn Glu Gly Tyr Ala Leu Ala Lys Leu Ser Val Met
    130                 135                 140

Lys Tyr Cys Glu Tyr Val Ser Ala Glu Lys Gly Val Phe Tyr Lys Thr
145                 150                 155                 160

Leu Val Pro Cys Asn Leu Tyr Gly Glu Phe Asp Lys Phe Glu Glu Lys
                165                 170                 175

Ile Ala His Met Ile Pro Gly Leu Ile Ala Arg Met His Thr Ala Lys
            180                 185                 190

Leu Lys Asn Glu Lys Glu Phe Ala Met Trp Gly Asp Gly Thr Ala Arg
        195                 200                 205

Arg Glu Tyr Leu Asn Ala Lys Asp Leu Ala Arg Phe Ile Ser Leu Ala
    210                 215                 220

Tyr Glu Asn Ile Ala Ser Ile Pro Ser Val Met Asn Val Gly Ser Gly
225                 230                 235                 240

Val Asp Tyr Ser Ile Glu Glu Tyr Tyr Glu Lys Val Ala Gln Val Leu
```

```
                    245                 250                 255
Asp Tyr Lys Gly Val Phe Val Lys Asp Leu Ser Lys Pro Val Gly Met
            260                 265                 270

Gln Gln Lys Leu Met Asp Ile Ser Lys Gln Arg Ala Leu Lys Trp Glu
        275                 280                 285

Leu Glu Ile Pro Leu Glu Gln Gly Ile Lys Glu Ala Tyr Glu Tyr Tyr
    290                 295                 300

Leu Lys Leu Leu Glu Val
305             310

<210> SEQ ID NO 14
<211> LENGTH: 933
<212> TYPE: DNA
<213> ORGANISM: Helicobacter pylori

<400> SEQUENCE: 14
atgaacgaga tcatcctcat taccggcgcc tacggcatgg tcggtcagaa cacggctctg      60
tacttcaaga agaacaagcc cgacgttacc ctccttactc ctaagaaaag cgagctgtgc     120
ctcttggaca aggataatgt ccaggcctac ctgaaagaat ataagccgac aggaatcatt     180
cactgcgcag gccgcgtcgg cgggatcgtg gcgaacatga cgacctctc cacgtacatg      240 gtcgagaacc ttctcatggg cctgtacctg ttttcgagcg ccctcgactc tggtgtgaag     300
aaggccatca acttggcctc atcctgtgct tatcccaagt cgcgcccaa tccactgaaa      360 gagtcggatc tgctcaacgg cagcctcgag cctaccaacg agggatacgc ccttgctaag     420
ctgtccgtca tgaagtactg cgaatacgtt agtgccgaga agggcgtgtt ctataagacc     480
ctcgtcccgt gcaacttgta cggcgagttc gacaagtttg aagaaagat cgcacacatg      540 atccccggcc tcattgcccg aatgcatacg gcgaagctga gaacgagaa agaattttgcc     600 atgtggggcg acggtactgc tcgccgggag tacctcaacg ccaaggatct ggcccgtttc     660
atttctcttg catacgagaa tatcgctagc attccctctg tcatgaacgt gggatcgggc     720
gttgactata gcatcgagga atactacgag aaggtcgcgc aagtgctcga ctacaagggg     780
gtgttcgtca aggacctgtc caagcctgtc ggtatgcagc aaaagctcat ggatatctcg     840
aagcagaggg ctctgaagtg ggagttggag attccgctcg agcagggcat caaagaggcc     900
tacgagtact atctgaagct gcttgaggtg taa                                  933

<210> SEQ ID NO 15
<211> LENGTH: 381
<212> TYPE: PRT
<213> ORGANISM: Helicobacter pylori

<400> SEQUENCE: 15

Met Lys Glu Lys Ile Ala Leu Ile Thr Gly Val Thr Gly Gln Asp Gly
1               5                   10                  15

Ser Tyr Leu Ala Glu Tyr Leu Leu Asn Leu Gly Tyr Glu Val His Gly
            20                  25                  30

Leu Lys Arg Arg Ser Ser Ile Asn Thr Ser Arg Ile Asp His Leu
        35                  40                  45

Tyr Glu Asp Leu His Ser Glu His Lys Arg Arg Phe Phe Leu His Tyr
    50                  55                  60

Gly Asp Met Thr Asp Ser Ser Asn Leu Ile His Leu Ile Ala Thr Thr
65                  70                  75                  80

Lys Pro Thr Glu Ile Tyr Asn Leu Ala Ala Gln Ser His Val Lys Val
                85                  90                  95
```

Ser Phe Glu Thr Pro Glu Tyr Thr Ala Asn Ala Asp Gly Ile Gly Thr
            100                 105                 110

Leu Arg Ile Leu Glu Ala Met Arg Ile Leu Gly Leu Glu Lys Lys Thr
            115                 120                 125

Arg Phe Tyr Gln Ala Ser Thr Ser Glu Leu Tyr Gly Glu Val Leu Glu
        130                 135                 140

Thr Pro Gln Asn Glu Asn Thr Pro Phe Asn Pro Arg Ser Pro Tyr Ala
145                 150                 155                 160

Val Ala Lys Met Tyr Ala Phe Tyr Ile Thr Lys Asn Tyr Arg Glu Ala
                165                 170                 175

Tyr Asn Leu Phe Ala Val Asn Gly Ile Leu Phe Asn His Glu Ser Arg
            180                 185                 190

Val Arg Gly Glu Thr Phe Val Thr Arg Lys Ile Thr Arg Ala Ala Ser
        195                 200                 205

Ala Ile Ala Tyr Asn Leu Thr Asp Cys Leu Tyr Leu Gly Asn Leu Asp
        210                 215                 220

Ala Lys Arg Asp Trp Gly His Ala Lys Asp Tyr Val Lys Met Met His
225                 230                 235                 240

Leu Met Leu Gln Ala Pro Thr Pro Gln Asp Tyr Val Ile Ala Thr Gly
                245                 250                 255

Lys Thr Thr Ser Val Arg Asp Phe Val Lys Met Ser Phe Glu Phe Ile
            260                 265                 270

Gly Ile Asp Leu Glu Phe Gln Asn Thr Gly Ile Lys Glu Ile Gly Leu
        275                 280                 285

Ile Lys Ser Val Asp Glu Lys Arg Ala Asn Ala Leu Gln Leu Asn Leu
        290                 295                 300

Ser His Leu Lys Thr Gly Lys Ile Val Val Arg Ile Asp Glu His Tyr
305                 310                 315                 320

Phe Arg Pro Thr Glu Val Asp Leu Leu Leu Gly Asp Pro Thr Gly Ala
                325                 330                 335

Glu Lys Glu Leu Gly Trp Val Arg Glu Tyr Asp Leu Lys Glu Leu Val
            340                 345                 350

Lys Asp Met Leu Glu Tyr Asp Leu Lys Glu Cys Gln Lys Asn Leu Tyr
        355                 360                 365

Leu Gln Asp Gly Gly Tyr Thr Leu Arg Asn Phe Tyr Glu
    370                 375                 380

<210> SEQ ID NO 16
<211> LENGTH: 1146
<212> TYPE: DNA
<213> ORGANISM: Helicobacter pylori

<400> SEQUENCE: 16
atgaaagaga agatcgccct cattaccggc gtcacgggcc aggacggtag ctacctggct        60
gagtacctcc tgaaccttgg atatgaagtg cacggcttga agcgccgatc ctcgagcatc       120
aacacttctc ggatcgatca cctctacgag gacctccatt ccgagcacaa gcgccgtttc       180
tttctgcact acggcgacat gaccgactcg tcaaatctga tccacctcat gccaccacg        240 aagcccacag atctacaa ccttgccgcg cagagccatg tcaaggttag tttcgaaacc         300
cctgagtata cggccaacgc agatggcatt ggactctca ggatcttgga ggctatgcgc        360
atcctgggcc tcgagaagaa aaccagattc taccaagcct ccacgtctga gctgtacggt       420
gaggtcctgg aaaccccgca gaacgagaac acacccttta accccgcag cccatacgcc       480

```
gtcgcgaaga tgtacgcttt ctatattacg aagaattacc gagaggccta caacctcttt      540
gcagtgaacg gaatcctttt caaccacgag tcgcgcgtcc ggggcgaaac cttcgttacc      600
cgtaagatta ctagggccgc tccgctatc gcgtacaacc tcacggactg cctgtatctg       660
ggcaatttgg acgccaagcg cgattggggc cacgccaagg actacgtcaa gatgatgcac      720
ctcatgctcc aggcacctac cccgcaggac tacgtgatcg ccaccggtaa gactacaagc     780
gtccgagact cgtcaagat gtccttcgag tttatcggca ttgatcttga gtttcagaac      840
acgggaatca aagagattgg cctgatcaag tcggttgaca gaagcgcgc gaacgcgctc      900 caactcaacc tgtctcatct caagaccggg aagatcgtcg tgcggattga cgaacactat     960
ttccgcccca ctgaggtcga cctgttgctg ggcgatccca cgggtgccga aaagagctt    1020 ggctgggtcc gagagtacga cctcaaagaa ctggtgaagg acatgctcga gtacgatctg    1080
aaagagtgcc agaagaacct ctacttgcag gacggcggat ataccttcg gaatttctac    1140 gagtaa                                                                 1146
```

<210> SEQ ID NO 17
<211> LENGTH: 407
<212> TYPE: PRT
<213> ORGANISM: Trichoderma reesei

<400> SEQUENCE: 17

Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
225                 230                 235                 240

His Gly Gln Asn Gly Ser Tyr Asn Phe Gly Tyr Ile Asp Thr Ser Val
                245                 250                 255

Ala Lys Gly Pro Val Ala Tyr Thr Pro Val Asp Asn Ser Gln Gly Phe
            260                 265                 270

Trp Glu Phe Thr Ala Ser Gly Tyr Ser Val Gly Gly Lys Leu Asn
        275                 280                 285

Arg Asn Ser Ile Asp Gly Ile Ala Asp Thr Gly Thr Thr Leu Leu Leu
    290                 295                 300

Leu Asp Asp Asn Val Val Asp Ala Tyr Ala Asn Val Gln Ser Ala
305                 310                 315                 320

Gln Tyr Asp Asn Gln Gln Gly Val Val Phe Asp Cys Asp Glu Asp
            325                 330                 335

Leu Pro Ser Phe Ser Phe Gly Val Gly Ser Ser Thr Ile Thr Ile Pro
        340                 345                 350

Gly Asp Leu Leu Asn Leu Thr Pro Leu Glu Glu Gly Ser Ser Thr Cys
        355                 360                 365

Phe Gly Gly Leu Gln Ser Ser Ser Gly Ile Gly Ile Asn Ile Phe Gly
    370                 375                 380

Asp Val Ala Leu Lys Ala Ala Leu Val Val Phe Asp Leu Gly Asn Glu
385                 390                 395                 400

Arg Leu Gly Trp Ala Gln Lys
            405

<210> SEQ ID NO 18
<211> LENGTH: 399
<212> TYPE: PRT
<213> ORGANISM: Trichoderma reesei

<400> SEQUENCE: 18

Met Gln Pro Ser Phe Gly Ser Phe Leu Val Thr Val Leu Ser Ala Ser
1               5                   10                  15

Met Ala Ala Gly Ser Val Ile Pro Ser Thr Asn Ala Asn Pro Gly Ser
            20                  25                  30

Phe Glu Ile Lys Arg Ser Ala Asn Lys Ala Phe Thr Gly Arg Asn Gly
        35                  40                  45

Pro Leu Ala Leu Ala Arg Thr Tyr Ala Lys Tyr Gly Val Glu Val Pro
    50                  55                  60

Lys Thr Leu Val Asp Ala Ile Gln Leu Val Lys Ser Ile Gln Leu Ala
65                  70                  75                  80

Lys Arg Asp Ser Ala Thr Val Thr Ala Thr Pro Asp His Asp Asp Ile
            85                  90                  95

Glu Tyr Leu Val Pro Val Lys Ile Gly Thr Pro Gln Thr Leu Asn
            100                 105                 110

Leu Asp Phe Asp Thr Gly Ser Ser Asp Leu Trp Val Phe Ser Ser Asp
        115                 120                 125

Val Asp Pro Thr Ser Ser Gln Gly His Asp Ile Tyr Thr Pro Ser Lys
130                 135                 140

Ser Thr Ser Ser Lys Lys Leu Glu Gly Ala Ser Trp Asn Ile Thr Tyr
145                 150                 155                 160

Gly Asp Arg Ser Ser Ser Gly Asp Val Tyr His Asp Ile Val Ser
            165                 170                 175

Val Gly Asn Leu Thr Val Lys Ser Gln Ala Val Glu Ser Ala Arg Asn
            180                 185                 190

Val Ser Ala Gln Phe Thr Gln Gly Asn Asn Asp Gly Leu Val Gly Leu
        195                 200                 205

Ala Phe Ser Ser Ile Asn Thr Val Lys Pro Thr Pro Gln Lys Thr Trp

```
                    210                 215                 220
Tyr Asp Asn Ile Val Gly Ser Leu Asp Ser Pro Val Phe Val Ala Asp
225                 230                 235                 240

Leu Arg His Asp Thr Pro Gly Ser Tyr His Phe Gly Ser Ile Pro Ser
                245                 250                 255

Glu Ala Ser Lys Ala Phe Tyr Ala Pro Ile Asp Asn Ser Lys Gly Phe
            260                 265                 270

Trp Gln Phe Ser Thr Ser Ser Asn Ile Ser Gly Gln Phe Asn Ala Val
        275                 280                 285

Ala Asp Thr Gly Thr Thr Leu Leu Leu Ala Ser Asp Asp Leu Val Lys
290                 295                 300

Ala Tyr Tyr Ala Lys Val Gln Gly Ala Arg Val Asn Val Phe Leu Gly
305                 310                 315                 320

Gly Tyr Val Phe Asn Cys Thr Thr Gln Leu Pro Asp Phe Thr Phe Thr
                325                 330                 335

Val Gly Glu Gly Asn Ile Thr Val Pro Gly Thr Leu Ile Asn Tyr Ser
            340                 345                 350

Glu Ala Gly Asn Gly Gln Cys Phe Gly Gly Ile Gln Pro Ser Gly Gly
        355                 360                 365

Leu Pro Phe Ala Ile Phe Gly Asp Ile Ala Leu Lys Ala Ala Tyr Val
370                 375                 380

Ile Phe Asp Ser Gly Asn Lys Gln Val Gly Trp Ala Gln Lys Lys
385                 390                 395

<210> SEQ ID NO 19
<211> LENGTH: 452
<212> TYPE: PRT
<213> ORGANISM: Trichoderma reesei

<400> SEQUENCE: 19

Met Glu Ala Ile Leu Gln Ala Gln Ala Lys Phe Arg Leu Asp Arg Gly
1               5                   10                  15

Leu Gln Lys Ile Thr Ala Val Arg Asn Lys Asn Tyr Lys Arg His Gly
            20                  25                  30

Pro Lys Ser Tyr Val Tyr Leu Leu Asn Arg Phe Gly Phe Glu Pro Thr
        35                  40                  45

Lys Pro Gly Pro Tyr Phe Gln Gln His Arg Ile His Gln Arg Gly Leu
    50                  55                  60

Ala His Pro Asp Phe Lys Ala Ala Val Gly Gly Arg Val Thr Arg Gln
65                  70                  75                  80

Lys Val Leu Ala Lys Lys Val Lys Glu Asp Gly Thr Val Asp Ala Gly
                85                  90                  95

Gly Ser Lys Thr Gly Glu Val Asp Ala Glu Asp Gln Gln Asn Asp Ser
            100                 105                 110

Glu Tyr Leu Cys Glu Val Thr Ile Gly Thr Pro Gly Gln Lys Leu Met
        115                 120                 125

Leu Asp Phe Asp Thr Gly Ser Ser Asp Leu Trp Val Phe Ser Thr Glu
    130                 135                 140

Leu Ser Lys His Leu Gln Glu Asn His Ala Ile Phe Asp Pro Lys Lys
145                 150                 155                 160

Ser Ser Thr Phe Lys Pro Leu Lys Asp Gln Thr Trp Gln Ile Ser Tyr
                165                 170                 175

Gly Asp Gly Ser Ser Ala Ser Gly Thr Cys Gly Ser Asp Thr Val Thr
            180                 185                 190
```

Leu Gly Gly Leu Ser Ile Lys Asn Gln Thr Ile Glu Leu Ala Ser Lys
            195                 200                 205

Leu Ala Pro Gln Phe Ala Gln Gly Thr Gly Asp Gly Leu Leu Gly Leu
        210                 215                 220

Ala Trp Pro Gln Ile Asn Thr Val Gln Thr Asp Gly Arg Pro Thr Pro
225                 230                 235                 240

Ala Asn Thr Pro Val Ala Asn Met Ile Gln Gln Asp Ile Pro Ser
                245                 250                 255

Asp Ala Gln Leu Phe Thr Ala Ala Phe Tyr Ser Glu Arg Asp Glu Asn
                260                 265                 270

Ala Glu Ser Phe Tyr Thr Phe Gly Tyr Ile Asp Gln Asp Leu Val Ser
            275                 280                 285

Ala Ser Gly Gln Glu Ile Ala Trp Thr Asp Val Asp Asn Ser Gln Gly
        290                 295                 300

Phe Trp Met Phe Pro Ser Thr Lys Thr Thr Ile Asn Gly Lys Asp Ile
305                 310                 315                 320

Ser Gln Glu Gly Asn Thr Ala Ile Ala Asp Thr Gly Thr Thr Leu Ala
                325                 330                 335

Leu Val Ser Asp Glu Val Cys Glu Ala Leu Tyr Lys Ala Ile Pro Gly
            340                 345                 350

Ala Lys Tyr Asp Asp Asn Gln Gln Gly Tyr Val Phe Pro Ile Asn Thr
        355                 360                 365

Asp Ala Ser Ser Leu Pro Glu Leu Lys Val Ser Val Gly Asn Thr Gln
    370                 375                 380

Phe Val Ile Gln Pro Glu Asp Leu Ala Phe Ala Pro Ala Asp Asp Ser
385                 390                 395                 400

Asn Trp Tyr Gly Gly Val Gln Ser Arg Gly Ser Asn Pro Phe Asp Ile
                405                 410                 415

Leu Gly Asp Val Phe Leu Lys Ser Val Tyr Ala Ile Phe Asp Gln Gly
            420                 425                 430

Asn Gln Arg Phe Gly Ala Val Pro Lys Ile Gln Ala Lys Gln Asn Leu
        435                 440                 445

Gln Pro Pro Gln
    450

<210> SEQ ID NO 20
<211> LENGTH: 395
<212> TYPE: PRT
<213> ORGANISM: Trichoderma reesei

<400> SEQUENCE: 20

Met Lys Ser Ala Leu Leu Ala Ala Ala Leu Val Gly Ser Ala Gln
1               5                   10                  15

Ala Gly Ile His Lys Met Lys Leu Gln Lys Val Ser Leu Glu Gln Gln
                20                  25                  30

Leu Glu Gly Ser Ser Ile Glu Ala His Val Gln Gln Leu Gly Gln Lys
            35                  40                  45

Tyr Met Gly Val Arg Pro Thr Ser Arg Ala Glu Val Met Phe Asn Asp
        50                  55                  60

Lys Pro Pro Lys Val Gln Gly Gly His Pro Val Pro Thr Asn Phe
65                  70                  75                  80

Met Asn Ala Gln Tyr Phe Ser Glu Ile Thr Ile Gly Thr Pro Pro Gln
                85                  90                  95

Ser Phe Lys Val Val Leu Asp Thr Gly Ser Ser Asn Leu Trp Val Pro
            100                 105                 110

-continued

```
Ser Gln Ser Cys Asn Ser Ile Ala Cys Phe Leu His Ser Thr Tyr Asp
            115                 120                 125

Ser Ser Ser Ser Ser Thr Tyr Lys Pro Asn Gly Ser Asp Phe Glu Ile
130                 135                 140

His Tyr Gly Ser Gly Ser Leu Thr Gly Phe Ile Ser Asn Asp Val Val
145                 150                 155                 160

Thr Ile Gly Asp Leu Lys Ile Lys Gly Gln Asp Phe Ala Glu Ala Thr
                165                 170                 175

Ser Glu Pro Gly Leu Ala Phe Ala Phe Gly Arg Phe Asp Gly Ile Leu
            180                 185                 190

Gly Leu Gly Tyr Asp Thr Ile Ser Val Asn Gly Ile Val Pro Pro Phe
            195                 200                 205

Tyr Gln Met Val Asn Gln Lys Leu Ile Asp Glu Pro Val Phe Ala Phe
            210                 215                 220

Tyr Leu Gly Ser Ser Asp Glu Gly Ser Glu Ala Val Phe Gly Gly Val
225                 230                 235                 240

Asp Asp Ala His Tyr Glu Gly Lys Ile Glu Tyr Ile Pro Leu Arg Arg
                245                 250                 255

Lys Ala Tyr Trp Glu Val Asp Leu Asp Ser Ile Ala Phe Gly Asp Glu
            260                 265                 270

Val Ala Glu Leu Glu Asn Thr Gly Ala Ile Leu Asp Thr Gly Thr Ser
            275                 280                 285

Leu Asn Val Leu Pro Ser Gly Leu Ala Glu Leu Leu Asn Ala Glu Ile
            290                 295                 300

Gly Ala Lys Lys Gly Phe Gly Gly Gln Tyr Thr Val Asp Cys Ser Lys
305                 310                 315                 320

Arg Asp Ser Leu Pro Asp Ile Thr Phe Ser Leu Ala Gly Ser Lys Tyr
                325                 330                 335

Ser Leu Pro Ala Ser Asp Tyr Ile Ile Glu Met Ser Gly Asn Cys Ile
            340                 345                 350

Ser Ser Phe Gln Gly Met Asp Phe Pro Glu Pro Val Gly Pro Leu Val
            355                 360                 365

Ile Leu Gly Asp Ala Phe Leu Arg Arg Tyr Tyr Ser Val Tyr Asp Leu
            370                 375                 380

Gly Arg Asp Ala Val Gly Leu Ala Lys Ala Lys
385                 390                 395

<210> SEQ ID NO 21
<211> LENGTH: 426
<212> TYPE: PRT
<213> ORGANISM: Trichoderma reesei

<400> SEQUENCE: 21

Met Lys Phe His Ala Ala Ala Leu Thr Leu Ala Cys Leu Ala Ser Ser
1               5                   10                  15

Ala Ser Ala Gly Val Ala Gln Pro Arg Ala Asp Glu Val Glu Ser Ala
            20                  25                  30

Glu Gln Gly Lys Thr Phe Ser Leu Glu Gln Ile Pro Asn Glu Arg Tyr
        35                  40                  45

Lys Gly Asn Ile Pro Ala Ala Tyr Ile Ser Ala Leu Ala Lys Tyr Ser
    50                  55                  60

Pro Thr Ile Pro Asp Lys Ile Lys His Ala Ile Glu Ile Asn Pro Asp
65                  70                  75                  80

Leu His Arg Lys Phe Ser Lys Leu Ile Asn Ala Gly Asn Met Thr Gly
```

```
                85                  90                  95
Thr Ala Val Ala Ser Pro Pro Gly Ala Asp Ala Glu Tyr Val Leu
            100                 105                 110
Pro Val Lys Ile Gly Thr Pro Gln Thr Leu Pro Leu Asn Leu Asp
            115                 120                 125
Thr Gly Ser Ser Asp Leu Trp Val Ile Ser Thr Asp Thr Tyr Pro Pro
130                 135                 140
Gln Val Gln Gly Gln Thr Arg Tyr Asn Val Ser Ala Ser Thr Thr Ala
145                 150                 155                 160
Gln Arg Leu Ile Gly Glu Ser Trp Val Ile Arg Tyr Gly Asp Gly Ser
                165                 170                 175
Ser Ala Asn Gly Ile Val Tyr Lys Asp Arg Val Gln Ile Gly Asn Thr
                180                 185                 190
Phe Phe Asn Gln Gln Ala Val Glu Ser Ala Val Asn Ile Ser Asn Glu
                195                 200                 205
Ile Ser Asp Asp Ser Phe Ser Ser Gly Leu Leu Gly Ala Ala Ser Ser
            210                 215                 220
Ala Ala Asn Thr Val Arg Pro Asp Arg Gln Thr Thr Tyr Leu Glu Asn
225                 230                 235                 240
Ile Lys Ser Gln Leu Ala Arg Pro Val Phe Thr Ala Asn Leu Lys Lys
                245                 250                 255
Gly Lys Pro Gly Asn Tyr Asn Phe Gly Tyr Ile Asn Gly Ser Glu Tyr
                260                 265                 270
Ile Gly Pro Ile Gln Tyr Ala Ala Ile Asn Pro Ser Ser Pro Leu Trp
            275                 280                 285
Glu Val Ser Val Ser Gly Tyr Arg Val Gly Ser Asn Asp Thr Lys Tyr
290                 295                 300
Val Pro Arg Val Trp Asn Ala Ile Ala Asp Thr Gly Thr Thr Leu Leu
305                 310                 315                 320
Leu Val Pro Asn Asp Ile Val Ser Ala Tyr Tyr Ala Gln Val Lys Gly
                325                 330                 335
Ser Thr Phe Ser Asn Asp Val Gly Met Met Leu Val Pro Cys Ala Ala
                340                 345                 350
Thr Leu Pro Asp Phe Ala Phe Gly Leu Gly Asn Tyr Arg Gly Val Ile
                355                 360                 365
Pro Gly Ser Tyr Ile Asn Tyr Gly Arg Met Asn Lys Thr Tyr Cys Tyr
            370                 375                 380
Gly Gly Ile Gln Ser Ser Glu Asp Ala Pro Phe Ala Val Leu Gly Asp
385                 390                 395                 400
Ile Ala Leu Lys Ala Gln Phe Val Val Phe Asp Met Gly Asn Lys Val
                405                 410                 415
Val Gly Phe Ala Asn Lys Asn Thr Asn Val
            420                 425

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
acccaaagcg tccttcatta                                              20

<210> SEQ ID NO 23
```

```
<211> LENGTH: 446
<212> TYPE: PRT
<213> ORGANISM: Trichoderma reesei

<400> SEQUENCE: 23
```

| | | | | | | | | | | | | | | | |
|---|---|---|---|---|---|---|---|---|---|---|---|---|---|---|---|
| Met | Thr | Leu | Pro | Val | Pro | Leu | Arg | Glu | His | Asp | Leu | Pro | Phe | Leu | Lys |
| 1 | | | | 5 | | | | | 10 | | | | | 15 | |
| Glu | Lys | Arg | Lys | Leu | Pro | Ala | Asp | Asp | Ile | Pro | Ser | Gly | Thr | Tyr | Thr |
| | | | 20 | | | | | 25 | | | | | 30 | | |
| Leu | Pro | Ile | Ile | His | Ala | Arg | Arg | Pro | Lys | Leu | Ala | Ser | Arg | Ala | Ile |
| | | 35 | | | | | 40 | | | | | 45 | | | |
| Glu | Val | Gln | Val | Glu | Asn | Arg | Ser | Asp | Val | Ser | Tyr | Tyr | Ala | Gln | Leu |
| 50 | | | | | 55 | | | | | 60 | | | | | |
| Asn | Ile | Gly | Thr | Pro | Pro | Gln | Thr | Val | Tyr | Ala | Gln | Ile | Asp | Thr | Gly |
| 65 | | | | | 70 | | | | | 75 | | | | | 80 |
| Ser | Phe | Glu | Leu | Trp | Val | Asn | Pro | Asn | Cys | Ser | Asn | Val | Gln | Ser | Ala |
| | | | | 85 | | | | | 90 | | | | | 95 | |
| Asp | Gln | Arg | Phe | Cys | Arg | Ala | Ile | Gly | Phe | Tyr | Asp | Pro | Ser | Ser | Ser |
| | | | | 100 | | | | | 105 | | | | | 110 | |
| Ser | Thr | Ala | Asp | Val | Thr | Ser | Gln | Ser | Ala | Arg | Leu | Arg | Tyr | Gly | Ile |
| | | | 115 | | | | | 120 | | | | | 125 | | |
| Gly | Ser | Ala | Asp | Val | Thr | Tyr | Val | His | Asp | Thr | Ile | Ser | Leu | Pro | Gly |
| | 130 | | | | | 135 | | | | | 140 | | | | |
| Ser | Gly | Ser | Gly | Ser | Lys | Ala | Met | Lys | Ala | Val | Gln | Phe | Gly | Val | Ala |
| 145 | | | | | 150 | | | | | 155 | | | | | 160 |
| Asp | Thr | Ser | Val | Asp | Glu | Phe | Ser | Gly | Ile | Leu | Gly | Leu | Gly | Ala | Gly |
| | | | | 165 | | | | | 170 | | | | | 175 | |
| Asn | Gly | Ile | Asn | Thr | Glu | Tyr | Pro | Asn | Phe | Val | Asp | Glu | Leu | Ala | Ala |
| | | | 180 | | | | | 185 | | | | | 190 | | |
| Gln | Gly | Val | Thr | Ala | Thr | Lys | Ala | Phe | Ser | Leu | Ala | Leu | Gly | Ser | Lys |
| | | 195 | | | | | 200 | | | | | 205 | | | |
| Ala | Glu | Glu | Glu | Gly | Val | Ile | Ile | Phe | Gly | Gly | Val | Asp | Thr | Ala | Lys |
| 210 | | | | | 215 | | | | | 220 | | | | | |
| Phe | His | Gly | Glu | Leu | Ala | His | Leu | Pro | Ile | Val | Pro | Ala | Asp | Asp | Ser |
| 225 | | | | 230 | | | | | 235 | | | | | 240 | |
| Pro | Asp | Gly | Val | Ala | Arg | Tyr | Trp | Val | Lys | Met | Lys | Ser | Ile | Ser | Leu |
| | | | 245 | | | | | 250 | | | | | 255 | | |
| Thr | Pro | Pro | Pro | Ser | Ser | Gly | Ser | Thr | Asp | Asn | Asn | Asn | | | |
| | | 260 | | | | | 265 | | | | | 270 | | | |
| Lys | Pro | Val | Ala | Phe | Pro | Gln | Thr | Ser | Met | Thr | Val | Phe | Leu | Asp | Ser |
| | 275 | | | | | 280 | | | | | 285 | | | | |
| Gly | Ser | Thr | Leu | Thr | Leu | Pro | Pro | Ala | Leu | Val | Arg | Gln | Ile | Ala |
| 290 | | | | | 295 | | | | | 300 | | | | | |
| Ser | Ala | Leu | Gly | Ser | Thr | Gln | Thr | Asp | Glu | Ser | Gly | Phe | Phe | Val | Val |
| 305 | | | | | 310 | | | | | 315 | | | | | 320 |
| Asp | Cys | Ala | Leu | Ala | Ser | Gln | Asp | Gly | Thr | Ile | Asp | Phe | Glu | Phe | Asp |
| | | | | 325 | | | | | 330 | | | | | 335 | |
| Gly | Val | Thr | Ile | Arg | Val | Pro | Tyr | Ala | Glu | Met | Ile | Arg | Gln | Val | Ser |
| | | | 340 | | | | | 345 | | | | | 350 | | |
| Thr | Leu | Pro | Pro | His | Cys | Tyr | Leu | Gly | Met | Met | Gly | Ser | Thr | Gln | Phe |
| | | 355 | | | | | 360 | | | | | 365 | | | |
| Ala | Leu | Leu | Gly | Asp | Thr | Phe | Leu | Arg | Ser | Ala | Tyr | Ala | Val | Phe | Asp |
| 370 | | | | | 375 | | | | | 380 | | | | | |
| Leu | Thr | Ser | Asn | Val | Val | His | Leu | Ala | Pro | Tyr | Ala | Asn | Cys | Gly | Thr |

```
                385                 390                 395                 400
Asn Val Lys Ser Ile Thr Ser Thr Ser Ser Leu Ser Asn Leu Val Gly
                405                 410                 415

Thr Cys Asn Asp Pro Ser Lys Pro Ser Ser Pro Ser Pro Ser Gln
            420                 425                 430

Thr Pro Ser Ala Ser Pro Ser Ser Thr Ala Thr Gln Lys Ala
            435                 440                 445

<210> SEQ ID NO 24
<211> LENGTH: 259
<212> TYPE: PRT
<213> ORGANISM: Trichoderma reesei

<400> SEQUENCE: 24

Met Ala Pro Ala Ser Gln Val Val Ser Ala Leu Met Leu Pro Ala Leu
1               5                   10                  15

Ala Leu Gly Ala Ala Ile Gln Pro Arg Gly Ala Asp Ile Val Gly Gly
                20                  25                  30

Thr Ala Ala Ser Leu Gly Glu Phe Pro Tyr Ile Val Ser Leu Gln Asn
            35                  40                  45

Pro Asn Gln Gly Gly His Phe Cys Gly Gly Val Leu Val Asn Ala Asn
        50                  55                  60

Thr Val Thr Ala Ala His Cys Ser Val Val Tyr Pro Ala Ser Gln
65                  70                  75                  80

Ile Arg Val Arg Ala Gly Thr Leu Thr Trp Asn Ser Gly Gly Thr Leu
                85                  90                  95

Val Gly Val Ser Gln Ile Ile Val Asn Pro Ser Tyr Asn Asp Arg Thr
            100                 105                 110

Thr Asp Phe Asp Val Ala Val Trp His Leu Ser Ser Pro Ile Arg Glu
        115                 120                 125

Ser Ser Thr Ile Gly Tyr Ala Thr Leu Pro Ala Gln Gly Ser Asp Pro
    130                 135                 140

Val Ala Gly Ser Thr Val Thr Thr Ala Gly Trp Gly Thr Thr Ser Glu
145                 150                 155                 160

Asn Ser Asn Ser Ile Pro Ser Arg Leu Asn Lys Val Ser Val Pro Val
                165                 170                 175

Val Ala Arg Ser Thr Cys Gln Ala Asp Tyr Arg Ser Gln Gly Leu Ser
            180                 185                 190

Val Thr Asn Asn Met Phe Cys Ala Gly Leu Thr Gln Gly Gly Lys Asp
        195                 200                 205

Ser Cys Ser Gly Asp Ser Gly Pro Ile Val Asp Ala Asn Gly Val
    210                 215                 220

Leu Gln Gly Val Val Ser Trp Gly Ile Gly Cys Ala Glu Ala Gly Phe
225                 230                 235                 240

Pro Gly Val Tyr Thr Arg Ile Gly Asn Phe Val Asn Tyr Ile Asn Gln
                245                 250                 255

Asn Leu Ala

<210> SEQ ID NO 25
<211> LENGTH: 882
<212> TYPE: PRT
<213> ORGANISM: Trichoderma reesei

<400> SEQUENCE: 25

Met Val Arg Ser Ala Leu Phe Val Ser Leu Leu Ala Thr Phe Ser Gly
1               5                   10                  15
```

-continued

```
Val Ile Ala Arg Val Ser Gly His Gly Ser Lys Ile Val Pro Gly Ala
             20                  25                  30
Tyr Ile Phe Glu Phe Glu Asp Ser Gln Asp Thr Ala Asp Phe Tyr Lys
             35                  40                  45
Lys Leu Asn Gly Glu Gly Ser Thr Arg Leu Lys Phe Asp Tyr Lys Leu
 50                  55                  60
Phe Lys Gly Val Ser Val Gln Leu Lys Asp Leu Asp Asn His Glu Ala
 65                  70                  75                  80
Lys Ala Gln Gln Met Ala Gln Leu Pro Ala Val Lys Asn Val Trp Pro
                 85                  90                  95
Val Thr Leu Ile Asp Ala Pro Asn Pro Lys Val Glu Trp Val Ala Gly
            100                 105                 110
Ser Thr Ala Pro Thr Leu Glu Ser Arg Ala Ile Lys Lys Pro Pro Ile
            115                 120                 125
Pro Asn Asp Ser Ser Asp Phe Pro Thr His Gln Met Thr Gln Ile Asp
130                 135                 140
Lys Leu Arg Ala Lys Gly Tyr Thr Gly Lys Gly Val Arg Val Ala Val
145                 150                 155                 160
Ile Asp Thr Gly Ile Asp Tyr Thr His Pro Ala Leu Gly Gly Cys Phe
                165                 170                 175
Gly Arg Gly Cys Leu Val Ser Phe Gly Thr Asp Leu Val Gly Asp Asp
                180                 185                 190
Tyr Thr Gly Phe Asn Thr Pro Val Pro Asp Asp Pro Val Asp Cys
                195                 200                 205
Ala Gly His Gly Ser His Val Ala Gly Ile Ile Ala Ala Gln Glu Asn
            210                 215                 220
Pro Tyr Gly Phe Thr Gly Gly Ala Pro Asp Val Thr Leu Gly Ala Tyr
225                 230                 235                 240
Arg Val Phe Gly Cys Asp Gly Gln Ala Gly Asn Asp Val Leu Ile Ser
                245                 250                 255
Ala Tyr Asn Gln Ala Phe Glu Asp Gly Ala Gln Ile Ile Thr Ala Ser
                260                 265                 270
Ile Gly Gly Pro Ser Gly Trp Ala Glu Glu Pro Trp Ala Val Ala Val
                275                 280                 285
Thr Arg Ile Val Glu Ala Gly Val Pro Cys Thr Val Ser Ala Gly Asn
            290                 295                 300
Glu Gly Asp Ser Gly Leu Phe Phe Ala Ser Thr Ala Ala Asn Gly Lys
305                 310                 315                 320
Lys Val Ile Ala Val Ala Ser Val Asp Asn Glu Asn Ile Pro Ser Val
                325                 330                 335
Leu Ser Val Ala Ser Tyr Lys Ile Asp Ser Gly Ala Ala Gln Asp Phe
                340                 345                 350
Gly Tyr Val Ser Ser Lys Ala Trp Asp Gly Val Ser Lys Pro Leu
            355                 360                 365
Tyr Ala Val Ser Phe Asp Thr Thr Ile Pro Asp Asp Gly Cys Ser Pro
370                 375                 380
Leu Pro Asp Ser Thr Pro Asp Leu Ser Asp Tyr Ile Val Leu Val Arg
385                 390                 395                 400
Arg Gly Thr Cys Thr Phe Val Gln Lys Ala Gln Asn Val Ala Ala Lys
                405                 410                 415
Gly Ala Lys Tyr Leu Leu Tyr Tyr Asn Asn Ile Pro Gly Ala Leu Ala
            420                 425                 430
```

-continued

Val Asp Val Ser Ala Val Pro Glu Ile Glu Ala Val Gly Met Val Asp
        435                 440                 445

Asp Lys Thr Gly Ala Thr Trp Ile Ala Ala Leu Lys Asp Gly Lys Thr
450                 455                 460

Val Thr Leu Thr Leu Thr Asp Pro Ile Glu Ser Glu Lys Gln Ile Gln
465                 470                 475                 480

Phe Ser Asp Asn Pro Thr Thr Gly Gly Ala Leu Ser Gly Tyr Thr Thr
                485                 490                 495

Trp Gly Pro Thr Trp Glu Leu Asp Val Lys Pro Gln Ile Ser Ser Pro
            500                 505                 510

Gly Gly Asn Ile Leu Ser Thr Tyr Pro Val Ala Leu Gly Gly Tyr Ala
            515                 520                 525

Thr Leu Ser Gly Thr Ser Met Ala Cys Pro Leu Thr Ala Ala Ala Val
        530                 535                 540

Ala Leu Ile Gly Gln Ala Arg Gly Thr Phe Asp Pro Ala Leu Ile Asp
545                 550                 555                 560

Asn Leu Leu Ala Thr Thr Ala Asn Pro Gln Leu Phe Asn Asp Gly Glu
                565                 570                 575

Lys Phe Tyr Asp Phe Leu Ala Pro Val Pro Gln Gln Gly Gly Gly Leu
            580                 585                 590

Ile Gln Ala Tyr Asp Ala Ala Phe Ala Thr Thr Leu Leu Ser Pro Ser
        595                 600                 605

Ser Leu Ser Phe Asn Asp Thr Asp His Phe Ile Lys Lys Lys Gln Ile
        610                 615                 620

Thr Leu Lys Asn Thr Ser Lys Gln Arg Val Thr Tyr Lys Leu Asn His
625                 630                 635                 640

Val Pro Thr Asn Thr Phe Tyr Thr Leu Ala Pro Gly Asn Gly Tyr Pro
                645                 650                 655

Ala Pro Phe Pro Asn Asp Ala Val Ala Ala His Ala Asn Leu Lys Phe
            660                 665                 670

Asn Leu Gln Gln Val Thr Leu Pro Ala Gly Arg Ser Ile Thr Val Asp
        675                 680                 685

Val Phe Pro Thr Pro Arg Asp Val Asp Ala Lys Arg Leu Ala Leu
        690                 695                 700

Trp Ser Gly Tyr Ile Thr Val Asn Gly Thr Asp Gly Thr Ser Leu Ser
705                 710                 715                 720

Val Pro Tyr Gln Gly Leu Thr Gly Ser Leu His Lys Gln Lys Val Leu
                725                 730                 735

Tyr Pro Glu Asp Ser Trp Ile Ala Asp Ser Thr Asp Glu Ser Leu Ala
            740                 745                 750

Pro Val Glu Asn Gly Thr Val Phe Thr Ile Pro Ala Pro Gly Asn Ala
        755                 760                 765

Gly Pro Asp Asp Lys Leu Pro Ser Leu Val Val Ser Pro Ala Leu Gly
        770                 775                 780

Ser Arg Tyr Val Arg Val Asp Leu Val Leu Ser Ala Pro Pro His
785                 790                 795                 800

Gly Thr Lys Leu Lys Thr Val Lys Phe Leu Asp Thr Thr Ser Ile Gly
                805                 810                 815

Gln Pro Ala Gly Ser Pro Leu Leu Trp Ile Ser Arg Gly Ala Asn Pro
            820                 825                 830

Ile Ala Trp Thr Gly Glu Leu Ser Asp Asn Lys Phe Ala Pro Pro Gly
        835                 840                 845

Thr Tyr Lys Ala Val Phe His Ala Leu Arg Ile Phe Gly Asn Glu Lys

```
                850                 855                 860
Lys Lys Glu Asp Trp Asp Val Ser Glu Ser Pro Ala Phe Thr Ile Lys
865                 870                 875                 880

Tyr Ala

<210> SEQ ID NO 26
<211> LENGTH: 541
<212> TYPE: PRT
<213> ORGANISM: Trichoderma reesei

<400> SEQUENCE: 26

Met Arg Ser Val Val Ala Leu Ser Met Ala Ala Val Ala Gln Ala Ser
1               5                   10                  15

Thr Phe Gln Ile Gly Thr Ile His Glu Lys Ser Ala Pro Val Leu Ser
                20                  25                  30

Asn Val Glu Ala Asn Ala Ile Pro Asp Ala Tyr Ile Ile Lys Phe Lys
            35                  40                  45

Asp His Val Gly Glu Asp Ala Ser Lys His Asp Trp Ile Gln
        50                  55                  60

Ser Ile His Thr Asn Val Glu Gln Glu Arg Leu Glu Leu Arg Lys Arg
65                  70                  75                  80

Ser Asn Val Phe Gly Ala Asp Asp Val Phe Asp Gly Leu Lys His Thr
                85                  90                  95

Phe Lys Ile Gly Asp Gly Phe Lys Gly Tyr Ala Gly His Phe His Glu
            100                 105                 110

Ser Val Ile Glu Gln Val Arg Asn His Pro Asp Val Glu Tyr Ile Glu
        115                 120                 125

Arg Asp Ser Ile Val His Thr Met Leu Pro Leu Glu Ser Lys Asp Ser
130                 135                 140

Ile Ile Val Glu Asp Ser Cys Asn Gly Glu Thr Glu Lys Gln Ala Pro
145                 150                 155                 160

Trp Gly Leu Ala Arg Ile Ser His Arg Glu Thr Leu Asn Phe Gly Ser
                165                 170                 175

Phe Asn Lys Tyr Leu Tyr Thr Ala Asp Gly Gly Glu Gly Val Asp Ala
            180                 185                 190

Tyr Val Ile Asp Thr Gly Thr Asn Ile Glu His Val Asp Phe Glu Gly
        195                 200                 205

Arg Ala Lys Trp Gly Lys Thr Ile Pro Ala Gly Asp Glu Asp Glu Asp
210                 215                 220

Gly Asn Gly His Gly Thr His Cys Ser Gly Thr Val Ala Gly Lys Lys
225                 230                 235                 240

Tyr Gly Val Ala Lys Lys Ala His Val Tyr Ala Val Lys Val Leu Arg
                245                 250                 255

Ser Asn Gly Ser Gly Thr Met Ser Asp Val Val Lys Gly Val Glu Tyr
            260                 265                 270

Ala Ala Leu Ser His Ile Glu Gln Val Lys Ala Lys Lys Gly Lys
        275                 280                 285

Arg Lys Gly Phe Lys Gly Ser Val Ala Asn Met Ser Leu Gly Gly Gly
    290                 295                 300

Lys Thr Gln Ala Leu Asp Ala Ala Val Asn Ala Val Arg Ala Gly
305                 310                 315                 320

Val His Phe Ala Val Ala Ala Gly Asn Asp Asn Ala Asp Ala Cys Asn
                325                 330                 335

Tyr Ser Pro Ala Ala Ala Thr Glu Pro Leu Thr Val Gly Ala Ser Ala
```

```
         340                 345                 350
Leu Asp Asp Ser Arg Ala Tyr Phe Ser Asn Tyr Gly Lys Cys Thr Asp
            355                 360                 365

Ile Phe Ala Pro Gly Leu Ser Ile Gln Ser Thr Trp Ile Gly Ser Lys
370                 375                 380

Tyr Ala Val Asn Thr Ile Ser Gly Thr Ser Met Ala Ser Pro His Ile
385                 390                 395                 400

Cys Gly Leu Leu Ala Tyr Tyr Leu Ser Leu Gln Pro Ala Gly Asp Ser
                405                 410                 415

Glu Phe Ala Val Ala Pro Ile Thr Pro Lys Lys Leu Lys Glu Ser Val
                420                 425                 430

Ile Ser Val Ala Thr Lys Asn Ala Leu Ser Asp Leu Pro Asp Ser Asp
                435                 440                 445

Thr Pro Asn Leu Leu Ala Trp Asn Gly Gly Cys Ser Asn Phe Ser
    450                 455                 460

Gln Ile Val Glu Ala Gly Ser Tyr Thr Val Lys Pro Lys Gln Asn Lys
465                 470                 475                 480

Gln Ala Lys Leu Pro Ser Thr Ile Glu Glu Leu Glu Glu Ala Ile Glu
                485                 490                 495

Gly Asp Phe Glu Val Val Ser Gly Glu Ile Val Lys Gly Ala Lys Ser
                500                 505                 510

Phe Gly Ser Lys Ala Glu Lys Phe Ala Lys Lys Ile His Asp Leu Val
            515                 520                 525

Glu Glu Glu Ile Glu Glu Phe Ile Ser Glu Leu Ser Glu
            530                 535                 540

<210> SEQ ID NO 27
<211> LENGTH: 391
<212> TYPE: PRT
<213> ORGANISM: Trichoderma reesei

<400> SEQUENCE: 27

Met Arg Leu Ser Val Leu Leu Ser Val Leu Pro Leu Val Leu Ala Ala
1               5                   10                  15

Pro Ala Ile Glu Lys Arg Ala Glu Pro Ala Pro Leu Leu Val Pro Thr
                20                  25                  30

Thr Lys His Gly Leu Val Ala Asp Lys Tyr Ile Val Lys Phe Lys Asp
            35                  40                  45

Gly Ser Ser Leu Gln Ala Val Asp Glu Ala Ile Ser Gly Leu Val Ser
        50                  55                  60

Asn Ala Asp His Val Tyr Gln His Val Phe Arg Gly Phe Ala Ala Thr
65                  70                  75                  80

Leu Asp Lys Glu Thr Leu Glu Ala Leu Arg Asn His Pro Glu Val Asp
                85                  90                  95

Tyr Ile Glu Gln Asp Ala Val Val Lys Ile Asn Ala Tyr Val Ser Gln
                100                 105                 110

Thr Gly Ala Pro Trp Gly Leu Gly Arg Ile Ser His Lys Ala Arg Gly
            115                 120                 125

Ser Thr Thr Tyr Val Tyr Asp Asp Ser Ala Gly Ala Gly Thr Cys Ser
        130                 135                 140

Tyr Val Ile Asp Thr Gly Val Asp Ala Thr His Pro Asp Phe Glu Gly
145                 150                 155                 160

Arg Ala Thr Leu Leu Arg Ser Phe Val Ser Gly Gln Asn Thr Asp Gly
                165                 170                 175
```

Asn Gly His Gly Thr His Val Ser Gly Thr Ile Ser Arg Thr Tyr
            180                 185                 190

Gly Val Ala Lys Lys Thr Gln Ile Tyr Gly Val Lys Val Leu Asp Asn
            195                 200                 205

Ser Gly Ser Gly Ser Phe Ser Thr Val Ile Ala Gly Met Asp Tyr Val
            210                 215                 220

Ala Ser Asp Ser Gln Thr Arg Asn Cys Pro Asn Gly Ser Val Ala Asn
225                 230                 235                 240

Met Ser Leu Gly Gly Gly Tyr Thr Ala Ser Val Asn Gln Ala Ala Ala
            245                 250                 255

Arg Leu Ile Gln Ala Gly Val Phe Leu Ala Val Ala Ala Gly Asn Asp
            260                 265                 270

Gly Val Asp Ala Arg Asn Thr Ser Pro Ala Ser Glu Pro Thr Val Cys
            275                 280                 285

Thr Val Gly Ala Ser Thr Ser Ser Asp Ala Arg Ala Ser Phe Ser Asn
            290                 295                 300

Tyr Gly Ser Val Val Asp Ile Phe Ala Pro Gly Gln Asp Ile Leu Ser
305                 310                 315                 320

Thr Trp Pro Asn Arg Gln Thr Asn Thr Ile Ser Gly Thr Ser Met Ala
            325                 330                 335

Thr Pro His Ile Val Gly Leu Gly Ala Tyr Leu Ala Gly Leu Glu Gly
            340                 345                 350

Phe Ser Asp Pro Gln Ala Leu Cys Ala Arg Ile Gln Ser Leu Ala Asn
            355                 360                 365

Arg Asn Leu Leu Ser Gly Ile Pro Ser Gly Thr Ile Asn Ala Ile Ala
            370                 375                 380

Phe Asn Gly Asn Pro Ser Gly
385                 390

<210> SEQ ID NO 28
<211> LENGTH: 387
<212> TYPE: PRT
<213> ORGANISM: Trichoderma reesei

<400> SEQUENCE: 28

Met Gly Leu Val Thr Asn Pro Phe Ala Lys Asn Ile Ile Pro Asn Arg
1               5                   10                  15

Tyr Ile Val Val Tyr Asn Asn Ser Phe Gly Glu Glu Ala Ile Ser Ala
            20                  25                  30

Lys Gln Ala Gln Phe Ala Ala Lys Ile Ala Lys Arg Asn Leu Gly Lys
            35                  40                  45

Arg Gly Leu Phe Gly Asn Glu Leu Ser Thr Ala Ile His Ser Phe Ser
        50                  55                  60

Met His Thr Trp Arg Ala Met Ala Leu Asp Ala Asp Ile Met Ile
65                  70                  75                  80

Lys Asp Ile Phe Asp Ala Glu Glu Val Ala Tyr Ile Glu Ala Asp Thr
            85                  90                  95

Lys Val Gln His Ala Ala Leu Val Ala Gln Thr Asn Ala Ala Pro Gly
            100                 105                 110

Leu Ile Arg Leu Ser Asn Lys Ala Val Gly Gly Gln Asn Tyr Ile Phe
            115                 120                 125

Asp Asn Ser Ala Gly Ser Asn Ile Thr Ala Tyr Val Val Asp Thr Gly
        130                 135                 140

Ile Arg Ile Thr His Ser Glu Phe Glu Gly Arg Ala Thr Phe Gly Ala
145                 150                 155                 160

```
Asn Phe Val Asn Asp Asp Thr Asp Glu Asn Gly His Gly Ser His Val
            165                 170                 175
Ala Gly Thr Ile Gly Gly Ala Thr Phe Gly Val Ala Lys Asn Val Glu
        180                 185                 190
Leu Val Ala Val Lys Val Leu Asp Ala Asp Gly Ser Gly Ser Asn Ser
    195                 200                 205
Gly Val Leu Asn Gly Met Gln Phe Val Val Asn Asp Val Gln Ala Lys
210                 215                 220
Lys Arg Ser Gly Lys Ala Val Met Asn Met Ser Leu Gly Gly Ser Phe
225                 230                 235                 240
Ser Thr Ala Val Asn Asn Ala Ile Thr Ala Leu Thr Asn Ala Gly Ile
                245                 250                 255
Val Pro Val Val Ala Gly Asn Glu Asn Gln Asp Thr Ala Asn Thr
            260                 265                 270
Ser Pro Gly Ser Ala Pro Gln Ala Ile Thr Val Gly Ala Ile Asp Ala
        275                 280                 285
Thr Thr Asp Ile Arg Ala Gly Phe Ser Asn Phe Gly Thr Gly Val Asp
    290                 295                 300
Ile Tyr Ala Pro Gly Val Asp Val Leu Ser Val Gly Ile Lys Ser Asp
305                 310                 315                 320
Ile Asp Thr Ala Val Leu Ser Gly Thr Ser Met Ala Ser Pro His Val
                325                 330                 335
Ala Gly Leu Ala Ala Tyr Leu Met Ala Leu Glu Gly Val Ser Asn Val
            340                 345                 350
Asp Asp Val Ser Asn Leu Ile Lys Asn Leu Ala Ala Lys Thr Gly Ala
        355                 360                 365
Ala Val Lys Gln Asn Ile Ala Gly Thr Thr Ser Leu Ile Ala Asn Asn
    370                 375                 380
Gly Asn Phe
385

<210> SEQ ID NO 29
<211> LENGTH: 409
<212> TYPE: PRT
<213> ORGANISM: Trichoderma reesei

<400> SEQUENCE: 29

Met Ala Ser Leu Arg Arg Leu Ala Leu Tyr Leu Gly Ala Leu Leu Pro
1               5                   10                  15
Ala Val Leu Ala Ala Pro Ala Val Asn Tyr Lys Leu Pro Glu Ala Val
            20                  25                  30
Pro Asn Lys Phe Ile Val Thr Leu Lys Asp Gly Ala Ser Val Asp Thr
        35                  40                  45
Asp Ser His Leu Thr Trp Val Lys Asp Leu His Arg Arg Ser Leu Gly
    50                  55                  60
Lys Arg Ser Thr Ala Gly Val Glu Lys Thr Tyr Asn Ile Asp Ser Trp
65                  70                  75                  80
Asn Ala Tyr Ala Gly Glu Phe Asp Glu Glu Thr Val Lys Gln Ile Lys
                85                  90                  95
Ala Asn Pro Asp Val Ala Ser Val Glu Pro Asp Tyr Ile Met Trp Leu
            100                 105                 110
Ser Asp Ile Val Glu Asp Lys Arg Ala Leu Thr Thr Gln Thr Gly Ala
        115                 120                 125
Pro Trp Gly Leu Gly Thr Val Ser His Arg Thr Pro Gly Ser Thr Ser
```

```
              130                 135                 140
Tyr Ile Tyr Asp Thr Ser Ala Gly Ser Gly Thr Phe Ala Tyr Val Val
145                 150                 155                 160

Asp Ser Gly Ile Asn Ile Ala His Gln Gln Phe Gly Gly Arg Ala Ser
                165                 170                 175

Leu Gly Tyr Asn Ala Ala Gly Gly Asp His Val Asp Thr Leu Gly His
                180                 185                 190

Gly Thr His Val Ser Gly Thr Ile Gly Gly Ser Thr Tyr Gly Val Ala
                195                 200                 205

Lys Gln Ala Ser Leu Ile Ser Val Lys Val Phe Gln Gly Asn Ser Ala
                210                 215                 220

Ser Thr Ser Val Ile Leu Asp Gly Tyr Asn Trp Ala Val Asn Asp Ile
225                 230                 235                 240

Val Ser Arg Asn Arg Ala Ser Lys Ser Ala Ile Asn Met Ser Leu Gly
                245                 250                 255

Gly Pro Ala Ser Ser Thr Trp Ala Thr Ala Ile Asn Ala Ala Phe Asn
                260                 265                 270

Lys Gly Val Leu Thr Ile Val Ala Ala Gly Asn Gly Asp Ala Leu Gly
                275                 280                 285

Asn Pro Gln Pro Val Ser Ser Thr Ser Pro Ala Asn Val Pro Asn Ala
                290                 295                 300

Ile Thr Val Ala Ala Leu Asp Ile Asn Trp Arg Thr Ala Ser Phe Thr
305                 310                 315                 320

Asn Tyr Gly Ala Gly Val Asp Val Phe Ala Pro Gly Val Asn Ile Leu
                325                 330                 335

Ser Ser Trp Ile Gly Ser Asn Thr Ala Thr Asn Thr Ile Ser Gly Thr
                340                 345                 350

Ser Met Ala Thr Pro His Val Val Gly Leu Ala Leu Tyr Leu Gln Ala
                355                 360                 365

Leu Glu Gly Leu Ser Thr Pro Thr Ala Val Thr Asn Arg Ile Lys Ala
                370                 375                 380

Leu Ala Thr Thr Gly Arg Val Thr Gly Ser Leu Asn Gly Ser Pro Asn
385                 390                 395                 400

Thr Leu Ile Phe Asn Gly Asn Ser Ala
                405

<210> SEQ ID NO 30
<211> LENGTH: 555
<212> TYPE: PRT
<213> ORGANISM: Trichoderma reesei

<400> SEQUENCE: 30

Met Arg Ala Cys Leu Leu Phe Leu Gly Ile Thr Ala Leu Ala Thr Ala
1               5                   10                  15

Ile Pro Ala Leu Lys Pro Pro His Gly Ser Pro Asp Arg Ala His Thr
                20                  25                  30

Thr Gln Leu Ala Lys Val Ser Ile Ala Leu Gln Pro Glu Cys Arg Glu
                35                  40                  45

Leu Leu Glu Gln Ala Leu His His Leu Ser Asp Pro Ser Ser Pro Arg
                50                  55                  60

Tyr Gly Arg Tyr Leu Gly Arg Glu Glu Ala Lys Ala Leu Leu Arg Pro
65                  70                  75                  80

Arg Arg Glu Ala Thr Ala Ala Val Lys Arg Trp Leu Ala Arg Ala Gly
                85                  90                  95
```

```
Val Pro Ala His Asp Val Leu Thr Asp Gly Gln Phe Ile His Val Arg
            100                 105                 110

Thr Leu Ala Glu Lys Ala Gln Ala Leu Leu Gly Phe Glu Tyr Asn Ser
        115                 120                 125

Thr Leu Gly Ser Gln Thr Ile Ala Ile Ser Thr Leu Pro Gly Lys Ile
    130                 135                 140

Arg Lys His Val Met Thr Val Gln Tyr Val Pro Leu Trp Thr Glu Ala
145                 150                 155                 160

Asp Trp Glu Glu Cys Lys Thr Ile Ile Thr Pro Ser Cys Leu Lys Arg
                165                 170                 175

Leu Tyr His Val Asp Ser Tyr Arg Ala Lys Tyr Glu Ser Ser Ser Leu
            180                 185                 190

Phe Gly Ile Val Gly Phe Ser Gly Gln Ala Ala Gln His Asp Glu Leu
        195                 200                 205

Asp Lys Phe Leu His Asp Phe Ala Pro Tyr Ser Thr Asn Ala Asn Phe
    210                 215                 220

Ser Ile Glu Ser Val Asn Gly Gly Gln Ser Pro Gln Gly Met Asn Glu
225                 230                 235                 240

Pro Ala Ser Glu Ala Asn Gly Asp Val Gln Tyr Ala Val Ala Met Gly
                245                 250                 255

Tyr His Val Pro Val Arg Tyr Tyr Ala Val Gly Gly Glu Asn His Asp
            260                 265                 270

Ile Ile Pro Asp Leu Asp Leu Val Asp Thr Thr Glu Tyr Leu Glu
        275                 280                 285

Pro Phe Leu Glu Phe Ala Ser His Leu Leu Asp Leu Asp Asp Glu
    290                 295                 300

Leu Pro Arg Val Val Ser Ile Ser Tyr Gly Ala Asn Glu Gln Leu Phe
305                 310                 315                 320

Pro Arg Ser Tyr Ala His Gln Val Cys Asp Met Phe Gly Gln Leu Gly
                325                 330                 335

Ala Arg Gly Val Ser Ile Val Val Ala Ala Gly Asp Leu Gly Pro Gly
            340                 345                 350

Val Ser Cys Gln Ser Asn Asp Gly Ser Ala Arg Pro Lys Phe Ile Pro
        355                 360                 365

Ser Phe Pro Ala Thr Cys Pro Tyr Val Thr Ser Val Gly Ser Thr Arg
    370                 375                 380

Gly Ile Met Pro Glu Val Ala Ala Ser Phe Ser Ser Gly Gly Phe Ser
385                 390                 395                 400

Asp Tyr Phe Ala Arg Pro Ala Trp Gln Asp Arg Ala Val Gly Ala Tyr
                405                 410                 415

Leu Gly Ala His Gly Glu Glu Trp Glu Gly Phe Tyr Asn Pro Ala Gly
            420                 425                 430

Arg Gly Phe Pro Asp Val Ala Ala Gln Gly Val Asn Phe Arg Phe Arg
        435                 440                 445

Ala His Gly Asn Glu Ser Leu Ser Ser Gly Thr Ser Leu Ser Ser Pro
    450                 455                 460

Val Phe Ala Ala Leu Ile Ala Leu Leu Asn Asp His Arg Ser Lys Ser
465                 470                 475                 480

Gly Met Pro Pro Met Gly Phe Leu Asn Pro Trp Ile Tyr Thr Val Gly
                485                 490                 495

Ser His Ala Phe Thr Asp Ile Ile Glu Ala Arg Ser Glu Gly Cys Pro
            500                 505                 510

Gly Gln Ser Val Glu Tyr Leu Ala Ser Pro Tyr Ile Pro Asn Ala Gly
```

-continued

```
            515                 520                 525
Trp Ser Ala Val Pro Gly Trp Asp Pro Val Thr Gly Trp Gly Thr Pro
    530                 535                 540

Leu Phe Asp Arg Met Leu Asn Leu Ser Leu Val
545                 550                 555

<210> SEQ ID NO 31
<211> LENGTH: 388
<212> TYPE: PRT
<213> ORGANISM: Trichoderma reesei

<400> SEQUENCE: 31

Met Ala Trp Leu Lys Lys Leu Ala Leu Val Leu Leu Ala Ile Val Pro
1               5                   10                  15

Tyr Ala Thr Ala Ser Pro Ala Leu Ser Pro Arg Ser Arg Glu Ile Leu
                20                  25                  30

Ser Leu Glu Asp Leu Glu Ser Glu Asp Lys Tyr Val Ile Gly Leu Lys
            35                  40                  45

Gln Gly Leu Ser Pro Thr Asp Leu Lys Lys His Leu Leu Arg Val Ser
        50                  55                  60

Ala Val Gln Tyr Arg Asn Lys Asn Ser Thr Phe Glu Gly Gly Thr Gly
65                  70                  75                  80

Val Lys Arg Thr Tyr Ala Ile Gly Asp Tyr Arg Ala Tyr Thr Ala Val
                85                  90                  95

Leu Asp Arg Asp Thr Val Arg Glu Ile Trp Asn Asp Thr Leu Glu Lys
            100                 105                 110

Pro Pro Trp Gly Leu Ala Thr Leu Ser Asn Lys Lys Pro His Gly Phe
        115                 120                 125

Leu Tyr Arg Tyr Asp Lys Ser Ala Gly Glu Gly Thr Phe Ala Tyr Val
    130                 135                 140

Leu Asp Thr Gly Ile Asn Ser Lys His Val Asp Phe Glu Gly Arg Ala
145                 150                 155                 160

Tyr Met Gly Phe Ser Pro Pro Lys Thr Glu Pro Thr Asp Ile Asn Gly
                165                 170                 175

His Gly Thr His Val Ala Gly Ile Ile Gly Lys Thr Phe Gly Val
            180                 185                 190

Ala Lys Lys Thr Gln Leu Ile Gly Val Lys Val Phe Leu Asp Asp Glu
        195                 200                 205

Ala Thr Thr Ser Thr Leu Met Glu Gly Leu Glu Trp Ala Val Asn Asp
    210                 215                 220

Ile Thr Thr Lys Gly Arg Gln Gly Arg Ser Val Ile Asn Met Ser Leu
225                 230                 235                 240

Gly Gly Pro Tyr Ser Gln Ala Leu Asn Asp Ala Ile Asp His Ile Ala
                245                 250                 255

Asp Met Gly Ile Leu Pro Val Ala Ala Ala Gly Asn Lys Gly Ile Pro
            260                 265                 270

Ala Thr Phe Ile Ser Pro Ala Ser Ala Asp Lys Ala Met Thr Val Gly
        275                 280                 285

Ala Ile Asn Ser Asp Trp Gln Glu Thr Asn Phe Ser Asn Phe Gly Pro
    290                 295                 300

Gln Val Asn Ile Leu Ala Pro Gly Glu Asp Val Leu Ser Ala Tyr Val
305                 310                 315                 320

Ser Thr Asn Thr Ala Thr Arg Val Leu Ser Gly Thr Ser Met Ala Ala
                325                 330                 335
```

```
Pro His Val Ala Gly Leu Ala Leu Tyr Leu Met Ala Leu Glu Phe
            340                 345                 350

Asp Ser Thr Gln Lys Leu Thr Asp Arg Ile Leu Gln Leu Gly Met Lys
        355                 360                 365

Asn Lys Val Val Asn Leu Met Thr Asp Ser Pro Asn Leu Ile Ile His
    370                 375                 380

Asn Asn Val Lys
385

<210> SEQ ID NO 32
<211> LENGTH: 256
<212> TYPE: PRT
<213> ORGANISM: Trichoderma reesei

<400> SEQUENCE: 32

Met Phe Ile Ala Gly Val Ala Leu Ser Ala Leu Leu Cys Ala Asp Thr
1               5                   10                  15

Val Leu Ala Gly Val Ala Gln Asp Arg Gly Leu Ala Ala Arg Leu Ala
            20                  25                  30

Arg Arg Ala Gly Arg Arg Ser Ala Pro Phe Arg Asn Asp Thr Ser His
        35                  40                  45

Ala Thr Val Gln Ser Asn Trp Gly Gly Ala Ile Leu Glu Gly Ser Gly
    50                  55                  60

Phe Thr Ala Ala Ser Ala Thr Val Asn Val Pro Arg Gly Gly Gly
65                  70                  75                  80

Ser Asn Ala Ala Gly Ser Ala Trp Val Gly Ile Asp Gly Ala Ser Cys
                85                  90                  95

Gln Thr Ala Ile Leu Gln Thr Gly Phe Asp Trp Tyr Gly Asp Gly Thr
            100                 105                 110

Tyr Asp Ala Trp Tyr Glu Trp Tyr Pro Glu Phe Ala Ala Asp Phe Ser
        115                 120                 125

Gly Ile Asp Ile Arg Gln Gly Asp Gln Ile Ala Met Ser Val Val Ala
    130                 135                 140

Thr Ser Leu Thr Gly Gly Ser Ala Thr Leu Glu Asn Leu Ser Thr Gly
145                 150                 155                 160

Gln Lys Val Thr Gln Asn Phe Asn Arg Val Thr Ala Gly Ser Leu Cys
                165                 170                 175

Glu Thr Ser Ala Glu Phe Ile Ile Glu Asp Phe Glu Gly Cys Asn Ser
            180                 185                 190

Asn Gly Ser Asn Cys Gln Pro Val Pro Phe Ala Ser Phe Ser Pro Ala
        195                 200                 205

Ile Thr Phe Ser Ser Ala Thr Ala Thr Arg Ser Gly Arg Ser Val Ser
    210                 215                 220

Leu Ser Gly Ala Glu Ile Thr Glu Val Ile Val Asn Asn Gln Asp Leu
225                 230                 235                 240

Thr Arg Cys Ser Val Ser Gly Ser Ser Thr Leu Thr Cys Ser Tyr Val
                245                 250                 255

<210> SEQ ID NO 33
<211> LENGTH: 236
<212> TYPE: PRT
<213> ORGANISM: Trichoderma reesei

<400> SEQUENCE: 33

Met Asp Ala Ile Arg Ala Arg Ser Ala Ala Arg Arg Ser Asn Arg Phe
1               5                   10                  15
```

-continued

Gln Ala Gly Ser Ser Lys Asn Val Asn Gly Thr Ala Asp Val Glu Ser
              20                  25                  30

Thr Asn Trp Ala Gly Ala Ala Ile Thr Thr Ser Gly Val Thr Glu Val
         35                  40                  45

Ser Gly Thr Phe Thr Val Pro Arg Pro Ser Val Pro Ala Gly Gly Ser
     50                  55                  60

Ser Arg Glu Glu Tyr Cys Gly Ala Ala Trp Val Gly Ile Asp Gly Tyr
65                  70                  75                  80

Ser Asp Ala Asp Leu Ile Gln Thr Gly Val Leu Trp Cys Val Glu Asp
                 85                  90                  95

Gly Glu Tyr Leu Tyr Glu Ala Trp Tyr Glu Tyr Leu Pro Ala Ala Leu
            100                 105                 110

Val Glu Tyr Ser Gly Ile Ser Val Thr Ala Gly Ser Val Val Thr Val
        115                 120                 125

Thr Ala Thr Lys Thr Gly Thr Asn Ser Gly Val Thr Thr Leu Thr Ser
    130                 135                 140

Gly Gly Lys Thr Val Ser His Thr Phe Ser Arg Gln Asn Ser Pro Leu
145                 150                 155                 160

Pro Gly Thr Ser Ala Glu Trp Ile Val Glu Asp Phe Thr Ser Gly Ser
                165                 170                 175

Ser Leu Val Pro Phe Ala Asp Phe Gly Ser Val Thr Phe Thr Gly Ala
            180                 185                 190

Thr Ala Val Val Asn Gly Ala Thr Val Thr Ala Gly Gly Asp Ser Pro
        195                 200                 205

Val Ile Ile Asp Leu Glu Asp Ser Arg Gly Asp Ile Leu Thr Ser Thr
    210                 215                 220

Thr Val Ser Gly Ser Thr Val Thr Val Glu Tyr Glu
225                 230                 235

<210> SEQ ID NO 34
<211> LENGTH: 612
<212> TYPE: PRT
<213> ORGANISM: Trichoderma reesei

<400> SEQUENCE: 34

Met Ala Lys Leu Ser Thr Leu Arg Leu Ala Ser Leu Ser Leu Val
1               5                   10                  15

Ser Val Gln Val Ser Ala Ser Val His Leu Leu Glu Ser Leu Glu Lys
                20                  25                  30

Leu Pro His Gly Trp Lys Ala Ala Glu Thr Pro Ser Pro Ser Ser Gln
            35                  40                  45

Ile Val Leu Gln Val Ala Leu Thr Gln Gln Asn Ile Asp Gln Leu Glu
        50                  55                  60

Ser Arg Leu Ala Ala Val Ser Thr Pro Thr Ser Ser Thr Tyr Gly Lys
65                  70                  75                  80

Tyr Leu Asp Val Asp Glu Ile Asn Ser Ile Phe Ala Pro Ser Asp Ala
                 85                  90                  95

Ser Ser Ser Ala Val Glu Ser Trp Leu Gln Ser His Gly Val Thr Ser
            100                 105                 110

Tyr Thr Lys Gln Gly Ser Ser Ile Trp Phe Gln Thr Asn Ile Ser Thr
        115                 120                 125

Ala Asn Ala Met Leu Ser Thr Asn Phe His Thr Tyr Ser Asp Leu Thr
    130                 135                 140

Gly Ala Lys Lys Val Arg Thr Leu Lys Tyr Ser Ile Pro Glu Ser Leu
145                 150                 155                 160

```
Ile Gly His Val Asp Leu Ile Ser Pro Thr Thr Tyr Phe Gly Thr Thr
                165                 170                 175
Lys Ala Met Arg Lys Leu Lys Ser Ser Gly Val Ser Pro Ala Ala Asp
                180                 185                 190
Ala Leu Ala Ala Arg Gln Glu Pro Ser Ser Cys Lys Gly Thr Leu Val
                195                 200                 205
Phe Glu Gly Glu Thr Phe Asn Val Phe Gln Pro Asp Cys Leu Arg Thr
                210                 215                 220
Glu Tyr Ser Val Asp Gly Tyr Thr Pro Ser Val Lys Ser Gly Ser Arg
225                 230                 235                 240
Ile Gly Phe Gly Ser Phe Leu Asn Glu Ser Ala Ser Phe Ala Asp Gln
                245                 250                 255
Ala Leu Phe Glu Lys His Phe Asn Ile Pro Ser Gln Asn Phe Ser Val
                260                 265                 270
Val Leu Ile Asn Gly Gly Thr Asp Leu Pro Gln Pro Pro Ser Asp Ala
                275                 280                 285
Asn Asp Gly Glu Ala Asn Leu Asp Ala Gln Thr Ile Leu Thr Ile Ala
                290                 295                 300
His Pro Leu Pro Ile Thr Glu Phe Ile Thr Ala Gly Ser Pro Pro Tyr
305                 310                 315                 320
Phe Pro Asp Pro Val Glu Pro Ala Gly Thr Pro Asn Glu Asn Glu Pro
                325                 330                 335
Tyr Leu Gln Tyr Tyr Glu Phe Leu Leu Ser Lys Ser Asn Ala Glu Ile
                340                 345                 350
Pro Gln Val Ile Thr Asn Ser Tyr Gly Asp Glu Glu Gln Thr Val Pro
                355                 360                 365
Arg Ser Tyr Ala Val Arg Val Cys Asn Leu Ile Gly Leu Leu Gly Leu
370                 375                 380
Arg Gly Ile Ser Val Leu His Ser Ser Gly Asp Glu Gly Val Gly Ala
385                 390                 395                 400
Ser Cys Val Ala Thr Asn Ser Thr Thr Pro Gln Phe Asn Pro Ile Phe
                405                 410                 415
Pro Ala Thr Cys Pro Tyr Val Thr Ser Val Gly Gly Thr Val Ser Phe
                420                 425                 430
Asn Pro Glu Val Ala Trp Ala Gly Ser Ser Gly Gly Phe Ser Tyr Tyr
                435                 440                 445
Phe Ser Arg Pro Trp Tyr Gln Gln Glu Ala Val Gly Thr Tyr Leu Glu
                450                 455                 460
Lys Tyr Val Ser Ala Glu Thr Lys Lys Tyr Tyr Gly Pro Tyr Val Asp
465                 470                 475                 480
Phe Ser Gly Arg Gly Phe Pro Asp Val Ala Ala His Ser Val Ser Pro
                485                 490                 495
Asp Tyr Pro Val Phe Gln Gly Gly Glu Leu Thr Pro Ser Gly Gly Thr
                500                 505                 510
Ser Ala Ala Ser Pro Val Val Ala Ala Ile Val Ala Leu Leu Asn Asp
                515                 520                 525
Ala Arg Leu Arg Glu Gly Lys Pro Thr Leu Gly Phe Leu Asn Pro Leu
                530                 535                 540
Ile Tyr Leu His Ala Ser Lys Gly Phe Thr Asp Ile Thr Ser Gly Gln
545                 550                 555                 560
Ser Glu Gly Cys Asn Gly Asn Asn Thr Gln Thr Gly Ser Pro Leu Pro
                565                 570                 575
```

```
Gly Ala Gly Phe Ile Ala Gly Ala His Trp Asn Ala Thr Lys Gly Trp
            580                 585                 590

Asp Pro Thr Thr Gly Phe Gly Val Pro Asn Leu Lys Lys Leu Leu Ala
        595                 600                 605

Leu Val Arg Phe
    610

<210> SEQ ID NO 35
<211> LENGTH: 57
<212> TYPE: DNA
<213> ORGANISM: Artificial Sequence
<220> FEATURE:
<223> OTHER INFORMATION: primer

<400> SEQUENCE: 35
gtaacgccag ggttttccca gtcacgacgg tttaaactca ggtcaaccac cgaggac        57

<210> SEQ ID NO 36
<211> LENGTH: 70
<212> TYPE: DNA
<213> ORGANISM: Artificial Sequence
<220> FEATURE:
<223> OTHER INFORMATION: primer

<400> SEQUENCE: 36
ttcttcttat tgatttgagc ctgtgtgtag agatacaagg atttaaattg aatgggatgg     60
ttcgattgct                                                            70

<210> SEQ ID NO 37
<211> LENGTH: 88
<212> TYPE: DNA
<213> ORGANISM: Artificial Sequence
<220> FEATURE:
<223> OTHER INFORMATION: primer

<400> SEQUENCE: 37
aagttccctt cctctggcag caatcgaacc atcccattca atttaaatcc ttgtatctct     60
acacacaggc tcaaatcaat aagaagaa                                        88

<210> SEQ ID NO 38
<211> LENGTH: 88
<212> TYPE: DNA
<213> ORGANISM: Artificial Sequence
<220> FEATURE:
<223> OTHER INFORMATION: primer

<400> SEQUENCE: 38
ttcttcttat tgatttgagc ctgtgtgtag agatacaagg atttaaattg aatgggatgg     60
ttcgattgct gccagaggaa gggaactt                                        88

<210> SEQ ID NO 39
<211> LENGTH: 88
<212> TYPE: DNA
<213> ORGANISM: Artificial Sequence
<220> FEATURE:
<223> OTHER INFORMATION: primer

<400> SEQUENCE: 39
aagcgcccac tccacatctc cactcgacct gcaggcatgc ggcgcgccac tgggagctgt     60
gccgagtttg ctggctactt acctagtc                                        88

<210> SEQ ID NO 40
```

```
<211> LENGTH: 88
<212> TYPE: DNA
<213> ORGANISM: Artificial Sequence
<220> FEATURE:
<223> OTHER INFORMATION: Primer

<400> SEQUENCE: 40
gactaggtaa gtagccagca aactcggcac agctcccagt ggcgcgccgc atgcctgcag      60
gtcgagtgga gatgtggagt gggcgctt                                        88

<210> SEQ ID NO 41
<211> LENGTH: 70
<212> TYPE: DNA
<213> ORGANISM: Artificial Sequence
<220> FEATURE:
<223> OTHER INFORMATION: Primer

<400> SEQUENCE: 41
aagcgcccac tccacatctc cactcgacct gcaggcatgc ggcgcgccac tgggagctgt      60
gccgagtttg                                                            70

<210> SEQ ID NO 42
<211> LENGTH: 65
<212> TYPE: DNA
<213> ORGANISM: Artificial Sequence
<220> FEATURE:
<223> OTHER INFORMATION: Primer

<400> SEQUENCE: 42
ccaccagacc agtgccgccc gtgacgagga tggttttcat tttgacggtt tgtgtgatgt      60
agcgt                                                                 65

<210> SEQ ID NO 43
<211> LENGTH: 63
<212> TYPE: DNA
<213> ORGANISM: Artificial Sequence
<220> FEATURE:
<223> OTHER INFORMATION: Primer

<400> SEQUENCE: 43
ccagtggttc gttgacaact acgaaaccgc ccggaagtaa cactctgagc tgaatgcaga      60
agc                                                                   63

<210> SEQ ID NO 44
<211> LENGTH: 27
<212> TYPE: DNA
<213> ORGANISM: Artificial Sequence
<220> FEATURE:
<223> OTHER INFORMATION: Primer

<400> SEQUENCE: 44
tacaataaca cagatctttt atgacgg                                         27

<210> SEQ ID NO 45
<211> LENGTH: 71
<212> TYPE: DNA
<213> ORGANISM: Artificial Sequence
<220> FEATURE:
<223> OTHER INFORMATION: Primer

<400> SEQUENCE: 45
ttgtaatgtt ctaccgtcat aaaagatctg tgttattgta gcgatcgcct agcatcgact      60
actgctgctc t                                                          71
```

<210> SEQ ID NO 46
<211> LENGTH: 58
<212> TYPE: DNA
<213> ORGANISM: Artificial Sequence
<220> FEATURE:
<223> OTHER INFORMATION: Primer

<400> SEQUENCE: 46
gcggataaca atttcacaca ggaaacagcg tttaaacctc caccgaccga tccgttgg        58

<210> SEQ ID NO 47
<211> LENGTH: 59
<212> TYPE: DNA
<213> ORGANISM: Artificial Sequence
<220> FEATURE:
<223> OTHER INFORMATION: Primer

<400> SEQUENCE: 47
gtaacgccag ggttttccca gtcacgacgg tttaaactca agctcatgga cctcaaggc       59

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
ccatgcaaag atacacatca atcg                                             24

<210> SEQ ID NO 49
<211> LENGTH: 63
<212> TYPE: DNA
<213> ORGANISM: Artificial Sequence
<220> FEATURE:
<223> OTHER INFORMATION: Primer

<400> SEQUENCE: 49
gattgtaccc cagctgcgat tgatgtgtat ctttgcatgg ggcatccgta gttgtcgcaa      60
gaa                                                                    63

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
tacaataaca cagatctttt atgacgg                                          27

<210> SEQ ID NO 51
<211> LENGTH: 63
<212> TYPE: DNA
<213> ORGANISM: Artificial Sequence
<220> FEATURE:
<223> OTHER INFORMATION: Primer

<400> SEQUENCE: 51
ttgtaatgtt ctaccgtcat aaaagatctg tgttattgta ggtctgaagg acgtggaatg      60
atg                                                                    63

<210> SEQ ID NO 52

<211> LENGTH: 26
<212> TYPE: DNA
<213> ORGANISM: Artificial Sequence
<220> FEATURE:
<223> OTHER INFORMATION: Primer

<400> SEQUENCE: 52
gttgagagaa gttgttggat tgatca						26

<210> SEQ ID NO 53
<211> LENGTH: 72
<212> TYPE: DNA
<213> ORGANISM: Artificial Sequence
<220> FEATURE:
<223> OTHER INFORMATION: Primer

<400> SEQUENCE: 53
aaccaaagac tttttgatca atccaacaac ttctctcaac ttaattaaat ggcgtcaaca		60 aatgcgcgct at								72

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
gttcattcga gggccggga							19

<210> SEQ ID NO 55
<211> LENGTH: 63
<212> TYPE: DNA
<213> ORGANISM: Artificial Sequence
<220> FEATURE:
<223> OTHER INFORMATION: Primer

<400> SEQUENCE: 55
caacgacctc gtcggcatcg ctcccggccc tcgaatgaac gacaacgacc accctgatca		60 ttc									63

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
ttacttctcg gcctcggggt ag						22

<210> SEQ ID NO 57
<211> LENGTH: 71
<212> TYPE: DNA
<213> ORGANISM: Artificial Sequence
<220> FEATURE:
<223> OTHER INFORMATION: Primer

<400> SEQUENCE: 57
gactgttaag tacccgacct accccgaggc cgagaagtaa ggccggccgg ctttcgtgac		60 cgggcttcaa a								71

<210> SEQ ID NO 58
<211> LENGTH: 24

-continued

<212> TYPE: DNA
<213> ORGANISM: Artificial Sequence
<220> FEATURE:
<223> OTHER INFORMATION: Primer

<400> SEQUENCE: 58
gtatcagtca gcgagcaagc catt                                            24

<210> SEQ ID NO 59
<211> LENGTH: 70
<212> TYPE: DNA
<213> ORGANISM: Artificial Sequence
<220> FEATURE:
<223> OTHER INFORMATION: Primer

<400> SEQUENCE: 59
atgatgcctt tgcagaaatg gcttgctcgc tgactgatac gcgatcgcag gtagacgctt     60
tgcgagtgtg                                                            70

<210> SEQ ID NO 60
<211> LENGTH: 55
<212> TYPE: DNA
<213> ORGANISM: Artificial Sequence
<220> FEATURE:
<223> OTHER INFORMATION: Primer

<400> SEQUENCE: 60
gcggataaca atttcacaca ggaaacagcg tttaaactga actgacgcgg actga          55

<210> SEQ ID NO 61
<211> LENGTH: 67
<212> TYPE: DNA
<213> ORGANISM: Artificial Sequence
<220> FEATURE:
<223> OTHER INFORMATION: Primer

<400> SEQUENCE: 61
gcctttgcag aaatggcttg ctcgctgact gatacgcgat cgcttggtgc tcgtattagt     60
gccaatg                                                               67

<210> SEQ ID NO 62
<211> LENGTH: 69
<212> TYPE: DNA
<213> ORGANISM: Artificial Sequence
<220> FEATURE:
<223> OTHER INFORMATION: Primer

<400> SEQUENCE: 62
cctcgaacag ggccttgttg ttttcctcgt ggagcttcat atttaaatct tggcggtatt     60
gcggctcgg                                                             69

<210> SEQ ID NO 63
<211> LENGTH: 72
<212> TYPE: DNA
<213> ORGANISM: Artificial Sequence
<220> FEATURE:
<223> OTHER INFORMATION: Primer

<400> SEQUENCE: 63
cctgggcaga gatggtaacg ccgccgagga atccgtttaa ggcgcgccgt tctgttgatg     60
ttgacttgga gt                                                         72

<210> SEQ ID NO 64

```
<211> LENGTH: 66
<212> TYPE: DNA
<213> ORGANISM: Artificial Sequence
<220> FEATURE:
<223> OTHER INFORMATION: Primer

<400> SEQUENCE: 64
cttcttagat acacacacac tcgcaaagcg tctacctgcg atcgctgggg gcggatagag     60
gagcag                                                               66

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
ggcgaaaggg ggatgtgctg                                                20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
cccaggcttt acactttatg                                                20

<210> SEQ ID NO 67
<211> LENGTH: 19
<212> TYPE: DNA
<213> ORGANISM: Artificial Sequence
<220> FEATURE:
<223> OTHER INFORMATION: Primer

<400> SEQUENCE: 67
tagcatcgac tactgctgc                                                 19

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
cagcctctct cagcctcatc                                                20

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
gccaaagcac ccaagtacc                                                 19

<210> SEQ ID NO 70
<211> LENGTH: 20
<212> TYPE: DNA
<213> ORGANISM: Artificial Sequence
<220> FEATURE:
<223> OTHER INFORMATION: Primer
```

<400> SEQUENCE: 70
gacgagcccg acattaaagc                                              20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
gcacggcttc ctcatcttcg                                              20

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
gaagtaatct ctgcagatct ttcg                                         24

<210> SEQ ID NO 73
<211> LENGTH: 19
<212> TYPE: DNA
<213> ORGANISM: Artificial Sequence
<220> FEATURE:
<223> OTHER INFORMATION: Primer

<400> SEQUENCE: 73
atttgctttc caggctgag                                               19

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
ccctacaacg accatcaaag tc                                           22

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
gagaatatgg agcttcatcg a                                            21

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76
cagtatattc atcttcccat cc                                           22

<210> SEQ ID NO 77

<210> SEQ ID NO 77
<211> LENGTH: 17
<212> TYPE: DNA
<213> ORGANISM: Artificial Sequence
<220> FEATURE:
<223> OTHER INFORMATION: Primer

<400> SEQUENCE: 77
ttctccctcc actacgg                                                  17

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
cgagtacgtc gaggctatgt g                                             21

<210> SEQ ID NO 79
<211> LENGTH: 17
<212> TYPE: DNA
<213> ORGANISM: Artificial Sequence
<220> FEATURE:
<223> OTHER INFORMATION: Primer

<400> SEQUENCE: 79
caagcagcaa agagtgc                                                  17

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
tttacaactc tcctatgagt cg                                            22

<210> SEQ ID NO 81
<211> LENGTH: 17
<212> TYPE: DNA
<213> ORGANISM: Artificial Sequence
<220> FEATURE:
<223> OTHER INFORMATION: Primer

<400> SEQUENCE: 81
caatcggaag ggtgtcg                                                  17

<210> SEQ ID NO 82
<211> LENGTH: 17
<212> TYPE: DNA
<213> ORGANISM: Artificial Sequence
<220> FEATURE:
<223> OTHER INFORMATION: Primer

<400> SEQUENCE: 82
agccactggc acttgca                                                  17

<210> SEQ ID NO 83
<211> LENGTH: 17
<212> TYPE: DNA
<213> ORGANISM: Artificial Sequence
<220> FEATURE:
<223> OTHER INFORMATION: Primer

<400> SEQUENCE: 83
ccggtgaagt cgattgc                                          17

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
cagtgcgaga acgttgtc                                         18

<210> SEQ ID NO 85
<211> LENGTH: 17
<212> TYPE: DNA
<213> ORGANISM: Artificial Sequence
<220> FEATURE:
<223> OTHER INFORMATION: Primer

<400> SEQUENCE: 85
ggcctcttcc acaacct                                          17

<210> SEQ ID NO 86
<211> LENGTH: 17
<212> TYPE: DNA
<213> ORGANISM: Artificial Sequence
<220> FEATURE:
<223> OTHER INFORMATION: Primer

<400> SEQUENCE: 86
ctcagcgtga acgagtc                                          17

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
tgtaactcag gttaattgtt gggc                                  24

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
tgaaggacgt ggaatgatgg                                       20

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
aaacaagcaa ccttgaacc                                        19

<210> SEQ ID NO 90
<211> LENGTH: 21
<212> TYPE: DNA

```
<213> ORGANISM: Artificial Sequence
<220> FEATURE:
<223> OTHER INFORMATION: Primer

<400> SEQUENCE: 90
acacagataa accaccaact c                                                    21

<210> SEQ ID NO 91
<211> LENGTH: 17
<212> TYPE: DNA
<213> ORGANISM: Artificial Sequence
<220> FEATURE:
<223> OTHER INFORMATION: Primer

<400> SEQUENCE: 91
cgattgacca aggccca                                                         17

<210> SEQ ID NO 92
<211> LENGTH: 17
<212> TYPE: DNA
<213> ORGANISM: Artificial Sequence
<220> FEATURE:
<223> OTHER INFORMATION: Primer

<400> SEQUENCE: 92
acgctgatct tggagtc                                                         17

<210> SEQ ID NO 93
<211> LENGTH: 17
<212> TYPE: DNA
<213> ORGANISM: Artificial Sequence
<220> FEATURE:
<223> OTHER INFORMATION: Primer

<400> SEQUENCE: 93
cctcgctgct caaagag                                                         17

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
ccgggcttca acaatgatg tg                                                    22

<210> SEQ ID NO 95
<211> LENGTH: 17
<212> TYPE: DNA
<213> ORGANISM: Artificial Sequence
<220> FEATURE:
<223> OTHER INFORMATION: Primer

<400> SEQUENCE: 95
ggagcatgag cctatgg                                                         17

<210> SEQ ID NO 96
<211> LENGTH: 22
<212> TYPE: DNA
<213> ORGANISM: Artificial Sequence
<220> FEATURE:
<223> OTHER INFORMATION: Primer

<400> SEQUENCE: 96
ctgaggacgg gcaattcaag tc                                                   22
```

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
cacatcaacc gttgacaagg                                               20

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
tttcttcctc ctacaccac                                                19

<210> SEQ ID NO 99
<211> LENGTH: 19
<212> TYPE: DNA
<213> ORGANISM: Artificial Sequence
<220> FEATURE:
<223> OTHER INFORMATION: Primer

<400> SEQUENCE: 99
acgtcgtctg cacctacct                                                19

<210> SEQ ID NO 100
<211> LENGTH: 17
<212> TYPE: DNA
<213> ORGANISM: Artificial Sequence
<220> FEATURE:
<223> OTHER INFORMATION: Primer

<400> SEQUENCE: 100
ctgttgtggt ggacgtc                                                  17

<210> SEQ ID NO 101
<211> LENGTH: 17
<212> TYPE: DNA
<213> ORGANISM: Artificial Sequence
<220> FEATURE:
<223> OTHER INFORMATION: Primer

<400> SEQUENCE: 101
ctgcgaggtc aagacgt                                                  17

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
cagggccagc agtacaacac                                               20

<210> SEQ ID NO 103
<211> LENGTH: 20
<212> TYPE: DNA
<213> ORGANISM: Artificial Sequence
<220> FEATURE:

<223> OTHER INFORMATION: Primer

<400> SEQUENCE: 103
gattcatcac aggggcagtc				20

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
gagcaggctc gacgtatttc				20

<210> SEQ ID NO 105
<211> LENGTH: 17
<212> TYPE: DNA
<213> ORGANISM: Artificial Sequence
<220> FEATURE:
<223> OTHER INFORMATION: Primer

<400> SEQUENCE: 105
ggagcatgag cctatgg				17

<210> SEQ ID NO 106
<211> LENGTH: 19
<212> TYPE: DNA
<213> ORGANISM: Artificial Sequence
<220> FEATURE:
<223> OTHER INFORMATION: Primer

<400> SEQUENCE: 106
acgccgttgc tgagccttg				19

<210> SEQ ID NO 107
<211> LENGTH: 17
<212> TYPE: DNA
<213> ORGANISM: Artificial Sequence
<220> FEATURE:
<223> OTHER INFORMATION: Primer

<400> SEQUENCE: 107
ctgttgtggt ggacgtc				17

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
gagcccatca tcaacacctc				20

<210> SEQ ID NO 109
<211> LENGTH: 19
<212> TYPE: DNA
<213> ORGANISM: Artificial Sequence
<220> FEATURE:
<223> OTHER INFORMATION: Primer

<400> SEQUENCE: 109
tgccaaggtc gtagacgga				19

-continued

```
<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
aagatcgccc tcattaccgg cgt                                               23

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
tccgaagggt atatccgccg t                                                 21

<210> SEQ ID NO 112
<211> LENGTH: 320
<212> TYPE: PRT
<213> ORGANISM: Ascaris suum

<400> SEQUENCE: 112

Met Ala Ser Glu Lys Gln Met Ile Val Leu Val Thr Gly Gly Thr Gly
1               5                   10                  15

Leu Val Gly Lys Ala Ile Glu Lys Ile Val Lys Thr Glu Glu Ser Arg
            20                  25                  30

Pro Asn Glu Arg Trp Ile Phe Ile Gly Ser Lys Asp Cys Asp Leu Ser
        35                  40                  45

Asp Leu Glu Ala Thr Arg Lys Leu Phe Ala Lys His Lys Pro Thr His
    50                  55                  60

Val Ile His Leu Ala Ala Met Val Gly Gly Leu Phe His Asn Leu Gln
65                  70                  75                  80

His Asn Leu Gln Phe Phe Arg Lys Asn Met Gln Ile Asn Asp Asn Val
                85                  90                  95

Leu Ala Val Cys Asp Glu Asn Asp Ile Glu Lys Cys Val Ser Cys Leu
            100                 105                 110

Ser Thr Cys Ile Phe Pro Asp Lys Thr Thr Tyr Pro Ile Asp Glu Thr
        115                 120                 125

Met Val His Asn Gly Pro Pro His Asp Ser Asn Phe Gly Tyr Ser Tyr
    130                 135                 140

Ala Lys Arg Met Ile Asp Val Leu Asn Arg Gly Tyr Ala Gln Glu Arg
145                 150                 155                 160

Gly Arg Lys Tyr Thr Ser Val Val Pro Cys Asn Val Phe Gly Pro Tyr
                165                 170                 175

Asp Asn Tyr Asn Leu Glu Tyr Gly His Val Ile Pro Ala Leu Ile His
            180                 185                 190

Lys Thr Phe Ile Ala Lys Arg Asp Gly Lys Pro Leu Glu Val Phe Gly
        195                 200                 205

Ser Gly Ala Pro Leu Arg Gln Phe Ile Tyr Ser Leu Asp Leu Ala Arg
    210                 215                 220

Leu Phe Val Trp Val Leu Arg Asn Tyr Glu Glu Ile Glu Pro Ile Ile
225                 230                 235                 240

Leu Ser Val Gly Glu Glu Asp Glu Val Ser Ile Met Asp Ala Val Asn
                245                 250                 255
```

-continued

```
Ala Ile Val Lys Ala Phe Asp Phe Lys Gly Gly Ile Val Gln Asp Lys
            260                 265                 270

Ser Lys Ala Asp Gly Gln Tyr Lys Lys Thr Ala Ser Asn Ala Lys Leu
        275                 280                 285

Arg Lys Tyr Leu Pro Asp Phe Lys Phe Thr Pro Phe Asp Val Ala Ile
    290                 295                 300

Lys Glu Ser Val Asp Trp Phe Val Ala Asn Tyr Glu Asp Ala Arg Lys
305                 310                 315                 320

<210> SEQ ID NO 113
<211> LENGTH: 483
<212> TYPE: PRT
<213> ORGANISM: Brugia malayi

<400> SEQUENCE: 113

Met Ala Ser Ser Ser Arg Arg Leu Lys Lys Glu Leu Thr Asp Ile Gln
1               5                   10                  15

Ser Ser Asp Ser Arg Thr Phe Cys Cys Val Glu Phe Asp Glu Asn Asn
            20                  25                  30

Leu Leu His Trp Thr Gly Leu Leu Val Pro Asp Lys Glu Pro Tyr Asn
        35                  40                  45

Lys Gly Ala Phe Lys Val Ala Ile Asp Phe Pro Val Glu Tyr Pro Phe
    50                  55                  60

Lys Pro Pro Lys Ile Thr Phe Leu Thr Lys Ile Tyr His Pro Asn Val
65                  70                  75                  80

Asp Glu Lys Gly Gln Val Cys Leu Pro Ile Ile Ser Pro Asp Asn Trp
                85                  90                  95

Lys Pro Ala Thr Lys Thr Glu Gln Val Met Asn Ala Leu Leu Gly Leu
            100                 105                 110

Ile Thr Glu Pro Glu Pro Asp His Pro Leu Arg Ala Asp Leu Ala Glu
        115                 120                 125

Glu Phe Thr Lys Asp Arg Lys Lys Phe Asn Lys Thr Ala Glu Asp Tyr
    130                 135                 140

Thr Lys Lys Tyr Ala Val Lys Arg Pro Asp Gly Trp Phe Glu Thr Arg
145                 150                 155                 160

His Lys Ile Met Asp Arg Glu Gln Ser Met Thr Val Leu Val Thr Gly
                165                 170                 175

Gly Thr Gly Leu Val Gly Arg Ser Ile Glu Lys Ile Ile Thr Thr Glu
            180                 185                 190

Glu Ala Arg Pro Asn Glu Thr Trp Ile Phe Val Gly Arg Asn Asp Cys
        195                 200                 205

Asp Leu Thr Asp Ile Glu Ala Thr Arg Lys Leu Phe Met Lys Cys Arg
    210                 215                 220

Pro Ser His Val Ile His Leu Ala Ala Met Val Gly Gly Leu Phe His
225                 230                 235                 240

Asn Leu His Cys Asn Leu Gln Phe Phe Arg Lys Asn Met Gln Ile Asn
                245                 250                 255

Asp Asn Val Leu Met Ala Cys Asn Glu Phe Asp Val Val Lys Cys Ile
            260                 265                 270

Ser Cys Leu Ser Thr Cys Val Phe Pro Asp Lys Thr Thr Tyr Pro Ile
        275                 280                 285

Asp Glu Thr Met Val His Asn Gly Pro Pro His Ser Ser Asn Phe Gly
    290                 295                 300

Tyr Ser Tyr Ala Lys Arg Met Ile Asp Val Leu Asn Arg Gly Tyr Ala
305                 310                 315                 320

```
Gln Glu Phe Gly Arg Lys Tyr Thr Ser Val Ile Pro Cys Asn Val Phe
            325                 330                 335

Gly Pro His Asp Asn Tyr Asn Leu Lys Asp Gly His Val Ile Pro Ala
            340                 345                 350

Leu Ile His Lys Thr Tyr Ile Ala Lys His Glu Gly Thr Pro Leu Glu
            355                 360                 365

Val Phe Gly Ser Gly Thr Pro Leu Arg Gln Phe Ile Tyr Ser Leu Asp
            370                 375                 380

Leu Ala Arg Leu Phe Ile Trp Val Ala Arg Ser Tyr Glu Glu Ile Asp
385                 390                 395                 400

Pro Ile Ile Leu Ser Val Gly Glu Glu Asp Glu Val Ser Ile Met Asp
                405                 410                 415

Ala Val His Ala Val Val Arg Ala Phe Asp Phe Lys Gly Glu Ile Val
            420                 425                 430

His Asp Lys Thr Lys Ala Asp Gly Gln Tyr Lys Lys Thr Ala Ser Asn
            435                 440                 445

Ala Lys Leu Arg Lys Tyr Leu Pro Asn Phe Lys Phe Thr Pro Phe Glu
            450                 455                 460

Ile Ala Ile Lys Glu Ser Val Asp Trp Phe Ile Asp Asn Tyr Asp Asn
465                 470                 475                 480

Ala Arg Lys

<210> SEQ ID NO 114
<211> LENGTH: 323
<212> TYPE: PRT
<213> ORGANISM: Gallus gallus

<400> SEQUENCE: 114

Met Thr Glu Ala Leu Gly Ala Lys Pro Lys Arg Ile Leu Val Thr Gly
1               5                   10                  15

Gly Thr Gly Leu Val Gly Arg Ala Ile Gln Glu Val Val Ala Asn Gly
            20                  25                  30

Glu Gly Arg Pro Asp Glu Glu Trp Val Phe Val Ser Ser Arg Asp Ala
        35                  40                  45

Asp Leu Thr Ser Ala Val Glu Thr Lys Ala Leu Phe Glu Lys His Lys
    50                  55                  60

Pro Thr His Val Ile His Leu Ala Ala Met Val Gly Gly Leu Phe Lys
65              70                  75                  80

Asn Ile Arg Cys Asn Leu Asp Phe Trp Arg Arg Asn Ile His Ile Asn
                85                  90                  95

Asp Asn Val Leu His Ser Ala Tyr Glu Cys Gly Val Gln Lys Val Val
            100                 105                 110

Ser Cys Leu Ser Thr Cys Ile Phe Pro Asp Lys Thr Thr Tyr Pro Ile
        115                 120                 125

Asp Glu Thr Met Ile His Asn Gly Pro Pro His Ser Ser Asn Phe Gly
    130                 135                 140

Tyr Ser Tyr Ala Lys Arg Met Ile Asp Val Gln Asn Arg Gly Tyr Phe
145                 150                 155                 160

Glu Gln His Gly Cys Arg Phe Thr Ala Val Ile Pro Thr Asn Val Phe
                165                 170                 175

Gly Pro His Asp Asn Phe Asn Ile Glu Asp Gly His Val Leu Pro Gly
            180                 185                 190

Leu Ile His Lys Val Tyr Leu Ala Lys Gln Asn Gly Ser Ala Leu Thr
        195                 200                 205
```

Val Trp Gly Thr Gly Lys Pro Arg Arg Gln Phe Ile Tyr Ser Leu Asp
        210                 215                 220

Leu Ala Arg Leu Phe Val Trp Val Leu Arg Glu Tyr Glu Glu Val Glu
225                 230                 235                 240

Pro Ile Ile Leu Ser Val Gly Glu Glu Asp Glu Val Ser Ile Arg Glu
                    245                 250                 255

Ala Ala Glu Ala Ile Val Glu Ala Met Asp Phe Arg Gly Glu Leu Ile
            260                 265                 270

Phe Asp Thr Thr Lys Ala Asp Gly Gln Phe Lys Lys Thr Ala Ser Asn
        275                 280                 285

Ala Lys Leu Arg His Tyr Leu Pro Asn Phe Gln Phe Thr Pro Phe Arg
    290                 295                 300

Gln Ala Val Lys Glu Thr Cys Thr Trp Phe Ser Thr Asn Tyr Ala Ser
305                 310                 315                 320

Ala Arg Lys

<210> SEQ ID NO 115
<211> LENGTH: 320
<212> TYPE: PRT
<213> ORGANISM: Danio rerio

<400> SEQUENCE: 115

Met Asn Gly Thr Val Glu Pro Met Arg Val Leu Val Thr Gly Gly Ser
1               5                   10                  15

Gly Leu Val Gly Arg Ala Ile Glu Arg Val Val Lys Asp Glu Gly Arg
            20                  25                  30

Glu Gly Glu Glu Trp Thr Phe Leu Ser Ser Lys Asp Ala Asn Leu Leu
        35                  40                  45

Ser Ala Glu Glu Thr Arg Ala Ile Phe Gln Lys Tyr Arg Pro Thr His
    50                  55                  60

Val Ile His Leu Ala Ala Met Val Gly Gly Leu Phe Arg Asn Met Arg
65                  70                  75                  80

Gln Asn Leu Asp Phe Trp Arg Asn Asn Val Phe Ile Asn Asp Asn Val
                85                  90                  95

Leu Gln Thr Ala Asn Glu Phe Gly Val Val Lys Val Ser Cys Leu
            100                 105                 110

Ser Thr Cys Ile Phe Pro Asp Lys Thr Thr Tyr Pro Ile Asp Glu Thr
        115                 120                 125

Met Ile His Asn Gly Pro Pro His Asp Ser Asn Phe Gly Tyr Ala Phe
    130                 135                 140

Ala Lys Arg Met Ile Asp Val Gln Asn Arg Thr Cys Phe Lys Gln Tyr
145                 150                 155                 160

Gly Arg Arg Tyr Thr Ser Val Ile Pro Thr Asn Val Phe Gly Ala His
                165                 170                 175

Asp Asn Phe Asn Ile Asp Asp Gly His Val Leu Pro Gly Leu Ile His
            180                 185                 190

Lys Thr Tyr Leu Ala Lys Lys Glu Gly Lys Pro Leu Gln Val Trp Gly
        195                 200                 205

Ser Gly Lys Pro Leu Arg Gln Phe Ile Tyr Ser Leu Asp Leu Ala Arg
    210                 215                 220

Leu Phe Leu Trp Val Leu Arg Glu Tyr Asp Glu Val Asp Pro Ile Ile
225                 230                 235                 240

Leu Ser Val Gly Glu Glu Asp Glu Leu Ser Ile Lys Asp Cys Ala Asp
                245                 250                 255

```
Ala Val Val Asp Ala Leu Gly Phe Lys Gly Asp Val Ile Tyr Asp Thr
            260                 265                 270

Ser Lys Ala Asp Gly Gln Phe Lys Thr Ala Ser Asn Ala Lys Leu
        275                 280                 285

Arg Gln Tyr Leu Pro Asp Phe Gln Phe Thr Pro Phe Arg Glu Ala Ile
    290                 295                 300

Lys Glu Thr Cys Asp Trp Phe Val Ala Asn Tyr Asp Ile Ala Arg Lys
305                 310                 315                 320

<210> SEQ ID NO 116
<211> LENGTH: 317
<212> TYPE: PRT
<213> ORGANISM: Xenopus laevis

<400> SEQUENCE: 116

Met Glu Gly Lys Arg Ile Leu Val Thr Gly Gly Ser Gly Leu Val Gly
1               5                   10                  15

Lys Ala Ile Glu Lys Val Val Ala Asp Gly Glu Gly Arg Pro Asp Glu
            20                  25                  30

Gln Trp Ile Phe Ile Ser Ser Lys Asp Ala Asp Leu Thr Asn Ala Ala
        35                  40                  45

Asp Thr Lys Cys Leu Phe Glu Lys His Lys Pro Thr His Val Ile His
    50                  55                  60

Leu Ala Ala Met Val Gly Gly Leu Phe Arg Asn Met Lys Tyr Asn Leu
65                  70                  75                  80

Asp Phe Leu Arg Asn Asn Leu His Ile Asn Asp Asn Val Leu His Ser
                85                  90                  95

Ala Tyr Glu Met Gly Val Gln Lys Val Val Ser Cys Leu Ser Thr Cys
            100                 105                 110

Ile Phe Pro Asp Lys Thr Thr Tyr Pro Ile Asp Glu Thr Met Ile His
        115                 120                 125

Asn Gly Pro Pro His Thr Ser Asn Phe Gly Tyr Ser Tyr Ala Lys Arg
    130                 135                 140

Met Ile Asp Val Gln Asn Arg Ala Tyr Tyr Glu Gln His Gly Cys Lys
145                 150                 155                 160

Phe Thr Ser Val Ile Pro Thr Asn Val Phe Gly Pro His Asp Asn Phe
                165                 170                 175

Asn Ile Asp Asp Gly His Val Leu Pro Gly Leu Ile His Lys Val Tyr
            180                 185                 190

Ser Ala Lys Gln Asn Gly Thr Ala Leu Ser Ile Trp Gly Thr Gly Gln
        195                 200                 205

Pro Arg Arg Gln Phe Ile Tyr Ser Leu Asp Leu Ala Arg Leu Phe Ile
    210                 215                 220

Trp Val Leu Arg Glu Tyr Asn Glu Val Asp Pro Ile Ile Leu Ser Val
225                 230                 235                 240

Gly Glu Glu Asp Glu Val Ser Ile Lys Glu Ala Ala Glu Ser Ile Val
                245                 250                 255

Ala Ala Met Glu Phe Lys Gly Glu Leu Ile Phe Asp Ser Thr Lys Ser
            260                 265                 270

Asp Gly Gln Phe Lys Thr Ala Ser Asn His Lys Leu Arg Lys Tyr
        275                 280                 285

Leu Pro Asp Phe Gln Phe Thr Pro Phe Asn Lys Ala Val Gln Glu Thr
    290                 295                 300

Cys Asn Trp Phe Asn Ser Asn Tyr Ala Gln Ala Arg Lys
```

<210> SEQ ID NO 117
<211> LENGTH: 321
<212> TYPE: PRT
<213> ORGANISM: Bos taurus

<400> SEQUENCE: 117

Met Gly Asp Pro Arg Gly Thr Arg Arg Ile Leu Val Thr Gly Gly Ser
1               5                   10                  15

Gly Leu Val Gly Arg Ala Ile Gln Lys Val Val Glu Asp Gly Ala Arg
            20                  25                  30

Leu Pro Gly Glu Asp Trp Val Phe Val Ser Ser Lys Asp Ala Asp Leu
        35                  40                  45

Thr Asp Ala Ala Gln Thr Arg Ala Leu Phe Gln Gln Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Ile His Ile Asn Asp Asn
                85                  90                  95

Val Leu His Ser Ala Phe Glu Val Gly Val Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Ser Ile Glu Asp Gly His Val Leu Pro Gly Leu Ile
            180                 185                 190

His Lys Val His Leu Ala Lys Ser Ser Gly Ser Ala Leu Thr Val Trp
        195                 200                 205

Gly Thr Gly Arg Pro Arg Arg Gln Phe Ile Tyr Ser Leu Asp Leu Ala
    210                 215                 220

Arg Leu Phe Ile Trp Ala Leu Arg Glu Tyr Asp Glu Val Glu Pro Ile
225                 230                 235                 240

Ile Leu Ser Val Gly Glu Glu Asp Glu Val Ser Val Gln Glu Ala Ala
                245                 250                 255

Glu Ala Val Val Glu Ala Met Asp Phe His Gly Glu Val Thr Phe Asp
            260                 265                 270

Thr Thr Lys Ser Asp Gly Gln Phe Lys Lys Thr Ala Ser Asn Ala Lys
        275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 118
<211> LENGTH: 321
<212> TYPE: PRT
<213> ORGANISM: Equus caballus

<400> SEQUENCE: 118

Met Gly Glu Pro Gln Gly Ser Met Arg Ile Leu Val Thr Gly Ser Ser
1               5                   10                  15

Gly Leu Val Gly Arg Ala Ile Gln Lys Val Val Ala Asp Gly Ala Arg
            20                  25                  30

Leu Pro Gly Glu Asp Trp Val Phe Val Ser Ser Lys Asp Ala Asp Leu
            35                  40                  45

Thr Asp Ala Ala Gln Thr Arg Ala Leu Phe Glu Lys Val Arg Pro Thr
50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Ala Arg Lys Val Val Ser Cys
            100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Ser Ser Asn Phe Gly Tyr Ser
130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
                180                 185                 190

His Lys Val His Leu Ala Lys Ser Ser Gly Ser Ala Leu Thr Val Trp
                195                 200                 205

Gly Thr Gly Lys Pro Arg Arg Gln Phe Ile Tyr Ser Leu Asp Leu Ala
            210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Gln Glu Ala Ala
                245                 250                 255

Glu Ala Val Val Glu Ala Met Asp Phe His Gly Asp Val Thr Phe Asp
            260                 265                 270

Thr Thr Lys Ser Asp Gly Gln Phe Lys Lys Thr Ala Ser Asn Gly Lys
            275                 280                 285

Leu Arg Ala Tyr Leu Pro Asp Phe Arg Phe Thr Pro Phe Lys Gln Ala
            290                 295                 300

Val Lys Glu Thr Cys Ala Trp Phe Thr Asp Asn Tyr Glu Gln Ala Arg
305                 310                 315                 320

Lys

<210> SEQ ID NO 119
<211> LENGTH: 321
<212> TYPE: PRT
<213> ORGANISM: Canis lupus familiaris

<400> SEQUENCE: 119

Met Ser Glu Pro Gly Gly Ser Val Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Asp Trp Val Phe Val Ser Ser Lys Asp Ala Asp Leu
            35                  40                  45

Thr Asp Ala Ala Gln Thr Arg Ala Leu Phe Glu Lys Val Arg Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Val Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Asn Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Ser Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Gln Glu Ala Ala
                245                 250                 255

Glu Ala Val Val Glu Ala Met Asp Phe His Gly Glu Val Thr Phe Asp
            260                 265                 270

Thr Thr Lys Ser Asp Gly Gln Phe Lys Lys Thr Ala Ser Asn Gly Lys
        275                 280                 285

Leu Arg Thr Tyr Leu Pro Asp Phe Arg Phe Thr Pro Phe Lys Gln Ala
    290                 295                 300

Val Lys Glu Thr Cys Ala Trp Phe Thr His Asn Tyr Glu Gln Ala Arg
305                 310                 315                 320

Lys

<210> SEQ ID NO 120
<211> LENGTH: 321
<212> TYPE: PRT
<213> ORGANISM: Homo sapiens

<400> SEQUENCE: 120

Met Gly Glu Pro Gln Gly Ser Met Arg Ile Leu Val Thr Gly Gly Ser
1               5                   10                  15

Gly Leu Val Gly Lys Ala Ile Gln Lys Val Val Ala Asp Gly Ala Gly
            20                  25                  30

Leu Pro Gly Glu Asp Trp Val Phe Val Ser Ser Lys Asp Ala Asp Leu
        35                  40                  45

Thr Asp Thr Ala Gln Thr Arg Ala Leu Phe Glu Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Met Asn Asp Asn
                85                  90                  95

```
Val Leu His Ser Ala Phe Glu Val Gly Ala Arg Lys Val Val Ser Cys
            100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Asn Ser Asn Phe Gly Tyr Ser
130             135                 140

Tyr Ala Lys Arg Met Ile Asp Val Gln Asn Arg Ala Tyr Phe Gln Gln
145                 150                 155                 160

Tyr Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Ser Gly Ser Ala Leu Thr Val Trp
            195                 200                 205

Gly Thr Gly Asn Pro Arg Arg Gln Phe Ile Tyr Ser Leu Asp Leu Ala
        210                 215                 220

Gln Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe His Gly Glu Val Thr Phe Asp
            260                 265                 270

Thr Thr Lys Ser Asp Gly Gln Phe Lys Lys Thr Ala Ser Asn Ser Lys
        275                 280                 285

Leu Arg Thr Tyr Leu Pro Asp Phe Arg Phe Thr Pro Phe Lys Gln Ala
        290                 295                 300

Val Lys Glu Thr Cys Ala Trp Phe Thr Asp Asn Tyr Glu Gln Ala Arg
305                 310                 315                 320

Lys

<210> SEQ ID NO 121
<211> LENGTH: 321
<212> TYPE: PRT
<213> ORGANISM: Cricetulus griseus

<400> SEQUENCE: 121

Met Gly Glu Pro Gln Gly Ser Arg Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Ser Ser Asn Phe Gly Tyr Ser
130             135                 140
```

```
Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 122
<211> LENGTH: 321
<212> TYPE: PRT
<213> ORGANISM: Rattus norvegicus

<400> SEQUENCE: 122

Met Gly Glu Pro His Gly Ser Met Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ser Val Ile Pro Thr Asn Val Phe Gly Pro
                165                 170                 175

Tyr Asp Asn Phe Asn Ile Glu Asp Gly His Val Leu Pro Gly Leu Ile
            180                 185                 190
```

His Lys Val His Leu Ala Lys Ser Ser Gly Ser Ala Leu Thr Val Trp
            195                 200                 205

Gly Thr Gly Lys Pro Arg Arg Gln Phe Ile Tyr Ser Leu Asp Leu Ala
        210                 215                 220

Arg Leu Phe Ile Trp Val Leu Arg Glu Tyr Asn Glu Val Glu Pro Ile
225                 230                 235                 240

Ile Leu Ser Val Gly Glu Asp Val Ser Ile Lys Glu Ala Ala
                245                 250                 255

Glu Ala Val Val Glu Ala Met Asp Phe Ser Gly Glu Val Thr Phe Asp
                260                 265                 270

Ser Thr Lys Ser Asp Gly Gln Tyr Lys Lys Thr Ala Ser Asn Gly Lys
                275                 280                 285

Leu Arg Ser Tyr Leu Pro Asp Phe Cys Phe Thr Pro Phe Lys Gln Ala
            290                 295                 300

Val Lys Glu Thr Cys Ala Trp Phe Thr Glu Asn Tyr Glu Gln Ala Arg
305                 310                 315                 320

Lys

<210> SEQ ID NO 123
<211> LENGTH: 321
<212> TYPE: PRT
<213> ORGANISM: Mus musculus

<400> SEQUENCE: 123

Met Gly Glu Pro His Gly Ser Met Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Ala Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

Tyr Asp Asn Phe Asn Ile Glu Asp Gly His Val Leu Pro Gly Leu Ile
            180                 185                 190

His Lys Val His Leu Ala Lys Ser Ser Asp Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Ser Glu Val Glu Pro Ile
225                 230                 235                 240

Ile Leu Ser Val Gly Glu Asp Glu Val Ser Ile Lys Glu Ala Ala
            245                 250                 255

Glu Ala Val Val Glu Ala Met Asp Phe Asn Gly Glu Val Thr Phe Asp
        260                 265                 270

Ser Thr Lys Ser Asp Gly Gln Tyr Lys Lys Thr Ala Ser Asn Gly Lys
    275                 280                 285

Leu Arg Ser Tyr Leu Pro Asp Phe Arg Phe Thr Pro Phe Lys Gln Ala
290                 295                 300

Val Lys Glu Thr Cys Thr Trp Phe Thr Asp Asn Tyr Glu Gln Ala Arg
305                 310                 315                 320

Lys

<210> SEQ ID NO 124
<211> LENGTH: 380
<212> TYPE: PRT
<213> ORGANISM: Loa loa

<400> SEQUENCE: 124

Met Asn Thr Glu Ala Leu Glu Asp Cys Leu Gly Asn Arg His Ser Met
1               5                   10                  15

Lys Pro Ile Ser Glu Val Glu Lys Cys Lys Phe Arg Thr Pro Lys Ile
            20                  25                  30

Ala Leu Ile Thr Gly Ile Ser Gly Gln Asp Gly Ser Tyr Leu Ala Glu
        35                  40                  45

Leu Leu Leu Ser Lys Gly Tyr Glu Val His Gly Ile Ile Arg Arg Ser
    50                  55                  60

Ser Ser Phe Asn Thr Ser Arg Ile Glu His Leu Tyr Ser Asn Pro Val
65                  70                  75                  80

Thr His His Ala Asp Ser Ser Phe Thr Leu His Tyr Gly Asp Met Thr
                85                  90                  95

Asp Ser Ser Cys Leu Ile Lys Leu Val Ser Gln Ile Gln Pro Thr Glu
            100                 105                 110

Val Tyr His Leu Ala Ala Gln Ser His Val Lys Val Ser Phe Asp Leu
        115                 120                 125

Pro Glu Tyr Thr Ala Glu Val Asp Ala Val Gly Thr Leu Arg Leu Leu
    130                 135                 140

Asp Ser Ile His Ala Cys Gly Leu Thr Asn Lys Val Arg Phe Tyr Gln
145                 150                 155                 160

Ala Ser Thr Ser Glu Leu Tyr Gly Lys Val Gln Glu Val Pro Gln Lys
                165                 170                 175

Glu Thr Thr Pro Phe Tyr Pro Arg Ser Pro Tyr Ala Ala Ala Lys Leu
            180                 185                 190

Tyr Ser Tyr Trp Ile Val Val Asn Tyr Arg Glu Ala Tyr Asn Met Phe
        195                 200                 205

Ala Cys Asn Gly Ile Leu Phe Asn His Glu Ser Pro Arg Arg Gly Glu
    210                 215                 220

Thr Phe Val Thr Arg Lys Ile Thr Arg Ala Val Ala Lys Ile Ala Leu
225                 230                 235                 240

Gly Gln Gln Glu Ile Leu Glu Leu Gly Asn Leu Ser Ser Ser Arg Asp
                245                 250                 255

Trp Gly His Ala Lys Glu Tyr Val Glu Ala Met Trp Lys Ile Leu Gln
            260                 265                 270

Tyr Asp Gln Pro Asp Asp Phe Val Ile Ala Thr Gly Lys Ser Tyr Thr
        275                 280                 285

```
Val Arg Arg Phe Ala Glu Leu Ala Phe Glu Glu Ile Gly Lys Thr Ile
    290                 295                 300

Ile Trp Glu Gly Glu Gly Val His Glu Val Gly Lys Glu Lys Asp Thr
305                 310                 315                 320

Gly Ile Ile Arg Val Arg Val Ser Pro Lys Tyr Tyr Arg Pro Thr Glu
                325                 330                 335

Val Asp Leu Leu Ile Gly Asp Pro Thr Lys Ala Lys Gln Lys Leu Asn
            340                 345                 350

Trp Glu Ala Lys Ile Thr Leu Glu Glu Leu Val Lys Glu Met Val Ala
        355                 360                 365

Ser Asp Leu Gln Leu Met Lys Ser Asn Pro Met Ala
    370                 375                 380

<210> SEQ ID NO 125
<211> LENGTH: 387
<212> TYPE: PRT
<213> ORGANISM: Brugia malayi

<400> SEQUENCE: 125

Met Thr Ile Asn Ala Thr Lys Met Asn Thr Glu Thr Gln Glu Asn Cys
1               5                   10                  15

Leu Gly Asn Arg Ser Ser Met Lys Thr Ile Ser Glu Val Glu Arg Tyr
            20                  25                  30

Lys Cys Arg Ala Arg Lys Ile Ala Leu Ile Thr Gly Ile Ser Gly Gln
        35                  40                  45

Asp Gly Ser Tyr Leu Ala Glu Leu Leu Leu Ser Lys Gly Tyr Glu Val
    50                  55                  60

His Gly Ile Ile Arg Arg Ser Ser Ser Phe Asn Thr Ala Arg Ile Glu
65                  70                  75                  80

His Leu Tyr Ser Asn Pro Ile Thr His His Ala Asp Ser Ser Phe Thr
                85                  90                  95

Leu His Tyr Gly Asp Met Thr Asp Ser Ser Cys Leu Ile Lys Ile Val
            100                 105                 110

Ser Gln Ile Gln Pro Thr Glu Val Tyr His Leu Ala Ala Gln Ser His
        115                 120                 125

Val Lys Val Ser Phe Asp Leu Pro Glu Tyr Thr Ala Glu Val Asp Ala
    130                 135                 140

Val Gly Thr Leu Arg Leu Leu Asp Ser Ile His Ala Cys Gly Leu Thr
145                 150                 155                 160

Asn Lys Val Lys Phe Tyr Gln Ala Ser Thr Ser Glu Leu Tyr Gly Lys
                165                 170                 175

Val Gln Glu Val Pro Gln Lys Glu Thr Thr Pro Phe Tyr Pro Arg Ser
            180                 185                 190

Pro Tyr Ala Ala Ala Lys Leu Tyr Ser Tyr Trp Ile Val Val Asn Tyr
        195                 200                 205

Arg Glu Ala Tyr Ser Met Phe Ala Cys Asn Gly Ile Leu Phe Asn His
    210                 215                 220

Glu Ser Pro Arg Arg Gly Glu Thr Phe Val Thr Arg Lys Ile Thr Arg
225                 230                 235                 240

Ala Val Ala Lys Ile Ala Leu Gly Gln Gln Glu Val Leu Glu Leu Gly
                245                 250                 255

Asn Leu Ser Ser Ser Arg Asp Trp Gly His Ala Lys Glu Tyr Val Glu
            260                 265                 270

Ala Met Trp Arg Ile Leu Gln Tyr Asp Lys Pro Asp Asp Phe Val Ile
```

```
                275                 280                 285
Ala Thr Gly Lys Ser Tyr Thr Val Arg Arg Phe Ala Glu Leu Ala Phe
    290                 295                 300
Glu Ile Gly Lys Lys Ile Ile Trp Glu Gly Gly Val His Glu
305                 310                 315                 320
Val Gly Lys Glu Glu Asp Thr Gly Ile Val Arg Val Arg Val Ser Ser
                325                 330                 335
Lys Tyr Tyr Arg Pro Thr Glu Val Asp Leu Leu Ile Gly Asp Ser Thr
            340                 345                 350
Lys Ala Lys Gln Lys Leu Asn Trp Glu Ala Lys Thr Thr Leu Glu Glu
                355                 360                 365
Leu Val Lys Glu Met Val Ala Ser Asp Leu Gln Leu Met Lys Ser Asn
            370                 375                 380
Pro Met Ala
385

<210> SEQ ID NO 126
<211> LENGTH: 362
<212> TYPE: PRT
<213> ORGANISM: Anopheles gambiae str. PEST

<400> SEQUENCE: 126

Met Glu Gly Glu Ala Ala Val Thr Asn Pro Val Asp Arg Lys Val Ala
1               5                   10                  15
Leu Ile Thr Gly Ile Thr Gly Gln Asp Gly Ser Tyr Leu Ala Glu Phe
                20                  25                  30
Leu Leu Asp Lys Gly Tyr Glu Val His Gly Ile Ile Arg Ala Ser
            35                  40                  45
Thr Phe Asn Thr Ser Arg Ile Glu His Leu Tyr Ala Asp Pro Arg Thr
    50                  55                  60
His Arg Glu Gly Lys Met Lys Leu His Tyr Gly Asp Met Thr Asp Ser
65                  70                  75                  80
Ser Ala Leu Val Lys Ile Ala Gln Val Arg Pro Ser Glu Ile Tyr
                85                  90                  95
Asn Leu Ala Ala Gln Ser His Val Lys Ile Ser Phe Asp Leu Ser Glu
                100                 105                 110
Tyr Thr Ala Glu Val Asp Ala Val Gly Thr Leu Arg Leu Leu Asp Ala
            115                 120                 125
Ile Arg Thr Val Gly Gln Glu Arg Thr Val Arg Phe Tyr Gln Ala Ser
    130                 135                 140
Thr Ser Glu Leu Tyr Gly Lys Val Ala Glu Thr Pro Gln Asn Glu Lys
145                 150                 155                 160
Thr Pro Phe Tyr Pro Arg Ser Pro Tyr Ala Cys Ala Lys Met Tyr Gly
                165                 170                 175
Tyr Trp Ile Val Ile Asn Tyr Arg Glu Ala Tyr Asp Met Phe Ala Cys
                180                 185                 190
Asn Gly Ile Leu Phe Asn His Glu Ser Pro Arg Arg Gly Glu Asn Phe
            195                 200                 205
Val Thr Arg Lys Ile Thr Arg Ser Val Ala Lys Ile Ser Leu Gly Gln
    210                 215                 220
Gln Glu Tyr Leu Glu Leu Gly Asn Leu Asp Ser Lys Arg Asp Trp Gly
225                 230                 235                 240
His Ala Lys Asp Tyr Val Glu Ala Met Trp Leu Met Gln Gln Glu
                245                 250                 255
```

```
Arg Pro Glu Asp Phe Val Ile Ala Thr Gly Thr His Ser Val Arg
            260                 265                 270

Glu Phe Val Glu Gln Ala Phe Arg Tyr Ile Gly Arg Glu Ile Glu Trp
        275                 280                 285

Arg Gly Thr Gly Val Asp Glu Val Gly Val Glu Lys Gly Thr Asp Thr
    290                 295                 300

Val Arg Val Arg Ile Asn Pro Lys Phe Phe Arg Pro Thr Glu Val Asp
305                 310                 315                 320

Leu Leu Leu Gly Asp Ala Ser Lys Ala Lys Ala Gln Leu Gly Trp Ser
                325                 330                 335

Pro Lys Val Thr Phe Leu Glu Leu Ile Ala Asp Met Met Ala Ala Asp
            340                 345                 350

Ile Gln Leu Met Lys Asn Asn Pro Ser Ala
        355                 360

<210> SEQ ID NO 127
<211> LENGTH: 382
<212> TYPE: PRT
<213> ORGANISM: Aedes aegypti

<400> SEQUENCE: 127

Met Ser Leu Glu Asn Gly Ser Asn Lys Lys Arg Arg Leu Ser Leu Glu
1               5                   10                  15

Asn His Leu Ala Thr Glu Ser Glu Gly Ser Ser Ser Asp Pro Asn
            20                  25                  30

Arg Arg Val Ala Leu Ile Thr Gly Ile Thr Gly Gln Asp Gly Ser Tyr
        35                  40                  45

Leu Ala Glu Phe Leu Leu Lys Lys Asp Tyr Glu Val His Gly Ile Ile
50                  55                  60

Arg Arg Ala Ser Thr Phe Asn Thr Ser Arg Ile Glu His Leu Tyr Ala
65                  70                  75                  80

Asp Pro His Ser His Lys Gln Gly Lys Met Lys Leu His Tyr Gly Asp
                85                  90                  95

Met Thr Asp Ser Ser Cys Leu Val Lys Ile Ile Ser Ser Val Arg Pro
            100                 105                 110

Ser Glu Ile Tyr Asn Leu Ala Ala Gln Ser His Val Lys Val Ser Phe
        115                 120                 125

Asp Leu Ser Glu Tyr Thr Ala Glu Val Asp Ala Val Gly Thr Leu Arg
    130                 135                 140

Leu Leu Asp Ala Ile Arg Thr Cys Gly Leu Glu Lys Ser Val Arg Phe
145                 150                 155                 160

Tyr Gln Ala Ser Thr Ser Glu Leu Tyr Gly Lys Val Val Glu Thr Pro
                165                 170                 175

Gln Asn Glu Lys Thr Pro Phe Tyr Pro Arg Ser Pro Tyr Ala Cys Ala
            180                 185                 190

Lys Met Tyr Gly Tyr Trp Ile Val Ile Asn Tyr Arg Glu Ala Tyr Asn
        195                 200                 205

Met Phe Ala Cys Asn Gly Ile Leu Phe Asn His Glu Ser Pro Arg Arg
    210                 215                 220

Gly Glu Asn Phe Val Thr Arg Lys Ile Thr Arg Ser Val Ala Lys Ile
225                 230                 235                 240

Ser Leu Asn Gln Met Asp Cys Leu Glu Leu Gly Asn Leu Asp Ser Lys
                245                 250                 255

Arg Asp Trp Gly His Ala Gln Asp Tyr Val Glu Ala Met Trp Met Met
            260                 265                 270
```

```
Leu Gln Gln Pro Gln Pro Gln Asp Tyr Val Ile Ala Thr Gly Glu Cys
        275                 280                 285

His Ser Val Arg Glu Phe Val Glu His Ser Phe Arg His Ile Gly Arg
    290                 295                 300

Glu Ile Glu Trp Arg Gly Glu Gly Leu Asn Glu Val Gly Val Glu Lys
305                 310                 315                 320

Gly Thr Asp Thr Val Arg Val Arg Ile Asn Pro Lys Phe Phe Arg Pro
            325                 330                 335

Thr Glu Val Asp Leu Leu Leu Gly Asp Ala Ser Lys Ala Lys Arg Glu
            340                 345                 350

Leu Gly Trp Thr Pro Lys Val Ser Phe Leu Gln Leu Val Ser Asp Met
        355                 360                 365

Met Val Ala Asp Ile Glu Leu Met Lys Lys Asn Pro Asn Ala
        370                 375                 380

<210> SEQ ID NO 128
<211> LENGTH: 370
<212> TYPE: PRT
<213> ORGANISM: Danio rerio

<400> SEQUENCE: 128

Met Ala Gln Cys Thr Ala Thr Thr Gly Gly Gly Met Asn Gly Asp
1               5                   10                  15

Ser Lys Arg Lys Arg Lys Val Ala Ile Ile Thr Gly Ile Thr Gly Gln
            20                  25                  30

Asp Gly Ser Tyr Leu Ala Glu Leu Leu Leu Ala Lys Gly Tyr Glu Val
        35                  40                  45

His Gly Ile Leu Arg Arg Ser Ser Ser Phe Asn Thr Gly Arg Ile Glu
    50                  55                  60

His Leu Tyr His Asn Pro Gln Thr His Thr Glu Gly Asn Met Lys Leu
65                  70                  75                  80

His Tyr Gly Asp Leu Thr Asp Ser Thr Cys Leu Val Lys Ile Ile Asn
                85                  90                  95

Glu Val Lys Pro Thr Glu Ile Tyr Asn Leu Gly Ala Gln Ser His Val
            100                 105                 110

Lys Ile Ser Phe Asp Leu Ala Glu Tyr Thr Ala Asp Val Asp Gly Val
        115                 120                 125

Gly Thr Leu Arg Leu Leu Asp Ala Val Lys Thr Cys Gly Leu Thr Asp
    130                 135                 140

Thr Val Arg Phe Tyr Gln Ala Ser Thr Ser Glu Leu Tyr Gly Lys Val
145                 150                 155                 160

Gln Glu Ile Pro Gln Lys Glu Thr Thr Pro Phe Tyr Pro Arg Ser Pro
                165                 170                 175

Tyr Gly Ala Ala Lys Leu Tyr Ala Tyr Trp Ile Val Ile Asn Phe Arg
            180                 185                 190

Glu Ala Tyr Asn Leu Phe Ala Val Asn Gly Ile Leu Phe Asn His Glu
        195                 200                 205

Ser Pro Arg Arg Gly Ser Asn Phe Val Thr Arg Lys Ile Ser Arg Ser
    210                 215                 220

Val Ala Lys Ile His Leu Gly Gln Leu Glu Cys Phe Ser Leu Gly Asn
225                 230                 235                 240

Leu Asp Ser Met Arg Asp Trp Gly His Ala Lys Asp Tyr Val Glu Ala
                245                 250                 255

Met Trp Leu Met Leu Gln Gln Glu Glu Pro Val Asp Phe Val Ile Ala
```

```
                  260                 265                 270
Thr Gly Glu Val His Ser Val Arg Glu Phe Val Glu Arg Ala Phe Lys
                275                 280                 285

His Val Gly Lys Thr Ile Val Trp Glu Gly Lys Asp Glu Lys Glu Val
            290                 295                 300

Gly Arg Cys Gln Glu Thr Gly Val Ile His Val Arg Val Asp Pro Lys
305                 310                 315                 320

Tyr Tyr Arg Pro Thr Glu Val Asp Tyr Leu Gln Gly Asp Ser Ser Lys
                325                 330                 335

Ala Phe Lys Val Leu Gly Trp Lys Pro Arg Val Thr Phe Glu Glu Leu
            340                 345                 350

Val Lys Glu Met Val Asp Ala Asp Ile Lys Leu Met Gln Asn Asn Pro
355                 360                 365

Asn Ala
    370

<210> SEQ ID NO 129
<211> LENGTH: 370
<212> TYPE: PRT
<213> ORGANISM: Salmo salar

<400> SEQUENCE: 129

Met Ala Gln Cys Thr Glu Pro Ser Thr Ser Thr Gly Ala Asn Gly Glu
1               5                   10                  15

Leu Lys Lys Pro Arg Lys Val Ala Val Ile Thr Gly Ile Thr Gly Gln
            20                  25                  30

Asp Gly Ser Tyr Leu Ala Glu Phe Leu Leu Glu Lys Gly Tyr Glu Val
        35                  40                  45

His Gly Ile Leu Arg Arg Ser Ser Ser Phe Asn Thr Gly Arg Ile Glu
    50                  55                  60

His Leu Tyr Gln Asn Pro Gln Thr His Thr Glu Gly Asn Met Lys Leu
65                  70                  75                  80

His Tyr Gly Asp Leu Thr Asp Ser Thr Cys Leu Val Lys Ile Ile Asn
                85                  90                  95

Gln Val Lys Pro Thr Glu Ile Tyr Asn Leu Gly Ala Gln Ser His Val
            100                 105                 110

Lys Ile Ser Phe Glu Leu Ala Glu Tyr Thr Ala Asn Val Asp Gly Val
        115                 120                 125

Gly Thr Leu Arg Leu Leu Asp Ala Ile Lys Thr Cys Gly Leu Thr Asn
    130                 135                 140

Ser Val Lys Phe Tyr Gln Ala Ser Thr Ser Glu Leu Tyr Gly Lys Val
145                 150                 155                 160

Gln Glu Ile Pro Gln Lys Glu Thr Thr Pro Phe Tyr Pro Arg Ser Pro
                165                 170                 175

Tyr Gly Ala Ala Lys Leu Tyr Ala Tyr Trp Ile Val Val Asn Phe Arg
            180                 185                 190

Glu Ala Tyr Asn Leu Phe Ala Val Asn Gly Ile Leu Phe Asn His Glu
        195                 200                 205

Ser Pro Arg Arg Gly Ala Asn Phe Val Thr Arg Lys Ile Ser Arg Ser
    210                 215                 220

Val Ala Lys Ile His Leu Gly Gln Leu Glu Ser Phe Ser Leu Gly Asn
225                 230                 235                 240

Leu Asp Ser Lys Arg Asp Trp Gly His Ala Lys Asp Tyr Val Glu Ala
                245                 250                 255
```

Met Trp Leu Met Leu Gln Gln Glu Glu Pro Glu Asp Leu Val Ile Ala
            260                 265                 270

Thr Gly Glu Val His Ser Val Arg Glu Phe Val Glu Lys Ser Phe Lys
        275                 280                 285

His Val Gly Lys Thr Ile Val Trp Gly Lys Asp Glu Asn Glu Val
        290                 295                 300

Gly Arg Cys Gln Glu Thr Gly Val Ile His Val Lys Val Asp Ser Lys
305                 310                 315                 320

Tyr Tyr Arg Pro Thr Glu Val Glu Tyr Leu Gln Gly Asp Ser Thr Lys
                325                 330                 335

Ala Leu Thr Lys Leu Gly Trp Lys Ala Lys Ile Thr Phe Glu Glu Leu
            340                 345                 350

Val Lys Glu Met Val Asp Ala Asp Ile His Leu Met Lys Asn Asn Pro
        355                 360                 365

Asn Ala
    370

<210> SEQ ID NO 130
<211> LENGTH: 358
<212> TYPE: PRT
<213> ORGANISM: Apis mellifera

<400> SEQUENCE: 130

Met Lys Met Ala Thr Asp Ser Arg Arg Val Ala Leu Ile Thr Gly
1               5                   10                  15

Ile Thr Gly Gln Asp Gly Ser Tyr Leu Ala Glu Phe Leu Leu Glu Lys
            20                  25                  30

Gly Tyr Asp Val His Gly Ile Ile Arg Arg Ala Ser Ser Phe Asn Thr
        35                  40                  45

Ala Arg Ile Gln His Leu Tyr Glu Asp Pro Lys Cys His Arg Gln Gly
    50                  55                  60

Lys Met Lys Leu His Tyr Gly Asp Met Thr Asp Ser Ser Ser Leu Ile
65                  70                  75                  80

Lys Val Ile Ser Ser Val Gln Pro Thr Glu Ile Tyr Asn Leu Ala Ala
                85                  90                  95

Gln Ser His Val Met Val Ser Phe Glu Val Ser Glu Tyr Thr Ala Glu
            100                 105                 110

Val Asp Ala Val Gly Thr Val Arg Leu Leu Asp Ala Ile Arg Thr Cys
        115                 120                 125

Gly Leu Glu Lys Ser Val Lys Phe Tyr His Ala Ser Thr Ser Glu Leu
    130                 135                 140

Tyr Gly Arg Val Thr Gln Val Pro Gln Asn Glu Lys Thr Pro Phe Tyr
145                 150                 155                 160

Pro Arg Ser Pro Tyr Ala Cys Ala Lys Leu Tyr Ser Phe Trp Ile Val
                165                 170                 175

Ile Asn Tyr Arg Glu Ala Tyr Asn Met Phe Ala Cys Asn Gly Ile Leu
            180                 185                 190

Phe Asn His Glu Ser Pro Arg Arg Gly Glu Asn Phe Val Thr Arg Lys
        195                 200                 205

Val Thr Arg Ser Ile Ala Lys Ile His Leu Gly Leu Gln Asp Ile Leu
    210                 215                 220

Glu Leu Gly Asn Leu Asp Ala Lys Arg Asp Trp Gly His Ala Lys Asp
225                 230                 235                 240

Tyr Val Glu Ala Met Trp Leu Met Leu Gln Gln Pro Thr Ala Asp Asp
                245                 250                 255

```
Tyr Val Ile Ala Thr Gly Glu Thr His Ser Val Arg Glu Phe Val Glu
            260                 265                 270

Ala Ala Phe Gln Tyr Val Gly Arg Thr Ile Lys Trp Glu Gly Glu Gly
            275                 280                 285

Ile Asn Glu Ile Gly Gln Asp Val Gln Thr Gly Gln Val Leu Val Lys
290                 295                 300

Val Asn Pro Lys Tyr Phe Arg Pro Thr Glu Val Asp Val Leu Leu Gly
305                 310                 315                 320

Asp Ala Thr Lys Ala Lys Glu Lys Ile Gly Trp Lys Pro Thr Ile Thr
                325                 330                 335

Phe Glu Asn Leu Val Lys Asp Met Met Asp Ser Asp Leu Glu Leu Met
                340                 345                 350

Ser Lys Asn Pro Asn Ala
        355

<210> SEQ ID NO 131
<211> LENGTH: 395
<212> TYPE: PRT
<213> ORGANISM: Drosophila melanogaster

<400> SEQUENCE: 131

Met Leu Asn Thr Arg Leu Ile Ala Met Ser Thr Ser Asp Gly Ala Pro
1               5                   10                  15

Glu Thr Lys Lys Gln Arg Pro Glu Ser Ser Asn Gly Ser Lys Asp
            20                  25                  30

Gln Asn Gly Thr Glu Ala Gly Ala Glu Gly Asp Ser Arg Asp Lys Val
        35                  40                  45

Ala Leu Ile Thr Gly Ile Thr Gly Gln Asp Gly Ser Tyr Leu Ala Glu
    50                  55                  60

Phe Leu Leu Lys Lys Asp Tyr Glu Val His Gly Ile Ile Arg Arg Ala
65                  70                  75                  80

Ser Thr Phe Asn Thr Thr Arg Ile Glu His Leu Tyr Ala Asp Pro Lys
                85                  90                  95

Ala His Lys Gly Gly Arg Met Lys Leu His Tyr Gly Asp Met Thr Asp
            100                 105                 110

Ser Ser Ser Leu Val Lys Ile Ile Asn Met Val Lys Pro Thr Glu Ile
        115                 120                 125

Tyr Asn Leu Ala Ala Gln Ser His Val Lys Val Ser Phe Asp Leu Ser
    130                 135                 140

Glu Tyr Thr Ala Glu Val Asp Ala Val Gly Thr Leu Arg Ile Leu Asp
145                 150                 155                 160

Ala Ile Arg Thr Cys Gly Met Glu Lys Asn Val Arg Phe Tyr Gln Ala
                165                 170                 175

Ser Thr Ser Glu Leu Tyr Gly Lys Val Val Glu Thr Pro Gln Asn Glu
            180                 185                 190

Gln Thr Pro Phe Tyr Pro Arg Ser Pro Tyr Ala Cys Ala Lys Met Tyr
        195                 200                 205

Gly Phe Trp Ile Val Ile Asn Tyr Arg Glu Ala Tyr Asn Met Tyr Ala
    210                 215                 220

Cys Asn Gly Ile Leu Phe Asn His Glu Ser Pro Arg Arg Gly Glu Asn
225                 230                 235                 240

Phe Val Thr Arg Lys Ile Thr Arg Ser Val Ala Lys Ile Tyr His Lys
                245                 250                 255

Gln Met Glu Tyr Phe Glu Leu Gly Asn Leu Asp Ser Lys Arg Asp Trp
```

```
            260                 265                 270
Gly His Ala Ser Asp Tyr Val Glu Ala Met Trp Met Leu Gln Arg
            275                 280                 285

Glu Ser Pro Ser Asp Tyr Val Ile Ala Thr Gly Thr His Ser Val
            290                 295                 300

Arg Glu Phe Val Glu Ala Phe Lys His Ile Asp Arg Glu Ile Thr
305                 310                 315                 320

Trp Lys Gly Lys Gly Val Asp Glu Val Gly Val Glu Asn Gly Thr Gly
                325                 330                 335

Ile Val Arg Val Arg Ile Asn Pro Lys Tyr Phe Arg Pro Thr Glu Val
                340                 345                 350

Asp Leu Leu Gln Gly Asp Ala Ser Lys Ala Asn Arg Glu Leu Asn Trp
                355                 360                 365

Thr Pro Lys Val Thr Phe Val Glu Leu Val Ser Asp Met Met Lys Ala
                370                 375                 380

Asp Ile Glu Leu Met Arg Lys Asn Pro Ile Ala
385                 390                 395

<210> SEQ ID NO 132
<211> LENGTH: 369
<212> TYPE: PRT
<213> ORGANISM: Xenopus laevis

<400> SEQUENCE: 132

Met Ala Gln Asn Gln Gly Asn Cys Ser Cys Ser Pro Ser Asn Ser Ser
1               5                   10                  15

Gly Lys Pro Arg Lys Val Ala Leu Ile Thr Gly Ile Thr Gly Gln Asp
                20                  25                  30

Gly Ser Tyr Leu Ala Glu Phe Leu Leu Glu Lys Gly Tyr Glu Val His
            35                  40                  45

Gly Ile Val Arg Arg Ser Ser Ser Phe Asn Thr Gly Arg Ile Glu His
        50                  55                  60

Leu Tyr Lys Asn Pro His Ala His Thr Glu Gly Asn Met Lys Leu His
65                  70                  75                  80

Tyr Gly Asp Leu Thr Asp Ser Thr Cys Leu Val Lys Ile Ile Asn Glu
                85                  90                  95

Val Lys Pro Thr Glu Ile Tyr Asn Leu Gly Ala Gln Ser His Val Lys
            100                 105                 110

Ile Ser Phe Asp Leu Ala Glu Tyr Thr Ala Asp Val Asp Gly Leu Gly
        115                 120                 125

Thr Leu Arg Leu Leu Asp Ala Thr Lys Thr Cys Gly Leu Ile Asn Thr
130                 135                 140

Val Lys Phe Tyr Gln Ala Ser Thr Ser Glu Leu Tyr Gly Lys Val Gln
145                 150                 155                 160

Glu Ile Pro Gln Lys Glu Thr Thr Pro Phe Tyr Pro Arg Ser Pro Tyr
                165                 170                 175

Gly Ala Ala Lys Leu Tyr Ala Tyr Trp Ile Val Val Asn Phe Arg Glu
            180                 185                 190

Ala Tyr Asn Leu Phe Ala Val Asn Gly Ile Leu Phe Asn His Glu Ser
        195                 200                 205

Pro Arg Arg Gly Ala Asn Phe Val Thr Arg Lys Ile Ser Arg Ser Val
    210                 215                 220

Ala Lys Ile His Leu Gly Gln Met Glu Ser Phe Ser Leu Gly Asn Leu
225                 230                 235                 240
```

```
Asp Ala Lys Arg Asp Trp Gly His Ala Lys Asp Tyr Val Glu Ala Met
                245                 250                 255

Trp Leu Met Leu Gln Thr Asp Glu Pro Glu Asp Phe Val Ile Ser Thr
        260                 265                 270

Gly Glu Val His Ser Val Arg Glu Phe Val Glu Lys Ala Phe Lys His
        275                 280                 285

Ile Gly Lys Thr Ile Val Trp Glu Gly Lys Asn Glu Asn Glu Val Gly
    290                 295                 300

Arg Cys Ser Glu Thr Gly Lys Ile His Val Lys Val Asp Leu Lys Tyr
305                 310                 315                 320

Tyr Arg Pro Thr Glu Val Asp Phe Leu Gln Gly Asp Cys Ser Gln Ala
                325                 330                 335

Lys Asn Lys Leu Gly Trp Thr Pro Lys Val Ser Phe Asp Glu Leu Val
            340                 345                 350

Lys Glu Met Val Glu Ser Asp Val Lys Leu Met Ala Thr Asn Pro Asn
        355                 360                 365

Ala

<210> SEQ ID NO 133
<211> LENGTH: 372
<212> TYPE: PRT
<213> ORGANISM: Bos taurus

<400> SEQUENCE: 133

Met Ala Gln Ala Ala His Tyr Pro Gly Ala Cys Gly Ala Gly Asp
1               5                   10                  15

Ala Glu Thr Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Val Lys Thr Cys Gly Leu
    130                 135                 140

Ile Ser Ser Val Arg Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile His Leu Gly Gln Leu Glu Cys Phe Ser Leu
225                 230                 235                 240
```

```
Gly Asn Leu Asp Ala Lys Arg Asp Trp Gly His Ala Lys Asp Tyr Val
                245                 250                 255

Glu Ala Met Trp Leu Met Leu Gln Lys Asp Glu Pro Gly Asp Phe Val
            260                 265                 270

Ile Ala Thr Gly Glu Val His Ser Val Arg Glu Phe Val Glu Lys Ser
        275                 280                 285

Phe Leu His Ile Gly Lys Thr Ile Val Trp Glu Gly Lys Asn Glu Asn
    290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Arg Gln Lys Leu Ser Trp Lys Pro Arg Val Ala Phe Asp
            340                 345                 350

Glu Leu Val Arg Glu Met Val Glu Ala Asp Val Glu Leu Met Arg Thr
        355                 360                 365

Asn Pro His Ala
    370

<210> SEQ ID NO 134
<211> LENGTH: 372
<212> TYPE: PRT
<213> ORGANISM: Cricetulus griseus

<400> SEQUENCE: 134

Met Ala His Ala Pro Ala Ser Cys Pro Ser Arg Asn Ser Gly Asp
1               5                   10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Lys Gly Tyr
            35                  40                  45

Glu Val His Gly Ile Val Arg Arg Ser Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240
```

```
Gly Asn Leu Asp Ala Lys Arg Asp Trp Gly His Ala Lys Asp Tyr Val
            245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
            275                 280                 285

Phe Met His Ile Gly Lys Thr Ile Val Trp Glu Gly Lys Asn Glu Asn
            290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                    325                 330                 335

Ser Lys Ala Gln Gln Lys Leu Asn Trp Lys Pro Arg Val Ala Phe Asp
                    340                 345                 350

Glu Leu Val Arg Glu Met Val Gln Ala Asp Val Glu Leu Met Arg Thr
                    355                 360                 365

Asn Pro Asn Ala
        370

<210> SEQ ID NO 135
<211> LENGTH: 372
<212> TYPE: PRT
<213> ORGANISM: Mus musculus

<400> SEQUENCE: 135

Met Ala Gln Ala Pro Ala Lys Cys Pro Ser Tyr Pro Gly Ser Gly Asp
1               5                   10                  15

Gly Glu Met Gly Lys Leu Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
            35                  40                  45

Glu Val His Gly Ile Val Arg Arg Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
            115                 120                 125

Gly Val Gly Thr Leu Arg Leu Leu Asp Ala Ile Lys Thr Cys Gly Leu
            130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                    165                 170                 175

Ser Pro Tyr Gly Ala Ala Lys Leu Tyr Ala Tyr Trp Ile Val Val Asn
                    180                 185                 190

Phe Arg Glu Ala Tyr Asn Leu Phe Ala Val Asn Gly Ile Leu Phe Asn
                    195                 200                 205

His Glu Ser Pro Arg Arg Gly Ala Asn Phe Val Thr Arg Lys Ile Ser
            210                 215                 220

Arg Ser Val Ala Lys Ile Tyr Leu Gly Gln Leu Glu Cys Phe Ser Leu
```

```
                225                 230                 235                 240
Gly Asn Leu Asp Ala Lys Arg Asp Trp Gly His Ala Lys Asp Tyr Val
                    245                 250                 255
Glu Ala Met Trp Leu Met Leu Gln Asn Asp Glu Pro Glu Asp Phe Val
                260                 265                 270
Ile Ala Thr Gly Glu Val His Ser Val Arg Glu Phe Val Glu Lys Ser
            275                 280                 285
Phe Met His Ile Gly Lys Thr Ile Val Trp Gly Lys Asn Glu Asn
        290                 295                 300
Glu Val Gly Arg Cys Lys Glu Thr Gly Lys Val His Val Thr Val Asp
305                 310                 315                 320
Leu Lys Tyr Tyr Arg Pro Thr Glu Val Asp Phe Leu Gln Gly Asp Cys
                325                 330                 335
Ser Lys Ala Gln Gln Lys Leu Asn Trp Lys Pro Arg Val Ala Phe Asp
                340                 345                 350
Glu Leu Val Arg Glu Met Val Gln Ala Asp Val Glu Leu Met Arg Thr
                355                 360                 365
Asn Pro Asn Ala
            370

<210> SEQ ID NO 136
<211> LENGTH: 372
<212> TYPE: PRT
<213> ORGANISM: Rattus norvegicus

<400> SEQUENCE: 136

Met Ala His Ala Pro Ala Ser Cys Arg Arg Tyr Pro Gly Ser Gly Asp
1               5                   10                  15
Gly Glu Met Gly Lys Leu Arg Lys Val Ala Leu Ile Thr Gly Ile Thr
                20                  25                  30
Gly Gln Asp Gly Ser Tyr Leu Ala Glu Phe Leu Leu Glu Lys Gly Tyr
            35                  40                  45
Glu Val His Gly Ile Val Arg Arg Ser Ser Ser Phe Asn Thr Gly Arg
        50                  55                  60
Ile Glu His Leu Tyr Lys Asn Pro Gln Ala His Ile Glu Gly Asn Met
65                  70                  75                  80
Lys Leu His Tyr Gly Asp Leu Thr Asp Ser Thr Cys Leu Val Lys Ile
                85                  90                  95
Ile Asn Glu Val Lys Pro Thr Glu Ile Tyr Asn Leu Gly Ala Gln Ser
                100                 105                 110
His Val Lys Ile Ser Phe Asp Leu Ala Glu Tyr Thr Ala Asp Val Asp
            115                 120                 125
Gly Val Gly Thr Leu Arg Leu Leu Asp Ala Ile Lys Thr Cys Gly Leu
        130                 135                 140
Ile Asn Ser Val Lys Phe Tyr Gln Ala Ser Thr Ser Glu Leu Tyr Gly
145                 150                 155                 160
Lys Val Gln Glu Ile Pro Gln Lys Glu Thr Thr Pro Phe Tyr Pro Arg
                165                 170                 175
Ser Pro Tyr Gly Ala Ala Lys Leu Tyr Ala Tyr Trp Ile Val Val Asn
                180                 185                 190
Phe Arg Glu Ala Tyr Asn Leu Phe Ala Val Asn Gly Ile Leu Phe Asn
            195                 200                 205
His Glu Ser Pro Arg Arg Gly Ala Asn Phe Val Thr Arg Lys Ile Ser
        210                 215                 220
```

```
Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
        290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
                340                 345                 350

Glu Leu Val Arg Glu Met Val Gln Ala Asp Val Glu Leu Met Arg Thr
            355                 360                 365

Asn Pro Asn Ala
    370

<210> SEQ ID NO 137
<211> LENGTH: 372
<212> TYPE: PRT
<213> ORGANISM: Homo sapiens

<400> SEQUENCE: 137

Met Ala His Ala Pro Ala Arg Cys Pro Ser Ala Arg Gly Ser Gly Asp
1               5                   10                  15

Gly Glu Met Gly Lys Pro Arg Asn Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Val Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220
```

```
Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
            245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
            275                 280                 285

Phe Leu His Ile Gly Lys Thr Ile Val Trp Glu Gly Lys Asn Glu Asn
            290                 295                 300

Glu Val Gly Arg Cys Lys Glu Thr Gly Lys Val His Val Thr Val Asp
305                 310                 315                 320

Leu Lys Tyr Tyr Arg Pro Thr Glu Val Asp Phe Leu Gln Gly Asp Cys
                325                 330                 335

Thr Lys Ala Lys Gln Lys Leu Asn Trp Lys Pro Arg Val Ala Phe Asp
            340                 345                 350

Glu Leu Val Arg Glu Met Val His Ala Asp Val Glu Leu Met Arg Thr
            355                 360                 365

Asn Pro Asn Ala
    370

<210> SEQ ID NO 138
<211> LENGTH: 373
<212> TYPE: PRT
<213> ORGANISM: Ciona intestinalis

<400> SEQUENCE: 138

Met Ala Asp Ser Ser Cys Asn Gly Lys Arg Lys Asn Gly Asp Ser Cys
1               5                   10                  15

Asp Thr Glu Thr Lys Lys Gln Lys Lys Thr Ala Leu Val Thr Gly Ile
            20                  25                  30

Thr Gly Gln Asp Gly Ser Tyr Leu Ala Glu Leu Leu Ile Glu Lys Gly
        35                  40                  45

Tyr Glu Val His Gly Ile Ile Arg Arg Ala Ser Gln Pro Asn Thr Ala
50                  55                  60

Arg Ile Glu His Leu Tyr Ala Asp Arg Ala Thr His Lys Glu Gly Ser
65                  70                  75                  80

Met Lys Leu His Tyr Gly Asp Leu Thr Asp Ser Ser Cys Leu Val Lys
                85                  90                  95

Ile Ile Asn Gln Val Lys Pro Asn Glu Ile Tyr Asn Leu Gly Ala Met
            100                 105                 110

Ser His Val Lys Val Ser Phe Asp Leu Ala Glu Tyr Thr Ala Asp Val
            115                 120                 125

Asp Gly Val Gly Thr Leu Arg Leu Leu Asp Ala Ile Arg Thr Cys Gly
        130                 135                 140

Met Ser Asp Ser Val Arg Phe Tyr Gln Ala Ser Thr Ser Glu Met Phe
145                 150                 155                 160

Gly Lys Val Gln Glu Ile Pro Gln Lys Glu Thr Thr Pro Phe Tyr Pro
                165                 170                 175

Arg Ser Pro Tyr Ala Ala Ala Lys Val Tyr Ala Tyr Trp Ile Val Val
            180                 185                 190

Asn Tyr Arg Glu Ala Tyr Gly Met His Ala Ser Asn Gly Ile Leu Phe
            195                 200                 205

Asn His Glu Ser Pro Arg Arg Gly Phe Asn Phe Val Thr Arg Lys Ile
```

```
            210                 215                 220
Thr Arg Ser Val Ala Lys Ile His Leu Gly Leu Gln Glu Leu Ile Thr
225                 230                 235                 240

Leu Gly Asn Leu Asp Ser Lys Arg Asp Trp Gly His Ala Arg Asp Tyr
                245                 250                 255

Val Lys Gly Met Trp Met Met Met Gln His Asp Glu Pro Gly Asp Tyr
            260                 265                 270

Val Leu Ser Thr Asn Glu Thr His Ser Val Arg Glu Phe Val Glu Lys
        275                 280                 285

Ser Phe Lys His Ile Gly Val Glu Leu Glu Trp Gln Gly Glu Gly Val
    290                 295                 300

Asn Glu Ile Gly Val Asp Lys Ser Thr Gly Val Lys Arg Val Gln Ile
305                 310                 315                 320

Ser Glu Arg Tyr Tyr Arg Pro Thr Glu Val Glu Phe Leu Leu Gly Asp
                325                 330                 335

Tyr Ser Lys Ala Lys Lys Val Leu Gly Trp Ser Pro Asp Ile Lys Phe
            340                 345                 350

Asn Glu Leu Val Lys Glu Met Val Glu Ala Asp Ile Asn Leu Met Lys
        355                 360                 365

Lys Thr Pro Asn Ala
    370

<210> SEQ ID NO 139
<211> LENGTH: 379
<212> TYPE: PRT
<213> ORGANISM: Francisella sp. T Ala Leu Asn Leu Gln Asp Lys Leu Tyr Leu Gly Asn Leu Asp Ala Lys
210                 215                 220

Arg Asp Trp Gly His Ala Lys Asp Tyr Val Arg Met Met Trp Met Ile
225                 230                 235                 240

Leu Gln Ala Asp Gln Pro Glu Asp Trp Val Ile Ala Thr Gly Gln Thr
            245                 250                 255

Thr Thr Val Arg Asp Phe Val Lys Leu Ser Phe Ala Tyr Ala Gly Ile
        260                 265                 270

Asn Leu Arg Phe Glu Gly Glu Gly Val Asp Glu Ile Gly Val Val Asp
    275                 280                 285

Ser Val Asp Ser Ala Arg Ala Glu Arg Ala Gly Val Asp Leu Ser His
290                 295                 300

Ile Ser Glu Gly Gln Val Val Val Cys Val Asp Pro Arg Tyr Phe Arg
305                 310                 315                 320

Pro Thr Glu Val Asp Leu Leu Leu Gly Asp Pro Thr Lys Ala Glu Gln
            325                 330                 335

Lys Leu Gly Trp Ser Arg Glu Tyr Asp Leu Glu His Leu Val Asn Asp
        340                 345                 350

Met Met Glu Ser Asp Leu Lys Leu Met Thr Lys Asp Val Tyr Leu Lys
    355                 360                 365

Asp Gly Gly Tyr Lys Ile Met Ser Tyr Phe Glu
370                 375

<210> SEQ ID NO 140
<211> LENGTH: 379
<212> TYPE: PRT
<213> ORGANISM: Campylobacter coli 59-2

<400> SEQUENCE: 140

Met Lys Lys Val Ala Leu Ile Thr Gly Val Thr Gly Gln Asp Gly Ala
1               5                   10                  15

Tyr Leu Ser Glu Phe Leu Leu Asn Lys Gly Tyr Glu Val His Gly Ile
            20                  25                  30

Lys Arg Arg Ser Ser Leu Phe Asn Thr Asp Arg Ile Asp His Leu Phe
        35                  40                  45

Glu Gly His His Asn Lys Lys Asn Asp Phe Tyr Leu His Tyr Gly Asp
    50                  55                  60

Met Thr Asp Ser Met Asn Leu Thr Arg Ile Ile Ala Glu Ile Lys Pro
65                  70                  75                  80

Asp Glu Ile Tyr Asn Leu Ala Ala Met Ser His Val His Val Ser Phe
                85                  90                  95

Glu Thr Pro Glu Tyr Thr Ala Asn Ala Asp Gly Ile Gly Thr Leu Arg
            100                 105                 110

Ile Leu Asp Ala Val Arg Phe Leu Asn Leu Thr Gln Lys Thr Lys Ile
        115                 120                 125

Tyr Gln Ala Ser Thr Ser Glu Leu Phe Gly Lys Val Gln Glu Ile Pro
    130                 135                 140

Gln Asn Glu Lys Thr Pro Phe Tyr Pro Arg Ser Pro Tyr Ala Val Ala
145                 150                 155                 160

Lys Met Tyr Ala Tyr Trp Ile Thr Val Asn Tyr Arg Glu Ala Tyr Asp
                165                 170                 175

Met Phe Ala Cys Asn Gly Ile Leu Phe Asn His Glu Ser Pro Val Arg
            180                 185                 190

Gly Glu Thr Phe Val Thr Arg Lys Ile Thr Arg Ala Thr Ala Lys Ile
        195                 200                 205

```
Ala Leu Asn Leu Asp Asp Met Leu Tyr Leu Gly Asn Leu Asp Ala Lys
            210                 215                 220

Arg Asp Trp Gly His Ala Lys Asp Tyr Val Arg Met Met Trp Met Ile
225                 230                 235                 240

Leu Gln His Glu Lys Ala Asp Asp Trp Val Ile Ala Thr Gly Lys Thr
            245                 250                 255

Thr Thr Val Arg Asp Phe Val Lys Leu Ala Phe Glu Tyr Cys Gly Ile
            260                 265                 270

Lys Leu Asn Phe Lys Gly Val Gly Val Asp Glu Glu Gly Phe Ile Glu
            275                 280                 285

Asp Leu Asp Gln Gln Arg Ala Lys Glu Leu Ser Leu Ser Phe Asn His
            290                 295                 300

Leu Gln Lys Gly Gln Val Val Lys Val Asn Pro Arg Tyr Phe Arg
305                 310                 315                 320

Pro Thr Glu Val Asp Leu Leu Leu Gly Asp Pro Ser Lys Ala Glu Lys
            325                 330                 335

Glu Leu Gly Trp Asn Arg Glu Tyr Asp Leu Lys Asn Leu Val Asp Asp
            340                 345                 350

Met Met Glu Asn Asp Leu Lys Leu Met Thr Lys Asp Val Tyr Leu Lys
            355                 360                 365

Gln Gly Gly Tyr Lys Ile Met Arg Tyr Tyr Glu
    370                 375

<210> SEQ ID NO 141
<211> LENGTH: 373
<212> TYPE: PRT
<213> ORGANISM: Cellulophaga lytica DSM 7489

<400> SEQUENCE: 141

Met Ser Asp Lys Lys Val Ala Leu Ile Thr Gly Val Thr Gly Gln Asp
1               5                   10                  15

Gly Ala Tyr Leu Ser Glu Phe Leu Leu Lys Lys Gly Tyr Glu Val His
            20                  25                  30

Gly Leu Lys Arg Arg Ser Ser Leu Phe Asn Thr Asp Arg Ile Asp His
        35                  40                  45

Leu Tyr Gln Asp Pro His Ile Glu Asn Arg Asn Phe Ile Leu His Tyr
    50                  55                  60

Gly Asp Met Thr Asp Ser Thr Asn Leu Ile Arg Leu Ile Gln Glu Ile
65                  70                  75                  80

Gln Pro Asp Glu Ile Tyr Asn Leu Ala Ala Met Ser His Val His Val
                85                  90                  95

Ser Phe Glu Val Pro Glu Tyr Thr Ala Asn Ala Asp Gly Ile Gly Thr
            100                 105                 110

Leu Arg Ile Leu Asp Ala Val Arg Met Leu Gly Leu Ser Asn Lys Thr
        115                 120                 125

Arg Ile Tyr Gln Ala Ser Thr Ser Glu Leu Tyr Gly Lys Val Gln Glu
    130                 135                 140

Val Pro Gln Ser Glu Thr Thr Pro Phe Tyr Pro Arg Ser Pro Tyr Ala
145                 150                 155                 160

Val Ala Lys Met Tyr Ala Tyr Trp Ile Thr Val Asn Tyr Arg Glu Ala
                165                 170                 175

Tyr Asn Met Tyr Ala Cys Asn Gly Ile Leu Phe Asn His Glu Ser Pro
            180                 185                 190

Ile Arg Gly Glu Thr Phe Val Thr Arg Lys Ile Thr Arg Ala Thr Ala
```

```
                195                 200                 205
Lys Ile Ala Leu Gly Leu Gln Asp Lys Phe Tyr Leu Gly Asn Leu Asp
210                 215                 220

Ala Glu Arg Asp Trp Gly His Ala Lys Asp Tyr Val Arg Met Met Trp
225                 230                 235                 240

Met Ile Leu Gln Ala Asp Glu Pro Glu Asp Trp Val Ile Ala Thr Gly
            245                 250                 255

Lys Thr Thr Lys Val Arg Glu Phe Val Lys Met Ser Phe Ala Glu Ala
        260                 265                 270

Gly Ile Glu Leu Glu Phe Lys Gly Ser Gly Val Glu Glu Lys Ala Tyr
    275                 280                 285

Val Val Lys Cys Ser Asn Pro Asp Tyr Gln Leu Glu Ile Gly Lys Glu
290                 295                 300

Val Leu Ser Val Asp Pro Lys Tyr Phe Arg Pro Thr Glu Val Glu Leu
305                 310                 315                 320

Leu Ile Gly Asp Pro Thr Lys Ala Lys Thr Lys Leu Gly Trp Thr Val
            325                 330                 335

Glu Tyr Glu Leu Ala Asp Leu Val Lys Asp Met Val Gln Ser Asp Leu
        340                 345                 350

Lys Leu Met Gln Lys Glu Gln Tyr Leu Lys Asp Gly Tyr Arg Ile
    355                 360                 365

Leu Asn Tyr Phe Glu
    370

<210> SEQ ID NO 142
<211> LENGTH: 575
<212> TYPE: PRT
<213> ORGANISM: Bos taurus

<400> SEQUENCE: 142

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Pro Ala Ser
65                  70                  75                  80

Gly Arg Ile Arg Ala Leu Glu Glu Gln Leu Val Lys Ala Lys Glu Gln
                85                  90                  95

Ile Glu Asn Tyr Lys Lys Gln Thr Arg Asn Gly Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Asn Leu Glu Gly Asn Glu
    130                 135                 140

Leu Gln Arg His Ala Asp Glu Phe Leu Ser Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190
```

Arg Arg Ile Thr Tyr Leu Gln Asn Pro Lys Asp Cys Ser Lys Ala Lys
            195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser His Asn Trp Arg Tyr Ala Thr Gly Gly Trp Glu
            245                 250                 255

Thr Val Phe Arg Pro Val Ser Glu Thr Cys Thr Asp Arg Ser Gly Val
            260                 265                 270

Ser Thr Gly His Trp Ser Gly Glu Ile Lys Asp Lys Asn Val Gln Val
            275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
            325                 330                 335

Arg Pro Gln Pro Trp Leu Glu Lys Glu Ile Glu Glu Ala Thr Lys Lys
            340                 345                 350

Leu Gly Phe Lys His Pro Val Ile Gly Val His Val Arg Arg Thr Asp
            355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
            405                 410                 415

Ala Lys Thr Lys Tyr Pro His Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Ile Tyr Pro
            500                 505                 510

His Glu Pro Arg Thr Ala Asp Glu Ile Pro Met Glu Pro Gly Asp Ile
            515                 520                 525

Ile Gly Val Ala Gly Asn His Trp Asp Gly Tyr Ser Lys Gly Val Asn
530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
            565                 570                 575

<210> SEQ ID NO 143
<211> LENGTH: 575
<212> TYPE: PRT
<213> ORGANISM: Canis lupus familiaris

<400> SEQUENCE: 143

```
Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Ala Pro Ala Ser
65                  70                  75                  80

Gly Arg Val Arg Ala Leu Glu Glu Gln Leu Leu Lys Ala Lys Glu Gln
                85                  90                  95

Ile Glu Asn Tyr Lys Lys Gln Thr Arg Asn Gly Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys Asn Leu Glu Gly Asn Val
    130                 135                 140

Leu Gln Arg His Ala Asp Glu Phe Leu Ser Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Lys
        195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Asn Glu Thr Cys Thr Asp Arg Ser Gly Thr
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
            340                 345                 350

Leu Gly Phe Asn Ile Pro Val Ile Gly Val His Val Arg Arg Thr Asp
        355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Arg Arg Val Tyr Leu Ala Thr Asp Asp Pro Ser Leu Leu Lys Glu
                405                 410                 415
```

Ala Lys Thr Lys Tyr Pro Thr Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Ile Tyr Pro
        500                 505                 510

His Gln Pro Arg Thr Ala Asp Glu Ile Pro Met Glu Pro Gly Asp Ile
    515                 520                 525

Ile Gly Val Ala Gly Asn His Trp Asp Gly Tyr Ser Lys Gly Val Asn
530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
            565                 570                 575

<210> SEQ ID NO 144
<211> LENGTH: 599
<212> TYPE: PRT
<213> ORGANISM: Mus musculus

<400> SEQUENCE: 144

Leu Glu Pro Glu Tyr Asn Val Ser Ser Ser Leu Ser Ser Arg Lys Ile
1               5                   10                  15

Glu Asp Arg Val Glu Thr Leu Lys Met Arg Ala Trp Thr Gly Ser Trp
            20                  25                  30

Arg Trp Ile Met Leu Ile Leu Phe Ala Trp Gly Thr Leu Leu Phe Tyr
        35                  40                  45

Ile Gly Gly His Leu Val Arg Asp Asn Asp His Pro Asp His Ser Ser
    50                  55                  60

Arg Glu Leu Ser Lys Ile Leu Ala Lys Leu Glu Arg Leu Lys Gln Gln
65                  70                  75                  80

Asn Glu Asp Leu Arg Arg Met Ala Glu Ser Leu Arg Ile Pro Glu Gly
            85                  90                  95

Pro Ile Asp Gln Gly Thr Ala Thr Gly Arg Val Arg Val Leu Glu Glu
        100                 105                 110

Gln Leu Val Lys Ala Lys Glu Gln Ile Glu Asn Tyr Lys Lys Gln Ala
    115                 120                 125

Arg Asn Gly Leu Gly Lys Asp His Glu Ile Leu Arg Arg Arg Ile Glu
130                 135                 140

Asn Gly Ala Lys Glu Leu Trp Phe Phe Leu Gln Ser Glu Leu Lys Lys
145                 150                 155                 160

Leu Lys His Leu Glu Gly Asn Glu Leu Gln Arg His Ala Asp Glu Ile
            165                 170                 175

Leu Leu Asp Leu Gly His His Glu Arg Ser Ile Met Thr Asp Leu Tyr
        180                 185                 190

Tyr Leu Ser Gln Thr Asp Gly Ala Gly Asp Trp Arg Glu Lys Glu Ala
    195                 200                 205

Lys Asp Leu Thr Glu Leu Val Gln Arg Arg Ile Thr Tyr Leu Gln Asn
210                 215                 220

-continued

```
Pro Lys Asp Cys Ser Lys Ala Arg Lys Leu Val Cys Asn Ile Asn Lys
225                 230                 235                 240

Gly Cys Gly Tyr Gly Cys Gln Leu His His Val Val Tyr Cys Phe Met
            245                 250                 255

Ile Ala Tyr Gly Thr Gln Arg Thr Leu Ile Leu Glu Ser Gln Asn Trp
        260                 265                 270

Arg Tyr Ala Thr Gly Gly Trp Glu Thr Val Phe Arg Pro Val Ser Glu
    275                 280                 285

Thr Cys Thr Asp Arg Ser Gly Leu Ser Thr Gly His Trp Ser Gly Glu
290                 295                 300

Val Asn Asp Lys Asn Ile Gln Val Val Glu Leu Pro Ile Val Asp Ser
305                 310                 315                 320

Leu His Pro Arg Pro Pro Tyr Leu Pro Leu Ala Val Pro Glu Asp Leu
                325                 330                 335

Ala Asp Arg Leu Leu Arg Val His Gly Asp Pro Ala Val Trp Trp Val
            340                 345                 350

Ser Gln Phe Val Lys Tyr Leu Ile Arg Pro Gln Pro Trp Leu Glu Lys
        355                 360                 365

Glu Ile Glu Glu Ala Thr Lys Lys Leu Gly Phe Lys His Pro Val Ile
370                 375                 380

Gly Val His Val Arg Arg Thr Asp Lys Val Gly Thr Glu Ala Ala Phe
385                 390                 395                 400

His Pro Ile Glu Glu Tyr Met Val His Val Glu His Phe Gln Leu
                405                 410                 415

Leu Ala Arg Arg Met Gln Val Asp Lys Lys Arg Val Tyr Leu Ala Thr
            420                 425                 430

Asp Asp Pro Thr Leu Leu Lys Glu Ala Lys Thr Lys Tyr Ser Asn Tyr
            435                 440                 445

Glu Phe Ile Ser Asp Asn Ser Ile Ser Trp Ser Ala Gly Leu His Asn
450                 455                 460

Arg Tyr Thr Glu Asn Ser Leu Arg Gly Val Ile Leu Asp Ile His Phe
465                 470                 475                 480

Leu Ser Gln Ala Asp Phe Leu Val Cys Thr Phe Ser Ser Gln Val Cys
                485                 490                 495

Arg Val Ala Tyr Glu Ile Met Gln Thr Leu His Pro Asp Ala Ser Ala
            500                 505                 510

Asn Phe His Ser Leu Asp Asp Ile Tyr Tyr Phe Gly Gly Gln Asn Ala
        515                 520                 525

His Asn Gln Ile Ala Val Tyr Pro His Lys Pro Arg Thr Glu Glu Glu
530                 535                 540

Ile Pro Met Glu Pro Gly Asp Ile Gly Val Ala Gly Asn His Trp
545                 550                 555                 560

Asp Gly Tyr Ser Lys Gly Ile Asn Arg Lys Leu Gly Lys Thr Gly Leu
            565                 570                 575

Tyr Pro Ser Tyr Lys Val Arg Glu Lys Ile Glu Thr Val Lys Tyr Pro
            580                 585                 590

Thr Tyr Pro Glu Ala Glu Lys
        595
```

<210> SEQ ID NO 145
<211> LENGTH: 575
<212> TYPE: PRT
<213> ORGANISM: Rattus norvegicus

```
<400> SEQUENCE: 145

Met Arg Ala Trp Thr Gly Ser Trp Arg Trp Ile Met Leu Ile Leu Phe
 1               5                  10                  15

Ala Trp Gly Thr Leu Leu Phe Tyr Ile Gly Gly His Leu Val Arg Asp
             20                  25                  30

Asn Asp His Pro Asp His Ser Arg Glu Leu Ser Lys Ile Leu Ala
         35                  40                  45

Lys Leu Glu Arg Leu Lys Gln Gln Asn Glu Asp Leu Arg Arg Met Ala
 50                  55                  60

Glu Ser Leu Arg Ile Pro Glu Gly Pro Ile Asp Gln Gly Thr Ala Thr
 65                  70                  75                  80

Gly Arg Val Arg Val Leu Glu Glu Gln Leu Val Lys Ala Lys Glu Gln
                 85                  90                  95

Ile Glu Asn Tyr Lys Lys Gln Ala Arg Asn Gly Leu Gly Lys Asp His
            100                 105                 110

Glu Ile Leu Arg Arg Ile Glu Asn Gly Ala Lys Glu Leu Trp Phe
            115                 120                 125

Phe Leu Gln Ser Glu Leu Lys Lys Leu Lys His Leu Glu Gly Asn Glu
        130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ala Leu Leu Lys Glu
                405                 410                 415
```

```
Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
                500                 505                 510

His Lys Pro Arg Thr Asp Glu Glu Ile Pro Met Glu Pro Gly Asp Ile
            515                 520                 525

Ile Gly Val Ala Gly Asn His Trp Asp Gly Tyr Ser Lys Gly Val Asn
530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575
```

<210> SEQ ID NO 146
<211> LENGTH: 575
<212> TYPE: PRT
<213> ORGANISM: Cricetulus griseus

<400> SEQUENCE: 146

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
                20                  25                  30

Asn Asp His Pro Asp His Ser Ser Arg Glu Leu Ser Lys Ile Leu Ala
            35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
```

```
            210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
                260                 265                 270

Ser Thr Gly His Trp Ser Gly Glu Val Lys Asp Lys Asn Val Gln Val
                275                 280                 285

Val Glu Leu Pro Ile Val Asp Ser Leu His Pro Arg Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Thr Thr Lys Lys
                340                 345                 350

Leu Gly Phe Lys His Pro Val Ile Gly Val His Val Arg Arg Thr Asp
                355                 360                 365

Lys Val Gly Thr Glu Ala Ala Phe His Pro Ile Glu Glu Tyr Met Val
    370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
                420                 425                 430

Ser Trp Ser Ala Gly Leu His Asn Arg Tyr Thr Glu Asn Ser Leu Arg
                435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
                500                 505                 510

His Gln Pro Arg Thr Lys Glu Glu Ile Pro Met Glu Pro Gly Asp Ile
                515                 520                 525

Ile Gly Val Ala Gly Asn His Trp Asn Gly Tyr Ser Lys Gly Val Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 147
<211> LENGTH: 575
<212> TYPE: PRT
<213> ORGANISM: Gallus gallus

<400> SEQUENCE: 147

Met Arg Pro Trp Thr Gly Ser Trp Arg Trp Ile Met Leu Ile Leu Phe
1               5                   10                  15
```

```
Ala Trp Gly Thr Leu Leu Phe Tyr Ile Gly Gly His Leu Val Arg Asp
             20                  25                  30

Ser Glu His Pro Asp His Ser Ser Arg Glu Leu Ser Lys Ile Leu Ala
         35                  40                  45

Lys Leu Glu Arg Leu Lys Gln Gln Asn Glu Asp Leu Arg Arg Met Ala
 50                  55                  60

Glu Ser Leu Arg Ile Pro Asp Gly Pro Ile Asp Gln Gly Pro Ala Ala
 65                  70                  75                  80

Gly Lys Val His Ala Leu Glu Glu Gln Leu Lys Ala Lys Glu Gln
                 85                  90                  95

Ile Glu Asn Tyr Lys Lys Gln Thr Gly Asp Gly Leu Gly Lys Asp His
                100                 105                 110

Glu Ile Leu Arg Arg Ile Glu Asn Gly Ala Lys Glu Leu Trp Phe
            115                 120                 125

Phe Leu Gln Ser Glu Leu Lys Lys Leu Lys Asn Leu Glu Gly Ser Glu
 130                 135                 140

Leu Gln Arg Arg Ile Asp Glu Phe Leu Ser Asp Leu Gly His Gln Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Asp Leu Val Gln
            180                 185                 190

Arg Arg Ile Thr Tyr Leu Gln Asn Pro Lys Asp Cys Ser Lys Ala Lys
            195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Thr
            260                 265                 270

Thr Thr Gly His Trp Ser Gly Glu Thr Asn Asp Lys Asp Val Gln Val
            275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Ile Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Ala Thr Arg Lys
            340                 345                 350

Leu Gly Phe Lys His Pro Val Ile Gly Val His Val Arg Arg Thr Asp
            355                 360                 365

Lys Val Gly Thr Glu Ala Ala Phe His Pro Ile Glu Glu Tyr Met Val
            370                 375                 380

His Val Glu Glu Arg Phe Glu Leu Leu Ala Arg Arg Met His Val Asp
385                 390                 395                 400

Lys Lys Arg Val Tyr Leu Ala Thr Asp Asp Pro Ser Leu Leu Gln Glu
                405                 410                 415

Ala Lys Ser Lys Tyr Pro Asn Tyr Glu Phe Ile Ser Asp Asn Ser Ile
            420                 425                 430

Ser Trp Ser Ala Gly Leu His Asn Arg Tyr Thr Glu Asn Ser Leu Arg
```

```
                    435                 440                 445
Gly Val Ile Leu Asp Ile His Phe Leu Ser Gln Ala Asp Phe Leu Val
450                 455                 460

Cys Thr Phe Ser Ser Gln Val Cys Arg Val Pro Tyr Glu Ile Met Gln
465                 470                 475                 480

Thr Leu His Pro Asp Ala Ser Ala Tyr Phe His Ser Leu Asp Asp Ile
                485                 490                 495

Tyr Tyr Phe Gly Gly Gln Asn Ala His Asn Gln Ile Ala Val Tyr Ala
                500                 505                 510

His His Pro Arg Thr Ala Asp Glu Ile Pro Met Glu Pro Gly Asp Ile
                515                 520                 525

Ile Gly Val Ala Gly Asn His Trp Asp Gly Tyr Ser Lys Gly Ile Asn
530                 535                 540

Arg Lys Leu Gly Lys Thr Gly Leu Tyr Pro Ser Tyr Lys Val Lys Glu
545                 550                 555                 560

Lys Ile Glu Thr Val Lys Tyr Pro Thr Tyr Pro Glu Ala Glu Lys
                565                 570                 575

<210> SEQ ID NO 148
<211> LENGTH: 578
<212> TYPE: PRT
<213> ORGANISM: Xenopus (Silurana) tropicalis

<400> SEQUENCE: 148

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
                20                  25                  30

Asn Glu Asn Pro Asp His Ser Ser Arg Glu Leu Ser Lys Ile Leu Ala
                35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Glu Gln Gly Ala Ala Ala
65                  70                  75                  80

Gly Arg Ile Arg Ala Leu Glu Glu Gln Leu Leu Lys Ala Lys Glu Gln
                85                  90                  95

Ile Glu Met Tyr Lys Gln Gln Ser Ser Asn Ala Val Ser Gly Leu Gly
                100                 105                 110

Lys Asp His Glu Ile Leu Arg Arg Ala Ile Glu Asn Gly Ala Lys Glu
                115                 120                 125

Phe Trp Tyr Phe Val Gln Ser Glu Val Lys Lys Leu Lys His Leu Asp
                130                 135                 140

Arg Asn Glu Leu Gln Arg His Val Asp Glu Ile Ile Asp Met Gly
145                 150                 155                 160

His Gln Gln Arg Ser Val Met Thr Asp Leu Tyr Tyr Leu Ser Gln Thr
                165                 170                 175

Asp Gly Ala Gly Asp Trp Arg Glu Arg Glu Ala Lys Asp Leu Thr Asp
                180                 185                 190

Leu Val Gln Arg Arg Ile Thr Tyr Leu Gln Asn Pro Lys Asp Cys Ser
                195                 200                 205

Lys Ala Lys Lys Leu Val Cys Asn Ile Asn Lys Gly Cys Gly Tyr Gly
                210                 215                 220

Cys Gln Leu His His Val Val Tyr Cys Phe Met Ile Ala Tyr Gly Thr
225                 230                 235                 240
```

Gln Arg Thr Leu Ile Leu Glu Ser Gln Ser Trp Arg Tyr Ala Thr Gly
                245                 250                 255

Gly Trp Glu Thr Val Phe Lys Pro Val Ser Glu Thr Cys Thr Asp Arg
            260                 265                 270

Ser Gly Ser Ser Thr Gly His Trp Ser Gly Glu Ala Asn Asp Lys Asn
        275                 280                 285

Val Gln Val Val Glu Leu Pro Ile Val Asp Ser Leu His Pro Arg Pro
    290                 295                 300

Pro Tyr Leu Pro Leu Gly Val Pro Glu Asp Leu Ala Asp Arg Leu Ile
305                 310                 315                 320

Arg Leu His Gly Asp Pro Ala Val Trp Trp Val Ser Gln Phe Val Lys
                325                 330                 335

Tyr Leu Ile Arg Pro Gln Pro Trp Leu Glu Lys Glu Ile Glu Glu Ser
            340                 345                 350

Thr Lys Lys Leu Gly Phe Lys His Pro Val Ile Gly Val His Val Arg
        355                 360                 365

Arg Thr Asp Lys Val Gly Thr Glu Ala Ala Phe His Pro Ile Glu Glu
    370                 375                 380

Tyr Met Val His Val Glu Glu His Phe Gln Leu Leu Ala Arg Arg Met
385                 390                 395                 400

Gln Ile Asp Lys Lys Arg Val Tyr Leu Ala Thr Asp Asp Pro Thr Leu
                405                 410                 415

Leu Gln Glu Ala Lys Ala Lys Tyr Pro Gln Tyr Glu Phe Ile Ser Asp
            420                 425                 430

Asn Ser Ile Ser Trp Ser Ala Gly Leu His Asn Arg Tyr Thr Glu Asn
        435                 440                 445

Ser Leu Arg Gly Val Ile Leu Asp Ile His Phe Leu Ser Gln Ala Asp
    450                 455                 460

Phe Leu Val Cys Thr Phe Ser Ser Gln Val Cys Arg Val Ala Tyr Glu
465                 470                 475                 480

Ile Met Gln Thr Leu His Pro Asp Ala Ser His Phe His Ser Leu
                485                 490                 495

Asp Asp Ile Tyr Tyr Phe Gly Gly Gln Asn Ala His Asn Gln Leu Ala
            500                 505                 510

Ile Tyr Pro His Gln Pro Arg Asn Ala Glu Glu Ile Pro Leu Glu Pro
        515                 520                 525

Gly Asp Ile Ile Gly Val Ala Gly Asn His Trp Asp Gly Tyr Ser Lys
    530                 535                 540

Gly Ile Asn Arg Lys Leu Gly Arg Thr Gly Leu Tyr Pro Ser Tyr Lys
545                 550                 555                 560

Val Lys Glu Lys Ile Glu Thr Val Lys Tyr Pro Thr Tyr Gln Glu Ala
                565                 570                 575

Glu Lys

<210> SEQ ID NO 149
<211> LENGTH: 580
<212> TYPE: PRT
<213> ORGANISM: Danio rerio

<400> SEQUENCE: 149

Met Arg Pro Trp Thr Gly Ser Trp Arg Trp Ile Ala Leu Val Leu Leu
1               5                   10                  15

Ala Trp Gly Thr Leu Leu Phe Tyr Ile Gly Gly His Leu Val Lys Asp
            20                  25                  30

```
Ser Glu His Ala Pro Arg Ser Ser Arg Glu Leu Ala Lys Ile Leu Thr
         35                  40                  45

Lys Leu Glu Arg Leu Lys Gln Gln Asn Glu Asp Leu Arg Arg Met Ala
 50                  55                  60

Gln Ser Leu Arg Ile Pro Glu Gly Gln Ser Asp Gly Pro Ile Ser Ser
 65                  70                  75                  80

Gly Arg Leu Arg Ser Leu Glu Glu Gln Leu Ser Arg Ala Lys Gln Lys
                 85                  90                  95

Ile Gln Ser Phe Gln Arg Leu Ser Gly Glu Gly Pro Gly Lys Asp His
            100                 105                 110

Glu Glu Leu Arg Arg Lys Val Glu Asn Gly Val Arg Glu Leu Trp Tyr
            115                 120                 125

Phe Val Arg Ser Glu Val Lys Lys Leu Pro Leu Met Glu Thr Gly Ala
130                 135                 140

Met His Lys His Val Asp Thr Leu Met Gln Asp Leu Gly His Gln Gln
145                 150                 155                 160

Arg Ser Val Met Thr Asp Leu Tyr His Leu Ser Gln Ala Asp Gly Ala
                165                 170                 175

Gly Asp Trp Arg Glu Lys Glu Ala Asn Glu Leu Ser Asp Leu Val Gln
            180                 185                 190

Asn Arg Ile Met Tyr Leu Gln Asn Pro Gln Asp Cys Ser Lys Ala Arg
            195                 200                 205

Lys Leu Val Cys Asn Ile Asn Lys Gly Cys Gly Tyr Gly Cys Gln Leu
            210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Lys Pro Val Ser Asp Thr Cys Thr Asp Arg Thr Gly Ala
            260                 265                 270

Ser Thr Gly His Trp Ser Gly Glu Ala His Asp Arg Asp Val Gln Val
            275                 280                 285

Val Glu Leu Pro Ile Val Asp Ser Leu His Pro Arg Pro Pro Tyr Leu
290                 295                 300

Pro Leu Ala Val Pro Glu Asp Leu Ala Pro Arg Leu Gln Arg Leu His
305                 310                 315                 320

Gly Asp Pro Ser Val Trp Trp Val Ser Gln Phe Val Lys Phe Leu Val
                325                 330                 335

Arg Pro Gln Ala Trp Leu Glu Lys Glu Ile Gln Glu Thr Cys Leu Lys
            340                 345                 350

Leu Gly Phe Lys His Pro Ile Ile Gly Val His Val Arg Arg Thr Asp
            355                 360                 365

Lys Val Gly Thr Glu Ala Ala Phe His Pro Ile Glu Glu Tyr Met Val
370                 375                 380

His Val Glu Asp His Tyr Gln Ser Leu Ala Gln Arg Met His Val Asp
385                 390                 395                 400

Lys Lys Arg Val Tyr Leu Ala Thr Asp Asp Pro Ser Leu Leu Gln Glu
                405                 410                 415

Ala Lys Thr Lys Tyr Pro Asp Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Arg Thr Asn Tyr Leu Val
```

```
                450             455             460
Cys Thr Phe Ser Ser Gln Val Cys Arg Val Ala Tyr Glu Ile Met Gln
465                 470                 475                 480

Thr Leu His Pro Asp Ala Ser Ser Tyr Phe Tyr Ser Leu Asp Asp Ile
                    485                 490                 495

Tyr Tyr Phe Gly Gly Gln Asn Ala His Asn Gln Ile Ala Ile Tyr Pro
                500                 505                 510

His Gln Pro Arg Asn Ser Asp Asp Ile Pro Leu Glu Pro Gly Asp Val
            515                 520                 525

Ile Gly Val Ala Gly Asn His Trp Asp Gly Tyr Ser Lys Gly Ile Asn
        530                 535                 540

Arg Lys Thr Gly Arg Thr Gly Leu Tyr Pro Ser Tyr Lys Val Lys Glu
545                 550                 555                 560

Lys Ile Glu Thr Val Lys Tyr Pro Thr Tyr Pro Glu Ala Asp Lys Leu
                565                 570                 575

Leu Lys Lys Pro
            580

<210> SEQ ID NO 150
<211> LENGTH: 385
<212> TYPE: PRT
<213> ORGANISM: Ascaris suum

<400> SEQUENCE: 150

Met His His Asp Ser Lys Ile Thr Pro Val Ala Thr Ile His Leu Leu
1               5                   10                  15

Pro Lys Gly Leu Gly Arg Gly Leu Leu Gln Gln Phe Ala Met Lys
            20                  25                  30

Asn Gly Arg Gln His Glu Thr Leu Ala Gln Lys Ser Ile Lys Ile Val
        35                  40                  45

Leu Ala Val Ser Ala Tyr Trp Ile Cys Ser Ile Gly Leu Val Phe Leu
    50                  55                  60

Asn Lys Tyr Leu Leu Ser Ser Glu Asn Leu Lys Leu Asn Ala Pro Leu
65                  70                  75                  80

Phe Ile Thr Trp Tyr Gln Cys Leu Val Thr Val Val Leu Cys Tyr Thr
                85                  90                  95

Cys Ser Tyr Leu Ser Arg Ile Phe Pro Ser Arg Phe Ser Phe Pro Ser
            100                 105                 110

Ile Ala Phe Asp His Arg Ile Ser Arg Glu Val Leu Pro Leu Ser Phe
        115                 120                 125

Val Phe Val Ala Met Ile Thr Thr Asn Asn Leu Cys Leu Lys Tyr Val
    130                 135                 140

Gly Val Ser Phe Tyr Tyr Val Gly Arg Ser Leu Thr Thr Val Phe Asn
145                 150                 155                 160

Val Val Cys Ser Tyr Leu Ile Leu Gly Gln Gly Thr Ser Trp Arg Ala
                165                 170                 175

Leu Leu Cys Cys Ala Val Ile Ile Gly Gly Phe Phe Leu Gly Val Asp
            180                 185                 190

Gln Glu Asp Ala Ala Gly Ser Leu Ser Val Leu Gly Val Val Tyr Gly
        195                 200                 205

Val Ala Ala Ser Leu Cys Val Ala Leu Asn Ala Ile Tyr Thr Gln Arg
    210                 215                 220

Thr Leu Pro Ala Val Gly Asp Ser Val Ala Arg Leu Thr Met Tyr Asn
225                 230                 235                 240
```

-continued

```
Asn Thr Asn Ala Val Val Leu Phe Ile Pro Leu Met Leu Phe Ser Gly
                245                 250                 255

Glu Phe Gly Glu Ile Ile Tyr Phe Pro Tyr Leu Leu Ser Thr His Phe
            260                 265                 270

Trp Ala Leu Met Thr Ile Ser Gly Val Phe Gly Phe Leu Met Gly Tyr
            275                 280                 285

Val Thr Gly Trp Gln Ile Gln Val Thr Ser Pro Leu Thr His Asn Ile
            290                 295                 300

Ser Gly Thr Ala Lys Ala Ala Gln Thr Val Ile Ala Val Ala Trp
305                 310                 315                 320

Trp Gln Glu Val Lys Ser Val Leu Trp Trp Val Ser Asn Val Val Val
                325                 330                 335

Leu Gly Gly Ser Ala Ala Tyr Thr Ala Val Lys Arg Lys Glu Met Ile
            340                 345                 350

Ala Asn His Glu Ser Asn Ala Lys Pro Arg Gly Ser Val Ser Pro Asp
            355                 360                 365

Arg Glu Pro Ile Leu Ser Ser Lys Ser Ser Gly Asp Thr Ser Glu Asp
    370                 375                 380

Val
385

<210> SEQ ID NO 151
<211> LENGTH: 331
<212> TYPE: PRT
<213> ORGANISM: Loa loa

<400> SEQUENCE: 151

Met Ser Lys Tyr Ser Leu Ser Ser Tyr Thr Gly Lys Leu Leu Asn
1               5                   10                  15

Ala Pro Leu Phe Val Thr Trp Tyr Gln Cys Phe Val Thr Val Leu Leu
            20                  25                  30

Cys Cys Val Phe Cys Trp Val Ser Lys Gln Tyr Pro Ser Leu Val Thr
            35                  40                  45

Phe Pro Phe Val Gly Phe Asp His Arg Ile Ser Arg Glu Val Leu Pro
    50                  55                  60

Leu Ser Phe Val Phe Val Ala Met Ile Ala Thr Asn Asn Leu Cys Leu
65                  70                  75                  80

Lys Tyr Val Gly Val Ser Phe Tyr Tyr Ile Gly Arg Ser Leu Thr Thr
                85                  90                  95

Val Phe Asn Val Ile Cys Ser Tyr Ile Ile Leu Gly Gln Leu Thr Ser
            100                 105                 110

Leu Lys Thr Ile Leu Cys Cys Ala Leu Ile Ile Gly Phe Val Leu
            115                 120                 125

Gly Val Asp Gln Glu Asp Ala Thr Ala Gln Phe Leu Pro Arg Thr
    130                 135                 140

Phe Leu Gly Thr Leu Ser Val Thr Gly Val Ile Phe Gly Val Ala Ala
145                 150                 155                 160

Ser Met Phe Val Ala Leu Asn Ala Ile Tyr Thr Gln Arg Thr Leu Pro
                165                 170                 175

Ser Val Gly Asp Ser Ile Thr Gln Leu Thr Leu Tyr Asn Asn Ile Asn
            180                 185                 190

Ala Leu Val Leu Phe Ile Pro Val Met Leu Phe Ser Gly Asp Ile Ser
            195                 200                 205

Glu Val Phe Tyr Phe Arg Tyr Ser Ser Leu Arg Phe Trp Thr Leu
    210                 215                 220
```

-continued

```
Met Thr Leu Ser Gly Ile Phe Gly Phe Leu Met Ser Tyr Val Thr Gly
225                 230                 235                 240

Trp Gln Ile Gln Val Thr Ser Ser Leu Thr His Asn Ile Ser Gly Thr
                245                 250                 255

Ala Lys Ala Ala Ala Gln Thr Val Ile Ala Val Val Trp Trp Gln Glu
            260                 265                 270

Met Lys Ser Leu Leu Trp Trp Ile Ser Asn Val Ile Val Leu Gly Gly
        275                 280                 285

Ser Ala Ile Tyr Thr Met Ile Lys Arg Lys Glu Met Val Asp Lys Tyr
    290                 295                 300

Asp Thr Asn Lys Ser Lys Leu Asn Glu Asn Ile Glu Arg Gln Ala Val
305                 310                 315                 320

Leu Phe Gly Leu Ser Asp Glu Asp Glu Thr Val
                325                 330

<210> SEQ ID NO 152
<211> LENGTH: 363
<212> TYPE: PRT
<213> ORGANISM: Rattus norvegicus

<400> SEQUENCE: 152

Met Asn Arg Val Pro Leu Lys Arg Ser Arg Ile Leu Arg Met Ala Leu
1               5                   10                  15

Thr Gly Ala Ser Ala Val Ser Glu Glu Ala Asp Ser Glu Asn Lys Pro
            20                  25                  30

Phe Leu Leu Arg Ala Leu Gln Ile Ala Leu Val Val Ser Leu Tyr Trp
        35                  40                  45

Val Thr Ser Ile Ser Met Val Phe Leu Asn Lys Tyr Leu Leu Asp Ser
    50                  55                  60

Pro Ser Leu Gln Leu Asp Thr Pro Ile Phe Val Thr Phe Tyr Gln Cys
65                  70                  75                  80

Leu Val Thr Ser Leu Leu Cys Lys Gly Leu Ser Thr Leu Ala Thr Cys
                85                  90                  95

Cys Pro Gly Met Val Asp Phe Pro Thr Leu Asn Leu Asp Leu Lys Val
            100                 105                 110

Ala Arg Ser Val Leu Pro Leu Ser Val Val Phe Ile Gly Met Ile Thr
        115                 120                 125

Phe Asn Asn Leu Cys Leu Lys Tyr Val Gly Val Ala Phe Tyr Asn Val
    130                 135                 140

Gly Arg Ser Leu Thr Thr Val Phe Asn Val Leu Leu Ser Tyr Leu Leu
145                 150                 155                 160

Leu Lys Gln Thr Thr Ser Phe Tyr Ala Leu Leu Thr Cys Ala Ile Ile
                165                 170                 175

Ile Gly Gly Phe Trp Leu Gly Ile Asp Gln Glu Gly Ala Glu Gly Thr
            180                 185                 190

Leu Ser Leu Thr Gly Thr Ile Phe Gly Val Leu Ala Ser Leu Cys Val
        195                 200                 205

Ser Leu Asn Ala Ile Tyr Thr Lys Lys Val Leu Pro Ala Val Asp His
    210                 215                 220

Ser Ile Trp Arg Leu Thr Phe Tyr Asn Asn Val Asn Ala Cys Val Leu
225                 230                 235                 240

Phe Leu Pro Leu Met Val Val Leu Gly Glu Leu His Ala Leu Leu Ala
                245                 250                 255

Phe Ala His Leu Asn Ser Ala His Phe Trp Val Met Met Thr Leu Gly
```

```
                    260                 265                 270
Gly Leu Phe Gly Phe Ala Ile Gly Tyr Val Thr Gly Leu Gln Ile Lys
                275                 280                 285
Phe Thr Ser Pro Leu Thr His Asn Val Ser Gly Thr Ala Lys Ala Cys
            290                 295                 300
Ala Gln Thr Val Leu Ala Val Leu Tyr Tyr Glu Ile Lys Ser Phe
305                 310                 315                 320
Leu Trp Trp Thr Ser Asn Leu Met Val Leu Gly Gly Ser Ser Ala Tyr
                325                 330                 335
Thr Trp Val Arg Gly Trp Glu Met Gln Lys Thr Gln Glu Asp Pro Ser
            340                 345                 350
Ser Lys Glu Gly Glu Lys Ser Ala Ile Gly Val
            355                 360

<210> SEQ ID NO 153
<211> LENGTH: 365
<212> TYPE: PRT
<213> ORGANISM: Cricetulus griseus

<400> SEQUENCE: 153

Met Asn Arg Ala Pro Leu Lys Arg Ser Arg Ile Leu Arg Met Ala Leu
1               5                   10                  15
Thr Gly Gly Ser Thr Ala Ser Glu Glu Ala Asp Glu Asp Ser Arg Asn
                20                  25                  30
Lys Pro Phe Leu Leu Arg Ala Leu Gln Ile Ala Leu Val Val Ser Leu
            35                  40                  45
Tyr Trp Val Thr Ser Ile Ser Met Val Phe Leu Asn Lys Tyr Leu Leu
50                  55                  60
Asp Ser Pro Ser Leu Gln Leu Asp Thr Pro Ile Phe Val Thr Phe Tyr
65                  70                  75                  80
Gln Cys Leu Val Thr Ser Leu Leu Cys Lys Gly Leu Ser Thr Leu Ala
                85                  90                  95
Thr Cys Cys Pro Gly Thr Val Asp Phe Pro Thr Leu Asn Leu Asp Leu
            100                 105                 110
Lys Val Ala Arg Ser Val Leu Pro Leu Ser Val Val Phe Ile Gly Met
            115                 120                 125
Ile Ser Phe Asn Asn Leu Cys Leu Lys Tyr Val Gly Val Ala Phe Tyr
130                 135                 140
Asn Val Gly Arg Ser Leu Thr Thr Val Phe Asn Val Leu Leu Ser Tyr
145                 150                 155                 160
Leu Leu Leu Lys Gln Thr Thr Ser Phe Tyr Ala Leu Leu Thr Cys Gly
                165                 170                 175
Ile Ile Ile Gly Gly Phe Trp Leu Gly Ile Asp Gln Glu Gly Ala Glu
            180                 185                 190
Gly Thr Leu Ser Leu Ile Gly Thr Ile Phe Gly Val Leu Ala Ser Leu
            195                 200                 205
Cys Val Ser Leu Asn Ala Ile Tyr Thr Lys Lys Val Leu Pro Ala Val
            210                 215                 220
Asp Asn Ser Ile Trp Arg Leu Thr Phe Tyr Asn Asn Val Asn Ala Cys
225                 230                 235                 240
Val Leu Phe Leu Pro Leu Met Val Leu Leu Gly Glu Leu Arg Ala Leu
                245                 250                 255
Leu Asp Phe Ala His Leu Tyr Ser Ala His Phe Trp Leu Met Met Thr
            260                 265                 270
```

Leu Gly Gly Leu Phe Gly Phe Ala Ile Gly Tyr Val Thr Gly Leu Gln
            275                 280                 285

Ile Lys Phe Thr Ser Pro Leu Thr His Asn Val Ser Gly Thr Ala Lys
        290                 295                 300

Ala Cys Ala Gln Thr Val Leu Ala Val Leu Tyr Tyr Glu Thr Lys
305                 310                 315                 320

Ser Phe Leu Trp Trp Thr Ser Asn Leu Met Val Leu Gly Ser Ser
                325                 330                 335

Ala Tyr Thr Trp Val Arg Gly Trp Glu Met Gln Lys Thr Gln Glu Asp
            340                 345                 350

Pro Ser Ser Lys Glu Gly Glu Lys Ser Ala Ile Arg Val
        355                 360                 365

<210> SEQ ID NO 154
<211> LENGTH: 363
<212> TYPE: PRT
<213> ORGANISM: Mus musculus

<400> SEQUENCE: 154

Met Asn Arg Ala Pro Leu Lys Arg Ser Arg Ile Leu Arg Met Ala Leu
1               5                   10                  15

Thr Gly Val Ser Ala Val Ser Glu Glu Ser Glu Ser Gly Asn Lys Pro
            20                  25                  30

Phe Leu Leu Arg Ala Leu Gln Ile Ala Leu Val Val Ser Leu Tyr Trp
        35                  40                  45

Val Thr Ser Ile Ser Met Val Phe Leu Asn Lys Tyr Leu Leu Asp Ser
    50                  55                  60

Pro Ser Leu Gln Leu Asp Thr Pro Ile Phe Val Thr Phe Tyr Gln Cys
65                  70                  75                  80

Leu Val Thr Ser Leu Leu Cys Lys Gly Leu Ser Thr Leu Ala Thr Cys
                85                  90                  95

Cys Pro Gly Met Val Asp Phe Pro Thr Leu Asn Leu Asp Val Lys Val
            100                 105                 110

Ala Arg Ser Val Leu Pro Leu Ser Val Val Phe Ile Gly Met Ile Thr
        115                 120                 125

Phe Asn Asn Leu Cys Leu Lys Tyr Val Gly Val Pro Phe Tyr Asn Val
    130                 135                 140

Gly Arg Ser Leu Thr Thr Val Phe Asn Val Leu Leu Ser Tyr Leu Leu
145                 150                 155                 160

Leu Lys Gln Thr Thr Ser Phe Tyr Ala Leu Leu Thr Cys Gly Val Ile
                165                 170                 175

Ile Gly Gly Phe Trp Leu Gly Ile Asp Gln Glu Gly Ala Glu Gly Thr
            180                 185                 190

Leu Ser Leu Thr Gly Thr Ile Phe Gly Val Leu Ala Ser Leu Cys Val
        195                 200                 205

Ser Leu Asn Ala Ile Tyr Thr Lys Lys Val Leu Pro Ala Val Asp His
    210                 215                 220

Ser Ile Trp Arg Leu Thr Phe Tyr Asn Asn Val Asn Ala Cys Val Leu
225                 230                 235                 240

Phe Leu Pro Leu Met Ile Val Leu Gly Glu Leu Arg Ala Leu Leu Ala
                245                 250                 255

Phe Thr His Leu Ser Ser Ala His Phe Trp Leu Met Met Thr Leu Gly
            260                 265                 270

Gly Leu Phe Gly Phe Ala Ile Gly Tyr Val Thr Gly Leu Gln Ile Lys
        275                 280                 285

```
Phe Thr Ser Pro Leu Thr His Asn Val Ser Gly Thr Ala Lys Ala Cys
            290                 295                 300

Ala Gln Thr Val Leu Ala Val Leu Tyr Tyr Glu Ile Lys Ser Phe
305                 310                 315                 320

Leu Trp Trp Thr Ser Asn Leu Met Val Leu Gly Gly Ser Ser Ala Tyr
                    325                 330                 335

Thr Trp Val Arg Gly Trp Glu Met Gln Lys Thr Gln Glu Asp Pro Ser
                340                 345                 350

Ser Lys Asp Gly Glu Lys Ser Ala Ile Arg Val
                355                 360

<210> SEQ ID NO 155
<211> LENGTH: 350
<212> TYPE: PRT
<213> ORGANISM: Mus musculus

<400> SEQUENCE: 155

Met Ala Leu Thr Gly Val Ser Ala Val Ser Glu Glu Ser Glu Ser Gly
1               5                   10                  15

Asn Lys Pro Phe Leu Leu Arg Ala Leu Gln Ile Ala Leu Val Val Ser
                20                  25                  30

Leu Tyr Trp Val Thr Ser Ile Ser Met Val Phe Leu Asn Lys Tyr Leu
            35                  40                  45

Leu Asp Ser Pro Ser Leu Gln Leu Asp Thr Pro Ile Phe Val Thr Phe
        50                  55                  60

Tyr Gln Cys Leu Val Thr Ser Leu Leu Cys Lys Gly Leu Ser Thr Leu
65                  70                  75                  80

Ala Thr Cys Cys Pro Gly Met Val Asp Phe Pro Thr Leu Asn Leu Asp
                85                  90                  95

Leu Lys Val Ala Arg Ser Val Leu Pro Leu Ser Val Val Phe Ile Gly
            100                 105                 110

Met Ile Thr Phe Asn Asn Leu Cys Leu Lys Tyr Val Gly Val Pro Phe
        115                 120                 125

Tyr Asn Val Gly Arg Ser Leu Thr Thr Val Phe Asn Val Leu Leu Ser
    130                 135                 140

Tyr Leu Leu Leu Lys Gln Thr Thr Ser Phe Tyr Ala Leu Leu Thr Cys
145                 150                 155                 160

Gly Val Ile Ile Gly Gly Phe Trp Leu Gly Ile Asp Gln Glu Gly Ala
                165                 170                 175

Glu Gly Thr Leu Ser Leu Thr Gly Thr Ile Phe Gly Val Leu Ala Ser
            180                 185                 190

Leu Cys Val Ser Leu Asn Ala Ile Tyr Thr Lys Lys Val Leu Pro Ala
        195                 200                 205

Val Asp His Ser Ile Trp Arg Leu Thr Phe Tyr Asn Asn Val Asn Ala
    210                 215                 220

Cys Val Leu Phe Leu Pro Leu Met Ile Val Leu Gly Glu Leu Arg Ala
225                 230                 235                 240

Leu Leu Ala Phe Thr His Leu Ser Ser Ala His Phe Trp Leu Met Met
                245                 250                 255

Thr Leu Gly Gly Leu Phe Gly Phe Ala Ile Gly Tyr Val Thr Gly Leu
            260                 265                 270

Gln Ile Lys Phe Thr Ser Pro Leu Thr His Asn Val Ser Gly Thr Ala
        275                 280                 285

Lys Ala Cys Ala Gln Thr Val Leu Ala Val Leu Tyr Tyr Glu Glu Ile
```

290                 295                 300
Lys Ser Phe Leu Trp Trp Thr Ser Asn Leu Met Val Leu Gly Gly Ser
305                 310                 315                 320

Ser Ala Tyr Thr Trp Val Arg Gly Trp Glu Met Gln Lys Thr Gln Glu
                325                 330                 335

Asp Pro Ser Ser Lys Asp Gly Glu Lys Ser Ala Ile Arg Val
                340                 345                 350

<210> SEQ ID NO 156
<211> LENGTH: 365
<212> TYPE: PRT
<213> ORGANISM: Gallus gallus

<400> SEQUENCE: 156

Met Ser Arg Ser Gln Leu Thr Arg Thr Gly Ile Leu Arg Met Ala Leu
1               5                   10                  15

Gly Gly Ala Ala Asp Pro Leu Leu Pro Ala Glu Gly Ala Gly Gly Arg
                20                  25                  30

Arg Thr Pro Phe Val Leu Arg Ala Leu Arg Ile Ala Leu Val Val Ser
                35                  40                  45

Leu Tyr Trp Phe Val Ser Ile Thr Met Val Phe Leu Asn Lys Tyr Leu
50                  55                  60

Leu Asp Ser Pro Ser Leu Arg Leu Asp Ala Pro Leu Phe Val Thr Phe
65                  70                  75                  80

Phe Gln Cys Ala Val Thr Ala Ala Leu Cys Leu Gly Leu Ser Leu Gly
                85                  90                  95

Ala Ala Cys Gly Pro Cys Ala Ala Leu Pro Ala Leu Arg Leu Asp Leu
                100                 105                 110

Lys Val Ser Arg Ser Val Leu Pro Leu Ser Val Val Phe Ile Gly Met
                115                 120                 125

Val Thr Ser Asn Asn Leu Cys Leu Lys His Val Gly Val Ala Phe Tyr
130                 135                 140

Asn Val Gly Arg Ser Leu Thr Thr Val Phe Asn Val Leu Leu Ser Tyr
145                 150                 155                 160

Leu Leu Leu Lys Gln Thr Thr Ser Leu Tyr Ala Leu Ala Cys Gly
                165                 170                 175

Ile Ile Ile Gly Gly Phe Trp Leu Gly Val Asp Gln Glu Gly Ala Glu
                180                 185                 190

Gly Thr Leu Ser Trp Thr Gly Ile Ile Phe Gly Ile Leu Ala Ser Leu
                195                 200                 205

Cys Val Ser Leu Asn Ala Ile Tyr Thr Lys Lys Val Leu Pro Val Val
                210                 215                 220

Asp Gly Ser Ile Trp His Leu Thr Phe Tyr Asn Asn Met Asn Ala Cys
225                 230                 235                 240

Val Leu Phe Leu Pro Leu Met Met Ile Thr Gly Glu Phe His Thr Leu
                245                 250                 255

Tyr His Phe Asp Lys Leu Gly Ser Pro Ser Phe Trp Gly Met Met Thr
                260                 265                 270

Leu Gly Gly Val Phe Gly Phe Ala Ile Gly Tyr Val Thr Gly Leu Gln
                275                 280                 285

Ile Lys Phe Thr Ser Pro Leu Thr His Asn Val Ser Gly Thr Ala Lys
                290                 295                 300

Ala Cys Ala Gln Thr Val Leu Ala Val Val Tyr Phe Glu Glu Thr Lys
305                 310                 315                 320

Ser Leu Leu Trp Trp Thr Ser Asn Leu Met Val Leu Gly Gly Ser Phe
            325                 330                 335

Ala Tyr Thr Trp Val Lys Gly Leu Glu Met Arg Lys Ala Gln Glu Asp
        340                 345                 350

Pro Asn Leu Lys Ser Ser Glu Lys Asn Glu Thr Gly Val
            355                 360                 365

<210> SEQ ID NO 157
<211> LENGTH: 362
<212> TYPE: PRT
<213> ORGANISM: Xenopus (Silurana) tropicalis

<400> SEQUENCE: 157

Met Asn Phe Lys Arg Ser Ser Ile Leu Arg Met Ala Leu Met Gly Ala
1               5                   10                  15

Gly Glu Gly Asp Gln Glu Lys Val Ser Arg Glu Ser Phe Leu Val Arg
            20                  25                  30

Ala Val Lys Ile Ala Leu Val Val Thr Leu Tyr Trp Phe Ile Ser Ile
        35                  40                  45

Thr Met Val Phe Leu Asn Lys Tyr Leu Leu Asp Ser Pro Ser Leu Lys
    50                  55                  60

Leu Asp Ala Pro Leu Phe Val Thr Phe Tyr Gln Cys Val Val Thr Val
65                  70                  75                  80

Val Leu Cys Lys Gly Leu Ser Leu Leu Thr His Val Pro Ser His
                85                  90                  95

Ile Leu Glu Phe Pro Ser Leu Arg Phe Asp Leu Lys Val Leu Arg Thr
            100                 105                 110

Val Leu Pro Leu Ser Ile Val Phe Ile Gly Met Ile Thr Phe Asn Asn
        115                 120                 125

Leu Cys Leu Lys Tyr Leu Gly Val Ala Phe Tyr Thr Val Gly Arg Cys
    130                 135                 140

Leu Ser Thr Val Phe Asn Val Leu Leu Ser Tyr Ile Met Leu Lys Gln
145                 150                 155                 160

Thr Thr Ser Met Tyr Ala Leu Met Ser Cys Gly Val Ile Leu Gly Gly
                165                 170                 175

Phe Trp Leu Gly Ile Asp Gln Glu Gly Ala Glu Gly Thr Leu Ser Trp
            180                 185                 190

Ala Gly Ile Phe Phe Gly Val Leu Ala Ser Leu Cys Val Ser Leu Asn
        195                 200                 205

Ala Ile Tyr Thr Lys Lys Val Leu Pro Ala Val Asp Gly Ser Ile Trp
    210                 215                 220

Arg Leu Thr Phe Tyr Asn Asn Val Asn Ala Cys Phe Leu Phe Thr Pro
225                 230                 235                 240

Leu Leu Phe Ile Phe Gly Glu Val Gly Thr Leu Phe Thr Phe Asp Lys
                245                 250                 255

Leu Phe Ala Phe Ser Phe Trp Gly Met Met Thr Leu Gly Gly Ile Phe
            260                 265                 270

Gly Phe Ala Ile Gly Tyr Val Thr Gly Leu Gln Ile Gln Phe Thr Ser
        275                 280                 285

Pro Leu Thr His Asn Ile Ser Gly Thr Ala Lys Ala Cys Ala Gln Thr
    290                 295                 300

Val Leu Ala Val Met Tyr Tyr His Gln Ile Lys Ser Phe Leu Trp Trp
305                 310                 315                 320

Thr Ser Asn Leu Met Val Leu Gly Gly Ser Phe Ser Tyr Thr Trp Val
                325                 330                 335

Lys Gly Leu Glu Met Lys Lys Ser Gln Gly Glu Thr Asn Gln Ser Gln
                340                 345                 350

Ser Asn Gly Glu Lys Asn Ser Val Gly Val
            355                 360

<210> SEQ ID NO 158
<211> LENGTH: 348
<212> TYPE: PRT
<213> ORGANISM: Danio rerio

<400> SEQUENCE: 158

Met Ala Phe Thr Asp Ser Thr Arg Pro Gly Asp Lys Glu Pro Phe
1               5                   10                  15

Phe Met Arg Ala Thr Lys Ile Ala Leu Val Val Thr Leu Tyr Trp Phe
                20                  25                  30

Ile Ser Ile Ser Met Val Phe Leu Asn Asn Tyr Leu Leu Asp Ser Lys
                35                  40                  45

Glu Leu Asp Ala Pro Val Phe Ile Thr Phe Phe Gln Cys Val Val Ser
    50                  55                  60

Val Gly Leu Cys Leu Leu Met Ser Phe Leu Ser Ser Leu Cys Pro Gly
65                  70                  75                  80

Ser Val Asp Phe Pro Ser Leu Lys Phe Asp Leu Arg Val Ser Arg Glu
                85                  90                  95

Ile Leu Pro Leu Thr Ile Val Phe Ile Ser Met Ile Thr Phe Asn Asn
                100                 105                 110

Leu Cys Leu Lys Tyr Val Gly Val Ala Phe Tyr Thr Val Gly Arg Ser
                115                 120                 125

Leu Ser Thr Val Phe Asn Val Ile Leu Ser Tyr Val Val Leu Lys Gln
    130                 135                 140

Thr Thr Ser Leu Tyr Ala Val Leu Cys Cys Gly Val Ile Leu Gly Gly
145                 150                 155                 160

Phe Trp Leu Gly Val Asp Gln Glu Ala Val Ala Gly Ser Leu Ser Trp
                165                 170                 175

Ala Gly Val Val Phe Gly Val Ile Ala Ser Leu Cys Val Ser Leu Asn
                180                 185                 190

Ala Ile Phe Thr Lys Lys Val Leu Pro Val Val Asp Gly Asn Ile Trp
                195                 200                 205

Lys Leu Ser Tyr Tyr Asn Asn Leu Asn Ala Ile Val Leu Phe Leu Pro
    210                 215                 220

Leu Leu Ile Ile Leu Gly Glu Val Lys Ser Val Phe Glu Phe Ser Arg
225                 230                 235                 240

Leu Thr Asp Leu His Phe Trp Gly Met Met Thr Leu Gly Gly Val Phe
                245                 250                 255

Gly Phe Ala Ile Gly Tyr Val Thr Gly Leu Gln Ile Lys Phe Thr Ser
                260                 265                 270

Pro Leu Thr His Asn Val Ser Gly Thr Ala Lys Ser Cys Ala Gln Thr
                275                 280                 285

Val Leu Ala Val Tyr Trp Ala Ser Glu Lys Ser Thr Leu Trp Trp
    290                 295                 300

Thr Ser Asn Leu Met Val Leu Gly Gly Ser Phe Ala Tyr Thr Trp Val
305                 310                 315                 320

Lys Gly Met Glu Met Lys Lys Ala Pro Val Pro Thr Glu Thr Gln Ser
                325                 330                 335

Leu Asn Pro Gln Lys Asn Lys Glu Asp Leu Gly Val

<210> SEQ ID NO 159
<211> LENGTH: 364
<212> TYPE: PRT
<213> ORGANISM: Bos taurus

<400> SEQUENCE: 159

| | | | | | | | | | | | | | | |
|---|---|---|---|---|---|---|---|---|---|---|---|---|---|---|
| Met | Asn | Arg | Ala | Ser | Leu | Lys | Arg | Ser | Lys | Ile | Leu | His | Met | Ala | Leu |
| 1 | | | | 5 | | | | | 10 | | | | | 15 | |
| Met | Gly | Thr | Ser | Asp | Pro | Ser | Gly | Glu | Ala | Glu | Ala | Ser | Gln | Glu | Lys |
| | | | 20 | | | | | 25 | | | | | 30 | | |
| Pro | Phe | Val | Leu | Arg | Ala | Leu | Gln | Ile | Ala | Leu | Val | Val | Ser | Leu | Tyr |
| | | 35 | | | | | 40 | | | | | 45 | | | |
| Trp | Val | Thr | Ser | Ile | Ser | Met | Val | Phe | Leu | Asn | Lys | Tyr | Leu | Leu | Asp |
| | 50 | | | | | 55 | | | | | 60 | | | | |
| Ser | Pro | Ser | Leu | Arg | Leu | Asp | Thr | Pro | Ile | Phe | Val | Thr | Phe | Tyr | Gln |
| 65 | | | | | 70 | | | | | 75 | | | | | 80 |
| Cys | Leu | Val | Thr | Val | Leu | Leu | Cys | Lys | Gly | Leu | Ser | Ser | Leu | Ala | Thr |
| | | | | 85 | | | | | 90 | | | | | 95 | |
| Cys | Cys | Pro | Gly | Thr | Val | Asp | Phe | Pro | Ala | Leu | His | Leu | Asp | Leu | Lys |
| | | | 100 | | | | | 105 | | | | | 110 | | |
| Val | Ala | Arg | Ser | Val | Leu | Pro | Leu | Ser | Val | Val | Phe | Ile | Gly | Met | Ile |
| | | 115 | | | | | 120 | | | | | 125 | | | |
| Thr | Phe | Asn | Asn | Leu | Cys | Leu | Lys | Tyr | Val | Gly | Val | Ala | Phe | Tyr | Asn |
| | 130 | | | | | 135 | | | | | 140 | | | | |
| Val | Gly | Arg | Ser | Leu | Thr | Thr | Val | Phe | Asn | Val | Leu | Leu | Ser | Tyr | Leu |
| 145 | | | | | 150 | | | | | 155 | | | | | 160 |
| Leu | Leu | Lys | Gln | Thr | Thr | Ser | Phe | Tyr | Ala | Leu | Leu | Thr | Cys | Ser | Val |
| | | | | 165 | | | | | 170 | | | | | 175 | |
| Ile | Ile | Gly | Gly | Phe | Trp | Leu | Gly | Val | Asp | Gln | Glu | Gly | Ala | Glu | Gly |
| | | | 180 | | | | | 185 | | | | | 190 | | |
| Thr | Leu | Ser | Trp | Thr | Gly | Thr | Leu | Phe | Gly | Val | Leu | Ala | Ser | Leu | Cys |
| | | 195 | | | | | 200 | | | | | 205 | | | |
| Val | Ser | Leu | Asn | Ala | Ile | Tyr | Thr | Lys | Lys | Val | Leu | Pro | Ala | Val | Asp |
| | 210 | | | | | 215 | | | | | 220 | | | | |
| Gly | Ser | Ile | Trp | Arg | Leu | Thr | Phe | Tyr | Asn | Asn | Ala | Asn | Ala | Cys | Val |
| 225 | | | | | 230 | | | | | 235 | | | | | 240 |
| Leu | Phe | Leu | Pro | Leu | Leu | Leu | Ala | Leu | Gly | Glu | Leu | Arg | Ala | Leu | Leu |
| | | | | 245 | | | | | 250 | | | | | 255 | |
| Ala | Phe | Pro | Gln | Leu | Gly | Ser | Ala | His | Phe | Trp | Ala | Met | Met | Thr | Leu |
| | | | 260 | | | | | 265 | | | | | 270 | | |
| Gly | Gly | Leu | Phe | Gly | Phe | Ala | Ile | Gly | Tyr | Val | Thr | Gly | Leu | Gln | Ile |
| | | 275 | | | | | 280 | | | | | 285 | | | |
| Lys | Phe | Thr | Ser | Pro | Leu | Thr | His | Asn | Val | Ser | Gly | Thr | Ala | Lys | Ala |
| | 290 | | | | | 295 | | | | | 300 | | | | |
| Cys | Ala | Gln | Thr | Val | Leu | Ala | Val | Leu | Tyr | Tyr | Glu | Glu | Ala | Lys | Ser |
| 305 | | | | | 310 | | | | | 315 | | | | | 320 |
| Phe | Leu | Trp | Trp | Thr | Ser | Asn | Met | Met | Val | Leu | Gly | Gly | Ser | Ser | Ala |
| | | | | 325 | | | | | 330 | | | | | 335 | |
| Tyr | Thr | Trp | Val | Arg | Gly | Arg | Glu | Met | Lys | Lys | Thr | Gln | Glu | Glu | Pro |
| | | | 340 | | | | | 345 | | | | | 350 | | |
| His | Pro | Arg | Glu | Asn | Glu | Lys | Ser | Asn | Met | Glu | Val | | | | |
| | | | 355 | | | | | 360 | | | | | | | |

<210> SEQ ID NO 160
<211> LENGTH: 364
<212> TYPE: PRT
<213> ORGANISM: Canis lupus familiaris

<400> SEQUENCE: 160

Met Asn Arg Ala Pro Leu Lys Arg Ser Arg Ile Leu His Met Ala Leu
1               5                   10                  15

Met Gly Ala Ser Asp Pro Leu Gly Glu Ala Glu Ala Ile Lys Glu Lys
            20                  25                  30

Pro Phe Leu Leu Arg Ala Leu Gln Ile Thr Leu Val Val Ser Leu Tyr
        35                  40                  45

Trp Val Thr Ser Ile Ser Met Val Phe Leu Asn Lys Tyr Leu Leu Asp
    50                  55                  60

Ser Pro Ser Leu Gln Leu Asp Thr Pro Ile Phe Val Thr Phe Tyr Gln
65                  70                  75                  80

Cys Leu Val Thr Thr Leu Leu Cys Lys Ser Leu Ser Thr Leu Ala Ala
                85                  90                  95

Phe Cys Pro Gly Ala Met Asp Phe Pro Thr Leu Arg Leu Asp Leu Arg
            100                 105                 110

Val Ala Arg Ser Val Leu Pro Leu Ser Val Val Phe Ile Gly Met Ile
        115                 120                 125

Thr Phe Asn Asn Leu Cys Leu Lys Tyr Val Gly Val Ala Phe Tyr Asn
    130                 135                 140

Val Gly Arg Ser Leu Thr Thr Val Phe Asn Val Leu Leu Ser Tyr Leu
145                 150                 155                 160

Leu Leu Lys Gln Thr Thr Ser Phe Tyr Ala Leu Leu Thr Cys Gly Ile
                165                 170                 175

Ile Ile Gly Gly Phe Trp Leu Gly Val Asp Gln Glu Ala Glu Gly
            180                 185                 190

Thr Leu Ser Trp Thr Gly Thr Leu Phe Gly Val Leu Ala Ser Leu Cys
        195                 200                 205

Val Ser Leu Asn Ala Ile Tyr Thr Lys Lys Val Leu Pro Ala Val Asp
    210                 215                 220

Gly Ser Ile Trp Arg Leu Thr Phe Tyr Asn Asn Val Asn Ala Cys Val
225                 230                 235                 240

Leu Phe Leu Pro Leu Leu Leu Leu Gly Glu Leu Gln Thr Leu Leu
                245                 250                 255

Asn Phe Ser Gln Leu Gly Ser Ala His Phe Trp Gly Met Met Thr Leu
            260                 265                 270

Gly Gly Leu Phe Gly Phe Ala Ile Gly Tyr Val Thr Gly Leu Gln Ile
        275                 280                 285

Lys Phe Thr Ser Pro Leu Thr His Asn Val Ser Gly Thr Ala Lys Ala
    290                 295                 300

Cys Ala Gln Thr Val Leu Ala Val Leu Tyr Tyr Glu Glu Thr Lys Ser
305                 310                 315                 320

Phe Leu Trp Trp Thr Ser Asn Met Met Val Leu Gly Gly Ser Ser Ala
                325                 330                 335

Tyr Thr Val Arg Gly Trp Glu Met Lys Lys Ile Gly Glu Asp Pro
            340                 345                 350

Ser Pro Lys Glu Asp Glu Lys Ser Ser Met Gly Val
        355                 360

<210> SEQ ID NO 161

```
<211> LENGTH: 364
<212> TYPE: PRT
<213> ORGANISM: Homo sapiens

<400> SEQUENCE: 161

Met Asn Arg Ala Pro Leu Lys Arg Ser Arg Ile Leu His Met Ala Leu
1               5                   10                  15

Thr Gly Ala Ser Asp Pro Ser Ala Glu Ala Glu Ala Asn Gly Glu Lys
            20                  25                  30

Pro Phe Leu Arg Ala Leu Gln Ile Ala Leu Val Val Ser Leu Tyr
        35                  40                  45

Trp Val Thr Ser Ile Ser Met Val Phe Leu Asn Lys Tyr Leu Leu Asp
50                  55                  60

Ser Pro Ser Leu Arg Leu Asp Thr Pro Ile Phe Val Thr Phe Tyr Gln
65                  70                  75                  80

Cys Leu Val Thr Thr Leu Leu Cys Lys Gly Leu Ser Ala Leu Ala Ala
                85                  90                  95

Cys Cys Pro Gly Ala Val Asp Phe Pro Ser Leu Arg Leu Asp Leu Arg
            100                 105                 110

Val Ala Arg Ser Val Leu Pro Leu Ser Val Val Phe Ile Gly Met Ile
            115                 120                 125

Thr Phe Asn Asn Leu Cys Leu Lys Tyr Val Gly Val Ala Phe Tyr Asn
130                 135                 140

Val Gly Arg Ser Leu Thr Thr Val Phe Asn Val Leu Leu Ser Tyr Leu
145                 150                 155                 160

Leu Leu Lys Gln Thr Thr Ser Phe Tyr Ala Leu Leu Thr Cys Gly Ile
                165                 170                 175

Ile Ile Gly Gly Phe Trp Leu Gly Val Asp Gln Glu Gly Ala Glu Gly
            180                 185                 190

Thr Leu Ser Trp Leu Gly Thr Val Phe Gly Val Leu Ala Ser Leu Cys
            195                 200                 205

Val Ser Leu Asn Ala Ile Tyr Thr Thr Lys Val Leu Pro Ala Val Asp
            210                 215                 220

Gly Ser Ile Trp Arg Leu Thr Phe Tyr Asn Asn Val Asn Ala Cys Ile
225                 230                 235                 240

Leu Phe Leu Pro Leu Leu Leu Leu Gly Glu Leu Gln Ala Leu Arg
                245                 250                 255

Asp Phe Ala Gln Leu Gly Ser Ala His Phe Trp Gly Met Met Thr Leu
            260                 265                 270

Gly Gly Leu Phe Gly Phe Ala Ile Gly Tyr Val Thr Gly Leu Gln Ile
            275                 280                 285

Lys Phe Thr Ser Pro Leu Thr His Asn Val Ser Gly Thr Ala Lys Ala
            290                 295                 300

Cys Ala Gln Thr Val Leu Ala Val Leu Tyr Tyr Glu Glu Thr Lys Ser
305                 310                 315                 320

Phe Leu Trp Trp Thr Ser Asn Met Met Val Leu Gly Ser Ser Ala
                325                 330                 335

Tyr Thr Trp Val Arg Gly Trp Glu Met Lys Lys Thr Pro Glu Glu Pro
            340                 345                 350

Ser Pro Lys Asp Ser Glu Lys Ser Ala Met Gly Val
            355                 360

<210> SEQ ID NO 162
<211> LENGTH: 351
<212> TYPE: PRT
```

<213> ORGANISM: Homo sapiens

<400> SEQUENCE: 162

```
Met Ala Leu Thr Gly Ala Ser Asp Pro Ser Ala Glu Ala Glu Ala Asn
1               5                   10                  15
Gly Glu Lys Pro Phe Leu Leu Arg Ala Leu Gln Ile Ala Leu Val Val
            20                  25                  30
Ser Leu Tyr Trp Val Thr Ser Ile Ser Met Val Phe Leu Asn Lys Tyr
        35                  40                  45
Leu Leu Asp Ser Pro Ser Leu Arg Leu Asp Thr Pro Ile Phe Val Thr
    50                  55                  60
Phe Tyr Gln Cys Leu Val Thr Thr Leu Leu Cys Lys Gly Leu Ser Ala
65                  70                  75                  80
Leu Ala Ala Cys Cys Pro Gly Ala Val Asp Phe Pro Ser Leu Arg Leu
                85                  90                  95
Asp Leu Arg Val Ala Arg Ser Val Leu Pro Leu Ser Val Val Phe Ile
            100                 105                 110
Gly Met Ile Thr Phe Asn Asn Leu Cys Leu Lys Tyr Val Gly Val Ala
            115                 120                 125
Phe Tyr Asn Val Gly Arg Ser Leu Thr Thr Val Phe Asn Val Leu Leu
    130                 135                 140
Ser Tyr Leu Leu Leu Lys Gln Thr Thr Ser Phe Tyr Ala Leu Leu Thr
145                 150                 155                 160
Cys Gly Ile Ile Ile Gly Gly Phe Trp Leu Gly Val Asp Gln Glu Gly
                165                 170                 175
Ala Glu Gly Thr Leu Ser Trp Leu Gly Thr Val Phe Gly Val Leu Ala
            180                 185                 190
Ser Leu Cys Val Ser Leu Asn Ala Ile Tyr Thr Thr Lys Val Leu Pro
            195                 200                 205
Ala Val Asp Gly Ser Ile Trp Arg Leu Thr Phe Tyr Asn Asn Val Asn
    210                 215                 220
Ala Cys Ile Leu Phe Leu Pro Leu Leu Leu Leu Gly Glu Leu Gln
225                 230                 235                 240
Ala Leu Arg Asp Phe Ala Gln Leu Gly Ser Ala His Phe Trp Gly Met
            245                 250                 255
Met Thr Leu Gly Gly Leu Phe Gly Phe Ala Ile Gly Tyr Val Thr Gly
            260                 265                 270
Leu Gln Ile Lys Phe Thr Ser Pro Leu Thr His Asn Val Ser Gly Thr
            275                 280                 285
Ala Lys Ala Cys Ala Gln Thr Val Leu Ala Val Leu Tyr Tyr Glu Glu
    290                 295                 300
Thr Lys Ser Phe Leu Trp Trp Thr Ser Asn Met Met Val Leu Gly Gly
305                 310                 315                 320
Ser Ser Ala Tyr Thr Trp Val Arg Gly Trp Glu Met Lys Lys Thr Pro
                325                 330                 335
Glu Glu Pro Ser Pro Lys Asp Ser Glu Lys Ser Ala Met Gly Val
            340                 345                 350
```

<210> SEQ ID NO 163
<211> LENGTH: 1263
<212> TYPE: DNA
<213> ORGANISM: Trichoderma reesei

<400> SEQUENCE: 163

```
atggcgtcac tcatcaaaac tgccgtggac attgccaacg ccgccatgc gctgtccaga    60
```

```
tatgtcatct ttgggctctg gcttgcggat gcggtgctgt gcgggctgat tatctggaaa      120
gtgccttata cggaaatcga ctgggtcgcc tacatggagc aagtcaccca gttcgtccac      180
ggagagcgag actacccaa gatggagggc ggcacagggc ccctggtgta cccgcggcc        240 catgtgtaca tctacacagg gctctactac ctgacgaaca agggcaccga catcctgctg      300
gcgcagcagc tctttgccgt gctctacatg gctactctgg cggtcgtcat gacatgctac      360
tccaaggcca aggtcccgcc gtacatcttc ccgcttctca tcctctccaa aagacttcac      420
agcgtcttcg tcctgagatg cttcaacgac tgcttcgccg ccttcttcct ctggctctgc      480
atcttcttct tccagaggcg agagtggacc atcggagctc tcgcatacag catcggcctg      540
ggcgtcaaaa tgtcgctgct actggttctc cccgccgtgg tcatcgtcct ctacctcggc      600
cgcggcttca agggcgccct gcggctgctc tggctcatgg tgcaggtcca gctcctcctc      660
gccataccct tcatcacgac aaattggcgc ggctacctcg gccgtgcatt cgagctctcg      720
aggcagttca gtttgaatg acagtcaat tggcgcatgc tgggcgagga tctgttcctc        780
agccggggct tctctatcac gctactggca tttcacgcca tcttcctcct cgcctttatc      840
ctcggccggt ggctgaagat tagggaacgg accgtactcg ggatgatccc ctatgtcatc      900
cgattcagat cgcccttac cgagcaggaa gagcgcgcca tctccaaccg cgtcgtcacg       960
cccggctatg tcatgtccac catcttgtcg gccaacgtgg tgggactgct gtttgcccgg      1020
tctctgcact accagttcta tgcatatctg gcgtgggcga ccccctatct cctgtggacg      1080
gcctgcccca tctttttggt ggtggccccc ctctgggcgg cgcaagaatg ggcctggaac      1140
gtcttcccca gcacgcctct tagctcgagc gtcgtggtga gcgtgctggc cgtgacggtg      1200
gccatggcgt ttgcaggttc aaatccgcag ccacgtgaaa catcgaagcc gaagcagcac      1260
taa                                                                    1263
```

<210> SEQ ID NO 164
<211> LENGTH: 420
<212> TYPE: PRT
<213> ORGANISM: Trichoderma reesei

<400> SEQUENCE: 164

```
Met Ala Ser Leu Ile Lys Thr Ala Val Asp Ile Ala Asn Gly Arg His
1               5                   10                  15

Ala Leu Ser Arg Tyr Val Ile Phe Gly Leu Trp Leu Ala Asp Ala Val
            20                  25                  30

Leu Cys Gly Leu Ile Ile Trp Lys Val Pro Tyr Thr Glu Ile Asp Trp
        35                  40                  45

Val Ala Tyr Met Glu Gln Val Thr Gln Phe Val His Gly Glu Arg Asp
    50                  55                  60

Tyr Pro Lys Met Glu Gly Gly Thr Gly Pro Leu Val Tyr Pro Ala Ala
65                  70                  75                  80

His Val Tyr Ile Tyr Thr Gly Leu Tyr Leu Thr Asn Lys Gly Thr
                85                  90                  95

Asp Ile Leu Leu Ala Gln Gln Leu Phe Ala Val Leu Tyr Met Ala Thr
            100                 105                 110

Leu Ala Val Val Met Thr Cys Tyr Ser Lys Ala Lys Val Pro Pro Tyr
        115                 120                 125

Ile Phe Pro Leu Leu Ile Leu Ser Lys Arg Leu His Ser Val Phe Val
    130                 135                 140

Leu Arg Cys Phe Asn Asp Cys Phe Ala Ala Phe Phe Leu Trp Leu Cys
```

-continued

```
            145                 150                 155                 160
Ile Phe Phe Gln Arg Arg Glu Trp Thr Ile Gly Ala Leu Ala Tyr
                165                 170                 175

Ser Ile Gly Leu Gly Val Lys Met Ser Leu Leu Val Leu Pro Ala
            180                 185                 190

Val Val Ile Val Leu Tyr Leu Gly Arg Gly Phe Lys Gly Ala Leu Arg
        195                 200                 205

Leu Leu Trp Leu Met Val Gln Val Gln Leu Leu Ala Ile Pro Phe
        210                 215                 220

Ile Thr Thr Asn Trp Arg Gly Tyr Leu Gly Arg Ala Phe Glu Leu Ser
225                 230                 235                 240

Arg Gln Phe Lys Phe Glu Trp Thr Val Asn Trp Arg Met Leu Gly Glu
                245                 250                 255

Asp Leu Phe Leu Ser Arg Gly Phe Ser Ile Thr Leu Leu Ala Phe His
            260                 265                 270

Ala Ile Phe Leu Leu Ala Phe Ile Leu Gly Arg Trp Leu Lys Ile Arg
        275                 280                 285

Glu Arg Thr Val Leu Gly Met Ile Pro Tyr Val Ile Arg Phe Arg Ser
    290                 295                 300

Pro Phe Thr Glu Gln Glu Arg Ala Ile Ser Asn Arg Val Val Thr
305                 310                 315                 320

Pro Gly Tyr Val Met Ser Thr Ile Leu Ser Ala Asn Val Val Gly Leu
                325                 330                 335

Leu Phe Ala Arg Ser Leu His Tyr Gln Phe Tyr Ala Tyr Leu Ala Trp
            340                 345                 350

Ala Thr Pro Tyr Leu Leu Trp Thr Ala Cys Pro Asn Leu Leu Val Val
        355                 360                 365

Ala Pro Leu Trp Ala Ala Gln Glu Trp Ala Trp Asn Val Phe Pro Ser
    370                 375                 380

Thr Pro Leu Ser Ser Val Val Val Ser Val Leu Ala Val Thr Val
385                 390                 395                 400

Ala Met Ala Phe Ala Gly Ser Asn Pro Gln Pro Arg Glu Thr Ser Lys
                405                 410                 415

Pro Lys Gln His
            420

<210> SEQ ID NO 165
<211> LENGTH: 445
<212> TYPE: PRT
<213> ORGANISM: Homo sapiens

<400> SEQUENCE: 165

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
                20                  25                  30

Ala Pro Gly Arg Pro Pro Ser Val Ser Ala Leu Asp Gly Asp Pro Ala
            35                  40                  45

Ser Leu Thr Arg Glu Val Ile Arg Leu Ala Gln Asp Ala Glu Val Glu
        50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Pro Ala Gln Pro Arg
                85                  90                  95
```

```
Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
            130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
            195                 200                 205

Glu Asp Asp Leu Glu Val Ala Pro Asp Phe Phe Glu Tyr Phe Arg Ala
            210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
            275                 280                 285

Asp Asp Trp Met Arg Arg Pro Glu Gln Arg Gln Gly Arg Ala Cys Ile
290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
            355                 360                 365

Gln Val Glu Lys Val Arg Thr Asn Asp Arg Lys Glu Leu Gly Glu Val
            370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Leu Thr Trp Glu Gly Tyr Asp Pro Ser Trp Asn
            435                 440                 445

<210> SEQ ID NO 166
<211> LENGTH: 447
<212> TYPE: PRT
<213> ORGANISM: Homo sapiens

<400> SEQUENCE: 166

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30
```

```
Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
            115                 120                 125

Glu Tyr Leu Arg Leu Leu Leu Asp Ser Leu Arg Lys Ala Gln Gly Ile
        130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln
        435                 440                 445
```

-continued

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
agcgagctgt gcctcttgga                                                     20

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
agtcgagcac ttgcgcgacc t                                                   21

<210> SEQ ID NO 169
<211> LENGTH: 21
<212> TYPE: DNA
<213> ORGANISM: Artificial Sequence
<220> FEATURE:
<223> OTHER INFORMATION: Primer

<400> SEQUENCE: 169
tttgttgcca tattttcctg c                                                   21

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
ttgccagtga tacacatggg                                                     20

<210> SEQ ID NO 171
<211> LENGTH: 10
<212> TYPE: PRT
<213> ORGANISM: Trichoderma reesei

<400> SEQUENCE: 171

Met Ala Ser Thr Asn Ala Arg Tyr Val Arg
1               5                   10

<210> SEQ ID NO 172
<211> LENGTH: 17
<212> TYPE: PRT
<213> ORGANISM: Trichoderma reesei

<400> SEQUENCE: 172

Tyr Leu Leu Ile Ala Phe Phe Thr Ile Leu Val Phe Tyr Phe Val Ser
1               5                   10                  15

Asn

<210> SEQ ID NO 173
<211> LENGTH: 379
<212> TYPE: PRT
<213> ORGANISM: Trichoderma reesei

<400> SEQUENCE: 173

```
Ser Lys Tyr Glu Gly Val Asp Leu Asn Lys Gly Thr Phe Thr Ala Pro
1               5                   10                  15

Asp Ser Thr Lys Thr Thr Pro Lys Pro Pro Ala Thr Gly Asp Ala Lys
            20                  25                  30

Asp Phe Pro Leu Ala Leu Thr Pro Asn Asp Pro Gly Phe Asn Asp Leu
                35                  40                  45

Val Gly Ile Ala Pro Gly Pro Arg Met Asn Ala Thr Phe Val Thr Leu
    50                  55                  60

Ala Arg Asn Ser Asp Val Trp Asp Ile Ala Arg Ser Ile Arg Gln Val
65                  70                  75                  80

Glu Asp Arg Phe Asn Arg Arg Tyr Asn Tyr Asp Trp Val Phe Leu Asn
                85                  90                  95

Asp Lys Pro Phe Asp Asn Thr Phe Lys Lys Val Thr Thr Ser Leu Val
                100                 105                 110

Ser Gly Lys Thr His Tyr Gly Glu Ile Ala Pro Glu His Trp Ser Phe
            115                 120                 125

Pro Asp Trp Ile Asp Gln Asp Lys Ala Lys Lys Val Arg Glu Asp Met
    130                 135                 140

Ala Glu Arg Lys Ile Ile Tyr Gly Asp Ser Val Ser Tyr Arg His Met
145                 150                 155                 160

Cys Arg Phe Glu Ser Gly Phe Phe Arg Gln Pro Leu Met Met Asn
                165                 170                 175

Tyr Glu Tyr Tyr Trp Arg Val Glu Pro Ser Ile Glu Leu Tyr Cys Asp
                180                 185                 190

Ile His Tyr Asp Pro Phe Arg Leu Met Val Glu Gln Gly Lys Lys Tyr
            195                 200                 205

Ser Phe Val Ile Ser Leu Tyr Glu Tyr Pro Ala Thr Ile Ala Thr Leu
210                 215                 220

Trp Glu Ser Thr Lys Lys Phe Met Lys Asn His Pro Glu His Ile Ala
225                 230                 235                 240

Pro Asp Asn Ser Met Arg Phe Leu Ser Asp Asp Gly Gly Glu Thr Tyr
                245                 250                 255

Asn Asn Cys His Phe Trp Ser Asn Phe Glu Ile Gly Ser Leu Glu Trp
                260                 265                 270

Leu Arg Ser Lys Gln Tyr Ile Asp Phe Phe Glu Ser Leu Asp Lys Asp
                275                 280                 285

Gly Gly Phe Phe Tyr Glu Arg Trp Gly Asp Ala Pro Val His Ser Ile
            290                 295                 300

Ala Ala Gly Leu Met Leu Asn Arg Ser Glu Ile His Phe Phe Asn Asp
305                 310                 315                 320

Ile Ala Tyr Trp His Val Pro Phe Thr His Cys Pro Thr Gly Glu Lys
                325                 330                 335

Thr Arg Leu Asp Leu Lys Cys His Cys Asp Pro Lys Glu Asn Phe Asp
                340                 345                 350

Trp Lys Gly Tyr Ser Cys Thr Ser Arg Phe Phe Glu Met Asn Gly Met
            355                 360                 365

Asp Lys Pro Glu Gly Trp Glu Asn Gln Gln Asp
    370                 375
```

<210> SEQ ID NO 174
<211> LENGTH: 8
<212> TYPE: PRT
<213> ORGANISM: Trichoderma reesei

<400> SEQUENCE: 174

Met Ala Ile Ala Arg Pro Val Arg
1               5

<210> SEQ ID NO 175
<211> LENGTH: 15
<212> TYPE: PRT
<213> ORGANISM: Trichoderma reesei

<400> SEQUENCE: 175

Ala Leu Gly Gly Leu Ala Ala Ile Leu Trp Cys Phe Phe Leu Tyr
1               5                   10                  15

<210> SEQ ID NO 176
<211> LENGTH: 371
<212> TYPE: PRT
<213> ORGANISM: Trichoderma reesei

<400> SEQUENCE: 176

Gln Leu Leu Arg Pro Ser Ser Tyr Asn Ser Pro Gly Asp Arg Tyr
1               5                   10                  15

Ile Asn Phe Glu Arg Asp Pro Asn Leu Asp Pro Thr Gly Glu Pro Glu
            20                  25                  30

Gly Ile Leu Val Arg Thr Ser Asp Arg Tyr Ala Pro Asp Ala Lys Asp
        35                  40                  45

Thr Asp Arg Ala Ser Ala Thr Leu Leu Ala Leu Val Arg Asn Glu Glu
50                  55                  60

Val Asp Asp Met Val Ala Ser Met Val Asp Leu Glu Arg Thr Trp Asn
65                  70                  75                  80

Ser Lys Phe Asn Tyr Pro Trp Thr Phe Phe Asn Asp Lys Pro Phe Ser
                85                  90                  95

Glu Glu Phe Lys Lys Lys Thr Ser Ala Val Thr Asn Ala Thr Cys Asn
            100                 105                 110

Tyr Glu Leu Ile Pro Lys Glu His Trp Asp Ala Pro Ser Trp Ile Asp
        115                 120                 125

Pro Ala Ile Phe Glu Glu Ser Ala Ala Val Leu Lys Lys Asn Gly Val
130                 135                 140

Gln Tyr Ala Asn Met Met Ser Tyr His Gln Met Cys Arg Trp Asn Ser
145                 150                 155                 160

Gly Met Phe Tyr Lys His Pro Ala Leu Lys Asp Val Arg Tyr Tyr Trp
                165                 170                 175

Arg Val Glu Pro Lys Val His Phe Phe Cys Asp Val Tyr Asp Val
            180                 185                 190

Phe Arg Tyr Met Gln Asp Asn Asn Lys Thr Tyr Gly Phe Thr Ile Asn
        195                 200                 205

Leu Tyr Asp Asp Pro His Thr Leu Pro Thr Leu Trp Pro Gln Thr Ala
210                 215                 220

Lys Phe Leu Ala Asp His Pro Asn Tyr Leu His Glu His Ser Ala Ile
225                 230                 235                 240

Lys Trp Val Ile Asp Asp Ala Arg Arg Pro Gln His Asn Arg Glu Ala
                245                 250                 255

Gln Gly Phe Ser Thr Cys His Phe Trp Ser Asn Phe Glu Val Ala Asp
            260                 265                 270

Met Glu Phe Trp Arg Ser Lys Val Tyr Glu Asp Tyr Phe Glu His Leu
        275                 280                 285

Asp Arg Ala Gly Gly Phe Phe Tyr Glu Arg Trp Gly Asp Ala Pro Val

```
            290                 295                 300
His Ser Ile Ala Leu Gly Leu Phe Glu Asp Ser Ser Lys Ile His Trp
305                 310                 315                 320

Phe Arg Asp Ile Gly Tyr Gln His Ile Pro Phe Phe Asn Cys Pro Asn
                325                 330                 335

Ser Pro Lys Cys Lys Gly Cys Val Thr Gly Arg Leu Thr Asp Gly Glu
                340                 345                 350

Pro Phe Leu His Arg Glu Asp Cys Arg Pro Asn Trp Phe Lys Tyr Ala
            355                 360                 365

Gly Met Gly
        370

<210> SEQ ID NO 177
<211> LENGTH: 6
<212> TYPE: PRT
<213> ORGANISM: Trichoderma reesei

<400> SEQUENCE: 177

Met Leu Asn Pro Arg Arg
1               5

<210> SEQ ID NO 178
<211> LENGTH: 15
<212> TYPE: PRT
<213> ORGANISM: Trichoderma reesei

<400> SEQUENCE: 178

Ala Leu Ile Ala Ala Ala Phe Ile Leu Thr Val Phe Phe Leu Ile
1               5                   10                  15

<210> SEQ ID NO 179
<211> LENGTH: 352
<212> TYPE: PRT
<213> ORGANISM: Trichoderma reesei

<400> SEQUENCE: 179

Ser Arg Ser His Asn Ser Glu Ser Ala Ser Thr Ser Glu Pro Lys Asp
1               5                   10                  15

Ala Glu Ala Glu Ala Leu Ser Ala Ala Asn Ala Gln Gln Arg Ala Ala
                20                  25                  30

Pro Pro Pro Pro Pro Gln Lys Pro Met Ile Asp Met Ser Gly Met Ser
                35                  40                  45

Thr Tyr Asp Lys Leu Ala Tyr Ala Tyr Glu Tyr Asp Ile Glu Ser Lys
            50                  55                  60

Phe Pro Ala Tyr Ile Trp Gln Thr Trp Arg Lys Thr Pro Ser Glu Gly
65              70                  75                  80

Asp Phe Glu Phe Arg Glu Gln Glu Ala Ser Trp Ser Ile Glu His Pro
                85                  90                  95

Gly Phe Ile His Glu Val Ile Thr Asp Ser Val Ala Asp Thr Leu Leu
                100                 105                 110

Gln Leu Leu Tyr Gly Ser Ile Pro Glu Val Leu Glu Ala Tyr His Ala
            115                 120                 125

Leu Pro Leu Pro Val Leu Lys Ala Asp Leu Phe Arg Tyr Leu Ile Leu
            130                 135                 140

Tyr Ala Arg Gly Gly Ile Tyr Ser Asp Ile Asp Thr Tyr Ala Ile Arg
145             150                 155                 160

Ser Ala Leu Glu Trp Ile Pro Pro Gln Ile Pro Lys Glu Thr Val Gly
                165                 170                 175
```

```
Leu Val Ile Gly Ile Glu Ala Asp Pro Asp Arg Pro Asp Trp Ala Asp
                180                 185                 190

Trp Tyr Ser Arg Arg Ile Gln Phe Cys Gln Trp Thr Ile Gln Ser Lys
            195                 200                 205

Pro Gly His Pro Val Leu Arg Asp Ile Ile Ser Arg Ile Thr Asn Gln
        210                 215                 220

Thr Leu Glu Met Lys Lys Ser Gly Lys Leu Ser Ala Phe Gln Gly Asn
225                 230                 235                 240

Arg Val Val Asp Leu Thr Gly Pro Ala Val Trp Thr Asp Thr Ile Met
                245                 250                 255

Asp Tyr Phe Asn Asp Glu Arg Tyr Phe Asp Met Glu Asn Ser Lys Gly
            260                 265                 270

Arg Ile Asp Tyr Arg Asn Phe Thr Gly Met Glu Thr Ser Lys Arg Val
        275                 280                 285

Gly Asp Val Val Leu Pro Ile Thr Ser Phe Ser Pro Gly Val Gly
290                 295                 300

Gln Met Gly Ala Lys Asp Tyr Asp Pro Met Ala Phe Val Lys His
305                 310                 315                 320

Asp Phe Glu Gly Thr Trp Lys Pro Glu Ser Glu Arg His Ile Gly Glu
            325                 330                 335

Ile Val Gln Glu Leu Gly Glu Gly Gln Gly Glu Ala Pro Lys Glu Gln
                340                 345                 350
```

<210> SEQ ID NO 180
<211> LENGTH: 22
<212> TYPE: PRT
<213> ORGANISM: Trichoderma reesei

<400> SEQUENCE: 180

```
Met Gly Met Gly Gln Cys Gln Trp Ser Pro Phe Arg Asn Lys Val Pro
1               5                   10                  15

Thr Gln Met Arg Arg Cys
            20
```

<210> SEQ ID NO 181
<211> LENGTH: 15
<212> TYPE: PRT
<213> ORGANISM: Trichoderma reesei

<400> SEQUENCE: 181

```
Leu Pro Leu Tyr Ile Thr Val Val Cys Val Phe Leu Val Ile Val
1               5                   10                  15
```

<210> SEQ ID NO 182
<211> LENGTH: 362
<212> TYPE: PRT
<213> ORGANISM: Trichoderma reesei

<400> SEQUENCE: 182

```
Asn Phe Asp Trp Ile Leu Ala Ile Pro Asn Pro Ala Ser Val Leu Arg
1               5                   10                  15

Arg Glu Pro Lys Ala Pro Pro Leu Pro Gly Ser Thr Phe Pro Gln Lys
            20                  25                  30

Ile Trp Gln Thr Trp Lys Val Asp Pro Leu Asn Phe Asp Glu Arg Asp
        35                  40                  45

Leu Val Thr Ala Arg Thr Trp Thr Thr Ile Asn Pro Gly Met Arg Tyr
50                  55                  60
```

```
Glu Val Val Thr Asp Ala Asn Glu Met Ala Tyr Ile Glu Asp Arg Tyr
 65                  70                  75                  80

Gly Pro Asn Gly Phe Asp Arg Pro Asp Ile Val Glu Phe Tyr Lys Met
                 85                  90                  95

Ile Asn Leu Pro Ile Ile Lys Ala Asp Leu Leu Arg Tyr Met Ile Met
            100                 105                 110

Tyr Ala Glu Gly Gly Ile Tyr Ala Asp Ile Asp Val Glu Thr Met Lys
        115                 120                 125

Pro Phe His Arg Phe Ile Pro Asp Arg Tyr Asp Glu Lys Asp Ile Asp
    130                 135                 140

Ile Ile Ile Gly Val Glu Ile Asp Gln Pro Asp Phe Lys Asp His Pro
145                 150                 155                 160

Ile Leu Gly Lys Lys Ser Met Ser Phe Cys Gln Trp Thr Phe Val Ala
                165                 170                 175

Arg Pro Gln Gln Pro Val Met Met Arg Leu Ile Glu Asn Ile Met Lys
            180                 185                 190

Trp Phe Lys Thr Val Ala Arg Asp Gln Gly Val Pro Leu Gly Glu Val
        195                 200                 205

Gln Leu Asp Phe Asp Gln Val Ile Ser Gly Thr Gly Pro Ser Ala Phe
    210                 215                 220

Thr Lys Ala Met Leu Glu Glu Met Asn Arg Lys Thr Lys Gly Pro Lys
225                 230                 235                 240

Val Thr Trp Asp Ala Phe His Asn Leu Asp Glu Ser Lys Leu Val Gly
                245                 250                 255

Gly Val Leu Val Leu Thr Val Glu Ala Phe Cys Ala Gly Gln Gly His
            260                 265                 270

Ser Asp Ser Gly Asn His Asn Ala Arg Asn Ala Leu Val Lys His His
        275                 280                 285

Phe His Ala Ser Asn Trp Pro Ser Arg His Pro Arg Tyr Lys His Pro
    290                 295                 300

Ala Tyr Gly Gln Val Glu Asp Cys Asn Trp Val Pro Glu Cys Val Arg
305                 310                 315                 320

Lys Trp Asp Glu Asp Thr Ser Asn Trp Asp Lys Tyr Ser Glu Asn Glu
                325                 330                 335

Gln Lys Lys Ile Leu Gln Asp Ile Glu Asn Ala Arg Leu Glu Arg Glu
            340                 345                 350

Arg Gln Gln Gln Ala Leu Ala Ala Leu Pro
        355                 360

<210> SEQ ID NO 183
<211> LENGTH: 17
<212> TYPE: PRT
<213> ORGANISM: Trichoderma reesei

<400> SEQUENCE: 183

Met Ala Arg Pro Met Gly Ser Val Arg Leu Lys Lys Ala Asn Pro Ser
1               5                   10                  15

Thr

<210> SEQ ID NO 184
<211> LENGTH: 16
<212> TYPE: PRT
<213> ORGANISM: Trichoderma reesei

<400> SEQUENCE: 184

Leu Ile Leu Gly Ala Val Leu Cys Ile Phe Ile Ile Ile Phe Leu Val
```

-continued

<210> SEQ ID NO 185
<211> LENGTH: 339
<212> TYPE: PRT
<213> ORGANISM: Trichoderma reesei

<400> SEQUENCE: 185

Ser Pro Ser Ser Pro Ala Ser Ala Ser Arg Leu Ser Ile Val Ser Ala
1               5                   10                  15

Gln His His Leu Ser Pro Pro Thr Ser Pro Tyr Gln Ser Pro Arg Ser
            20                  25                  30

Gly Ala Val Gln Gly Pro Pro Val Thr Arg Tyr Asn Leu Asn Lys
        35                  40                  45

Val Thr Val Thr Ser Asp Pro Val Arg Asn Gln Glu His Ile Leu Ile
    50                  55                  60

Leu Thr Pro Met Ala Arg Phe Tyr Gln Glu Tyr Trp Asp Asn Leu Leu
65                  70                  75                  80

Arg Leu Asn Tyr Pro His Glu Leu Ile Thr Leu Gly Phe Ile Leu Pro
                85                  90                  95

Lys Thr Lys Glu Gly Asn Gln Ala Thr Ser Met Leu Gln Lys Gln Ile
            100                 105                 110

Gln Lys Thr Gln Asn Tyr Gly Pro Glu Lys Asp Arg Phe Lys Ser Ile
        115                 120                 125

Ile Ile Leu Arg Gln Asp Phe Asp Pro Ala Val Val Ser Gln Asp Glu
130                 135                 140

Ser Glu Arg His Lys Leu Ala Asn Gln Lys Ala Arg Arg Glu Val Met
145                 150                 155                 160

Ala Lys Ala Arg Asn Ser Leu Leu Phe Thr Thr Leu Gly Pro Ser Thr
                165                 170                 175

Ser Trp Val Leu Trp Leu Asp Ala Asp Ile Thr Glu Thr Ala Pro Thr
            180                 185                 190

Leu Ile Gln Asp Leu Ala Ser His Asp Lys Pro Ile Ile Val Ala Asn
        195                 200                 205

Cys Phe Gln Lys Tyr Tyr Asp Pro Glu Ser Lys Lys Met Ala Glu Arg
    210                 215                 220

Pro Tyr Asp Phe Asn Ser Trp Gln Asp Ser Glu Thr Ala Leu Lys Met
225                 230                 235                 240

Ala Glu Gln Met Gly Pro Asp Asp Ile Leu Leu Glu Gly Tyr Ala Glu
                245                 250                 255

Met Ala Thr Tyr Arg Thr Leu Leu Ala Tyr Met Ser Thr Pro Gly Gly
            260                 265                 270

Ser Lys Asp Leu Val Val Pro Leu Asp Gly Val Gly Thr Ala Leu
        275                 280                 285

Leu Val Lys Ala Asp Val His Arg Asp Gly Ala Met Phe Pro Pro Phe
290                 295                 300

Ala Phe Tyr His Leu Ile Glu Ser Glu Gly Phe Ala Lys Met Ala Lys
305                 310                 315                 320

Arg Leu Gly Trp Gln Pro Tyr Gly Leu Pro Asn Tyr Lys Val Tyr His
                325                 330                 335

Tyr Asn Glu

<210> SEQ ID NO 186
<211> LENGTH: 31
<212> TYPE: PRT

<213> ORGANISM: Trichoderma reesei

<400> SEQUENCE: 186

Met Leu Leu Pro Lys Gly Gly Leu Asp Trp Arg Ser Ala Arg Ala Gln
1               5                   10                  15

Ile Pro Pro Thr Arg Ala Leu Trp Asn Ala Val Thr Arg Thr Arg
            20                  25                  30

<210> SEQ ID NO 187
<211> LENGTH: 15
<212> TYPE: PRT
<213> ORGANISM: Trichoderma reesei

<400> SEQUENCE: 187

Phe Ile Leu Leu Val Gly Ile Thr Gly Leu Ile Leu Leu Leu Trp
1               5                   10                  15

<210> SEQ ID NO 188
<211> LENGTH: 358
<212> TYPE: PRT
<213> ORGANISM: Trichoderma reesei

<400> SEQUENCE: 188

Arg Gly Val Ser Thr Ser Ala Ser Glu Met Gln Ser Phe Tyr Cys Trp
1               5                   10                  15

Gly Pro Ala Lys Pro Pro Met Glu Met Ser Pro Asn Glu His Asn Arg
            20                  25                  30

Trp Asn Gly His Leu Gln Thr Pro Val Ile Phe Asn His His Ala Pro
        35                  40                  45

Val Glu Val Asn Ser Ser Thr Ile Glu His Val Asp Leu Asn Pro Ile
50                  55                  60

Asn Ser Thr Lys Gln Ala Val Thr Lys Glu Arg Ile Leu Ile Leu
65                  70                  75                  80

Thr Pro Leu Lys Asp Ala Ala Pro Tyr Leu Ser Lys Tyr Phe Glu Leu
                85                  90                  95

Leu Ala Glu Leu Thr Tyr Pro His Arg Leu Ile Asp Leu Ala Phe Leu
            100                 105                 110

Val Ser Asp Ser Thr Asp Asp Thr Leu Ala Val Leu Ala Ser Glu Leu
        115                 120                 125

Asp Arg Ile Gln Lys Arg Pro Asp Gln Ile Pro Phe His Ser Ala Thr
130                 135                 140

Val Ile Glu Lys Asp Phe Gly Phe Lys Leu Ser Gln Asn Val Glu Glu
145                 150                 155                 160

Arg His Ser Phe Glu Ala Gln Gly Pro Arg Arg Lys Ala Met Gly Arg
                165                 170                 175

Ala Arg Asn Tyr Leu Leu Tyr Thr Ala Leu Lys Pro Glu His Ser Trp
            180                 185                 190

Val Tyr Trp Arg Asp Val Asp Ile Val Asp Ser Pro Thr Gly Ile Leu
        195                 200                 205

Glu Asp Phe Ile Ala His Asp Arg Asp Ile Leu Val Pro Asn Ile Trp
210                 215                 220

Phe His Arg Tyr Arg Asp Gly Val Asp Ile Glu Gly Arg Phe Asp Tyr
225                 230                 235                 240

Asn Ser Trp Val Glu Ser Asp Lys Gly Arg Lys Leu Ala Asn Ser Leu
                245                 250                 255

Asp Lys Asp Val Val Leu Ala Glu Gly Tyr Lys Gln Tyr Asp Thr Gly
            260                 265                 270

```
Arg Thr Tyr Met Ala Lys Met Gly Asp Trp Arg Glu Asn Lys Asp Val
            275                 280                 285

Glu Leu Glu Leu Asp Gly Ile Gly Gly Val Asn Ile Leu Val Lys Ala
            290                 295                 300

Asp Val His Arg Ser Gly Ile Asn Phe Pro Cys Tyr Ala Phe Glu Asn
305                 310                 315                 320

Gln Ala Glu Thr Glu Gly Phe Ala Lys Met Ala Lys Arg Ala Gly Tyr
                325                 330                 335

Glu Val Tyr Gly Leu Pro Asn Tyr Val Val Trp His Ile Asp Thr Glu
            340                 345                 350

Glu Lys Gly Gly Asn Ala
            355

<210> SEQ ID NO 189
<211> LENGTH: 45
<212> TYPE: PRT
<213> ORGANISM: Trichoderma reesei

<400> SEQUENCE: 189

Met Met Pro Arg His His Ser Ser Gly Phe Ser Asn Gly Tyr Pro Arg
1               5                   10                  15

Ala Asp Thr Phe Glu Ile Ser Pro His Arg Phe Gln Pro Arg Ala Thr
            20                  25                  30

Leu Pro Pro His Arg Lys Arg Lys Arg Thr Ala Ile Arg
        35                  40                  45

<210> SEQ ID NO 190
<211> LENGTH: 16
<212> TYPE: PRT
<213> ORGANISM: Trichoderma reesei

<400> SEQUENCE: 190

Val Gly Ile Ala Val Val Ile Leu Val Leu Val Leu Trp Phe Gly
1               5                   10                  15

<210> SEQ ID NO 191
<211> LENGTH: 407
<212> TYPE: PRT
<213> ORGANISM: Trichoderma reesei

<400> SEQUENCE: 191

Gln Pro Arg Ser Val Ala Ser Leu Ile Ser Leu Gly Ile Leu Ser Gly
1               5                   10                  15

Tyr Asp Asp Leu Lys Leu Glu Thr Val Arg Tyr Tyr Asp Leu Ser Asn
            20                  25                  30

Val Gln Gly Thr Ala Arg Gly Trp Glu Arg Glu Glu Arg Ile Leu Leu
        35                  40                  45

Cys Val Pro Leu Arg Asp Ala Glu Gln His Leu Pro Met Phe Phe Ser
    50                  55                  60

His Leu Lys Asn Phe Thr Tyr Pro His Asn Leu Ile Asp Leu Ala Phe
65                  70                  75                  80

Leu Val Ser Asp Ser Lys Asp His Thr Leu Glu Ser Leu Thr Glu His
                85                  90                  95

Leu Glu Ala Ile Gln Ala Asp Pro Asp Pro Lys Gln Pro Tyr Gly Glu
            100                 105                 110

Ile Ser Ile Ile Glu Lys Asp Phe Gly Gln Lys Val Asn Gln Asp Val
        115                 120                 125
```

```
Glu Ser Arg His Gly Phe Ala Ala Gln Ala Ser Arg Arg Lys Leu Met
130                 135                 140

Ala Gln Ala Arg Asn Trp Leu Leu Ser Ala Ala Leu Arg Pro Tyr His
145                 150                 155                 160

Ser Trp Val Tyr Trp Arg Asp Val Asp Val Glu Thr Ala Pro Phe Thr
                165                 170                 175

Ile Leu Glu Asp Leu Met Arg His Asn Lys Asp Val Ile Val Pro Asn
                180                 185                 190

Val Trp Arg Pro Leu Pro Asp Trp Leu Gly Gly Glu Gln Pro Tyr Asp
                195                 200                 205

Leu Asn Ser Trp Gln Glu Ser Glu Thr Ala Leu Ala Leu Ala Asp Thr
210                 215                 220

Leu Asp Glu Asp Ala Val Ile Val Glu Gly Tyr Ala Glu Tyr Ala Thr
225                 230                 235                 240

Trp Arg Pro His Leu Ala Tyr Leu Arg Asp Pro Tyr Gly Asp Pro Asp
                245                 250                 255

Met Glu Met Glu Ile Asp Gly Val Gly Gly Val Ser Ile Leu Ala Lys
                260                 265                 270

Ala Lys Val Phe Arg Ala Gly Val His Phe Pro Ala Phe Ser Phe Glu
            275                 280                 285

Lys His Ala Glu Thr Glu Gly Phe Gly Lys Met Ala Lys Arg Met His
        290                 295                 300

Phe Ser Val Val Gly Leu Pro His Tyr Thr Ile Trp His Leu Tyr Glu
305                 310                 315                 320

Pro Ser Val Asp Asp Ile Lys His Met Glu Glu Met Glu Arg Glu Arg
                325                 330                 335

Ile Ala Arg Glu Lys Glu Glu Glu Arg Lys Lys Lys Glu Ala Gln
                340                 345                 350

Ile Lys Glu Glu Phe Gly Asp Ala Asn Ser Gln Trp Glu Gln Asp Lys
            355                 360                 365

Gln Gln Met Gln Asp Leu Lys Leu Gln Asp Arg Gly Gly Asp Lys Glu
        370                 375                 380

Ala Ala Ala Ala Gly Val Asn Gln Gly Ala Ala Ala Lys Ala Ala Gly
385                 390                 395                 400

Ala Met Glu Gly Gln Lys Asn
                405

<210> SEQ ID NO 192
<211> LENGTH: 119
<212> TYPE: PRT
<213> ORGANISM: Trichoderma reesei

<400> SEQUENCE: 192

Met Ser Leu Ser Arg Ser Pro Ser Val Pro Gly Gly Gly Trp Ser
1               5                   10                  15

Ser Pro Gly Leu Asn Ile Asn Ser Gly Arg Ser Ser Pro Ser Asn Ala
                20                  25                  30

Ala Gly Ser Ser Val Ser Trp Glu Ser Ala Lys Met Arg Lys Gln Gly
            35                  40                  45

Ala Asn Gly Tyr Pro Ser Phe Ser Thr Gln Asn Gln Gly Phe Phe Thr
        50                  55                  60

Arg His Met Arg Arg Ile Ser Ser Ser Leu Pro Arg Phe Ala Ala Gly
65                  70                  75                  80

Pro Gly Asn Thr Tyr Ala Glu Arg Glu Lys Tyr Glu Arg Gly Gly His
                85                  90                  95
```

```
Ser Pro His Ala Gly Gly Arg Leu Arg Ala Phe Leu Ala Arg Ile
            100                 105                 110

Gly Arg Arg Leu Lys Trp Arg
        115

<210> SEQ ID NO 193
<211> LENGTH: 15
<212> TYPE: PRT
<213> ORGANISM: Trichoderma reesei

<400> SEQUENCE: 193

Ile Leu Leu Pro Leu Ile Ile Ile Cys Thr Ile Val Ala Tyr Tyr
1               5                   10                  15

<210> SEQ ID NO 194
<211> LENGTH: 325
<212> TYPE: PRT
<213> ORGANISM: Trichoderma reesei

<400> SEQUENCE: 194

Gly Thr His Glu Ala Pro Gly Phe Val His Trp Trp Arg Arg Ile Ser
1               5                   10                  15

Met Gly Gly Gly Gly Glu Lys Phe Val Ile Ile Leu Gly Ala Asn Val
            20                  25                  30

Gly Gly Gly Val Met Glu Trp Lys Gly Ala Arg Glu Trp Ala Ile Glu
        35                  40                  45

Arg Asp Ser Val Arg Asn Lys Arg Lys Tyr Ala Thr Arg Trp Gly Tyr
    50                  55                  60

Asp Leu Glu Ile Val Asp Met Lys Thr Lys Lys Arg Tyr Ala His Glu
65                  70                  75                  80

Trp Arg Glu Ser Trp Glu Lys Val Asp Phe Ile Arg Ala Ala Met Arg
                85                  90                  95

Lys Tyr Pro Lys Ala Glu Trp Phe Trp Trp Leu Asp Leu Asn Thr Tyr
            100                 105                 110

Val Met Glu Pro Ser Tyr Ser Leu Gln Arg His Leu Phe Asn His Leu
        115                 120                 125

Asp Arg His Val Tyr Arg Asp Ile Asn Val Phe Asn Pro Leu Asn Ile
    130                 135                 140

Thr His Pro Pro Thr Glu Glu Tyr Leu Asp Ala Glu Ala Arg Ser Pro
145                 150                 155                 160

Val Gly Asp Gly Asn Ile Asn Ser Val Asn Leu Met Leu Thr Gln Asp
                165                 170                 175

Cys Ser Gly Phe Asn Leu Gly Ser Phe Phe Ile Arg Arg Ser Ala Trp
            180                 185                 190

Thr Glu Gln Leu Leu Asp Ile Trp Trp Asp Pro Val Leu Tyr Glu Gln
        195                 200                 205

Lys His Met Glu Trp Glu His Lys Glu Gln Asp Ala Leu Glu Gln Leu
    210                 215                 220

Tyr Arg Thr Gln Pro Trp Ile Arg Gln His Thr Gly Phe Leu Pro Gln
225                 230                 235                 240

Arg Leu Ile Asn Ser Phe Pro Pro Ala Ala Cys Ala Asp Glu Ser Gly
                245                 250                 255

Leu Asn Asn Thr Arg Ile His Tyr Asn Glu Lys Asp Arg Asp Phe Val
            260                 265                 270

Val Asn Met Ala Gly Cys Glu Trp Gly Arg Asp Cys Trp Gly Glu Met
        275                 280                 285
```

```
Tyr His Tyr Arg Glu Phe Ser Tyr Trp Leu Asn Arg Asn Pro Trp Glu
        290                 295                 300

Leu Phe Lys Glu Glu Ile Val Ala Val Ile Trp Tyr Lys Leu Thr Gly
305                 310                 315                 320

Gln Arg Val Lys Leu
                325

<210> SEQ ID NO 195
<211> LENGTH: 33
<212> TYPE: PRT
<213> ORGANISM: Trichoderma reesei

<400> SEQUENCE: 195

Met His Phe Ala Tyr Pro Ser Arg Lys Ser Ser Asn Pro Pro Phe
1                5                  10                  15

Arg Pro Arg Ser Thr Arg Leu Pro Gly Leu Arg Arg Ser Arg Ile Lys
                20                  25                  30

Thr

<210> SEQ ID NO 196
<211> LENGTH: 15
<212> TYPE: PRT
<213> ORGANISM: Trichoderma reesei

<400> SEQUENCE: 196

Ile Gly Ile Val Leu Phe Leu Val Leu Ala Thr Leu Trp Phe Phe
1                5                  10                  15

<210> SEQ ID NO 197
<211> LENGTH: 262
<212> TYPE: PRT
<213> ORGANISM: Trichoderma reesei

<400> SEQUENCE: 197

Ser Asn Pro Arg Val Pro Arg Pro Asp Pro Glu Arg Val Pro Ser Gly
1                5                  10                  15

Arg Pro Pro Val Val Leu Val Thr Val Ile Asp Pro Thr Gln Tyr Pro
                20                  25                  30

Asn Ala Tyr Leu Lys Thr Ile Lys Glu Asn Arg Glu Gln Tyr Ala Ala
            35                  40                  45

Lys His Gly Tyr Glu Ala Phe Ile Val Lys Ala Tyr Asp Tyr Asp Thr
        50                  55                  60

Gln Gly Ala Pro Gln Ser Trp Ser Lys Leu Met Ala Met Arg His Ala
65                  70                  75                  80

Leu Thr Lys Phe Pro Glu Cys Arg Phe Val Trp Tyr Leu Asp Gln Asp
                85                  90                  95

Ala Tyr Ile Met Asp Met Ser Lys Ser Leu Glu Glu Gln Leu Leu Asn
            100                 105                 110

Arg Gln Lys Leu Glu Ser Leu Met Ile Lys Asn Tyr Pro Val Val Pro
        115                 120                 125

Pro Asp Ser Ile Ile Lys Thr Phe Ser His Leu Arg Pro Asp Glu Val
    130                 135                 140

Asp Leu Ile Val Ser Gln Asp Ser Ser Gly Leu Val Ala Gly Ser Val
145                 150                 155                 160

Val Val Arg Asn Ser Gln Trp Ser Lys Phe Leu Leu Glu Thr Trp Met
                165                 170                 175

Asp Pro Leu Tyr Arg Ser Tyr Asn Phe Gln Lys Ala Glu Arg His Ala
```

```
                180             185             190
Leu Glu His Ile Val Gln Trp His Pro Thr Ile Leu Ser Lys Leu Ala
            195                 200                 205
Leu Val Pro Gln Arg Thr Leu Gly Pro Tyr Thr Arg Thr Asp Gln Gly
        210                 215                 220
Asp Ala Tyr Gln Asp Gly Asp Phe Val Val Met Phe Thr Gly Cys Thr
225                 230                 235                 240
Lys Ser Gly Glu Gln Ser Cys Glu Thr Val Ser Ala Ser Tyr Tyr Gln
                245                 250                 255
Lys Trp Ser Ser Ser Leu
                260

<210> SEQ ID NO 198
<211> LENGTH: 90
<212> TYPE: PRT
<213> ORGANISM: Trichoderma reesei

<400> SEQUENCE: 198

Met Ile Arg Asp Pro Phe Gly Ile His Ser Lys Asn Ala Phe Lys Ala
1               5                   10                  15
Thr Ala Leu Arg Ala Ala Arg Asp Ile Lys Glu Ala Ala Thr Gln Ala
            20                  25                  30
Gly Ala Asn Ala Leu Glu Met Ser Phe Ser Leu Pro Lys His Val Pro
        35                  40                  45
Asp Phe Gly Asp Pro Ser Arg Ala Leu Glu Asp Arg Ala Trp Ala Ala
    50                  55                  60
Leu Leu Pro Met Tyr Lys Asp Lys Pro Tyr Ala Tyr Ala Pro Ser Met
65                  70                  75                  80
Arg Leu Arg Pro Trp Trp Arg Arg Lys
                85                  90

<210> SEQ ID NO 199
<211> LENGTH: 19
<212> TYPE: PRT
<213> ORGANISM: Trichoderma reesei

<400> SEQUENCE: 199

Val Leu Gly Met Ile Ala Ala Val Met Phe Val Leu Tyr Val Thr
1               5                   10                  15
Gly Phe Phe

<210> SEQ ID NO 200
<211> LENGTH: 565
<212> TYPE: PRT
<213> ORGANISM: Trichoderma reesei

<400> SEQUENCE: 200

Ser Ser Gly Gln Thr Glu Glu Ala Lys Lys Lys Ala Ser Gly Ser Ala
1               5                   10                  15
Phe Ser Trp Leu Gly Leu Ser Gln Glu Arg Gly Val Asp Trp Asp
            20                  25                  30
Glu Arg Arg Lys Ser Val Val Glu Ala Phe Glu Val Trp Asp Ala Tyr
        35                  40                  45
Glu Arg Tyr Ala Trp Gly Lys Asp Glu Phe His Pro Ile Ser Lys Asn
    50                  55                  60
Gly Arg Asn Met Ala Pro Lys Gly Leu Gly Trp Ile Ile Ile Asp Ser
65                  70                  75                  80
```

```
Leu Asp Thr Met Met Leu Met Asn Gln Thr Thr Arg Leu Gln His Ala
                 85                  90                  95

Arg Glu Trp Ile Ser Thr Ser Leu Thr Trp Asp Gln Asp Gln Asp Val
            100                 105                 110

Asn Thr Phe Glu Thr Thr Ile Arg Met Leu Gly Gly Leu Leu Ser Ala
            115                 120                 125

His Tyr Leu Ser Thr Glu Phe Pro Glu Leu Ala Pro Leu Thr Glu Asp
            130                 135                 140

Asp Glu Gly Ala Pro Gly Glu Asp Leu Tyr Leu Glu Lys Ala Lys Asp
145                 150                 155                 160

Leu Ala Asp Arg Leu Leu Ser Ala Phe Glu Ser Glu Ser Gly Ile Pro
                165                 170                 175

Tyr Ala Ser Val Asn Ile Gly Glu Tyr Lys Gly Pro Ser His Ser Asp
                180                 185                 190

Asn Gly Ala Ser Ser Thr Ala Glu Ala Thr Thr Leu Gln Leu Glu Phe
                195                 200                 205

Lys Tyr Leu Ala Lys Leu Thr Gly Glu Lys Asn Phe Trp Asp Lys Val
            210                 215                 220

Glu Lys Val Met Glu Val Val Asp Asp Asn Gln Pro Glu Asp Gly Leu
225                 230                 235                 240

Val Pro Ile Tyr Ile Tyr Ala Thr Thr Gly Glu Phe Arg Gly Gln Asn
                245                 250                 255

Ile Arg Leu Gly Ser Arg Gly Asp Ser Tyr Tyr Glu Tyr Leu Ile Lys
                260                 265                 270

Gln Tyr Leu Gln Thr Asn Lys Gln Glu Pro Ile Tyr Glu Glu Met Trp
            275                 280                 285

Asp Glu Ala Leu Ala Gly Val Arg Lys His Leu Val Thr Tyr Thr Glu
290                 295                 300

Pro Ser Glu Phe Thr Ile Ile Ala Glu Arg Pro Asp Gly Leu Glu His
305                 310                 315                 320

Pro Met Ser Pro Lys Met Asp His Leu Val Cys Phe Met Pro Gly Thr
                325                 330                 335

Ile Ala Leu Ala Ala Thr Gly Gly Leu Thr Glu Ala Glu Ala Arg Lys
                340                 345                 350

Leu Ser Thr Trp Asn Lys Lys Asp Asp Asp Met Gln Leu Ala Arg
            355                 360                 365

Glu Leu Met His Thr Cys Trp Gly Met Tyr Lys Tyr Met Lys Thr Gly
            370                 375                 380

Leu Ala Pro Glu Ile Met Tyr Phe Asn Ile Pro Asn Pro Pro Glu
385                 390                 395                 400

Ser Ser Ala Pro His Gln Ala Pro Ala Ala Phe Asp Glu Asp Pro His
                405                 410                 415

Ala Glu Trp Arg Lys Asp Phe Val Val His Ser Asn Asp Val His Asn
            420                 425                 430

Leu Gln Arg Pro Glu Thr Val Glu Ser Leu Phe Tyr Met Trp Arg Ile
            435                 440                 445

Thr Gly Asp Val Lys Tyr Arg Glu Trp Gly Trp Asp Met Phe Lys Ser
            450                 455                 460

Phe Val Asn Tyr Thr Ala Val Glu Asp Gln Gly Gly Phe Thr Ser Leu
465                 470                 475                 480

Leu Asp Ala Asn Ser Ile Pro Pro Thr Pro Lys Asp Asn Met Glu Ser
                485                 490                 495

Phe Trp Leu Ala Glu Thr Leu Lys Tyr Met Tyr Leu Leu Phe Ser Pro
```

```
                  500                 505                 510
Asn Asp Val Leu Pro Leu His Lys Ile Val Leu Asn Thr Glu Ala His
            515                 520                 525

Pro Phe Pro Arg Phe Asp Met Gly Pro Leu Phe Ser Thr Gly Trp Lys
        530                 535                 540

Arg Lys Pro Arg Asp Gly Ser Ala Lys Lys Ala Thr Thr Ala Ala
545                 550                 555                 560

Thr Thr Asp Ala Glu
            565

<210> SEQ ID NO 201
<211> LENGTH: 7
<212> TYPE: PRT
<213> ORGANISM: Trichoderma reesei

<400> SEQUENCE: 201

Met Ala Arg Arg Arg Tyr Arg
1               5

<210> SEQ ID NO 202
<211> LENGTH: 15
<212> TYPE: PRT
<213> ORGANISM: Trichoderma reesei

<400> SEQUENCE: 202

Leu Phe Met Ile Cys Ala Ala Val Ile Leu Phe Leu Leu Tyr Arg
1               5                   10                  15

<210> SEQ ID NO 203
<211> LENGTH: 871
<212> TYPE: PRT
<213> ORGANISM: Trichoderma reesei

<400> SEQUENCE: 203

Val Ser Gln Asn Thr Trp Asp Asp Ser Ala His Tyr Ala Thr Leu Arg
1               5                   10                  15

His Pro Pro Ala Ser Asn Pro Pro Ala Ala Gly Gly Glu Ser Pro Leu
            20                  25                  30

Lys Pro Ala Ala Lys Pro Glu His Glu His Glu Asn Gly Tyr
        35                  40                  45

Ala Pro Glu Ser Lys Pro Lys Pro Gln Ser Glu Pro Lys Pro Glu Ser
    50                  55                  60

Lys Pro Ala Pro Glu His Ala Ala Gly Gly Gln Lys Ser Gln Gly Lys
65                  70                  75                  80

Pro Ser Tyr Glu Asp Asp Glu Glu Thr Gly Lys Asn Pro Pro Lys Ser
                85                  90                  95

Ala Val Ile Pro Ser Asp Thr Arg Leu Pro Pro Asp Asn Lys Val His
            100                 105                 110

Trp Arg Pro Val Lys Glu His Phe Pro Val Pro Ser Glu Ser Val Ile
        115                 120                 125

Ser Leu Pro Thr Gly Lys Pro Leu Lys Val Pro Arg Val Gln His Glu
    130                 135                 140

Phe Gly Val Glu Ser Pro Glu Ala Lys Ser Arg Arg Val Ala Arg Gln
145                 150                 155                 160

Glu Arg Val Gly Lys Glu Ile Glu Arg Ala Trp Ser Gly Tyr Lys Lys
                165                 170                 175

Phe Ala Trp Met His Asp Glu Leu Ser Pro Val Ser Ala Lys His Arg
            180                 185                 190
```

```
Asp Pro Phe Cys Gly Trp Ala Ala Thr Leu Val Asp Ser Leu Asp Thr
        195                 200                 205

Leu Trp Ile Ala Gly Leu Lys Glu Gln Phe Asp Glu Ala Ala Arg Ala
        210                 215                 220

Val Glu Gln Ile Asp Phe Thr Thr Thr Pro Arg Asn Asn Ile Pro Val
225                 230                 235                 240

Phe Glu Thr Thr Ile Arg Tyr Leu Gly Gly Leu Leu Gly Ala Phe Asp
                245                 250                 255

Val Ser Gly Gly His Asp Gly Gly Tyr Pro Met Leu Leu Thr Lys Ala
                260                 265                 270

Val Glu Leu Ala Glu Ile Leu Met Gly Ile Phe Asp Thr Pro Asn Arg
        275                 280                 285

Met Pro Ile Leu Tyr Tyr Gln Trp Gln Pro Glu Tyr Ala Ser Gln Pro
        290                 295                 300

His Arg Ala Gly Ser Val Gly Ile Ala Glu Leu Gly Thr Leu Ser Met
305                 310                 315                 320

Glu Phe Thr Arg Leu Ala Gln Leu Thr Ser Gln Tyr Lys Tyr Tyr Asp
                325                 330                 335

Ala Val Asp Arg Ile Thr Asp Ala Leu Ile Glu Leu Lys Gln Gly
                340                 345                 350

Thr Ser Ile Pro Gly Leu Phe Pro Glu Asn Leu Asp Ala Ser Gly Cys
        355                 360                 365

Asn His Thr Ala Thr Ala Leu Arg Ser Ser Leu Ser Glu Ala Ala Gln
        370                 375                 380

Lys Gln Met Asp Glu Asp Leu Ser Asn Lys Pro Glu Asn Tyr Arg Pro
385                 390                 395                 400

Gly Lys Asn Ser Lys Ala Asp Pro Gln Thr Val Glu Lys Gln Pro Ala
                405                 410                 415

Lys Lys Gln Asn Glu Pro Val Glu Lys Ala Lys Gln Val Pro Thr Gln
                420                 425                 430

Gln Thr Ala Lys Arg Gly Lys Pro Pro Phe Gly Ala Asn Gly Phe Thr
        435                 440                 445

Ala Asn Trp Asp Cys Val Pro Gln Gly Leu Val Val Gly Gly Tyr Gly
        450                 455                 460

Phe Gln Gln Tyr His Met Gly Gly Gly Gln Asp Ser Ala Tyr Glu Tyr
465                 470                 475                 480

Phe Pro Lys Glu Tyr Leu Leu Leu Gly Gly Leu Glu Ser Lys Tyr Gln
                485                 490                 495

Lys Leu Tyr Val Asp Ala Val Glu Ala Ile Asn Glu Trp Leu Leu Tyr
                500                 505                 510

Arg Pro Met Thr Asp Gly Asp Trp Asp Ile Leu Phe Pro Ala Lys Val
        515                 520                 525

Ser Thr Ala Gly Asn Pro Ser Gln Asp Leu Val Ala Thr Phe Glu Val
        530                 535                 540

Thr His Leu Thr Cys Phe Ile Gly Gly Met Tyr Gly Leu Gly Gly Lys
545                 550                 555                 560

Ile Phe Gly Arg Glu Lys Asp Leu Glu Thr Ala Lys Arg Leu Thr Asp
                565                 570                 575

Gly Cys Val Trp Ala Tyr Gln Ser Thr Val Ser Gly Ile Met Pro Glu
                580                 585                 590

Gly Ser Gln Val Leu Ala Cys Pro Thr Leu Glu Lys Cys Asp Phe Asn
        595                 600                 605
```

```
Glu Thr Leu Trp Trp Glu Lys Leu Asp Pro Ala Lys Asp Trp Arg Asp
            610                 615                 620

Lys Gln Val Ala Asp Lys Asp Lys Ala Thr Val Gly Glu Ala Leu
625                 630                 635                 640

Lys Glu Thr Ala Asn Ser His Asp Ala Ala Gly Gly Ser Lys Ala Val
                    645                 650                 655

His Lys Arg Ala Ala Val Pro Leu Pro Lys Pro Gly Ala Asp Asp Asp
                660                 665                 670

Val Gly Ser Glu Leu Pro Gln Ser Leu Lys Asp Lys Ile Gly Phe Lys
            675                 680                 685

Asn Gly Glu Gln Lys Lys Pro Thr Gly Ser Ser Val Gly Ile Gln Arg
690                 695                 700

Asp Pro Asp Ala Pro Val Asp Ser Val Leu Glu Ala His Arg Leu Pro
705                 710                 715                 720

Pro Gln Glu Pro Glu Glu Gln Val Ile Leu Pro Asp Lys Pro Gln
                    725                 730                 735

Thr His Glu Glu Phe Val Lys Gln Arg Ile Ala Glu Met Gly Phe Ala
                740                 745                 750

Pro Gly Val Val His Ile Gln Ser Arg Gln Tyr Ile Leu Arg Pro Glu
            755                 760                 765

Ala Ile Glu Ser Val Trp Tyr Met Tyr Arg Ile Thr Gly Asp Pro Ile
770                 775                 780

Trp Met Glu Lys Gly Trp Lys Met Phe Glu Ala Thr Ile Arg Ala Thr
785                 790                 795                 800

Arg Thr Glu Ile Ala Asn Ser Ala Ile Asp Asp Val Asn Ser Glu Glu
                    805                 810                 815

Pro Gly Leu Lys Asp Glu Met Glu Ser Phe Trp Leu Ala Glu Thr Leu
                820                 825                 830

Lys Tyr Tyr Tyr Leu Leu Phe Ser Glu Pro Ser Val Ile Ser Leu Asp
            835                 840                 845

Glu Trp Val Leu Asn Thr Glu Ala His Pro Phe Lys Arg Pro Gly Gly
850                 855                 860

Ser Val Ile Gly His Ser Ile
865                 870

<210> SEQ ID NO 204
<211> LENGTH: 13
<212> TYPE: PRT
<213> ORGANISM: Trichoderma reesei

<400> SEQUENCE: 204

Met Leu Asn Gln Leu Gln Gly Arg Val Pro Arg Arg Tyr
1               5                   10

<210> SEQ ID NO 205
<211> LENGTH: 15
<212> TYPE: PRT
<213> ORGANISM: Trichoderma reesei

<400> SEQUENCE: 205

Ile Ala Leu Val Ala Phe Ala Phe Phe Val Ala Phe Leu Leu Trp
1               5                   10                  15

<210> SEQ ID NO 206
<211> LENGTH: 542
<212> TYPE: PRT
<213> ORGANISM: Trichoderma reesei
```

```
<400> SEQUENCE: 206

Ser Gly Tyr Asp Phe Val Pro Arg Thr Ala Thr Val Gly Arg Phe Lys
1               5                   10                  15

Tyr Val Pro Ser Ser Tyr Asp Trp Ser Lys Ala Lys Val Tyr Tyr Pro
            20                  25                  30

Val Lys Asp Met Lys Thr Leu Pro Gln Gly Thr Pro Val Thr Phe Pro
        35                  40                  45

Arg Leu Gln Leu Arg Asn Gln Ser Glu Ala Gln Asp Asp Thr Lys
    50                  55                  60

Ala Arg Lys Gln Ala Val Lys Asp Ala Phe Val Lys Ser Trp Glu Ala
65                  70                  75                  80

Tyr Lys Thr Tyr Ala Trp Thr Lys Asp Gln Leu Gln Pro Leu Ser Leu
                85                  90                  95

Ser Gly Lys Glu Thr Phe Ser Gly Trp Ser Ala Gln Leu Val Asp Ala
            100                 105                 110

Leu Asp Thr Leu Trp Ile Met Asp Leu Lys Asp Asp Phe Phe Leu Ala
        115                 120                 125

Val Lys Glu Val Ala Val Ile Asp Trp Ser Lys Thr Lys Asp Asn Lys
130                 135                 140

Val Ile Asn Leu Phe Glu Val Thr Ile Arg Tyr Leu Gly Gly Leu Ile
145                 150                 155                 160

Ala Ala Tyr Asp Leu Ser Gln Glu Pro Val Leu Arg Ala Lys Ala Ile
                165                 170                 175

Glu Leu Gly Asp Thr Leu Tyr Ala Thr Phe Asp Thr Pro Asn Arg Leu
            180                 185                 190

Pro Ser His Trp Leu Asp Tyr Ser Lys Ala Lys Lys Gly Thr Gln Arg
        195                 200                 205

Ala Asp Asp Ser Met Ser Gly Ala Ala Gly Gly Thr Leu Cys Met Glu
210                 215                 220

Phe Thr Arg Leu Ser Gln Ile Thr Gly Asp Pro Lys Tyr Tyr Asp Ala
225                 230                 235                 240

Thr Glu Arg Ile Lys Gln Phe Phe Tyr Arg Phe Gln Asn Glu Thr Thr
                245                 250                 255

Leu Pro Gly Met Trp Pro Val Met Met Asn Tyr Arg Glu Glu Thr Met
            260                 265                 270

Val Glu Ser Arg Tyr Ser Met Gly Gly Ser Ala Asp Ser Leu Tyr Glu
        275                 280                 285

Tyr Leu Val Lys Met Pro Ala Leu Leu Gly Gly Leu Asp Pro Gln Tyr
    290                 295                 300

Pro Glu Met Ala Ile Arg Ala Leu Asp Thr Ala Arg Asp Asn Leu Leu
305                 310                 315                 320

Phe Arg Pro Met Thr Glu Lys Gly Asp Asn Ile Leu Ala Leu Gly Asn
                325                 330                 335

Ala Leu Val Asp His Gly Asn Val Gln Arg Ile Thr Glu Met Gln His
            340                 345                 350

Leu Thr Cys Phe Ala Gly Gly Met Tyr Ala Met Ala Gly Lys Leu Phe
        355                 360                 365

Lys Arg Asp Asp Tyr Val Asp Leu Gly Ser Arg Ile Ser Ser Gly Cys
    370                 375                 380

Val Trp Ala Tyr Asp Ser Phe Pro Ser Gly Ile Met Pro Glu Ser Ala
385                 390                 395                 400

Asp Met Ala Ala Cys Ala Lys Leu Asp Gly Pro Cys Pro Tyr Asp Glu
                405                 410                 415
```

```
Val Lys Ala Pro Val Asp Pro Asp Gly Arg Pro His Gly Phe Ile
            420             425             430

His Val Lys Ser Arg His Tyr Leu Arg Pro Glu Ala Ile Glu Ser
            435             440             445

Val Phe Tyr Met Trp Arg Ile Thr Gly Asp Gln Val Trp Arg Asp Thr
450             455             460

Ala Trp Arg Met Trp Glu Asn Ile Val Arg Glu Ala Glu Thr Glu His
465             470             475             480

Ala Phe Ala Ile Val Glu Asp Val Thr Arg Thr Ala Ser Lys Leu Thr
                485             490             495

Asn Asn Tyr Leu Leu Gln Thr Phe Trp Leu Ala Glu Thr Leu Lys Tyr
                500             505             510

Phe Tyr Leu Ile Phe Asp Asp Glu Ser Ala Ile Asp Leu Asp Lys Trp
            515             520             525

Val Phe Asn Thr Glu Ala His Pro Phe Lys Arg Pro Ala Val
            530             535             540

<210> SEQ ID NO 207
<211> LENGTH: 13
<212> TYPE: PRT
<213> ORGANISM: Trichoderma reesei

<400> SEQUENCE: 207

Met Leu Val Val Gly Arg Pro Arg Leu Val Arg Asn Ser
1               5                   10

<210> SEQ ID NO 208
<211> LENGTH: 16
<212> TYPE: PRT
<213> ORGANISM: Trichoderma reesei

<400> SEQUENCE: 208

Ile Ile Leu Thr Leu Ala Ile Leu Ser Ile Trp His Leu Gly Leu Leu
1               5                   10                  15

<210> SEQ ID NO 209
<211> LENGTH: 576
<212> TYPE: PRT
<213> ORGANISM: Trichoderma reesei

<400> SEQUENCE: 209

Ser Arg Thr Pro Thr Ser Ala Ser Ala Leu Val Ser Ala Ser Val Ser
1               5                   10                  15

Ala Ser Ser Glu Trp Ser Arg Leu Glu Arg Leu Met Asn Arg Gly Ala
            20                  25                  30

Pro Leu Thr Pro Tyr Pro Asp Ser Asn Ser Ser Phe Asp Trp Ser Ala
        35                  40                  45

Ile Pro Phe Arg Tyr Pro Pro His Asn Thr Thr His Leu Pro Pro Arg
    50                  55                  60

His Lys Gln Pro Pro Leu Pro Arg Ile Gln His Arg Phe Gly Pro Glu
65                  70                  75                  80

Ser Pro Ala Ala Ala Lys Glu Arg Ile Lys Arg Leu Lys Ala Val Lys
                85                  90                  95

Gln Val Phe Leu Arg Ala Trp Gln Ala Tyr Lys Gly Tyr Ala Trp Lys
            100                 105                 110

Gln Asp Ala Leu Leu Pro Ile Ser Gly Gly Gly Arg Glu Gln Phe Ser
        115                 120                 125
```

-continued

```
Gly Trp Ala Ala Thr Leu Val Asp Ala Leu Asp Thr Leu Trp Ile Met
130                 135                 140

Gly Leu Arg Glu Glu Phe Asp Glu Ala Val Ala Val Ala Glu Ile
145                 150                 155                 160

Asp Phe Gly Ser Ser Thr Ser Ser Arg Val Asn Ile Phe Glu Thr Asn
                165                 170                 175

Ile Arg Tyr Leu Gly Leu Leu Ala Ala Tyr Asp Leu Ser Gly Arg
            180                 185                 190

Glu Val Leu Leu Lys Lys Ala Val Glu Leu Gly Asp Leu Ile Tyr Ala
                195                 200                 205

Gly Phe Asn Thr Glu Asn Gly Met Pro Val Asp Phe Leu Asn Phe Tyr
210                 215                 220

Ser Ala Lys Ser Gly Glu Gly Leu Val Val Glu Ser Ser Val Val Ser
225                 230                 235                 240

Ala Ser Pro Gly Thr Leu Ser Leu Glu Leu Ala His Leu Ser Gln Val
                245                 250                 255

Thr Gly Asp Asp Lys Tyr Tyr Ser Ala Val Ser Gln Val Met Asp Val
                260                 265                 270

Phe Tyr Gln Gly Gln Asn Lys Thr Arg Leu Pro Gly Val Trp Pro Ile
            275                 280                 285

Asp Val Asn Met Arg Ala Lys Asp Val Val Ser Gly Ser Arg Phe Thr
290                 295                 300

Leu Gly Gly Cys Ala Asp Ser Leu Tyr Glu Tyr Leu Pro Lys Met His
305                 310                 315                 320

Gln Leu Leu Gly Gly Gly Glu Pro Lys Tyr Glu Thr Met Ser Arg Thr
                325                 330                 335

Phe Leu Gln Ala Ala Asp Arg His Phe Val Phe Arg Pro Met Leu Pro
                340                 345                 350

Gly Ala Glu Glu Asp Val Leu Met Pro Gly Asn Val Asn Val Asp Glu
                355                 360                 365

Asp Ser Gly Glu Ala Val Leu Asp Pro Glu Thr Glu His Leu Ala Cys
            370                 375                 380

Phe Val Gly Gly Met Phe Gly Leu Ala Gly Arg Leu Phe Ser Arg Pro
385                 390                 395                 400

Asp Asp Val Glu Thr Gly Val Arg Leu Thr Asn Gly Cys Val Tyr Ala
                405                 410                 415

Tyr Arg Ala Phe Pro Thr Gly Met Met Pro Glu Arg Leu Asp Leu Ala
            420                 425                 430

Pro Cys Arg Asp Arg Ser Ser Arg Cys Pro Trp Asp Glu Glu His Trp
            435                 440                 445

Leu Glu Glu Arg Ala Lys Arg Pro Glu Trp Glu Pro His Leu Pro Arg
450                 455                 460

Gly Phe Thr Ser Ala Lys Asp Pro Arg Tyr Leu Leu Arg Pro Glu Ala
465                 470                 475                 480

Ile Glu Ser Val Phe Tyr Ser Tyr Arg Ile Thr Gly Arg Gln Glu Phe
                485                 490                 495

Gln Thr Ala Ala Trp Asp Met Phe Thr Ala Val Glu Lys Gly Thr Arg
                500                 505                 510

Thr Gln Phe Ala Asn Ala Ala Val Leu Asp Val Thr Arg Ala Ala Asp
            515                 520                 525

Glu Leu Pro Gln Glu Asp Tyr Met Glu Ser Phe Trp Leu Ala Glu Thr
                530                 535                 540

Leu Lys Tyr Phe Tyr Leu Met Phe Thr Thr Pro Asp Ile Ile Ser Leu
```

```
            545                 550                 555                 560
Asp Asp Tyr Val Leu Asn Thr Glu Ala His Pro Phe Lys Leu Val Gly
                565                 570                 575
```

<210> SEQ ID NO 210
<211> LENGTH: 17
<212> TYPE: PRT
<213> ORGANISM: Trichoderma reesei

<400> SEQUENCE: 210

```
Met Val Met Leu Val Ala Ile Ala Leu Ala Trp Leu Gly Cys Ser Leu
1               5                   10                  15

Leu
```

<210> SEQ ID NO 211
<211> LENGTH: 1053
<212> TYPE: PRT
<213> ORGANISM: Trichoderma reesei

<400> SEQUENCE: 211

```
Arg Pro Val Asp Ala Met Arg Ala Asp Tyr Leu Ala Gln Leu Arg Gln
1               5                   10                  15

Glu Thr Val Asp Met Phe Tyr His Gly Tyr Ser Asn Tyr Met Glu His
                20                  25                  30

Ala Phe Pro Glu Asp Glu Leu Arg Pro Ile Ser Cys Thr Pro Leu Thr
            35                  40                  45

Arg Asp Arg Asp Asn Pro Gly Arg Ile Ser Leu Asn Asp Ala Leu Gly
    50                  55                  60

Asn Tyr Ser Leu Thr Leu Ile Asp Ser Leu Ser Thr Leu Ala Ile Leu
65                  70                  75                  80

Ala Gly Gly Pro Gln Asn Gly Pro Tyr Thr Pro Gln Ala Leu Ser
                85                  90                  95

Asp Phe Gln Asp Gly Val Ala Glu Phe Val Arg His Tyr Gly Asp Gly
            100                 105                 110

Arg Ser Gly Pro Ser Gly Ala Gly Ile Arg Ala Arg Gly Phe Asp Leu
        115                 120                 125

Asp Ser Lys Val Gln Val Phe Glu Thr Val Ile Arg Gly Val Gly Gly
    130                 135                 140

Leu Leu Ser Ala His Leu Phe Ala Ile Gly Glu Leu Pro Ile Thr Gly
145                 150                 155                 160

Tyr Val Pro Arg Pro Glu Gly Val Ala Gly Asp Asp Pro Leu Glu Leu
                165                 170                 175

Ala Pro Ile Pro Trp Pro Asn Gly Phe Arg Tyr Asp Gly Gln Leu Leu
            180                 185                 190

Arg Leu Ala Leu Asp Leu Ser Glu Arg Leu Leu Pro Ala Phe Tyr Thr
        195                 200                 205

Pro Thr Gly Ile Pro Tyr Pro Arg Val Asn Leu Arg Ser Gly Ile Pro
    210                 215                 220

Phe Tyr Val Asn Ser Pro Leu His Gln Asn Leu Gly Glu Ala Val Glu
225                 230                 235                 240

Glu Gln Ser Gly Arg Pro Glu Ile Thr Glu Thr Cys Ser Ala Gly Ala
                245                 250                 255

Gly Ser Leu Val Leu Glu Phe Thr Val Leu Ser Arg Leu Thr Gly Asp
            260                 265                 270

Ala Arg Phe Glu Gln Ala Ala Lys Arg Ala Phe Trp Glu Val Trp His
        275                 280                 285
```

```
Arg Arg Ser Glu Ile Gly Leu Ile Gly Asn Gly Ile Asp Ala Glu Arg
    290                 295                 300

Gly Leu Trp Ile Gly Pro His Ala Gly Ile Gly Ala Gly Met Asp Ser
305                 310                 315                 320

Phe Phe Glu Tyr Ala Leu Lys Ser His Ile Leu Leu Ser Gly Leu Gly
                325                 330                 335

Met Pro Asn Ala Ser Thr Ser Arg Arg Gln Ser Thr Thr Ser Trp Leu
                340                 345                 350

Asp Pro Asn Ser Leu His Pro Pro Leu Pro Pro Glu Met His Thr Ser
            355                 360                 365

Asp Ala Phe Leu Gln Ala Trp His Gln Ala His Ala Ser Val Lys Arg
    370                 375                 380

Tyr Leu Tyr Thr Asp Arg Ser His Phe Pro Tyr Tyr Ser Asn Asn His
385                 390                 395                 400

Arg Ala Thr Gly Gln Pro Tyr Ala Met Trp Ile Asp Ser Leu Gly Ala
                405                 410                 415

Phe Tyr Pro Gly Leu Leu Ala Leu Ala Gly Glu Val Glu Glu Ala Ile
                420                 425                 430

Glu Ala Asn Leu Val Tyr Thr Ala Leu Trp Thr Arg Tyr Ser Ala Leu
            435                 440                 445

Pro Glu Arg Trp Ser Val Arg Glu Gly Asn Val Glu Ala Gly Ile Gly
    450                 455                 460

Trp Trp Pro Gly Arg Pro Glu Phe Ile Glu Ser Thr Tyr His Ile Tyr
465                 470                 475                 480

Arg Ala Thr Arg Asp Pro Trp Tyr Leu His Val Gly Glu Met Val Leu
                485                 490                 495

Arg Asp Ile Arg Arg Arg Cys Tyr Ala Glu Cys Gly Trp Ala Gly Leu
            500                 505                 510

Gln Asp Val Gln Thr Gly Glu Lys Gln Asp Arg Met Glu Ser Phe Phe
    515                 520                 525

Leu Gly Glu Thr Ala Lys Tyr Met Tyr Leu Leu Phe Asp Pro Asp His
    530                 535                 540

Pro Leu Asn Lys Leu Asp Ala Ala Tyr Val Phe Thr Thr Glu Gly His
545                 550                 555                 560

Pro Leu Ile Ile Pro Lys Ser Lys Arg Gly Ser Gly Ser His Asn Arg
                565                 570                 575

Gln Asp Arg Ala Arg Lys Ala Lys Lys Ser Arg Asp Val Ala Val Tyr
            580                 585                 590

Thr Tyr Tyr Asp Glu Ser Phe Thr Asn Ser Cys Pro Ala Pro Arg Pro
    595                 600                 605

Pro Ser Glu His His Leu Ile Gly Ser Ala Thr Ala Ala Arg Pro Asp
610                 615                 620

Leu Phe Ser Val Ser Arg Phe Thr Asp Leu Tyr Arg Thr Pro Asn Val
625                 630                 635                 640

His Gly Pro Leu Glu Lys Val Glu Met Arg Asp Lys Lys Lys Gly Arg
                645                 650                 655

Val Val Arg Tyr Arg Ala Thr Ser Asn His Thr Ile Phe Pro Trp Thr
                660                 665                 670

Leu Pro Pro Ala Met Leu Pro Glu Asn Gly Thr Cys Ala Ala Pro Pro
            675                 680                 685

Glu Arg Ile Ile Ser Leu Ile Glu Phe Pro Ala Asn Asp Ile Thr Ser
    690                 695                 700
```

```
Gly Ile Thr Ser Arg Phe Gly Asn His Leu Ser Trp Gln Thr His Leu
705                 710                 715                 720

Gly Pro Thr Val Asn Ile Leu Glu Gly Leu Arg Leu Gln Leu Glu Gln
            725                 730                 735

Val Ser Asp Pro Ala Thr Gly Glu Asp Lys Trp Arg Ile Thr His Ile
        740                 745                 750

Gly Asn Thr Gln Leu Gly Arg His Glu Thr Val Phe Phe His Ala Glu
    755                 760                 765

His Val Arg His Leu Lys Asp Glu Val Phe Ser Cys Arg Arg Arg Arg
770                 775                 780

Asp Ala Val Glu Ile Glu Leu Leu Val Asp Lys Pro Ser Asp Thr Asn
785                 790                 795                 800

Asn Asn Asn Thr Leu Ala Ser Ser Asp Asp Val Val Asp Ala
            805                 810                 815

Lys Ala Glu Glu Gln Asp Gly Met Leu Ala Asp Asp Gly Asp Thr
        820                 825                 830

Leu Asn Ala Glu Thr Leu Ser Ser Asn Ser Leu Phe Gln Ser Leu Leu
    835                 840                 845

Arg Ala Val Ser Ser Val Phe Glu Pro Val Tyr Thr Ala Ile Pro Glu
850                 855                 860

Ser Asp Pro Ser Ala Gly Thr Ala Lys Val Tyr Ser Phe Asp Ala Tyr
865                 870                 875                 880

Thr Ser Thr Gly Pro Gly Ala Tyr Pro Met Pro Ser Ile Ser Asp Thr
                885                 890                 895

Pro Ile Pro Gly Asn Pro Phe Tyr Asn Phe Arg Asn Pro Ala Ser Asn
            900                 905                 910

Phe Pro Trp Ser Thr Val Phe Leu Ala Gly Gln Ala Cys Glu Gly Pro
        915                 920                 925

Leu Pro Ala Ser Ala Pro Arg Glu His Gln Val Ile Val Met Leu Arg
    930                 935                 940

Gly Gly Cys Ser Phe Ser Arg Lys Leu Asp Asn Ile Pro Ser Phe Ser
945                 950                 955                 960

Pro His Asp Arg Ala Leu Gln Leu Val Val Leu Asp Glu Pro Pro
                965                 970                 975

Pro Pro Pro Pro Pro Pro Ala Asn Asp Arg Arg Asp Val Thr Arg
            980                 985                 990

Pro Leu Leu Asp Thr Glu Gln Thr  Thr Pro Lys Gly Met  Lys Arg Leu
        995                 1000                1005

His Gly Ile Pro Met Val Leu  Val Arg Ala Ala Arg  Gly Asp Tyr
    1010                1015                1020

Glu Leu Phe Gly His Ala Ile  Gly Val Gly Met Arg  Arg Lys Tyr
    1025                1030                1035

Arg Val Glu Ser Gln Gly Leu  Val Val Glu Asn Ala  Val Val Leu
    1040                1045                1050

<210> SEQ ID NO 212
<211> LENGTH: 45
<212> TYPE: PRT
<213> ORGANISM: Trichoderma reesei

<400> SEQUENCE: 212

Met Met Pro Arg His His Ser Ser Gly Phe Ser Asn Gly Tyr Pro Arg
1               5                   10                  15

Ala Asp Thr Phe Glu Ile Ser Pro His Arg Phe Gln Pro Arg Ala Thr
            20                  25                  30
```

Leu Pro Pro His Arg Lys Arg Lys Arg Thr Ala Ile Arg
            35                  40                  45

<210> SEQ ID NO 213
<211> LENGTH: 16
<212> TYPE: PRT
<213> ORGANISM: Trichoderma reesei

<400> SEQUENCE: 213

Val Gly Ile Ala Val Val Ile Leu Val Leu Val Leu Trp Phe Gly
1               5                   10                  15

<210> SEQ ID NO 214
<211> LENGTH: 407
<212> TYPE: PRT
<213> ORGANISM: Trichoderma reesei

<400> SEQUENCE: 214

Gln Pro Arg Ser Val Ala Ser Leu Ile Ser Leu Gly Ile Leu Ser Gly
1               5                   10                  15

Tyr Asp Asp Leu Lys Leu Glu Thr Val Arg Tyr Tyr Asp Leu Ser Asn
            20                  25                  30

Val Gln Gly Thr Ala Arg Gly Trp Glu Arg Glu Arg Ile Leu Leu
        35                  40                  45

Cys Val Pro Leu Arg Asp Ala Glu Gln His Leu Pro Met Phe Phe Ser
50                  55                  60

His Leu Lys Asn Phe Thr Tyr Pro His Asn Leu Ile Asp Leu Ala Phe
65                  70                  75                  80

Leu Val Ser Asp Ser Lys Asp His Thr Leu Glu Ser Leu Thr Glu His
            85                  90                  95

Leu Glu Ala Ile Gln Ala Asp Pro Asp Pro Lys Gln Pro Tyr Gly Glu
        100                 105                 110

Ile Ser Ile Ile Glu Lys Asp Phe Gly Gln Lys Val Asn Gln Asp Val
        115                 120                 125

Glu Ser Arg His Gly Phe Ala Ala Gln Ala Ser Arg Arg Lys Leu Met
130                 135                 140

Ala Gln Ala Arg Asn Trp Leu Leu Ser Ala Ala Leu Arg Pro Tyr His
145                 150                 155                 160

Ser Trp Val Tyr Trp Arg Asp Val Asp Val Glu Thr Ala Pro Phe Thr
                165                 170                 175

Ile Leu Glu Asp Leu Met Arg His Asn Lys Asp Val Ile Val Pro Asn
            180                 185                 190

Val Trp Arg Pro Leu Pro Asp Trp Leu Gly Gly Glu Gln Pro Tyr Asp
        195                 200                 205

Leu Asn Ser Trp Gln Glu Ser Glu Thr Ala Leu Leu Ala Asp Thr
    210                 215                 220

Leu Asp Glu Asp Ala Val Ile Val Glu Gly Tyr Ala Glu Tyr Ala Thr
225                 230                 235                 240

Trp Arg Pro His Leu Ala Tyr Leu Arg Asp Pro Tyr Gly Asp Pro Asp
                245                 250                 255

Met Glu Met Glu Ile Asp Gly Val Gly Gly Val Ser Ile Leu Ala Lys
            260                 265                 270

Ala Lys Val Phe Arg Ala Gly Val His Phe Pro Ala Phe Ser Phe Glu
        275                 280                 285

Lys His Ala Glu Thr Glu Gly Phe Gly Lys Met Ala Lys Arg Met His
        290                 295                 300

-continued

```
Phe Ser Val Val Gly Leu Pro His Tyr Thr Ile Trp His Leu Tyr Glu
305                 310                 315                 320

Pro Ser Val Asp Asp Ile Lys His Met Glu Glu Met Glu Arg Glu Arg
            325                 330                 335

Ile Ala Arg Glu Lys Glu Glu Glu Arg Lys Lys Lys Glu Ala Gln
        340                 345                 350

Ile Lys Glu Glu Phe Gly Asp Ala Asn Ser Gln Trp Glu Gln Asp Lys
    355                 360                 365

Gln Gln Met Gln Asp Leu Lys Leu Gln Asp Arg Gly Gly Asp Lys Glu
370                 375                 380

Ala Ala Ala Ala Gly Val Asn Gln Gly Ala Ala Ala Lys Ala Ala Gly
385                 390                 395                 400

Ala Met Glu Gly Gln Lys Asn
                405

<210> SEQ ID NO 215
<211> LENGTH: 31
<212> TYPE: PRT
<213> ORGANISM: Trichoderma reesei

<400> SEQUENCE: 215

Met Leu Leu Pro Lys Gly Gly Leu Asp Trp Arg Ser Ala Arg Ala Gln
1               5                   10                  15

Ile Pro Pro Thr Arg Ala Leu Trp Asn Ala Val Thr Thr Arg
            20                  25                  30

<210> SEQ ID NO 216
<211> LENGTH: 15
<212> TYPE: PRT
<213> ORGANISM: Trichoderma reesei

<400> SEQUENCE: 216

Phe Ile Leu Leu Val Gly Ile Thr Gly Leu Ile Leu Leu Leu Trp
1               5                   10                  15

<210> SEQ ID NO 217
<211> LENGTH: 358
<212> TYPE: PRT
<213> ORGANISM: Trichoderma reesei

<400> SEQUENCE: 217

Arg Gly Val Ser Thr Ser Ala Ser Glu Met Gln Ser Phe Tyr Cys Trp
1               5                   10                  15

Gly Pro Ala Lys Pro Pro Met Glu Met Ser Pro Asn Glu His Asn Arg
            20                  25                  30

Trp Asn Gly His Leu Gln Thr Pro Val Ile Phe Asn His His Ala Pro
        35                  40                  45

Val Glu Val Asn Ser Ser Thr Ile Glu His Val Asp Leu Asn Pro Ile
    50                  55                  60

Asn Ser Thr Lys Gln Ala Val Thr Lys Glu Glu Arg Ile Leu Ile Leu
65                  70                  75                  80

Thr Pro Leu Lys Asp Ala Ala Pro Tyr Leu Ser Lys Tyr Phe Glu Leu
                85                  90                  95

Leu Ala Glu Leu Thr Tyr Pro His Arg Leu Ile Asp Leu Ala Phe Leu
            100                 105                 110

Val Ser Asp Ser Thr Asp Asp Thr Leu Ala Val Leu Ala Ser Glu Leu
        115                 120                 125
```

```
Asp Arg Ile Gln Lys Arg Pro Asp Gln Ile Pro Phe His Ser Ala Thr
    130                 135                 140
Val Ile Glu Lys Asp Phe Gly Phe Lys Leu Ser Gln Asn Val Glu Glu
145                 150                 155                 160
Arg His Ser Phe Glu Ala Gln Gly Pro Arg Arg Lys Ala Met Gly Arg
                165                 170                 175
Ala Arg Asn Tyr Leu Leu Tyr Thr Ala Leu Lys Pro Glu His Ser Trp
            180                 185                 190
Val Tyr Trp Arg Asp Val Asp Ile Val Asp Ser Pro Thr Gly Ile Leu
        195                 200                 205
Glu Asp Phe Ile Ala His Asp Arg Asp Ile Leu Val Pro Asn Ile Trp
    210                 215                 220
Phe His Arg Tyr Arg Asp Gly Val Asp Ile Glu Gly Arg Phe Asp Tyr
225                 230                 235                 240
Asn Ser Trp Val Glu Ser Asp Lys Gly Arg Lys Leu Ala Asn Ser Leu
                245                 250                 255
Asp Lys Asp Val Val Leu Ala Glu Gly Tyr Lys Gln Tyr Asp Thr Gly
            260                 265                 270
Arg Thr Tyr Met Ala Lys Met Gly Asp Trp Arg Glu Asn Lys Asp Val
        275                 280                 285
Glu Leu Glu Leu Asp Gly Ile Gly Gly Val Asn Ile Leu Val Lys Ala
    290                 295                 300
Asp Val His Arg Ser Gly Ile Asn Phe Pro Cys Tyr Ala Phe Glu Asn
305                 310                 315                 320
Gln Ala Glu Thr Glu Gly Phe Ala Lys Met Lys Arg Ala Gly Tyr
                325                 330                 335
Glu Val Tyr Gly Leu Pro Asn Tyr Val Val Trp His Ile Asp Thr Glu
            340                 345                 350
Glu Lys Gly Gly Asn Ala
        355

<210> SEQ ID NO 218
<211> LENGTH: 17
<212> TYPE: PRT
<213> ORGANISM: Trichoderma reesei

<400> SEQUENCE: 218

Met Ala Arg Pro Met Gly Ser Val Arg Leu Lys Lys Ala Asn Pro Ser
1               5                   10                  15
Thr

<210> SEQ ID NO 219
<211> LENGTH: 16
<212> TYPE: PRT
<213> ORGANISM: Trichoderma reesei

<400> SEQUENCE: 219

Leu Ile Leu Gly Ala Val Leu Cys Ile Phe Ile Ile Phe Leu Val
1               5                   10                  15

<210> SEQ ID NO 220
<211> LENGTH: 339
<212> TYPE: PRT
<213> ORGANISM: Trichoderma reesei

<400> SEQUENCE: 220

Ser Pro Ser Ser Pro Ala Ser Ala Ser Arg Leu Ser Ile Val Ser Ala
1               5                   10                  15
```

-continued

```
Gln His His Leu Ser Pro Pro Thr Ser Pro Tyr Gln Ser Pro Arg Ser
             20                  25                  30

Gly Ala Val Gln Gly Pro Pro Val Thr Arg Tyr Asn Leu Asn Lys
         35                  40                  45

Val Thr Val Thr Ser Asp Pro Val Arg Asn Gln Glu His Ile Leu Ile
 50                  55                  60

Leu Thr Pro Met Ala Arg Phe Tyr Gln Glu Tyr Trp Asp Asn Leu Leu
 65                  70                  75                  80

Arg Leu Asn Tyr Pro His Glu Leu Ile Thr Leu Gly Phe Ile Leu Pro
             85                  90                  95

Lys Thr Lys Glu Gly Asn Gln Ala Thr Ser Met Leu Gln Lys Gln Ile
            100                 105                 110

Gln Lys Thr Gln Asn Tyr Gly Pro Glu Lys Asp Arg Phe Lys Ser Ile
            115                 120                 125

Ile Ile Leu Arg Gln Asp Phe Asp Pro Ala Val Val Ser Gln Asp Glu
130                 135                 140

Ser Glu Arg His Lys Leu Ala Asn Gln Lys Ala Arg Arg Glu Val Met
145                 150                 155                 160

Ala Lys Ala Arg Asn Ser Leu Leu Phe Thr Thr Leu Gly Pro Ser Thr
                165                 170                 175

Ser Trp Val Leu Trp Leu Asp Ala Asp Ile Thr Glu Thr Ala Pro Thr
            180                 185                 190

Leu Ile Gln Asp Leu Ala Ser His Asp Lys Pro Ile Ile Val Ala Asn
        195                 200                 205

Cys Phe Gln Lys Tyr Tyr Asp Pro Glu Ser Lys Lys Met Ala Glu Arg
210                 215                 220

Pro Tyr Asp Phe Asn Ser Trp Gln Asp Ser Glu Thr Ala Leu Lys Met
225                 230                 235                 240

Ala Glu Gln Met Gly Pro Asp Asp Ile Leu Leu Glu Gly Tyr Ala Glu
                245                 250                 255

Met Ala Thr Tyr Arg Thr Leu Leu Ala Tyr Met Ser Thr Pro Gly Gly
            260                 265                 270

Ser Lys Asp Leu Val Val Pro Leu Asp Gly Val Gly Thr Ala Leu
            275                 280                 285

Leu Val Lys Ala Asp Val His Arg Asp Gly Ala Met Phe Pro Pro Phe
290                 295                 300

Ala Phe Tyr His Leu Ile Glu Ser Glu Gly Phe Ala Lys Met Ala Lys
305                 310                 315                 320

Arg Leu Gly Trp Gln Pro Tyr Gly Leu Pro Asn Tyr Lys Val Tyr His
                325                 330                 335

Tyr Asn Glu
```

<210> SEQ ID NO 221
<211> LENGTH: 33
<212> TYPE: PRT
<213> ORGANISM: Trichoderma reesei

<400> SEQUENCE: 221

```
Met His Phe Ala Tyr Pro Ser Arg Lys Ser Ser Asn Pro Pro Pro Phe
 1               5                  10                  15

Arg Pro Arg Ser Thr Arg Leu Pro Gly Leu Arg Ser Arg Ile Lys
             20                  25                  30

Thr
```

-continued

<210> SEQ ID NO 222
<211> LENGTH: 15
<212> TYPE: PRT
<213> ORGANISM: Trichoderma reesei

<400> SEQUENCE: 222

Ile Gly Ile Val Leu Phe Leu Val Leu Ala Thr Leu Trp Phe Phe
1               5                   10                  15

<210> SEQ ID NO 223
<211> LENGTH: 262
<212> TYPE: PRT
<213> ORGANISM: Trichoderma reesei

<400> SEQUENCE: 223

Ser Asn Pro Arg Val Pro Arg Pro Asp Pro Glu Arg Val Pro Ser Gly
1               5                   10                  15

Arg Pro Pro Val Val Leu Val Thr Val Ile Asp Pro Thr Gln Tyr Pro
                20                  25                  30

Asn Ala Tyr Leu Lys Thr Ile Lys Glu Asn Arg Glu Gln Tyr Ala Ala
            35                  40                  45

Lys His Gly Tyr Glu Ala Phe Ile Val Lys Ala Tyr Asp Tyr Asp Thr
50                  55                  60

Gln Gly Ala Pro Gln Ser Trp Ser Lys Leu Met Ala Met Arg His Ala
65                  70                  75                  80

Leu Thr Lys Phe Pro Glu Cys Arg Phe Val Trp Tyr Leu Asp Gln Asp
                85                  90                  95

Ala Tyr Ile Met Asp Met Ser Lys Ser Leu Glu Glu Gln Leu Leu Asn
            100                 105                 110

Arg Gln Lys Leu Glu Ser Leu Met Ile Lys Asn Tyr Pro Val Val Pro
        115                 120                 125

Pro Asp Ser Ile Ile Lys Thr Phe Ser His Leu Arg Pro Asp Glu Val
    130                 135                 140

Asp Leu Ile Val Ser Gln Asp Ser Ser Gly Leu Val Ala Gly Ser Val
145                 150                 155                 160

Val Val Arg Asn Ser Gln Trp Ser Lys Phe Leu Leu Glu Thr Trp Met
                165                 170                 175

Asp Pro Leu Tyr Arg Ser Tyr Asn Phe Gln Lys Ala Glu Arg His Ala
            180                 185                 190

Leu Glu His Ile Val Gln Trp His Pro Thr Ile Leu Ser Lys Leu Ala
        195                 200                 205

Leu Val Pro Gln Arg Thr Leu Gly Pro Tyr Thr Arg Thr Asp Gln Gly
    210                 215                 220

Asp Ala Tyr Gln Asp Gly Asp Phe Val Val Met Phe Thr Gly Cys Thr
225                 230                 235                 240

Lys Ser Gly Glu Gln Ser Cys Glu Thr Val Ser Ala Ser Tyr Tyr Gln
                245                 250                 255

Lys Trp Ser Ser Ser Leu
            260

<210> SEQ ID NO 224
<211> LENGTH: 119
<212> TYPE: PRT
<213> ORGANISM: Trichoderma reesei

<400> SEQUENCE: 224

Met Ser Leu Ser Arg Ser Pro Ser Pro Val Pro Gly Gly Gly Trp Ser

```
1               5                   10                  15
Ser Pro Gly Leu Asn Ile Asn Ser Gly Arg Ser Ser Pro Ser Asn Ala
            20                  25                  30

Ala Gly Ser Ser Val Ser Trp Glu Ser Ala Lys Met Arg Lys Gln Gly
            35                  40                  45

Ala Asn Gly Tyr Pro Ser Phe Ser Thr Gln Asn Gln Gly Phe Phe Thr
            50                  55                  60

Arg His Met Arg Arg Ile Ser Ser Ser Leu Pro Arg Phe Ala Ala Gly
65                  70                  75                  80

Pro Gly Asn Thr Tyr Ala Glu Arg Glu Lys Tyr Glu Arg Gly Gly His
                85                  90                  95

Ser Pro His Ala Gly Gly Arg Leu Arg Ala Phe Leu Ala Arg Ile
            100                 105                 110

Gly Arg Arg Leu Lys Trp Arg
            115

<210> SEQ ID NO 225
<211> LENGTH: 16
<212> TYPE: PRT
<213> ORGANISM: Trichoderma reesei

<400> SEQUENCE: 225

Ile Leu Leu Pro Leu Ile Ile Ile Cys Thr Ile Val Ala Tyr Tyr Gly
1               5                   10                  15

<210> SEQ ID NO 226
<211> LENGTH: 324
<212> TYPE: PRT
<213> ORGANISM: Trichoderma reesei

<400> SEQUENCE: 226

Thr His Glu Ala Pro Gly Phe Val His Trp Trp Arg Arg Ile Ser Met
1               5                   10                  15

Gly Gly Gly Gly Glu Lys Phe Val Ile Leu Gly Ala Asn Val Gly
            20                  25                  30

Gly Gly Val Met Glu Trp Lys Gly Ala Arg Glu Trp Ala Ile Glu Arg
            35                  40                  45

Asp Ser Val Arg Asn Lys Arg Lys Tyr Ala Thr Arg Trp Gly Tyr Asp
            50                  55                  60

Leu Glu Ile Val Asp Met Lys Thr Lys Lys Arg Tyr Ala His Glu Trp
65                  70                  75                  80

Arg Glu Ser Trp Glu Lys Val Asp Phe Ile Arg Ala Ala Met Arg Lys
            85                  90                  95

Tyr Pro Lys Ala Glu Trp Phe Trp Leu Asp Leu Asn Thr Tyr Val
            100                 105                 110

Met Glu Pro Ser Tyr Ser Leu Gln Arg His Leu Phe Asn His Leu Asp
            115                 120                 125

Arg His Val Tyr Arg Asp Ile Asn Val Phe Asn Pro Leu Asn Ile Thr
            130                 135                 140

His Pro Pro Thr Glu Glu Tyr Leu Asp Ala Glu Ala Arg Ser Pro Val
145                 150                 155                 160

Gly Asp Gly Asn Ile Asn Ser Val Asn Leu Met Leu Thr Gln Asp Cys
                165                 170                 175

Ser Gly Phe Asn Leu Gly Ser Phe Phe Ile Arg Arg Ser Ala Trp Thr
            180                 185                 190

Glu Gln Leu Leu Asp Ile Trp Trp Asp Pro Val Leu Tyr Glu Gln Lys
```

```
                195                 200                 205
His Met Glu Trp Glu His Lys Glu Gln Asp Ala Leu Glu Gln Leu Tyr
210                 215                 220

Arg Thr Gln Pro Trp Ile Arg Gln His Thr Gly Phe Leu Pro Gln Arg
225                 230                 235                 240

Leu Ile Asn Ser Phe Pro Ala Ala Cys Ala Asp Glu Ser Gly Leu
                245                 250                 255

Asn Asn Thr Arg Ile His Tyr Asn Glu Lys Asp Arg Asp Phe Val Val
                260                 265                 270

Asn Met Ala Gly Cys Glu Trp Gly Arg Asp Cys Trp Gly Glu Met Tyr
                275                 280                 285

His Tyr Arg Glu Phe Ser Tyr Trp Leu Asn Arg Asn Pro Trp Glu Leu
                290                 295                 300

Phe Lys Glu Glu Ile Val Ala Val Ile Trp Tyr Lys Leu Thr Gly Gln
305                 310                 315                 320

Arg Val Lys Leu

<210> SEQ ID NO 227
<211> LENGTH: 339
<212> TYPE: PRT
<213> ORGANISM: Saccharomyces cerevisiae

<400> SEQUENCE: 227

Met Ala Gly Ser Thr Ser Ser Leu Val Ile Cys Ala Ile Gly Ile Tyr
1               5                   10                  15

Ala Thr Phe Leu Thr Trp Ala Leu Val Gln Glu Pro Leu Ala Thr Arg
                20                  25                  30

Thr Trp Pro Asn Ser Met Gly Lys Phe Gln Phe Pro Asn Val Ile Ser
            35                  40                  45

Leu Ile Gln Ala Ser Val Ala Met Met Met Gly Tyr Leu Tyr Leu Asn
50                  55                  60

Trp Lys Lys Val Glu Tyr Pro Pro Arg Lys Met Ile Lys Asp His Trp
65                  70                  75                  80

Lys Gln Leu Met Leu Ile Ser Phe Thr Gln Ser Ser Ser Gly Pro Leu
                85                  90                  95

Ala Thr Thr Ser Leu Lys His Val Asp Tyr Leu Thr Tyr Met Leu Ala
                100                 105                 110

Lys Ser Cys Lys Met Ile Pro Val Leu Leu Val His Leu Leu Leu Tyr
            115                 120                 125

Arg Thr Pro Ile Ala Ser Gln Lys Lys Val Val Ala Leu Leu Val Ser
130                 135                 140

Leu Gly Val Thr Ile Phe Thr Ile Gly Gly Asn Asp Gly Lys Lys Leu
145                 150                 155                 160

Lys Arg Ser Phe Asn Glu Ser Gly Asn Asp Asn Lys Leu Gln Gly Phe
                165                 170                 175

Gly Leu Leu Phe Ser Ser Leu Phe Leu Asp Gly Leu Thr Asn Ala Thr
                180                 185                 190

Gln Asp Lys Leu Leu Lys Ala Asn Lys Ala Lys Glu Lys Gly Lys Gln
            195                 200                 205

Thr Leu Ile Thr Gly Ala His Leu Met Phe Thr Leu Asn Leu Phe Val
210                 215                 220

Ile Leu Trp Asn Ile Leu Tyr Phe Ile Val Ile Asp Cys Lys Gln Trp
225                 230                 235                 240

Asp Asn Ala Val Ser Val Leu Thr Met Asp Pro Gln Val Trp Gly Tyr
```

245                 250                 255
Leu Met Leu Tyr Ser Phe Cys Gly Ala Met Gly Gln Cys Phe Ile Phe
                260                 265                 270

Tyr Thr Leu Glu Gln Phe Gly Ser Leu Val Leu Ile Met Ile Thr Val
            275                 280                 285

Thr Arg Lys Met Val Ser Met Ile Leu Ser Ile Ile Val Phe Gly Lys
        290                 295                 300

Ser Val Arg Phe Gln Gln Trp Val Gly Met Phe Ile Val Phe Gly Gly
305                 310                 315                 320

Ile Thr Trp Glu Ala Leu Asn Lys Lys Ala Asn Ile Pro Lys Ala
                325                 330                 335

Lys Ser Ala

<210> SEQ ID NO 228
<211> LENGTH: 348
<212> TYPE: PRT
<213> ORGANISM: Homo sapiens

<400> SEQUENCE: 228

Met Ala Glu Lys Val Leu Val Thr Gly Gly Ala Gly Tyr Ile Gly Ser
1               5                   10                  15

His Thr Val Leu Glu Leu Leu Glu Ala Gly Tyr Leu Pro Val Val Ile
            20                  25                  30

Asp Asn Phe His Asn Ala Phe Arg Gly Gly Gly Ser Leu Pro Glu Ser
        35                  40                  45

Leu Arg Arg Val Gln Glu Leu Thr Gly Arg Ser Val Glu Phe Glu Glu
    50                  55                  60

Met Asp Ile Leu Asp Gln Gly Ala Leu Gln Arg Leu Phe Lys Lys Tyr
65                  70                  75                  80

Ser Phe Met Ala Val Ile His Phe Ala Gly Leu Lys Ala Val Gly Glu
                85                  90                  95

Ser Val Gln Lys Pro Leu Asp Tyr Tyr Arg Val Asn Leu Thr Gly Thr
            100                 105                 110

Ile Gln Leu Leu Glu Ile Met Lys Ala His Gly Val Lys Asn Leu Val
        115                 120                 125

Phe Ser Ser Ser Ala Thr Val Tyr Gly Asn Pro Gln Tyr Leu Pro Leu
    130                 135                 140

Asp Glu Ala His Pro Thr Gly Gly Cys Thr Asn Pro Tyr Gly Lys Ser
145                 150                 155                 160

Lys Phe Phe Ile Glu Glu Met Ile Arg Asp Leu Cys Gln Ala Asp Lys
                165                 170                 175

Thr Trp Asn Val Val Leu Leu Arg Tyr Phe Asn Pro Thr Gly Ala His
            180                 185                 190

Ala Ser Gly Cys Ile Gly Glu Asp Pro Gln Gly Ile Pro Asn Asn Leu
        195                 200                 205

Met Pro Tyr Val Ser Gln Val Ala Ile Gly Arg Arg Glu Ala Leu Asn
    210                 215                 220

Val Phe Gly Asn Asp Tyr Asp Thr Glu Asp Gly Thr Gly Val Arg Asp
225                 230                 235                 240

Tyr Ile His Val Asp Leu Ala Lys Gly His Ile Ala Ala Leu Arg
                245                 250                 255

Lys Leu Lys Glu Gln Cys Gly Cys Arg Ile Tyr Asn Leu Gly Thr Gly
            260                 265                 270

Thr Gly Tyr Ser Val Leu Gln Met Val Gln Ala Met Glu Lys Ala Ser

```
                275                 280                 285
Gly Lys Lys Ile Pro Tyr Lys Val Val Ala Arg Arg Glu Gly Asp Val
    290                 295                 300
Ala Ala Cys Tyr Ala Asn Pro Ser Leu Ala Gln Glu Glu Leu Gly Trp
305                 310                 315                 320
Thr Ala Ala Leu Gly Leu Asp Arg Met Cys Glu Asp Leu Trp Arg Trp
                325                 330                 335
Gln Lys Gln Asn Pro Ser Gly Phe Gly Thr Gln Ala
            340                 345

<210> SEQ ID NO 229
<211> LENGTH: 106
<212> TYPE: PRT
<213> ORGANISM: Trichoderma reesei

<400> SEQUENCE: 229

Met Ala Ser Thr Asn Ala Arg Tyr Val Arg Tyr Leu Leu Ile Ala Phe
1               5                   10                  15
Phe Thr Ile Leu Val Phe Tyr Phe Val Ser Asn Ser Lys Tyr Glu Gly
                20                  25                  30
Val Asp Leu Asn Lys Gly Thr Phe Thr Ala Pro Asp Ser Thr Lys Thr
            35                  40                  45
Thr Pro Lys Pro Pro Ala Thr Gly Asp Ala Lys Asp Phe Pro Leu Ala
50                  55                  60
Leu Thr Pro Asn Asp Pro Gly Phe Asn Asp Leu Val Gly Ile Ala Pro
65                  70                  75                  80
Gly Pro Arg Met Asn Ala Thr Phe Val Thr Leu Ala Arg Asn Ser Asp
                85                  90                  95
Val Trp Asp Ile Ala Arg Ser Ile Arg Gln
            100                 105

<210> SEQ ID NO 230
<211> LENGTH: 83
<212> TYPE: PRT
<213> ORGANISM: Trichoderma reesei

<400> SEQUENCE: 230

Met Ala Ser Thr Asn Ala Arg Tyr Val Arg Tyr Leu Leu Ile Ala Phe
1               5                   10                  15
Phe Thr Ile Leu Val Phe Tyr Phe Val Ser Asn Ser Lys Tyr Glu Gly
                20                  25                  30
Val Asp Leu Asn Lys Gly Thr Phe Thr Ala Pro Asp Ser Thr Lys Thr
            35                  40                  45
Thr Pro Lys Pro Pro Ala Thr Gly Asp Ala Lys Asp Phe Pro Leu Ala
50                  55                  60
Leu Thr Pro Asn Asp Pro Gly Phe Asn Asp Leu Val Gly Ile Ala Pro
65                  70                  75                  80
Gly Pro Arg

<210> SEQ ID NO 231
<211> LENGTH: 51
<212> TYPE: PRT
<213> ORGANISM: Trichoderma reesei

<400> SEQUENCE: 231

Met Ala Ser Thr Asn Ala Arg Tyr Val Arg Tyr Leu Leu Ile Ala Phe
1               5                   10                  15
```

```
Phe Thr Ile Leu Val Phe Tyr Phe Val Ser Asn Ser Lys Tyr Glu Gly
                20                  25                  30

Val Asp Leu Asn Lys Gly Thr Phe Thr Ala Pro Asp Ser Thr Lys Thr
            35                  40                  45

Thr Pro Lys
        50

<210> SEQ ID NO 232
<211> LENGTH: 722
<212> TYPE: PRT
<213> ORGANISM: Homo sapiens

<400> SEQUENCE: 232

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335
```

-continued

```
Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
            355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
            435                 440                 445

Ile Leu Gln Met Cys Val Glu Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
            515                 520                 525

Gly Gln Gly Lys Gly Leu Glu Asn Phe Val Thr Leu Ile Thr Gly Thr
    530                 535                 540

Gly Ile Gly Gly Gly Ile Ile His Gln His Glu Leu Ile His Arg Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
    595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr
```

<210> SEQ ID NO 233
<211> LENGTH: 753
<212> TYPE: PRT

<213> ORGANISM: Homo sapiens

<400> SEQUENCE: 233

| | | | | | | | | | | | | | | |
|---|---|---|---|---|---|---|---|---|---|---|---|---|---|---|
| Met | Glu | Thr | Tyr | Gly | Tyr | Leu | Gln | Arg | Glu | Ser | Cys | Phe | Gln | Gly | Pro |
| 1 | | | | 5 | | | | | 10 | | | | | 15 | |
| His | Glu | Leu | Tyr | Phe | Lys | Asn | Leu | Ser | Lys | Arg | Asn | Lys | Gln | Ile | Met |
| | | | 20 | | | | | 25 | | | | | 30 | | |
| Glu | Lys | Asn | Gly | Asn | Asn | Arg | Lys | Leu | Arg | Val | Cys | Val | Ala | Thr | Cys |
| | | | 35 | | | | 40 | | | | | 45 | | | |
| Asn | Arg | Ala | Asp | Tyr | Ser | Lys | Leu | Ala | Pro | Ile | Met | Phe | Gly | Ile | Lys |
| | 50 | | | | | 55 | | | | | 60 | | | | |
| Thr | Glu | Pro | Glu | Phe | Phe | Glu | Leu | Asp | Val | Val | Leu | Gly | Ser | His | |
| 65 | | | | | 70 | | | | | 75 | | | | | 80 |
| Leu | Ile | Asp | Asp | Tyr | Gly | Asn | Thr | Tyr | Arg | Met | Ile | Glu | Gln | Asp | Asp |
| | | | | 85 | | | | | 90 | | | | | 95 | |
| Phe | Asp | Ile | Asn | Thr | Arg | Leu | His | Thr | Ile | Val | Arg | Gly | Asp | Glu | |
| | | | 100 | | | | | 105 | | | | | 110 | | |
| Ala | Ala | Met | Val | Glu | Ser | Val | Gly | Leu | Ala | Leu | Val | Lys | Leu | Pro | Asp |
| | | | 115 | | | | | 120 | | | | | 125 | | |
| Val | Leu | Asn | Arg | Leu | Lys | Pro | Asp | Ile | Met | Ile | Val | His | Gly | Asp | Arg |
| | 130 | | | | | 135 | | | | | 140 | | | | |
| Phe | Asp | Ala | Leu | Ala | Leu | Ala | Thr | Ser | Ala | Ala | Leu | Met | Asn | Ile | Arg |
| 145 | | | | | 150 | | | | | 155 | | | | | 160 |
| Ile | Leu | His | Ile | Glu | Gly | Gly | Glu | Val | Ser | Gly | Thr | Ile | Asp | Asp | Ser |
| | | | | 165 | | | | | 170 | | | | | 175 | |
| Ile | Arg | His | Ala | Ile | Thr | Lys | Leu | Ala | His | Tyr | His | Val | Cys | Cys | Thr |
| | | | 180 | | | | | 185 | | | | | 190 | | |
| Arg | Ser | Ala | Glu | Gln | His | Leu | Ile | Ser | Met | Cys | Glu | Asp | His | Asp | Arg |
| | | | 195 | | | | | 200 | | | | | 205 | | |
| Ile | Leu | Leu | Ala | Gly | Cys | Pro | Ser | Tyr | Asp | Lys | Leu | Leu | Ser | Ala | Lys |
| | 210 | | | | | 215 | | | | | 220 | | | | |
| Asn | Lys | Asp | Tyr | Met | Ser | Ile | Ile | Arg | Met | Trp | Leu | Gly | Asp | Asp | Val |
| 225 | | | | | 230 | | | | | 235 | | | | | 240 |
| Lys | Ser | Lys | Asp | Tyr | Ile | Val | Ala | Leu | Gln | His | Pro | Val | Thr | Thr | Asp |
| | | | | 245 | | | | | 250 | | | | | 255 | |
| Ile | Lys | His | Ser | Ile | Lys | Met | Phe | Glu | Leu | Thr | Leu | Asp | Ala | Leu | Ile |
| | | | 260 | | | | | 265 | | | | | 270 | | |
| Ser | Phe | Asn | Lys | Arg | Thr | Leu | Val | Leu | Phe | Pro | Asn | Ile | Asp | Ala | Gly |
| | | | 275 | | | | | 280 | | | | | 285 | | |
| Ser | Lys | Glu | Met | Val | Arg | Val | Met | Arg | Lys | Lys | Gly | Ile | Glu | His | His |
| | 290 | | | | | 295 | | | | | 300 | | | | |
| Pro | Asn | Phe | Arg | Ala | Val | Lys | His | Val | Pro | Phe | Asp | Gln | Phe | Ile | Gln |
| 305 | | | | | 310 | | | | | 315 | | | | | 320 |
| Leu | Val | Ala | His | Ala | Gly | Cys | Met | Ile | Gly | Asn | Ser | Ser | Cys | Gly | Val |
| | | | | 325 | | | | | 330 | | | | | 335 | |
| Arg | Glu | Val | Gly | Ala | Phe | Gly | Thr | Pro | Val | Ile | Asn | Leu | Gly | Thr | Arg |
| | | | 340 | | | | | 345 | | | | | 350 | | |
| Gln | Ile | Gly | Arg | Glu | Thr | Gly | Glu | Asn | Val | Leu | His | Val | Arg | Asp | Ala |
| | | | 355 | | | | | 360 | | | | | 365 | | |
| Asp | Thr | Gln | Asp | Lys | Ile | Leu | Gln | Ala | Leu | His | Leu | Gln | Phe | Gly | Lys |
| | 370 | | | | | 375 | | | | | 380 | | | | |
| Gln | Tyr | Pro | Cys | Ser | Lys | Ile | Tyr | Gly | Asp | Gly | Asn | Ala | Val | Pro | Arg |
| 385 | | | | | 390 | | | | | 395 | | | | | 400 |

```
Ile Leu Lys Phe Leu Lys Ser Ile Asp Leu Gln Glu Pro Leu Gln Lys
                405                 410                 415

Lys Phe Cys Phe Pro Val Lys Glu Asn Ile Ser Gln Asp Ile Asp
        420                 425                 430

His Ile Leu Glu Thr Leu Ser Ala Leu Ala Val Asp Leu Gly Gly Thr
            435                 440                 445

Asn Leu Arg Val Ala Ile Val Ser Met Lys Gly Glu Ile Val Lys Lys
450                 455                 460

Tyr Thr Gln Phe Asn Pro Lys Thr Tyr Glu Arg Ile Asn Leu Ile
465                 470                 475                 480

Leu Gln Met Cys Val Glu Ala Ala Glu Ala Val Lys Leu Asn Cys
                485                 490                 495

Arg Ile Leu Gly Val Gly Ile Ser Thr Gly Gly Arg Val Asn Pro Arg
                500                 505                 510

Glu Gly Ile Val Leu His Ser Thr Lys Leu Ile Gln Glu Trp Asn Ser
            515                 520                 525

Val Asp Leu Arg Thr Pro Leu Ser Asp Thr Leu His Leu Pro Val Trp
            530                 535                 540

Val Asp Asn Asp Gly Asn Cys Ala Ala Leu Ala Glu Arg Lys Phe Gly
545                 550                 555                 560

Gln Gly Lys Gly Leu Glu Asn Phe Val Thr Leu Ile Thr Gly Thr Gly
                565                 570                 575

Ile Gly Gly Gly Ile Ile His Gln His Glu Leu Ile His Gly Ser Ser
                580                 585                 590

Phe Cys Ala Ala Glu Leu Gly His Leu Val Val Ser Leu Asp Gly Pro
            595                 600                 605

Asp Cys Ser Cys Gly Ser His Gly Cys Ile Glu Ala Tyr Ala Ser Gly
            610                 615                 620

Met Ala Leu Gln Arg Glu Ala Lys Lys Leu His Asp Glu Asp Leu Leu
625                 630                 635                 640

Leu Val Glu Gly Met Ser Val Pro Lys Asp Glu Ala Val Gly Ala Leu
                645                 650                 655

His Leu Ile Gln Ala Ala Lys Leu Gly Asn Ala Lys Ala Gln Ser Ile
                660                 665                 670

Leu Arg Thr Ala Gly Thr Ala Leu Gly Leu Gly Val Val Asn Ile Leu
            675                 680                 685

His Thr Met Asn Pro Ser Leu Val Ile Leu Ser Gly Val Leu Ala Ser
            690                 695                 700

His Tyr Ile His Ile Val Lys Asp Val Ile Arg Gln Gln Ala Leu Ser
705                 710                 715                 720

Ser Val Gln Asp Val Asp Val Val Ser Asp Leu Val Asp Pro Ala
                725                 730                 735

Leu Leu Gly Ala Ala Ser Met Val Leu Asp Tyr Thr Thr Arg Arg Ile
                740                 745                 750

Tyr
```

<210> SEQ ID NO 234
<211> LENGTH: 359
<212> TYPE: PRT
<213> ORGANISM: Homo sapiens

<400> SEQUENCE: 234

```
Met Pro Leu Glu Leu Glu Leu Cys Pro Gly Arg Trp Val Gly Gly Gln
1               5                   10                  15
```

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
        35                  40                  45

Asp Cys Ala Lys Phe Gln Lys Ser Glu Leu Glu Phe Lys Phe Asn Arg
    50                  55                  60

Lys Ala Leu Glu Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
            100                 105                 110

Gly Met Asp Glu Met Ala Val Glu Phe Leu His Glu Leu Asn Val Pro
        115                 120                 125

Phe Phe Lys Val Gly Ser Gly Asp Thr Asn Asn Phe Pro Tyr Leu Glu
    130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Phe Leu Gln Cys Thr Ser Ala Tyr Pro Leu Gln Pro
            180                 185                 190

Glu Asp Val Asn Leu Arg Val Ile Ser Glu Tyr Gln Lys Leu Phe Pro
        195                 200                 205

Asp Ile Pro Ile Gly Tyr Ser Gly His Glu Thr Gly Ile Ala Ile Ser
    210                 215                 220

Val Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
                245                 250                 255

Gly Glu Leu Ala Glu Leu Val Arg Ser Val Arg Leu Val Glu Arg Ala
            260                 265                 270

Leu Gly Ser Pro Thr Lys Gln Leu Leu Pro Cys Glu Met Ala Cys Asn
        275                 280                 285

Glu Lys Leu Gly Lys Ser Val Val Ala Lys Val Lys Ile Pro Glu Gly
    290                 295                 300

Thr Ile Leu Thr Met Asp Met Leu Thr Val Lys Val Gly Glu Pro Lys
305                 310                 315                 320

Gly Tyr Pro Pro Glu Asp Ile Phe Asn Leu Val Gly Lys Lys Val Leu
                325                 330                 335

Val Thr Val Glu Glu Asp Asp Thr Ile Met Glu Glu Leu Val Asp Asn
            340                 345                 350

His Gly Lys Lys Ile Lys Ser
        355

<210> SEQ ID NO 235
<211> LENGTH: 248
<212> TYPE: PRT
<213> ORGANISM: Homo sapiens

<400> SEQUENCE: 235

Met Gly Leu Ser Arg Val Arg Ala Val Phe Phe Asp Leu Asp Asn Thr
1               5                   10                  15

Leu Ile Asp Thr Ala Gly Ala Ser Arg Arg Gly Met Leu Glu Val Ile
            20                  25                  30

-continued

```
Lys Leu Leu Gln Ser Lys Tyr His Tyr Lys Glu Glu Ala Glu Ile Ile
            35                  40                  45

Cys Asp Lys Val Gln Val Lys Leu Ser Lys Glu Cys Phe His Pro Tyr
 50                  55                  60

Asn Thr Cys Ile Thr Asp Leu Arg Thr Ser His Trp Glu Glu Ala Ile
 65                  70                  75                  80

Gln Glu Thr Lys Gly Ala Ala Asn Arg Lys Leu Ala Glu Glu Cys
                85                  90                  95

Tyr Phe Leu Trp Lys Ser Thr Arg Leu Gln His Met Thr Leu Ala Glu
                100                 105                 110

Asp Val Lys Ala Met Leu Thr Glu Leu Arg Lys Glu Val Arg Leu Leu
                115                 120                 125

Leu Leu Thr Asn Gly Asp Arg Gln Thr Gln Arg Glu Lys Ile Glu Ala
            130                 135                 140

Cys Ala Cys Gln Ser Tyr Phe Asp Ala Val Val Gly Gly Glu Gln
145                 150                 155                 160

Arg Glu Glu Lys Pro Ala Pro Ser Ile Phe Tyr Tyr Cys Cys Asn Leu
                165                 170                 175

Leu Gly Val Gln Pro Gly Asp Cys Val Met Val Gly Asp Thr Leu Glu
                180                 185                 190

Thr Asp Ile Gln Gly Gly Leu Asn Ala Gly Leu Lys Ala Thr Val Trp
            195                 200                 205

Ile Asn Lys Asn Gly Ile Val Pro Leu Lys Ser Ser Pro Val Pro His
210                 215                 220

Tyr Met Val Ser Val Leu Glu Leu Pro Ala Leu Leu Gln Ser Ile
225                 230                 235                 240

Asp Cys Lys Val Ser Met Ser Thr
                245
```

<210> SEQ ID NO 236
<211> LENGTH: 434
<212> TYPE: PRT
<213> ORGANISM: Homo sapiens

<400> SEQUENCE: 236

```
Met Asp Ser Val Glu Lys Gly Ala Ala Thr Ser Val Ser Asn Pro Arg
 1               5                  10                  15

Gly Arg Pro Ser Arg Gly Arg Pro Lys Leu Gln Arg Asn Ser Arg
                20                  25                  30

Gly Gly Gln Gly Arg Gly Val Glu Lys Pro Pro His Leu Ala Ala Leu
            35                  40                  45

Ile Leu Ala Arg Gly Gly Ser Lys Gly Ile Pro Leu Lys Asn Ile Lys
 50                  55                  60

His Leu Ala Gly Val Pro Leu Ile Gly Trp Val Leu Arg Ala Ala Leu
 65                  70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
                100                 105                 110

Ser Glu Val Ser Lys Asp Ser Ser Thr Ser Leu Asp Ala Ile Ile Glu
            115                 120                 125

Phe Leu Asn Tyr His Asn Glu Val Asp Ile Val Gly Asn Ile Gln Ala
            130                 135                 140

Thr Ser Pro Cys Leu His Pro Thr Asp Leu Gln Lys Val Ala Glu Met
```

```
            145                 150                 155                 160
        Ile Arg Glu Gly Tyr Asp Ser Val Phe Ser Val Arg Arg His
                        165                 170                 175
        Gln Phe Arg Trp Ser Glu Ile Gln Lys Gly Val Arg Glu Val Thr Glu
                    180                 185                 190

Pro Leu Asn Leu Asn Pro Ala Lys Arg Pro Arg Gln Asp Trp Asp
                195                 200                 205

Gly Glu Leu Tyr Glu Asn Gly Ser Phe Tyr Ala Lys Arg His Leu
            210                 215                 220

Ile Glu Met Gly Tyr Leu Gln Gly Gly Lys Met Ala Tyr Glu Met
        225                 230                 235                 240

Arg Ala Glu His Ser Val Asp Ile Asp Val Asp Ile Asp Trp Pro Ile
                        245                 250                 255

Ala Glu Gln Arg Val Leu Arg Tyr Gly Tyr Phe Gly Lys Glu Lys Leu
                    260                 265                 270

Lys Glu Ile Lys Leu Leu Val Cys Asn Ile Asp Gly Cys Leu Thr Asn
                275                 280                 285

Gly His Ile Tyr Val Ser Gly Asp Gln Lys Glu Ile Ser Tyr Asp
            290                 295                 300

Val Lys Asp Ala Ile Gly Ile Ser Leu Leu Lys Ser Gly Ile Glu
        305                 310                 315                 320

Val Arg Leu Ile Ser Glu Arg Ala Cys Ser Lys Gln Thr Leu Ser Ser
                        325                 330                 335

Leu Lys Leu Asp Cys Lys Met Glu Val Ser Val Ser Asp Lys Leu Ala
                    340                 345                 350

Val Val Asp Glu Trp Arg Lys Glu Met Gly Leu Cys Trp Lys Glu Val
                355                 360                 365

Ala Tyr Leu Gly Asn Glu Val Ser Asp Glu Glu Cys Leu Lys Arg Val
            370                 375                 380

Gly Leu Ser Gly Ala Pro Ala Asp Ala Cys Ser Thr Ala Gln Lys Ala
        385                 390                 395                 400

Val Gly Tyr Ile Cys Lys Cys Asn Gly Gly Arg Gly Ala Ile Arg Glu
                        405                 410                 415

Phe Ala Glu His Ile Cys Leu Leu Met Glu Lys Val Asn Asn Ser Cys
                    420                 425                 430

Gln Lys

<210> SEQ ID NO 237
<211> LENGTH: 336
<212> TYPE: PRT
<213> ORGANISM: Mus musculus

<400> SEQUENCE: 237

Met Ala Pro Ala Arg Glu Asn Val Ser Leu Phe Phe Lys Leu Tyr Cys
1               5                   10                  15

Leu Thr Val Met Thr Leu Val Ala Ala Tyr Thr Val Ala Leu Arg
            20                  25                  30

Tyr Thr Arg Thr Thr Ala Glu Glu Leu Tyr Phe Ser Thr Thr Ala Val
        35                  40                  45

Cys Ile Thr Glu Val Ile Lys Leu Leu Ile Ser Val Gly Leu Leu Ala
    50                  55                  60

Lys Glu Thr Gly Ser Leu Gly Arg Phe Lys Ala Ser Leu Ser Glu Asn
65                  70                  75                  80

Val Leu Gly Ser Pro Lys Glu Leu Ala Lys Leu Ser Val Pro Ser Leu
```

```
                     85                  90                  95

Val Tyr Ala Val Gln Asn Asn Met Ala Phe Leu Ala Leu Ser Asn Leu
                100                 105                 110

Asp Ala Ala Val Tyr Gln Val Thr Tyr Gln Leu Lys Ile Pro Cys Thr
            115                 120                 125

Ala Leu Cys Thr Val Leu Met Leu Asn Arg Thr Leu Ser Lys Leu Gln
        130                 135                 140

Trp Ile Ser Val Phe Met Leu Cys Gly Gly Val Thr Leu Val Gln Trp
145                 150                 155                 160

Lys Pro Ala Gln Ala Thr Lys Val Val Ala Gln Asn Pro Leu Leu
                165                 170                 175

Gly Phe Gly Ala Ile Ala Ile Ala Val Leu Cys Ser Gly Phe Ala Gly
                180                 185                 190

Val Tyr Phe Glu Lys Val Leu Lys Ser Ser Asp Thr Ser Leu Trp Val
            195                 200                 205

Arg Asn Ile Gln Met Tyr Leu Ser Gly Ile Val Val Thr Leu Ala Gly
        210                 215                 220

Thr Tyr Leu Ser Asp Gly Ala Glu Ile Gln Glu Lys Gly Phe Phe Tyr
225                 230                 235                 240

Gly Tyr Thr Tyr Tyr Val Trp Phe Val Ile Phe Leu Ala Ser Val Gly
                245                 250                 255

Gly Leu Tyr Thr Ser Val Val Lys Tyr Thr Asp Asn Ile Met Lys
                260                 265                 270

Gly Phe Ser Ala Ala Ala Ile Val Leu Ser Thr Ile Ala Ser Val
            275                 280                 285

Leu Leu Phe Gly Leu Gln Ile Thr Leu Ser Phe Ala Leu Gly Ala Leu
        290                 295                 300

Leu Val Cys Val Ser Ile Tyr Leu Tyr Gly Leu Pro Arg Gln Asp Thr
305                 310                 315                 320

Thr Ser Ile Gln Gln Glu Ala Thr Ser Lys Glu Arg Ile Ile Gly Val
                325                 330                 335

<210> SEQ ID NO 238
<211> LENGTH: 403
<212> TYPE: PRT
<213> ORGANISM: Mus musculus

<400> SEQUENCE: 238

Met Ile His Thr Asn Leu Lys Arg Lys Phe Ser Cys Phe Val Leu Val
1               5                   10                  15

Phe Leu Leu Phe Ala Ile Ile Cys Val Trp Lys Lys Gly Ser Asp Tyr
            20                  25                  30

Glu Ala Leu Thr Leu Gln Ala Lys Val Phe Gln Met Pro Lys Ser Gln
        35                  40                  45

Glu Lys Val Ala Val Gly Pro Ala Pro Gln Ala Val Phe Ser Asn Ser
    50                  55                  60

Lys Gln Asp Pro Lys Glu Gly Val Gln Ile Leu Ser Tyr Pro Arg Val
65                  70                  75                  80

Thr Ala Lys Val Lys Pro Gln Pro Ser Leu Gln Val Trp Asp Lys Asp
                85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Pro
        115                 120                 125
```

Gly Val Lys Phe Ser Val Glu Ala Leu Arg Cys His Leu Arg Asp His
130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Ala Gly
                165                 170                 175

Pro Trp His Lys Cys Ala Val Val Ser Ser Ala Gly Ser Leu Lys Asn
                180                 185                 190

Ser Gln Leu Gly Arg Glu Ile Asp Asn His Asp Ala Val Leu Arg Phe
                195                 200                 205

Asn Gly Ala Pro Thr Asp Asn Phe Gln Gln Asp Val Gly Thr Lys Thr
210                 215                 220

Thr Ile Arg Leu Val Asn Ser Gln Leu Val Thr Thr Glu Lys Arg Phe
225                 230                 235                 240

Leu Lys Asp Ser Leu Tyr Thr Glu Gly Ile Leu Ile Leu Trp Asp Pro
                245                 250                 255

Ser Val Tyr His Ala Asp Ile Pro Gln Trp Tyr Gln Lys Pro Asp Tyr
                260                 265                 270

Asn Phe Phe Glu Thr Tyr Lys Ser Tyr Arg Arg Leu His Pro Ser Gln
                275                 280                 285

Pro Phe Tyr Ile Leu Lys Pro Gln Met Pro Trp Glu Leu Trp Asp Ile
290                 295                 300

Ile Gln Glu Ile Ser Pro Asp Leu Ile Gln Pro Asn Pro Pro Ser Ser
305                 310                 315                 320

Gly Met Leu Gly Ile Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr
                340                 345                 350

His Gln Lys Phe Phe Asp Ser Ala Cys Thr Met Gly Ala Tyr His Pro
                355                 360                 365

Leu Leu Phe Glu Lys Asn Met Val Lys His Leu Asn Glu Gly Thr Asp
370                 375                 380

Glu Asp Ile Tyr Leu Phe Gly Lys Ala Thr Leu Ser Gly Phe Arg Asn
385                 390                 395                 400

Asn Arg Cys

<210> SEQ ID NO 239
<211> LENGTH: 329
<212> TYPE: PRT
<213> ORGANISM: Homo sapiens

<400> SEQUENCE: 239

Met Val Ser Lys Ser Arg Trp Lys Leu Leu Ala Met Leu Ala Leu Val
1               5                   10                  15

Leu Val Val Met Val Trp Tyr Ser Ile Ser Arg Glu Asp Ser Phe Tyr
                20                  25                  30

Phe Pro Ile Pro Glu Lys Lys Glu Pro Cys Leu Gln Gly Glu Ala Glu
                35                  40                  45

Ser Lys Ala Ser Lys Leu Phe Gly Asn Tyr Ser Arg Asp Gln Pro Ile
                50                  55                  60

Phe Leu Arg Leu Glu Asp Tyr Phe Trp Val Lys Thr Pro Ser Ala Tyr
65                  70                  75                  80

Glu Leu Pro Tyr Gly Thr Lys Gly Ser Glu Asp Leu Leu Leu Arg Val
                85                  90                  95

```
Leu Ala Ile Thr Ser Ser Ile Pro Lys Asn Ile Gln Ser Leu Arg
            100                 105                 110

Cys Arg Arg Cys Val Val Gly Asn Gly His Arg Leu Arg Asn Ser
        115                 120                 125

Ser Leu Gly Asp Ala Ile Asn Lys Tyr Asp Val Val Ile Arg Leu Asn
    130                 135                 140

Asn Ala Pro Val Ala Gly Tyr Glu Gly Asp Val Gly Ser Lys Thr Thr
145                 150                 155                 160

Met Arg Leu Phe Tyr Pro Glu Ser Ala His Phe Asp Pro Lys Val Glu
                165                 170                 175

Asn Asn Pro Asp Thr Leu Leu Val Leu Val Ala Phe Lys Ala Met Asp
            180                 185                 190

Phe His Trp Ile Glu Thr Ile Leu Ser Asp Lys Lys Arg Val Arg Lys
        195                 200                 205

Gly Phe Trp Lys Gln Pro Leu Ile Trp Asp Val Asn Pro Lys Gln
    210                 215                 220

Ile Arg Ile Leu Asn Pro Phe Met Glu Ile Ala Ala Asp Lys Leu
225                 230                 235                 240

Leu Ser Leu Pro Met Gln Gln Pro Arg Lys Ile Lys Gln Lys Pro Thr
                245                 250                 255

Thr Gly Leu Leu Ala Ile Thr Leu Ala Leu His Leu Cys Asp Leu Val
            260                 265                 270

His Ile Ala Gly Phe Gly Tyr Pro Asp Ala Tyr Asn Lys Lys Gln Thr
        275                 280                 285

Ile His Tyr Tyr Glu Gln Ile Thr Leu Lys Ser Met Ala Gly Ser Gly
    290                 295                 300

His Asn Val Ser Gln Glu Ala Leu Ala Ile Lys Arg Met Leu Glu Met
305                 310                 315                 320

Gly Ala Ile Lys Asn Leu Thr Ser Phe
                325

<210> SEQ ID NO 240
<211> LENGTH: 863
<212> TYPE: PRT
<213> ORGANISM: Artificial Sequence
<220> FEATURE:
<223> OTHER INFORMATION: Primer

<400> SEQUENCE: 240

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
            35                  40                  45

Gly Ala Gly Gly Arg Gly Gly Asp His Pro Ser Val Ala Val Gly Ile
        50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125
```

-continued

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
210                 215                 220

Ala Lys Phe Ser Gln Thr Lys His His Trp Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln Thr
        435                 440                 445

Arg Pro Ala Pro Gly Arg Pro Pro Ser Val Ser Ala Leu Asp Gly Asp
450                 455                 460

Pro Ala Ser Leu Thr Arg Glu Val Ile Arg Leu Ala Gln Asp Ala Glu
465                 470                 475                 480

Val Glu Leu Glu Arg Gln Arg Gly Leu Leu Gln Gln Ile Gly Asp Ala
                485                 490                 495

Leu Ser Ser Gln Arg Gly Arg Val Pro Thr Ala Ala Pro Pro Ala Gln
            500                 505                 510

Pro Arg Val Pro Val Thr Pro Ala Pro Ala Val Ile Pro Ile Leu Val
        515                 520                 525

Ile Ala Cys Asp Arg Ser Thr Val Arg Arg Cys Leu Asp Lys Leu Leu
530                 535                 540

His Tyr Arg Pro Ser Ala Glu Leu Phe Pro Ile Ile Val Ser Gln Asp

```
                545                 550                 555                 560
Cys Gly His Glu Glu Thr Ala Gln Ala Ile Ala Ser Tyr Gly Ser Ala
                565                 570                 575
Val Thr His Ile Arg Gln Pro Asp Leu Ser Ser Ile Ala Val Pro Pro
580                 585                 590
Asp His Arg Lys Phe Gln Gly Tyr Tyr Lys Ile Ala Arg His Tyr Arg
                595                 600                 605
Trp Ala Leu Gly Gln Val Phe Arg Gln Phe Arg Phe Pro Ala Ala Val
                610                 615                 620
Val Val Glu Asp Asp Leu Glu Val Ala Pro Asp Phe Glu Tyr Phe
625                 630                 635                 640
Arg Ala Thr Tyr Pro Leu Leu Lys Ala Asp Pro Ser Leu Trp Cys Val
                645                 650                 655
Ser Ala Trp Asn Asp Asn Gly Lys Glu Gln Met Val Asp Ala Ser Arg
                660                 665                 670
Pro Glu Leu Leu Tyr Arg Thr Asp Phe Phe Pro Gly Leu Gly Trp Leu
                675                 680                 685
Leu Leu Ala Glu Leu Trp Ala Glu Leu Glu Pro Lys Trp Pro Lys Ala
                690                 695                 700
Phe Trp Asp Asp Trp Met Arg Arg Pro Glu Gln Arg Gln Gly Arg Ala
705                 710                 715                 720
Cys Ile Arg Pro Glu Ile Ser Arg Thr Met Thr Phe Gly Arg Lys Gly
                725                 730                 735
Val Ser His Gly Gln Phe Phe Asp Gln His Leu Lys Phe Ile Lys Leu
                740                 745                 750
Asn Gln Gln Phe Val His Phe Thr Gln Leu Asp Leu Ser Tyr Leu Gln
                755                 760                 765
Arg Glu Ala Tyr Asp Arg Asp Phe Leu Ala Arg Val Tyr Gly Ala Pro
                770                 775                 780
Gln Leu Gln Val Glu Lys Val Arg Thr Asn Asp Arg Lys Glu Leu Gly
785                 790                 795                 800
Glu Val Arg Val Gln Tyr Thr Gly Arg Asp Ser Phe Lys Ala Phe Ala
                805                 810                 815
Lys Ala Leu Gly Val Met Asp Asp Leu Lys Ser Gly Val Pro Arg Ala
                820                 825                 830
Gly Tyr Arg Gly Ile Val Thr Phe Gln Phe Arg Gly Arg Val His
                835                 840                 845
Leu Ala Pro Pro Pro Thr Trp Glu Gly Tyr Asp Pro Ser Trp Asn
850                 855                 860

<210> SEQ ID NO 241
<211> LENGTH: 57
<212> TYPE: DNA
<213> ORGANISM: Artificial Sequence
<220> FEATURE:
<223> OTHER INFORMATION: Primer

<400> SEQUENCE: 241
gtaacgccag ggttttccca gtcacgacgg tttaaacgta ttgcgatgag cagcaga      57

<210> SEQ ID NO 242
<211> LENGTH: 43
<212> TYPE: DNA
<213> ORGANISM: Artificial Sequence
<220> FEATURE:
<223> OTHER INFORMATION: Primer
```

```
<400> SEQUENCE: 242
atccacttaa cgttactgaa atctggtctc ctaacccacc aag                43

<210> SEQ ID NO 243
<211> LENGTH: 43
<212> TYPE: DNA
<213> ORGANISM: Artificial Sequence
<220> FEATURE:
<223> OTHER INFORMATION: Primer

<400> SEQUENCE: 243
ctccttcaat atcatcttct gtctgtgaaa tgaggtccct tcc                43

<210> SEQ ID NO 244
<211> LENGTH: 57
<212> TYPE: DNA
<213> ORGANISM: Artificial Sequence
<220> FEATURE:
<223> OTHER INFORMATION: Primer

<400> SEQUENCE: 244
gcggataaca atttcacaca ggaaacagcg tttaaaccaa acgcagcaga aaccata   57

<210> SEQ ID NO 245
<211> LENGTH: 51
<212> TYPE: DNA
<213> ORGANISM: Artificial Sequence
<220> FEATURE:
<223> OTHER INFORMATION: Primer

<400> SEQUENCE: 245
gatttcagta acgttaagtg gatgcggccg cgacagaaga tgatattgaa g         51

<210> SEQ ID NO 246
<211> LENGTH: 50
<212> TYPE: DNA
<213> ORGANISM: Artificial Sequence
<220> FEATURE:
<223> OTHER INFORMATION: Primer

<400> SEQUENCE: 246
gacagaagat gatattgaag gaggcggccg cttaagtgga tcccggtgac           50

<210> SEQ ID NO 247
<211> LENGTH: 68
<212> TYPE: DNA
<213> ORGANISM: Artificial Sequence
<220> FEATURE:
<223> OTHER INFORMATION: Primer

<400> SEQUENCE: 247
ggtgggttag gagaccagat ttcagtaacg ttaagtggat gcggccgcct agcatcgact 60
actgctgc                                                         68

<210> SEQ ID NO 248
<211> LENGTH: 46
<212> TYPE: DNA
<213> ORGANISM: Artificial Sequence
<220> FEATURE:
<223> OTHER INFORMATION: Primer

<400> SEQUENCE: 248
gcagcagtag tcgatgctag gcgcgccatg caaagataca catcaa              46
```

```
<210> SEQ ID NO 249
<211> LENGTH: 46
<212> TYPE: DNA
<213> ORGANISM: Artificial Sequence
<220> FEATURE:
<223> OTHER INFORMATION: Primer

<400> SEQUENCE: 249
ttgatgtgta tctttgcatg gcgcgcctag catcgactac tgctgc            46

<210> SEQ ID NO 250
<211> LENGTH: 68
<212> TYPE: DNA
<213> ORGANISM: Artificial Sequence
<220> FEATURE:
<223> OTHER INFORMATION: Primer

<400> SEQUENCE: 250
agggacctca tttcacagac agaagatgat attgaaggag gcggccgcgg ctgatgaggc    60
tgagagag                                                            68

<210> SEQ ID NO 251
<211> LENGTH: 20
<212> TYPE: DNA
<213> ORGANISM: Artificial Sequence
<220> FEATURE:
<223> OTHER INFORMATION: Primer

<400> SEQUENCE: 251
tcgctgtaac gaacttctgt                                               20

<210> SEQ ID NO 252
<211> LENGTH: 20
<212> TYPE: DNA
<213> ORGANISM: Artificial Sequence
<220> FEATURE:
<223> OTHER INFORMATION: Primer

<400> SEQUENCE: 252
cattgttgac ctccactagc                                               20

<210> SEQ ID NO 253
<211> LENGTH: 20
<212> TYPE: DNA
<213> ORGANISM: Artificial Sequence
<220> FEATURE:
<223> OTHER INFORMATION: Primer

<400> SEQUENCE: 253
gctgctgatc ggacattttt                                               20

<210> SEQ ID NO 254
<211> LENGTH: 18
<212> TYPE: DNA
<213> ORGANISM: Artificial Sequence
<220> FEATURE:
<223> OTHER INFORMATION: Primer

<400> SEQUENCE: 254
gtttctggca gctggact                                                 18

<210> SEQ ID NO 255
<211> LENGTH: 20
<212> TYPE: DNA
<213> ORGANISM: Artificial Sequence
<220> FEATURE:
```

```
<223> OTHER INFORMATION: Primer

<400> SEQUENCE: 255
tcgctgtaac gaacttctgt                                              20

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
tgcgtcgccg tctcgctcct                                              20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
cgacgatcta cagccatctg                                              20

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
ccggtagcgt tagagagacg                                              20

<210> SEQ ID NO 259
<211> LENGTH: 58
<212> TYPE: DNA
<213> ORGANISM: Artificial Sequence
<220> FEATURE:
<223> OTHER INFORMATION: Primer

<400> SEQUENCE: 259
gtaacgccag ggttttccca gtcacgacgg tttaaactgc tgttgctgtt tgttgatg    58

<210> SEQ ID NO 260
<211> LENGTH: 69
<212> TYPE: DNA
<213> ORGANISM: Artificial Sequence
<220> FEATURE:
<223> OTHER INFORMATION: Primer

<400> SEQUENCE: 260
cccgtcaccg agatctgatc cgtcaccggg atccacttaa gcggccgcct gtggtgagat   60
ctccagacg                                                          69

<210> SEQ ID NO 261
<211> LENGTH: 69
<212> TYPE: DNA
<213> ORGANISM: Artificial Sequence
<220> FEATURE:
<223> OTHER INFORMATION: Primer

<400> SEQUENCE: 261
gccaagccca aaaagtgctc cttcaatatc atcttctgtc gcggccgcac tgtgcccaac   60
``` aataagcag                                                                 69

<210> SEQ ID NO 262
<211> LENGTH: 55
<212> TYPE: DNA
<213> ORGANISM: Artificial Sequence
<220> FEATURE:
<223> OTHER INFORMATION: Primer

<400> SEQUENCE: 262
gcggataaca atttcacaca ggaaacagcg tttaaaccca aggcgctggc tgtta            55

<210> SEQ ID NO 263
<211> LENGTH: 20
<212> TYPE: DNA
<213> ORGANISM: Artificial Sequence
<220> FEATURE:
<223> OTHER INFORMATION: Primer

<400> SEQUENCE: 263
gatcgacaaa ggttccagcg                                                     20

<210> SEQ ID NO 264
<211> LENGTH: 20
<212> TYPE: DNA
<213> ORGANISM: Artificial Sequence
<220> FEATURE:
<223> OTHER INFORMATION: Primer

<400> SEQUENCE: 264
aattgtatca ttccgaggct                                                     20

<210> SEQ ID NO 265
<211> LENGTH: 19
<212> TYPE: DNA
<213> ORGANISM: Artificial Sequence
<220> FEATURE:
<223> OTHER INFORMATION: Primer

<400> SEQUENCE: 265
ctgtttggcc ctcgaaact                                                      19

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
tgcgtcgccg tctcgctcct                                                     20

<210> SEQ ID NO 267
<211> LENGTH: 20
<212> TYPE: DNA
<213> ORGANISM: Artificial Sequence
<220> FEATURE:
<223> OTHER INFORMATION: Primer

<400> SEQUENCE: 267
ttcgccatcc aaatttcttc                                                     20

<210> SEQ ID NO 268
<211> LENGTH: 19
<212> TYPE: DNA

<213> ORGANISM: Artificial Sequence
<220> FEATURE:
<223> OTHER INFORMATION: Primer

<400> SEQUENCE: 268
catcctcaag gcctcagac                                          19

<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
cccaagtcgt ctcagctctc                                         20

<210> SEQ ID NO 270
<211> LENGTH: 21
<212> TYPE: DNA
<213> ORGANISM: Artificial Sequence
<220> FEATURE:
<223> OTHER INFORMATION: Primer

<400> SEQUENCE: 270
tcgaaggctt cagtgaggta a                                       21

<210> SEQ ID NO 271
<211> LENGTH: 57
<212> TYPE: DNA
<213> ORGANISM: Artificial Sequence
<220> FEATURE:
<223> OTHER INFORMATION: Primer

<400> SEQUENCE: 271
gtaacgccag ggttttccca gtcacgacgg tttaaacatc tcggagtgat gcttcct    57

<210> SEQ ID NO 272
<211> LENGTH: 68
<212> TYPE: DNA
<213> ORGANISM: Artificial Sequence
<220> FEATURE:
<223> OTHER INFORMATION: Primer

<400> SEQUENCE: 272
gcgctggcaa cgagagcaga gcagcagtag tcgatgctag gcggccgcat cagacgaaac    60
cagacgag                                                      68

<210> SEQ ID NO 273
<211> LENGTH: 68
<212> TYPE: DNA
<213> ORGANISM: Artificial Sequence
<220> FEATURE:
<223> OTHER INFORMATION: Primer

<400> SEQUENCE: 273
caaccagccg cagcctcagc ctctctcagc ctcatcagcc gcggccgcgc gaatcgagtt    60
gatgattc                                                      68

<210> SEQ ID NO 274
<211> LENGTH: 57
<212> TYPE: DNA
<213> ORGANISM: Artificial Sequence
<220> FEATURE:
<223> OTHER INFORMATION: Primer

<400> SEQUENCE: 274
gcggataaca atttcacaca ggaaacagcg tttaaacctg gttgggatct gaccact    57

<210> SEQ ID NO 275
<211> LENGTH: 19
<212> TYPE: DNA
<213> ORGANISM: Artificial Sequence
<220> FEATURE:
<223> OTHER INFORMATION: Primer

<400> SEQUENCE: 275
ctgtttggcc ctcgaaact    19

<210> SEQ ID NO 276
<211> LENGTH: 20
<212> TYPE: DNA
<213> ORGANISM: Artificial Sequence
<220> FEATURE:
<223> OTHER INFORMATION: Primer

<400> SEQUENCE: 276
ccatgagctt gaacaggtaa    20

<210> SEQ ID NO 277
<211> LENGTH: 20
<212> TYPE: DNA
<213> ORGANISM: Artificial Sequence
<220> FEATURE:
<223> OTHER INFORMATION: Primer

<400> SEQUENCE: 277
ttcgccatcc aaatttcttc    20

<210> SEQ ID NO 278
<211> LENGTH: 19
<212> TYPE: DNA
<213> ORGANISM: Artificial Sequence
<220> FEATURE:
<223> OTHER INFORMATION: Primer

<400> SEQUENCE: 278
catcctcaag gcctcagac    19

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
gcagacaaac agagcaacga    20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
ccatgagctt gaacaggtaa    20

<210> SEQ ID NO 281

```
<211> LENGTH: 20
<212> TYPE: DNA
<213> ORGANISM: Artificial Sequence
<220> FEATURE:
<223> OTHER INFORMATION: Primer

<400> SEQUENCE: 281
tagagggtgt cgatggaagc                                                 20

<210> SEQ ID NO 282
<211> LENGTH: 19
<212> TYPE: DNA
<213> ORGANISM: Artificial Sequence
<220> FEATURE:
<223> OTHER INFORMATION: Primer

<400> SEQUENCE: 282
catcctcaag gcctcagac                                                  19

<210> SEQ ID NO 283
<211> LENGTH: 20
<212> TYPE: DNA
<213> ORGANISM: Artificial Sequence
<220> FEATURE:
<223> OTHER INFORMATION: Primer

<400> SEQUENCE: 283
ggtctcttct ttgccagcac                                                 20

<210> SEQ ID NO 284
<211> LENGTH: 20
<212> TYPE: DNA
<213> ORGANISM: Artificial Sequence
<220> FEATURE:
<223> OTHER INFORMATION: Primer

<400> SEQUENCE: 284
tgtcgctgaa ctgaatttgc                                                 20

<210> SEQ ID NO 285
<211> LENGTH: 67
<212> TYPE: DNA
<213> ORGANISM: Artificial Sequence
<220> FEATURE:
<223> OTHER INFORMATION: Primer

<400> SEQUENCE: 285
gattaagttg ggtaacgcca gggttttccc agtcacgacg gtttaaacac ctcatgaggg     60
actatgg                                                               67

<210> SEQ ID NO 286
<211> LENGTH: 69
<212> TYPE: DNA
<213> ORGANISM: Artificial Sequence
<220> FEATURE:
<223> OTHER INFORMATION: Primer

<400> SEQUENCE: 286
gcgctggcaa cgagagcaga gcagcagtag tcgatgctag gcggccgcca agaagaggca     60
gagggtaat                                                             69

<210> SEQ ID NO 287
<211> LENGTH: 68
<212> TYPE: DNA
<213> ORGANISM: Artificial Sequence
```

-continued

```
<220> FEATURE:
<223> OTHER INFORMATION: Primer

<400> SEQUENCE: 287
caaccagccg cagcctcagc ctctctcagc ctcatcagcc gcggccgcct atacatactg   60
atgataca                                                            68

<210> SEQ ID NO 288
<211> LENGTH: 68
<212> TYPE: DNA
<213> ORGANISM: Artificial Sequence
<220> FEATURE:
<223> OTHER INFORMATION: Primer

<400> SEQUENCE: 288
tggaattgtg agcggataac aatttcacac aggaaacagc gtttaaacgc cccatgtatg   60
gactctac                                                            68

<210> SEQ ID NO 289
<211> LENGTH: 20
<212> TYPE: DNA
<213> ORGANISM: Artificial Sequence
<220> FEATURE:
<223> OTHER INFORMATION: Primer

<400> SEQUENCE: 289
gcagacaaac agagcaacga                                               20

<210> SEQ ID NO 290
<211> LENGTH: 20
<212> TYPE: DNA
<213> ORGANISM: Artificial Sequence
<220> FEATURE:
<223> OTHER INFORMATION: Primer

<400> SEQUENCE: 290
ccatgagctt gaacaggtaa                                               20

<210> SEQ ID NO 291
<211> LENGTH: 20
<212> TYPE: DNA
<213> ORGANISM: Artificial Sequence
<220> FEATURE:
<223> OTHER INFORMATION: Primer

<400> SEQUENCE: 291
tagagggtgt cgatggaagc                                               20

<210> SEQ ID NO 292
<211> LENGTH: 19
<212> TYPE: DNA
<213> ORGANISM: Artificial Sequence
<220> FEATURE:
<223> OTHER INFORMATION: Primer

<400> SEQUENCE: 292
catcctcaag gcctcagac                                                19

<210> SEQ ID NO 293
<211> LENGTH: 22
<212> TYPE: DNA
<213> ORGANISM: Artificial Sequence
<220> FEATURE:
<223> OTHER INFORMATION: Primer
```

```
<400> SEQUENCE: 293
ctcagaaagg ttgtagttgt ga                                              22

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
ccatgagctt gaacaggtaa                                                 20

<210> SEQ ID NO 295
<211> LENGTH: 22
<212> TYPE: DNA
<213> ORGANISM: Artificial Sequence
<220> FEATURE:
<223> OTHER INFORMATION: Primer

<400> SEQUENCE: 295
gatgttgtgt tttcagtctg ca                                              22

<210> SEQ ID NO 296
<211> LENGTH: 19
<212> TYPE: DNA
<213> ORGANISM: Artificial Sequence
<220> FEATURE:
<223> OTHER INFORMATION: Primer

<400> SEQUENCE: 296
catcctcaag gcctcagac                                                  19

<210> SEQ ID NO 297
<211> LENGTH: 19
<212> TYPE: DNA
<213> ORGANISM: Artificial Sequence
<220> FEATURE:
<223> OTHER INFORMATION: Primer

<400> SEQUENCE: 297
atgttcatcg ctggcgtcg                                                  19

<210> SEQ ID NO 298
<211> LENGTH: 21
<212> TYPE: DNA
<213> ORGANISM: Artificial Sequence
<220> FEATURE:
<223> OTHER INFORMATION: Primer

<400> SEQUENCE: 298
ctaaacgtaa gagcaggtca a                                               21

<210> SEQ ID NO 299
<211> LENGTH: 67
<212> TYPE: DNA
<213> ORGANISM: Artificial Sequence
<220> FEATURE:
<223> OTHER INFORMATION: Primer

<400> SEQUENCE: 299
gattaagttg ggtaacgcca gggttttccc agtcacgacg gtttaaacgc tactacgcga     60
gcaagtg                                                               67
```

```
<210> SEQ ID NO 300
<211> LENGTH: 66
<212> TYPE: DNA
<213> ORGANISM: Artificial Sequence
<220> FEATURE:
<223> OTHER INFORMATION: Primer

<400> SEQUENCE: 300
ggaactgtcg gcgattggga gaatttcgtg cgatcgcggc ggccgccgga tgaagatgtg      60
cagttg                                                                66

<210> SEQ ID NO 301
<211> LENGTH: 69
<212> TYPE: DNA
<213> ORGANISM: Artificial Sequence
<220> FEATURE:
<223> OTHER INFORMATION: Primer

<400> SEQUENCE: 301
agggaacata tcaccctcgg gcatttttca tttggtaggc ggccgctaag atatcttcaa      60
gcttatgcg                                                             69

<210> SEQ ID NO 302
<211> LENGTH: 20
<212> TYPE: DNA
<213> ORGANISM: Artificial Sequence
<220> FEATURE:
<223> OTHER INFORMATION: Primer

<400> SEQUENCE: 302
cggatgaaga tgtgcagttg                                                 20

<210> SEQ ID NO 303
<211> LENGTH: 61
<212> TYPE: DNA
<213> ORGANISM: Artificial Sequence
<220> FEATURE:
<223> OTHER INFORMATION: Primer

<400> SEQUENCE: 303
tgtctcactt ccacccatct caactgcaca tcttcatccg agcaacaaca tgaggttcga      60
a                                                                     61

<210> SEQ ID NO 304
<211> LENGTH: 69
<212> TYPE: DNA
<213> ORGANISM: Artificial Sequence
<220> FEATURE:
<223> OTHER INFORMATION: Primer

<400> SEQUENCE: 304
cctatgttgt gtggaattgt gagcggataa caatttcaca gtttaaacac aacgcatgtc      60
cagcttttg                                                             69

<210> SEQ ID NO 305
<211> LENGTH: 22
<212> TYPE: DNA
<213> ORGANISM: Artificial Sequence
<220> FEATURE:
<223> OTHER INFORMATION: Primer

<400> SEQUENCE: 305
ctcagaaagg ttgtagttgt ga                                              22
```

```
<210> SEQ ID NO 306
<211> LENGTH: 20
<212> TYPE: DNA
<213> ORGANISM: Artificial Sequence
<220> FEATURE:
<223> OTHER INFORMATION: Primer

<400> SEQUENCE: 306
ccatgagctt gaacaggtaa                                               20

<210> SEQ ID NO 307
<211> LENGTH: 22
<212> TYPE: DNA
<213> ORGANISM: Artificial Sequence
<220> FEATURE:
<223> OTHER INFORMATION: Primer

<400> SEQUENCE: 307
gatgttgtgt tttcagtctg ca                                            22

<210> SEQ ID NO 308
<211> LENGTH: 19
<212> TYPE: DNA
<213> ORGANISM: Artificial Sequence
<220> FEATURE:
<223> OTHER INFORMATION: Primer

<400> SEQUENCE: 308
catcctcaag gcctcagac                                                19

<210> SEQ ID NO 309
<211> LENGTH: 19
<212> TYPE: DNA
<213> ORGANISM: Artificial Sequence
<220> FEATURE:
<223> OTHER INFORMATION: Primer

<400> SEQUENCE: 309
gcttggcatc acggaagct                                                19

<210> SEQ ID NO 310
<211> LENGTH: 20
<212> TYPE: DNA
<213> ORGANISM: Artificial Sequence
<220> FEATURE:
<223> OTHER INFORMATION: Primer

<400> SEQUENCE: 310
ccatgagctt gaacaggtaa                                               20

<210> SEQ ID NO 311
<211> LENGTH: 21
<212> TYPE: DNA
<213> ORGANISM: Artificial Sequence
<220> FEATURE:
<223> OTHER INFORMATION: Primer

<400> SEQUENCE: 311
ttgacaagaa aggtccggtt g                                             21

<210> SEQ ID NO 312
<211> LENGTH: 19
<212> TYPE: DNA
<213> ORGANISM: Artificial Sequence
<220> FEATURE:
<223> OTHER INFORMATION: Primer
```

<400> SEQUENCE: 312
catcctcaag gcctcagac                                                19

<210> SEQ ID NO 313
<211> LENGTH: 20
<212> TYPE: DNA
<213> ORGANISM: Artificial Sequence
<220> FEATURE:
<223> OTHER INFORMATION: Primer

<400> SEQUENCE: 313
atggatgcta tccgagccag                                               20

<210> SEQ ID NO 314
<211> LENGTH: 22
<212> TYPE: DNA
<213> ORGANISM: Artificial Sequence
<220> FEATURE:
<223> OTHER INFORMATION: Primer

<400> SEQUENCE: 314
ctattcatac tcaacagtca ca                                            22

<210> SEQ ID NO 315
<211> LENGTH: 68
<212> TYPE: DNA
<213> ORGANISM: Artificial Sequence
<220> FEATURE:
<223> OTHER INFORMATION: Primer

<400> SEQUENCE: 315
aagttccctt cctctggcag caatcgaacc atcccattca gcggccgcct agcatcgact   60
actgctgc                                                            68

<210> SEQ ID NO 316
<211> LENGTH: 68
<212> TYPE: DNA
<213> ORGANISM: Artificial Sequence
<220> FEATURE:
<223> OTHER INFORMATION: Primer

<400> SEQUENCE: 316
tgattgtacc ccagctgcga ttgatgtgta tctttgcatg gcggccgctc aatgttgact   60
gccccagg                                                            68

<210> SEQ ID NO 317
<211> LENGTH: 68
<212> TYPE: DNA
<213> ORGANISM: Artificial Sequence
<220> FEATURE:
<223> OTHER INFORMATION: primer

<400> SEQUENCE: 317
gcacttctta gatacacaca cactcgcaaa gcgtctacct ggcgcgcctg aatgggatgg   60
ttcgattg                                                            68

<210> SEQ ID NO 318
<211> LENGTH: 21
<212> TYPE: DNA
<213> ORGANISM: Artificial Sequence
<220> FEATURE:
<223> OTHER INFORMATION: Primer

<400> SEQUENCE: 318
ggcaggtcgc agagcaagac a                                    21

<210> SEQ ID NO 319
<211> LENGTH: 21
<212> TYPE: DNA
<213> ORGANISM: Artificial Sequence
<220> FEATURE:
<223> OTHER INFORMATION: Primer

<400> SEQUENCE: 319
ttgacaagaa aggtccggtt g                                    21

<210> SEQ ID NO 320
<211> LENGTH: 20
<212> TYPE: DNA
<213> ORGANISM: Artificial Sequence
<220> FEATURE:
<223> OTHER INFORMATION: Primer

<400> SEQUENCE: 320
gattcatcac aggggcagtc                                      20

<210> SEQ ID NO 321
<211> LENGTH: 20
<212> TYPE: DNA
<213> ORGANISM: Artificial Sequence
<220> FEATURE:
<223> OTHER INFORMATION: Primer

<400> SEQUENCE: 321
tgcgtcgccg tctcgctcct                                      20

<210> SEQ ID NO 322
<211> LENGTH: 19
<212> TYPE: DNA
<213> ORGANISM: Artificial Sequence
<220> FEATURE:
<223> OTHER INFORMATION: Primer

<400> SEQUENCE: 322
acgccgttgc tgagccttg                                       19

<210> SEQ ID NO 323
<211> LENGTH: 20
<212> TYPE: DNA
<213> ORGANISM: Artificial Sequence
<220> FEATURE:
<223> OTHER INFORMATION: Primer

<400> SEQUENCE: 323
ttaggcgacc tcttttcca                                       20

<210> SEQ ID NO 324
<211> LENGTH: 20
<212> TYPE: DNA
<213> ORGANISM: Artificial Sequence
<220> FEATURE:
<223> OTHER INFORMATION: Primer

<400> SEQUENCE: 324
gagcccatca tcaacacctc                                      20

<210> SEQ ID NO 325
<211> LENGTH: 19

<212> TYPE: DNA
<213> ORGANISM: Artificial Sequence
<220> FEATURE:
<223> OTHER INFORMATION: Primer

<400> SEQUENCE: 325
tgccaaggtc gtagacgga                                          19

<210> SEQ ID NO 326
<211> LENGTH: 58
<212> TYPE: DNA
<213> ORGANISM: Artificial Sequence
<220> FEATURE:
<223> OTHER INFORMATION: Primer

<400> SEQUENCE: 326
ggtaacgcca gggttttccc agtcacgacg gtttaaacgt cgagccccct ggacacct    58

<210> SEQ ID NO 327
<211> LENGTH: 68
<212> TYPE: DNA
<213> ORGANISM: Artificial Sequence
<220> FEATURE:
<223> OTHER INFORMATION: Primer

<400> SEQUENCE: 327
gcgctggcaa cgagagcaga gcagcagtag tcgatgctag gcggccgcca tcgccgtcgc    60
ggacatga                                                           68

<210> SEQ ID NO 328
<211> LENGTH: 68
<212> TYPE: DNA
<213> ORGANISM: Artificial Sequence
<220> FEATURE:
<223> OTHER INFORMATION: Primer

<400> SEQUENCE: 328
tgattgtacc ccagctgcga ttgatgtgta tctttgcatg gcggccgctc gacgttgtat    60
ctgcactc                                                            68

<210> SEQ ID NO 329
<211> LENGTH: 68
<212> TYPE: DNA
<213> ORGANISM: Artificial Sequence
<220> FEATURE:
<223> OTHER INFORMATION: Primer

<400> SEQUENCE: 329
gtacgttctg attgccaact acggaccaga ccagggctcc ggcgcgccca tcgccgtcgc    60
ggacatga                                                            68

<210> SEQ ID NO 330
<211> LENGTH: 20
<212> TYPE: DNA
<213> ORGANISM: Artificial Sequence
<220> FEATURE:
<223> OTHER INFORMATION: Primer

<400> SEQUENCE: 330
ggagccctgg tctggtccgt                                         20

<210> SEQ ID NO 331
<211> LENGTH: 58
<212> TYPE: DNA

<213> ORGANISM: Artificial Sequence
<220> FEATURE:
<223> OTHER INFORMATION: Primer

<400> SEQUENCE: 331
agcggataac aatttcacac aggaaacagc gtttaaacac gcgcttcaac atgcccca    58

<210> SEQ ID NO 332
<211> LENGTH: 60
<212> TYPE: DNA
<213> ORGANISM: Artificial Sequence
<220> FEATURE:
<223> OTHER INFORMATION: Primer

<400> SEQUENCE: 332
gctggccgct gggaatagcg tcatgtccgc gacggcgatg gaattcggtc tgaaggacgt    60

<210> SEQ ID NO 333
<211> LENGTH: 22
<212> TYPE: DNA
<213> ORGANISM: Artificial Sequence
<220> FEATURE:
<223> OTHER INFORMATION: Primer

<400> SEQUENCE: 333
gttgagagaa gttgttggat tg    22

<210> SEQ ID NO 334
<211> LENGTH: 62
<212> TYPE: DNA
<213> ORGANISM: Artificial Sequence
<220> FEATURE:
<223> OTHER INFORMATION: Primer

<400> SEQUENCE: 334
aaccaaagac tttttgatca atccaacaac ttctctcaac atgaagattt cctcgatcct    60
tg    62

<210> SEQ ID NO 335
<211> LENGTH: 19
<212> TYPE: DNA
<213> ORGANISM: Artificial Sequence
<220> FEATURE:
<223> OTHER INFORMATION: Primer

<400> SEQUENCE: 335
tcagcgccgt aacctctgc    19

<210> SEQ ID NO 336
<211> LENGTH: 61
<212> TYPE: DNA
<213> ORGANISM: Artificial Sequence
<220> FEATURE:
<223> OTHER INFORMATION: Primer

<400> SEQUENCE: 336
tgatggtgat gaggcggaaa agcagaggtt acggcgctga ggatccactt aacgttactg    60
a    61

<210> SEQ ID NO 337
<211> LENGTH: 71
<212> TYPE: DNA
<213> ORGANISM: Artificial Sequence
<220> FEATURE:
<223> OTHER INFORMATION: Primer

<400> SEQUENCE: 337
tctctcaaag gaagaatccc ttcagggttg cgtttccagt gcggccgctc tccttctaga    60
aagaaggatt a    71

<210> SEQ ID NO 338
<211> LENGTH: 20
<212> TYPE: DNA
<213> ORGANISM: Artificial Sequence
<220> FEATURE:
<223> OTHER INFORMATION: Primer

<400> SEQUENCE: 338
actggaaacg caaccctgaa    20

<210> SEQ ID NO 339
<211> LENGTH: 58
<212> TYPE: DNA
<213> ORGANISM: Artificial Sequence
<220> FEATURE:
<223> OTHER INFORMATION: Primer

<400> SEQUENCE: 339
tctgattgcc aactacggac cagaccaggg ctccggcgcg gcggccgcta gatctacg    58

<210> SEQ ID NO 340
<211> LENGTH: 66
<212> TYPE: DNA
<213> ORGANISM: Artificial Sequence
<220> FEATURE:
<223> OTHER INFORMATION: Primer

<400> SEQUENCE: 340
gtacacttgt ttagaggtaa tccttctttc tagaaggaga gcggccgcgg agccctggtc    60
tggtcc    66

<210> SEQ ID NO 341
<211> LENGTH: 59
<212> TYPE: DNA
<213> ORGANISM: Artificial Sequence
<220> FEATURE:
<223> OTHER INFORMATION: Primer

<400> SEQUENCE: 341
gcgctggcaa cgagagcaga gcagcagtag tcgatgctag aagctgacgg gcgtcaacg    59

<210> SEQ ID NO 342
<211> LENGTH: 19
<212> TYPE: DNA
<213> ORGANISM: Artificial Sequence
<220> FEATURE:
<223> OTHER INFORMATION: Primer

<400> SEQUENCE: 342
tagcatcgac tactgctgc    19

<210> SEQ ID NO 343
<211> LENGTH: 70
<212> TYPE: DNA
<213> ORGANISM: Artificial Sequence
<220> FEATURE:
<223> OTHER INFORMATION: Primer

<400> SEQUENCE: 343

```
gtacgttctg attgccaact acggaccaga ccagggctcc gcggccgcca tgcaaagata      60
cacatcaatc                                                             70
```

<210> SEQ ID NO 344
<211> LENGTH: 20
<212> TYPE: DNA
<213> ORGANISM: Artificial Sequence
<220> FEATURE:
<223> OTHER INFORMATION: Primer

<400> SEQUENCE: 344

```
gattcatcac aggggcagtc                                                  20
```

<210> SEQ ID NO 345
<211> LENGTH: 20
<212> TYPE: DNA
<213> ORGANISM: Artificial Sequence
<220> FEATURE:
<223> OTHER INFORMATION: Primer

<400> SEQUENCE: 345

```
ccgctctcaa actgcccaaa                                                  20
```

<210> SEQ ID NO 346
<211> LENGTH: 19
<212> TYPE: DNA
<213> ORGANISM: Artificial Sequence
<220> FEATURE:
<223> OTHER INFORMATION: Primer

<400> SEQUENCE: 346

```
acgtgaagtt gcccatcaa                                                   19
```

<210> SEQ ID NO 347
<211> LENGTH: 24
<212> TYPE: DNA
<213> ORGANISM: Artificial Sequence
<220> FEATURE:
<223> OTHER INFORMATION: Primer

<400> SEQUENCE: 347

```
taacttgtac gctctcagtt cgag                                             24
```

<210> SEQ ID NO 348
<211> LENGTH: 20
<212> TYPE: DNA
<213> ORGANISM: Artificial Sequence
<220> FEATURE:
<223> OTHER INFORMATION: Primer

<400> SEQUENCE: 348

```
gaccaatggc ttcacgaagt                                                  20
```

<210> SEQ ID NO 349
<211> LENGTH: 20
<212> TYPE: DNA
<213> ORGANISM: Artificial Sequence
<220> FEATURE:
<223> OTHER INFORMATION: Primer

<400> SEQUENCE: 349

```
ttaggcgacc tcttttccca                                                  20
```

<210> SEQ ID NO 350
<211> LENGTH: 20

```
<212> TYPE: DNA
<213> ORGANISM: Artificial Sequence
<220> FEATURE:
<223> OTHER INFORMATION: Primer

<400> SEQUENCE: 350
cagcagcacc gcatccacca                                          20

<210> SEQ ID NO 351
<211> LENGTH: 20
<212> TYPE: DNA
<213> ORGANISM: Artificial Sequence
<220> FEATURE:
<223> OTHER INFORMATION: Primer

<400> SEQUENCE: 351
gccgaatcgc tggttgccct                                          20

<210> SEQ ID NO 352
<211> LENGTH: 58
<212> TYPE: DNA
<213> ORGANISM: Artificial Sequence
<220> FEATURE:
<223> OTHER INFORMATION: Primer

<400> SEQUENCE: 352
ggtaacgcca gggttttccc agtcacgacg gtttaaacgg aggctgcgac accgtctg  58

<210> SEQ ID NO 353
<211> LENGTH: 68
<212> TYPE: DNA
<213> ORGANISM: Artificial Sequence
<220> FEATURE:
<223> OTHER INFORMATION: Primer

<400> SEQUENCE: 353
gcgctggcaa cgagagcaga gcagcagtag tcgatgctag gcggccgccc ggcctgaaac  60
gacctccc                                                         68

<210> SEQ ID NO 354
<211> LENGTH: 68
<212> TYPE: DNA
<213> ORGANISM: Artificial Sequence
<220> FEATURE:
<223> OTHER INFORMATION: Primer

<400> SEQUENCE: 354
cccgtcaccg agatctgatc cgtcaccggg atccacttaa gcggccgcga gagagaaaca  60
aaacagtg                                                         68

<210> SEQ ID NO 355
<211> LENGTH: 68
<212> TYPE: DNA
<213> ORGANISM: Artificial Sequence
<220> FEATURE:
<223> OTHER INFORMATION: Primer

<400> SEQUENCE: 355
acattccgac cgtttactga tccaagccgt gcaaccgact ggcgcgcccc ggcctgaaac  60
gacctccc                                                         68

<210> SEQ ID NO 356
<211> LENGTH: 20
<212> TYPE: DNA
```

```
<213> ORGANISM: Artificial Sequence
<220> FEATURE:
<223> OTHER INFORMATION: Primer

<400> SEQUENCE: 356
agtcggttgc acggcttgga                                              20

<210> SEQ ID NO 357
<211> LENGTH: 58
<212> TYPE: DNA
<213> ORGANISM: Artificial Sequence
<220> FEATURE:
<223> OTHER INFORMATION: Primer

<400> SEQUENCE: 357
agcggataac aatttcacac aggaaacagc gtttaaacga gacggacgcc tgcaccac    58

<210> SEQ ID NO 358
<211> LENGTH: 68
<212> TYPE: DNA
<213> ORGANISM: Artificial Sequence
<220> FEATURE:
<223> OTHER INFORMATION: Primer

<400> SEQUENCE: 358
tgattgtacc ccagctgcga ttgatgtgta tctttgcatg gcgatcgcga cagaagatga  60
tattgaag                                                            68

<210> SEQ ID NO 359
<211> LENGTH: 20
<212> TYPE: DNA
<213> ORGANISM: Artificial Sequence
<220> FEATURE:
<223> OTHER INFORMATION: Primer

<400> SEQUENCE: 359
ttaagtggat cccggtgacg                                              20

<210> SEQ ID NO 360
<211> LENGTH: 57
<212> TYPE: DNA
<213> ORGANISM: Artificial Sequence
<220> FEATURE:
<223> OTHER INFORMATION: Primer

<400> SEQUENCE: 360
gtaacgccag ggttttccca gtcacgacgg tttaaaccat aaacttgcgc agtcgaa     57

<210> SEQ ID NO 361
<211> LENGTH: 68
<212> TYPE: DNA
<213> ORGANISM: Artificial Sequence
<220> FEATURE:
<223> OTHER INFORMATION: Primer

<400> SEQUENCE: 361
gcgctggcaa cgagagcaga gcagcagtag tcgatgctag gcggccgcct tctaggatgg  60
agcgcttg                                                            68

<210> SEQ ID NO 362
<211> LENGTH: 68
<212> TYPE: DNA
<213> ORGANISM: Artificial Sequence
<220> FEATURE:
<223> OTHER INFORMATION: Primer
```

<400> SEQUENCE: 362
caaccagccg cagcctcagc ctctctcagc ctcatcagcc gcggccgcag acggcttctt    60
ccaaaaca    68

<210> SEQ ID NO 363
<211> LENGTH: 57
<212> TYPE: DNA
<213> ORGANISM: Artificial Sequence
<220> FEATURE:
<223> OTHER INFORMATION: Primer

<400> SEQUENCE: 363
gcggataaca atttcacaca ggaaacagcg tttaaacccc cagggaggct attctac    57

<210> SEQ ID NO 364
<211> LENGTH: 20
<212> TYPE: DNA
<213> ORGANISM: Artificial Sequence
<220> FEATURE:
<223> OTHER INFORMATION: Primer

<400> SEQUENCE: 364
ctttccaagc gtttgagtcc    20

<210> SEQ ID NO 365
<211> LENGTH: 20
<212> TYPE: DNA
<213> ORGANISM: Artificial Sequence
<220> FEATURE:
<223> OTHER INFORMATION: Primer

<400> SEQUENCE: 365
ccatgagctt gaacaggtaa    20

<210> SEQ ID NO 366
<211> LENGTH: 20
<212> TYPE: DNA
<213> ORGANISM: Artificial Sequence
<220> FEATURE:
<223> OTHER INFORMATION: Primer

<400> SEQUENCE: 366
gcgtgtttta tcctggtgct    20

<210> SEQ ID NO 367
<211> LENGTH: 19
<212> TYPE: DNA
<213> ORGANISM: Artificial Sequence
<220> FEATURE:
<223> OTHER INFORMATION: Primer

<400> SEQUENCE: 367
catcctcaag gcctcagac    19

<210> SEQ ID NO 368
<211> LENGTH: 20
<212> TYPE: DNA
<213> ORGANISM: Artificial Sequence
<220> FEATURE:
<223> OTHER INFORMATION: Primer

<400> SEQUENCE: 368
cacctccgtc gatgagtttt    20

-continued

```
<210> SEQ ID NO 369
<211> LENGTH: 20
<212> TYPE: DNA
<213> ORGANISM: Artificial Sequence
<220> FEATURE:
<223> OTHER INFORMATION: Primer

<400> SEQUENCE: 369
agaagaaggt ggtggtggtg                                               20

<210> SEQ ID NO 370
<211> LENGTH: 57
<212> TYPE: DNA
<213> ORGANISM: Artificial Sequence
<220> FEATURE:
<223> OTHER INFORMATION: Primer

<400> SEQUENCE: 370
gtaacgccag ggttttccca gtcacgacgg tttaaacgtt tgagcattct cccaagc      57

<210> SEQ ID NO 371
<211> LENGTH: 68
<212> TYPE: DNA
<213> ORGANISM: Artificial Sequence
<220> FEATURE:
<223> OTHER INFORMATION: Primer

<400> SEQUENCE: 371
gcgctggcaa cgagagcaga gcagcagtag tcgatgctag gcggccgccg ccattttgaa   60
gaagatgc                                                            68

<210> SEQ ID NO 372
<211> LENGTH: 68
<212> TYPE: DNA
<213> ORGANISM: Artificial Sequence
<220> FEATURE:
<223> OTHER INFORMATION: Primer

<400> SEQUENCE: 372
caaccagccg cagcctcagc ctctctcagc ctcatcagcc gcggccgcat gctccctcgt   60
cattaagc                                                            68

<210> SEQ ID NO 373
<211> LENGTH: 57
<212> TYPE: DNA
<213> ORGANISM: Artificial Sequence
<220> FEATURE:
<223> OTHER INFORMATION: Primer

<400> SEQUENCE: 373
gcggataaca atttcacaca ggaaacagcg tttaaacaca acaccttctc cgacacc      57

<210> SEQ ID NO 374
<211> LENGTH: 20
<212> TYPE: DNA
<213> ORGANISM: Artificial Sequence
<220> FEATURE:
<223> OTHER INFORMATION: Primer

<400> SEQUENCE: 374
atgcccaagt ttcgtacctg                                               20

<210> SEQ ID NO 375
<211> LENGTH: 20
```

```
<212> TYPE: DNA
<213> ORGANISM: Artificial Sequence
<220> FEATURE:
<223> OTHER INFORMATION: Primer

<400> SEQUENCE: 375
ccatgagctt gaacaggtaa                                              20

<210> SEQ ID NO 376
<211> LENGTH: 20
<212> TYPE: DNA
<213> ORGANISM: Artificial Sequence
<220> FEATURE:
<223> OTHER INFORMATION: Primer

<400> SEQUENCE: 376
ggcgcattca gaagaagaac                                              20

<210> SEQ ID NO 377
<211> LENGTH: 19
<212> TYPE: DNA
<213> ORGANISM: Artificial Sequence
<220> FEATURE:
<223> OTHER INFORMATION: Primer

<400> SEQUENCE: 377
catcctcaag gcctcagac                                               19

<210> SEQ ID NO 378
<211> LENGTH: 20
<212> TYPE: DNA
<213> ORGANISM: Artificial Sequence
<220> FEATURE:
<223> OTHER INFORMATION: Primer

<400> SEQUENCE: 378
cacttgatga acgctggcta                                              20

<210> SEQ ID NO 379
<211> LENGTH: 20
<212> TYPE: DNA
<213> ORGANISM: Artificial Sequence
<220> FEATURE:
<223> OTHER INFORMATION: Primer

<400> SEQUENCE: 379
cgtaatggcg ttgttgacag                                              20

<210> SEQ ID NO 380
<211> LENGTH: 57
<212> TYPE: DNA
<213> ORGANISM: Artificial Sequence
<220> FEATURE:
<223> OTHER INFORMATION: Primer

<400> SEQUENCE: 380
gtaacgccag ggttttccca gtcacgacgg tttaaacgag gcagccaaaa agtgaag     57

<210> SEQ ID NO 381
<211> LENGTH: 68
<212> TYPE: DNA
<213> ORGANISM: Artificial Sequence
<220> FEATURE:
<223> OTHER INFORMATION: Primer

<400> SEQUENCE: 381
```

```
gcgctggcaa cgagagcaga gcagcagtag tcgatgctag gcggccgctg aaagaaggca    60
ggaccagt                                                              68

<210> SEQ ID NO 382
<211> LENGTH: 68
<212> TYPE: DNA
<213> ORGANISM: Artificial Sequence
<220> FEATURE:
<223> OTHER INFORMATION: Primer

<400> SEQUENCE: 382
caaccagccg cagcctcagc ctctctcagc ctcatcagcc gcggccgcaa gaggctcgga    60
caaagaca                                                              68

<210> SEQ ID NO 383
<211> LENGTH: 57
<212> TYPE: DNA
<213> ORGANISM: Artificial Sequence
<220> FEATURE:
<223> OTHER INFORMATION: Primer

<400> SEQUENCE: 383
gcggataaca atttcacaca ggaaacagcg tttaaacgat cgtggtgcac gagacta       57

<210> SEQ ID NO 384
<211> LENGTH: 20
<212> TYPE: DNA
<213> ORGANISM: Artificial Sequence
<220> FEATURE:
<223> OTHER INFORMATION: Primer

<400> SEQUENCE: 384
gcactgcgtt gcctttctat                                                 20

<210> SEQ ID NO 385
<211> LENGTH: 20
<212> TYPE: DNA
<213> ORGANISM: Artificial Sequence
<220> FEATURE:
<223> OTHER INFORMATION: Primer

<400> SEQUENCE: 385
ccatgagctt gaacaggtaa                                                 20

<210> SEQ ID NO 386
<211> LENGTH: 20
<212> TYPE: DNA
<213> ORGANISM: Artificial Sequence
<220> FEATURE:
<223> OTHER INFORMATION: Primer

<400> SEQUENCE: 386
gaaagcatgg ctcgtttctc                                                 20

<210> SEQ ID NO 387
<211> LENGTH: 19
<212> TYPE: DNA
<213> ORGANISM: Artificial Sequence
<220> FEATURE:
<223> OTHER INFORMATION: Primer

<400> SEQUENCE: 387
catcctcaag gcctcagac                                                  19
```

```
<210> SEQ ID NO 388
<211> LENGTH: 20
<212> TYPE: DNA
<213> ORGANISM: Artificial Sequence
<220> FEATURE:
<223> OTHER INFORMATION: Primer

<400> SEQUENCE: 388
acccggctca actagctaca                                              20

<210> SEQ ID NO 389
<211> LENGTH: 20
<212> TYPE: DNA
<213> ORGANISM: Artificial Sequence
<220> FEATURE:
<223> OTHER INFORMATION: Primer

<400> SEQUENCE: 389
agctggcctt tcgttacaga                                              20

<210> SEQ ID NO 390
<211> LENGTH: 57
<212> TYPE: DNA
<213> ORGANISM: Artificial Sequence
<220> FEATURE:
<223> OTHER INFORMATION: Primer

<400> SEQUENCE: 390
gtaacgccag ggttttccca gtcacgacgg tttaaacttg gtttgaacag ctgcaag     57

<210> SEQ ID NO 391
<211> LENGTH: 68
<212> TYPE: DNA
<213> ORGANISM: Artificial Sequence
<220> FEATURE:
<223> OTHER INFORMATION: Primer

<400> SEQUENCE: 391
gcgctggcaa cgagagcaga gcagcagtag tcgatgctag gcggccgctt tgcagcaaga  60
tgtcgttc                                                           68

<210> SEQ ID NO 392
<211> LENGTH: 68
<212> TYPE: DNA
<213> ORGANISM: Artificial Sequence
<220> FEATURE:
<223> OTHER INFORMATION: Primer

<400> SEQUENCE: 392
caaccagccg cagcctcagc ctctctcagc ctcatcagcc gcggccgcgc tgtgaagacg  60
ggcttatc                                                           68

<210> SEQ ID NO 393
<211> LENGTH: 57
<212> TYPE: DNA
<213> ORGANISM: Artificial Sequence
<220> FEATURE:
<223> OTHER INFORMATION: Primer

<400> SEQUENCE: 393
gcggataaca atttcacaca ggaaacagcg tttaaaccaa gaacagcatc gaggaca     57

<210> SEQ ID NO 394
<211> LENGTH: 19
<212> TYPE: DNA
```

<213> ORGANISM: Artificial Sequence
<220> FEATURE:
<223> OTHER INFORMATION: Primer

<400> SEQUENCE: 394
gggcgacgac gagttttat                                      19

<210> SEQ ID NO 395
<211> LENGTH: 20
<212> TYPE: DNA
<213> ORGANISM: Artificial Sequence
<220> FEATURE:
<223> OTHER INFORMATION: Primer

<400> SEQUENCE: 395
ccatgagctt gaacaggtaa                                     20

<210> SEQ ID NO 396
<211> LENGTH: 20
<212> TYPE: DNA
<213> ORGANISM: Artificial Sequence
<220> FEATURE:
<223> OTHER INFORMATION: Primer

<400> SEQUENCE: 396
gaatggatca agtcgctgct                                     20

<210> SEQ ID NO 397
<211> LENGTH: 19
<212> TYPE: DNA
<213> ORGANISM: Artificial Sequence
<220> FEATURE:
<223> OTHER INFORMATION: Primer

<400> SEQUENCE: 397
catcctcaag gcctcagac                                      19

<210> SEQ ID NO 398
<211> LENGTH: 20
<212> TYPE: DNA
<213> ORGANISM: Artificial Sequence
<220> FEATURE:
<223> OTHER INFORMATION: Primer

<400> SEQUENCE: 398
ctcaggctct gcttggattc                                     20

<210> SEQ ID NO 399
<211> LENGTH: 20
<212> TYPE: DNA
<213> ORGANISM: Artificial Sequence
<220> FEATURE:
<223> OTHER INFORMATION: Primer

<400> SEQUENCE: 399
atgccaaaaa gactgctgct                                     20

<210> SEQ ID NO 400
<211> LENGTH: 57
<212> TYPE: DNA
<213> ORGANISM: Artificial Sequence
<220> FEATURE:
<223> OTHER INFORMATION: Primer

<400> SEQUENCE: 400
gtaacgccag ggttttccca gtcacgacgg tttaaacgcc tccctggtat tcagaca      57

-continued

```
<210> SEQ ID NO 401
<211> LENGTH: 68
<212> TYPE: DNA
<213> ORGANISM: Artificial Sequence
<220> FEATURE:
<223> OTHER INFORMATION: Primer

<400> SEQUENCE: 401
gcgctggcaa cgagagcaga gcagcagtag tcgatgctag gcggccgcga cgccagaaag      60
aaatgctc                                                              68

<210> SEQ ID NO 402
<211> LENGTH: 68
<212> TYPE: DNA
<213> ORGANISM: Artificial Sequence
<220> FEATURE:
<223> OTHER INFORMATION: Primer

<400> SEQUENCE: 402
caaccagccg cagcctcagc ctctctcagc ctcatcagcc gcggccgcga cctggtcagc      60
tgctcttt                                                              68

<210> SEQ ID NO 403
<211> LENGTH: 57
<212> TYPE: DNA
<213> ORGANISM: Artificial Sequence
<220> FEATURE:
<223> OTHER INFORMATION: Primer

<400> SEQUENCE: 403
gcggataaca atttcacaca ggaaacagcg tttaaactgg aaccacatcg acttcac        57

<210> SEQ ID NO 404
<211> LENGTH: 20
<212> TYPE: DNA
<213> ORGANISM: Artificial Sequence
<220> FEATURE:
<223> OTHER INFORMATION: Primer

<400> SEQUENCE: 404
aaccaccttg tcaccgtctc                                                 20

<210> SEQ ID NO 405
<211> LENGTH: 20
<212> TYPE: DNA
<213> ORGANISM: Artificial Sequence
<220> FEATURE:
<223> OTHER INFORMATION: Primer

<400> SEQUENCE: 405
ccatgagctt gaacaggtaa                                                 20

<210> SEQ ID NO 406
<211> LENGTH: 20
<212> TYPE: DNA
<213> ORGANISM: Artificial Sequence
<220> FEATURE:
<223> OTHER INFORMATION: Primer

<400> SEQUENCE: 406
gtcgtcgagg ctgctttatc                                                 20
```

```
<210> SEQ ID NO 407
<211> LENGTH: 19
<212> TYPE: DNA
<213> ORGANISM: Artificial Sequence
<220> FEATURE:
<223> OTHER INFORMATION: Primer

<400> SEQUENCE: 407
catcctcaag gcctcagac                                              19

<210> SEQ ID NO 408
<211> LENGTH: 20
<212> TYPE: DNA
<213> ORGANISM: Artificial Sequence
<220> FEATURE:
<223> OTHER INFORMATION: Primer

<400> SEQUENCE: 408
gatctcgaat ccgaggacaa                                             20
```